US009682153B2

(12) United States Patent
Bossard et al.

(10) Patent No.: US 9,682,153 B2
(45) Date of Patent: Jun. 20, 2017

(54) POLYMER CONJUGATES OF THERAPEUTIC PEPTIDES

(71) Applicant: NEKTAR THERAPEUTICS, San Francisco, CA (US)

(72) Inventors: Mary J. Bossard, Madison, AL (US); Steven O. Roczniak, Greensboro, NC (US); Harold Zappe, Harvest, AL (US); Yujun Wang, Fremont, CA (US); Ping Zhang, Millbrae, CA (US); Dawei Sheng, Madison, AL (US); C. Simone Jude-Fishburn, Redwood City, CA (US); Elizabeth Louise Minamitani, Lacey's Spring, AL (US); Xiaofeng Liu, Belmont, CA (US); Haim Moskowitz, San Diego, CA (US); Dennis G. Fry, Pacifica, CA (US); Cherie F. Ali, Burlingame, CA (US); Christine Taylor Brew, Pacifica, CA (US)

(73) Assignee: Nektar Therapeutics, San Francisco, CA (US)

(*) Notice: Subject to any disclaimer, the term of this patent is extended or adjusted under 35 U.S.C. 154(b) by 0 days.

(21) Appl. No.: 14/664,582

(22) Filed: Mar. 20, 2015

(65) Prior Publication Data

US 2016/0022828 A1    Jan. 28, 2016

Related U.S. Application Data

(63) Continuation of application No. 13/119,297, filed as application No. PCT/US2009/005192 on Sep. 17, 2009, now abandoned.

(60) Provisional application No. 61/153,966, filed on Feb. 19, 2009, provisional application No. 61/208,089, filed on Feb. 18, 2009, provisional application No. 61/192,672, filed on Sep. 19, 2008.

(51) Int. Cl.
A61K 38/00      (2006.01)
A61K 47/48      (2006.01)
A61K 38/10      (2006.01)
A61K 38/16      (2006.01)
A61K 38/28      (2006.01)

(52) U.S. Cl.
CPC ........ *A61K 47/48215* (2013.01); *A61K 38/10* (2013.01); *A61K 38/16* (2013.01); *A61K 38/28* (2013.01); *A61K 47/4823* (2013.01)

(58) Field of Classification Search
None
See application file for complete search history.

(56) References Cited

U.S. PATENT DOCUMENTS

| | | |
|---|---|---|
| 3,906,950 A | 9/1975 | Cocozza |
| 4,010,148 A | 3/1977 | Goldstein |
| 4,013,075 A | 3/1977 | Cocozza |
| 4,148,788 A | 4/1979 | Wang |
| 4,247,066 A | 1/1981 | Frost et al. |
| 4,321,260 A | 3/1982 | Auclair |
| 4,461,724 A | 7/1984 | Konishi |
| 4,554,101 A | 11/1985 | Hopp |
| 4,585,754 A | 4/1986 | Meisner et al. |
| 4,608,364 A | 8/1986 | Grau |
| 4,652,548 A | 3/1987 | Chance et al. |
| 4,667,668 A | 5/1987 | Wetterlin |
| 4,668,281 A | 5/1987 | Levitt |
| 4,801,612 A | 1/1989 | Wei et al. |
| 4,805,811 A | 2/1989 | Wetterlin |
| 4,810,646 A | 3/1989 | Jamas et al. |
| 4,846,876 A | 7/1989 | Draber et al. |
| 4,868,122 A | 9/1989 | Kominek et al. |
| 4,966,753 A | 10/1990 | McMichael |
| 4,992,540 A | 2/1991 | Jamas et al. |
| 5,028,703 A | 7/1991 | Jamas et al. |
| 5,049,656 A | 9/1991 | Lewis et al. |
| 5,118,494 A | 6/1992 | Schultz et al. |
| 5,137,871 A | 8/1992 | Wei |
| 5,221,736 A | 6/1993 | Coolidge et al. |
| 5,252,714 A | 10/1993 | Harris et al. |
| 5,256,549 A | 10/1993 | Urdea et al. |
| 5,288,708 A | 2/1994 | Sikiric et al. |
| 5,320,094 A | 6/1994 | Laube et al. |
| 5,359,030 A | 10/1994 | Ekwuribe |
| 5,388,572 A | 2/1995 | Mulhauser et al. |
| 5,438,040 A | 8/1995 | Ekwuribe |
| 5,440,013 A | 8/1995 | Kahn |
| 5,446,128 A | 8/1995 | Kahn |
| 5,457,044 A | 10/1995 | Cipolla et al. |

(Continued)

FOREIGN PATENT DOCUMENTS

| | | |
|---|---|---|
| EP | 0 076 676 | 4/1983 |
| EP | 0 132 769 | 2/1985 |

(Continued)

OTHER PUBLICATIONS

US RE37,917, 12/2002, Furuhata et al. (withdrawn)
Abe, et al., "Versatile synthesis of oligosaccharide-containing fullerenes", Tetrahedron: Asymmetry, vol. 16, pp. 15-19, (2005).
Altschul, et al., "Basic Local Alignment Search Tool", J. Mol. Biol., vol. 215, pp. 403-410, (1990).
Angell, "Formation of Glasses from Liquids and Biopolymers", Science, vol. 267, pp. 1924-1935, (Mar. 31, 1995).

(Continued)

*Primary Examiner* — James H Alstrum Acevedo
*Assistant Examiner* — Sergio Coffa

(57) ABSTRACT

The invention provides peptides that are chemically modified by covalent attachment of a water-soluble oligomer. A conjugate of the invention, when administered by any of a number of administration routes, exhibits characteristics that are different from the characteristics of the peptide not attached to the water-soluble oligomer.

12 Claims, 84 Drawing Sheets

(56) References Cited

U.S. PATENT DOCUMENTS

| | | |
|---|---|---|
| 5,458,135 A | 10/1995 | Patton et al. |
| 5,468,481 A | 11/1995 | Sharma et al. |
| 5,470,831 A | 11/1995 | Whitman et al. |
| 5,475,085 A | 12/1995 | Kahn |
| 5,492,688 A | 2/1996 | Byron et al. |
| 5,521,184 A | 5/1996 | Zimmermann |
| 5,522,385 A | 6/1996 | Lloyd et al. |
| 5,545,719 A | 8/1996 | Shashoua |
| 5,571,789 A | 11/1996 | Fluge et al. |
| 5,605,674 A | 2/1997 | Purewal et al. |
| 5,607,677 A | 3/1997 | Jamas et al. |
| 5,610,136 A | 3/1997 | McMichael |
| 5,612,460 A | 3/1997 | Zalipsky |
| 5,618,914 A | 4/1997 | Kahn |
| 5,629,384 A | 5/1997 | Veronese et al. |
| 5,650,234 A | 7/1997 | Dolence et al. |
| 5,654,007 A | 8/1997 | Johnson et al. |
| 5,670,155 A | 9/1997 | Kahn |
| 5,672,581 A | 9/1997 | Rubsamen et al. |
| 5,672,662 A | 9/1997 | Harris et al. |
| 5,672,681 A | 9/1997 | Kahn |
| 5,674,976 A | 10/1997 | Kahn |
| 5,683,677 A | 11/1997 | Purewal et al. |
| 5,692,095 A | 11/1997 | Young |
| 5,710,245 A | 1/1998 | Kahn |
| 5,739,208 A | 4/1998 | Harris |
| 5,740,794 A | 4/1998 | Smith et al. |
| 5,741,495 A | 4/1998 | Jamas et al. |
| 5,758,637 A | 6/1998 | Ivri et al. |
| 5,767,254 A | 6/1998 | Polt |
| 5,785,049 A | 7/1998 | Smith et al. |
| 5,795,864 A | 8/1998 | Amstutz et al. |
| 5,817,628 A | 10/1998 | Kreek |
| 5,834,590 A | 11/1998 | Vinik et al. |
| 5,840,833 A | 11/1998 | Kahn |
| 5,840,900 A | 11/1998 | Greenwald et al. |
| 5,859,184 A | 1/1999 | Kahn et al. |
| 5,880,131 A | 3/1999 | Greenwald et al. |
| 5,888,762 A | 3/1999 | Joliot et al. |
| 5,922,675 A | 7/1999 | Baker et al. |
| 5,929,237 A | 7/1999 | Kahn |
| 5,932,462 A | 8/1999 | Harris et al. |
| 5,932,548 A | 8/1999 | Deghenghi |
| 5,938,117 A | 8/1999 | Ivri |
| 5,976,574 A | 11/1999 | Gordon |
| 5,985,248 A | 11/1999 | Gordon et al. |
| 5,990,237 A | 11/1999 | Bentley et al. |
| 5,998,367 A | 12/1999 | Gaeta et al. |
| 6,001,336 A | 12/1999 | Gordon |
| 6,014,970 A | 1/2000 | Ivri et al. |
| 6,080,762 A | 6/2000 | Allen et al. |
| 6,083,909 A | 7/2000 | Sommermeyer et al. |
| 6,085,740 A | 7/2000 | Ivri et al. |
| 6,136,346 A | 10/2000 | Eljamal et al. |
| 6,162,046 A | 12/2000 | Young et al. |
| 6,205,999 B1 | 3/2001 | Ivri et al. |
| 6,214,966 B1 | 4/2001 | Harris |
| 6,257,233 B1 | 7/2001 | Burr et al. |
| 6,302,331 B1 | 10/2001 | Dvorsky et al. |
| 6,309,671 B1 | 10/2001 | Foster et al. |
| 6,347,936 B1 | 2/2002 | Young et al. |
| 6,348,558 B1 | 2/2002 | Harris et al. |
| 6,357,490 B1 | 3/2002 | Johnston et al. |
| 6,362,254 B2 | 3/2002 | Harris et al. |
| 6,376,470 B1 | 4/2002 | Greenwald et al. |
| 6,376,604 B2 | 4/2002 | Kozlowski |
| 6,379,670 B1 | 4/2002 | Gaur et al. |
| 6,413,507 B1 | 7/2002 | Bentley et al. |
| 6,448,369 B1 | 9/2002 | Bentley et al. |
| 6,495,659 B2 | 12/2002 | Bentley et al. |
| 6,504,005 B1 | 1/2003 | Fridkin et al. |
| 6,515,100 B2 | 2/2003 | Harris |
| 6,518,239 B1 | 2/2003 | Kuo et al. |
| 6,524,591 B2 | 2/2003 | Schmid |
| 6,579,968 B1 | 6/2003 | Blood et al. |
| 6,583,408 B2 | 6/2003 | Smith et al. |
| 6,585,509 B2 | 7/2003 | Young et al. |
| 6,602,498 B2 | 8/2003 | Shen |
| 6,610,649 B2 | 8/2003 | Wahren et al. |
| 6,634,864 B1 | 10/2003 | Young et al. |
| 6,653,442 B1 | 11/2003 | Chang et al. |
| 6,701,922 B2 | 3/2004 | Hindle et al. |
| 6,706,289 B2 | 3/2004 | Lewis et al. |
| 6,794,489 B2 | 9/2004 | Blood et al. |
| 6,800,611 B2 | 10/2004 | Fujii et al. |
| 6,803,565 B2 | 10/2004 | Smith et al. |
| 6,815,530 B2 | 11/2004 | Ekwuribe et al. |
| 6,828,297 B2 | 12/2004 | Ekwuribe et al. |
| 6,831,064 B1 | 12/2004 | Forssmann et al. |
| 6,835,802 B2 | 12/2004 | Ekwuribe et al. |
| 6,838,259 B2 | 1/2005 | Suenaga et al. |
| 6,858,580 B2 | 2/2005 | Ekwuribe et al. |
| 6,864,350 B2 | 3/2005 | Harris |
| 6,878,689 B2 | 4/2005 | Murata et al. |
| 6,890,518 B2 | 5/2005 | Patton et al. |
| 6,899,867 B2 | 5/2005 | Bentley et al. |
| 6,943,151 B2 | 9/2005 | Henriksen et al. |
| 7,026,440 B2 | 4/2006 | Bentley et al. |
| 7,030,084 B2 | 4/2006 | Ekwuribe et al. |
| 7,060,675 B2 | 6/2006 | Ekwuribe et al. |
| 7,084,114 B2 | 8/2006 | Ekwuribe et al. |
| 7,112,662 B2 | 9/2006 | Matsumoto et al. |
| 7,268,109 B2 | 9/2007 | Ellis et al. |
| 7,297,676 B2 | 11/2007 | Rudolph et al. |
| 7,314,754 B2 | 1/2008 | Watanabe et al. |
| 7,431,570 B2 | 10/2008 | Young et al. |
| 8,252,275 B2 | 8/2012 | Bentley et al. |
| 2001/0044526 A1 | 11/2001 | Shen |
| 2002/0013266 A1 | 1/2002 | Bentley et al. |
| 2002/0028189 A1 | 3/2002 | Jo et al. |
| 2002/0065397 A1 | 5/2002 | Roberts et al. |
| 2003/0069170 A1 | 4/2003 | Soltero et al. |
| 2003/0143596 A1 | 7/2003 | Bentley et al. |
| 2003/0228652 A1 | 12/2003 | Radhakrishnan et al. |
| 2003/0229010 A1 | 12/2003 | Ekwuribe |
| 2004/0038899 A1 | 2/2004 | Bentley et al. |
| 2004/0096402 A1 | 5/2004 | Hodges et al. |
| 2004/0116649 A1 | 6/2004 | Kozlowski |
| 2004/0203081 A1 | 10/2004 | James et al. |
| 2004/0262513 A1 | 12/2004 | Karol et al. |
| 2005/0009988 A1 | 1/2005 | Harris et al. |
| 2005/0014903 A1 | 1/2005 | Kozlowski et al. |
| 2005/0059600 A1 | 3/2005 | Burnett et al. |
| 2005/0074425 A1 | 4/2005 | Waugh et al. |
| 2005/0217666 A1 | 10/2005 | Fink et al. |
| 2005/0229927 A1 | 10/2005 | Fink et al. |
| 2005/0229928 A1 | 10/2005 | Ivri et al. |
| 2005/0281781 A1 | 12/2005 | Ostroff |
| 2006/0074009 A1 | 4/2006 | James et al. |
| 2006/0105948 A1 | 5/2006 | Kodra et al. |
| 2006/0121062 A1 | 6/2006 | Eichner et al. |
| 2006/0171920 A1 | 8/2006 | Shechter et al. |
| 2006/0199759 A1 | 9/2006 | Ekwuribe et al. |
| 2006/0216301 A1 | 9/2006 | Tahara et al. |
| 2006/0239960 A1 | 10/2006 | Bossard et al. |
| 2006/0239961 A1 | 10/2006 | Bentley et al. |
| 2006/0264376 A1 | 11/2006 | Mitrovic et al. |
| 2006/0293499 A1 | 12/2006 | Bentley et al. |
| 2007/0071764 A1 | 3/2007 | Sullivan et al. |
| 2008/0044438 A1 | 2/2008 | Ostroff et al. |
| 2008/0085862 A1 | 4/2008 | Kim et al. |
| 2008/0090758 A1 | 4/2008 | Guenther et al. |
| 2008/0139459 A1 | 6/2008 | Bos et al. |
| 2008/0152668 A1 | 6/2008 | Rudolph et al. |
| 2008/0207505 A1 | 8/2008 | James |
| 2008/0241102 A1 | 10/2008 | Hersel et al. |
| 2009/0221487 A1 | 9/2009 | Liu et al. |
| 2011/0165111 A1 | 7/2011 | Zappe et al. |
| 2011/0165112 A1 | 7/2011 | Bossard et al. |
| 2011/0165113 A1 | 7/2011 | Roczniak et al. |
| 2011/0171160 A1 | 7/2011 | Minamitani et al. |
| 2011/0171161 A1 | 7/2011 | Wang et al. |
| 2011/0171162 A1 | 7/2011 | Zappe et al. |
| 2011/0171163 A1 | 7/2011 | Sheng et al. |

(56) References Cited

U.S. PATENT DOCUMENTS

| | | |
|---|---|---|
| 2011/0171164 A1 | 7/2011 | Bossard et al. |
| 2011/0171165 A1 | 7/2011 | Fry et al. |
| 2011/0171166 A1 | 7/2011 | Roczniak et al. |
| 2011/0171312 A1 | 7/2011 | Kuo et al. |
| 2011/0206633 A1 | 8/2011 | Bossard |
| 2011/0237524 A1 | 9/2011 | Ali et al. |
| 2012/0195847 A1 | 8/2012 | Wang et al. |

FOREIGN PATENT DOCUMENTS

| | | |
|---|---|---|
| EP | 0 078 228 | 1/1987 |
| EP | 0 129 985 | 9/1988 |
| EP | 0 400 472 | 12/1990 |
| EP | 0 467 172 | 4/1994 |
| EP | 0 472 598 | 7/1996 |
| EP | 1 239 037 | 9/2002 |
| EP | 1 066 850 | 8/2006 |
| EP | 1 797 901 | 6/2007 |
| EP | 1 529 057 | 5/2008 |
| EP | 2 070 950 | 6/2009 |
| JP | 2008-156283 | 7/2008 |
| WO | WO 91/04011 | 4/1991 |
| WO | WO 91/11173 | 8/1991 |
| WO | WO 91/14468 | 10/1991 |
| WO | WO 92/00107 | 1/1992 |
| WO | WO 95/00162 | 1/1995 |
| WO | WO 95/09616 | 4/1995 |
| WO | WO 95/10531 | 4/1995 |
| WO | WO 95/17195 | 6/1995 |
| WO | WO 95/24183 | 9/1995 |
| WO | WO 96/32096 | 10/1996 |
| WO | WO 96/32149 | 10/1996 |
| WO | WO 96/37508 | 11/1996 |
| WO | WO 97/12687 | 4/1997 |
| WO | WO 97/41031 | 11/1997 |
| WO | WO 97/41833 | 11/1997 |
| WO | WO 98/29096 | 7/1998 |
| WO | WO 99/12969 | 3/1999 |
| WO | WO 99/16419 | 4/1999 |
| WO | WO 99/16422 | 4/1999 |
| WO | WO 00/01417 | 1/2000 |
| WO | WO 00/07572 | 2/2000 |
| WO | WO 00/09073 | 2/2000 |
| WO | WO 00/24890 | 5/2000 |
| WO | WO 00/29427 | 5/2000 |
| WO | WO 01/21197 | 3/2001 |
| WO | WO 01/24831 | 4/2001 |
| WO | WO 01/33977 | 5/2001 |
| WO | WO 01/44284 | 6/2001 |
| WO | WO 01/62827 | 8/2001 |
| WO | WO 01/75104 | 10/2001 |
| WO | WO 02/36169 | 5/2002 |
| WO | WO 02/085399 | 10/2002 |
| WO | WO 02/094200 | 11/2002 |
| WO | WO 02/098446 | 12/2002 |
| WO | WO 03/037272 | 5/2003 |
| WO | WO 03/059413 | 7/2003 |
| WO | WO 2004/024761 | 3/2004 |
| WO | WO 2004/047871 | 6/2004 |
| WO | WO 2004/060299 | 7/2004 |
| WO | WO 2004/060300 | 7/2004 |
| WO | WO 2004/089280 | 10/2004 |
| WO | WO 2004/091494 | 10/2004 |
| WO | WO 2004/094991 | 11/2004 |
| WO | WO 2005/014024 | 2/2005 |
| WO | WO 2005/016973 | 2/2005 |
| WO | WO 2005/028539 | 3/2005 |
| WO | WO 2005/097158 | 10/2005 |
| WO | WO 2005/099768 | 10/2005 |
| WO | WO 2005/105151 | 11/2005 |
| WO | WO 2005/116655 | 12/2005 |
| WO | WO 2005/117939 | 12/2005 |
| WO | WO 2006/019950 | 2/2006 |
| WO | WO 2006/065977 | 6/2006 |
| WO | WO 2006/076471 | 7/2006 |
| WO | WO 2006/077397 | 7/2006 |
| WO | WO 2006/082184 | 8/2006 |
| WO | WO 2006/097521 | 9/2006 |
| WO | WO 2006/110776 | 10/2006 |
| WO | WO 2006/127181 | 11/2006 |
| WO | WO 2007/028632 | 3/2007 |
| WO | WO 2007/034498 | 3/2007 |
| WO | WO 2007/054030 | 5/2007 |
| WO | WO 2007/075534 | 7/2007 |
| WO | WO 2007/149686 | 12/2007 |
| WO | WO 2008/011165 | * 1/2008 |
| WO | WO 2008/082669 | 7/2008 |
| WO | WO 2008/088401 | 7/2008 |
| WO | WO 2009/045122 | 4/2009 |
| WO | WO 2009/047500 | 4/2009 |
| WO | WO 2010/033204 | 3/2010 |
| WO | WO 2010/033205 | 3/2010 |
| WO | WO 2010/033215 | 3/2010 |
| WO | WO 2010/033216 | 3/2010 |
| WO | WO 2010/033217 | 3/2010 |
| WO | WO 2010/033218 | 3/2010 |
| WO | WO 2010/033220 | 3/2010 |
| WO | WO 2010/033221 | 3/2010 |
| WO | WO 2010/033222 | 3/2010 |
| WO | WO 2010/033223 | 3/2010 |
| WO | WO 2010/033224 | 3/2010 |
| WO | WO 2010/033227 | 3/2010 |
| WO | WO 2010/033239 | 3/2010 |
| WO | WO 2010/033240 | 3/2010 |
| WO | WO 2010/042145 | 4/2010 |

OTHER PUBLICATIONS

Asada, et al., "Stability of Acyl Derivatives of Insulin in the Small Intestine: Relative Importance of Insulin Association Characteristics in Aqueous Solution", Pharmaceu. Res., vol. 11, No. 8, pp. 1115-1120, (1994).

Bab, et al., "Osteogenic Growth Peptide: From Concept to Drug Design", Biopolymers, vol. 66, pp. 33-48, (2002).

Baker, et al., "A randomized phase 2 study of the thrombospondin-mimetic peptide ABT-510 in patients with advanced soft tissue sarcoma (STS)", J. of Clin. Oncol., vol. 23, No. 16S, Part I of II, pp. 9013, (Jun. 1, 2005).

Baudys, et al., "Extending Insulin Action in Vivo by Conjugation to Carboxylmethyl Dextran", Bioconj. Chem., vol. 9, pp. 176-183, (1998).

Bowersox, et al., "Pharmacotherapeutic Potential of Omega-Conotoxin MVIIA (SNX-111), An N-Type Neuronal Calcium Channel Blocker Found in the Venom of Conus Magus", Toxicon, vol. 36, No. 11, pp. 1651-1658, (1998).

Bowie, et al., "A Method to Identify Protein Sequences That Fold into a Known Three-Dimensional Structure", Science, vol. 253 pp. 164-170, (1991).

Boyd, et al., "A Urokinase-Derived Peptide (Å6) Increases Survival of Mice Bearing Orthotopically Grown Prostate Cancer and Reduces Lymph Node Metastasis", Am. J. of Pathol., vol. 162, No. 2, pp. 619-626, (Feb. 2003).

Brange, et al., "Neutral Insulin Solutions Physically Stabilized by Addition of Zn2+", Diabetic Med., vol. 3, pp. 532-536, (1986).

Brenner, et al., "Population statistics of protein structures: lessons from structural classifications", Curr. Opin. in Struct. Biol., vol. 7, pp. 369-376, (1997).

Calceti, et al., "Development and in vivo evaluation of an oral insulin-PEG delivery system", European Journal of Pharmaceutical Sciences, vol. 22, pp. 315-323, (2004).

Caliceti, et al., "Improvement of the physicochemical and biopharmaceutical properties of insulin by poly(ethylene glycol) conjugation", S.T.P. Pharma Sciences, vol. 9, No. 1, pp. 107-113, (1999).

Carillo, et al., "The Multiple Sequence Alignment Problem in Biology", SIAM J. Appl. Math., vol. 48, No. 5, pp. 1073-1082, (Oct. 1988).

Castronovo, et al., "Functional Domains of the 67-kDa Laminin Receptor Precursor", The J. of Biol. Chem., Issue of Oct. 25, vol. 266, No. 30, pp. 20440-20446, (1991).

(56) References Cited

OTHER PUBLICATIONS

Castronovo, et al., "Laminin Receptor Complementary DNA-deduced Synthetic Peptide Inhibits Cancer Cell Attachment to Endothelium", Cancer Res., vol. 51, pp. 5672-5678, (Oct. 15, 1991).
Cervigni, et al., "Synthesis of Glycopeptides and Lipopeptides by Chemoselective Ligation", Angew. Chem. Int. Ed. Engl., vol. 35, No. 11, pp. 1230-1232, (1996).
Chapman, "PEGylated antibodies and antibody fragments for improved therapy: a review", Adv. Drug Del. Rev., vol. 54, No. 4, pp. 531-545, (2002).
Chen, et al., "Rational Design of α-Helical Antimicrobial Peptides with Enhanced Activities and Specificity/Therapeutic Index", The J. of Biol. Chem., vol. 280, No. 13, Issue of Apr. 1, pp. 12316-12329, (2005).
Cheng, et al., "The Opioid Growth Factor (OGF)—OGF Receptor Axis Uses the p16 Pathway to Inhibit Head and Neck Cancer", Cancer Res., vol. 67, No. 21, pp. 10511-10518, (Nov. 1, 2007).
Chou, et al., "Conformational Parameters for Amino Acids in Helical, β-Sheet, and Random Coil Regions Calculated from Proteins", Biochemistry, vol. 13, No. 2, pp. 211-222, (1974).
Chou, et al., "Empirical Predictions of Protein Conformation", Ann. Rev. Biochem., vol. 47, pp. 251-276, (1978).
Chou, et al., "Prediction of Protein Conformation", Biochemistry, vol. 13, No. 2, pp. 222-245, (1974).
Chou, et al., "Prediction of the Secondary Structure of Proteins from their Amino Acid Sequence", Adv. Enzymol. Relat. Areas Mol. Biol., pp. 45-148, (1978).
Chou, et al., "Prediction of β-Turns", Biophys. J., vol. 26, pp. 367-384, (1979).
Cohen, et al., "Oxyntomodulin Suppresses Appetite and Reduces Food Intake in Humans", The J. of Clin. Endocrin. & Metabolism, vol. 88, No. 10, pp. 4696-4701, (2003).
Coleman, et al., "Angiocol, A Type IV Collagen Fragment, Modulates Retinal Angiogenesis In Vitro", Microcirculation, pp. 530, (OC4), (Apr. 2004).
Colombo, et al., "Liquid-Phase Synthesis of Naturally Occurring Peptides, I: Syntheses of Leucine-Enkephalin and Methionine-Enkephalin on a p-Alkoxybenzyl-Modified Soluble Support", Hoppe-Seyler's Z. Physiol. Chem., vol. 362, pp. 1385-1391, (Oct. 1981).
Colonna, et al., "Cardiac ischemia and impairment of vascular endothelium function in hearts from growth hormone-deficient rats: Protection by hexarelin", Euro. J. of Pharmacol., vol. 334, pp. 201-207, (1997).
Crowe, et al., "NBI-5788, an Altered MBP83-99 Peptide, Induces a T-Helper 2-Like Immune Response in Multiple Sclerosis Patients", Ann. Neurol., vol. 48, pp. 758-765, (2000).
Davis, "The origin of pegnology", Adv. Drug Del. Rev., vol. 54, No. 4, pp. 457-458, (2002).
Devereux, et al., "A comprehensive set of sequence analysis programs for the VAX", Nucl. Acids Res., vol. 12, No. 1, pp. 387-395, (1984).
Donovan, et al., "Absorption of Polyethylene Glycols 600 Through 2000: The Molecular Weight Dependence of Gastrointestinal and Nasal Absorption", Pharmaceu. Res., vol. 7, No. 8, pp. 863-868, (1990).
Doores, et al., "Direct deprotected glycosyl-asparagine ligation", Chem. Commun., pp. 1401-1403, (2006).
Dorner, et al., "Hemodynamic effects of continuous urodilatin infusion: A dose-finding study", Clin. Pharmacol. & Therp., vol. 64, No. 3, pp. 322-330, (1998).
Dou, et al., "Synthesis and Purification of Mono-PEGylated Insulin", Chem. Biol. Drug Des., vol. 69, pp. 132-138, (2007).
Ehrat, et al., "Synthesis and Spectroscopic Characterization of Insulin Derivatives Containing One or Two Poly(ethylene oxide) Chains at Specific Positions", Biopolymers, vol. 22, pp. 569-573, (1983).
Ellis, et al., "In Vitro Bioactivity of Insulin Analogues: Lipogenic and Anti-Lipolytic Potency and Their Interaction with the Effect of Native Insulin", Diabetologia, vol. 15, pp. 403-410, (1978).

Elsner, et al., "Efficacy of prolonged infusion of urodilatin [ANP-(95-126)] in patients with congestive heart failure", Am. Heart J., vol. 129, pp. 766-773, (Apr. 1995).
Ferron, et al., "Osteocalcin differentially regulates β cell and adipocyte gene expression and affects the development of metabolic diseases in wild-type mice", PNAS, vol. 105, No. 13, pp. 5266-5270, (Apr. 1, 2008).
Filpula, et al., "Releasable PEGylation of proteins with customized linkers", Adv. Drug Del. Rev., vol. 60, pp. 29-49, (2008).
Fineberg, "Antibodies to Insulin and Other Biologics: Implications for Clinicians and Development Scientists", Respiratory Drug Del. VIII, pp. 43-49, (2002).
Forbes, et al., "Temporal dependence of ectopeptidase expression in alveolar epithelial cell culture: implications for study of peptide absorption", Int. J. of Pharmaceu., vol. 180, pp. 225-234, (1999).
Furata, et al., "General Pharmacology of KP-102 (GHRP-2), a Potent Growth Hormone-Releasing Peptide", Arzneim.-Forsch./Drug Res., vol. 54, No. 12, pp. 868-880, (2004).
Gershonov, et al., "New Concept for Long-Acting Insulin", Diabetes, vol. 48, pp. 1437-1442, (Jul. 1999).
Gibbs, et al., "Nature of the Glass Transition and the Glassy State", The J. of Chem. Phys., vol. 28, No. 3, pp. 373-383, (Mar. 1958).
Gietema, et al., "A phase I study assessing the safety and pharmacokinetics of the thrombospondin-1-mimetic angiogenesis inhibitor ABT-510 with gemcitabine and cisplatin in patients with solid tumors", Annals. of Oncol., vol. 17, pp. 1320-1327, (2006).
Gluud, et al., "Terlipressin for hepatorenal syndrome", Cochrane Database of Sys. Revs., Issue 4., Art. No. CD005162. DOI: 10.1002/14651858.CD005162.pub2, (23 Pages), (2006).
Gohil, et al., "Neuroanatomical distribution of receptors for a novel voltage-sensitive calcium-channel antagonist, SNX-230 (ω-conopeptide MVIIC)", Brain Res., vol. 653, pp. 258-266, (1994).
Gray, et al., "Cloning of the cDNA of a Human Neutrophil Bactericidal Protein", The J. of Biol. Chem., Issue of Jun. 5, vol. 264, No. 16, pp. 9505-9509, (1989).
Gribskov, et al., "Profile Analysis", Meth. in Enzymol., vol. 183, pp. 146-159, (1990).
Gribskov, et al., "Profile analysis: Detection of distantly related proteins", Proc. Natl. Acad. Sci. USA, vol. 84, pp. 4355-4358, (Jul. 1987).
Harada, et al., "Detection of Genetic Alterations in Pancreatic Cancers by Comparative Genomic Hybridization Coupled with Tissue Microdissection and Degenerate Oligonucleotide Primed Polymerase Chain Reaction", Oncology, vol. 62, pp. 251-258, (2002).
Harris, et al., "Poly(ethylene glycol) Chemistry and Biological Applications", ACS Symposium Series, 11 pages, (1997).
Harris, et al., "Effect of Pegylation on Pharmaceuticals", Nature, vol. 2, pp. 214-221, (Mar. 2003).
Harris, "Laboratory Synthesis of Polyethylene Glycol Derivatives", JMS-Rev. Macromol. Chem. Phys., vol. C25, No. 3, pp. 325-373, (1985).
Hatanaka, et al., "One-Step Synthesis of Biotinyl Photoprobes from Unprotected Carbohydrates", J. Org. Chem., vol. 65, pp. 5639-5643, (2000).
Haviv, et al., "Thrombospondin-1 Mimetic Peptide Inhibitors of Angiogenesis and Tumor Growth: Design, Synthesis, and Optimization of Pharmacokinetics and Biological Activities", J. Med. Chem., vol. 48, pp. 2838-2846, (2005).
Heise, et al., "Time-Action Profiles of Novel Premixed Preparations of Insulin Lispro and NPL Insulin", Diabetes Care, vol. 21, No. 5, pp. 800-803, (May 1998).
Henikoff, et al., "Amino acid substitution matrices from protein blocks", Proc. Natl. Acad. Sci. USA, vol. 89, pp. 10915-10919, (Nov. 1992).
Hinds, et al., "Effects of PEG conjugation on insulin properties", Adv. Drug Del. Rev., vol. 54, No. 4, pp. 505-530, (2002).
Hinds, et al., "Synthesis and Characterization of Poly(ethylene gylcol)-Insulin Conjugates", Bioconj. Chem., vol. 11, pp. 195-201, (2000).
Holm, et al., "Protein folds and families: sequence and structure alignments", Nucl. Acids. Res., vol. 27, No. 1, pp. 244-247, (1999).

(56) References Cited

OTHER PUBLICATIONS

Horan, et al., "Antinociceptive Profile of Biphalin, a Dimeric Enkephalin Analog", The J. of Pharmacol. And Exper. Therapeu., vol. 265, No. 3, pp. 1446-1454, (1993).
Hori, et al., "Metastin Suppresses the Motility and Growth of CHO Cells Transfected with Its Receptor", Biochem. and Biophys. Res. Commun., vol. 286, pp. 958-963, (2001).
Huber, et al., "Conjugation of Low Molecular Weight Poly(ethylene glycol) to Biphalin Enhances Antinociceptive Profile", Journal of Pharmaceutical Sciences, vol. 92, No. 7, pp. 1377-1385, (Jul. 2003).
Ioannou, et al., "Terlipressin for acute esophageal variceal hemorrhage", Cochrane Database of Sys. Revs., Issue 1., Art. No. CD002147. DOI: 10.1002/14651858.CD002147, (92 Pages), (2003).
Jeppesen, et al., "Glucagon-like Peptide 2 Improves Nutrient Absorption and Nutritional Status in Short-Bowel Patients With No Colon", Gastroenterology, vol. 120, pp. 806-815, (2001).
Jiang, et al., "Effects of Net Charge and the Number of Positively Charged Residues on the Biological Activity of Amphipathic α-Helical Cationic Antimicrobial Peptides", Biopoly. Pep. Sci., vol. 90, No. 3, pp. 369-383, (2008).
Jones, et al., "Biological Properties of Chemically Modified Insulins", Diabetologia, vol. 12, pp. 601-608, (1976).
Jones, "Progress in protein structure prediction", Curr. Opin. in Struct. Biol., vol. 7, pp. 377-387, (1997).
Kentsch, et al., "Haemodynamic and renal effects of urodilatin bolus injections in patients with congestive heart failure", Euro. J. of Clin. Invest., vol. 22, pp. 662-669, (1992).
Kentsch, et al., "Severe hypotension and bradycardia after continuous intravenous infusion of urodilatin (ANP 95-126) in a patient with congestive heart failure", Eur. J. Clin. Invest., vol. 54, pp. 251-283, (1995).
Kinstler, et al., "Mono-N-terminal poly(ethylene glycol)-protein conjugates", Adv. Drug Del. Rev., vol. 54, No. 4, pp. 477-485, (2002).
Kocsis, et al., "The concept of internal solubilization in peptide synthesis: ethylene glycol-based protecting groups", Tetrahed. Lett., vol. 49, pp. 7015-7017, (2008).
Kosson, et al., "Antinociception after intrathecal biphalin application in rats: a reevaluation and novel, rapid method to confirm correct catheter tip position", Pharmacol. Rep., vol. 57, pp. 545-549, (2005).
Kotani, et al., "The Metastasis Suppressor Gene KiSS-1 Encodes Kisspeptins, the Natural Ligands of the Orphan G Protein-coupled Receptor GPR54", The J. of Biol. Chem., vol. 276, No. 37, Issue of Sep. 14, pp. 34631-34636, (2001).
Koutkia, et al., "Growth Hormone-Releasing Hormone in HIV-Infected Men With Lipodystrophy", JAMA, vol. 292, No. 2, pp. 210-218, (Jul. 14, 2004).
Krishnan, et al., "Stability and Physical Characteristics of Orally Active Amphiphilic Human Insulin Analog, Methoxy (Polyethylene Glycol) Hexanoyl Human Recombinant Insulin (HIM2)", Proceed. Int'l. Symp. Control. Rel. Bioact. Mater., vol. 27, pp. 1038-1039, (2000).
Kurtz, et al., "Circulating IgG Antibody to Protamine in Patients Treated with Protamine-Insulins", Diabetologia, vol. 25, pp. 322-324, (1983).
Kyte, et al., "A Simple Method for Displaying the Hydropathic Character of a Protein", J. Mol. Biol., vol. 157, pp. 105-132, (1982).
Lee, et al., "Discovery of a receptor related to the galanin receptors", FEBS Lett., vol. 446. pp. 103-107, (1999).
Lee, et al., "KiSS-1, a Novel Human Malignant Melanoma Metastasis-Suprressor Gene", J. of the Nat. Cancer Inst., vol. 88, No. 23, pp. 1731-1737, (Dec. 4, 1996).
Lee, et al., "Suppression of Metastasis in Human Breast Carcinoma MDA-MB-435 Cells after Transfection with the Metastasis Suppressor Gene, KiSS-1", Cancer Res., vol. 57, pp. 2384-2387, (Jun. 15, 1997).
Lehmann, "Ecallantide (DX-88), a plasma kallikrein inhibitor for the treatment of hereditary angioedema and the prevention of blood loss in on-pump cardiothoracic surgery", Expert. Opin. Biol. Ther., vol. 8, No. 8, pp. 1187-1199, (2008).
Leteux, et al., "Biotinyl-L-3-(2-naphthyl)-alanine hydrazide derivatives of N-glycans: versatile solid-phase probes for carbohydrate-recognition studies", Glycobiology, vol. 8, No. 3, pp. 227-236, (1998).
Liddle, et al., "Regulation of Gastric Emptying in Humans by Cholecystokinin", J. Clin. Invest., vol. 77, pp. 992-996, (Mar. 1986).
Lipsett, et al., "The role of Islet Neogenesis-Associated Protein (INGAP) in islet neogenesis", Cell Biochem. Biophys., vol. 48, pp. 127-137, (2007).
Liu, et al., "Glucose-Induced Release of Glycosylpoly(ethylene glycol) Insulin Bound to a Soluble Conjugate of Concanavalin A", Bioconjugate Chem., vol. 8, pp. 664-672, (1997).
Liu, et al., "Poly(ethylene glycol( (PEG) Modifications and Conformational Analysis of Thymosin Alpha 1", Understanding Biology Using Peptides, pp. 70-71, (2005).
Liu, et al., "Poly(ethylene glycol) (PEG) Modification and Conformation Analysis of Thymosin Alpha 1", Biopolymers, vol. 80, No. 4, pp. 518, (2005).
Lloyd, et al., "Activation of somatostatin receptor subtype 2 inhibits acid secretion in rats", Am. J. Physiol., vol. 268, pp. G102-G106, (1995).
Maeda, et al., "Amino Acids and Peptides. XXIV.[1)] Preparation and Antinociceptive Effect of [D-Ala$^2$,(N-Me)Phe$^4$]Enkephalin Analog-Poly(Ethylene Glycol) Hybrids", Chem. Pharm. Bull., vol. 42, No. 9, pp. 1859-1863, (1994).
Merrifield, "Solid Phase Peptide Synthesis. I. The Synthesis of a Tetrapeptide", J. Am. Chem. Soc., vol. 85, No. 14, pp. 2149-2154, (1963).
Meyer, et al., "Effects of tendamistate (an α-amylase inactivator), guar and placebo on starch metabolism", SA Med. J., vol. 66, No. 11, pp. 222-223, (Aug. 11, 1984).
Miljanich, et al., "Antagonists of Neuronal Calcium Channels: Structure, Function, and Therapeutic Implications", Annu. Rev. Pharmacol. Toxicol., vol. 35, pp. 707-734,(1995).
Miljanich, "Ziconotide: Neuronal Calcium Channel Blocker for Treating Severe Chronic Pain", Curr. Med. Chem., vol. 11, pp. 3029-3040, (2004).
Miller, et al., "Amphiphilic Conjugates of Human Brain Natriuretic Peptide Design for Oral Delivery: In Vitro Activity Screening", Bioconj. Chem., vol. 17, pp. 267-274, (2006).
Moult, "The current state of the art protein structure prediction", Curr. Opin. in Biotechnol., vol. 7, pp. 422-427, (1996).
Muir, et al., "AXOR12, a Novel Human G Protein-coupled Receptor, Activated by the Peptide KiSS-1", The J. of Biol. Chem., vol. 276, No. 31, Issue of Aug. 3, pp. 28969-28975, (2001).
Murray-Rust, et al., "Structure and Evolution of Insulins: Implications for Receptor Binding", BioEssays, vol. 14, No. 5, pp. 325-331, (May 1992).
Musse, et al., "Molecular "Negativity" May Underlie Multiple Sclerosis: Role of the Myelin Basic Protein Family in the Pathogenesis of MS", Intl. Rev. of Neurobiol., vol. 79, pp. 149-172, (2007).
Myers, et al., "Acylation of Human Insulin With Palmitic Acid Extends the Time Action of Human Insulin in Diabetic Dogs", Diabetes, vol. 46, pp. 637-642, (Apr. 1997).
Nakao, et al., "A new function of calphobindin I (annexin V). Promotion of both migration and urokinase-type plasminogen activator activity of normal human keratinocytes", Eur. J. Biochem., vol. 223, pp. 901-908, (1994).
Nash, et al., "Requirement of KISS1 Secretion for Multiple Organ Metastasis Suppression and Maintenance of Tumor Dormancy", J. Natl. Cancer. Inst., vol. 99, pp. 309-321, (2007).
Nash, et al., "The KISS1 metastasis suppressor: mechanistic insights and clinical utility", NIH Pub. Acc. Aut. Manu., vol. 11, pp. 647-659, (2006).
Needleman, et al., "Atriopeptin: A Cardiac Hormone Intimately Involved in Fluid, Electrolyte, and Blood-Pressure Homeostasis", The New Engl. J. of Med., vol. 314, No. 13, pp. 828-834, (Mar. 27, 1986).

(56) References Cited

OTHER PUBLICATIONS

Nesher, et al., "Reversible Pegylation Prolongs the Hypotensive Effect of Atrial Natriuretic Peptide", Bioconj. Chem., vol. 19, pp. 342-348, (2008).
Niven, et al., "The Pulmonary Absorption of Aerosolized and Intratracheally Instilled rhG-CSF and monoPEGylated rhG-CSF", Pharmaceu. Res., vol. 12, No. 9, pp. 1343-1349, (1995).
O'Brien, et al., "Terlipressin for norepinephrine-resistant septic shock", Lancet, vol. 359, pp. 1209-1210, (2002).
Ohtaki, et al., "Metastasis suppressor gene KiSS-1 encodes peptide ligand of a G-protein-coupled receptor", Nature, vol. 411, pp. 613-617, (May 31, 2001).
Otero, et al., "Reversal of thermal hyperalgesia in rat partial sciatic nerve ligation model by Prosaptide™ TX14(A)", Neurosci. Lett., vol. 270, pp. 29-32, (1999).
Ouchi, et al., "Design of Antitumor Agent-Terminated Poly(Ethylene Glycol) Conjugate as Macromolecular Prodrug", Polymer Preprints, vol. 38, No. 1, pp. 582-583,(1997).
Pace, et al., "GnRH Agonists: Gonadorelin, Leuprolide and Nafarelin", AFP, Clinical Pharmacology, vol. 44, No. 5, pp. 1777-1782, (Nov. 1991).
Park, et al., "Therapeutic Potential of Atrial Natriuretic Peptide Administration on Peripheral Arterial Diseases", Endocrinology, vol. 149, No. 2, pp. 483-491, (2008).
Pasut, et al., "Protein, peptide and non-peptide drug PEGylation for therapeutic application", Exp. Opin. Ther. Patents, vol. 14, No. 6, pp. 859-894, (2004).
Peyrin-Biroulet, et al., "Crohn's disease: beyond antagonists of tumour necrosis factor", Lancet, vol. 372, pp. 67-81, (2008).
Prakash, et al., "Sermorelin: A Review of its Use in the Diagnosis and Treatment of Children with Idiopathic Growth Hormone Deficiency", Biodrugs, vol. 12, No. 2, pp. 139-157, (Aug. 1999).
Qu, et al., "Protegrin Structure and Activity against Neisseria gonorrhoeae", Infection and Immun., vol. 65, No. 2, pp. 636-639, (Feb. 1997).
Rattan, et al., "Protein Synthesis, Posttranslational Modifications, and Aging", Ann. N.Y. Acad. Sci., pp. 48-62, (1992).
Raynor, et al., "Cloned Somatostatin Receptors: Identification of Subtype-Selective Peptides and Demonstration of High Affinity Binding of Linear Peptides", Mol. Pharmacol., vol. 43, pp. 838-844, (1993).
Reddy, et al., "Use of peginterferon alfa-2a (40 KD) (Pegasys®) for the treatment of hepatitis C", Adv. Drug Del. Rev., vol. 54, No. 4, pp. 571-586, (2002).
Rigaud, et al., "Allelotype of Pancreatic Acinar Cell Carcinoma", Int. J. Cancer, vol. 88, pp. 772-777, (2000).
Roberts, et al., "Chemistry for peptide and protein PEGylation", Adv. Drug Del. Rev., vol. 54, No. 4, pp. 459-476, (2002).
Sadamoto, et al., "Control of Bacteria Adhesion by Cell-Wall Engineering", J. Am. Chem. Soc., vol. 126, pp. 3755-3761, (2004).
Samuel, et al., "Studies on the immunogenicity of protamines in humans and experimental animals by means of a micro-complement fixation test", Clin. Exp. Immunol., vol. 33, pp. 252-260, (1978).
Sasaki-Yagi, et al., "Binding of enkephalin/dextran conjugates to opioid receptors", Int. J. Peptide Protein Res., vol. 43, pp. 219-224, (1994).
Sato, "Enzymatic procedure for site-specific pegylation of proteins", Adv. Drug Del. Rev., vol. 54, No. 4, pp. 487-504, (2002).
Seifter, et al., "Analysis for Protein Modifications and Nonprotein Cofactors", Meth. in Enzymol., vol. 182, pp. 626-646, (1990).
Shinohara, et al., "Bifunctional Labeling Reagent for Oligosaccharides to Incorporate Both Chromophore and Biotin Groups", Anal. Chem., vol. 68, pp. 2573-2579, (1996).
Sims, et al., "A Method for the Estimation of Polyethylene Glycol in Plasma Protein Fractions", Anal. Biochem., vol. 107, pp. 60-63, (1980).
Sippl, et al., "Threading thrills and threats", Structure, vol. 4, pp. 15-19, (Jan. 15, 1996).

Sjogren, "Thymalfasin: an immune system enhancer for the treatment of liver disease", J. of Gastroenterol. And Hepatol, vol. 19, pp. S69-S72, (2004).
Spatola, "Peptide Backbone Modifications: A Structure-Activity Analysis of Peptides Containing Amide Bond Surrogates", Chem. and Biochem. of Amino Acids, Peptides, and Proteins, Weinstein, Marcel Dekker, New York, pp. 267-357, (1983).
Steinberg, et al., "Protegrin-1: A Broad-Spectrum, Rapidly Microbicidal Peptide with In Vivo Activity", Antimicrob. Agents and Chemother. , vol. 41, No. 8, pp. 1738-742, (Aug. 1997).
Streicher, et al., "The Organization of the Human Myelin Basic Protein Gene", Biol. Chem. Hoppe-Seyler, vol. 370, pp. 503-510, (May 1989).
Syeda, et al., "Assessment of the Safety and Efficacy of the Novel Tetrapeptide ITF-1697 on Infarct Size after Primary PTCA in Acute Myocardial Infarction", Drugs R&D, vol. 5, No. 3, pp. 141-151, (2004).
Takahashi, et al., "Structure of human cholecystokinin gene and its chromosomal location", Gene, vol. 50, pp. 353-360, (1986).
Tessmar, et al., "Toward the Development of Biomimetic Polymers by Protein Immobilization: PEGylation of Insulin as a Model Reaction", Tissue Engineering, vol. 10, No. 3/4, pp. 441-453, (2004).
Tompkins, et al., "Mechanism of Action of Insulin and Insulin Analogues", Diabetologia, vol. 20, pp. 94-101, (1981).
Tran, et al., "Microbicidal Properties and Cytocidal Selectivity of Rhesus Macaque Theta Defensins", Antimicrob. Agents and Chemotherp., vol. 52, No. 3, pp. 944-953, (Mar. 2008).
Uchio, et al., "Site-specific insulin conjugates with enhanced stability and extended action profile", Adv. Drug Del. Rev., vol. 35, pp. 289-306, (1999).
Vale, et al., "Characterization of a 41-Residue Ovine Hypothalamic Peptide That Stimulates Secretion of Corticotropin and β-Endorphin", Science, vol. 213, pp. 1394-1397, (Sep. 18, 1981).
Vanbever, et al., "Sustained Release of Insulin From Insoluble Inhaled Particles", Drug Dev. Res., vol. 48, pp. 178-185, (1999).
Veronese, et al., "New PEGs for Peptide and Protein Modification, Suitable for Identification of the PEGylation Site", Bioconjugate Chem., vol. 12, pp. 62-70, (2001).
Veronese, et al., "Introduction and overview of peptide and protein pegylation", Adv. Drug Del. Rev., vol. 54, No. 4, pp. 453-456, (2002).
Veronese, et al., "Peptide and protein PEGylation: a review of problems and solutions", Biomaterials, vol. 22, pp. 405-417, (2001).
Veronese, et al., "Polyethylene glycol-superoxide dismutase, a conjugate in search of exploitation", Adv. Drug Del. Rev., vol. 54, No. 4, pp. 587-606, (2002).
Vlasov, et al., "Synthesis, and Conformational and Biological Study of 2-D-Ala,5-des-Met-Enkephalin Hydrazide Modified at the Carboxylic End by Poly-N-Vinylimidazole", Biopolymers, vol. 26, pp. 1489-1498, (1987).
Wall, et al., "High levels of exopeptidase activity are present in rat and canine bronchoalveolar lavage fluid", Int. J. of Pharmaceu., vol. 97, pp. 171-181, (1993).
Wang, et al., "Structural and biological characterization of pegylated recombinant interferon alpha-2b and its therapeutic implications", Adv. Drug Del. Rev., vol. 54, No. 4, pp. 547-570, (2002).
Witt, et al., "Pharmacodynamic and Pharmacokinetic Characterization of Poly(Ethylene glycol) Conjugation to Met-Enkephalin Analog [D -Pen$^2$,D -Pen$^5$]-enkephalin (DPDPE)", The J. of Pharmacol. and Exp. Therap., vol. 298, No. 2, pp. 848-856, (2001).
Wolanczyk, "Differential Scanning Calorimetry Analysis of Glass Transitions", Cryo-Lett., vol. 10, pp. 73-76, (1989).
Wold, "Posttranslational Protein Modifications: Perspective and Prospectives", Posttrans. Cov. Mod. of Proteins, Academic Press, Inc., pp. 1-15, (1983).
Yan, et al., "KiSS-1 Represses 92-kDa Type IV Collagenase Expression by Down-regulating NF-κB Binding to the Promoter as a Consequence of IκBα-induced Block of p65/p50 Nuclear Translocation", The J. of Biol. Chem., vol. 276, No. 2, pp. 1164-1172, (Jan. 12, 2001).

(56) References Cited

OTHER PUBLICATIONS

Yatsuoka, et al., "Association of Poor Prognosis With Loss of 12q, 17p, and 18q, and Concordant Loss of 6q/17p and 12q/18q in Human Pancreatic Ductal Adenocarcinoma", The Amer. J. of Gastroenterol., vol. 95, No. 8, pp. 2080-2085,(2000).
You, et al., "Tunable Inhibition and Denaturation of α-Chymotrypsin with Amino Acid-Functionalized Gold Nanoparticles", JACS, vol. 127, pp. 12873-12881, (2005).
Zalipsky, "Chemistry of polyethylene glycol conjugates with biologically active molecules", Adv. Drug Del. Rev., vol. 16, pp. 157-182, (1995).
Zalipsky, et al., "Use of Functionalized Poly(Ethylene Glycol)s for Modification of Polypeptides", Poly(Ethylene Glycol) Chemistry: Biotechnical and Biomedical Applications, Eds. J.M. Harris, Plenum Press, New York, 13 pages, (1992).
Zhang, et al., "Influence of Proline Residues on the Antibacterial and Synergistic Activities of α-Helical Peptides", Biochemistry, vol. 38, pp. 8102-8111, (1999).
Zhang, et al., "Obestatin, a Peptide Encoded by the Ghrelin Gene, Opposes Ghrelin's Effects on Food Intake", Science, vol. 310, pp. 996-999, (Nov. 11, 2005).
Zhao, et al., "Novel Degradable Poly(ethylene glycol) Esters for Drug Delivery", Amer. Chem. Soc., Chapter, 28, pp. 458-472, (1997).
Zhao, et al., "Rapid, sensitive structure analysis of oligosaccharides", Proc. Natl. Acad. Sci., vol. 94, pp. 1629-1633, (Mar. 1997).
PCT International Search Report corresponding to PCT Application No. PCT/US2009/005192 date of mailing Jan. 27, 2010.
PCT International Preliminary Report on Patentability corresponding to PCT Application No. PCT/US2009/005192 date of mailing Mar. 31, 2011.
PCT International Search Report and Written Opinion corresponding to PCT Application No. PCT/US2009/005209 date of mailing Apr. 19, 2010.
PCT International Preliminary Report on Patentability corresponding to PCT Application No. PCT/US2009/005209 date of mailing Mar. 31, 2011.
PCT International Search Report corresponding to PCT Application No. PCT/US2009/005213 date of mailing Feb. 15, 2010.
PCT International Preliminary Report on Patentability corresponding to PCT Application No. PCT/US2009/005213 date of mailing Mar. 31, 2011.
PCT International Search Report corresponding to PCT Application No. PCT/US2009/005211 date of mailing Mar. 11, 2010.
PCT International Preliminary Report on Patentability corresponding to PCT Application No. PCT/US2009/005211 date of mailing Mar. 31, 2011.
PCT International Search Report corresponding to PCT Application No. PCT/US2009/005232 date of mailing Feb. 11, 2010.
PCT International Preliminary Report on Patentability corresponding to PCT Application No. PCT/US2009/005232 date of mailing Mar. 31, 2011.
PCT International Search Report corresponding to PCT Application No. PCT/US2009/005205 date of mailing Nov. 26, 2009.
PCT International Preliminary Report on Patentability corresponding to PCT Application No. PCT/US2009/005205 date of mailing Mar. 31, 2011.
PCT International Search Report corresponding to PCT Application No. PCT/US2009/005210 date of mailing Nov. 16, 2009.
PCT International Preliminary Report on Patentability corresponding to PCT Application No. PCT/US2009/005210 date of mailing Mar. 31, 2011.
PCT International Search Report corresponding to PCT Application No. PCT/US2009/005190 date of mailing Nov. 16, 2009.
PCT International Preliminary Report on Patentability corresponding to PCT Application No. PCT/US2009/005190 date of mailing Mar. 31, 2011.
PCT International Search Report corresponding to PCT Application No. PCT/US2009/005217 date of mailing Jan. 27, 2010.
PCT International Preliminary Report on Patentability corresponding to PCT Application No. PCT/US2009/005217 date of mailing Mar. 31, 2011.
PCT International Search Report corresponding to PCT Application No. PCT/US2009/005204 date of mailing Mar. 12, 2010.
PCT International Preliminary Report on Patentability corresponding to PCT Application No. PCT/US2009/005204 date of mailing Mar. 31, 2011.
PCT International Search Report corresponding to PCT Application No. PCT/US2009/005189 date of mailing Mar. 31, 2010.
PCT International Preliminary Report on Patentability corresponding to PCT Application No. PCT/US2009/005189 date of mailing Mar. 31, 2011.
PCT International Search Report corresponding to PCT Application No. PCT/US2009/005218 date of mailing Nov. 17, 2009.
PCT International Preliminary Report on Patentability corresponding to PCT Application No. PCT/US2009/005218 date of mailing Mar. 31, 2011.
PCT International Search Report corresponding to PCT Application No. PCT/US2009/005233 date of mailing May 4, 2010.
PCT International Preliminary Report on Patentability corresponding to PCT Application No. PCT/US2009/005233 date of mailing Mar. 31, 2011.
PCT International Search Report corresponding to PCT Application No. PCT/US2009/005212 date of mailing Feb. 11, 2010).
PCT International Preliminary Report on Patentability corresponding to PCT Application No. PCT/US2009/005212 date of mailing Mar. 31, 2011.
PCT International Search Report corresponding to PCT Application No. PCT/US2009/005207 date of mailing Dec. 22, 2009.
PCT International Preliminary Report on Patentability corresponding to PCT Application No. PCT/US2009/005207 date of mailing Mar. 31, 2011.
PCT International Search Report corresponding to PCT Application No. PCT/US2009/005206 date of mailing Dec. 14, 2009.
PCT International Preliminary Report on Patentability corresponding to PCT Application No. PCT/US2009/005206 date of mailing Mar. 31, 2011.
Enzon Pharmaceuticals, Macromolecular Engineering Technologies, 16 pages, (2004).
Nektar™—Transforming Therapeutics, Nektar Molecule Engineering: Polyethylene Glycol and Derivatives for Advanced PEGylation, 24 pages, Catalog—2003, (Jul. 2003).
Nektar™—Transforming Therapeutics, Nektar Advanced PEGylation: Polyethylene Glycol and Derivatives for Advanced PEGylation, 27 pages, Catalog—2004, (Jul. 2004).
Nektar™—Transforming Therapeutics, Nektar Advanced PEGylation: Polyethylene Glycol and Derivatives for Advanced PEGylation, 33 pages, (Catalog 2005-2006).
NOF Corporation, PEG Derivatives, Phospholipid and Drug Delivery Materials for Pharmaceuticals, 46 pages, Catalogue 2003-$1^{st}$, (Jan. 2003).
NOF Corporation, PEG Derivatives, Phospholipid and Drug Delivery Materials for Pharmaceuticals, 27 pages, Catalogue 2003-$2^{nd}$, (Mar. 2004).
NOF Corporation, PEG Derivatives, Phospholipids and Drug Delivery Materials for Pharmaceutical Products and Formulations, 60 pages, Catalogue Ver. 8, (Apr. 2006).
Polypure Products, PEG amines; PEG acids and amino acids; PEG thiols and disulfides; Biotins, 5 pages, (Apr. 2004).
Polypure Products, PEG amines; PEG acids and amino acids; PEG thiols and disulfides; Biotins, 5 pages, (Apr. 2005).
Quanta Biodesign, Labeling, Derivatization and Crosslinking Reagents for Biological and Related Materials with dPEG™, 38 pages, (Mar. 12, 2004).
Quanta Biodesign, Labeling, Modification and Crosslinking Reagents incorporating our unique monodispersed dPEG™ Technology, 31 pages, (Nov. 5, 2004).
Quanta Biodesign, Ltd., Leading innovator, producer and provider of monodisperse discrete PEG™ (dPEG™) derivatives, (Product Catalog), 26 pages, (Updated: Jul. 18, 2005).

(56) References Cited

OTHER PUBLICATIONS

Quanta Biodesign, Ltd., Leading innovator, producer and provider of monodisperse discrete PEG™ (dPEG™) derivatives, (Product Catalog), 26 pages, (Updated: Nov. 17, 2005).
Shearwater Polymers, Inc., Polyethylene Glycol Derivatives, 50 pages, Catalog—(Mar. 1995).
Shearwater Polymers, Inc., Polyethylene Glycol Derivatives, 55 pages, Catalog 1997-1998, (Jul. 1997).
Shearwater Polymers, Inc., Polyethylene Glycol and Derivatives: Functionalized Biocompatible Polymers for Research and Pharmaceuticals, 50 pages, Catalog—(Jan. 2000).
Shearwater Corporation, Polyethylene Glycol and Derivatives for Biomedical Applications, 20 pages, Catalog—(Jul. 2001).
European Communication corresponding to European Patent Application No. 09 789 327.5 dated Sep. 5, 2012.
European Communication corresponding to European Patent Application No. 09 789 327.5 dated Jul. 19, 2013.
English Translation of Japanese Notice of Reasons for Rejection corresponding to Japanese Patent No. 2011-527822 mailing date Jan. 30, 2014.
English Translation of Mexican Official Letter corresponding to Mexican Patent Application No. MX/a/2011/003117 dated Feb. 13, 2014.
Australia Patent Examination Report No. 1 corresponding to Australian Patent Application No. 2009292643 date of issue Oct. 3, 2014.
European Summons to attend oral proceedings corresponding to European Patent Application No. 09789327.5 dated Oct. 14, 2014.
European Decision to refuse a European Patent application corresponding to European Patent Application No. 09789327.5 dated Feb. 17, 2015.
European Extended Search Report corresponding to European Patent Application No. 14200659.2 dated Apr. 15, 2015.
English Translation of Japanese Notice of Reasons for Rejection corresponding to Japanese Patent Application No. 2011-527822 mailing date Jan. 30, 2015.
English Translation of Mexican Official Letter corresponding to Mexican Patent Application No. MX/a/2011/003117 dated Aug. 2, 2013.
English Translation of Mexican Official Letter corresponding to Mexican Patent Application No. MX/a/2011/003117 dated Sep. 23, 2014.
Canadian Office Communication in Canadian Patent Application No. 2,737,040 dated May 7, 2015.
Australian Patent Examination Report No. 2 in Australian Patent Application No. 2009292643 date of issue Nov. 14, 2015.
Canadian Communication in Canadian Patent Application No. 2,737,040 dated Jan. 12, 2016.

\* cited by examiner

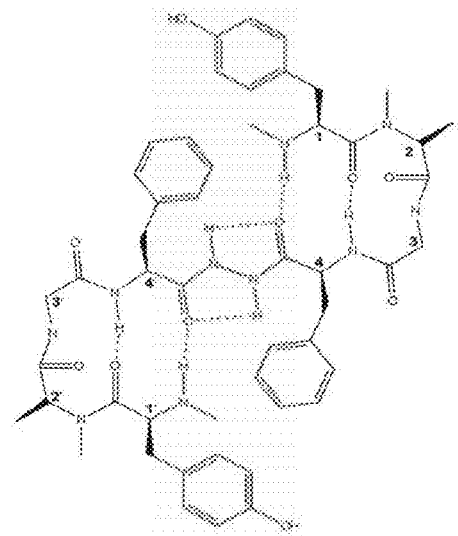
Figure 35    Biphalin structure
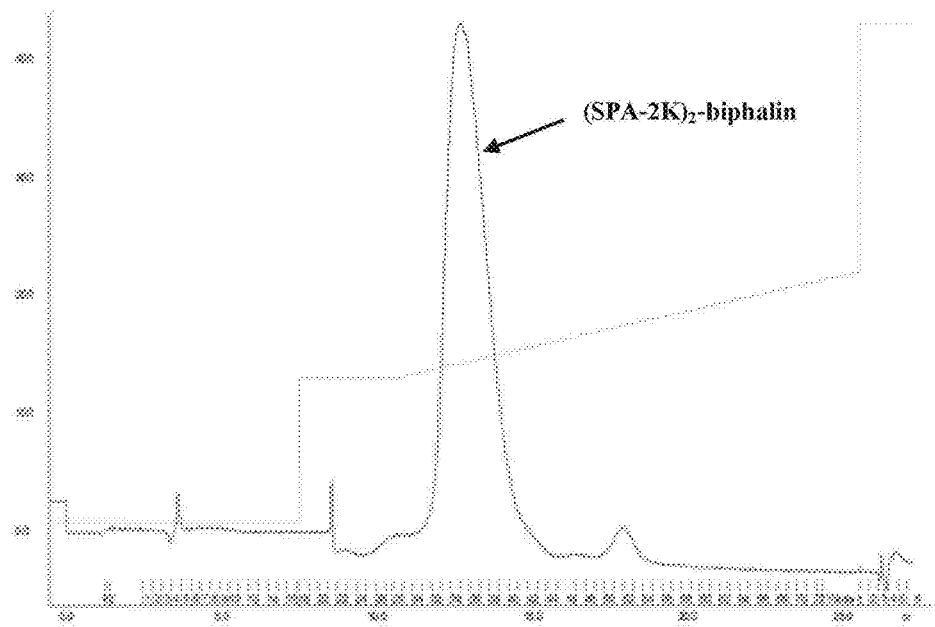
Figure 36

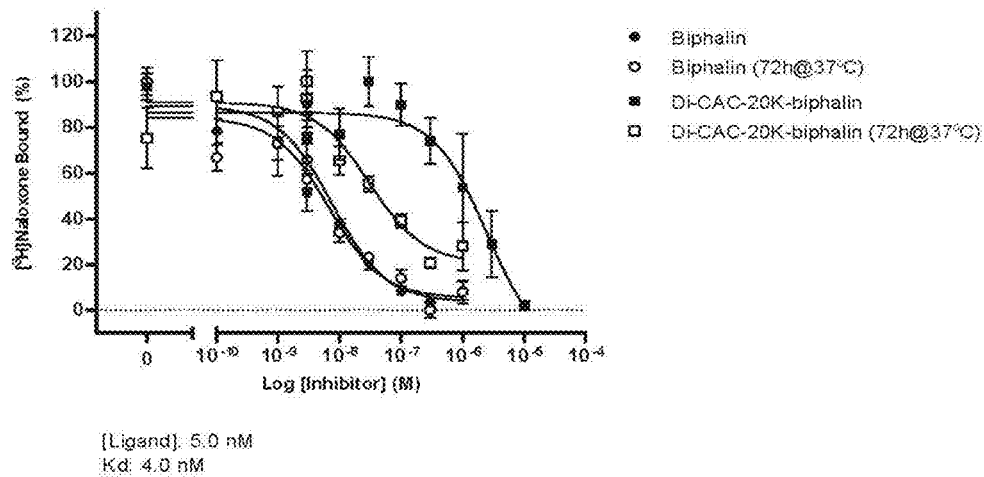
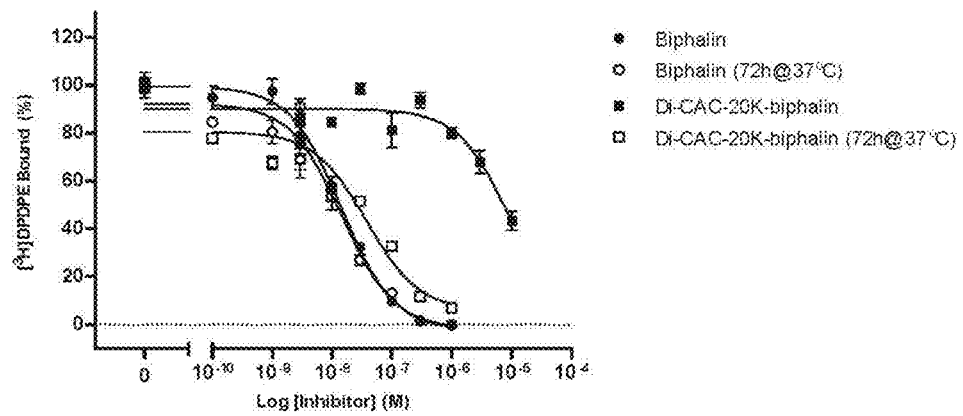
Figure 48

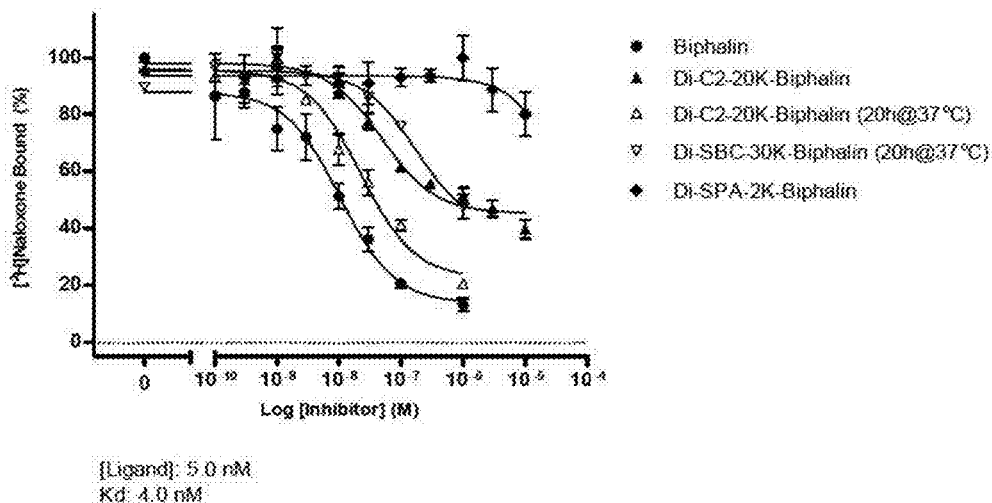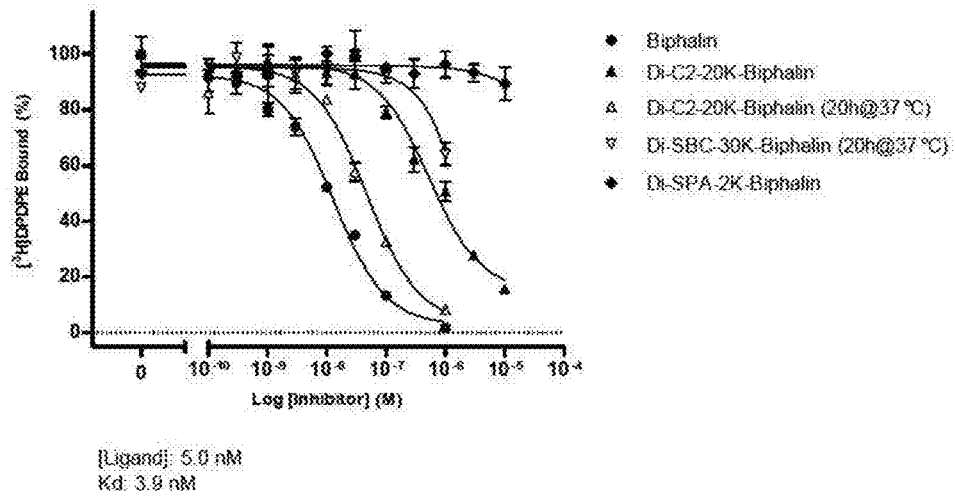
Figure 49

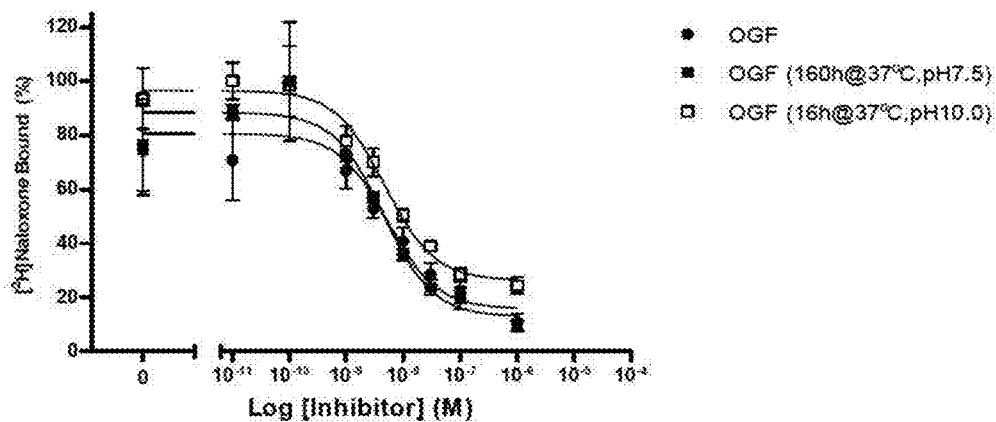
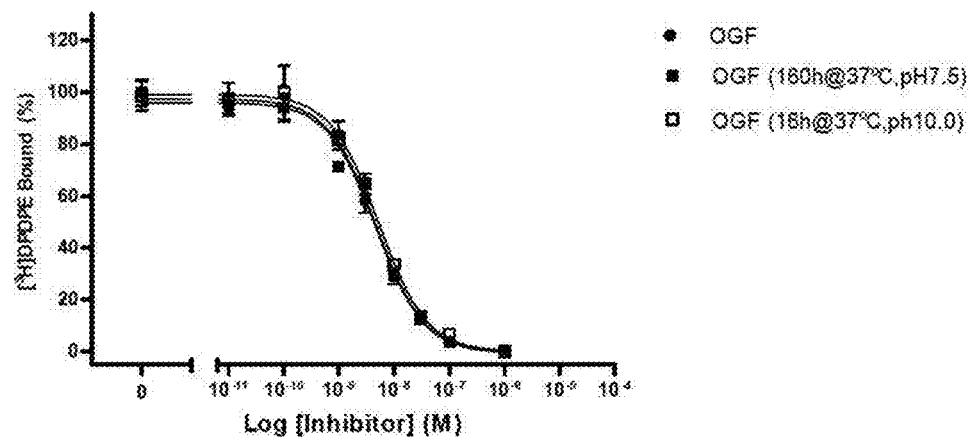
Figure 140

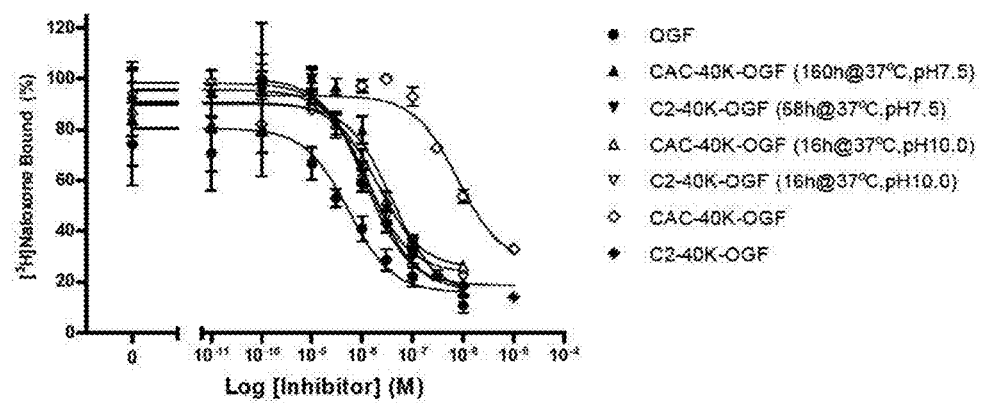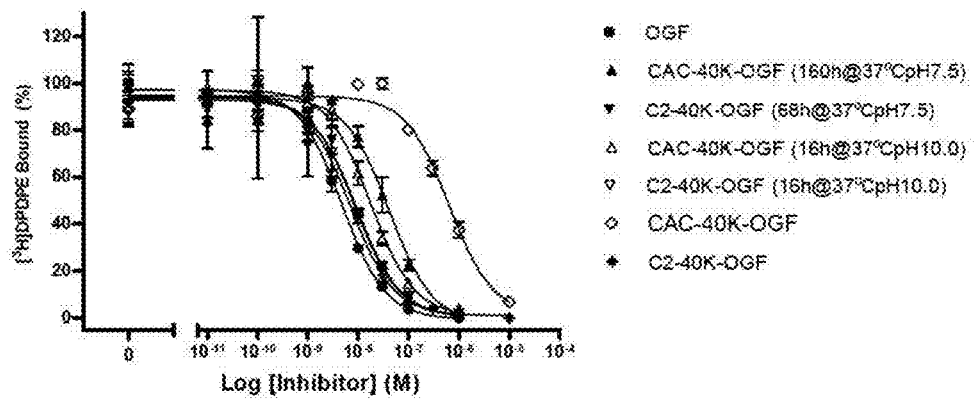
Figure 141

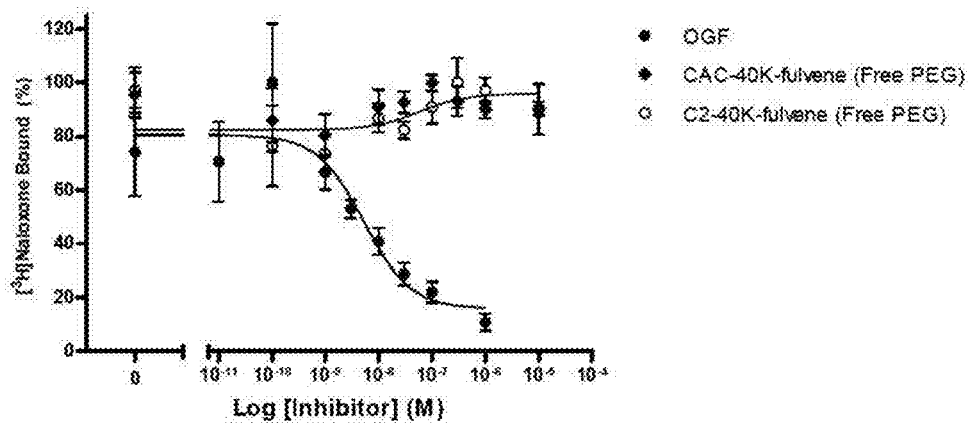
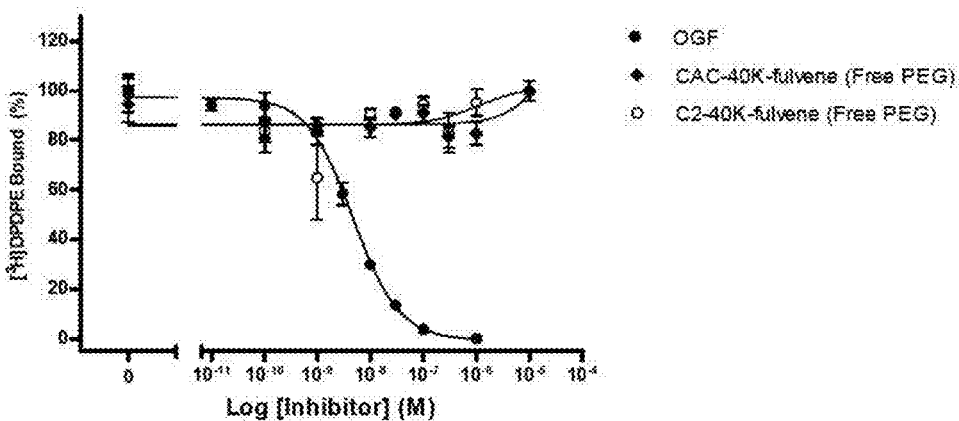
Figure 142

POLYMER CONJUGATES OF THERAPEUTIC PEPTIDES

CROSS REFERENCE TO RELATED APPLICATIONS

This application is a Continuation of U.S. application Ser. No. 13/119,297, filed 16 Mar. 2011, now Abandoned, which is a 35 U.S.C. 0371 application of International Application No. PCT/US2009/005192, filed 17 Sep. 2009, designating the United States, which claims the benefit of priority under 35 U.S.C. §119(e) to U.S. Provisional Patent Application Ser. No. 61/153,966, filed 19 Feb. 2009, to U.S. Provisional Patent Application Ser. No. 61/208,089, filed 18 Feb. 2009, to U.S. Provisional Patent Application Ser. No. 61/192,672, filed 19 Sep. 2008, the disclosures of which are incorporated herein by reference in their entirety.

FIELD OF THE INVENTION

Among other things, the present invention relates to conjugates comprising a therapeutic peptide moiety covalently attached to one or more water-soluble polymers.

BACKGROUND OF THE INVENTION

In many ways, the chemical and biological properties of peptides make them very attractive candidates for use as therapeutic agents. Peptides are naturally occurring molecules made up of amino acid building blocks, and are involved in countless physiological processes. With 20 naturally occurring amino acids, and any number of non-naturally occurring amino acids, a nearly endless variety of peptides may be generated. Additionally, peptides display a high degree of selectivity and potency, and may not suffer from potential adverse drug-drug interactions or other negative side effects. Moreover, recent advances in peptide synthesis techniques have made the synthesis of peptides practical and economically viable. Thus peptides hold great promise as a highly diverse, highly potent, and highly selective class of therapeutic molecules with low toxicity.

A number of peptides have been identified as therapeutically promising; however in vitro results have often not proven to bear out in vivo. Significantly, peptides suffer from a short in vivo half life, sometimes mere minutes, making them generally impractical, in their native form, for therapeutic administration. Thus there exists a need in the art for modified therapeutic peptides having an enhanced half-life and/or reduced clearance as well as additional therapeutic advantages as compared to the therapeutic peptides in their unmodified form.

SUMMARY OF THE INVENTION

Accordingly, the present invention provides conjugates comprising a therapeutic peptide moiety covalently attached to one or more water-soluble polymers. The water-soluble polymer may be stably bound to the therapeutic peptide moiety, or it may be releasably attached to the therapeutic peptide moiety.

The invention further provides methods of synthesizing such therapeutic peptide polymer conjugates and compositions comprising such conjugates. The invention further provides methods of treating, preventing, or ameliorating a disease, disorder or condition in a mammal comprising administering a therapeutically effective amount of a therapeutic peptide polymer conjugate of the invention.

Additional embodiments of the present conjugates, compositions, methods, and the like will be apparent from the following description, examples, and claims. As can be appreciated from the foregoing and following description, each and every feature described herein, and each and every combination of two or more of such features, is included within the scope of the present disclosure provided that the features included in such a combination are not mutually inconsistent. In addition, any feature or combination of features may be specifically excluded from any embodiment of the present invention. Additional aspects and advantages of the present invention are set forth in the following description and claims, particularly when considered in conjunction with the accompanying examples and drawings.

BRIEF DESCRIPTION OF DRAWINGS

FIG. 35. Biphalin structure.

FIG. 36: (SPA-2K)2-biphalin purification with CG-71S resin.

FIG. 48. Competition binding assay of biphalin and di-CAC-20K-biphalin conjugate at human (A) μ opioid and (B) δ opioid receptors.

FIG. 49. Competition binding assay of biphalin and di-C2-20K-biphalin, di-SBC-30K-biphalin, and di-SPA-2K-biphalin conjugate at human (A) μ opioid and (B) δ opioid receptors.

FIG. 1 FIGS. 99 and 100 show the mean plasma concentration-time profiles for CG-PEG$_2$-FMOC-40K-PG-1 and CAC-PEG$_2$-FMOC-40K-PG-1, their corresponding PEG-metabolite and released Protegrin-1.

Figure 123:
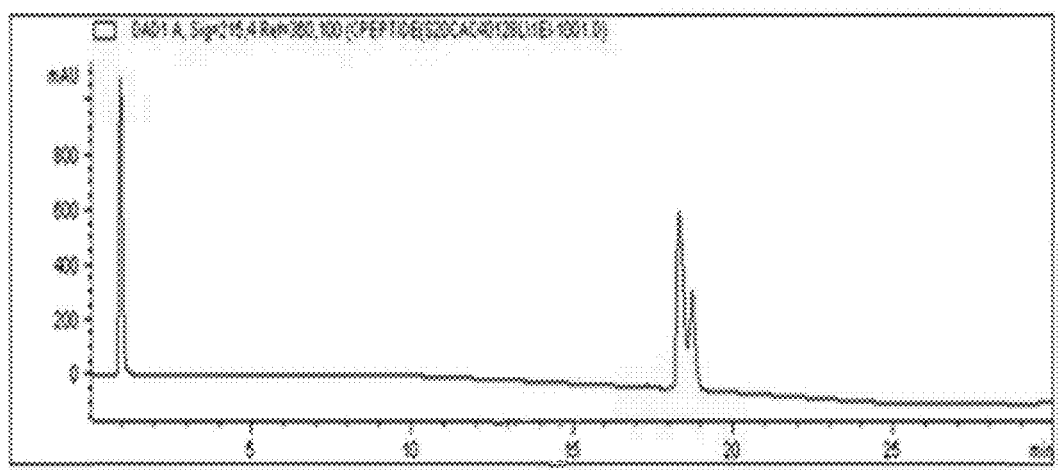

FIG. 123. Purity analysis of [mono]-[CAC-PEG2-FMOC-40K]-[C-peptide(S20C)] by reversed phase HPLC.

Figure 124:
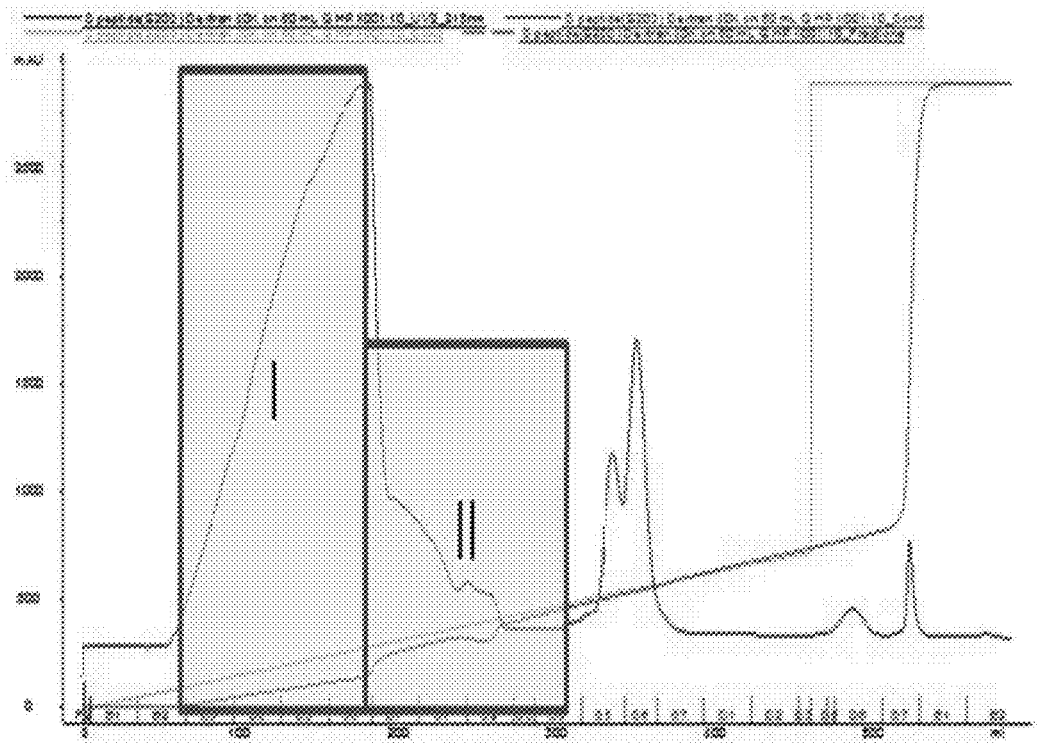

FIG. 124 Typical anion-exchange chromatography profile of dextran-butryaldehyde-40K-C-peptide(S20C).

Figure 125:
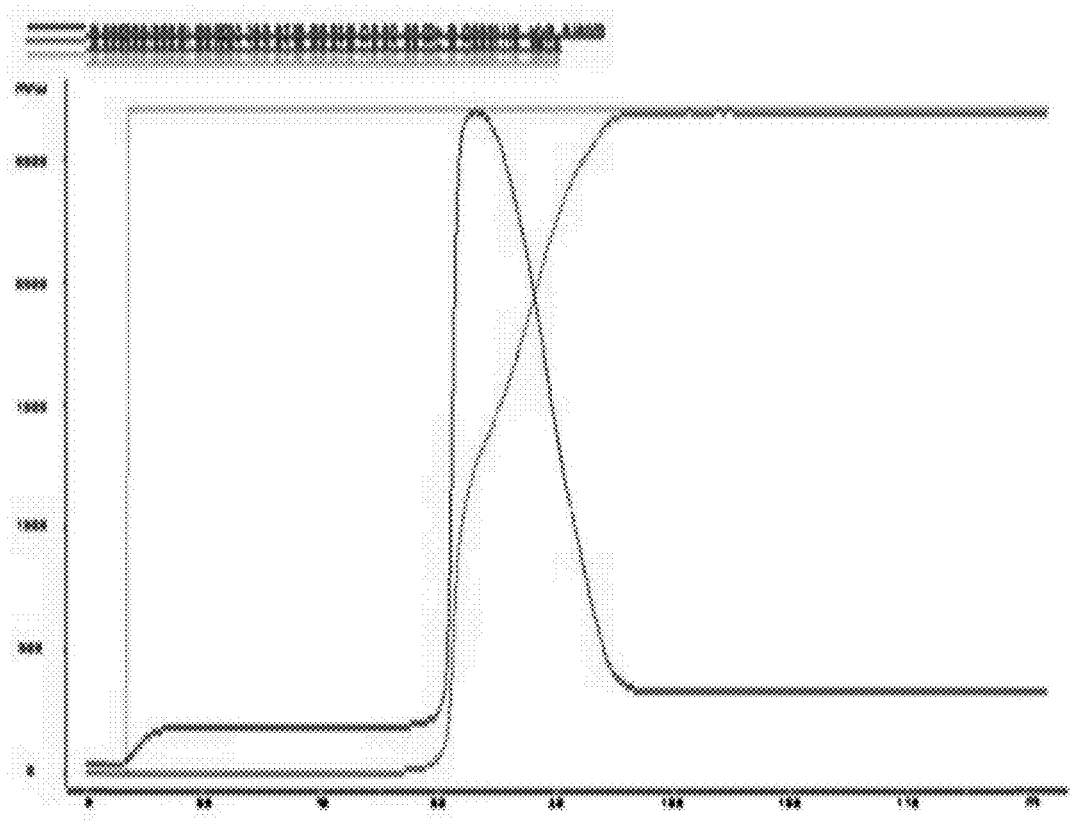

FIG. 125. Concentration of fraction II from the anion-exchange chromatogram shown in FIG. 124 by a second anion-exchange chromatography run.

Figure 126:
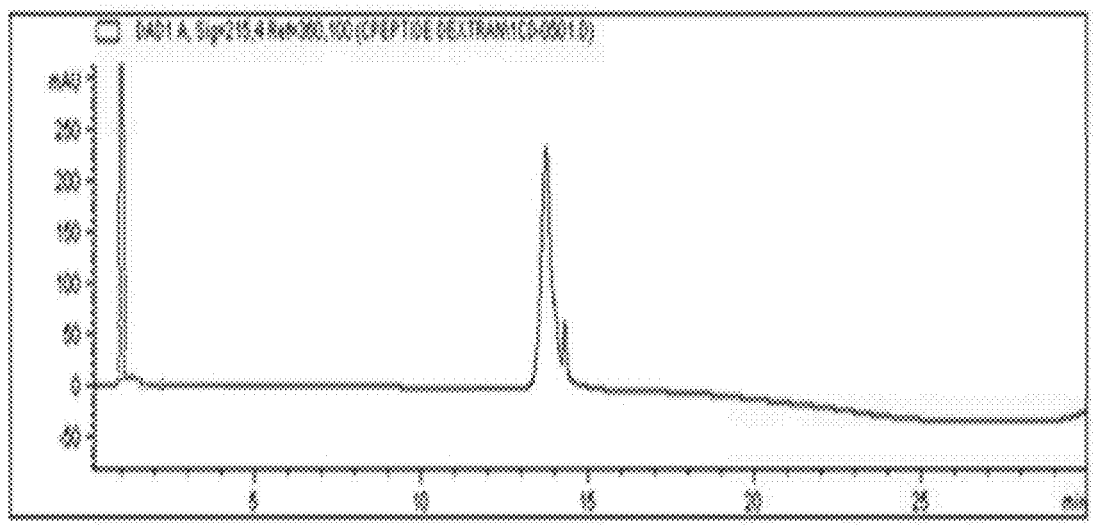

FIG. 126. Purity analysis of [[mono]-[Dextran-40K]-[C-peptide(S20C)] by reversed phase HPLC.

Figure 127:
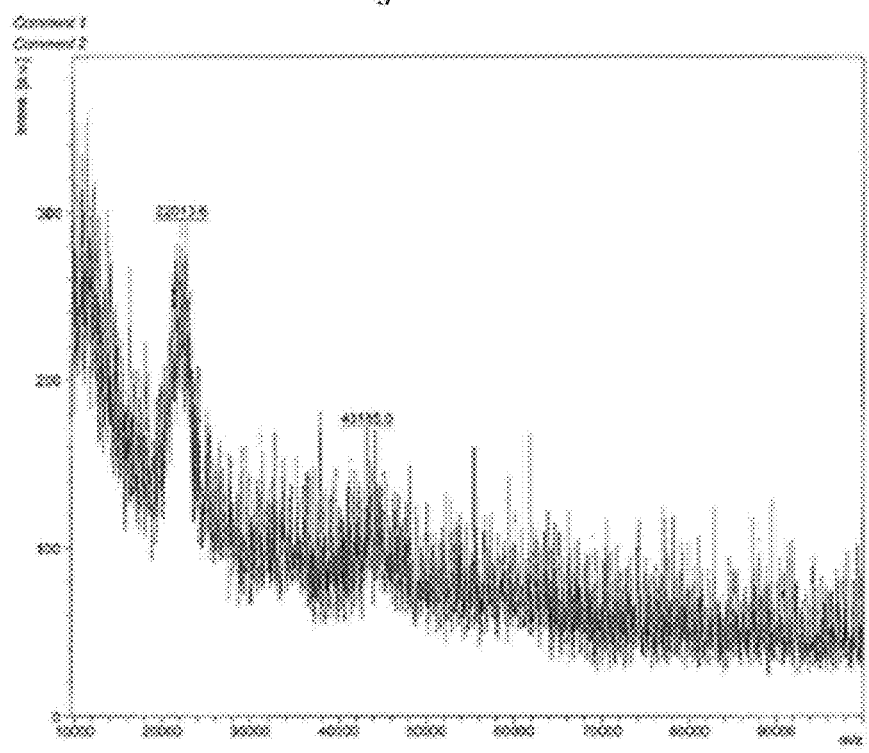

FIG. 127. MALDI-TOF spectrum for [mono]-[Dextran-40K]-[C-peptide(S20C)].

Figure 128:
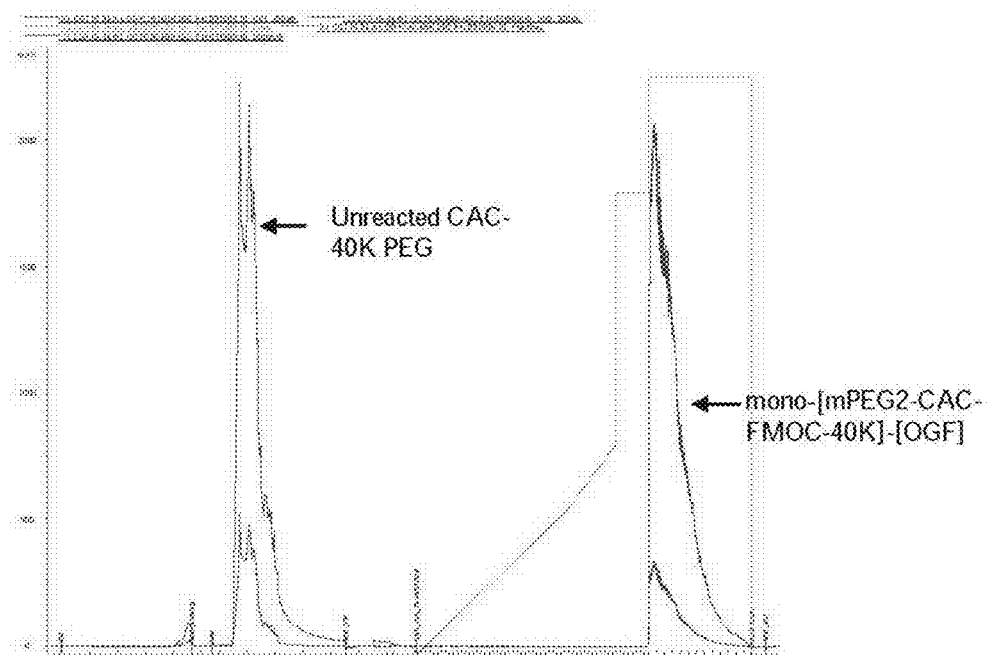

FIG. 128. Typical CG71S reversed phase purification profile of mono-[mPEG2-CAC-FMOC-40K]-[OGF].

Figure 129:
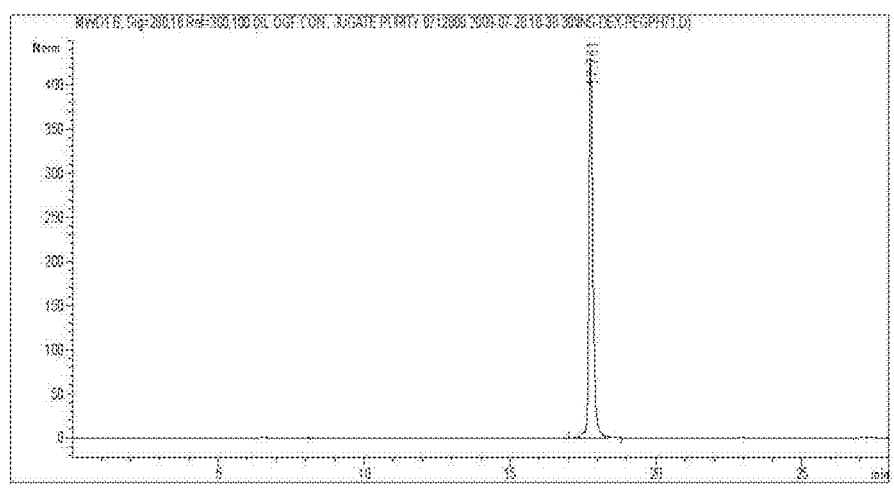

FIG. 129. Purity analysis of [mono]-[CAC-PEG2-FOMC-40K]-[OGF] by reversed phase HPLC.

Figure 130:
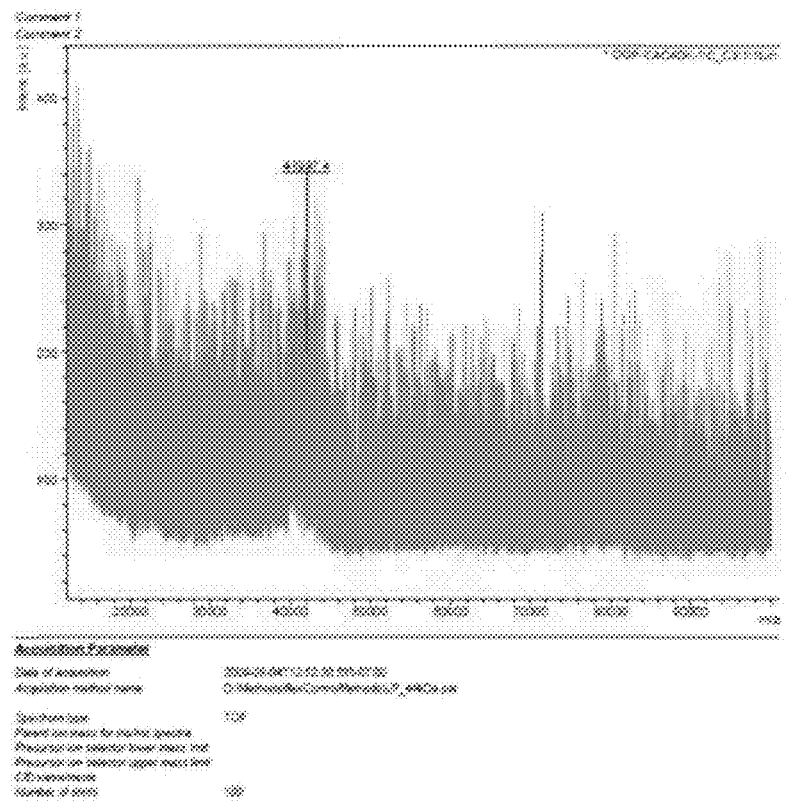

FIG. 130. MALDI-TOF spectrum of purified mono-[mPEG2-FMOC-CAC-40K]-[OGF].

Figure 131:
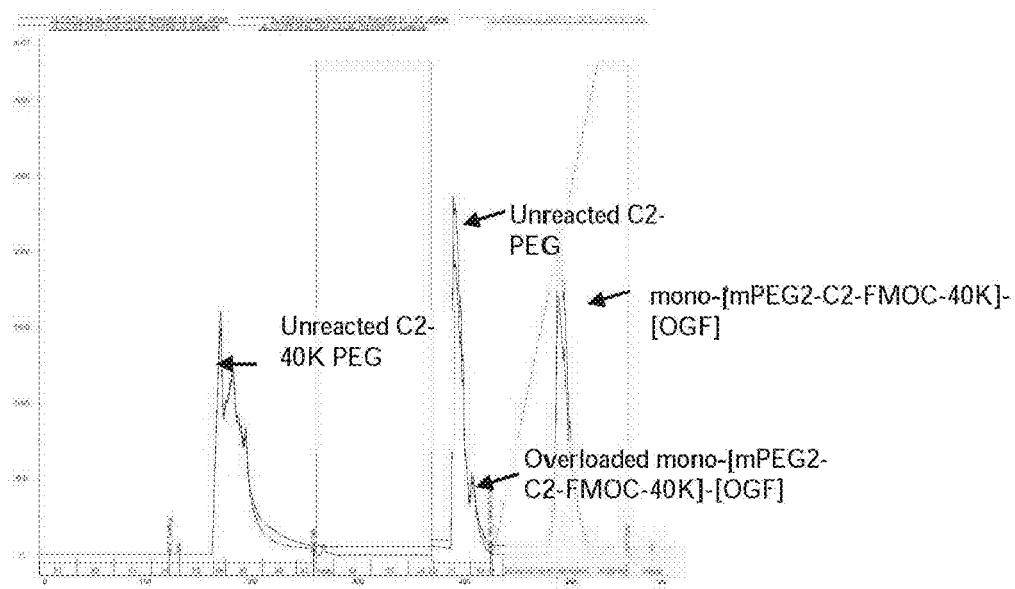

FIG. 131. Typical CG71S reverse phase purification profile of mono-[mPEG2-C2-FMOC-40K]-[OGF].

Figure 132:
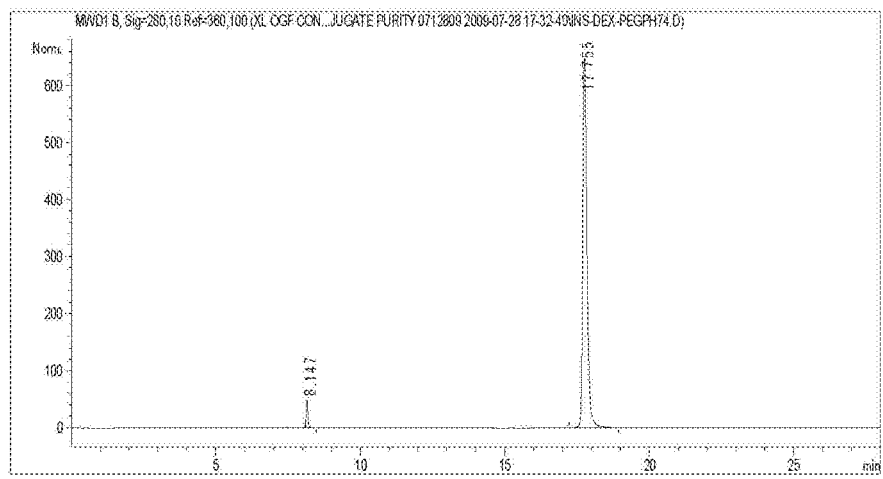

FIG. 132. Purity analysis of mono-[mPEG2-FMOC-C2-40K]-[OGF] by reversed phase HPLC.

Figure 133:
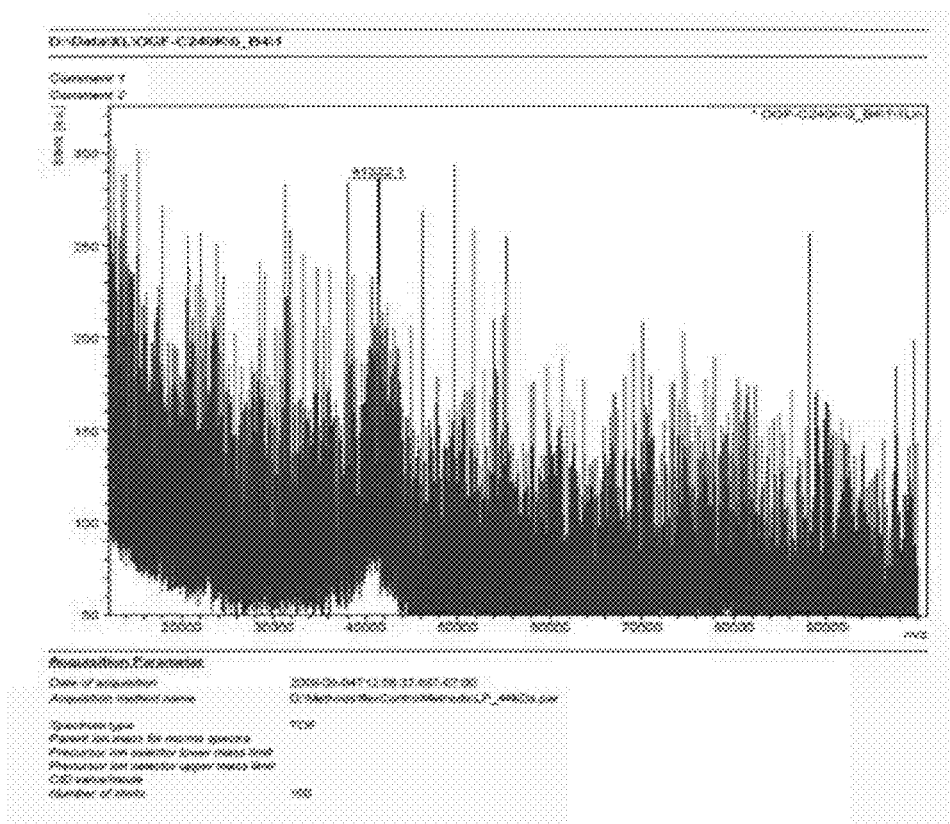

FIG. 133. MALDI-TOF spectrum of purified mono-[mPEG2-FMOC-C2-40K]-[OGF].

Figure 134:
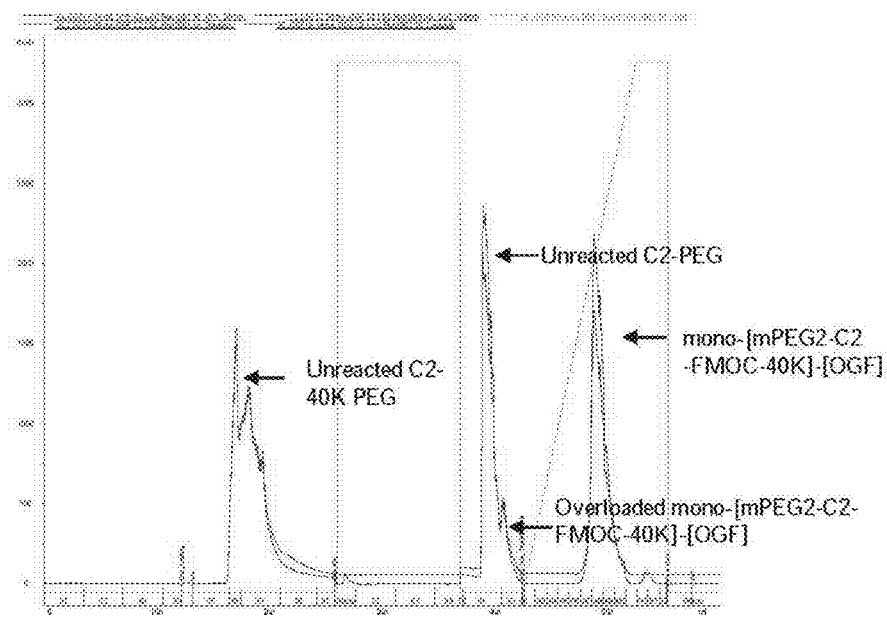

FIG. 134. Typical CG71S reversed phase purification profile of mono-[mPEG-Butyraldehyde-30K]-[OGF].

Figure 135:
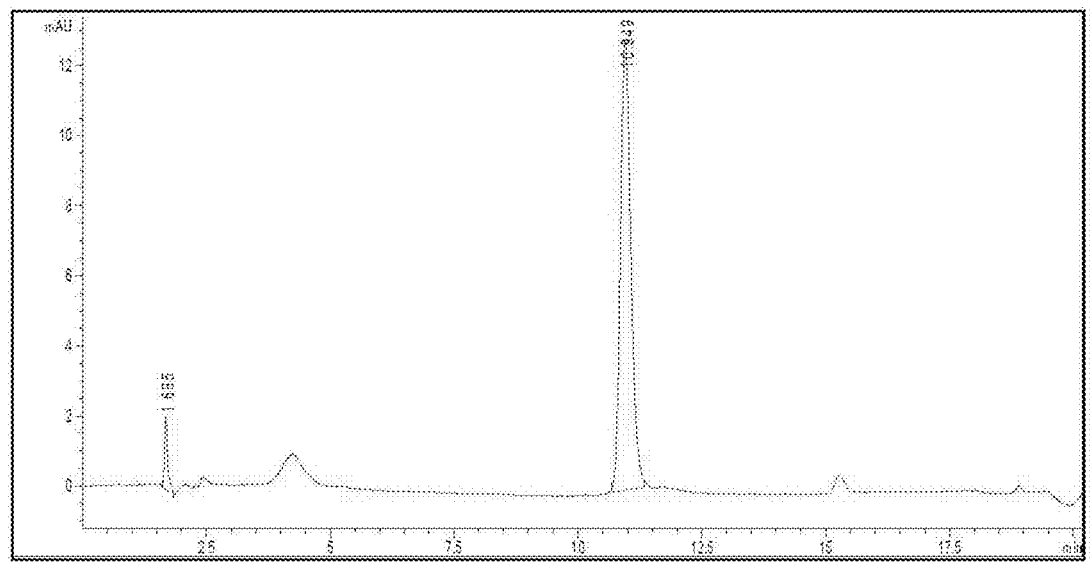

FIG. 135. Purity analysis of mono-[mPEG-ButyrAldehyde-30K]-[OGF] by reversed phase HPLC.

Figure 136:
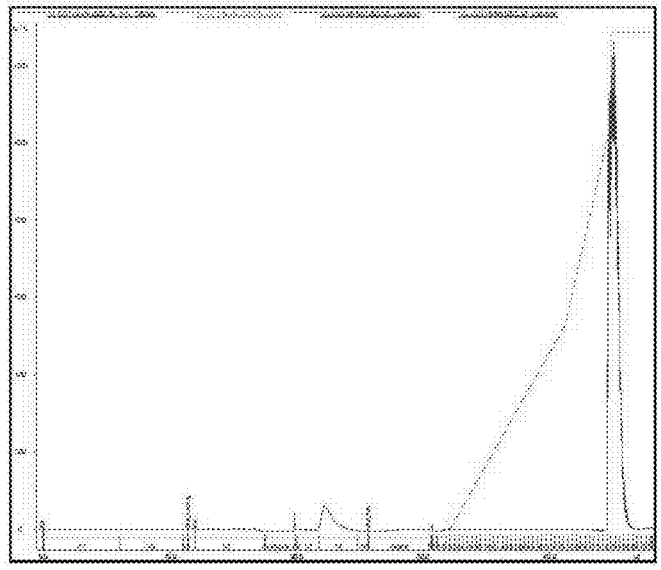

FIG. 136. Typical CG71S reversed phase purification profile of mono-[mPEG-epoxide-5K]-[OGF].

Figure 137:
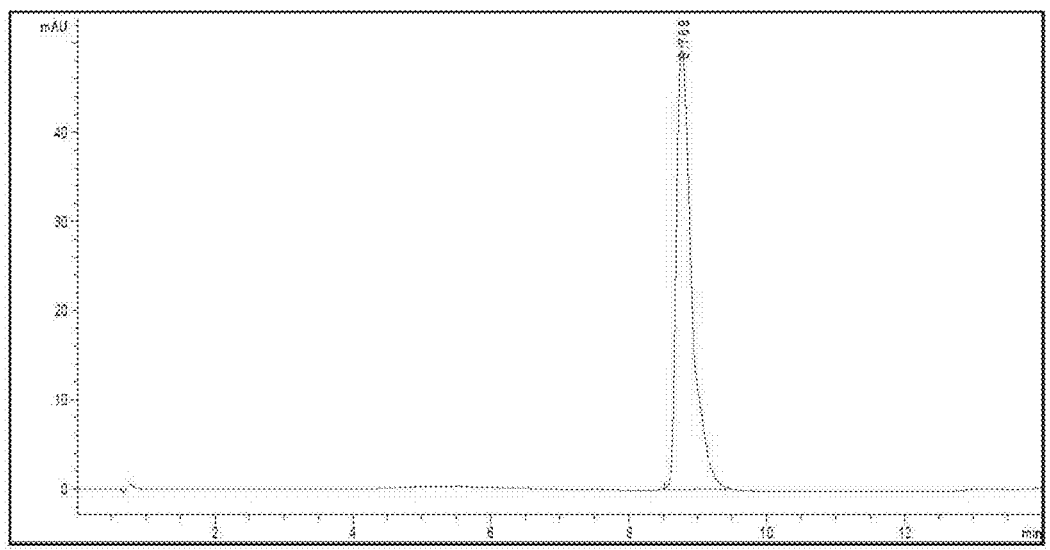

FIG. 137. Purity analysis of mono-[mPEG-epoxide-5K]-[OGF] by reversed phase HPLC.

Figure 138:
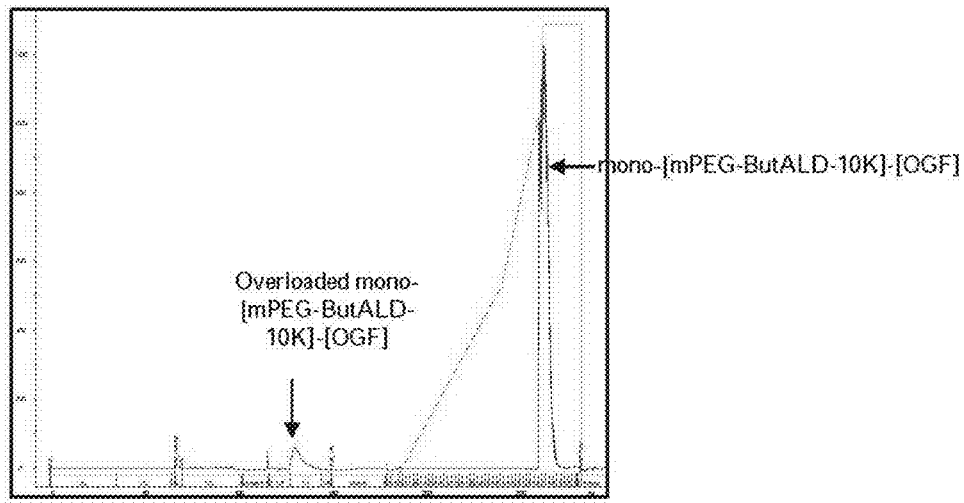

FIG. 138. Typical CG71S reversed phase purification profile of mono-[mPEG-Butyraldehyde-10K]-[OGF].

Figure 139:
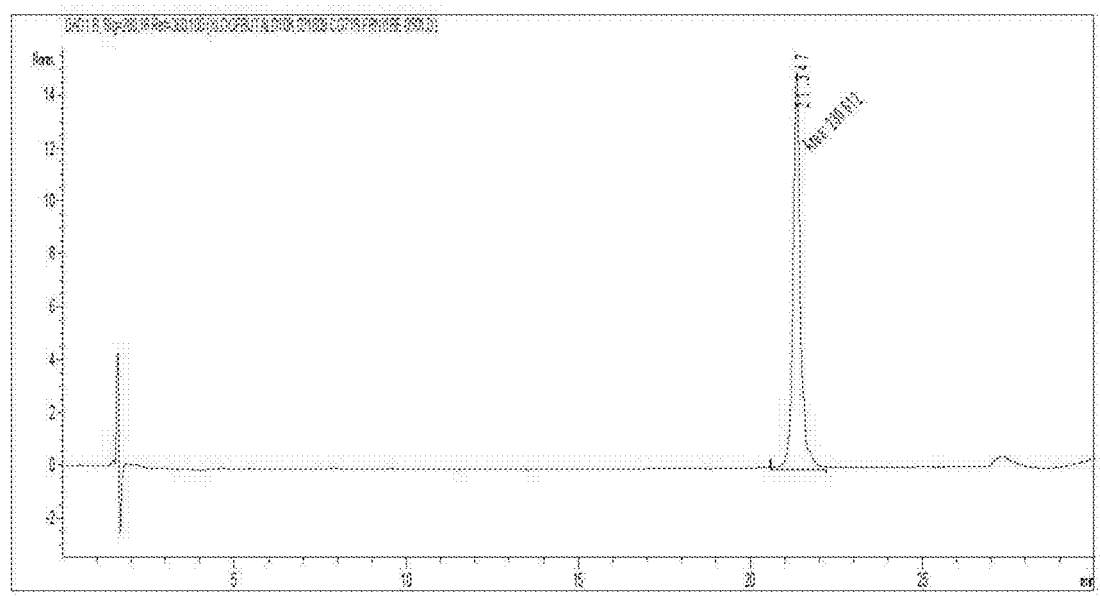

FIG. 139. Purity analysis of mono-[mPEG-ButyrAldehyde-10K]-[OGF] by reversed phase HPLC.

FIG. 140. Competition binding assay of OGF at human (A) μ opioid and (B) δ opioid receptors: effects of incubation treatment conditions.

FIG. 141. Competition binding assay of OGF and PEG-OGF conjugates (released and unreleased) at human (A) μ opioid and (B) δ opioid receptors.

FIG. 142. Competition binding assay of OGF and free PEGs at human (A) μ opioid and (B) δ opioid receptors.

Figure 143:
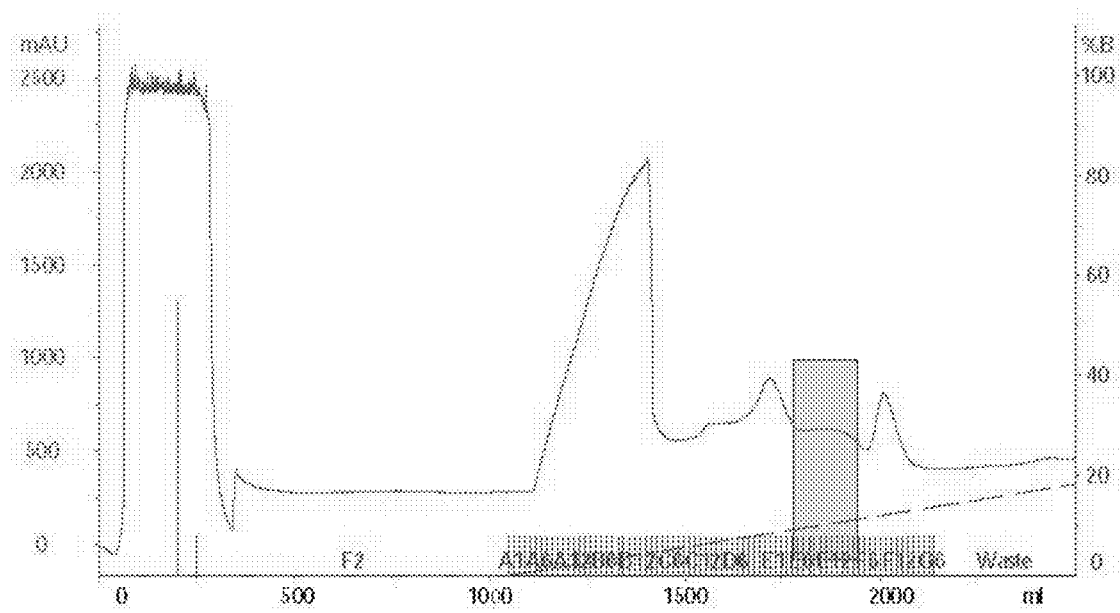

FIG. 143 Typical anion-exchange chromatography profile of the conjugation reaction mixture with partially acetylated insulin.

Figure 144:
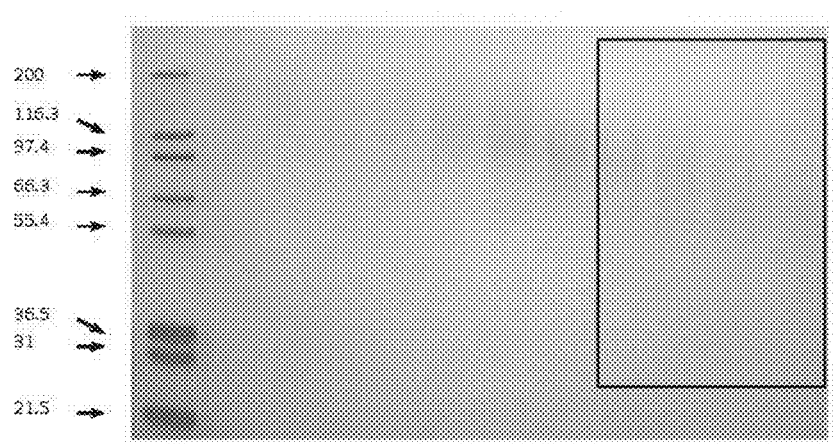

FIG. 144 SDS-PAGE analysis of fractions containing dextran-butyrALD-40K-insulin collected from anion-exchange chromatography.

Figure 145:
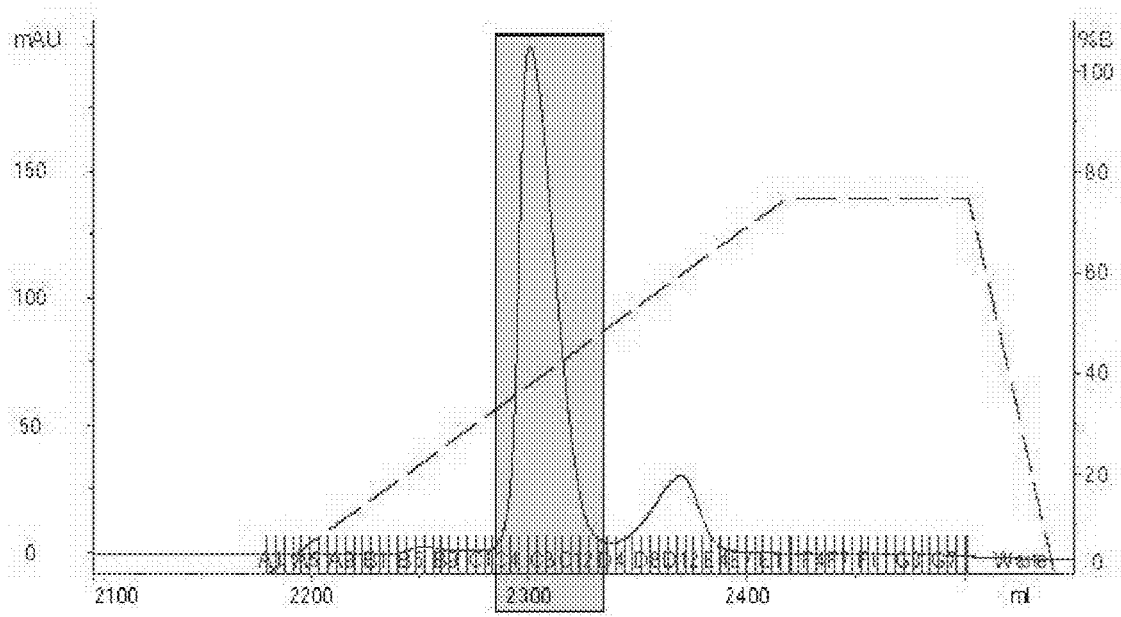

FIG. 145 Concentration of purified dextran-butyrALD-40K-insulin by anion-exchange chromatography.

Figure 146:
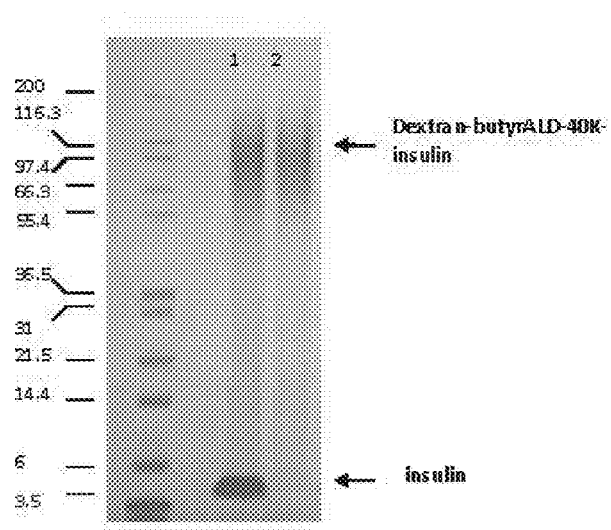

FIG. 146. SDS-PAGE analysis of purified dextran-butyrALD-40K-insulin.

Figure 147:
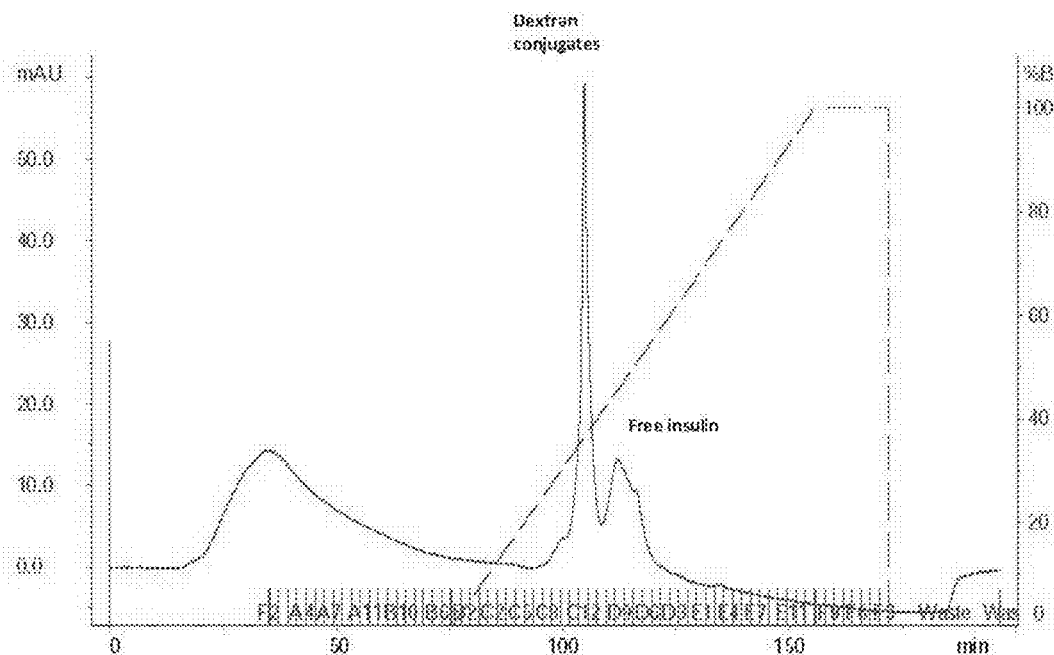

FIG. 147 Typical anion-exchange chromatography profile of the conjugation reaction mixture with non-acetylated insulin.

Figure 148:
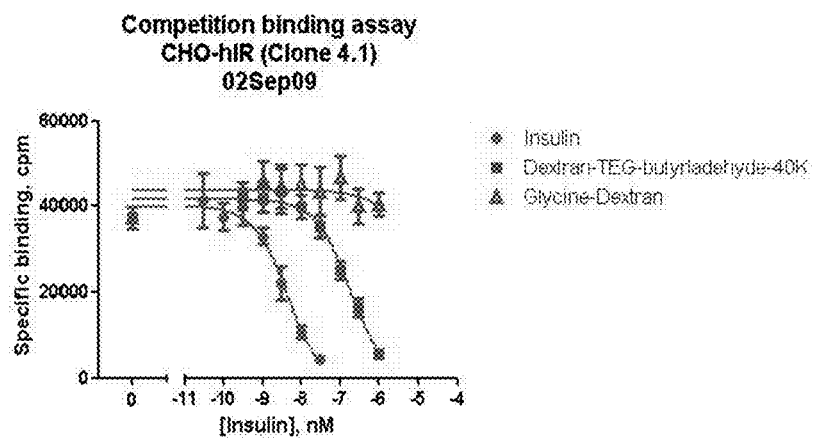

FIG. 148 In vitro binding of the Insulin-dextran conjugate.

Figure 149:
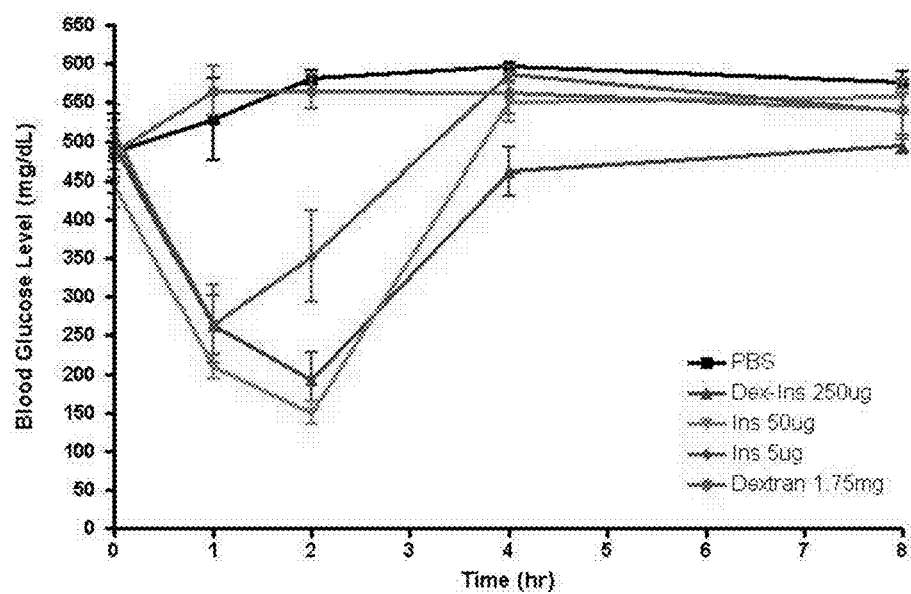

FIG. 149. Glucose levels after compound administration (0-8 hr).

DETAILED DESCRIPTION

As used in this specification and the intended claims, the singular forms "a," "an," and "the" include plural referents unless the context clearly dictates otherwise. Thus, for example, reference to "a polymer" includes a single polymer as well as two or more of the same or different polymers; reference to "an optional excipient" or to "a pharmaceutically acceptable excipient" refers to a single optional excipient as well as two or more of the same or different optional excipients, and the like.

In describing and claiming one or more embodiments of the present invention, the following terminology will be used in accordance with the definitions described below.

As used herein, the terms "therapeutic peptide" and "therapeutic peptides" mean one or more peptides having demonstrated or potential use in treating, preventing, or ameliorating one or more diseases, disorders, or conditions in a subject in need thereof, as well as related peptides. These terms may be used to refer to therapeutic peptides prior to conjugation to a water-soluble polymer as well as following the conjugation. Therapeutic peptides include, but are not limited to, those disclosed herein, including in Table 1. Therapeutic peptides include peptides found to have use in treating, preventing, or ameliorating one or more diseases, disorders, or conditions after the time of filing of this application. Related peptides include fragments of therapeutic peptides, therapeutic peptide variants, and therapeutic peptide derivatives that retain some or all of the therapeutic activities of the therapeutic peptide. As will be known to one of skill in the art, as a general principle, modifications may be made to peptides that do not alter, or only partially abrogate, the properties and activities of those peptides. In some instances, modifications may be made that result in an increase in therapeutic activities. Thus, in the spirit of the invention, the terms "therapeutic peptide" or "therapeutic peptides" are meant to encompass modifications to the therapeutic peptides defined and/or disclosed herein that do not alter, only partially abrogate, or increase the therapeutic activities of the parent peptide.

The term "therapeutic activity" as used herein refers to a demonstrated or potential biological activity whose effect is consistent with a desirable therapeutic outcome in humans, or to desired effects in non-human mammals or in other species or organisms. A given therapeutic peptide may have one or more therapeutic activities, however the term "therapeutic activities" as used herein may refer to a single therapeutic activity or multiple therapeutic activites. "Therapeutic activity" includes the ability to induce a response in vitro, and may be measured in vivo or in vitro. For example, a desirable effect may be assayed in cell culture, or by clinical evaluation, $EC_{50}$ assays, $IC_{50}$ assays, or dose response curves. In vitro or cell culture assays, for example, are commonly available and known to one of skill in the art for many therapeutic peptides as defined and/or disclosed herein. Therapeutic activity includes treatment, which may be prophylactic or ameliorative, or prevention of a disease, disorder, or condition. Treatment of a disease, disorder or condition can include improvement of a disease, disorder or condition by any amount, including elimination of a disease, disorder or condition.

As used herein, the terms "peptide," "polypeptide," and "protein," refer to polymers comprised of amino acid monomers linked by amide bonds. Peptides may include the standard 20 α-amino acids that are used in protein synthesis by cells (i.e. natural amino acids), as well as non-natural amino acids (non-natural amino acids nay be found in nature, but not used in protein synthesis by cells, e.g., ornithine, citrulline, and sarcosine, or may be chemically synthesized), amino acid analogs, and peptidomimetics. Spatola, (1983) in Chemistry and Biochemistry of Amino Acids, Peptides, and Proteins, Weinstein, ed., Marcel Dekker, New York, p. 267. The amino acids may be D- or L-optical isomers. Peptides may be formed by a condensation or coupling reaction between the α-carbon carboxyl group of one amino acid and the amino group of another amino acid. The terminal amino acid at one end of the chain (amino terminal) therefore has a free amino group, while the terminal amino acid at the other end of the chain (carboxy terminal) has a free carboxyl group. Alternatively, the peptides may be non-linear, branched peptides or cyclic peptides. Moreover, the peptides may optionally be modified or protected with a variety of functional groups or protecting groups, including on the amino and/or carboxy terminus.

Amino acid residues in peptides are abbreviated as follows: Phenylalanine is Phe or F; Leucine is Leu or L; Isoleucine is Ile or I; Methionine is Met or M; Valine is Val or V; Serine is Ser or S; Proline is Pro or P; Threonine is Thr or T; Alanine is Ala or A; Tyrosine is Tyr or Y; Histidine is His or H; Glutamine is Gln or Q; Asparagine is Asn or N; Lysine is Lys or K; Aspartic Acid is Asp or D; Glutamic Acid is Glu or E; Cysteine is Cys or C; Tryptophan is Trp or W; Arginine is Arg or R; and Glycine is Gly or G.

The terms "therapeutic peptide fragment" or "fragments of therapeutic peptides" refer to a polypeptide that comprises a truncation at the amino-terminus and/or a truncation at the carboxyl-terminus of a therapeutic peptide as defined herein. The terms "therapeutic peptide fragment" or "fragments of therapeutic peptides" also encompasses amino-terminal and/or carboxyl-terminal truncations of therapeutic peptide variants and therapeutic peptide derivatives. Therapeutic peptide fragments may be produced by synthetic techniques known in the art or may arise from in vivo protease activity on longer peptide sequences. It will be understood that therapeutic peptide fragments retain some or all of the therapeutic activities of the therapeutic peptides.

As used herein, the terms "therapeutic peptide variants" or "variants of therapeutic peptides" refer to therapeutic peptides having one or more amino acid substitutions, including conservative substitutions and non-conservative substitutions, amino acid deletions (either internal deletions and/or C- and/or N-terminal truncations), amino acid additions (either internal additions and/or C- and/or N-terminal additions, e.g., fusion peptides), or any combination thereof. Variants may be naturally occurring (e.g. homologs or orthologs), or non-natural in origin. The term "therapeutic peptide variants" may also be used to refer to therapeutic peptides incorporating one or more non-natural amino acids, amino acid analogs, and peptidomimetics. It will be understood that, in accordance with the invention, therapeutic peptide fragments retain some or all of the therapeutic activities of the therapeutic peptides.

The terms "therapeutic peptide derivatives" or "derivatives of therapeutic peptides" as used herein refer to therapeutic peptides, therapeutic peptide fragments, and therapeutic peptide variants that have been chemically altered other than through covalent attachment of a water-soluble polymer. It will be understood that, in accordance with the invention, therapeutic peptide derivatives retain some or all of the therapeutic activities of the therapeutic peptides.

As used herein, the terms "amino terminus protecting group" or "N-terminal protecting group," "carboxy terminus protecting group" or "C-terminal protecting group;" or "side chain protecting group" refer to any chemical moiety capable of addition to and optionally removal from a functional group on a peptide (e.g., the N-terminus, the C-terminus, or a functional group associated with the side chain of an amino acid located within the peptide) to allow for chemical manipulation of the peptide.

"PEG," "polyethylene glycol" and "poly(ethylene glycol)" as used herein, are interchangeable and encompass any nonpeptidic water-soluble poly(ethylene oxide). Typically, PEGs for use in accordance with the invention comprise the following structure "—$(OCH_2CH_2)_n$—" where (n) is 2 to 4000. As used herein, PEG also includes "—$CH_2CH_2$—O$(CH_2CH_2O)_n$—$CH_2CH_2$—" and "—$(OCH_2CH_2)_nO$—," depending upon whether or not the terminal oxygens have been displaced. Throughout the specification and claims, it should be remembered that the term "PEG" includes structures having various terminal or "end capping" groups and so forth. The term "PEG" also means a polymer that contains a majority, that is to say, greater than 50%, of —$OCH_2CH_2$— repeating subunits. With respect to specific forms, the PEG can take any number of a variety of molecular weights, as well as structures or geometries such as "branched," "linear," "forked," "multifunctional," and the like, to be described in greater detail below.

The terms "end-capped" and "terminally capped" are interchangeably used herein to refer to a terminal or endpoint of a polymer having an end-capping moiety. Typically, although not necessarily, the end-capping moiety comprises a hydroxy or $C_{1-20}$ alkoxy group, more preferably a $C_{1-10}$ alkoxy group, and still more preferably a $C_{1-5}$ alkoxy group. Thus, examples of end-capping moieties include alkoxy (e.g., methoxy, ethoxy and benzyloxy), as well as aryl, heteroaryl, cyclo, heterocyclo, and the like. It must be remembered that the end-capping moiety may include one or more atoms of the terminal monomer in the polymer [e.g., the end-capping moiety "methoxy" in $CH_3O(CH_2CH_2O)_n$— and $CH_3(OCH_2CH_2)_n$—]. In addition, saturated, unsaturated, substituted and unsubstituted forms of each of the foregoing are envisioned. Moreover, the end-capping group can also be a silane. The end-capping group can also advantageously comprise a detectable label. When the polymer has an end-capping group comprising a detectable label, the amount or location of the polymer and/or the moiety (e.g., active agent) to which the polymer is coupled can be determined by using a suitable detector. Such labels include, without limitation, fluorescers, chemiluminescers, moieties used in enzyme labeling, colorimetric (e.g., dyes), metal ions, radioactive moieties, gold particles, quantum dots, and the like. Suitable detectors include photometers, films, spectrometers, and the like. The end-capping group can also advantageously comprise a phospholipid. When the polymer has an end-capping group comprising a phospholipid, unique properties are imparted to the polymer and the resulting conjugate. Exemplary phospholipids include, without limitation, those selected from the class of phospholipids called phosphatidylcholines. Specific phospholipids include, without limitation, those selected from the group consisting of dilauroylphosphatidylcholine, dioleylphosphatidylcholine, dipalmitoylphosphatidylcholine, disteroylphosphatidylcholine, behenoylphosphatidylcholine, arachidoylphosphatidylcholine, and lecithin.

The term "targeting moiety" is used herein to refer to a molecular structure that helps the conjugates of the invention to localize to a targeting area, e.g., help enter a cell, or bind a receptor. Preferably, the targeting moiety comprises of vitamin, antibody, antigen, receptor, DNA, RNA, sialyl Lewis X antigen, hyaluronic acid, sugars, cell specific lectins, steroid or steroid derivative, RGD peptide, ligand for a cell surface receptor, serum component, or combinatorial molecule directed against various intra- or extracellular receptors. The targeting moiety may also comprise a lipid or a phospholipid. Exemplary phospholipids include, without limitation, phosphatidylcholines, phospatidylserine, phospatidylinositol, phospatidylglycerol, and phospatidylethanolamine. These lipids may be in the form of micelles or liposomes and the like. The targeting moiety may further comprise a detectable label or alternately a detectable label may serve as a targeting moiety. When the conjugate has a targeting group comprising a detectable label, the amount and/or distribution/location of the polymer and/or the moiety (e.g., active agent) to which the polymer is coupled can be determined by using a suitable detector. Such labels include, without limitation, fluorescers, chemiluminescers, moieties used in enzyme labeling, colorimetric (e.g., dyes), metal ions, radioactive moieties, gold particles, quantum dots, and the like.

"Non-naturally occurring" with respect to a polymer as described herein, means a polymer that in its entirety is not found in nature. A non-naturally occurring polymer of the invention may, however, contain one or more monomers or segments of monomers that are naturally occurring, so long as the overall polymer structure is not found in nature.

The term "water soluble" as in a "water-soluble polymer" is any polymer that is soluble in water at room temperature. Typically, a water-soluble polymer will transmit at least about 75%, more preferably at least about 95%, of light transmitted by the same solution after filtering. On a weight basis, a water-soluble polymer will preferably be at least about 35% (by weight) soluble in water, more preferably at least about 50% (by weight) soluble in water, still more preferably about 70% (by weight) soluble in water, and still more preferably about 85% (by weight) soluble in water. It is most preferred, however, that the water-soluble polymer is about 95% (by weight) soluble in water or completely soluble in water.

"Hydrophilic," e.g, in reference to a "hydrophilic polymer," refers to a polymer that is characterized by its solubility in and compatibility with water. In non-cross linked form, a hydrophilic polymer is able to dissolve in, or be dispersed in water. Typically, a hydrophilic polymer possesses a polymer backbone composed of carbon and hydrogen, and generally possesses a high percentage of oxygen in either the main polymer backbone or in pendent groups substituted along the polymer backbone, thereby leading to its "water-loving" nature. The water-soluble polymers of the present invention are typically hydrophilic, e.g., non-naturally occurring hydrophilic.

Molecular weight in the context of a water-soluble polymer, such as PEG, can be expressed as either a number average molecular weight or a weight average molecular weight. Unless otherwise indicated, all references to molecular weight herein refer to the weight average molecular weight. Both molecular weight determinations, number average and weight average, can be measured using gel permeation chromatography or other liquid chromatography techniques. Other methods for measuring molecular weight values can also be used, such as the use of end-group analysis or the measurement of colligative properties (e.g., freezing-point depression, boiling-point elevation, and osmotic pressure) to determine number average molecular weight, or the use of light scattering techniques, ultracentrifugation or viscometry to determine weight average molecular weight. The polymers of the invention are typically polydisperse (i.e., number average molecular weight and weight average molecular weight of the polymers are not equal), possessing low polydispersity values of preferably less than about 1.2, more preferably less than about 1.15, still more preferably less than about 1.10, yet still more preferably less than about 1.05, and most preferably less than about 1.03.

The term "active" or "activated" when used in conjunction with a particular functional group refers to a reactive functional group that reacts readily with an electrophile or a nucleophile on another molecule. This is in contrast to those groups that require strong catalysts or highly impractical reaction conditions in order to react (i.e., a "non-reactive" or "inert" group).

As used herein, the term "functional group" or any synonym thereof is meant to encompass protected forms thereof as well as unprotected forms.

The terms "spacer moiety," "linkage" and "linker" are used herein to refer to an atom or a collection of atoms optionally used to link interconnecting moieties such as a terminus of a polymer segment and a therapeutic peptide or an electrophile or nucleophile of a therapeutic peptide. The spacer moiety may be hydrolytically stable or may include a physiologically hydrolyzable or enzymatically degradable linkage. Unless the context clearly dictates otherwise, a spacer moiety optionally exists between any two elements of a compound (e.g., the provided conjugates comprising a residue of a therapeutic peptide and a water-soluble polymer that can be attached directly or indirectly through a spacer moiety).

A "monomer" or "mono-conjugate," in reference to a polymer conjugate of a therapeutic peptide, refers to a therapeutic peptide having only one water-soluble polymer molecule covalently attached thereto, whereas a therapeutic peptide "dimer" or "di-conjugate" is a polymer conjugate of a therapeutic peptide having two water-soluble polymer molecules covalently attached thereto, and so forth.

"Alkyl" refers to a hydrocarbon, typically ranging from about 1 to 15 atoms in length. Such hydrocarbons are preferably but not necessarily saturated and may be branched or straight chain, although typically straight chain is preferred. Exemplary alkyl groups include methyl, ethyl, propyl, butyl, pentyl, 2-methylbutyl, 2-ethylpropyl, 3-methylpentyl, and the like. As used herein, "alkyl" includes cycloalkyl as well as cycloalkylene-containing alkyl.

"Lower alkyl" refers to an alkyl group containing from 1 to 6 carbon atoms, and may be straight chain or branched, as exemplified by methyl, ethyl, n-butyl, i-butyl, and t-butyl.

"Cycloalkyl" refers to a saturated or unsaturated cyclic hydrocarbon chain, including bridged, fused, or spiro cyclic compounds, preferably made up of 3 to about 12 carbon atoms, more preferably 3 to about 8 carbon atoms. "Cycloalkylene" refers to a cycloalkyl group that is inserted into an alkyl chain by bonding of the chain at any two carbons in the cyclic ring system.

"Alkoxy" refers to an —O—R group, wherein R is alkyl or substituted alkyl, preferably $C_{1-6}$ alkyl (e.g., methoxy, ethoxy, propyloxy, and so forth).

The term "substituted" as in, for example, "substituted alkyl," refers to a moiety (e.g., an alkyl group) substituted with one or more noninterfering substituents, such as, but not limited to: alkyl; $C_{3-8}$ cycloalkyl, e.g., cyclopropyl, cyclobutyl, and the like; halo, e.g., fluoro, chloro, bromo, and iodo; cyano; alkoxy, lower phenyl; substituted phenyl; and the like. "Substituted aryl" is aryl having one or more noninterfering groups as a substituent. For substitutions on a phenyl ring, the substituents may be in any orientation (i.e., ortho, meta, or para).

"Noninterfering substituents" are those groups that, when present in a molecule, are typically nonreactive with other functional groups contained within the molecule.

"Aryl" means one or more aromatic rings, each of 5 or 6 core carbon atoms. Aryl includes multiple aryl rings that may be fused, as in naphthyl or unfused, as in biphenyl. Aryl rings may also be fused or unfused with one or more cyclic hydrocarbon, heteroaryl, or heterocyclic rings. As used herein, "aryl" includes heteroaryl.

"Heteroaryl" is an aryl group containing from one to four heteroatoms, preferably sulfur, oxygen, or nitrogen, or a combination thereof. Heteroaryl rings may also be fused with one or more cyclic hydrocarbon, heterocyclic, aryl, or heteroaryl rings.

"Heterocycle" or "heterocyclic" means one or more rings of 5-12 atoms, preferably 5-7 atoms, with or without unsaturation or aromatic character and having at least one ring atom that is not a carbon. Preferred heteroatoms include sulfur, oxygen, and nitrogen.

"Substituted heteroaryl" is heteroaryl having one or more noninterfering groups as substituents.

"Substituted heterocycle" is a heterocycle having one or more side chains formed from noninterfering substituents.

An "organic radical" as used herein shall include alkyl, substituted alkyl, alkenyl, substituted alkenyl, alkynyl, substituted alkynyl, aryl, and substituted aryl.

"Electrophile" and "electrophilic group" refer to an ion or atom or collection of atoms, that may be ionic, having an electrophilic center, i.e., a center that is electron seeking, capable of reacting with a nucleophile.

"Nucleophile" and "nucleophilic group" refers to an ion or atom or collection of atoms that may be ionic having a nucleophilic center, i.e., a center that is seeking an electrophilic center or with an electrophile.

A "physiologically cleavable" or "hydrolyzable" or "degradable" bond is a bond that reacts with water (i.e., is hydrolyzed) under physiological conditions. The tendency of a bond to hydrolyze in water will depend not only on the general type of linkage connecting two central atoms but also on the substituents attached to these central atoms. Appropriate hydrolytically unstable or weak linkages include but are not limited to carboxylate ester, phosphate ester, anhydrides, acetals, ketals, acyloxyalkyl ether, imines, orthoesters, peptides and oligonucleotides.

"Releasably attached," e.g., in reference to a therapeutic peptide releasably attached to a water-soluble polymer, refers to a therapeutic peptide that is covalently attached via a linker that includes a degradable linkage as disclosed herein, wherein upon degradation (e.g., hydrolysis), the therapeutic peptide is released. The therapeutic peptide thus released will typically correspond to the unmodified parent or native therapeutic peptide, or may be slightly altered, e.g., possessing a short organic tag. Preferably, the unmodified parent therapeutic peptide is released.

An "enzymatically degradable linkage" means a linkage that is subject to degradation by one or more enzymes.

A "hydrolytically stable" linkage or bond refers to a chemical bond, typically a covalent bond, that is substantially stable in water, that is to say, does not undergo hydrolysis under physiological conditions to any appreciable extent over an extended period of time. Examples of hydrolytically stable linkages include, but are not limited to, the following: carbon-carbon bonds (e.g., in aliphatic chains), ethers, amides, urethanes, and the like. Generally, a hydrolytically stable linkage is one that exhibits a rate of hydrolysis of less than about 1-2% per day under physiological conditions. Hydrolysis rates of representative chemical bonds can be found in most standard chemistry textbooks. It must be pointed out that some linkages can be hydrolytically stable or hydrolyzable, depending upon (for example) adjacent and neighboring atoms and ambient conditions. One of ordinary skill in the art can determine whether a given linkage or bond is hydrolytically stable or hydrolyzable in a given context by, for example, placing a linkage-containing molecule of interest under conditions of interest and testing for evidence of hydrolysis (e.g., the presence and amount of two molecules resulting from the cleavage of a single molecule). Other approaches known to those of ordinary skill in the art for determining whether a given linkage or bond is hydrolytically stable or hydrolyzable can also be used.

The terms "pharmaceutically acceptable excipient" and "pharmaceutically acceptable carrier" refer to an excipient that may optionally be included in the compositions of the invention and that causes no significant adverse toxicological effects to the patient.

"Pharmacologically effective amount," "physiologically effective amount," and "therapeutically effective amount" are used interchangeably herein to mean the amount of a polymer-(therapeutic peptide) conjugate that is needed to provide a desired level of the conjugate (or corresponding unconjugated therapeutic peptide) in the bloodstream or in the target tissue. The precise amount will depend upon numerous factors, e.g., the particular therapeutic peptide, the components and physical characteristics of the therapeutic composition, intended patient population, individual patient considerations, and the like, and can readily be determined by one skilled in the art, based upon the information provided herein.

"Multi-functional" means a polymer having three or more functional groups contained therein, where the functional groups may be the same or different. Multi-functional polymeric reagents of the invention will typically contain from about 3-100 functional groups, or from 3-50 functional groups, or from 3-25 functional groups, or from 3-15 functional groups, or from 3 to 10 functional groups, or will contain 3, 4, 5, 6, 7, 8, 9 or 10 functional groups within the polymer backbone. A "difunctional" polymer means a polymer having two functional groups contained therein, either the same (i.e., homodifunctional) or different (i.e., heterodifunctional).

The terms "subject," "individual," or "patient" are used interchangeably herein and refer to a vertebrate, preferably a mammal. Mammals include, but are not limited to, murines, rodents, simians, humans, farm animals, sport animals, and pets.

"Optional" or "optionally" means that the subsequently described circumstance may or may not occur, so that the description includes instances where the circumstance occurs and instances where it does not.

"Substantially" (unless specifically defined for a particular context elsewhere or the context clearly dictates otherwise) means nearly totally or completely, for instance, satisfying one or more of the following: greater than 50%, 51% or greater, 75% or greater, 80% or greater, 90% or greater, and 95% or greater of the condition.

Unless the context clearly dictates otherwise, when the term "about" precedes a numerical value, the numerical value is understood to mean the stated numerical value and also ±10% of the stated numerical value.

Turning now to one or more aspects of the invention, conjugates are provided, the conjugates comprising a therapeutic peptide covalently attached (either directly or through a spacer moiety or linker) to a water-soluble polymer. The conjugates generally have the following formula:

PEP-[—X-POLY]$_k$ wherein PEP is a therapeutic peptide as defined herein, X is a covalent bond or is a spacer moiety or linker, POLY is a water soluble polymer, and k in an integer ranging from 1-10, preferably 1-5, and more preferably 1-3.

Therapeutic Peptides

As previously stated, the conjugates of the invention comprise a therapeutic peptide as disclosed and/or defined herein. Therapeutic peptides include those currently known to have demonstrated or potential use in treating, preventing, or ameliorating one or more diseases, disorders, or conditions in a subject in need thereof as well as those discovered after the filing of this application. Therapeutic peptides also include related peptides.

In some embodiments of the invention, PEP is a therapeutic peptide selected from the group consisting of carperitide; alpha-neoendorphin; 348U87; A-3847; A-4114; A-68552; A-75998; A-84861; AN-1792; AAMP-1; exenatide; AC-625; ACE-inhibitors, Aventis; ACE-inhibitors, SRI; ACTH, Amgen; ruprintrivir; AI-102; AI-202; NeuroVax; AI-402; AI-502; AIDS therapeutic vaccine, Repl; AIDS therapy, Inst Pasteur; AIDS vaccine, J&J; AIDS vaccine, Liposome Co; AIDS vaccine, Arana; AIDS vaccine, Peptimmune; AIDS vaccine, Sanofi Past-3; AIDS vaccine, Protherics; AIDS vaccine, SSVI; AIDS vaccine, SWFBR; AIDS vaccine, United-1; AIDS vaccine, United-2; AIDS vaccine-2, Yokohama; AIDS vaccine-3, NIH; AIDS vaccine-4, NIH; AIT-083; teduglutide; Skelite; Allotrap-2702; Alzheimer's imaging agent, Dia; AM-425; AN-238; AnergiX.RA; AnervaX.RA; AS-109; AV-9; AZM-134; addressin, Lilly; allergy vaccine, BioResearch; ambamustine; amylin antagonists, Amylin; anaritide analogues, Bio-Mega; anaritide, Bayer; anaritide, Bristol; anaritide, Aventis-2; anaritide, Astellas; anaritide, GlaxoSmithKline-2; anaritide, Aventis-1; anaritide, Mitsubishi Tanabe; anaritide, Novartis; anaritide, OmniGene; anaritide, Sankyo; anaritide, Scios; angiotensin II antagonists; anti-inflammatories, Affymax; anti-inflammatory peptide, BTG; anti-integrin peptides, Burnha; anti-TCR vaccines; antiallergy peptides, Ajin; antiallergy vaccine, Acambis-1; anticancer matrix, Telios; anticancer peptides, Micrologix; antiflammins; antifungal peptides, BTG; antifungal tripeptides, BTG; antiGnRH immunogen, Aphton; Gastrimmune; antirenin vaccine; antirheumatic peptides, Acambis; antithrombin polypeptides; antiviral peptide, Bio-Mega; antiviral peptides, Non-indust; antiviral peptides, Yeda; apolipoprotein, NeuroSearch; apoptosis technology, Receptag; BCH-143; arthritis antigen; atrial natriuretic peptide, Ph; atrial natriuretic peptide, Ra; avorelin; B-956; BCH-2687; BCH-2763; frakefamide; BIM-22015; BIM-26028; BIM-44002; BIO-1006; BIO-1211; Bio-Flow; BPC-15; Britistatin; BST-2001; bivalirudin; bombesin antagonist; brain natriuretic peptide; brain natriuretic peptide, Phar; C-peptide analogues, UCB; C5a antagonist, Abbott; C68-22; Casocidin, Pharis; CBT-101; CCK(27-32), Organon; CD4, Genelabs; CD4-liposome conjugate, Sumito; CEE-04-420; CEP-079; CEP-903; CETP vaccine, Avant; mifamurtide; CGRP analogues, Asahi Chemical; CGRP, CSL; CGRP, Celltech; CGRP, Novartis; CGRP, Asahi Kasei; CGRP, SmithKline Beecham; CGRP, Unigene; rusalatide acetate; CI-782; CKS-17; CMV peptides, City of Hope; CNTF, Fidia; CP-95253; corticorelin acetate; CT-112, BTG; CT-1508; CTAP-III, Creative; CTP-37; PMD-2850; CVFM; CVT-857; CY-725; CY-726; CYC101; CYC103; CYC102; calcitonin, Peptitrol; calcitonin, Rockefeller; calciseptine; calcitonin analogues, SB; calcitonin, Amgen; calcitonin, Armour; calcitonin, Beaufour; calcitonin, Inhale; calcitonin, Bridgelock; calcitonin, microspheres; calcitonin, Nazdel; calcitonin, Novartis; calcitonin, nasal, Novartis; calcitonin, oral, Mannkind; calcitonin, Panoderm; calcitonin, Pharma Bissendorf; calcitonin, Pharmos; calcitonin, Anesiva; calcitonin, Aventis; calcitonin, Teijin; calcitonin, Teikoku; calcitonin, TheraTech; calcitonin, Yissum; calf thymus derived peptides; calpain inhibitors, ResCo; calphobindin I; cancer vaccines, Argonex; cargutocin; casokefamide; cekropin-P; chemokines, Dompe; tasidotin hydrochloride; ceruletide diethylamine; ceruletide, Fukuoka; cetrorelix acetate; chimaeric peptides, NIH; cholecystokinin, Ferring; collagenase IV inhibitors; collamers; contraceptive vaccine, Cephalo; contraceptive vaccine, Novarti; corplatin S compounds; corticoliberin, Pharma Bissend; corticoliberin, Salk; corticoliberin, Unigene; corticoliberin, Vanderbilt; D-21775; D-22213; Demegel; DAP inhibitors; DP-640; DP-107; DSIP; DU-728; Dynorphin A; daniplestim; defensins, LSB; desirudin; detirelix; dialytic oligopeptides; disagregin; E-2078; ECE inhibitor, SmithKline; ELS-1; EMD-73495; Enhancins; ecallantide; ES-1005; ES-305; echistatin; efegatran; eglin derivatives; elafin derivatives; elcatonin; eledoisin; encapsulated insulin, INSERM; endorphin, β-, Antigenics; endorphin, pancreatic; endorphin, β-, Mitsubishi; endorphin, β-, Amgen; endothelial cell growth factor; endothelin antagonists, ResCo; eptifibatide; examorelin; Factor VIII fragments, Pharma; FG-002; FG-003; FG-004; FG-005; FR-113680; FTS-Zn; fibrin-binding peptides, ISIS; fibronectin inhibitors, AstraZ; fibronectin-related peptide; follicular regulatory protein; G-4120; GAG-V3-VDP vaccine, Vern; GDL-peptides, Cytogen; EP-51216; GLP-1+ exendin-4, NIH; GLP-1, Amylin; GLP-1, TheraTech; GM-1986; GM-CSF blocker, Hospira; GnRH-associated peptide; GPCR antagonists, NIH; GPIIb/IIIa antags, Selectide; GRF1-44; GRF, Lilly; GT2342; GT2501; GYKI-14451; galanin; gastrin antagonists; gastrin, Novo; glaspimod; glicentin; glucagon antagonists, Synvista; glucagon, Lilly; glucagon, ZymoGenetics; glucagon-121; glycoprotein 1balpha fragments; gonadorelin analogues, Syntex; gonadorelin antagonist, Ortho; gonadorelin preparations; gonadorelin, Arana; gonadorelin-MDP vaccine; goralatide; gp120-V3 peptides; growth factor peptides, Biothe; ENMD-0996; H-142, AstraZeneca; Her-2/Neu peptides, GSK; herpes simplex vaccine, Wistar; AIDS vaccine, Cel-Sci; HP-101; vitespen; HSV vaccine, Cel-Sci; HSV-1gD/vaccinia vaccine; heparin binding peptides, NCI; hepatitis-B receptor; hepatitis-B vaccine, Tokyo; hepatitis-B vaccine, Protherics; hepatitis-B vaccine-2, BTG; hirugen; I5B2; iseganan hydrochloride; IgE peptides; IgG binding factor, Hoechst Ma; netamiftide; Insulin Aspart; Zorcell; icrocaptide; icatibant; immunomodulating peptides, Bio; infertility, E-TRANS; influenza vaccine, GSK-1; influenza vaccine, Yeda; instimulin; insulin analogue, Lilly; insulin analogues, Lilly; insulin analogues, Scios; insulin formulation, Pasteur; insulin glargine; insulin, Nektar, inhaled; insulin molecules, Novo; insulin oral, Inovax; insulin transdermal; insulin, Organon; insulin, ocular; insulin, AERx; insulin, AutoImmune; insulin, BEODAS; insulin, Biobras; insulin, Ferring Pharma; insulin, CJ Corp; insulin, Chiron; insulin, Chong Kun Dang; insulin, Sanofi Pasteur; insulin, Di-Arg, Hoechst Mario; insulin, E-TRANS; insulin, Forest; insulin, Hoechst, semisynth; insulin, Lilly, iodinated; insulin, Genentech, recombi; insulin, Provalis; insulin, Novartis; insulin, nasal; insulin, Ohio; insulin, Nazdel; insulin, Novo, synthetic; insulin, nasal, Novo Nordisk; insulin, oral; insulin, buccal, Generex; insulin, Arana; insulin, Anesiva; insulin, Procter & Gamble; insulin, Qmax; insulin, Innovata; insulin, Roche; insulin, recombinant, Aventis; insulin, Shionogi; insulin, Shire; insulin, Spiros; insulin, SRI; insulin, Structured Biological; insulin, semisynthetic, Biobra; insulin, synthetic, Powerpatch; insulin, Zymo, recombinant; insulin, monocomponent, Novo; IL-1 receptor antagonist, Affym; interleukin-1β, Sclavo; interleukin-8 antags, Select; J015X; J018X; AG-1776; KNI-549; pralmorelin; KPI-022; katacalcin; ketomethylureas; L-346670; L-364210; L-659837; L-693549; L-709049; L-75; L-761191; L-histidyl peptides; LDV-containing peptides, Antiso; LEAPS-101; LHRH antagonists, Abbott; PD-6735; Lys-Phe; hLF1-11; lagatide; laminin A peptides, NIH; laminin technology, NIH; lanreotide; leuprolide acetate, Atrigel; leuprorelin, Takeda; leuprorelin, Merck Serono; leuprorelin, DUROS; leuprorelin, Powerpatch; lipid-linked anchor technology; lysozyme metabolites, SPA; MCI-826; omiganan pentahydrochloride; MBP, ImmuLogic; MCI-536; MDL-104238; MDL-28050; Metascan; MMP inhibitors, NIH; MN-10006; MOL-376; MR-988; MSH derivatives; MUC-1 vaccine, Pittsburgh; malaria vaccine, Axis; malaria vaccine, Vernalis; malaria vaccine, Cel-Sci; malaria vaccine, Roche; melanoma vaccine, Nobilon; meningitis vaccine, Acambis; mertiatide; metkephamide; metorphamide; monocyte chemotactic factor; montirelin hydrate; motyline; murabutide; muramyl dipeptide derivatives; myelopid; N-acetyl[Leu-28Leu-31]NPY24-36; N-carbobenzoxy peptides; NAGA; tiplimotide; opebecan; insulin detemir; liraglutide; Nona CCK; NP-06; NPC-18545; Nva-FMDP; nacartocin; natural peptide BPC, Pliva; nerve growth factor, Synergen; nesiritide citrate; neuropeptides, Protherics; neuropeptides, Pfizer; neurotensin, Merck; neurotrophic factors, CereMedix; nifalatide; CL22, Innovata; nootropic, Yakult; nociceptin, Euroscreen; Org-2766; Org-30035; OSA peptides, Osteopharm; octreotide; opioid peptides, Unigene; osteogenic growth peptide; osteoporosis peptides, Telios; oxyntomodulin; P-113, Demegen; PACAP 27; PAPP; PD-83176; PD-122264; PD-132002; PEP-F; Penetratin; Peptigen agents; Phe-X-Gly, ResCo; PL-030; PN1 antagonists, Allelix; POL-443; POL-509; PPA, ResCo; PR-39; Prodaptin-M technology; PSP; tigapotide triflutate; PT-14; PT-5; semparatide; PTL-78968; parathyroid hormone fragments; pancreastatin; papillomavirus vaccine constru; parathyroid antagonist, Merck; enfuvirtide; peptide heterodimers, Cortech; peptide imaging, Diatide; pentapeptide 6A; pentigetide; peptide analogues, ResCo; peptide 6, NY Medical College; peptide G, Arana; peptide inhibitors, ICRT; peptide T analogue, Carl; peptide T analogues; peptide T, Arana; peptide/drug vehicle, BTG; peptides, Sanofi-Aventis; peptides, Scios; peptides, Yeda; peptomers, NIH; pertussis vaccine-1, TRION; ph-914; ph-921; ph-9313; phospholipase inhibitors, Poli; prolactin, Genzyme; pramlintide; pranlukast; proinsulin, Lilly; proinsulin-2, Novartis; progenitor cell inhibitor, RCT; proinsulin fragments, Lilly; proinsulin analogues, Lilly; proinsulin, Genentech; prostate cancer vaccine, United; prostate cancer vaccine, GSK; protirelin; protirelin, Takeda; *Pseudomonas* elastase inhibitor; QRS-10-001; QRS-5-005; Quilimmune-M; Retropep; RGD peptides; RHAMM targeting peptides, Cange; Ro-25-1553; RP-128; RSV vaccine, Avant; RSV vaccine, Acambis; RWJ-51438; TRH, Ferring; renin inhibitors, Pfizer-2; relaxin, Novartis; renin inhibitors, INSERM; romurtide; rubella vaccine, Protherics; S-17162; S-2441; SC-40476; SC-44900; SDZ-CO-611; SIDR-1204; SK&F-101926; SK&F-110679; SLPI, Synergen; edotreotide; SP-1; SPAAT; SR-41476; SR-42128; SR-42654; SRIF-A; *Streptococcus* A vaccine, ID; *Streptococcus* A vaccine, SIGA; calcitonin, PPL; salmon calcitonin, Therapicon; sermorelin, Kabi; saralasin acetate; secretin, Eisai; secretin, Ferring; secretin, Wakunaga; sermorelin, Novartis; sermorelin peptides, Sanofi-Ave; sermorelin, Antigenics; sermorelin, Molecular Genetics; sermorelin acetate, Merck Ser; sermorelin, Sanofi-Aventis; sermorelin, Unigene; sinapultide; sleep inducing peptide, Bissen; small peptides, Centocor; somatoliberin, Takeda; PTR-3173; somatostatin analogue, Shira; somatostatin analogues, Merck; somatostatin analogues, Tulane; somatostatin derivatives; somatostatin, Merck Serono; somatostatin, Ferring; somatostatin, Arana; somatostatin, Sanofi-Synthelabo; somatostatin, BayerScheringPhar; T-205; *Streptococcus* A vaccine, Active; sulglicotide; syndyphalin; synthetic p16, Dundee; synthetic peptide BPC, Pliva; synthetic peptides, ICRT; T cell receptor peptide vaccin; T-118; T-786; T-cell receptor peptides, Xoma; T22; TA-3712; TASP inhibitors; TCMP-80; Tc-99m P215; Tc-99m P483H; Tc-99m P773; Tc-99m depreotide; Tc-99m-P280; TEI-1345; THF, Pfizer; Theradigm-HBV; Theradigm-HIV; Theratides; Stimuvax; ThGRF 1-29; tesamorelin acetate; ThromboScan; TIMP, Creative BioMolecules; TIMP, Sanofi-Aventis; TJN-135; TNF inhibitor, Genelabs; TP-9201; TRH analogues, Roche; TRH, Daiichi; TRH, Japan Tobacco; TRH, Medicis; TRH, Arana; TRH-R, Medical Research Counci; TT-235; tabilautide; tendamistat; terlipressin; terlipressin, Nordic; teverelix; INKP-2001; thymic peptide; thymoleptic peptides; thymopentin; thymopentin analogues; thymosin alpha-2; thymosin β4; thymosin fraction 5; tolerizing peptide, Acambis; trefoil peptides, ICRT; triletide; tuftsin, Abic; tuftsin, Sclavo; Type I diabetes vaccine, RCT; tyrosine kinase antags, ICRT; tyrosine-containing dipeptides; UA 1041; UA 1155; UA 1248; Uroguanylin, Pharis; urodilatin; V.F.; VIC, Astellas; VIP analogues, TRION; VIP derivative, Eisai; VIP fusion protein, Kabi; vapreotide, immediate-release; varicella vaccine, ResCo; vitronectin receptor antag; vicalcins; Mycoprex; YIGSR-Stealth; Yissum Project No. 11607; Pharmaprojects No. 1088; Pharmaprojects No. 1113; Pharmaprojects No. 1269; Pharmaprojects No. 1448; Pharmaprojects No. 1507; Pharmaprojects No. 1573; Pharmaprojects No. 1583; Pharmaprojects No. 1626; Pharmaprojects No. 1779; Pharmaprojects No. 1797; Pharmaprojects No. 1843; Pharmaprojects No. 1876; Pharmaprojects No. 1913; Pharmaprojects No. 1939; Pharmaprojects No. 1994; Pharmaprojects No. 2043; Pharmaprojects No. 2044; Pharmaprojects No. 2063; Pharmaprojects No. 2100; Pharmaprojects No. 2122; Pharmaprojects No. 2202; Pharmaprojects No. 2363; Pharmaprojects No. 2388; Pharmaprojects No. 2425; Pharmaprojects No. 2476; Pharmaprojects No. 2527; Pharmaprojects No. 2560; Pharmaprojects No. 2571; Pharmaprojects No. 2825; Pharmaprojects No. 2866; C-type natriuretic peptide, Sun; Pharmaprojects No. 2909; Pharmaprojects No. 2912; Pharmaprojects No. 2913; Pharmaprojects No. 3009; Pharmaprojects No. 3020; Pharmaprojects No. 3051; Pharmaprojects No. 3127; Pharmaprojects No. 3284; Pharmaprojects No. 3341; Pharmaprojects No. 3392; Pharmaprojects No. 3393; Pharmaprojects No. 3400; Pharmaprojects No. 3415; Pharmaprojects No. 3472; Pharmaprojects No. 3503; Pharmaprojects No. 3581; Pharmaprojects No. 3597; Pharmaprojects No. 3654; Pharmaprojects No. 3667; Pharmaprojects No. 3777; Pharmaprojects No. 3862; Pharmaprojects No. 3863; Pharmaprojects No. 3891; Pharmaprojects No. 3903; Pharmaprojects No. 3939; Pharmaprojects No. 3963; Pharmaprojects No. 3989; Pharmaprojects No. 4004; Pharmaprojects No. 4093; Pharmaprojects No. 4098; Pharmaprojects No. 4113; Pharmaprojects No. 4182; Pharmaprojects No. 4209; Pharmaprojects No. 4246; Pharmaprojects No. 4251; Pharmaprojects No. 4300; Pharmaprojects No. 4323; Pharmaprojects No. 4347; Pharmaprojects No. 4367; Pharmaprojects No. 4385; Pharmaprojects No. 4402; Pharmaprojects No. 4445; Pharmaprojects No. 4544; Pharmaprojects No. 4625; Pharmaprojects No. 4626; Pharmaprojects No. 4643; Pharmaprojects No. 4705; Pharmaprojects No. 4708; Pharmaprojects No. 4766; GHRP-1, QLT; Pharmaprojects No. 4865; Pharmaprojects No. 491; Pharmaprojects No. 4915; Pharmaprojects No. 4936; Pharmaprojects No. 494; Hematide; Pharmaprojects No. 4975; Pharmaprojects No. 5048; Pharmaprojects No. 5055; Pharmaprojects No. 5076; anti-HER2/neu mimetic, Cyclacel; Pharmaprojects No. 5131; Pharmaprojects No. 5173; Pharmaprojects No. 5181; Pharmaprojects No. 5200; Pharmaprojects No. 5216; Pharmaprojects No. 5292; Pharmaprojects No. 5348; Pharmaprojects No. 5356; Pharmaprojects No. 5412; DMP-444; Pharmaprojects No. 5657; Pharmaprojects No. 5728; Pharmaprojects No. 5839; Pharmaprojects No. 5910; TGF-β antagonists, Inspiraplex; Pharmaprojects No. 5961; Pharmaprojects No. 5991; Pharmaprojects No. 6021; Pharmaprojects No. 6063; Pharmaprojects No. 6083; PI-0824; RIP-3, Rigel; NBI-6024; Pharmaprojects No. 892; Pharmaprojects No. 955; IR-501; A6, Angstrom; leuprolide, ProMaxx; Orolip DP; edratide; 131-I-TM-601; Prosaptide TX14(A), Savient; insulin, Flamel; p1025; NIH; protein kinase R antags, NIH; GLP-1, Daiichi; EMD-249590; secretin, RepliGen; RANTES inhibitor, Milan; Pharmaprojects No. 6236; NY ESO-1/CAG-3 antigen, NIH; BILN-504 SE; NIPs, RCT; insulin, Biphasix; ZRXL peptides, Novartis; BIM-23190; leuprorelin, TheriForm; β-amyloid peptides, CeNeS; oglufanide disodium; amyloid inhibiting peptides, Ax; iprP13; PN-277; differentiation inducers, Topo; immune privilege factor, Proneu; TASP-V; anticancer vaccine, NIH; Pharmaprojects No. 6281; HAV peptide matrix, Adherex; calcitonin, oral, Biocon; analgesic, Nobex; PTH 1-34, Biocon; insulin, oral, Biocon-2; BLS-0597; leuprorelin, Depocore; IDPS; AIDS vaccine, Hollis-Eden; insulin, NovaDel; insulin, Orasome; Pharmaprojects No. 6310; TRP-2. NIH; Pharmaprojects No. 6320; Re-188 P2045; calcitonin, Inovio; golotimod; angiotensin-II, topical, Trine; ETRX-101; antiallergy vaccine, Acambis-2; Tc-99m-P424; Tc-99m-P1666; insulin, Transfersome; Yissum Project No. 11649; SP(V5.2)C; melanoma vaccine, Therion-2; insulin Aspart, biphasic, Novo; Tat peptide analogues, NIH; Pharmaprojects No. 6365; Pharmaprojects No. 6373; Ramot project No. 981; ESP-24218; Pharmaprojects No. 6395; calcitonin, oral, Emisphere; omiganan, topical; AIDS vaccine, United-3; leuprorelin, Archimedes; HPV16 E6+E7 vaccine, NIH; peptide vaccine, NCI; *Chlamydia* vaccines, Argonex; delmitide acetate; RSV vaccine, Pierre Fabre-2; F-50040; CPI-1500; AIDS vaccine, BioQuest; insulin, BioSante, inhaled; antiangiogenics, GPC; TNF degradation product, Oncot; insulin, Emisphere; ozarelix; bremelanotide; *Pseudomonas* vaccine, Millenium; AIDS vaccine, CIBG; AIDS vaccine, Wyeth Vaccines-3; HCV serine protease inhib, BI; insulin, Wockhardt; cat PAD, Circassia; NOV-002; PPI-3088; insulin 24 hr, Altea; AP-811; hNLP, Pharis; ANUP-1, Pharis; serine protease inhibs, Pharis; Pharmaprojects No. 6523; respiratory mucus inhibitor, Em; CLX-0100; AIDS vaccine, Panacos; SPHERE peptide vaccine, Genzyme; P-16 peptide, Transition; EP-51389; insulin, ProMaxx; ET-642; P-50 peptide, Transition Ther; Famoxin; insulin, Alkermes, inhaled; GPCR peptide ligand, Synaptic; DiaPep227; alpha-1-antitrypsin, Cortech; IC-41; tuberculosis vaccine, Intercell; immunosuppressant vaccine, Aixl; malaria vaccine, NYU-2; netupitant; AG-702; insulin, AeroDose; anti-inflammatory, TapImmune; insulin glulisine; GPG-NH2; hepatitis-B therapy, Tripep; *Staphylococcus* therapy, Tripep; angiogenesis inhibitor, Tripep; bone marrow inhibitor, Tripep; melanoma vaccine, Biovector; lipopeptides, Cubist; ABT-510; parathyroid analogue, Unigene; Adageon-E; A-443654; CJC-1131; FE200 665; insulin, TranXenoGen; Gilatide; TFPI, EntreMed; desmopressin, Unigene; leuprorelin, oral, Unigene; antimicrobials, Isogenica; insulin, oral, Unigene; metastin; TRI-1144; DBI-4022; HM-9239; insulin, Bentley, intranasal; F-992; ZP-10; E1-INT; DEBIO-0513; spinal cord injury vacc, Weizm; DAC:GLP-2; uPAR inhibitors, Message; MBP-8298; PL-14736; anaritide peptides, BTG; SP-1000, Samaritan; leuprorelin, Ardana; melanocyte modulators, IsoTis; HF-1020; leucocyte immobilizing peptide; Dentonin; MET-1000; SGS-111; 5-Helix; HPV vaccine, Ludwig; caries vaccine, Forsyth; taltobulin; ATN-161; T05; LY-307161; *S. pneumoniae* vaccine, Milleniu; Alphastatin; anticancer peptides, Wockhardt; PGN-0052; INNO-201; leuprolide, Nektar; insulin, BioSante, oral; ADD-9903; viral vaccines, Bio-Virus; AOD-9604; calcitonin, oral, Pfizer; insulin, INJEX; ETD-XXXX; analgesic, Sigyn; anti-infectives, AM-Pharma; human AMPs, AM-Pharma; INGAP peptide; osteomyelitis peptides, AM-Phar; XOMA-629; XMP-293 derivatives; BlockAide/VP; EradicAide; BlockAide/CR; VAC-12; leuprolide, oral, DOR BioPharm; synthetic erythropoiesis pro; β-amyloid vaccine, Intellect; CEL-1000; sincalide; PankoPep; albiglutide; insulin, Bharat; leuprorelin, Norwood; Reversin 121, Solvo; SB-144; SB-29, STiL; cancer vaccine, Sedac; SDT-021; malaria vaccine, Sedac, ther; malaria vaccine, Seda, prophyl; hepatitis-C cellular ther, Seda; Factor XIIIa inhib, Curacyte; insulin, Micronix; AIDS vaccine, Antigen Express-1; exenatide LAR; AIDS vaccine, Bionor Immuno-1; GV-1002; GV-1001; MSI vaccine, GemVax; PEP-14; PV-267; antibacterials, Provid; hepatitis-B vaccine, Innovata; BA-058; BIM-51077; malaria vaccine, Immunogenics; TM-701; VG-104; AC-162352; antivirals, Genencor; leuprolide acetate, Voyager; calcitonin, nasal, Archimedes; insulin, nasal, West; calcitonin, oral, Unigene; calcitonin, nasal, Unigene; IMX-735; IMX-775; PPI-01; anti-IgE peptide, Allergy Ther; BZK-111; TH-0318; Enkastim; antibiotics, Bayer; Cerebrolysin; colorectal cancer therapy, IDM; wound growth factor, NephRx; JPD-105; osteoporosis drugs, Ferring; PN-951; CZEN-002; ZP-120; pasireotide; HerVac; CTT; LLG peptide, CTT; Pharmaprojects No. 6779; meptides, Senexis; Q-8008; FX-06; PhG-alpha-1; insulin, oral, Biocon; PP-0102; GTP-010; PAR-2 antagonists, EntreMed; parathyroid analogue, Zelos; K-1020; CTCE-9908; CTCE-0214; urocortin-II, Neurocrine; telomerase vaccine, Dendreon; AKL-0707; PYY3-36, Nastech; prostate cancer vaccine, Pepsca; AEZS-130; LYN-001; CUV-1647; AL-108; AL-309; HNTP-15; BIM-28131; CSF-G agonists, Affymax; IL-5 antagonists, Affymax; TRAIL agonists, Affymax; IgE inhibitors, Affymax; TM-801; TM-901; BN-054; APTA-01; HB-107; AVE cancer vaccine; PxSR; STD peptides, Helix; CF anti-infectives, Helix; HB-50; Homspera; S-0373; PYY3-36, oral, Emisphere; XG-101; XG-201CS; XG-102; insulin, oral, Coremed; Alzheimer's vaccine, Prana; AIDS vaccine, Bionor Immuno; leuprolide acetate, ALZAmer; AUX-202; AR-H044178; PYY3-36, Thiakis; lanreotide SR; malaria vaccine, Pevion; Alzheimer's vaccine, Pevion; melanoma vaccine, Antigen Expr; melanoma vaccine, Pevion; OGP-(10-14)-L; ABS-13; ABS-17; cancer therapeutics, Argolyn; substance P-saporin; diabetes therapeutic, Thera; CGX-1051; OTS-102; Xen-2174; insulin, inhaled, Coremed; WP9QY; osteoporosis treatment, Fulcr; AHNP, Fulcrum; insulin, Technosphere, Mannkind; FX-07; CBP-501; E7 vaccine, Neovacs; LSI-518P; aviptadil, Mondobiotech; anticancer peptide, OrthoLogic; AL-209; OP-145; AT-001; AT-008; CHP-105; AMEP, BioAlliance; cardiovascular ther, Argolyn; TEIPP-03; mental retardation ther, Argol; IMX-002; IMX-942; NLC-001; octreotide, Indevus; DRF-7295; opioid peptide derivatives, Ka; CDX-110; ALT-212; desmopressin, Orexo; IMA-901; obinepitide; TM-30335; HIV therapy, OyaGen-1; calcitonin, oral, ThioMatrix; insulin, oral, ThioMatrix; BRX-00585; Insulin Aspart, biphasic-2, No; CG-55069-11; GLP-1, Emisphere; linaclotide acetate; NPT-002; terlipressin, Orphan Therapeut; ZT-153; SciClone; FGLL; Syn-1002; MIP-160; PI-2301; PI-3101; BDM-E; insulin, Medtronic; ST-03; TH-0312; hepatitis-C vaccines, Kochi; cetrorelix acetate, once-weekly; RPI-MN; neurodegenerative ther, Recepto; RPI-78M; β-amyloid inhibitor, Alzhyme; DMI-3798; DMI-4983; ruzam; CT-319; EN-122004; glyponectin; EN-122001; EN-122002; KAI-9803; insulin, Advancell; larazotide acetate; calcitonin, oral, Bone Medical; parathyroid hormone, Bone Medi; calcitonin, Merrion; desmopressin, Merrion; acyline, Merrion; IMX-503; AP-214; *Streptococcus* vaccine, Vaccine; cytomegalovirus vaccine, Vacc; RHS-08; AG-707; antiallergics, Phylogica; PYC-36S; anticancers, Phylogica; Glypromate; NNZ-4945; calcitonin, intranasal, ITI; Peptide T, Advanced Immuni T; APTA-02; CGRP, Akela; TKS-1225; GalR2 peptide agonist, NeuroTa; botulinum vaccine, Emergent; HIV fusion inhibitors, Sequoia; AL-208; APP-018; BKT-RP3; smallpox vaccine, Antigen Expr; CMLVAX-100; INNO-105; insulin, Intravail; leptin, Intravail; calcitonin, Intravail; somatropin, Intravail; heparin, Intravail; erythropoietin, Intravail; CT-201; telomerase variants, GemVax; INT, transplantation; INT-3; SPI-1620; BIO-037; anticancers, Bracco; BIO-023; ZT-100; MC-4R agonists, Lilly; LT-1951; PTH (1-34), IGI; CGRP, VasoGenix; BIO-145; BIO-142; stem cell factor, Affymax; VEGFR-2 antagonist, Affymax; KGF receptor agonist, Affymax; YM-216391; AT-007; AT-011; EK2700; EK900-1800; EK900-12; FGLm; ABS-201; Mdbt-12; autoimmune therapy, Antigen; VX-001; IPP-102199; IPP-201101; CTA1-DD; Factor VIIa inhibitor, ProTher; antiangiogenic, ProTherapeutic; IMT-1012; colon cancer vaccine, Immunoto; prohanin, ProTherapeutics; smallpox vaccine, BioDefense; heart failure therapy, ElaCor; PA-401; 802-2; insulin, nasal, Nastech; SEN-304; IMA-920; IMA-940; IMA-910; influenza vaccine, Antigen, H5N1; Primacoll; octreotide, PR Pharmaceuticals; female infertility th, Vyteris; FAR-404; athlete's foot therapy, Helix; leishmaniasis ther, Helix; INNO-305; ALS-02; sNN-0465; NN-5401; TRI-999; Org-214444; Org-33409; IMA-930; YH-APC; PYC-35B; Rev-D4F; insulin, Phosphagenics; coeliac disease ther, Nexpep; coeliac disease therapy, BTG; exendin-4, PC-DAC; exenatide, nasal spray; CAP-232; ACE-011; Cardeva; BL-3020; FM-TP-2000; GGTI-2418; TM-30339; DP-74; DP-68; PPH ther, GeoPharma; MPL-TLB100; AZX-100; Alloferon; S2; S3; S4; PAC-G31P; PAC-745; PAC-525; PAC-113; VEBv; lipopeptide, Combinature; mondopeptide-1; mondopeptide-2; mondopeptide-2+mondopeptide-3; mondopeptide-4; MLIF; carfilzomib; Affitope AD-01; LT-ZP001; LT-ZMP001; CGX-1204; C3d, Enkam; C5a antagonist, Eucodis; adenocarcinoma vacc, ImmvaRx; insulin, oral, Apollo; renin inhibitors, Servier; Factor VIIa, GTC; ABS-212; NAFB001; NAFB002; insulin, MediVas; ZT-181; anti-inflammatory, Forbes; labour inhibitor, Theratechnolo; glaucoma therapy, Theratechnolo; AG-EM-0040; MS therapy, AplaGen; interleukin-2 mimetic, AplaGen; CNS therapy, AplaGen; Mesd-based peptides, Raptor; paratohormone, Sidus; asthma therapy, Synairgen; dekafin-1; anticancer vaccine, Ulm; BT-15; cancer imaging agent, Speci; cardiovascular imaging, Speci; E-75; Prothyx;

anticancer, Prothyx, Stealthyx; IL12-NGR; allergy vaccine, China Bio; amylin mimetic, 2nd-gen, Amylin; influenza vaccines, Variation; VLP-0012M; PLT-101; AL-408; anticancers, Aileron; antivirals, Ambrx; hSPN-16; HDL, Cerenis; enterostatin; BSc-2118; SB-006; antimicrobials, Spider Biotech; peptide therapy, Angioblast; octreotide, Ambrilia; GAP-134; Alzheimer's therapy, Il Dong; BL-4020; von Willebrand factor, Baxter; IL-1aQb; POT-4; gamma-secretase inhibitors, BMS; ISCOMATRIX; enfuvirtide, needle-free; connexin modulators, NeuroSol; BT-25; BT-20; Amp-Tide; HepTide; antimicrobial peptides, Helix; NPY2 agonists, Bayer; ragweed PAD, Circassia; dust mite PAD, Circassia; grass PAD, Circassia; transplant rejection PAD; insulin, oral, Oramed; cardiac ischaemia therapy, Phy; PYC-18; antidiabetics, Phylogica; PEP-35; ACE-041; ACE-031; ovarian cancer vaccine, Generex; ATX-MS-1467; iATX FVIII; diabetes vaccine, Apitope; allergy vaccine, Apitope; FX-06 analogue; PR-22G; PR-21, Pharmaxon; LT-1945; LT-1942; XG-414; XG-517; AC-163794; MDPTQ; B27PD; AC-2307; sedatives, ProTherapeutics; L-Type Ca channel blocker, Pro; phospholipase A2 inhibitor, Pro; PGL-3001; PGL-1001; influenza vaccine, Variation-2; Homspera nanoparticle, Immune; CVX-096; COR-1; survivin-2B; imMucin; GLP-1, PharmaN; atherosclerosis vaccine, Affir; adeptide; somatostatin antagonists, Preg; Casimax; CD-NP, Nile; PRX-111; ACT1-C; PRX-102; ACT1-G; AIDS vaccine, ITS; influenza vaccine, ITS; hepatitis-C vaccine, ITS; ALTY-0601; BGLP-40; somatropin, INB; trypansomal vaccine, INB; RU-COH, Pantarhei; LH-COH, Pantarhei; GLP-1 analogues, Unigene; Polyfensin; VIR-576; Xen-0568; Xen-0495; Xen-0468; LEKTI-6; leukaemia vaccine, MD Anderson; Met receptor agonists, MRCT; insulin HDV, short-acting, Dia; glucagon antagonists, CoGene; GLP-1 agonists, CoGenesys; insulin HDV, oral, Diasome; insulin HDV, long-acting, Dia; glucagon, Particle Therapeutics; GLP-1, Mannkind; insulin, next-generation, Flamel; Ostabolin-C, topical; DAC:HIV; antiviral, HepTide; Insulin Aspart, biphasic-3, No; Innotide; influenza vaccine, Bionor; HPV vaccine, Bionor Immuno; hepatitis-C vaccine, Bionor; Affitope AD-02; Affitope AD-03; RHS-02; RHS-03; insulin, Access; inherbins, Enkam; Dekafin-2; BL-4050; ALS vaccine, Amorfix; cancer vaccine, Canopus; relaxin, Corthera; rhNRG-1; rhErbB3-f; hepatitis-C vacc, Green Cross-3; androgen receptor antag, CRT; GLP-1 analogue CR, OctoPlus; AIDS vaccine, Sanofi Past-12; insulin, Diabetology; Combulin; AIDS vaccine, Sanofi Past-11; AnergiX.MG; AnergiX.MS; insulin, CritiTech; YP-20; NDR/NCE-18; CLT-002; CLT-007; CLT-008, Charlesson; CLT-009; PYC-38; AIM-101; AIM-102; AIM-501; APL-180; metabolic disease therapy, Xen; NP-213; NP-339; antimicrobial peptides, NovaB; lung anti-infectives, NovaBiot; c-peptide analogue, Diabetology; CGEN-855; NN-1250; NN-9535; insulin, rectal, Oramed; insulin, 12 hr, Altea; pancreatic cancer vaccine, Onco; SB-101; L-glutamine, Emmaus; glucagon antagonists, Kisspeptin-54; Kisspeptin-14; Kisspeptin-13; Kisspeptin-10; Ziconotide; Biphalin; Nesiritide; Protegrin-1; Protegrin-2; Protegrin-3; Protegrin-4; Protegrin-5; Preprotegrin; V681; V681 (V13A$_D$); GLP-2; GLP-2 (A2G); GLP-2 (A2G/C34); AOD-9604; Ac-AOD-9604(S8K); Ac-AOD-9604(K17); C-peptide; CR845; and Marcadia.

In certain embodiments of the invention, PEP is a therapeutic peptide selected from the therapeutic peptides listed in Table 1.

TABLE 1

This table lists the SEQ ID NOs., names, sequences, and known or suspected therapeutic activities of various peptides described herein. The SEQ ID NOs. 1-301 describe sequences that are required to be provided with the Sequence Listing and are therefore appended with the instant Specification. In some instances, these peptides contain features that are either inconsistent with or not amenable to inclusion in the Sequence Listing. For example, a sequence with less than four-amino acids; a sequence with a D-amino acid; or certain modification that cannot be described in the Sequence Listing presently, and therefore are not provided in the Sequence Listing. However, for the ease of use and description, a SEQ ID NO. has been provided to these peptides (i.e., SEQ ID NOs: 302-469).

| SEQ ID NO: | Name | Family | Sequence and/or other Identifying Information | Therapeutic Activity |
|---|---|---|---|---|
| 1 | carperitide | ANP | SLRRSSCFGGRMDRIGAQSGLGCNSFRY; human alpha-atrial natriuretic peptide; Atriopeptin-28 (human); | Cardiostimulant Respiratory |
| 2 | alpha-neoendorphin | Endorphin | H-Tyr-Gly-Gly-Phe-Leu-Arg-Lys-Tyr-Pro-Lys-OH | Analgesic, other |
| 3 | A-3847 | Insulin | gi\|386828\|gb\|AAA59172.1\| insulin [*Homo sapiens*] MALWMRLLPLLALLALWGPDPAAAFVNQHLCGSHL VEALYLVCGERGFFYTPKTRREAEDLQVGQVELGGG PGAGSLQPLALEGSLQKRGIVEQCCTSICSLYQLENYCN | Antidiabetic |
| 4 | A-4114 | Insulin | MALWMRLLPLLALLALWGPDPAAAFVNQHLCGSHL VEALYLVCGERGFFYTPKTRREAEDLQVGQVELGG | Antidiabetic |
| 5 | A-68552 | | GPGAGSLQPLALEGSLQKRGIVEQCCTSICSLYQLENYCN | Anorectic/Antiobesity |
| 302 and 303 | A-75998 | | [Ac-D-Nal1-D-4ClPhe2-D-3Pal3-NMeTyr5-D-Lys(Nic)6-Lys(Isp)8-D-Ala10]GnRH; N-acetyl-D-2-naphthylalanyl-D-4-chlorophenylalanyl-D-3-pyridylalanyl-seryl-N-methyltyrosyl-D-N(epsilon)-nicotinyllysyl-leucyl-N(epsilon)-isopropyllysyl-prolyl-alaninamide acetate | Releasing hormone Reproductive/gonadal, general |
| 6 | AN-1792 | beta-amyloid peptide | gi\|8176533\|gb\|AAB26264.2\| beta-amyloid peptide precursor; beta APP [*Homo sapiens*] GSGLTNIKTEEISEVKMDAEFRHDSGYEVHHQKLVFF AEDVGSNKGAIIGLMVGGVVIATVIIITLVMLK KQYTSNHHGVVE | Cognition enhancer |
| 7 | AAMP-1 | | MESESESGAAADTPPLETLSFHGDEEIIEVVELDPGPPD PDDLAQEMEDVDFEEEEEEEGNEEGWVLEPQEGVVG SMEGPDDSEVTFALHSASVFCVSLDPKTNTLAVTGGE DDKAFVWRLSDGELLFECAGHKDSVTCAGFSHDSTL | Anticoagulant Anti-inflammatory Immunological Anticancer, other |

TABLE 1-continued

This table lists the SEQ ID NOs., names, sequences, and known or suspected therapeutic activities of various peptides described herein. The SEQ ID NOs. 1-301 describe sequences that are required to be provided with the Sequence Listing and are therefore appended with the instant Specification. In some instances, these peptides contain features that are either inconsistent with or not amenable to inclusion in the Sequence Listing. For example, a sequence with less than four-amino acids; a sequence with a D-amino acid; or certain modification that cannot be described in the Sequence Listing presently, and therefore are not provided in the Sequence Listing. However, for the ease of use and description, a SEQ ID NO. has been provided to these peptides (i.e., SEQ ID NOs: 302-469).

| SEQ ID NO: | Name | Family | Sequence and/or other Identifying Information | Therapeutic Activity |
|---|---|---|---|---|
| | | | VATGDMSGLLKVWQVDTKEEVWSFEAGDLEWMEW HPRAPVLLAGTADGNTWMWKVPNGDCKTFQGPNCP ATCGRVLPDGKRAVVGYEDGTIRIWDLKQGSPIHVLK GTEGHQGPLTCVAANQDGSLILTGSVDCQAKLVSATT GKVVGVFRPETVASQPSLGEGEESESNSVESLGFCSV MPLAAVGYLDGTLAIYDLATQTLRHQCQHQSGIVQLL WEAGTAVVYTC SLDGIVRLWDARTGRLLTDYRGHTA EILDFALSKDASLVVTTSGDHKAKVFCVQRPDR | Vulnerary |
| 8 | Exenatide | GLP-1 | HGEGTFTSDLSKQMEEEAVRLFIEWLKNGGPSSGAPP PS | Antidiabetic Anorectic/Antiobesity |
| 9 | AC-625 | | Acetyl-ATQRLANELVRLQTYPRTNVGSNTY-NH$_2$ | Antihypertensive, renin system Symptomatic antidiabetic |
| 10 | ACTH | | gi|80861463|ref|NP_001030333.1| proopiomelanocortin preproprotein [Homo sapiens] MPRSCCSRSGALLLALLLQASMEVRGWCLESSQCQD LTTESNLLECIRACKPDLSAETPMFPGNGDEQPLTENP RKYVMGHFRWDRFGRRNSSSSGSSGAGQKREDVSAG EDCGPLPEGGPEPRSDGAKPGPREGKRSYSMEHFRWG KPVGKKRRPVKVYPNGAEDESAEAFPLEFKRELTGQR LREGDGPDGPADDGAGAQADLEHSLLVAAEKKDEGP YRMEHFRWGSPPKDKRYGGFMTSEKSQTPLVTLFKN AIIKNAYKKGE | Adrenal and pituitary disorders |
| 11 | AIDS therapeutic vaccine | | gi|288842|emb|CAA78890.1| V3 loop [Human immunodeficiency virus type 1] CTRPSNNTRKSIPVGPGKALYATGAIIGNIRQAHC | Therapeutic vaccine |
| 12 | AIDS therapy | | gi|5081475|0AAD39400.1|AF128998_1 gag [Human immunodeficiency virus type 1] MGARASVLSGGKLDKWEKIRLRPGGKKTYQLKHIVW ASRELERFAVNPGLLETGGGCKQILVQLQPSLQTGSEE LKSLYNAVATLYCVHQGIEVRDTKEALDKIEEEQNKS KKKAQQAAADTGNSSQVSQNYPIVQNLQGQMVHQAI SPRTLNAWVKVIEEKAFSPEVIPMFSALSEGATPQDLN TMLNTVGGHQAAMQMLKETINEEAAEWDRLHPAHA GPNAPGQMREPRGSDIAGTTSTLQEQIGWMTSNPPVP VGEIYKRWIILGLNKIVRMYSPVSILDIRQGPKEPFRDY VDRFYKTLRAEQASQDVKNWMTETLLVQNANPDCK TILKALGPAATLEEMMTACQGVGGPSHKARILAEAMS QVTSPANIMMQRGNFRNQRKTIKCFNCGKEGHLARH CRAPRKKGCWKCGREGHQMKDCTERQANFLGKIWP SHKGRPGNFLQSRPEPTAPPEESFRFGEETTTPPQKQEP LPSQKQETIDKDLYPLASLKSLFGNDPSLQ | Antiviral, anti-HIV |
| 13 and 14 | Allotrap-2702 | | Allotrap 1258; Allotrap 2702; Allotrap E; Allotrap G; RDP58; peptide Bc-1nl; NLRIALR/RLAIRLN | Immunosuppressant |
| 15 and 16 | Alzheimer's imaging agent | | H-DAEFRHDSGYEVHHQKLVFFAEDVGSNKGAIIGLMV GGVV-OH; or H-DAEFRHDSGYEVHHQKLVFFAEDVGSNKGAIIGLMV GGVVIA-OH | Imaging agent |
| 17 | AM-425 | | gi|4504991|ref|NP_002300.1| leukemia inhibitory factor (cholinergic differentiation factor) [Homo sapiens] MKVLAAGVVPLLLVLHWKHGAGSPLPITPVNATCAIR HPCHNNLMNQIRSQLAQLNGSANALFILYYTAQGEPF PNNLDKLCGPNVTDFPPFHANGTEKAKLVELYRIVVY LGTSLGNITRDQKILNPSALSHSKLNATADILRGLLSN VLCRLCSKYHVGHVDVTYGPDTSGKDVFQKKKLGCQ LLGKYKQIIAVLAQAF | Antiarthritic, immunological |
| 304 | AN-238 | | L-Threoninamide, N-[5-[2-[(2S,4S)-1,2,3,4,6,11-hexahydro-2,5,12-trihydroxy-7-methoxy-6,11-dioxo-4-[[2,3,6-trideoxy-3-(2,3-dihydro-1H-pyrrol-1-yl)-alpha-L-lyxo-hexopyranosyl]oxy]-2-naphthacenyl]-2-oxoethoxy]-1,5-dioxopentyl]-D-phenylalanyl-L-cysteinyl-L-tyrosyl-D-tryptophyl-L-lysyl-L-valyl-L-cysteinyl-, cyclic (2-7)-disulfide | Somatostatin Anticancer, hormonal |
| 305 | AV-9 | | [D-Arg]9-NH2 | Antiviral, other |
| 8 | AZM-134 | GLP-1 | HGEGTFTSDLSKQMEEEAVRLFIEWLKNGGPSSGAPP PS | Anorectic/Antiobesity Antidiabetic |

TABLE 1-continued

This table lists the SEQ ID NOs., names, sequences, and known or suspected therapeutic activities of various peptides described herein. The SEQ ID NOs. 1-301 describe sequences that are required to be provided with the Sequence Listing and are therefore appended with the instant Specification. In some instances, these peptides contain features that are either inconsistent with or not amenable to inclusion in the Sequence Listing. For example, a sequence with less than four-amino acids; a sequence with a D-amino acid; or certain modification that cannot be described in the Sequence Listing presently, and therefore are not provided in the Sequence Listing. However, for the ease of use and description, a SEQ ID NO. has been provided to these peptides (i.e., SEQ ID NOs: 302-469).

| SEQ ID NO: | Name | Family | Sequence and/or other Identifying Information | Therapeutic Activity |
| --- | --- | --- | --- | --- |
| 18 | Addressin | | gi\|109633022\|ref\|NP_570116.2\| mucosal vascular addressin cell adhesion molecule 1 isoform a precursor [*Homo sapiens*]<br>MDFGLALLLAGLLGLLLGQSLQVKPLQVEPPEPVVAV ALGASRQLTCRLACADRGASVQWRGLDTSLGAVQSD TGRSVLTVRNASLSAAGTRVCVGSCGGRTFQHTVQLL VYAFPDQLTVSPAALVPGDPEVACTAHKVTPVDPNAL SFSLLVGGQELEGAQALGPEVQEEEEEPQGDEDVLFR VTERWRLPPLGTPVPPALYCQATMRLPGLELSHRQAI PVLHSPTSPEPPDTTSPESPDTTSPESPDTTSQEPPDTTS PEPPDKTSPEPAPQQGSTHTPRSPGSTRTRRPEISQAGP TQGEVIPTGSSKPAGDQLPAALWTSSAVLGLLLLALPT YHLWKRCRHLAEDDTHPPASLRLLPQVSAWAGLRGT GQVGISPS | Recombinant, other<br>Anti-inflammatory |
| 306 | ambamustine | | L-Methionine, N-[3-[bis(2-chloroethyl)amino]-N-(4-fluoro-L-phenylalanyl]-L-phenylalanyl]-, ethyl ester | Anticancer, alkylating<br>Anticancer, antimetabolite |
| 19 | amylin antagonists | | DTTVSEPAPSCVTLYQSWRYSQADNGCAETVTVKVV YEDDTEGLCYAVAPGQITTVGDGYIGSHGHARYLAR CL | Antidiabetic |
| 20 | anaritide analogues | ANP | gi\|178638\|gb\|AAA35529.1\| atrial natriuretic peptide<br>MSSFSTTTVSFLLLLAFQLLGQTRANPMYNAVSNADL MDFKNLLDHLEEKMPLEDEVVPPQVLSDPNEEAGAA LSPLPEVPPWTGEVSPAQRDGGALGRGPWDSSDRSAL LKSKLRALLTAPRSLRRSSCFGGRMDRIGAQSGLGCN SFRY | Antihypertensive, diuretic |
| 21-28 | anti-inflammatory peptide | | As disclosed in U.S. Pat. No. 5,470,831:<br>Thr-Thr-Ser-Gln-Val-Arg-Pro-Arg<br>Val-Lys-Thr-Thr-Ser-Gln-Val-Arg-Pro-Arg.<br>Ser-Gln-Val-Arg-Pro-Arg<br>Val-Arg-Pro-Arg<br>Thr-Thr-Ser-Gln-Val-Arg-Pro-Arg-His-Ile-Thr.<br>Thr-Thr-Ser-Gln-Val<br>Thr-Ser-Gln-Val-Arg<br>Thr-Thr-Ser-Gly-Ile-His-Pro-Lys | Anti-inflammatory<br>Immunosuppressant<br>Multiple sclerosis treatment<br>Antiarthritic, other<br>Stomatological<br>Dermatological |
| 307 | antiflammins | | L-Leucine, N-[N-[N-[N-[N2-[N2-[N-(N-L-histidyl-L-alpha-aspartyl)-L-methionyl]-L-asparaginy]-L-lysyl]-L-valyl]-L-leucyl]-L-alpha-aspartyl]- | Anti-inflammatory |
| 308 | antifungal tripeptides | | tripeptides of N3-4-methoxyfumanyl<br>and di- and tripeptides of N3-D-trans 2,3-epoxysuccinamoyl-L-2,3-diaminopropanoic acid | Antifungal |
| 29 | Gastrimmune | | G17-DT; G17DT (vaccine); Gastrimmune; Glu-Gly-Pro-Trp-Leu-Glu-Glu-Glu-Glu -diphtheria toxoid; anti-gastrin 17 immunogen; gastrin 17 vaccine; gastrin-17-diphtheria toxoid conjugate | Anticancer, immunological |
| 30 | antithrombin polypeptides | | gi\|312673\|emb\|CAA51292.1\| Hirudin [*Hirudinaria manillensis*]<br>MFSLKLFVVFLAVCICVSQAVSYTDCTESGQNYCLCV GGNLCGGGKHCEMDGSGNKCVDGEGTPKPKSQT EGDFEEIPDEDILN | Antithrombotic<br>Anticoagulant |
| 31 | antiviral peptides | | NH2-Tyr-Ala-Gly-Ala-Val-Val-Asn-Asp-Leu-COOH | Antiviral, other |
| 32 | apolipoprotein | | gi\|671882\|emb\|CAA28583.1\| apolipoprotein [*Homo sapiens*]<br>MKLLAATVLLLTICSLEGALVRRQAKEPCVESLVSQY FQTVTDYGKDLMEKVKSPELQAEAKSYFEKSKE QLTPLIKKAGTELVNFLSYFVELGTHPATQ | Hypolipaemic/Antiatheroscle rosis |
| 33 | arthritis antigen | | gi\|46369603\|gb\|AAS89650.1\| secreted antigen 85A precursor [*Mycobacterium bovis* BCG]<br>MQLVDRVRGAVTGMSRRLVVGAVGAALVSGLVGAV GGTATAGAFSRPGLPVEYLQVPSPSMGRDIKVQFQSG GANSPALYLLDGLRAQDDFSGWDINTPAFEWYDQSG LSVVMPVGGQSSFYSDWYQPACGKAGCQTYKWETF LTSELPGWLQANRHVKPTGSAVVGLSMAASSALTLAI YHPQQFVYAGAMSGLLDPSQAMGPTLIGLAMGDAGG YKASDMWGPKEDPAWQRNDPLLNVGKLIANNTRVW VYCGNGKPSDLGGNNLPAKFLEGFVRTSNIKFQDAYN AGGGHNGVFDFPDSGTHSWEYWGAQLNAMKPDLQR ALGATPNTGPAPQGA | Recombinant, other<br>Antiarthritic, immunological<br>Immunosuppressant |
| 309 | Avorelin | | 5-Oxo-L-prolyl-L-histidyl-L-tryptophyl-L-seryl-L-tyrosyl-2-methyl-D-tryptophyl-L-leucyl-L-arginyl-N-ethyl-L-prolinamide | Releasing hormone<br>Anticancer, hormonal<br>Menstruation disorders |

TABLE 1-continued

This table lists the SEQ ID NOs., names, sequences, and known or suspected therapeutic activities of various peptides described herein. The SEQ ID NOs. 1-301 describe sequences that are required to be provided with the Sequence Listing and are therefore appended with the instant Specification. In some instances, these peptides contain features that are either inconsistent with or not amenable to inclusion in the Sequence Listing. For example, a sequence with less than four-amino acids; a sequence with a D-amino acid; or certain modification that cannot be described in the Sequence Listing presently, and therefore are not provided in the Sequence Listing. However, for the ease of use and description, a SEQ ID NO. has been provided to these peptides (i.e., SEQ ID NOs: 302-469).

| SEQ ID NO: | Name | Family | Sequence and/or other Identifying Information | Therapeutic Activity |
|---|---|---|---|---|
| 310 | B-956 | | N-[8(R)-Amino-2(S)-benzyl-5(S)-isopropyl-9-sulfanyl-3(Z),6(E)-nonadienoyl]-L-methionine | Anticancer, other |
| 311 | BCH-2687 | | L-Tyrosyl-D-arginyl-L-phenylalanyl-L-phenylalaninamide | Analgesic, other |
| 34 | BCH-2763 | | L-Leucine, D-phenylalanyl-L-prolyl-5-aminopentanoyl-5-aminopentanoyl-L-alpha-aspartyl-L-phenylalanyl-L-alpha-glutamyl-L-prolyl-L-isoleucyl-L-prolyl-; BCH-2763; Phe-Pro-(NH(CH$_2$)$_4$CO)$_2$-Asp-Phe-Glu-Pro-Ile-Pro-Leu; phenylalanyl-prolyl-(NH(CH$_2$)$_4$CO)$_2$-aspartyl-phenylalanyl-glutamyl-prolyl-isoleucyl-prolyl-leucine | Antithrombotic Anticoagulant |
| 312 | frakefamide | | L-phenylalaninamide, L-tyrosyl-D-alanyl-4-fluoro-L-phenylalanyl- | Analgesic, other |
| 313 | BIM-22015 | | Glycinamide, D-alanyl-L-glutaminyl-L-tyrosyl-L-phenylalanyl-L-arginyl-L-tryptophyl- | ACTH Neurological |
| 35 | BIM-26028 | | Pyroglutamyl-glutaminyl-arginyl-leucyl-glycyl-asparaginyl-glutaminyl-tryptyl-alanyl-valyl-glycyl-histidinyl-leucyl-leucyl-NH$_2$ | Releasing hormone Respiratory Anorectic/Antiobesity Anticancer, hormonal |
| 314 | BIM-44002 | | L-Tyrosinamide, L-phenylalanyl-L-norleucyl-L-histidyl-L-asparaginyl-L-leucyl-D-tryptophyl-L-lysyl-L-histidyl-L-leucyl-L-seryl-L-seryl-L-norleucyl-L-alpha-glutamyl-L-arginyl-L-valyl-L-.alpha.-glutamyl-L-tryptophyl-L-leucyl-L-arginyl-L-lysyl-L-lysyl-L-leucyl-L-glutaminyl-L-alpha-aspartyl-L-valyl-L-histidyl-L-asparaginyl- | Hormone Osteoporosis treatment |
| 36 | BIO-1211 | | L-Proline, N-((4-((((2-methylphenyl)aminocarbonyl)amino)phenyl)acetyl)-L-leucyl-L-alpha-aspartyl-L-valyl-; BIO-1211; N-((4-((((2-methylphenyl)amino)carbonyl)amino)phenyl)acetyl)-leucyl-aspartyl-valyl-proline | Antiasthma GI inflammatory/bowel disorders Multiple sclerosis treatment |
| 37 | BPC-15 | | BPC 15; BPC-15; BPC-157; booly protection compound 15; L-Valine, glycyl-L-alpha-glutamyl-L-prolyl-L-prolyl-L-prolylglycyl-L-lysyl-L-prolyl-L-alanyl-L-alpha-aspartyl-L-alpha-aspartyl-L-alanylglycyl-L-leucyl- | Anti-inflammatory |
| 315 | bivalirudin | | L-Leucine, D-phenylalanyl-L-prolyl-L-arginyl-L-prolylglycylglycylglycylglycylglycyl-L-asparaginylglycl-L-alpha-aspartyl-L-phenylalanyl-L-alpha-glutamyl-L-alpha-glutamyl-L-isoleucyl-L-prolyl-L-alpha-glutamyl-L-tyrosyl-; D-phenylalanyl-L-prolyl-L-arginyl-L-prolyl-glycylglycyl-glycyl-glycyl-L-asparagyl-glycyl-L-aspartyl-L-phenylalanyl-L-glutamyl-L-glutamyl-L-isoleucyl-Lprolyl-L-glutamyl-L-glutamyl-L-tyrosyl-L-leucine trifluoroacetate (salt) hydrate | Anticoagulant Antianginal |
| 38 | bombesin antagonist | | 5-oxoPro-Gln-Arg-Leu-Gly-Asn-Gln-Trp-Ala-Val-Gly-His-Leu-MetNH$_2$ [CAS], Bombesin 14; Bombesin Dihydrochloride; Dihydrochloride, Bombesin | Anticancer, other |
| 39 | brain natriuretic peptide | BNP | SPKMVQGSGCFGRKMDRISSSSGLGCKVLRRH | COPD treatment, cardiac |
| 41 | C-peptide analogues | C-peptide | Glu-Ala-Glu-Asp-Leu-Gln-Val-Gly-Gln-Val-Glu-Leu-Gly-Gly-Gly-Pro-Gly-Ala-Gly-Ser-Leu-Gln-Pro-Leu-Ala-Leu-Glu-Gly-Ser-Leu-Gln | Symptomatic antidiabetic Ophthalmological Neurological |
| 316 | C5a antagonist | | Me-Phe-Lys-Pro-D-Cha-L-Cha-D-Phe | Anti-inflammatory |
| 42 | CBT-101 | | L-Cysteinamide, L-asparaginyl-L-leucylglycyl-L-valyl-S-[(acetylamino)methyl]-, monoacetate | Antiglaucoma |
| 43 | CCK(27-32) | | Tyr(SO$_3$)-Met-Gly-Trp-Met-Asp; CBZ-CCK (27-32)-NH$_2$; cholecystokinin (27-32) amide, benzoyloxycarbonyl-, D-Trp | Analgesic, obesity, other |
| 44 | CD4 | | CD4 (81-92), D-Ile; CD4 (81-92), D-Tyr; CD4 (81-92), D-Tyr,D-Cys,D-Glu(5); CD4(81-92); TYICEVEDQKEE; Thr-Tyr-Ile-Cys-Glu-Val-Glu-Asp-Gln-Lys-Glu-Glu; threonyl-tyrosyl-isoleucyl-cysteinyl-glutamyl-valyl-glutamyl-aspartyl-glutaminyl-lysyl-glutamyl-glutamic acid | Antiviral, anti-HIV |
| 317 | CEE-04-420 | | Lys-D-Pro-Thr and Lys-D-Pro-Val | Analgesic, other |
| 45 | CEP-079 | | gi|108796063|ref|NP_001007140.2| insulin-like growth factor 2 isoform 1 precursor [Homo sapiens] MGIPMGKSMLVLLTFLAFASCCIAAYRPSETLCGGEL VDTLQFVCGDRGFYFSRPASRVSRRSRGIVEEC CFRSCDLALLETYCATPAKSERDVSTPPTVLPDNFPRY PVGKFFQYDTWKQSTQRLRRGLPALLRARRGH VLAKELEAFREAKRHRPLIALPTQDPAHGGAPPEMAS NRK | Ophthalmological |

TABLE 1-continued

This table lists the SEQ ID NOs., names, sequences, and known or suspected therapeutic activities of various peptides described herein. The SEQ ID NOs. 1-301 describe sequences that are required to be provided with the Sequence Listing and are therefore appended with the instant Specification. In some instances, these peptides contain features that are either inconsistent with or not amenable to inclusion in the Sequence Listing. For example, a sequence with less than four-amino acids; a sequence with a D-amino acid; or certain modification that cannot be described in the Sequence Listing presently, and therefore are not provided in the Sequence Listing. However, for the ease of use and description, a SEQ ID NO. has been provided to these peptides (i.e., SEQ ID NOs: 302-469).

| SEQ ID NO: | Name | Family | Sequence and/or other Identifying Information | Therapeutic Activity |
|---|---|---|---|---|
| 318 | mifamurtide | | L-Alaninamide, N-(N-acetylmuramoyl)-L-alanyl-D-alpha-glutaminyl-N-[4-hydroxy-10-oxo-7-[(1-oxohexadecyl)oxy]-3,5,9-trioxa-4-phosphapentacos-1-yl]-, P-oxide, monosodium salt, (R)- | Anticancer, immunological |
| 46 | CGRP analogues | CGRP | ACDTATCVTHRLAGLLSRSGGVVKNNFVPTNVGSKAF-NH$_2$ | Hormone Cardiovascular |
| 47 | rusalatide acetate | | gi\|4503635\|ref\|NP_000497.1\| coagulation factor II preproprotein [*Homo sapiens*]<br>MAHVRGLQLPGCLALAALCSLVHSQHVFLAPQQARSLLQRVRRANTFLEEVRKGNLERECVEETCSYEEAFEALESSTATDVFWAKYTACETARTPRDKLAACLEGNCAEGLGTNYRGHVNITRSGIECQLWRSRYPHKPEINSTTHPGADLQENFCRNPDSSTTGPWCYTTDPTVRRQECSIPVCGQDQVTVAMTPRSEGSSVNLSPPLEQCVPDRGQQYQGRLAVTTHGLPCLAWASAQAKALSKHQDFNSAVQLVENFCRNPDGDEEGVWCYVAGKPGDFGYCDLNYCEEAVEEETGDGLDEDSDRAIEGRTATSEYQTFFNPRTFGSGEADCGLRPLFEKKSLEDKTERELLESYIDGRIVEGSDAEIGMSPWQVMLFRKSPQELLCGASLISDRWVLTAAHCLLYPPWDKNFTENDLLVRIGKHSRTRYERNIEKISMLEKIYIHPRYNWRENLDRDIALMKLKKPVAFSDYIHPVCLPDRETAASLLQAGYKGRVTGWGNLKETWTANVGKGQPSVLQVVNLPIVERPVCKDSTRIRITDNMFCAGYKPDEGKRGDACEGDSGGPFVMKSPFNNRWYQMGIVSWGEGCDRDGKYGFYTHVFRLKKWIQKVIDQFGE | Musculoskeletal Vulnerary Symptomatic antidiabetic Cardiovascular Anti-infective, other Ophthalmological |
| 48 | CKS-17 | | L-Leucine, L-leucyl-L-glutaminyl-L-asparaginyl-L-arginyl-L-arginylglycyl-L-leucyl-L-alpha-aspartyl-L-leucyl-L-leucyl-L-phenylalanyl-L-leucyl-L-lysyl-L-alpha-glutamylglycylglycyl-; CKS-17; CKS-17 peptide | Immunosuppressant Anticancer, immunological |
| 10 | corticorelin acetate | corticotropin | gi\|80861463\|ref\|NP_001030333.1\| proopiomelanocortin preproprotein [*Homo sapiens*]<br>MPRSCCSRSGALLLALLLQASMEVRGWCLESSQCQDLTTESNLLECIRACKPDLSAETPMFPGNGDEQPLTENPRKYVMGHFRWDRFGRRNSSSSGSSGAGQKREDVSAGEDCGPLPEGGPEPRSDGAKPGPREGKRSYSMEHFRWGKPVGKKRRPVKVYPNGAEDESAEAFPLEFKRELTGQRLREGDGPDGPADDGAGAQADLEHSLLVAAEKKDEGPYRMEHFRWGSPPKDKRYGGFMTSEKSQTPLVTLFKNAIIKNAYKKGE | Neuroprotective Antiasthma Anti-inflammatory |
| 49 | CT-112 | | L-Arginine, L-threonyl-L-threonyl-L-seryl-L-glutaminyl-L-valyl-L-arginyl-L-prolyl-; 5-(3-ethoxy-4-pentyloxyphenyl)-2,4-thiazolidinedione | Antiarthritic, immunological |
| 50 | CTAP-III | | phenylalanyl--cysteinyl--tyrosyl-tryptophyl-arginyl-threonyl-penicillaminyl-threoninamide; rCTAP-III-Leu-21 (des 1-15); somatostatin analog CTAP | Vulnerary Antiarthritic, other Musculoskeletal Recombinant, other |
| 51 | CVFM | | Cys-Val-Phe-Met | Anticancer, other |
| 52 and 53 | calcitonin | calcitonin | CGNLSTCMLGTYTQDFNKFHTFPQTAIGVGAP (human)<br>H-Cys-Ser-Asn-Leu-Ser-Thr-Cys-Val-Leu-Gly-Lys-Leu-Ser-Gln-Glu-Leu-His-Lys-Leu-Gln-Thr-Tyr-Pro-Arg-Thr-Asn-Thr-Gly-Ser-Gly-Thr-Pro-NH2 (salmon) | Formulation, oral, other Hormone Osteoporosis treatment |
| 54 | calciseptine | | sp\|P22947\|TXCAS—DENPO Calciseptin OS = *Dendroaspis polylepis polylepis* PE = 1 SV = 1<br>RICYIHKASLPRATKTCVENTCYKMFIRTQREYISERGCGCPTAMWPYQTECCKGDRCNK | Antihypertensive, other |
| 52 and 53 | calcitonin analogues | calcitonin | CGNLSTCMLGTYTQDFNKFHTFPQTAIGVGAP (human)<br>H-Cys-Ser-Asn-Leu-Ser-Thr-Cys-Val-Leu-Gly-Lys-Leu-Ser-Gln-Glu-Leu-His-Lys-Leu-Gln-Thr-Tyr-Pro-Arg-Thr-Asn-Thr-Gly-Ser-Gly-Thr-Pro-NH2 (salmon) | Hormone Osteoporosis treatment |
| 55 | calphobindin I | | gi\|186680508\|ref\|NM_001154.3\| *Homo sapiens* annexin A5 (ANXA5),<br>MAQVLRGTVTDFPGFDERADAETLRKAMKGLGTDEESILTLLTSRSNAQRQEISAAFKTLFGRDLLDDLKSELTGKFEKLIVALMKPSRLYDAYELKHALKGAGTNEKVLTEIIASRTPEELRAIKQVYEEEYGSSLEDDVVGDTSGYYQRMLVVLLQANRDPDAGIDEAQVEQDAQALFQAGELKWGTDEEKFITIFGTRSVSHLRKVFDKYMTISGFQIEE | Ophthalmological, Vulnerary |

TABLE 1-continued

This table lists the SEQ ID NOs., names, sequences, and known or suspected therapeutic activities of various peptides described herein. The SEQ ID NOs. 1-301 describe sequences that are required to be provided with the Sequence Listing and are therefore appended with the instant Specification. In some instances, these peptides contain features that are either inconsistent with or not amenable to inclusion in the Sequence Listing. For example, a sequence with less than four-amino acids; a sequence with a D-amino acid; or certain modification that cannot be described in the Sequence Listing presently, and therefore are not provided in the Sequence Listing. However, for the ease of use and description, a SEQ ID NO. has been provided to these peptides (i.e., SEQ ID NOs: 302-469).

| SEQ ID NO: | Name | Family | Sequence and/or other Identifying Information | Therapeutic Activity |
|---|---|---|---|---|
| | | | TIDRETSGNLEQLLLAVVKSIRSIPAYLAETLYYAMKG AGTDDHTLIRVMVSRSEIDLFNIRKEFRKNFATSLYSM IKGDTSGDYKKALLLLCGEDD | |
| 319 | cargutocin | | 1,6-Dicarbaoxytocin, 1-butanoic acid-7-glycine- | Labour inducer |
| 320 | casokefamide | | L-Tyrosinamide, L-tyrosyl-D-alanyl-L-phenylalanyl-D-alanyl- | Antidiarrhoeal |
| 56 | cekropin-P | | sp|1314661|CECP1_PIG Cecropin-P1 OS = Sus scrofa PE = 1 SV = 1 SWLSKTAKKLENSAKKRISEGIAIAIQGGPR | Antibacterial, other |
| 57 | tasidotin hydrochloride | | N,N-Dimethyl-L-valyl-L-valyl-N-methyl-L-valyl-L-propyl-L-proline-tert-butylamide | Anticancer, other |
| 58 | ceruletide diethylamine | | Pyr-Gln-Asp-Tyr(SO3H)-Thr-Gly-Trp-Met-Asp-Phe-C(O)-NH$_2$ | Analgesic, other Gastroprokinetic |
| 321 | cetrorelix acetate | | D-Alaninamide, N-acetyl-3-(2-naphthalenyl)-D-alanyl-4-chloro-D-phenylalanyl-3-(3-pyridinyl)-D-alanyl-L-seryl-L-tyrosyl-N5-(aminocarbonyl)-D-ol-L-leucyl-L-arginyl-L-prolyl- | Fertility enhancer Prostate disorders Menstruation disorders Anticancer, hormonal |
| 59 | corticoliberin | corticoliberin | SQEPPISLDLTFHLLREVLEMTKADQLAQQAHSNRKL LDIA | Releasing hormone |
| 322 | D-22213 | | L-Histidinamide, N2-[(2,3,4,9-tetrahydro-1H-pyrido[3,4-b]indol-3-yl)carbonyl]-L-glutaminyl-L-tryptophyl-L-alanyl-L-valylglycyl-N-[1-[[[1-(aminocarbonyl)-3-methylbutyl]amino]methyl]-3-methylbutyl]-, [1(R),6[5-(R*,R*)]]-, monoacetate | Anticancer, other |
| 323 | DAP inhibitors | | L-AP-L-Ala and L-Ala-L-Ala-DL-AP; | Antibacterial, other |
| 60 | DP-640 | insulin | L-Tyrosinamide, β-alanyl-L-arginylglycyl-L-phenylalanyl-L-phenylalanyl-, diacetate (salt) | Insulin Antidiabetic |
| 61 | DP-107 | | L-Leucine, L-methionyl-L-threonyl-L-leucyl-L-threonyl-L-valyl-L-glutaminyl-L-alanyl-L-arginyl-L-glutaminyl-L-leucyl-L-leucyl-L-seryl-L-glutaminyl-L-isoleucyl-L-valyl-L-glutaminyl-L-glutaminyl-L-glutaminyl-L-asparaginyl-L-asparaginyl-L-leucyl-L-leucyl-L-arginyl-L-alanyl-L-isoleucyl-L-.alpha.-glutamyl-L-alanyl-L-glutaminyl-L-glutaminyl-L-histidyl-L-leucyl-L-leucyl-L-glutaminyl-L-leucyl-L-threonyl-L-valyl-L-tryptophylglycyl-L-isoleucyl-L-lysyl-L-glutaminyl- | Antiviral, anti-HIV |
| 62 | DU-728 | | Arg-Gly-Asp-Ser | Antithrombotic |
| 63 | Dynorphin A | | H-Tyr-Gly-Gly-Phe-Leu-Arg-Arg-Ile-Arg-Pro-Lys-Leu-Lys-Trp-Asp-Asn-Gln-OH | Analgesic, other Neuroprotective Dependence treatment |
| 64 | defensins | | gi|181535|gb|AAA52304.1| defensin precursor MRTLAILAAILLVALQAQAEPLQARADEVAAAPEQIA ADIPEVVVSLAWDESLAPKHPGSRKNMDCYCRIPACI AGERRYGTCIYQGRLWAFCC | Antibiotic, other Antifungal Vulnerary |
| 324 | detirelix | | D-Alaninamide, N-acetyl-3-(2-naphthalenyl)-D-alanyl-4-chloro-D-phenylalanyl-D-tryptophyl-L-seryl-L-tyrosyl-N6-[bis(ethylamino)methylene]-D-lysyl-L-leucyl-L-arginyl-L-prolyl- | Releasing hormone Abortifacient Male contraceptive |
| 65 | disagregin | | gi|545738|gb|AAB30092.1| disagregin = fibrinogen receptor antagonist [Ornithodoros moubata = tick, salivary gland, Peptide, 60 aa] SDDKCQGRPMYGCREDDDSVFGWTYDSNHGQCWKG SYCKHRRQPSNYFASQQECRNTCGA | Antithrombotic Cardiovascular |
| 66 and 65 | E-2078 | | D-Leucinamide, N-methyl-L-tyrosylglycylglycyl-L-phenylalanyl-L-leucyl-L-arginyl-N2-methyl-L-arginyl-N-ethyl- SDDKCQGRPMYGCREDDDSVFGWTYDSNHGQCWKG SYCKHRRQPSNYFASQQECRNTCGA | Analgesic, other |
| | ELS-1 | | Arg-Lys-Glu | Immunostimulant, other |
| 67 | ecallantide | | Glu-Ala-Met-His-Ser-Phe-Cys-Ala-Phe-Lys-Ala-Asp-Asp-Gly-Pro-Cys-Arg-Ala-Ala-His-Pro-Arg-Trp-Phe-Phe-Asn-Ile-Phe-Thr-Arg-Gln-Cys-Glu-Glu-Phe-Ile-Tyr-Gly-Gly-Cys-Glu-Gly-Asn-Gln-Asn-Asn-Phe-Glu-Ser-Leu-Glu-Glu-Cys-Lys-Lys-Met-Cys-Thr-Arg-Asp | Angioedema, Anti-inflammatory, Haemostatic, Antiarthritic, other |
| 325 | ES-1005 | | bis-(1-naphthyl)methylacetyl-His-Sta-Leu-E-Lys diHCl | Antihypertensive, renin system |
| 326 | efegatran | | L-prolinamide, N-methyl-D-phenylalanyl-n-(4-((aminoiminomethyl)amino)-1-formylbutyl), (S)- | Antithrombotic Antianginal |

TABLE 1-continued

This table lists the SEQ ID NOs., names, sequences, and known or suspected therapeutic activities of various peptides described herein. The SEQ ID NOs. 1-301 describe sequences that are required to be provided with the Sequence Listing and are therefore appended with the instant Specification. In some instances, these peptides contain features that are either inconsistent with or not amenable to inclusion in the Sequence Listing. For example, a sequence with less than four-amino acids; a sequence with a D-amino acid; or certain modification that cannot be described in the Sequence Listing presently, and therefore are not provided in the Sequence Listing. However, for the ease of use and description, a SEQ ID NO. has been provided to these peptides (i.e., SEQ ID NOs: 302-469).

| SEQ ID NO: | Name | Family | Sequence and/or other Identifying Information | Therapeutic Activity |
|---|---|---|---|---|
| 68 and 69 | elafin derivatives | | gi\|999146\|gb\|AAB34627.1\| elafin [Homo sapiens] MRASSFLIVVVFLIAGTLVLE H-Ala-Gln-Glu-Pro-Val-Lys-Gly-Pro-Val-Ser-Thr-Lys-Pro-Gly-Ser-Cys-Pro-Ile-Ile-Leu-Ile-Arg-Cys-Ala-Met-Leu-Asn-Pro-Pro-Asn-Arg-Cys-Leu-Lys-Asp-Thr-Asp-Cys-Pro-Gly-Ile-Lys-Lys-Cys-Cys-Glu-Gly-Ser-Cys-Gly-Met-Ala-Cys-Phe-Val-Pro-Gln-OH (Disulfide bonds between Cys16-Cys45, Cys23-Cys49, Cys32-Cys44, Cys38-Cys53) | Respiratory COPD treatment Antiarthritic, other |
| 70 and 52 | elcatonin | calcitonin | Ser-Asn-Leu-Ser-Thr-Asn-Val-Leu-Gly-Lys-Leu-Ser-Gln-Glu-Leu-His-Lys-Leu-Gln-Thr-Tyr-Pro-Arg-Thr-Asn-Val-Gly-Ala-Gly-Thr-Pro-NH$_2$ CGNLSTCMLGTYTQDFNKFHTFPQTAIGVGAP (human) | Hormone Osteoporosis treatment Analgesic, other |
| 71 | eledoisin | | 5-oxo-L-Pro-L-Pro-L-Ser-L-Lys-L-Asp-L-Ala-L-Phe-L-Ala-L-isoleucylglycyl-L-Leu-L-methionin-amide | Ophthalmological |
| 3 | encapsulated insulin | insulin | gi\|386828\|gb\|AAA59172.1\| insulin [Homo sapiens] MALWMRLLPLLALLALWGPDPAAAFVNQHLCGSHLV EALYLVCGERGFFYTPKTRREAEDLQVGQVELGGGPG AGSLQPLALEGSLQKRGIVEQCCTSICSLYQLENYCN | Formulation, optimized, nanoparticles Insulin Antidiabetic |
| 72 | endorphin, β- | | YGGFMTSEKSQTPLVTLFKNAIIKNAYKKGE | Analgesic, other |
| 72 | endorphin, pancreatic | | YGGFMTSEKSQTPLVTLFKNAIIKNAYKKGE | Analgesic, other |
| 73 | endothelial cell growth factor | | gi\|189701\|gb\|AAA60043.1\| endothelial cell growth factor MAALMTPGTGAPPAPGDFSGEGSQGLPDPSPEPKQLP ELIRMKRDGGRLSEADIRGFVAAVVNGSAQGAQIGA MLMAIRLRGMDLEETSVLTQALAQSGQQLEWPEAWR QQLVDKHSTGGVGDKVSLVLAPALAACGCKVPMISG RGLGHTGGTLDKLESIPGFNVIQSPEQMQVLLDQAGC CIVGQSEQLVPADGILYAARDVTATVDSLPLITASILSK KLVEGLSALVVDVKFGGAAVFPNQEQARELAKTLVG VGASLGLRVAAALTAMDKPLGRCVGHALEVEEALLC MDGAGPPDLRDLVTTLGGALLWLSGHAGTQAQGAA RVAAALDDGSALGRFERMLAAQGVDPGLARALCSGS PAERRQLLPRAREQEELLAPADGTVELVRALPLALVL HELGAGRSRAGEPLRLGVGAELLVDVGQRLRRGTPW LRVHRDGPALSGPQSRALQEALVLSDRAPFAAPSPFA ELVLPPQQ | Cardiovascular |
| 74 | eptifibatide | | MAP-HAR-GLY-ASP-TRP-PRO-CYS-NH$_2$ | Antianginal Cardiovascular |
| 327 | examorelin | GHRP | L-Lysinamide, L-histidyl-2-methyl-D-tryptophyl-L-alanyl-L-tryptophyl-D-phenylalanyl- | Releasing hormone Vulnerary Cardiovascular |
| 75 | FG-005 | | SMR1-QHNPR | Male sexual dysfunction |
| 328 | FR-113680 | | L-Phenylalaninamide, N-acetyl-L-threonyl-1-formyl-D-tryptophyl-N-methyl-N-(phenylmethyl)- | Antiasthma |
| 76 | fibronectin-related peptide | | Gly-Arg-Gly-Asp-Ser | Anticancer, other |
| 329 | G-4120 | | L-Cysteine, N-(mercaptoacetyl)-D-tyrosyl-L-arginylglycyl-L-alpha-aspartyl-, cyclic (1-5)-sulfide, S-oxide | Antithrombotic |
| 330 | EP-51216 | | 2S)-6-amino-2-[[(2S)-2-[[(2R)-2-[[(2R)-2-(4-aminobutanoylamino)-3-(2-methyl-1H-indol-3-yl)propanoyl]amino]-3-(2-methyl-1H-indol-3-yl)propanoyl]amino]-3-(2-methyl-1H-indol-3-yl)propanoyl]amino]hexanamide | GH Releasing hormone Vulnerary, endocrine |
| 8 | GLP-1 + exendin-4 | GLP-1 | HGEGTFTSDLSKQMEEEAVRLFIEWLKNGGPSSGAPP PS | Antidiabetic |
| 77 | GM-1986 | | YYWIGIR | Anti-inflammatory |
| 78 | GnRH-associated peptide | GnRH | gi\|133908612\|ref\|NP_001076580.1\| gonadotropin-releasing hormone 1 precursor [Homo sapiens] MKPIQKLLAGLILLTWCVEGCSSQHWSYGLRPGGKR DAENLIDSFQEIVKEVGQLAETQRFECTTHQPRSPLRD LKGALESLIEEETGQKKI | Antiprolactin Menstruation disorders Fertility enhancer |
| 79 | GRF1-44 | | gi\|11034841\|ref\|NP_066567.1\| growth hormone releasing hormone preproprotein [Homo sapiens] MPLWVFFFVILTLSNSSHCSPPPPLTLRMRRYADAIFT NSYRKV | Musculoskeletal |
| 80 | GRF | GHRF | gi\|337133\|gb\|AAA52609.1\| growth hormone releasing factor MPLWVFFFVILTLSNSSHCSPPPPLTLRMRRYADAIFT NSYRKVLGQLSARKLLQDIMSRQQGESNQERGARAR LGRQVDSMWAEQKQMELESILVALLQKHRNSQG | Idiopathic growth hormone deficiency; cachexia |

TABLE 1-continued

This table lists the SEQ ID NOs., names, sequences, and known or suspected therapeutic activities of various peptides described herein. The SEQ ID NOs. 1-301 describe sequences that are required to be provided with the Sequence Listing and are therefore appended with the instant Specification. In some instances, these peptides contain features that are either inconsistent with or not amenable to inclusion in the Sequence Listing. For example, a sequence with less than four-amino acids; a sequence with a D-amino acid; or certain modification that cannot be described in the Sequence Listing presently, and therefore are not provided in the Sequence Listing. However, for the ease of use and description, a SEQ ID NO. has been provided to these peptides (i.e., SEQ ID NOs: 302-469).

| SEQ ID NO: | Name | Family | Sequence and/or other Identifying Information | Therapeutic Activity |
|---|---|---|---|---|
| 331 | GYKI-14451 | | L-Prolinamide, N-[(1,1-dimethylethoxy)carbonyl]-D-phenylalanyl-N-[4-[(aminoiminomethyl)amino]-1-formylbutyl]-, (S)- | Antithrombotic |
| 81 | galanin | | gi\|1247490\|emb\|CAA01907.1\| galanin [*Homo sapiens*] MARGSALLLASLLLAAALSASAGLWSPAKEKRGWTL NSAGYLLGPHAVGNHRSFSDKNGLTSKRELRPEDDM KPGSFDRSIPENNIMRTIIEFLSFLHLKEAGALDRLLDL PAAASSEDIERS | Releasing hormone |
| 82 | gastrin antagonists | | (benzyloxycarbonyl)-L-Glu-L-Ala-L-Tyr-Gly-L-Tyr-L-Met-L-aspartic acid amide | Antiulcer |
| 332 | glaspimod | | N2,N2'-[2,7-Bis(pyroglutamyl-glutamyl-aspartylamino)-octanediolyl]bis(lysine) | Immunomodulator, anti-infective Immunostimulant, other Radio/chemoprotective |
| 83 | glicentin | | gi\|125987831\|sp\|P01275.3\|GLUC__HUMAN Glucagon precursor [Contains: Glicentin; Glicentin-related polypeptide (GRPP); Oxyntomodulin (OXY) (OXM); Glucagon; Glucagon-like peptide 1 (GLP-1); Glucagon-like peptide 1(7-37) (GLP-1(7-37)); Glucagon-like peptide 1(7-36) (GLP-1(7-36)); Glucagon-like peptide 2 (GLP-2)] MKSIYFVAGLFVMLVQGSWQRSLQDTEEKSRSFSASQ ADPLSDPDQMNEDKRHSQGTFTSDYSKYLDSRRAQD FVQWLMNTKRNRNNIAKRHDEFERHAEGTFTSDVSS YLEGQAAKEFIAWLVKGRGRRDFPEEVAIVEELGRRH ADGSFSDEMNTILDNLAARDFINWLIQTKITDRK | Insulin Antiulcer Antidiabetic |
| 84 | glucagon | | H2N-His-Ser-Gln-Gly-Thr-Phe-Thr-Ser-Asp-Tyr-Ser-Lys-Tyr-Leu-Asp-Ser-Arg-Arg-Ala-Gln-Asp-Phe-Val-Gln-Trp-Leu-Met-Asn-Thr-COOH | hypoglycemia Diagnostic |
| 84 | glucagon | glucagon | His-Ser-Gln-Gly-Thr-Phe-Thr-Ser-Asp-Tyr-Ser-Lys-Tyr-Leu-Asp-Ser-Arg-Arg-Ala-Gln-Asp-Phe-Val-Gln-Trp-Leu-Met-Asn-Thr | Hypoglycemia |
| 85 | gonadorelin analogues | gonadorelin | gi\|121522\|sp\|P01148.1\|GON1__HUMAN Progonadoliberin-1 precursor (Progonadoliberin I) [Contains: Gonadoliberin-1 (Gonadoliberin I) (Luteinizing hormone-releasing hormone I) (LH-RH I) (Gonadotropin-releasing hormone I) (GnRH-I) (Luliberin I) (Gonadorelin); GnRH-associated peptide 1 (GnRH-associated peptide I)] MKPIQKLLAGLILLTWCVEGCSSQHWSYGLRPGGKR DAENLIDSFQEIVKEVGQLAETQRFECTTHQPRSPLRD LKGALESLIEEETGQKKI | Female contraceptive; enometiosis, uterine leiomyoma, precocious puberty, prostate and breast cancer |
| 333 | gonadorelin antagonist | | [Ac-DNAL1(2),4FDPhe2,D-Trp3,D-Arg6]-LHRH | Female contraceptive; enometiosis, uterine leiomyoma, precocious puberty, prostate and breast cancer |
| 86 | gonadorelin | gonadorelin | 5-oxo-L-His-L-Trp-L-Ser-L-Tyr-Gly-L-Leu-L-Arg-L-Pro-glycinamide | Female contraceptive; enometiosis, uterine leiomyoma, precocious puberty, prostate and breast cancer |
| 334 | goralatide | | L-Proline, 1-[N2-[N-(N-acetyl-L-seryl)-L-α-aspartyl]-lysyl]- | Haematological Immunological Radio/chemoprotective |
| 335 | H-142 | | L-Lysine, N2-[N-[N-[N-[4-methy1-2-[[N-[N-[1-(N-L-prolyl-L-histidyl)-L-prolyl]-L-phenylalanyl]-R-histidyl]amino]pentyl]-L-valyl]-isoleucyl]-L-histidyl]-, (S)- | Antihypertensive, renin system |
| 336 | I5B2 | | L-Tyrosinamide, N-methyl-L-valyl-N-[2-(4-hydroxyphenyl)-1-phosphonoethyl]- | Antihypertensive, renin system |
| 87 | iseganan hydrochloride | | L-Argininamide, L-arginylglycylglycyl-L-leucyl-L-cysteinyl-L-tyrosyl-L-cysteinyl-L-arginylglycyl-L-arginyl-L-phenylalanyl-L-cysteinyl-L-valyl-L-cysteinyl-L-valylglycyl-, cyclic (5-14),(7-12)-bis(disulfide) hydrochloride | Antibacterial, other Antifungal Antiviral, other |
| 88 | netamiftide | | L-Tryptophanamide, 4-fluoro-L-phenylalanyl-(4R)-4-hydroxy-L-prolyl-L-arginylglycyl-, bis(trifluoroacetate) (salt) | Antidepressant Anxiolytic |
| 337 | icrocaptide | | L-Arginine, glycyl-N2-ethyl-L-lysyl-L-prolyl- | Cardiovascular Septic shock treatment |

TABLE 1-continued

This table lists the SEQ ID NOs., names, sequences, and known or suspected therapeutic activities of various peptides described herein. The SEQ ID NOs. 1-301 describe sequences that are required to be provided with the Sequence Listing and are therefore appended with the instant Specification. In some instances, these peptides contain features that are either inconsistent with or not amenable to inclusion in the Sequence Listing. For example, a sequence with less than four-amino acids; a sequence with a D-amino acid; or certain modification that cannot be described in the Sequence Listing presently, and therefore are not provided in the Sequence Listing. However, for the ease of use and description, a SEQ ID NO. has been provided to these peptides (i.e., SEQ ID NOs: 302-469).

| SEQ ID NO: | Name | Family | Sequence and/or other Identifying Information | Therapeutic Activity |
|---|---|---|---|---|
| 338 | icatibant | | L-Arginine, D-arginyl-L-arginyl-L-prolyl-trans-4-hydroxy-L-prolylglycyl-3-(2-thienyl)-L-alanyl-L-seryl-D-1,2,3,4-tetrahydro-3-isoquinolinecarbany-L-(2α,3aβ,7aβ)-octahydro-1H-indole-2-carbonyl- | Cardiovascular Hepatoprotective Vulnerary |
| 339 | AG-1776 | | 3-[2(S)-Hydroxy-3(S)-(3-hydroxy-2-methylbenzamido)-4-phenylbutanoyl]-5,5-dimethyl-N-(2-methylbenzyl)thiazolidine-4(R)-carboxamide | Antiviral, anti-HIV |
| 340 | pralmorelin | | L-Lysinamide, D-alanyl-3-(2-naphthalenyl)-D-alanyl-L-alanyl-L-tryptophyl-D-phenylalanyl- | Diagnostic Releasing hormone |
| 89 | katacalcin | calcitonin | gi\|115478\|sp\|1301258.1\|CALC_HUMAN Calcitonin precursor [Contains: Calcitonin; Katacalcin (Calcitonin carboxyl-terminal peptide) (CCP) (PDN-21)] MGFQKFSPFLALSILVLLQAGSLHAAPFRSALESSPAD PATLSEDEARLLLAALVQDYVQMKASELEQEQEREGS SLDSPRSKRCGNLSTCMLGTYTQDFNKFHTFPQTAIG VGAPGKKRDMSSDLERDHRPHVSMPQAN | Osteoporosis treatment Hormone Recombinant, other |
| 341 | ketomethylureas | | N-[N-[3-benzoylamino-4-phenyl-2-oxobutyl]-N-methylaminocarbonyl]proline | Antihypertensive, renin system |
| 90 | L-346670 | | N-L-arginyl-8-L-methionine-21a-L-phenylalanine-21b-L-arginine-21c-L-tyrosine- | Antihypertensive, diuretic |
| 91 | L-364210 | | N-isovaleryl-L-histidyl-L-prolyl-L-phenylalanyl-L-histidyl-(3S,4S)-4-amino-5-cyclohexyl-3-hydroxypentanoic acid)-L-leucyl-L-phenylalanylamide | Antihypertensive, renin system |
| 342 | L-659837 | | L-Phenylalanine, N-[2-(3-amino-2-oxo-1-pyrrolidinyl)-4-methyl-1-oxopentyl]-L-methionyl-L-glutaminyl-L-tryptophyl-, cyclic (4-1)-peptide, [S-(R*,S*)]- | Analgesic, other |
| 343 | L-693549 | | 5(S)-(tert-butoxycarbonylamino)-4(S)-hydroxy-N-[2(R)-hydroxyindan-1(S)-yl]-2(R)-[4-(3-hydroxypropyl)benzyl]-6-phenylhexamide | Antiviral, anti-HIV |
| 344 | L-709049 | | L-Alaninamide, N-acetyl-L-tyrosyl-L-valyl-N-(2-carboxy-1-formylethyl)-, (S)- | Anti-inflammatory |
| 92 | LDV-containing peptides | | 4-((N'-2-methylphenyl)ureido)phenylalanyl-leucyl-alpha-aspartyl-valyl-prolyl-alanyl-alanyl-lysine | Anticancer, other |
| | Lys-Phe | | L-Phenylalanine, N-L-lysyl- | Haematological Antisickling |
| 93 | lagatide | | D-Alaninamide, L-prolyl-L-valyl-L-threonyl-L-lysyl-L-prolyl-L-glutaminyl- | Antidiarrhoeal |
| 94 | laminin A peptide | | seryl-isoleucyl-lysyl-valyl-alanyl-valinamide | Anticancer, other Neurological |
| 95 | laminin | | tyrosyl-isoleucyl-glycyl-serylarginine | Anticancer, other |
| 345 | lanreotide | somatostatin | L-Threoninamide, 3-(2-naphthaleny1)-D-alanyl-L-cysteinyl-L-tyrosyl-D-tryptophyl-L-lysyl-L-valyl-L-cysteinyl-, cyclic (2-7)-disulfide; L-Threoninamide, 3-(1-naphthalenyl)-D-alanyl-L-cysteinyl-L-tyrosyl-D-tryptophyl-L-lysyl-L-valyl-L-cysteinyl-, cyclic (2-7)-disulfide | Acromegaly Anticancer, hormonal Cardiovascular Antidiarrhoeal |
| 346 | leuprolide acetate | | Luteinizing hormone-releasing factor (pig), 6-D-leucine-9-(N-ethyl-L-prolinamide)-10-deglycinamide- | Formulation, implant Anticancer, hormonal Menstruation disorders |
| 347 | MCI-826 | | Butanoic acid, 2,2-diethyl-4-[[3-[2-[4-(1-methylethyl)-2-thiazolyl]ethenyl]phenyl]amino]-4-oxo-, (E)- | Antiasthma |
| 96 | omiganan pentahydro-chloride | | L-lysinamide, L-isoleucyl-L-leucyl-L-arginyl-L-tryptophyl-L-prolyl-L-tryptophyl-L-tryptophyl-L-prolyl-L-tryptophyl-L-arginyl-L-arginyl, pentahydrochloride | Peptide antibiotic |
| 97-100 | MBP | | gi\|68509940\|ref\|NP_001020272.1\| Golli-mbp isoform 1 [Homo sapiens] MGNHAGKRELNAEKASTNSETNRGESEKKRNLGELS RTTSEDNEVFGEADANQNNGTSSQDTAVTDSKRTAD PKNAWQDAHPADPGSRPHLIRLFSRDAPGREDNTFKD RPSESDELQTIQEDSAATSESLDVMASQKRPSQRHGSK YLATASTMDHARHGFLPRHRDTGILDSIGRFFGGDRG APKRGSGKDSHHPARTAHYGSLPQKSHGRTQDENPV VHFFKNIVTPRTPPPSQGKGRGLSLSRFSWGAEGQRPG FGYGGRASDYKSAHKGFKGVDAQGTLSKIFKLGGRD SRSGSPMARR gi\|68509938\|ref\|NP_001020271.1\| Golli-mbp isoform 2 [Homo sapiens] MGNHAGKRELNAEKASTNSETNRGESEKKRNLGELS RTTSEDNEVFGEADANQNNGTSSQDTAVTDSKRTAD PKNAWQDAHPADPGSRPHLIRLFSRDAPGREDNTFKD | Multiple sclerosis treatment Immunosuppressant |

TABLE 1-continued

This table lists the SEQ ID NOs., names, sequences, and known or suspected therapeutic activities of various peptides described herein. The SEQ ID NOs. 1-301 describe sequences that are required to be provided with the Sequence Listing and are therefore appended with the instant Specification. In some instances, these peptides contain features that are either inconsistent with or not amenable to inclusion in the Sequence Listing. For example, a sequence with less than four-amino acids; a sequence with a D-amino acid; or certain modification that cannot be described in the Sequence Listing presently, and therefore are not provided in the Sequence Listing. However, for the ease of use and description, a SEQ ID NO. has been provided to these peptides (i.e., SEQ ID NOs: 302-469).

| SEQ ID NO: | Name | Family | Sequence and/or other Identifying Information | Therapeutic Activity |
|---|---|---|---|---|
| | | | RPSESDELQTIQEDSAATSESLDVMASQKRPSQRHGSK YLATASTMDHARHGFLPRHRDTGILDSIGRFFGGDRG APKRGSGKVSSEE gi\|68509930\|ref\|NP_001020252.1\| myelin basic protein isoform 1 [Homo sapiens] MASQKRPSQRHGSKYLATASTMDHARHGFLPRHRDT GILDSIGRFFGGDRGAPKRGSGKVPWLKPGRSPLPSHA RSQPGLCNMYKDSHHPARTAHYGSLPQKSHGRTQDE NPVVHFFKNIVTPRTPPPSQGKGRGLSLSRFSWGAEGQ RPGFGYGGRASDYKSAHKGFKGVDAQGTLSKIFKLG GRDSRSGSPMARR gi\|4505123\|ref\|NP_002376.1\| myelin basic protein isoform 2 [Homo sapiens] MASQKRPSQRHGSKYLATASTM | |
| 348 | MDL-104238 | | N-[4-(4-morpholinylcarbonyl)benzoyl]-L-valyl-N'-[3,3,4,4,4-pentafluoro-1-(1-methylethyl)-2-oxobutyl]-L-2-azetamide | Anti-inflammatory |
| 349 | MDL-28050 | | D-Glutamic acid, N-[N-[N-[N-[N-[1-[N-[1-[N-[N-(3-carboxy-1-oxopropyl)-L-tyrosyl]-L-alpha-glutamyl]-prolyl]-L-isoleucyl]-L-prolyl]-L-alpha-glutamyl]-L-alpha-glutamyl]-L-alanyl]-3-cyclohexyl-L-alanyl]- | Antithrombotic Anticoagulant |
| 101 | MMP inhibitors | | FN 439; FN-439; H2N—C6H4—CO-Gly-Pro-Leu-Ala-NHOH; MMP-inhibitor I; p-NH$_2$-Bz-Gly-Pro-D-Leu-D-Ala-NHOH | Antiarthritic,Anticancer, Anti-inflammatory |
| 350 | MR-988 | | N-pivaloyl-leucyl-gamma-aminobutyric acid | Antiepileptic |
| 351 | mertiatide | | Glycine, N-[N-[N-(mercaptoacetyl)glycyl]glycyl]- | Diagnostic |
| 352 | metkephamide | | L-Methioninamide, L-tyrosyl-D-alanylglycyl-L-phenylalanyl-N2-methyl-, monoacetate (salt) | Analgesic, other |
| 353 | murabutide | | D-Glutamine, N2-[N-(N-acetylmuramoyl)-L-alanyl]-, butyl ester | Immunomodulator, anti-infective Anticancer, immunological Immunostimulant, other |
| 354 | muramyl dipeptide derivatives | | D-alpha-Glutamine, N2-[N-(N-acetylmuramoyl)-L-alanyl]- | Immunomodulator, anti-infective Anticancer, immunological Immunostimulant, other |
| 355 | NPY24-36 | | N-acetyl[Leu-28Leu-31]NPY24-36 | Antihypotensive |
| 102 | NAGA | | Asn-Ala-Gly-Ala | Analgesic, other |
| 356 | tiplimotide | | L-Proline, D-alanyl-L-lysyl-L-prolyl-L-valyl-L-valyl-L-histidyl-L-leucyl-L-phenylalanyl-L-alanyl-L-asparaginyl-L-isoleucyl-L-valyl-L-threonyl-L-prolyl-L-arginyl-L-threonyl- | Multiple sclerosis treatment |
| 103 | opebecan | | gi\|157276599\|ref\|NP_001716.2\| bactericidal/permeability-increasing protein precursor [Homo sapiens] MRENMARGPCNAPRWASLMVLVAIGTAVTAAVNPG VVVRISQKGLDYASQQGTAALQKELKRIKIPDYSDSF KIKHLGKGHYSFYSMDIREFQLPSSQISMVPNVGLKFS ISNANIKISGKWKAQKRFLKMSGNFDLSIEGMSISADL KLGSNPTSGKPTITCSSCSSHINSVHVHISKSKVGWLIQ LFHKKIESALRNKMNSQVCEKVTNSVSSELQPYFQTL PVMTKID SVAGINYGLVAPPATTAETLDVQMKGEFYS ENHHNPPPFAPPVMEFPAAHDRMVYLGLSDYFFNTA GLVYQEAGVLKMTLRDDMIPKESKFRLTTKFFGTFLP EVAKKFPNMKIQIHVSASTPPHLSVQPTGLTFYPAVDV QAFAVLPNSSLASLFLIGMHTTGSMEVSAESNRLVGE LKLDRLLLELKHSNIGPFPVELLQDIMNYIVPILVLPRV NEKLQKGFPLPTPARVQLYNVVLQPHQNFLLFGADV VYK | Recombinant, other Antibacterial, other GI inflammatory/bowel disorders Vulnerary Anti-inflammatory Symptomatic antidiabetic Ophthalmological |
| 104 and 105 | liraglutide | GLP-1 | Glycine, L-histidyl-L-alanyl-L-alpha-glutamylglycyl-L-threonyl-L-phenylalanyl-L-threonyl-L-seryl-L-alpha-aspartyl-L-valyl-L-seryl-L-seryl-L-tyrosyl-L-leucyl-L-alpha-glutamylglycyl-L-glutaminyl-L-alanyl-L-alanyl-N6-[N-(1-oxohexadecyl)-L-gamma-glutamyl]-L-lysyl-L-alpha-glutamyl-L-phenylalanyl-L-isoleucyl-L-alanyl-L-tryptophyl-L-leucyl-L-valyl-L-arginylglycyl-L-arginyl- | Antidiabetic Anorectic/Antiobesity |
| 106 | Nona CCK | | SFKIKHLGKGHYSFYSMDIREFQLPSSQISMVPNVGLK FSISNANIKISGKWKAQKRFLKMSGNFDLSIE GMSISADLKLGSNPTSGKPTITCSSCSSHINSVHVHISK SKVGWLIQLFHKKIESALRNKMNSQVCEKVT | Diagnostic Neuroleptic Anorectic/Antiobesity Antidepressant |

TABLE 1-continued

This table lists the SEQ ID NOs., names, sequences, and known or suspected therapeutic activities of various peptides described herein. The SEQ ID NOs. 1-301 describe sequences that are required to be provided with the Sequence Listing and are therefore appended with the instant Specification. In some instances, these peptides contain features that are either inconsistent with or not amenable to inclusion in the Sequence Listing. For example, a sequence with less than four-amino acids; a sequence with a D-amino acid; or certain modification that cannot be described in the Sequence Listing presently, and therefore are not provided in the Sequence Listing. However, for the ease of use and description, a SEQ ID NO. has been provided to these peptides (i.e., SEQ ID NOs: 302-469).

| SEQ ID NO: | Name | Family | Sequence and/or other Identifying Information | Therapeutic Activity |
|---|---|---|---|---|
| 107 and 108 | NP-06 | | Cysteinyl-leucyl-glycyl-valyl-glycyl-seryl-cysteinyl-asparaginyl-aspartyl-phenylalanyl-alanyl-glycyl-cysteinyl-glycyl-tyrosyl-alanyl-isoleucyl-valyl-cysteinyl-phenylalanyl-tryptophan S-3.1-S-3.13:S-3.7-S-3.19-bis(disulfide)N-2.1-C-4.9-lactam NSVSSELQPYFQTLPVMTKIDSVAGINYGLVAPPATTA ETLDVQMKGEFYSENHHNPPPFAPPVMEFPAA | Antiviral, anti-HIV |
| 109 | NPC-18545 | | Bradykinin, N2-D-arginyl-3-(trans-4-hydroxy-L-proline)-7-(D-1,2,3,4-tetrahydro-3-isoquinolinecarboxylic acid)-8-[L-(2alpha,3aβ,7a.beta.)-octahydro-1H-indole-2-carboxylic acid]- HDRMVYLGLSDYFFNTAGLVYQEAGVLKMTLRDDM IPKESKFRLTTKFFGTFLPEVAKKFPNMKIQIHVS | Anti-inflammatory |
| 110 | Nva-FMDP | | Nva-N3-4-methoxyfumaroyl-L-2,3-diaminopropanoic acid ASTPPHLSVQPTGLTFYPAVDVQAFAVLPNSSLASLFL IGMHTTGSMEVSAESNRLVGELKLDRLLLELK | Antifungal |
| 111 | nacartocin | | 6-Carbaoxytocin, 1-(3-mercaptopropanoic acid)-2-(4-ethyl-L-phenylalanine)- HSNIGPFPVELLQDIMNYIVPILVLPRVNEKLQKGFPLP TPARVQLYNVVLQPHQNFLLFGADVVYK | Hormone Labour inducer Antihypertensive, diuretic |
| 112 | natural peptide | | U.S. Pat. No. 5,288,708 Partial N terminal sequence: H$_2$N-Gly-Glu-Pro-Pro-Pro-Gly-Lys-Pro-Ala-Asp-Asp-Ala-Gly-Leu-Val-- . . . —COOH | Antiulcer Hepatoprotective Vulnerary Anti-inflammatory Antiparkinsonian Urological |
| 39 | nesiritide citrate | BNP | SPKMVQGSGCFGRKMDRISSSSGLGCKVLRRH | Cardiostimulant Vasodilator, coronary |
| 113-141 | neurotrophic factors | | U.S. Pat. No. 5,545,719: AspLeuGlnValPheVal; GlyGluLysLysAsp; AlaThrHisGluSer; CysLeuProValSerGly; LeuProValSerGlySer; ProCysHisAlaProPro; GlyGlyHisAspLeuGluSerGly; AspAspLeuGlnValPhe 15 ProLeuThrSerGly 15 LeuIleHisPheGluGluGlyVal 15 (2) INFORMATION FOR SEQ ID NO: 11: (i) SEQUENCE CHARACTERISTICS: (A) LENGTH: 7 amino acids (B) TYPE: amino acid (D) TOPOLOGY: linear (ii) MOLECULE TYPE: peptide (v) FRAGMENT TYPE: internal (xi) SEQUENCE DESCRIPTION: SEQ ID NO: 11: GlyGluPheSerTyrAspSer 15 (2) INFORMATION FOR SEQ ID NO: 12: (i) SEQUENCE CHARACTERISTICS: (A) LENGTH: 7 amino acids (B) TYPE: amino acid (D) TOPOLOGY: linear (ii) MOLECULE TYPE: peptide (v) FRAGMENT TYPE: internal (xi) SEQUENCE DESCRIPTION: SEQ ID NO: 12: HisAlaProProLeuThrSer 15 (2) INFORMATION FOR SEQ ID NO: 13: (i) SEQUENCE CHARACTERISTICS: (A) LENGTH: 7 amino acids (B) TYPE: amino acid (D) TOPOLOGY: linear (ii) MOLECULE TYPE: peptide (v) FRAGMENT TYPE: internal (xi) SEQUENCE DESCRIPTION: SEQ ID NO: 13: AspLeuGluSerGlyGluPhe 15 (2) INFORMATION FOR SEQ ID NO: 14: (i) SEQUENCE CHARACTERISTICS: (A) LENGTH: 8 amino acids (B) TYPE: amino acid (D) TOPOLOGY: linear (ii) MOLECULE TYPE: peptide (v) FRAGMENT TYPE: internal (xi) SEQUENCE DESCRIPTION: SEQ ID NO: 14: GlyGluPheSerValCysAspSer 15 (2) INFORMATION FOR SEQ ID NO: 15: (i) SEQUENCE CHARACTERISTICS: (A) LENGTH: 10 amino acids (B) TYPE: amino acid (D) TOPOLOGY: linear (ii) MOLECULE TYPE: peptide (v) FRAGMENT TYPE: internal (xi) SEQUENCE DESCRIPTION: SEQ ID NO: 15: LysLysGlyGluPheSerValAlaAspSer 1510 (2) INFORMATION FOR SEQ ID NO: 16: (i) SEQUENCE CHARACTERISTICS: (A) LENGTH: 9 amino acids (B) TYPE: amino acid (D) TOPOLOGY: linear (ii) MOLECULE TYPE: peptide (v) FRAGMENT TYPE: internal (xi) SEQUENCE DESCRIPTION: SEQ ID NO: 16: LysLysGlyGluPheTyrCysSerArg 15 (2) INFORMATION FOR SEQ ID NO: 17: (i) SEQUENCE | Cognition enhancer Neuroprotective |

TABLE 1-continued

This table lists the SEQ ID NOs., names, sequences, and known or suspected therapeutic activities of various peptides described herein. The SEQ ID NOs. 1-301 describe sequences that are required to be provided with the Sequence Listing and are therefore appended with the instant Specification. In some instances, these peptides contain features that are either inconsistent with or not amenable to inclusion in the Sequence Listing. For example, a sequence with less than four-amino acids; a sequence with a D-amino acid; or certain modification that cannot be described in the Sequence Listing presently, and therefore are not provided in the Sequence Listing. However, for the ease of use and description, a SEQ ID NO. has been provided to these peptides (i.e., SEQ ID NOs: 302-469).

| SEQ ID NO: | Name | Family | Sequence and/or other Identifying Information | Therapeutic Activity |
|---|---|---|---|---|
| | | | CHARACTERISTICS: (A) LENGTH: 13 amino acids (B) TYPE: amino acid (D) TOPOLOGY: linear (ii) MOLECULE TYPE: peptide (v) FRAGMENT TYPE: internal (xi) SEQUENCE DESCRIPTION: SEQ ID NO: 17: GlyLeuArgValArgValTrpAsnGlyLysPheProLys 1510 (2) INFORMATION FOR SEQ ID NO: 18: (i) SEQUENCE CHARACTERISTICS: (A) LENGTH: 16 amino acids (B) TYPE: amino acid (D) TOPOLOGY: linear (ii) MOLECULE TYPE: peptide (v) FRAGMENT TYPE: internal (xi) SEQUENCE DESCRIPTION: SEQ ID NO: 18: GlyValAlaPheGluGluAlaProAspAspHisSerPheLeuPhe 151015 (2) INFORMATION FOR SEQ ID NO: 19: (i) SEQUENCE CHARACTERISTICS: (A) LENGTH: 7 amino acids (B) TYPE: amino acid (D) TOPOLOGY: linear (ii) MOLECULE TYPE: peptide (v) FRAGMENT TYPE: internal (xi) SEQUENCE DESCRIPTION: SEQ ID NO: 19: GlyGlyHisAspLeuSerGly 15 (2) INFORMATION FOR SEQ ID NO: 20: (i) SEQUENCE CHARACTERISTICS: (A) LENGTH: 8 amino acids (B) TYPE: amino acid (D) TOPOLOGY: linear (ii) MOLECULE TYPE: peptide (v) FRAGMENT TYPE: internal (xi) SEQUENCE DESCRIPTION: SEQ ID NO: 20: GlyGlyHisAspLeuGluSerGly 15 (2) INFORMATION FOR SEQ ID NO: 21: (i) SEQUENCE CHARACTERISTICS: (A) LENGTH: 14 amino acids (B) TYPE: amino acid (D) TOPOLOGY: linear (ii) MOLECULE TYPE: peptide (v) FRAGMENT TYPE: internal (xi) SEQUENCE DESCRIPTION: SEQ ID NO: 21: GlyGlyHisAspLeuGluSerGlyGluPheSerTyrAspSer 1510 (2) INFORMATION FOR SEQ ID NO: 22: (i) SEQUENCE CHARACTERISTICS: (A) LENGTH: 14 amino acids (B) TYPE: amino acid (D) TOPOLOGY: linear (ii) MOLECULE TYPE: peptide (v) FRAGMENT TYPE: internal (xi) SEQUENCE DESCRIPTION: SEQ ID NO: 22: GlyGlySerAspLeuSerGlyGluPheSerValCysAspSer 1510 (2) INFORMATION FOR SEQ ID NO: 23: (i) SEQUENCE CHARACTERISTICS: (A) LENGTH: 15 amino acids (B) TYPE: amino acid (D) TOPOLOGY: linear (ii) MOLECULE TYPE: peptide (v) FRAGMENT TYPE: internal (xi) SEQUENCE DESCRIPTION: SEQ ID NO: 23: GlyGlySerAspLeuSerGlyGlyGluPheSerValCysAspSer 151015 (2) INFORMATION FOR SEQ ID NO: 24: (i) SEQUENCE CHARACTERISTICS: (A) LENGTH: 15 amino acids (B) TYPE: amino acid (D) TOPOLOGY: linear (ii) MOLECULE TYPE: peptide (v) FRAGMENT TYPE: internal (xi) SEQUENCE DESCRIPTION: SEQ ID NO: 24: GlyGlySerAspLeuSerGlyGlyGluPheSerValAlaAspSer 151015 (2) INFORMATION FOR SEQ ID NO:25: (i) SEQUENCE CHARACTERISTICS: (A) LENGTH: 14 amino acids (B) TYPE: amino acid (D) TOPOLOGY: linear (ii) MOLECULE TYPE: peptide (v) FRAGMENT TYPE: internal (xi) SEQUENCE DESCRIPTION: SEQ ID NO: 25: GlyGlySerAspLeuSerGlyGluPheSerValAlaAspSer 1510 (2) INFORMATION FOR SEQ ID NO: 26: (i) SEQUENCE CHARACTERISTICS: (A) LENGTH: 6 amino acids (B) TYPE: amino acid (D) TOPOLOGY: linear (ii) MOLECULE TYPE: peptide (v) FRAGMENT TYPE: internal (xi) SEQUENCE DESCRIPTION: SEQ ID NO: 26: GluThrLeuGlnPheArg 15 (2) INFORMATION FOR SEQ ID NO: 27: (i) SEQUENCE CHARACTERISTICS: (A) LENGTH: 8 amino acids (B) TYPE: amino acid (D) TOPOLOGY: linear (ii) MOLECULE TYPE: peptide (v) FRAGMENT TYPE: internal (xi) SEQUENCE DESCRIPTION: SEQ ID NO: 27: LysLysGluThrLeuGlnPheArg 15 (2) INFORMATION FOR SEQ ID NO: 28: (i) SEQUENCE CHARACTERISTICS: (A) LENGTH: 8 amino acids (B) TYPE: amino acid (D) TOPOLOGY: linear (ii) MOLECULE TYPE: peptide (v) FRAGMENT TYPE: internal (xi) SEQUENCE DESCRIPTION: SEQ ID NO: 28: | |

TABLE 1-continued

This table lists the SEQ ID NOs., names, sequences, and known or suspected therapeutic activities of various peptides described herein. The SEQ ID NOs. 1-301 describe sequences that are required to be provided with the Sequence Listing and are therefore appended with the instant Specification. In some instances, these peptides contain features that are either inconsistent with or not amenable to inclusion in the Sequence Listing. For example, a sequence with less than four-amino acids; a sequence with a D-amino acid; or certain modification that cannot be described in the Sequence Listing presently, and therefore are not provided in the Sequence Listing. However, for the ease of use and description, a SEQ ID NO. has been provided to these peptides (i.e., SEQ ID NOs: 302-469).

| SEQ ID NO: | Name | Family | Sequence and/or other Identifying Information | Therapeutic Activity |
|---|---|---|---|---|
| | | | GluThrLeuGlnPheArgLysLys 15 (2) INFORMATION FOR SEQ ID NO: 29: (i) SEQUENCE CHARACTERISTICS: (A) LENGTH: 9 amino acids (B) TYPE: amino acid (D) TOPOLOGY: linear (ii) MOLECULE TYPE: peptide (v) FRAGMENT TYPE: internal (xi) SEQUENCE DESCRIPTION: SEQ ID NO: 29: LysAlaSerThrThrThrAsnTyrThr 15 | |
| 357 | nifalatide | | L-Prolinamide, L-tyrosyl-4-(methylsulfinyl)-D-2-aminobutanoylglycyl-4-nitro-L-phenylalanyl- | Antidiarrhoeal Analgesic, other |
| 358 | Org-2766 | | L-Phenylalanine, 4-(methylsulfonyl)-L-2-aminobutanoyl-L-alpha-glutamyl-L-histidyl-L-phenylalanyl-D-lysyl- | ACTH Symptomatic antidiabetic Radio/chemoprotective Neurological |
| 359 | Org-30035 | | L-Phenylalanine, glycylglycyl-L-phenylalanyl-4-(methylsulfonyl)-L-2-aminobutanoyl-D-lysyl- | Neuroleptic Anxiolytic |
| 360 | octreotide | somatostatin | L-Cysteinamide, D-phenylalanyl-L-cysteinyl-L-phenylalanyl-D-tryptophyl-L-lysyl-L-threonyl-N-[2-hydroxy-1-(hydroxymethyl)propyl]-, cyclic (2-7)-disulfide, [R-(R*,R*)]-; L-Cysteinamide, D-phenylalanyl-L-cysteinyl-L-phenylalanyl-D-tryptophyl-L-lysyl-L-threonyl-N-(2-hydroxy-1-(hydroxymethyl)propyl)-, cyclic (2-7)-disulfide, (R-(R*,R*))- | Acromegaly Antidiarrhoeal Anticancer, hormonal |
| 142 | osteogenic growth peptide | | Glycine, L-alanyl-L-leucyl-L-lysyl-L-arginyl-L-glutaminylglycyl-L-arginyl-L-threonyl-L-leucyl-L-tyrosylglycyl-L-phenylalanylglycyl- | Osteoporosis treatment |
| 143 | P-113 | | Angiotensin II, 1-(N-methylglycine)-5-L-valine-8-L-alanine-[CAS]; (Sar(1),Ala(8))ANGII; (Sar1,Val5,Ala8)Angiotensin II; 1 Sar 8 Ala Angiotensin II; 1 Sarcosine 8 Alanine Angiotensin II; 1-Sar-8-Ala Angiotensin II; 1-Sar-8-Ala-angiotensin II; 1-Sarcosine-8-Alanine Angiotensin II; Acetate, Hydrated Saralasin; Angiotensin II, 1-Sar-8-Ala; Angiotensin II, 1-Sarcosine-8-Alanine; Anhydrous Saralasin Acetate; Hydrated Saralasin Acetate; P-113; P-113 Acetate; Sar Arg Val Tyr Val His Pro Ala; Sar-Arg-Val-Tyr-Val-His-Pro-Ala; Saralasin Acetate; Saralasin Acetate, Anhydrous; Saralasin Acetate, Hydrated; angiotensin II, Sar(1)-Ala(8)-; angiotensin II, sarcosyl(1)-alanine(8)- | Stomatological Antibacterial, other Antifungal |
| 361 | PACAP 27 | | Pituitary adenylate cyclase-activating peptide-27 | Antiviral, anti-HIV |
| 362 | PAPP | | N-(dibenzyloxyphosphophionyl)-L-alanyl-L-prolyl-L-proline | Antihypertensive, other |
| 363 | PD-83176 | | CBZ-his-tyr(OBn)-ser(OBn)-trp-D-ala-NH$_2$ | Anticancer, other |
| 364 | PD-122264 | | N-[(1,1-dimethylethoxy)carbonyl]-alpha-methyltryptophyl-L-phenylalaninamide | Anorectic/Antiobesity Analgesic, other |
| 365 | PD-132002 | | DL-Serinamide, N-(4-morpholinylsulfonyl)-L-phenylalanyl-N-[1-(cyclohexylmethyl)-2,3-dihydroxy-5-methylhexyl]-O-methyl-3-oxo-, [1S-(1R*,2S*,3R*)]- | Antihypertensive, renin system |
| 144 | Penetratin | | U.S. Pat. Nos. 5,888,762 and 6,080,762; PCT Pub. Nos. WO/2000/29427 and WO/2000/01417: NH2-Arg Lys Arg Gly Arg Gln Thr Tyr Thr Arg Tyr Gln Thr Leu Glu Leu Glu Lys Glu Phe His Phe Asn Arg Tyr Leu Thr Arg Arg Arg Arg Ile Glu Ile Ala His Ala Leu Cys Leu Thr Glu Arg Gln Ile Lys Ile Trp Phe Gln Asn Arg Arg Met Lys Trp Lys Lys Glu Asn-COOH. | Formulation technology |
| 366 | PL-030 | | Glycinamide, L-tyrosyl-L-prolyl-N-methyl-L-phenylalanyl-D-prolyl- | Analgesic, other |
| 367 | POL-443 | | Z-prolyl-leucyl-tryptophan | Antihypertensive, renin system |
| 368 | POL-509 | | L-Tryptophan, N-[N-(5-oxo-L-prolyl)-L-leucyl]-, methyl ester- | Immunostimulant, other |
| 369 | PPA | | D-phenylalanine-L-proline-L-arginylchloromethane | Anticoagulant Diagnostic Antithrombotic |
| 145 | PR-39 | | L-Prolinamide, L-arginyl-L-arginyl-L-arginyl-L-prolyl-L-arginyl-L-prolyl-L-prolyl-L-tyrosyl-L-leucyl-L-prolyl-L-arginyl-L-prolyl-L-arginyl-L-prolyl-L-prolyl-L-prolyl-L-phenylalanyl-L-phenylalanyl-L-prolyl-L-prolyl-L-arginyl-L-leucyl-L-prolyl-L-prolyl-L-arginyl-L-isoleucyl-L-prolyl-L-prolylglycyl-L-phenylalanyl-L-prolyl-L-prolyl-L-arginyl-L-phenylalanyl-L-prolyl-L-prolyl-L-arginyl-L-phenylalanyl- | Antibacterial, other |

TABLE 1-continued

This table lists the SEQ ID NOs., names, sequences, and known or suspected therapeutic activities of various peptides described herein. The SEQ ID NOs. 1-301 describe sequences that are required to be provided with the Sequence Listing and are therefore appended with the instant Specification. In some instances, these peptides contain features that are either inconsistent with or not amenable to inclusion in the Sequence Listing. For example, a sequence with less than four-amino acids; a sequence with a D-amino acid; or certain modification that cannot be described in the Sequence Listing presently, and therefore are not provided in the Sequence Listing. However, for the ease of use and description, a SEQ ID NO. has been provided to these peptides (i.e., SEQ ID NOs: 302-469).

| SEQ ID NO: | Name | Family | Sequence and/or other Identifying Information | Therapeutic Activity |
|---|---|---|---|---|
| 146 | tigapotide triflutate | | L-Threonine, L-alpha-glutamyl-L-tryptophyl-L-glutaminyl-L-threonyl-L-alpha-aspartyl-L-asparaginyl-S-[(acetylamino)methyl]-L-cysteinyl-L-alpha-glutamyl-L-threonyl-S-[(acetylamino)methyl]-L-cysteinyl-L-threonyl-S-[(acetylamino)methyl]-L-cysteinyl-L-tyrosyl-L-alpha-glutamyl-, mono(trifluoroacetate) | Anticancer, other |
| 370 | PT-14 | | L-Lysinamide, N-acetyl-L-norleucyl-L-alpha-aspartyl-L-histidyl-D-phenylalanyl-L-arginyl-L-tryptophyl-, cyclic (2-7)-peptide | Male sexual dysfunction Female sexual dysfunction |
| 147 | PT-5 | somatostatin | gi\|21619156\|gb\|AAH32625.1\| Somatostatin [Homo sapiens] MLSCRLQCALAALSIVLALGCVTGAPSDPRLRQFLQK SLAAAAGKQELAKYFLAELLSEPNQTENDALEPEDLS QAAEQDEMRLELQRSANSNPAMAPRERKAGCKNFF WKTFTSC | Anticancer, other |
| 148 | semparatide | PTHrP | gi\|131542\|sp\|P12272.1\|PTHR_HUMAN Parathyroid hormone-related protein precursor (PTH-rP) (PTHrP) [Contains: PTHrP[1-36]; PTHrP[38-94]; Osteostatin (PTHrP[107-139])] MQRRLVQQWSVAVFLLSYAVPSCGRSVEGLSRRLKR AVSEHQLLHDKGKSIQDLRRRFFLHHLIAEIHTAEIRA TSEVSPNSKPSPNTKNHPVFGSDDEGRYLTQETNKVE TYKEQPLKTPGKKKKGKPGKRKEQEKKKRRTRSAWL DSGVTGSGLEGDHLSDTSTTSLELDSRRH | Hormone Osteoporosis treatment |
| 149 | parathyroid hormone fragments | PTH | SVSEIQLMHNLGKHLNSMERVEWLRKKLQDVHNF | Osteoporosis treatment |
| 150 | enfuvirtide | | L-Phenylalaninamide, N-acetyl-L-tyrosyl-L-threonyl-L-seryl-L-leucyl-L-isoleucyl-L-histidyl-L-seryl-L-leucyl-L-isoleucyl-L-alpha-glutamyl-L-alpha-glutamyl-L-seryl-L-glutaminyl-L-asparaginyl-L-glutaminyl-L-glutaminyl-L-alpha-glutamyl-L-lysyl-L-asparaginyl-L-alpha-glutamyl-L-glutaminyl-L-alpha-glutamyl-L-leucyl-L-leucyl-L-alpha-glutamyl-L-leucyl-L-alpha-aspartyl-L-lysyl-L-tryptophyl-L-alanyl-L-seryl-L-leucyl-L-tryptophyl-L-asparaginyl-L-tryptophyl- | Antiviral, anti-HIV |
| 151 | pentapeptide 6A | | Ala-Arg-Pro-Ala-Lys | Vasodilator, coronary |
| 371 | pentigetide | | L-Arginine, N2-[1-[N-(N-L-alpha-aspartyl-L-seryl)-L-alpha-aspartyl]-L-prolyl]- | Antiallergic, non-asthma Ophthalmological Antiasthma |
| 372 | peptide analogues | | N1,N3-bis(2,3-dihydroxypropyl)-2,4,6-triiodo-5-(2-methoxyacetamido)-N1-methylisophthalamide | Ophthalmological Antiarthritic, other Antiulcer Antihypertensive, other Multiple sclerosis treatment COPD treatment |
| 373 | peptide G | | [Arg(6),D-Trp(7,9),MePhe(8)]substance P | Anticancer, other |
| 374 | peptide T analogue | | D-Ala1-peptide T | Antiviral, anti-HIV |
| 375 | peptide T | | L-Threonine, N-[N-[N2-[N-[N-[N-(N-L-alanyl-L-seryl)-L-threonyl]-L-threonyl]-L-threonyl]-L-asparaginyl]-L-tyrosyl]- | Analgesic, other Antiviral, other Antiarthritic, other GI inflammatory/bowel disorders Anti-inflammatory |
| 152 | pramlintide | | 1,2-Dithia-5,8,11,14,17-pentaazacycloeicosane, cyclic peptide derivative U.S. Pat. No. 5,998,367 gi\|10066209\|gb\|AAE39671.1\| Sequence 1 from patent U.S. Pat. No. 5,998,367 KCNTATCATQRLANFLVHSSNNFGAILSSTNVGSNTY; | Antidiabetic Anorectic/Antiobesity |
| 376 | pranlukast | | Benzamide, N-[4-oxo-2-(1H-tetrazol-5-yl)-4H-1-benzopyran-8-yl]-4-(4-phenylbutoxy)-; 8-(4 (4-phenylbutoxy)benzoyl)amino-2-(tetrazol-5'-yl)-4-oxo-4H-1-benzopyran | Antiasthma Antiallergic, non-asthma |

TABLE 1-continued

This table lists the SEQ ID NOs., names, sequences, and known or suspected therapeutic activities of various peptides described herein. The SEQ ID NOs. 1-301 describe sequences that are required to be provided with the Sequence Listing and are therefore appended with the instant Specification. In some instances, these peptides contain features that are either inconsistent with or not amenable to inclusion in the Sequence Listing. For example, a sequence with less than four-amino acids; a sequence with a D-amino acid; or certain modification that cannot be described in the Sequence Listing presently, and therefore are not provided in the Sequence Listing. However, for the ease of use and description, a SEQ ID NO. has been provided to these peptides (i.e., SEQ ID NOs: 302-469).

| SEQ ID NO: | Name | Family | Sequence and/or other Identifying Information | Therapeutic Activity |
|---|---|---|---|---|
| 3 | proinsulin | proinsulin | gi\|59036749\|gb\|AAW83741.1\| proinsulin [*Homo sapiens*] MALWMRLLPLLALLALWGPDPAAAFVNQHLCGSHL VEALYLVCGERGFFYTPKTRREAEDLQVGQVELGGG PGAGSLQPLALEGSLQKRGIVEQCCTSICSLYQLENYC N | Antidiabetic |
| 377 | protirelin | TRH | L-Prolinamide, 5-oxo-L-prolyl-L-histidyl-; 2-Nle-3-Prot-protirelin; TRH, Nle(2)-Prot(3)-; pyroglutamyl-norleucyl-proline thioamide | Releasing hormone Diagnostic |
| 378 | protirelin | TRH | prolinamide, 5-oxo-L-prolyl-L-histidyl- | Releasing hormone Cognition enhancer |
| 153 | Ro-25-1553 | | L-Threoninamide, N-acetyl-L-histidyl-L-seryl-L-alpha-aspartyl-L-alanyl-L-valyl-L-phenylalanyl-L-threonyl-L-alpha-glutamyl-L-asparaginyl-L-tyrosyl-L-threonyl-L-lysyl-L-leucyl-L-arginyl-L-lysyl-L-glutaminyl-L-norleucyl-L-alanyl-L-alanyl-L-lysyl-L-lysyl-L-tyrosyl-L-leucyl-L-asparaginyl-L-alpha-aspartyl-L-leucyl-L-lysyl-L-lysylglycylglycyl-, (25-21)-lactam | Antiasthma Anti-inflammatory |
| 379 | RWJ-51438 | | N-methylphenylalanyl-N-(4-((aminoiminomethyl)amino)-1-(((6-carboxy-2-benzothiazolyl)carbonyl)butyl)prolinamide | Antithrombotic |
| 380 | TRH | TRH | L-Prolinamide, 5-oxo-L-prolyl-L-histidyl-3,3-dimethyl-; pyroGlu-His-Pro-NH$_2$ (or 5-oxo-L-prolyl-L-histidyl-L-prolinamide) | Diagnostic Thyroid hormone Releasing hormone |
| 154 | renin inhibitors | | Boc-Leu-Lys-Arg-Met-Pro-OMe | Antihypertensive, |
| 381 | romurtide | | L-Lysine, N2-[N2-[N-(N-acetylmuramoyl)-L-alanyl]-D-alpha-glutaminyl]-N6-(1-oxooctadecyl)-; L-Lysine, N2-(N2-(N-(N-acetylmuramoyl)-L-alanyl)-D-alpha-glutaminyl)-N6-(1-oxooctadecyl)- | Radio/chemoprotective Immunostimulant, other |
| 382 | S-17162 | | L-Tryptophan, N-[(2,3-dihydroxypropoxy)hydroxyphosphinyl]-L-leucyl-, disodium salt | Urological |
| 383 | S-2441 | | L-Argininamide, D-prolyl-L-phenylalanyl-N-heptyl- | Antimigraine Antigout Septic shock treatment |
| 384 | SDZ-CO-611 | somatostatin | L-Cysteinamide, N-(1-deoxy-4-O-.alpha.-D-glucopyranosyl-D-fructopyranos-1-yl)-D-phenylalanyl-L-cysteinyl-L-phenylalanyl-D-tryptophyl-L-lysyl-L-threonyl-N-[2-hydroxy-1-(hydroxymethyl)propyl]-, cyclic (2.fwdarw.7)-disulfide, [R-(R*,R*)]- | Somatostatin |
| 385 | SK&F-101926 | | L-Argininamide, O-ethyl-N-[(1-mercaptocyclohexyl)acetyl]-D-tyrosyl-L-phenylalanyl-L-valyl-L-asparaginyl-L-cysteinyl-L-prolyl-, cyclic (1-5)-disulfide | Antihypertensive, diuretic |
| 386 | SK&F-110679 | | His-D-Trp-Ala-Trp-D-Phe-LysNH$_2$ | Releasing hormone Vulnerary |
| 387 | edotreotide | | [N-[2[4,7-Bis[(carboxy-kappaO)methyl]-10-(carboxymethyl)-1,4,7,10-tetraazacyclododec-1-yl-kappaN1,kappaN4,kappaN10]acetyl]-D-phenylalanyl-L-cysteinyl-L-tyrosyl-D-tryptophyl-L-lysyl-L-threonyl-L-cysteinyl-L-threoninol cyclic (2-7)-disulfidato(3-)]yttrium | Anticancer, hormonal |
| 155 | SP-1 | | pGlu-Glu-Asp-Cys-Lys | Anticancer, other |
| 156 | SPAAT | | L-Lysine, L-methionyl-L-phenylalanyl-L-leucyl-L-alpha-glutamyl-L-alanyl-L-isoleucyl-L-prolyl-L-methionyl-L-seryl-L-isoleucyl-L-prolyl-L-prolyl-L-alpha-glutamyl-L-valyl-L-lysyl-L-phenylalanyl-L-asparaginyl-L-lysyl-L-prolyl-L-phenylalanyl-L-valyl-L-phenylalanyl-L-leucyl-L-methionyl-L-isoleucyl-L-alpha-glutamyl-L-glutaminyl-L-asparaginyl-L-threonyl-L-lysyl-L-seryl-L-prolyl-L-leucyl-L-phenylalanyl-L-methionylglycyl-L-lysyl-L-valyl-L-valyl-L-asparaginyl-L-prolyl-L-threonyl-L-glutaminyl- | COPD treatment |
| 388 | SR-41476 | | Z-Tyr-Val-Sta-Ala-Sta-OMe | Antiviral, anti-HIV |
| 389 | SR-42128 | | 1-[N-(3-methyl-1-oxobutyl)-L-phenylalanine]-2-L-norleucine- | Antihypertensive, renin system |
| 157 | SR-42654 | | isoval-phe-norleu-sta-ala-sta-lys | Antihypertensive, renin system |
| 147 | SRIF-A | somatostatin | gi\|21619156\|gb\|AAH32625.1\| Somatostatin [*Homo sapiens*] MLSCRLQCALAALSIVLALGCVTGAPSDPRLRQFLQK SLAAAAGKQELAKYFLAELLSEPNQTENDALEPEDLS QAAEQDEMRLELQRSANSNPAMAPRERKAGCKNFF WKTFTSC 8-D-tryptophan-14-D-cysteinesomatostatin (sheep) | Somatostatin Haemostatic Alimentary/Metabolic, other |

TABLE 1-continued

This table lists the SEQ ID NOs., names, sequences, and known or suspected therapeutic activities of various peptides described herein. The SEQ ID NOs. 1-301 describe sequences that are required to be provided with the Sequence Listing and are therefore appended with the instant Specification. In some instances, these peptides contain features that are either inconsistent with or not amenable to inclusion in the Sequence Listing. For example, a sequence with less than four-amino acids; a sequence with a D-amino acid; or certain modification that cannot be described in the Sequence Listing presently, and therefore are not provided in the Sequence Listing. However, for the ease of use and description, a SEQ ID NO. has been provided to these peptides (i.e., SEQ ID NOs: 302-469).

| SEQ ID NO: | Name | Family | Sequence and/or other Identifying Information | Therapeutic Activity |
|---|---|---|---|---|
| 158 | calcitonin | calcitonin | CSNLSTCVLGKLSQELHKLQTYPRTNTGSGTP | Osteoporosis treatment |
| 390 | salmon calcitonin | calcitonin | 11,18-Arg-14-Lys-salmon calcitonin; 11,18-arginyl-14-lysine-salmon calcitonin; Arg-Lys-Arg-CT; calcitonin, salmon, arginyl(11,18)-lysine(14)- | Osteoporosis treatment |
| 159 | sermorelin | | Tyr-Ala-Asp-Ala-Ile-Phe-Thr-Asn-Ser-Tyr-Arg-Lys-Val-Leu-Gly-Gln-Leu-Ser-Ala-Arg-Lys-Leu-Leu-Gln-Asp-Ile-Met-Ser-Arg-NH$_2$ | Idiopathic growth hormone deficiency Imaging agent |
| 391 | saralasin acetate | | 1-Sar-8-Ala-angiotensin; Angiotensin II, 1-(N-methylglycine)-5-L-valine-8-L-alanine- | Antihypertensive, renin system |
| 160 | secretin | | His-Ser-Asp-Gly-Thr-Phe-OMe; histidyl-seryl-aspartyl-glycyl-threonyl-phenylalanine-O-methyl- | Haemostatic; pancreatic dysfunction (diagnostic), asthma, COPD, others |
| 159 | sermorelin acetate | | Tyr-Ala-Asp-Ala-Ile-Phe-Thr-Asn-Ser-Tyr-Arg-Lys-Val-Leu-Gly-Gln-Leu-Ser-Ala-Arg-Lys-Leu-Leu-Gln-Asp-Ile-Met-Ser-Arg-NH$_2$ | Releasing hormone Diagnostic |
| 159 | sermorelin | | Tyr-Ala-Asp-Ala-Ile-Phe-Thr-Asn-Ser-Tyr-Arg-Lys-Val-Leu-Gly-Gln-Leu-Ser-Ala-Arg-Lys-Leu-Leu-Gln-Asp-Ile-Met-Ser-Arg-NH$_2$ | |
| 161 | sinapultide | | L-Lysine, L-lysyl-L-leucyl-L-leucyl-L-leucyl-L-leucyl-L-lysyl-L-leucyl-L-leucyl-L-leucyl-L-leucyl-L-lysyl-L-leucyl-L-leucyl-L-leucyl-L-leucyl-L-lysyl-L-leucyl-L-leucyl-L-leucyl-L-leucyl- | Lung Surfactant |
| 162 | sleep inducing peptide | | Trp-Ala-Gly-Gly-Asp-Ala-Ser-Gly-Glu | Hypnotic/Sedative Dependence treatment |
| 163 | somatoliberin | | gi\|11034841\|ref\|NP_066567.1\| growth hormone releasing hormone preproprotein [Homo sapiens] MPLWVFFFVILTLSNSSHCSPPPPLTLRMRRYADAIFT NSYRKVLGQLSARKLLQDIMSRQQGESNQERGARAR LGRQVDSMWAEQKQMELESILVALLQKHSRNSQG | Growth hormone Releasing hormone |
| 164 | PTR-3173 | somatostatin | Cyclic[(R)-βMeNphe-Phe-DTrp-Lys-Thr-Phe], MPLWVFFFVILTLSNSSHCSPPPPLTLRMRRYADAIFT NSYRKVLGQLSARKLLQDIMSRQQGESNQERG | Acoegaly Symptomatic antidiabetic Ophthalmological Urological Anticancer, hormonal |
| 165 | somatostatin analogue | somatostatin | des-(Ala1,Gly2)-(D-Trp8,D-Asu(3,14))-somatostatin, ARARLGRQVDSMWAEQKQMELESILVALLQKHSRNS QG | Acromegaly Antidiabetic Diagnostic |
| 392 | somatostatin analogues | somatostatin | cyclo-(N-Me-Ala-Tyr-D-Trp-Lys-Val-Phe)-somatostatin | Acromegaly Antidiabetic |
| 393 | somatostatin | somatostatin | 3,14-Dicarbasomatostatin, 1-de-L-alanine-2-deglycine-3-butanoic acid-11-L-tyrosine- | Acromegaly |
| 394 | somatostatin | somatostatin | 3,14-Dicarbasomatostatin, 1-de-L-alanine-2-deglycine-3-butanoic acid-11-L-tyrosine- | Acromegaly |
| 395 | syndyphalin | | Glycinamide, L-tyrosyl-4-(methylsulfinyl)-D-2-aminobutanoyl-N-methyl-N-(2-phenylethyl)- | Analgesic, other |
| 166 | synthetic peptide BPC | | gi\|109948285\|ref\|NP_001035971.1\| poly(A) binding protein, cytoplasmic 1-like 2B [Homo sapiens] MASLYVGDLHPEVTEAMLYEKFSPAGPILSIRICRDKI TRRSLGYAYVNYQQPVDAKRALETLNFDVIKG RPVRIMWSQRDPSLRKSGVGNVFIKNLGKTIDNKALY NIFSAFGNILSCKVACDEKGPKGYGFVHFQKQE SAERAIDVMNGMFLNYRKIFVGRFKSHKEREAERGA WARQSTSADVKDFEEDTDEEATLR | Antiulcer Hepatoprotective Vulnerary Anti-inflammatory Antiparkinsonian Musculoskeletal |
| 167 | T22 | | L-Argininamide, L-arginyl-L-arginyl-L-tryptophyl-L-cysteinyl-L-tyrosyl-L-arginyl-L-lysyl-L-cysteinyl-L-tyrosyl-L-lysylglycyl-L-tyrosyl-L-cysteinyl-L-tyrosyl-L-arginyl-L-lysyl-L-cysteinyl-, cyclic (4-17),(8-13)-bis(disulfide) | Antiviral, anti-HIV |
| 396 | Tc-99m depreotide | | Technetium-99Tc, (cyclo(L-homocysteinyl-N-methyl-L-phenylalanyl-L-tyrosyl-D-tryptophyl-L-lysyl-L-valyl) (1-1')-thioether with 3-((mercaptoacetyl)amino)-L-alanyl-L-lysyl-L-cysteinyl-L-lysinamidato(3-))oxo-, (SP-5-24)- | Imaging agent |
| 397 | Tc-99m-P280 | | 13,13'-[Oxybis[methylene(2,5-dioxo-1,3-pyrrolidinediyl)]]bis[N-(mercaptoacetyl)-D-tyrosyl-S-(3-aminopropyl)-L-cysteinylglycyl-L-alpha-aspartyl-L-cysteinylglycylglycyl-S-[(acetylamino)mehtyl]-L-cysteinylglycyl-S-[(acetylamino)methyl-L-cysteinylglycylglycyl-L-cysteinamide], cyclic (1 --> 5), (1' --> 5'), -bis(sulfide) | Imaging agent Antithrombotic |
| 398 | TEI-1345 | | (7E)-8-(2-naphthyl)-5,6-trans-5,6-methano-7-octenyl 3-(3,4-dimethoxyphenyl)-2-propenoate | Anti-inflammatory |

TABLE 1-continued

This table lists the SEQ ID NOs., names, sequences, and known or suspected therapeutic activities of various peptides described herein. The SEQ ID NOs. 1-301 describe sequences that are required to be provided with the Sequence Listing and are therefore appended with the instant Specification. In some instances, these peptides contain features that are either inconsistent with or not amenable to inclusion in the Sequence Listing. For example, a sequence with less than four-amino acids; a sequence with a D-amino acid; or certain modification that cannot be described in the Sequence Listing presently, and therefore are not provided in the Sequence Listing. However, for the ease of use and description, a SEQ ID NO. has been provided to these peptides (i.e., SEQ ID NOs: 302-469).

| SEQ ID NO: | Name | Family | Sequence and/or other Identifying Information | Therapeutic Activity |
|---|---|---|---|---|
| 168 | THF | | Leu-Glu-Asp-Gly-Pro-Lys-Phe-Leu;leucyl-glutamyl-aspartyl-glycyl-proly-lysyl-phenylalanyl-leucine | Immunomodulator, anti-infective, Immunostimulant, anti-AIDS |
| 169 | Theradigm-HBV | | Dipalmitoyl-Lys-Ser-Ser-Gln-Tyr-Ile-Lys-Ala-Asn-Ser-Lys-Phe-Ile-Gly-Ile-Thr-Glu-Ala-Ala-Ala-Phe-Leu-Pro-Ser-Asp-Phe-Phe-Pro-Ser-Val-OH | Immunomodulator, anti-infective Immunostimulant |
| 80 | tesamorelin acetate | GHRF | gi\|337133\|gb\|AAA52609.1\| growth hormone releasing factor MPLWVFFFVILTLSNSSHCSPPPPLTLRMRRYADAIFT NSYRKVLGQLSARKLLQDIMSRQQGESNQERGARAR LGRQVDSMWAEQKQMELESILVALLQKHRNSQG (3E)-Hex-3-enoylsomatoliberin (human) acetate (salt) | Musculoskeletal, COPD, Hypnotic/Sedative, Immunostimulant, Antidiabetic, Anabolic, Symptomatic antidiabetic, Vulnerary |
| 170 | TP-9201 | | L-Cysteinamide, N-acetyl-L-cysteinyl-L-asparaginyl-L-prolyl-L-arginylglycyl-L-alpha-aspartyl-O-methyl-L-tyrosyl-L-arginyl-, cyclic (1-9)-disulfide | Neuroprotective, Antithrombotic, Antianginal, Cardiovascular |
| 399 | TRH analogues | TRH | pyroGlu-His-Pro-NH2 (or 5-oxo-L-prolyl-L-histidyl-L-prolinamide) | Cognition enhancer |
| 400 | TT-235 | | [β,β-(3-Thiapentamethylene)-β-sulfanylpropionic acid, D-Trp2,Pen6,Arg8]-oxytocin acetate | Labour inhibitor |
| 401 | tabilautide | | L-Lysinamide, 6-carboxy-N6-[N-[N-(1-oxododecyl)-L-alanyl]-D-gamma-glutamyl]-, (S)- | Immunomodulator, anti-infective Radio/chemoprotective Immunostimulant, other |
| 171 and 172 | terlipressin | | N-[N-(N-glycylglycyl)glycyl]-8-L-lysine-; Gly-Gly-Gly-8-Lys-vasopressin; N-(alpha)-glycyl-glycyl-glycyl-8-lysine vasopressin; Gly-Gly-Gly-c[Cys-Tyr-Phe-Gln-Asn-Cys]-Pro-Lys-Gly-NH$_2$; N-(N-(N-glycylglycyl)glycyl)-8-L-lysinevasopressin | Haemostatic; GI bleeding |
| 171 and 172 | terlipressin | | N-[N-(N-glycylglycyl)glycyl]-8-L-lysine-; Gly-Gly-Gly-8-Lys-vasopressin; N-(alpha)-glycyl-glycyl-glycyl-8-lysine vasopressin; Gly-Gly-Gly-c[Cys-Tyr-Phe-Gln-Asn-Cys]-Pro-Lys-Gly-NH$_2$ | Haemostatic; GI bleeding |
| 402 | teverelix | | D-Alaninamide, N-acetyl-3-(2-naphthalenyl)-D-alanyl-4-chloro-D-phenylalanyl-3-(3-pyridinyl)-D-alanyl-L-seryl-L-tyrosyl-N6-(aminocarbonyl)-D-lysyl-L-leucyl-N6-(1-methylethyl)-L-lysyl-L-prolyl- | Anticancer, hormonal Prostate disorders Menstruation disorders Fertility enhancer Male contraceptive |
| 403 | thymopentin | | L-Tyrosine, N-[N-[N-(N2-L-arginyl-L-lysyl)-L-alpha-aspartyl]-L-valyl]-; L-Tyrosine, N-(N-(N-(N2-L-arginyl-L-lysyl)-L-alpha-aspartyl)-L-valyl)- | Immunostimulant, other Immunomodulator, anti-infective |
| 404 | triletide | | L-Histidine, N-[N-(N-acetyl-L-phenylalanyl)-L-phenylalanyl]-, methylester | Antiulcer |
| 405 | tuftsin | | L-Arginine, N2-[1-(N2-L-threonyl-L-lysyl)-L-prolyl]- | Anticancer, immunological Immunostimulant, other |
| 173 | Uroguanylin | | Guanylin (rat reduced), 1-L-glutamine-2-L-glutamic acid-3-L-aspartic acid-6-L-leucine-8-L-isoleucine-9-L-asparagine-10-L-valine- | Alimentary/Metabolic, other Antidiarrhoeal Diagnostic |
| 174 | VIC | | gi\|6681267\|ref\|NP_031929.1\| endothelin 3 [*Mus musculus*] MEPGLWLLLGLTVTSAAGLVPCPQSGDSGRASVSQGP PEAGSERGCEETVAGPGERIVSPTVALPAQPESAGQER APGRSGKQEDKGLPAHHRPRRCTCFTYKDKECVYYC HLDIIWINTPEQTVPYGLSNYRESLRGKRSLGPVPESSQ PSPWTRLRCTCMGADDKACAHFCARTRDVTSYSGRA ERPAAEEMRETGGPRQRLMSRTDKAHRP | Gastroprokinetic |
| 175 | VIP derivative | | gi\|5803023\|ref\|NP_006807.1\| lectin, mannose-binding 2 [*Homo sapiens*] MAAEGWIWRWGWGRRCLGRPGLLGPGPGPTTPLFLL LLLGSVTADITDGNSEHLKREHSLIKPYQGVGSSSMPL WDFQGSTMLTSQYVRLTPDERSKEGSIWNHQPCFLKD WEMHVHFKVHGTGKKNLHGDGIALWYTRDRLVPGP VFGSKDNFHGLAIFLDTYPNDETTERVFPYISVMVNN GSLSYDHSKDGRWTELAGCTADFRNRDHDTFLAVRY SRGRLTVMTDLEDKNEWKNCIDITGVRLPTGYYFGAS AGTGDLSDNHDIISMKLFQLMVEHTPDEESIDWTKIEP SVNFLKSPKDNVDDPTGNFRSGPLTGWRVFLLLLCAL LGIVVCAVVGAVVFQKRQERNKRFY | Antiasthma Vasodilator, peripheral |

TABLE 1-continued

This table lists the SEQ ID NOs., names, sequences, and known or suspected therapeutic activities of various peptides described herein. The SEQ ID NOs. 1-301 describe sequences that are required to be provided with the Sequence Listing and are therefore appended with the instant Specification. In some instances, these peptides contain features that are either inconsistent with or not amenable to inclusion in the Sequence Listing. For example, a sequence with less than four-amino acids; a sequence with a D-amino acid; or certain modification that cannot be described in the Sequence Listing presently, and therefore are not provided in the Sequence Listing. However, for the ease of use and description, a SEQ ID NO. has been provided to these peptides (i.e., SEQ ID NOs: 302-469).

| SEQ ID NO: | Name | Family | Sequence and/or other Identifying Information | Therapeutic Activity |
|---|---|---|---|---|
| 147 | vapreotide, immediate-release | somatostatin | gi\|21619156\|gb\|AAH32625.1\| Somatostatin [Homo sapiens] MLSCRLQCALAALSIVLALGCVTGAPSDPRLRQFLQK SLAAAAGKQELAKYFLAELLSEPNQTENDALEPEDLS QAAEQDEMRLELQRSANSNPAMAPRERKAGCKNFF WKTFTSC L-Tryptophanamide, D-phenylalanyl-L-cysteinyl-L-tyrosyl-D-tryptophyl-L-lysyl-L-valyl-L-cysteinyl-, cyclic (2-7)-disulfide- | Formulation, modified-release, immediate Somatostatin Haemostatic Anticancer, hormonal Antidiarrhoeal GI inflammatory/bowel disorders |
| 406 | Pharmaprojects No. 1269 | | L-Proline, 1-[N-[N-[1-[4-(4-hydroxyphenyl)-1-oxobutyl]-L-prolyl]-.alpha.-methyl-DL-phenylalanyl]glycyl]- | Vasodilator, renal |
| 407 | Pharmaprojects No. 1583 | | N(α)-((3S)-1-oxo-1,2,3,4-tetrahydroisoquinoline-3-carbonyl)-L-histidyl-L-prolinamide | Neuroleptic Antiparkinsonian |
| 408 | Pharmaprojects No. 1626 | | D-2-phenylglycyl-D-2-phenylglycine | Anticancer, immunological Immunostimulant, other |
| 409 | Pharmaprojects No. 1779 | | N-acyl-D-glutamyl-1-meso-diaminopimelyl-1-lysine tripeptide derivatives | Immunomodulator, anti-infective Immunostimulant, other |
| 176 | Pharmaprojects No. 1876 | | Thr-Asp-Ser-Phe-Val-Gly-Leu-Methionylamide | Antihypertensive, other |
| 410 | Pharmaprojects No. 1913 | | L-leucyl-D-methionyl-glucyl-N-(2-adamantyl)-L-phenylalanylamide | Antihypertensive, renin system |
| 177 | Pharmaprojects No. 1939 | | Lys-Pro-Gly-Glu-Pro-Gly-Pro-Lys | Anticoagulant |
| 178-182, 178, 183-185 and 178 | Pharmaprojects No. 2063 | | U.S. Pat. No. 4,461,724 and European Patent No. EP0078228: GSHK; ASHK; ADSHK; LSHK; TSHK; YSHK; GSHKCH₃COOH•H₂O; SAR-SHK; PSHK; (PYR)ESHK; WSHK; GSHK.2TosOH | Antiulcer Antithrombotic |
| 411 | Pharmaprojects No. 2363 | | N-methyl-D-Phe-Pro-Arg-H | Antithrombotic |
| 186 | Pharmaprojects No. 2388 | | N-3-(4-hydroxyphenyl)propionyl-Pro-Hyp-Gly-Ala-Gly | Antiarrhythmic |
| 412 | Pharmaprojects No. 2425 | | Glp-lys-NH₂-L-mandelate | Anticancer, immunological Immunostimulant, other |
| 413 | Pharmaprojects No. 3341 | | D-1-Tiq-Pro-Arg-H-sulfate | Antithrombotic |
| 414 | Pharmaprojects No. 3415 | | (2R,4S,5S,1'S)-5-(t-butoxycarbonyl)amino-4-hydroxy-N-[1'-isopropyl-1'-(4-isopropylcarbonylimidazol-2-yl)]methyl-6-phenyl-2-phenylmethyl-hexanamide | Antiviral, anti-HIV |
| 415 | Pharmaprojects No. 4004 | | Piv-1-Ser-Leu-GABA, and Piv-Ser-Leu-GABA | Neurological |
| 416 | Pharmaprojects No. 4323 | | (1R,4aR,8aR)-1,2,3,4,5,6,7,8-perhydroisoquinolin-1-carbonyl-(L)-prolinyl-(L)-arinine aldehyde | Antithrombotic Anticoagulant |
| 187, and 417 | Pharmaprojects No. 491 | | H-Trp-Ala-Ser-Gly-L-Asn-OH & H-Trp-D-Ala-Ser-Gly-Asp(OH)₂ | Hypnotic/Sedative Antidepressant Neuroprotective |
| 188 | Pharmaprojects No. 4975 | | H₂N-Asp-Ala-Asp-Pro-Arg-Gln-Tyr-Ala-COOH | Anti-inflammatory |
| 418 | Pharmaprojects No. 5200 | | 2-Amino-N-{1-(R)-benzyloxymethyl-2-[4-(morpholine-4-carbonyl)-4-phenyl-piperidin-1-yl]-2-oxo-ethyl}-isobutyramide | Osteoporosis treatment |
| 419 | Pharmaprojects No. 5356 | | 4-chloro-phenylcarbamoyl-thienylalanyl-leucyl-phenylalanine | Anti-inflammatory Anti-infective, other |
| 420 | DMP-444 | | synthetic cyclic pentapeptide (cyclo(D-Val-NMeArg-Gly-Asp-Mamb))with a tethered hydrazinonicotinyl (HYNIC) chelator for radiolabelling with 99mTc | Imaging agent |
| 189 | RIP-3 | | MSCVKLWPSGAPAPLVSIEELENQELVGKGGFGTVFR AQHRKWGYDVAVKIVNSKAISREVKAMASLDNEFVL RLEGVIEKVNWDQDPKPALVTKFMENGSLSGLLQSQ CPRPWPLLCRLLKEVVLGMFYLHDQNPVLLHRDLKPS NVLLDPELHVKLADFGLSTFQGGSQSGTGSGEPGGTL GYLAPELFVNVNRKASTASDVYSFGILMWAVLAGRE VELPTEPSLVYEAVCNRQNRPSLAELPQAGPETPGLEG LKELMQLCWSSEPKDRPSFQECLPKTDEVFQMVENN MNAAVSTVKDFLSQLRSSNRRFSIPESGQGGTEMDGF RRTIENQHSRNDVMVSEWLNKLNLEEPPSSVPKKCPS LTKRSRAQEEQVPQAWTAGTSSDSMAQPPQTPETSTF RNQMPSPTSTGTPSPGPRGNQGAERQGMNWSCRTPEP NPVTGRPLVNIYNCSGVQVGDNNYLTMQQTTALPTW GLAPSGKGRGLQHPPPVGSQEGPKDPEAWSRPQGWY NHSGK | Anticancer, other |

TABLE 1-continued

This table lists the SEQ ID NOs., names, sequences, and known or suspected therapeutic activities of various peptides described herein. The SEQ ID NOs. 1-301 describe sequences that are required to be provided with the Sequence Listing and are therefore appended with the instant Specification. In some instances, these peptides contain features that are either inconsistent with or not amenable to inclusion in the Sequence Listing. For example, a sequence with less than four-amino acids; a sequence with a D-amino acid; or certain modification that cannot be described in the Sequence Listing presently, and therefore are not provided in the Sequence Listing. However, for the ease of use and description, a SEQ ID NO. has been provided to these peptides (i.e., SEQ ID NOs: 302-469).

| SEQ ID NO: | Name | Family | Sequence and/or other Identifying Information | Therapeutic Activity |
|---|---|---|---|---|
| 421 | Pharmaprojects No. 955 | | N-(N-acetyl-1-isoleucyl-L-tyrosyl)-(−)-1-amino-2-(4-hydroxyphenyl)ethylphosphonic acid | Antihypertensive, other |
| 422 | leuprolide | | 6-D-leucine-9-(N-ethyl-L-prolinamide)-10-deglycinamide- | Formulation, modified-release, Anticancer |
| 190 | edratide | | L-glycyl-L-tyrosyl-L-tyrosyl- L-tryptophyl-L-seryl-L-tryptophyl-L-isoleucyl-L-arginyl-L-glutaminyl-Lprolyl-L-prolyl-L-glycyl-L-lysyl-L-glycyl-L-glutamyl-L-glutamyl-L-tryptophyl-L-isoleucyl-L-glycine | Immunosuppressant |
| 423 | Prosaptide TX14(A) | | H-Thr-D-Ala-Leu-Ile-Asp-Asn-Asn-Ala-Thr-Glu-Glu-Ile-Leu-Tyr-OH | Symptomatic antidiabetic Neurological Analgesic, other |
| 8 | GLP-1 | GLP-1 | HGEGTFTSDLSKQMEEEAVRLFIEWLKNGGPSSGAPPPS | Antidiabetic |
| 160 | secretin | | His-Ser-Asp-Gly-Thr-Phe-OMe; histidyl-seryl-aspartyl-glycyl-threonyl-phenylalanine-O-methyl- | Hormone, Diagnostic, GI inflammatory/bowel disorders, Neurological, Neuroleptic |
| 147 | BIM-23190 | somatostatin | gi\|21619156\|gb\|AAH32625.1\| Somatostatin [Homo sapiens] MLSCRLQCALAALSIVLALGCVTGAPSDPRLRQFLQK SLAAAAGKQELAKYFLAELLSEPNQTENDALEPEDLS QAAEQDEMRLELQRSANSNPAMAPRERKAGCKNFF WKTFTSC L-Threoninamide, N-[[4-(2-hydroxyethyl)-1-piperazinyl]acetyl]-D-phenylalanyl-L-cysteinyl-L-tyrosyl-D-tryptophyl-L-lysyl-(2S)-2-aminobutanoyl-L-cysteinyl-, cyclic (2-7)-disulfide | Acromegaly Antidiabetic |
| 424 | leuprorelin | | 6-D-leucine-9-(N-ethyl-L-prolinamide)-10-deglycinamide- | Formulation, Anticancer |
| 191 | β-amyloid peptides | beta-amyloid peptide | gi\|8176533\|gb\|AAB26264.2\| beta-amyloid peptide precursor; beta APP [Homo sapiens] GSGLTNIKTEEISEVKMDAEFRHDSGYEVHHQKLVFF AEDVGSNKGAIIGLMVGGVVIATVIIITLVMLK KQYTSNHHGVVE | Cognition enhancer |
| 425 | oglufanide disodium | | L-tryptophan, L-alpha-glutamyl-, disodium salt | Immunomodulator, anti-infective Anticancer, immunological |
| 192 | HAV peptide matrix | | leucyl-arginyl-alanyl-histidyl-alanyl-valyl-aspartyl-valyl-asparaginyl-glycinamide | Neurological |
| 149 | PTH 1-34 | PTH | SVSEIQLMHNLGKHLNSMERVEWLRKKLQDVHNF | Hormone |
| | leuprorelin | | 6-D-leucine-9-(N-ethyl-L-prolinamide)-10-deglycinamide- | Anticancer |
| 193 | TRP-2 | | H-Leu-Leu-Pro-Gly-Gly-Arg-Pro-Tyr-Arg-OH | Anticancer, immunological |
| 426 | golotimod | | (2R)-2-amino-5-[[(1S)-1-carboxy-2-(1H-indol-3-yl)ethyl]amino]-5-oxopentanoic acid | Immunostimulant, other Immunomodulator, anti-infective Anticancer, immunological Stomatological |
| 194 | angiotensin-II | Angiotensin II | gi\|28710\|emb\|CAA77513.1\| angiotensin II [Homo sapiens] MILNSSTEDGIKRIQDDCPKAGRHNYIFVMIPTLYSIIF VVGIFGNSLVVIVIYFYMKLKTVASVFLLNLALADLCF LLTLPLWAVYTAMEYRWPFGNYLCKIASASVSFNLY ASVFLLTCLSIDRYLAIVHPMKSRLRRTMLVAKVTCIII WLLAGLASLPAIIHRNVFFIENTNITVCAFHYESQNSTL PIGLGLTKNILGFLFPFLIILTSYTLIWKALKKAYEIQKN KPRNDDIFKIIMAIVLFFFFSWIPHQIFTFLDVLIQLGIIR DCRIADIVDTAMPITICIAYFNNCLNPLFYGFLGKKFKR YFLQLLKYIPPKAKSHSNLSTKMSTLSYRPSDNVSSST KKPAPCFEVE | Vulnerary Symptomatic antidiabetic |
| 195 | omiganan | | L-lysinamide, L-isoleucyl-L-leucyl-L-arginyl-L-tryptophyl-L-prolyl-L-tryptophyl-L-tryptophyl-L-prolyl-L-tryptophyl-L-arginyl-L-arginyl, pentahydrochloride | Formulation, dermal, topical Peptide antibiotic Antiacne |
| 427 | leuprorelin | | 6-D-leucine-9-(N-ethyl-L-prolinamide)-10-deglycinamide- | Transmucosal, nasal, Menstruation disorders, Anticancer, hormonal, Fertility enhancer |
| 428 | delmitide acetate | | D-Tyrosinamide, D-arginyl-D-norleucyl-D-norleucyl-D-norleucyl-D-arginyl-D-norleucyl-D-norleucyl-D-norleucylglycyl-, monoacetate | GI inflammatory/bowel disorders, Radio/chemoprotective, Antipsoriasis, Antipruritic/inflamm, allergic, Multiple sclerosis |

TABLE 1-continued

This table lists the SEQ ID NOs., names, sequences, and known or suspected therapeutic activities of various peptides described herein. The SEQ ID NOs. 1-301 describe sequences that are required to be provided with the Sequence Listing and are therefore appended with the instant Specification. In some instances, these peptides contain features that are either inconsistent with or not amenable to inclusion in the Sequence Listing. For example, a sequence with less than four-amino acids; a sequence with a D-amino acid; or certain modification that cannot be described in the Sequence Listing presently, and therefore are not provided in the Sequence Listing. However, for the ease of use and description, a SEQ ID NO. has been provided to these peptides (i.e., SEQ ID NOs: 302-469).

| SEQ ID NO: | Name | Family | Sequence and/or other Identifying Information | Therapeutic Activity |
|---|---|---|---|---|
| | | | | treatment, Alimentary/ Metabolic, other, Antiviral, anti-HIV, Antiasthma, COPD treatment, Respiratory Stomatological |
| 196 | cat PAD | | MRGALLVLALLVTQALGVKMAETCPIFYDVFFAVAN GNELLLDLSLTKVNATEPERTAMKKIQDCYVENGLIS RVLDGLVMTTISSSKDCMGEAVQNTVEDLKLNTLGR | Antiasthma Antiallergic, non-asthma |
| 429 | NOV-002 | | bis-(gamma-L-glutamyl)-L-cysteinyl-bis-glycin disodium salt | Anticancer, immunological Radio/chemosensitizer Antidote |
| 430 | GPG-NH2 | | glycyl-prolyl-glycine amide | Antiviral, anti-HIV |
| 431 | ABT-510 | | NAc-Sar-Gly-ValDalloIleThrNValIeArgProNHE | Anticancer, other |
| 8 | CJC-1131 | GLP-1 | HGEGTFTSDLSKQMEEEAVRLFIEWLKNGGPSSGAPP PS | Antidiabetic |
| 432 | desmopressin | | Vasopressin, 1-(3-mercaptopropanoic acid)-8-D-arginine- | Formulation, oral, Hormone, Antidiabetic, Urological |
| 197 | metastin | | MNSLVSWQLLLFLCATHFGEPLEKVASVGNSRPTGQQ LESLGLLAPGEQSLPCTERKPAATARLSRRGTSLSPPPE SSGSPQQPGLSAPHSRQIPAPQGAVLVQREKDLPNYN WNSFGLRFGKREAAPGNHGRSAGRG | Anticancer, other |
| 433 | leuprorelin | | 5-Oxo-L-prolyl-L-histidyl-L-tryptophyl-L-seryl-L-tyrosyl-D-leucyl-L-leucyl-L-arginyl-N-ethyl-L-prolinamide acetate (salt) | Anticancer |
| 434 | SGS-111 | | N-phenylacetylprolylglycine ethyl ester | Cognition enhancer Neuroprotective |
| 435 | taltobulin | | (4S)-4-[[(2S)-3,3-dimethy1-2-[[(25)-3-methy1-2-(methylamino)-3-phenylbutanoyl]amino]butanoyl]methylamino]-2,5-dimethylhex-2-enoic acid | Anticancer, other |
| 436 | leuprolide | | 6-D-leucine-9-(N-ethyl-L-prolinamide)-10-deglycinamide- | inhalable, systemic, Anticancer, Menstruation disorders |
| 103 | XOMA-629 | | gi\|157276599\|ref\|NP_001716.2\| bactericidal/permeability-increasing protein precursor [Homo sapiens] MRENMARGPCNAPRWASLMVLVAIGTAVTAAVNPG VVVRISQKGLDYASQQGTAALQKELKRIKIPDYSDSF KIKHLGKGHYSFYSMDIREFQLPSSQISMVPNVGLKFS ISNANIKISGKWKAQKRFLKMSGNFDLSIEGMSISADL KLGSNPTSGKPTITCSSCSSHINSVHVHISKSKVGWLIQ LFHKKIESALRNKMNSQVCEKVTNSVSSELQPYFQTL PVMTKID SVAGINYGLVAPPATTAETLDVQMKGEFYS ENHHNPPPFAPPVMEFPAAHDRMVYLGLSDYFFNTA GLVYQEAGVLKMTLRDDMIPKESKFRLTTKFFGTFLP EVAKKFPNMKIQIHVSASTPPHLSVQPTGLTFYPAVDV QAFAVLPNSSLASLFLIGMHTTGSMEVSAESNRLVGE LKLDRLLLELKHSNIGPFPVELLQDIMNYIVPILVLPRV NEKLQKGFPLPTPARVQLYNVVLQPHQNFLLFGADV VYK | Antiacne Anti-infective, other |
| 198 | synthetic erythropoiesis pro | | gi\|8393713\|ref\|NP_058651.1\| Sep (O-phosphoserine) tRNA: Sec (selenocysteine) tRNA synthase isoform 1 [Homo sapiens] MSTSYGCFWRRFIHGIGRSGDISAVQPKAAGSSLLNKI TNSLVLDIIKLAGVHTVANCFVVPMATGMSLTLCFLT LRHKRPKAKYIIWPRIDQKSCFKSMITAGFEPVVIENV LEGDELRTDLKAVEAKVQELGPDCILCIHSTTSCFAPR VPDRLEELAVICANYDIPHIVNNAYGVQSSKCMHLIQ QGARVGRIDAFVQSLDKNFMVPVGGAIIAGFNDSFIQE ISKMYPGRASASPSLDVLITLLSLGSNGYKKLLKERKE MFSYLSNQIKKLSEAYNERLLHTPHNPISLAMTLKTLD EHRDKAVTQLGSMLFTKQVSGARVVPLGSMQTVSGY TFRGFMSHTNNYPCAYLNAASAIGMKMQDVDLFINR LDRCLKAVRKERSKESDDNYDKTEDVDIEEMALKLD NVLLDTYQDA SS | Antianaemic Radio/chemoprotective |

TABLE 1-continued

This table lists the SEQ ID NOs., names, sequences, and known or suspected therapeutic activities of various peptides described herein. The SEQ ID NOs. 1-301 describe sequences that are required to be provided with the Sequence Listing and are therefore appended with the instant Specification. In some instances, these peptides contain features that are either inconsistent with or not amenable to inclusion in the Sequence Listing. For example, a sequence with less than four-amino acids; a sequence with a D-amino acid; or certain modification that cannot be described in the Sequence Listing presently, and therefore are not provided in the Sequence Listing. However, for the ease of use and description, a SEQ ID NO. has been provided to these peptides (i.e., SEQ ID NOs: 302-469).

| SEQ ID NO: | Name | Family | Sequence and/or other Identifying Information | Therapeutic Activity |
|---|---|---|---|---|
| 191 | β-amyloid vaccine | beta-amyloid peptide | gi|8176533|gb|AAB26264.2| beta-amyloid peptide precursor; beta APP [Homo sapiens] GSGLTNIKTEEISEVKMDAEFRHDSGYEVHHQKLVFF AEDVGSNKGAIIGLMVGGVVIATVIIITLVMLKKQYTS NHHGVVE | Cognition enhancer |
| 437 | sincalide | | 1-De-(5-oxo-L-proline)-2-de-L-glutamine-5-L-methioninecaerulein | Imaging agent Alimentary/Metabolic |
| 438 | albiglutide | | ([8-glycine]human glucagon-like peptide 1-(7-36)-peptidyl)([8-glycine]human glucagon-like peptide 1-(7-36)-peptidyl)(human serum albumin (585 residues)) | Antidiabetic Anorectic/Antiobesity |
| 199 | SB-144 | | gi|13899257|ref|NP_113622.1| transmembrane and ubiquitin-like domain containing 1 [Homo sapiens] MTLIEGVGDEVTVLFSVLACLLVLALAWVSTHTAEG GDPLPQPSGTPTPSQPSAAMAATDSMRGEAPGAETPS LRHRGQAAQPEPSTGFTATPPAPDSPQEPLVLRLKFLN DSEQVARAWPHDTIGSLKRTQFPGREQQVRLIYQGQL LGDDTQTLGSLHLPPNCVLHCHVSTRVGPPNPPCPPGS EPGPSGLEIGSLLLPLLLLLLLLLWYCQIQYRPFFPLTA TLGLAGFTLLLSLLAFAMYRP | Anticancer, other Radio/chemosensitizer |
| 200 | exenatide LAR | | L-histidylglycyl-L-glutamylglycyl-L-threonyl-L-phenylalanyl-L-threonyl-L-seryl-L-aspartyl-L-leucyl-L-seryl-L-lysyl-L-glutaminyl-L-methionyl-L-glutamyl-L-glutamyl-L-glutamyl-L-alanyl-L-valyl-L-arginyl-L-leucyl-L-phenylalanyl-L-isoleucyl-L-glutamyl-L-tryptophyl-L-leucyl-L-lysyl-L-asparaginylglycylglycyl-L-prolyl-L-seryl-L-serylglycyl-L-alanyl-L-prolyl-L-prolyl-L-prolyl-L-serinamide | Antidiabetic |
| 201 | BA-058 | PTHrP | gi|131542|sp|P12272.1|PTHR_HUMAN Parathyroid hormone-related protein precursor (PTH-rP) (PTHrP) [Contains: PTHrP[1-36]; PTHrP[38-94]; Osteostatin (PTHrP[107-139])] MQRRLVQQWSVAVFLLSYAVPSCGRSVEGLSRRLKR AVSEHQLLHDKGKSIQDLRRRFFLHHLIAEIHTAEIRA TSEVSPNSKPSPNTKNHPVRFGSDDEGRYLTQETNKV ETYKEQPLKTPGKKKKGKPGKRKEQEKKKRRTRSAW LDSGVTGSGLEGDHLSDTSTTSLELDSRRH | Osteoporosis treatment |
| 8 | BIM-51077 | GLP-1 | HGEGTFTSDLSKQMEEEAVRLFIEWLKNGGPSSGAPP PS [(aminoisobutyric acid) 8,35]hGLP-1(1-36)NH 2, has the same amino acid sequence as human GLP-1(7-36 amide) except for the replacement of amino acids 8 and 35 with α-aminoisobutyric acid (Aib) to reduce protease susceptibility. | Antidiabetic |
| 202 | TM-701 | | H-Met-Cys-Met-Pro-Cys-Phe-Thr-Thr-Asp-His-Gln-Met-Ala-Arg-Lys-Cys-Asp-Asp-Cys-Cys-Gly-Gly-Lys-Gly-Arg-Gly-Lys-Cys-Tyr-Gly-Pro-Gln-Cys-Leu-Cys-Arg-NH$_2$ (Disulfide bridge: 2-19, 5-28, 16-33, 20-35) | Anticancer, other Radio/chemosensitizer |
| 439 | CZEN-002 | | [dNal(2')-7,Phe-12]-α-MSH 6-13 | Antifungal, Antibacterial, other, Antiviral, anti-HIV, Immunosuppressant, Metabolic and enzyme disorders, Anti-inflammatory, Antiarthritic, otherGI inflammatory/bowel disorders |
| 203 | ZP-120 | | Ac-RYYRWKKKKKKK-NH$_2$ | Cardiostimulant |
| 204 | CTT | | H-Cys-Thr-Thr-His-Trp-Gly-Phe-Thr-Leu-Cys-OH | Formulation technology |
| 205 | PYY3-36 | | gi|71361686|ref|NP_004151.2| peptide YY [Homo sapiens] MVFVRRPWPALTTVLLALLVCLGALVDAYPIKPEAPR EDASPEELNRYYASLRHYLNLVTRQRYGKRDGPDTLL SKTFFPDGEDRPVRSRSEGPDLW | Anorectic/Antiobesity |
| | AEZS-130 | | EP1572 UMV1843 [Aib-DTrp-DgTrp-CHO] | Growth hormone Anabolic Musculoskeletal |
| 206 | AL-108 | | H-Asn-Ala-Pro-Val-Ser-Ile-Pro-Gln-OH | Neuroprotective Cognition enhancer Antiparkinsonian Ophthalmological |

TABLE 1-continued

This table lists the SEQ ID NOs., names, sequences, and known or suspected therapeutic activities of various peptides described herein. The SEQ ID NOs. 1-301 describe sequences that are required to be provided with the Sequence Listing and are therefore appended with the instant Specification. In some instances, these peptides contain features that are either inconsistent with or not amenable to inclusion in the Sequence Listing. For example, a sequence with less than four-amino acids; a sequence with a D-amino acid; or certain modification that cannot be described in the Sequence Listing presently, and therefore are not provided in the Sequence Listing. However, for the ease of use and description, a SEQ ID NO. has been provided to these peptides (i.e., SEQ ID NOs: 302-469).

| SEQ ID NO: | Name | Family | Sequence and/or other Identifying Information | Therapeutic Activity |
| --- | --- | --- | --- | --- |
| 202 | TM-801 | | H-Met-Cys-Met-Pro-Cys-Phe-Thr-Thr-Asp-His-Gln-Met-Ala-Arg-Lys-Cys-Asp-Asp-Cys-Cys-Gly-Gly-Lys-Gly-Arg-Gly-Lys-Cys-Tyr-Gly-Pro-Gln-Cys-Leu-Cys-Arg-NH2 (Disulfide bridge: 2-19, 5-28, 16-33, 20-35) | Imaging agent |
| 202 | TM-901 | | H-Met-Cys-Met-Pro-Cys-Phe-Thr-Thr-Asp-His-Gln-Met-Ala-Arg-Lys-Cys-Asp-Asp-Cys-Cys-Gly-Gly-Lys-Gly-Arg-Gly-Lys-Cys-Tyr-Gly-Pro-Gln-Cys-Leu-Cys-Arg-NH2 (Disulfide bridge: 2-19, 5-28, 16-33, 20-35) | Anticancer, other Imaging agent |
| 440 | S-0373 | TRH | pyroGlu-His-Pro-NH2 (or 5-oxo-L-prolyl-L-histidyl-L-prolinamide) | Neurological Psychostimulant Antiparkinsonian |
| 205 | PYY3-36 | | gi|71361686|ref|NP_004151.2| peptide YY [Homo sapiens] MVFVRRPWPALTTVLLALLVCLGALVDAYPIKPEAPR EDASPEELNRYYASLRHYLNLVTRQRYGKRDGPDTLL SKTFFPDGEDRPVRSRSEGPDLW | Formulation, oral, other Anorectic/Antiobesity |
| 207 | XG-101 | | gi|4885433|ref|NP_005447.1| mitogen-activated protein kinase 8 interacting protein 1 [Homo sapiens] MAERESGGLGGGAASPPAASPFLGLHIASPPNFRLTHD ISLEEFEDEDLSEITDECGISLQCKDTLSLRPPRAGLLSA GGGGAGSRLQAEMLQMDLIDATGDTPGAEDDEEDDD EERAARRPGAGPPKAESGQEPASRGQGQSQGQSQGPG SGDTYRPKRPTTLNLFPQVPRSQDTLNNNSLGKKHSW QDRVSRSSSPLKTGEQTPPHEHICLSDELPPQSGPAPTT DRGTSTDSPCRRSTATQMAPPGGPPAAPPGGRGHSHR DRIHYQADVRLEATEEIYLTPVQRPPDAAEPTSAFLPP TESRMSVSSDPDPAAYPSTAGRPHPSISEEEEGFDCLSS PERAEPPGGGWRGSLGEPPPPPRASLSSDTSALSYDSV YTLVVDEHAQLELVSLRPCFGDYSDESDSATVYDNC ASVSSPYESAIGEEYEEAPRPQPPACLSEDSTPDEPDVH SKKKFLNVFMSGRSRSSSAESFGLFSCIINGEEQEQTHR AIFRFVPRHEDELELEVDDPLLVELQAEDYWYEAYN MRTGARGVFPAYYAIEVTKEPEHMAALAKNSDWVD QFRVKFLGSVQVPYHKGNDVLCAAMQKIATTRRLTV HFNPPSSCVLEISVRGVKIGVKADDSQEAKGNKCSHFF QLKNISFCGYHPKNNKYFGFITKHPADHRFACHVFVS EDSTKALAESVGRAFQQFYKQFVEYTCPTEDIYLE | Immunological Cardiovascular Neuroprotective Immunosuppressant |
| 208 | XG-102 | | gi|4885433|ref|NP_005447.1| mitogen-activated protein kinase 8 interacting protein 1 [Homo sapiens] MAERESGGLGGGAASPPAASPFLGLHIASPPNFRLTHD ISLEEFEDEDLSEITDECGISLQCKDTLSLRPPRAGLLSA GGGGAGSRLQAEMLQMDLIDATGDTPGAEDDEEDDD EERAARRPGAGPPKAESGQEPASRGQGQSQGQSQGPG SGDTYRPKRPTTLNLFPQVPRSQDTLNNNSLGKKHSW QDRVSRSSSPLKTGEQTPPHEHICLSDELPPQSGPAPTT DRGTSTDSPCRRSTATQMAPPGGPPAAPPGGRGHSHR DRIHYQADVRLEATEEIYLTPVQRPPDAAEPTSAFLPP TESRMSVSSDPDPAAYPSTAGRPHPSISEEEEGFDCLSS PERAEPPGGGWRGSLGEPPPPPRASLSSDTSALSYDSV KYTLVVDEHAQLELVSLRPCFGDYSDESDSATVYDNC ASVSSPYESAIGEEYEEAPRPQPPACLSEDSTPDEPDVH FSKKKFLNVFMSGRSRSSSAESFGLFSCIINGEEQEQTHR AIFRFVPRHEDELELEVDDPLLVELQAEDYWYEAYN MRTGARGVFPAYYAIEVTKEPEHMAALAKNSDWVD QFRVKFLGSVQVPYHKGNDVLCAAMQKIATTRRLTV HFNPPSSCVLEISVRGVKGVKADDSQEAKGNKCSHFF QLKNISFCGYHPKNNKYFGFITKHPADHRFACHVFVS EDSTKALAESVGRAFQQFYKQFVEYTCPTEDIYLE | Neuroprotective Cardiovascular Otological Ophthalmological Antiparkinsonian Immunosuppressant |
| 441 | lanreotide SR | | L-Threonamide,3-(2-naphthalenyl)-D-alanyl-L-cysteinyl-L-tyrosyl-D-tryptophyl-L-lysyl-L-valyl-L-cysteinyl, cyclic (2-7)-disulfide | Formulation, modified-release, other Somatostatin Antihypertensive, other |
| 209 | OGP-(10-14)-L | | H-Tyrosine-Glycine-Phenylalanine-Glycine-Glycine-OH | Haematological Musculoskeletal |
| 210 | WP9QY | | cyclo(Tyr-Cys-Trp-Ser-Gln-Tyr-Leu-Cys-Tyr); cyclo(tyrosyl-cysteinyl-tryptophyl-seryl-glutaminyl-tyrosyl-leucyl-cysteinyl-tyrosyl) | Antiarthritic, other Anti-inflammatory |
| 211 | aviptadil | | His-Ser-Asp-Ala-Val-Phe-Thr-Asp-Asn-Tyr-Thr-Arg-Leu-Arg-Lys-Gln-Met-Ala-Val-Lys-Lys-Tyr-Leu-Asn-Ser-Ile-Leu-Asn | Antihypertensive, other Respiratory Immunosuppressant |

TABLE 1-continued

This table lists the SEQ ID NOs., names, sequences, and known or suspected therapeutic activities of various peptides described herein. The SEQ ID NOs. 1-301 describe sequences that are required to be provided with the Sequence Listing and are therefore appended with the instant Specification. In some instances, these peptides contain features that are either inconsistent with or not amenable to inclusion in the Sequence Listing. For example, a sequence with less than four-amino acids; a sequence with a D-amino acid; or certain modification that cannot be described in the Sequence Listing presently, and therefore are not provided in the Sequence Listing. However, for the ease of use and description, a SEQ ID NO. has been provided to these peptides (i.e., SEQ ID NOs: 302-469).

| SEQ ID NO: | Name | Family | Sequence and/or other Identifying Information | Therapeutic Activity |
|---|---|---|---|---|
| 212 | AL-209 | | Ser-Ala-Leu-Leu-Arg-Ser-Ile-Pro-Ala | Neuroprotective Cognition enhancer Ophthalmological |
| 442 | octreotide | | L-Cysteinamide, D-phenylalanyl-L-cysteinyl-L-phenylalanyl-D-tryptophyl-L-lysyl-L-threonyl-N-[2-hydroxy-1-(hydroxymethyl)propyl]-, cyclic (2-7)-disulfide, [R-(R*,R*)]- | Formulation, implant Formulation, modified-release, >24 hr Somatostatin |
| 213 | CDX-110 | | Leu-Glu-Glu-Lys-Lys-Gly-Asn-Tyr-Val-Val-Thr-Asp-His-Cys-KLH | Recombinant vaccine Anticancer, immunological |
| 444 | desmopressin | | Vasopressin, 1-(3-mercaptopropanoic acid)-8-D-arginine- | Hormone, Urological, Reproductive/gonadal, general |
| 445 | obinepitide Insulin | | [34-L-glutamine]pancreatic hormone (human) Insulin (ox), 8A-L-threonine-10A-L-isoleucine-30B-L-threonine- | Anorectic/Antiobesity solubility-enhanced Insulin |
| 171 | terlipressin | | N-(N-(N-glycylglycyl)glycyl)-8-L-lysinevasopressin [CAS]; Gly-Gly-Gly-8-Lys-vasopressin; N-(alpha)-glycyl-glycyl-glycyl-8-lysine vasopressin; Remestyp; TGLVP; glipressin; glycylpressin; glypressin; terlypressin; triglycyl lysine vasopressin; triglycyl-(8-lysine)vasopressin; triglycylvasopressin; vasopressin, tri-Gly-8-Lys- | Hepatoprotective, Urological, Gi bleeding |
| 214 | ZT-153 | | Asn-Phe-Gly-Ala-Ile-Leu; NFGAIL; asparagyl-phenylalanyl-glycyl-alanyl-isoleucyl-leucine; islet amyloid polypeptide (22-27) | Antidiabetic |
| 215, 215 and 216 | FGLL | | gi|42544189|ref|NP_004458.3| fibrinogen-like 1 precursor [Homo sapiens] MAKVFSFILVTTALTMGREISALEDCAQEQMRLRAQV RLLETRVKQQQVKIKQLLQENEVQFLDKGDENTVIDL GSKRQYADCSEIFNDGYKLSGFYKIKPLQSPAEFSVYC DMSDGGGWTVIQRRSDGSENFNRGWKDYENGFGNF VQKHGEYWLGNKNLHFLTTQEDYTLKIDLADFEKNS RYAQYKNFKVGDEKNFYELNIGEYSGTAGDSLAGNF HPEVQWWASHQRMKFSTWDRDHDNYEGNCAEEDQS GWWFNRCHSANLNGVYYSGPYTAKTDNGIVWYTWH GWWYSLKSVVMKIRPNDFIPNVI gi|42544200|ref|NP_963846.1| fibrinogen-like 1 precursor [Homo sapiens] MAKVFSFILVTTALTMGREISALEDCAQEQMRLRAQV RLLETRVKQQQVKIKQLLQENEVQFLDKGDENTVIDL GSKRQYADCSEIFNDGYKLSGFYKIKPLQSPAEFSVYC DMSDGGGWTVIQRRSDGSENFNRGWKDYENGFGNF VQKHGEYWLGNKNLHFLTTQEDYTLKIDLADFEKNS RYAQYKNFKVGDEKNFYELNIGEYSGTAGDSLAGNF HPEVQWWASHQRMKFSTWDRDHDNYEGNCAEEDQS GWWFNRCHSANLNGVYYSGPYTAKTDNGIVWYTWH GWWYSLKSVVMKIRPNDFIPNVI gi|42544198|ref|NP_671736.2| fibrinogen-like 1 precursor [Homo sapiens] MAKVFSFILVTTALTMGREISALEDCAQEQMRLRAQV RLLETRVKQQQVKIKQLLQENEVQFLD | Cognition enhancer Neurological |
| 217 | ST-03 | | gi|386634|gb|AAB27460.1| 01-ST-3 = heat-stable enterotoxin [Vibrio cholerae, 01, Peptide, 19 aa] NLIDCCEICCNPACFGCLN | Recombinant growth factor Musculoskeletal Osteoporosis treatment |
| 446 | cetrorelix acetate | | D-Alaninamide, N-acetyl-3-(2-naphthalenyl)-D-alanyl-4-chloro-D-phenylalanyl-3-(3-pyridinyl)-D-alanyl-L-seryl-L-tyrosyl-N5-(aminocarbonyl)-D-ol-L-leucyl-L-arginyl-L-prolyl- | Formulation, modified-release, >24 hr Menstruation disorders |
| 218 | neurodegenerative ther | | alpha toxin, Naja; cobra alpha toxin; cobra toxin alpha; toxin alpha, cobra; gi|64054|emb|CAA26373.1| unnamed protein product [Laticauda semifasciata] MKTLLLTLVVVTIVCLDLGYTRICFNHQSSQPQTTKTC SPGESSCYNKQWSDFRGTIIERGCGCPTVKPGIKLSCC ESEVCNN gi|4519816|dbj|BAA75752.1| short chain neurotoxin [Laticauda semifasciata] MKTLLLTLVVVTIVCLDLGYTRICFNHQSSQPQTTKTC SPGESSCYNKQWSDFRGTIIERGCGCPTVKPGIKLSCC ESEVCNN | Cognition enhancer |

TABLE 1-continued

This table lists the SEQ ID NOs., names, sequences, and known or suspected therapeutic activities of various peptides described herein. The SEQ ID NOs. 1-301 describe sequences that are required to be provided with the Sequence Listing and are therefore appended with the instant Specification. In some instances, these peptides contain features that are either inconsistent with or not amenable to inclusion in the Sequence Listing. For example, a sequence with less than four-amino acids; a sequence with a D-amino acid; or certain modification that cannot be described in the Sequence Listing presently, and therefore are not provided in the Sequence Listing. However, for the ease of use and description, a SEQ ID NO. has been provided to these peptides (i.e., SEQ ID NOs: 302-469).

| SEQ ID NO: | Name | Family | Sequence and/or other Identifying Information | Therapeutic Activity |
|---|---|---|---|---|
| | | | gi\|32140561\|dbj\|BAC78199.1\| erabutoxin a [*Laticauda semifasciata*] MKTLLLTLVVVTIVCLDLGYTRICFNHQSSQPQTTKTC SPGESSCYNKQWSDFRGTIIERGCGCPTVKPGIKLSCC ESEVCNN gi\|32140563\|dbj\|BAC78200.1\| erabutoxin a [*Laticauda semifasciata*] MKTLLLTLVVVTIVCLDLGYTRICFNHQSSQPQTTKTC SPGESSCYNKQWSDFRGTIIERGCGCPTVKPGIKLSCC ESEVCNN | |
| 219 | CT-319 | | MSNKKIIKIIKLQIPGGKANPAPPIGPALGAAGVNIMGF CKEFNAATQDRPGDLLPVVIT VYSDKTFSFVMKQSPVSSLIKKALGLESGSKIPNRNKV GKLTRAQITVIAEQKMKDMDVV LLESAERMVEGTARSMGVDVE | Antiviral, anti-HIV |
| 447 | Peptide T | | L-Threonine, N-(N-(N2-(N-(N-(N-D-alanyl-L-seryl)-L-threonyl)-L-threonyl)-L-threonyl)-L-asparaginyl)-L-tyrosyl)-[CAS]; HIV Peptide T; Peptide T, HIV | Antipsoriasis Multiple sclerosis treatment Cognition enhancer Musculoskeletal |
| 220 and 221 | APP-018 | | pallidin [*Mus musculus*] gi\|9790039\|ref\|NP_062762.1\|[9790039] MSVPEPPPPDGVLTGPSDSLEAGEPTPGLSDTSPDEGLI EDFPVDDRAVEHLVGGLLSHY LPDLQRSKRALQELTQNQVVLLDTLEQEISKFKECHS MLDINALFTEAKHYHAKLVTIRK EMLLLHEKTSKLKKRALKLQQKRQREELEREQQREK EFEREKQLTAKPAKRT envelope glycoprotein [Human immunodeficiency virus type 1] gi\|4205319\|gb\|AAD11044.1\|[4205319] KLTPLCVTLNCTDLDLRNTTNNTTTEERGEMKNCSFN ITTNIRDRYQKEYALFYKLDVIP IKEDNTSDNTSYRLISCNTSVITQACPKIS | Hypolipaemic/Antiatherosclerosis |
| 222 | somatropin | | gi\|60651145\|gb\|AAX31661.1\| somatotropin [*Bubalus bubalis*] AFPAMSLSSLFANAVLRAQHLHQLAADTFKEFERTYI PEGGQRYSIQNTQVAFCFSETIPA PTGKNEAQQKSDLELLRISLLLIQSWLGPLQFLSRVFT NSLVFGTSDRVYEKLKDLEEGI LALMRELEDGTPRAGQILKRTYDKFDTNMRSDDALL KNYGLLSCFRKDLHKTETYLRVMKCRRFGEASCAF | Formulation, transmucosal, nasal Growth hormone Anabolic Reproductive/gonadal, general |
| 448 | heparin | | 6-[5-acetamido-4,6-dihydroxy-2-(sulfooxymethyl)oxan-3-yl]oxy-3-[5-(6-carboxy-4,5-dihydroxy-3-sulfooxyoxan-2-yl)oxy-6-(hydroxymethyl)-3-(sulfoamino)-4-sulfooxyoxan-2-yl]oxy-4-hydroxy-5-sulfooxyoxane-2-carboxylic acid | Formulation, transmucosal, nasal Anticoagulant |
| 46 | CGRP | CGRP | ACDTATCVTHRLAGLLSRSGGVVKNNFVPTNVGSKAF-NH$_2$ | Cardiovascular Cardiostimulant |
| 449 | YM-216391 | | A concise total synthesis of the unusual oxazole-based cyclopeptide structure YM-216391, which also establishes the stereochemistry of the natural product i.e. 1, is described. The unusual polyoxazole-thiazole-based cyclopeptide 1, designated YM-216391, was recently isolated from Streptomyces nobilis.1 It shares both a structural and biological homology with the potent telomerase inhibitor telomestatin 2 which is showing promise in cancer chemotherapy.2 The structure of YM-216391 comprises a continuum of five azoles which have their origins in serine, cysteine and phenylalanine, linked via a glycine- valine-isoleucine tripeptide tether. The complete stereochemical assignment of YM-216391 has not been established. In this communication we describe a concise total synthesis of the cyclopeptide, which not only confirms its unique structure but also allows the assignment of its stereochemistry, shown in formula 1. Thus, the 2,4-disubstituted oxazoles 3 and 4 and the trisubstituted oxazole 5 were first elaborated | Anticancer, other |
| 223 | FGLm | | LSENDEWTQDRAKP | Cognition enhancer Neurological |

TABLE 1-continued

This table lists the SEQ ID NOs., names, sequences, and known or suspected therapeutic activities of various peptides described herein. The SEQ ID NOs. 1-301 describe sequences that are required to be provided with the Sequence Listing and are therefore appended with the instant Specification. In some instances, these peptides contain features that are either inconsistent with or not amenable to inclusion in the Sequence Listing. For example, a sequence with less than four-amino acids; a sequence with a D-amino acid; or certain modification that cannot be described in the Sequence Listing presently, and therefore are not provided in the Sequence Listing. However, for the ease of use and description, a SEQ ID NO. has been provided to these peptides (i.e., SEQ ID NOs: 302-469).

| SEQ ID NO: | Name | Family | Sequence and/or other Identifying Information | Therapeutic Activity |
|---|---|---|---|---|
| 224 | prohanin | | NPFPTWRKRPG | Analgesic, other |
| 225 | heart failure therapy | NP | gi\|189079\|gb\|AAA36355.1\| natriuretic peptide MDPQTAPSRALLLLLFLHLAFLGGRSHPLGSPGSASDL ETSGLQEQRNHLQGKLSELQVEQTSLEPLQES PRPTGVWKSREVATEGIRGHRKMVLYTLRAPRSPKM VQGSGCFGRKMDRISSSSGLGCKVLRRH | Cardiostimulant |
| 450 | SEN-304 | | D-[(chG)Y-(chG)(chG)(MeL)]-NH$_2$, where chG is R-cyclohexylglycine | Cognition enhancer Anti-inflammatory |
| 451 | Primacoll | | Synthetic growth factor | Musculoskeletal |
| 452 | Octreotide | | L-Cysteinamide, D-phenylalanyl-L-cysteinyl-L-phenylalanyl-D-tryptophyl-L-lysyl-L-threonyl-N-[2-hydroxy-1-(hydroxymethyl)propyl]-, cyclic (2-7)-disulfide, [R-(R*,R*)]- | Formulation, modified-release, >24 hr Symptomatic antidiabetic Ophthalmological Somatostatin |
| 453 | ALS-02 | | Glycine, N-(aminoiminomethyl)-N-methyl- | Neuroprotective |
| 200 | exendin-4, PC-DAC | GLP-1 | L-histidylglycyl-L-glutamylglycyl-L-threonyl-L-phenylalanyl-L-threonyl-L-seryl-L-aspartyl-L-leucyl-L-seryl-L-lysyl-L-glutaminyl-L-methionyl-L-glutamyl-L-glutamyl-L-glutamyl-L-alanyl-L-valyl-L-arginyl-L-leucyl-L-phenylalanyl-L-isoleucyl-L-glutamyl-L-tryptophyl-L-leucyl-L-lysyl-L-asparaginylglycylglycyl-L-prolyl-L-seryl-L-serylglycyl-L-alanyl-L-prolyl-L-prolyl-L-prolyl-L-serinamide | Antidiabetic |
| 226 | Exenatide | | gi\|1916067\|gb\|AAB51130.1\| exendin 4 [*Heloderma suspectum*] MKIILWLCVFGLFLATLFPISWQMPVESGLSSEDSASS ESFASKIKRHGEGTFTSDLSKQMEEEAVRLFIEWLKNG GPSSGAPPPSG | Formulation, transmucosal, nasal Antidiabetic |
| 225 | Cardeva | BNP | gi\|113836\|sp\|P16860.1\|ANFB__HUMAN Natriuretic peptides B precursor [Contains: Gamma-brain natriuretic peptide; Brain natriuretic peptide 32 (BNP-32)] MDPQTAPSRALLLLLFLHLAFLGGRSHPLGSPGSASDL ETSGLQEQRNHLQGKLSELQVEQTSLEPLQES PRPTGVWKSREVATEGIRGHRKMVLYTLRAPRSPKM VQGSGCFGRKMDRISSSSGLGCKVLRRH | Cardiostimulant |
| 227 | Alloferon | | H-His-Gly-Val-Ser-Gly-His-Gly-Gln-His-Gly-Val-His-Gly-OH | Immunomodulator, anti-infective |
| 454 | PAC-G31P | | AMCF-I; Alveolar Macrophage Chemotactic Factor I; Alveolar Macrophage Chemotactic Factor-I; Anionic Neutrophil Activating Peptide; Anionic Neutrophil-Activating Peptide; CXCL8 Chemokine; CXCL8 Chemokines; CXCL8, Chemokine; Chemokine CXCL8; Chemokine, CXCL8; Chemokines, CXCL8; Chemotactic Factor, Macrophage Derived; Chemotactic Factor, Macrophage-Derived; Chemotactic Factor, Neutrophil; Chemotactic Factor, Neutrophil, Monocyte-Derived; Chemotactic Peptide-Interleukin-8, Granulocyte; Granulocyte Chemotactic Peptide Interleukin 8; Granulocyte Chemotactic Peptide-Interleukin-8; IL-8; IL8; Interleukin 8; Lymphocyte-Derived Neutrophil-Activating Peptide; Macrophage-Derived Chemotactic Factor; Monocyte-Derived Neutrophil Chemotactic Factor; Monocyte-Derived Neutrophil-Activating Peptide; Neutrophil Activating Peptide, Lymphocyte Derived; Neutrophil Activating Peptide, Monocyte Derived; Neutrophil Activation Factor; Neutrophil Chemotactic Factor; Neutrophil-Activating Peptide, Anionic; Neutrophil-Activating Peptide | Recombinant interleukin Respiratory Antiasthma COPD treatment |
| 228 | PAC-525 | | Ac-KWRRWVRWI-NH$_2$ | Antibacterial, other |
| 229, 229 and 230 | PAC-113 | | Lys-Phe-His-Glu-Lys-His-His-Ser-His-Arg-Gly-Tyr histatin 10, human; histatin 11, human; histatin 12, human; histatin 3, human; histatin 4, human; histatin 5, human; histatin 6, human; histatin 7, human; histatin 8, human; histatin 9, human; histatin-3 (1-24), human; histatin-3 (1-25), human; histatin-3 (12-24), human; histatin-3 (12-25), human; histatin-3 (12-32), human; histatin-3 (13-25), human; histatin-3 (5-11), human; histatin-3 (5-12), human; lysyl-phenylalanyl-histidyl-glutamyl-lysyl-histidyl-histidyl-seryl-histidyl-arginyl-glycyl-tyrosine | Antifungal |

TABLE 1-continued

This table lists the SEQ ID NOs., names, sequences, and known or suspected therapeutic activities of various peptides described herein. The SEQ ID NOs. 1-301 describe sequences that are required to be provided with the Sequence Listing and are therefore appended with the instant Specification. In some instances, these peptides contain features that are either inconsistent with or not amenable to inclusion in the Sequence Listing. For example, a sequence with less than four-amino acids; a sequence with a D-amino acid; or certain modification that cannot be described in the Sequence Listing presently, and therefore are not provided in the Sequence Listing. However, for the ease of use and description, a SEQ ID NO. has been provided to these peptides (i.e., SEQ ID NOs: 302-469).

| SEQ ID NO: | Name | Family | Sequence and/or other Identifying Information | Therapeutic Activity |
|---|---|---|---|---|
|  |  |  | gi\|4557653\|ref\|NP_000191.1\| histatin 3 [Homo sapiens] MKFFVFALILALMLSMTGADSHAKRHHGYKRKFHEK HHSHRGYRSNYLYDN |  |
| 231 | MLIF |  | Met-Gln-Cys-Asn-Ser U.S. Pat. No. 6,524,591 | Anti-inflammatory |
| 454 | carfilzomib |  | L-Phenylalaninamide, (alphaS)-alpha-[(4-morpholinylacetyl)amino]benzenebutanoyl-L-leucyl-N-[(1S)-3-methyl-1-[[(2R)-2-methyloxiranyl]carbonyl]butyl]- | Anticancer, other |
| 232 | NAFB001 |  | gi\|63025222\|ref\|NP_000651.3\| transforming growth factor, beta 1 [Homo sapiens] MPPSGLRLLPLLLPLLWLLVLTPGRPAAGLSTCKTIDM ELVKRKRIEAIRGQILSKLRLASPPSQGEVPP GPLPEAVLALYNSTRDRVAGESAEPEPEPEADYYAKE VTRVLMVETHNEIYDKFKQSTHSIYMFFNTSEL REAVPEPVLLSRAELRLLRLKLKVEQHVELYQKYSNN SWRYLSNRLLAPSDSPEWLSFDVTGVVRQWLSR GGEIEGFRLSAHCSCDSRDNTLQVDINGFTTGRRGDL ATIHGMNRPFLLLMATPLERAQHLQSSRHRRAL DTNYCFSSTEKNCCVRQLYIDFRKDLGWKWIHEPKG YHANFCLGPCPYIWSLDTQYSKVLALYNQHNPGA SAAPCCVPQALEPLPIVYYVGRKPKVEQLSNMIVRSC KCS [PIR] | Ophthalmological Hepatoprotective |
| 233 | IL12-NGR |  | H-Cys-Asn-Gly-Arg-Cys-Gly-OH (Disulfide bridge: 1-5) | Recombinant, other Cytokine Anticancer, immunological |
| 234 and 235 | enterostatin |  | Val-Pro-Val-Asp; Val-Pro-Asp-Pro-Arg | Anorectic/Antiobesity |
| 455 | octreotide |  | L-Cysteinamide, D-phenylalanyl-L-cysteinyl-L-phenylalanyl-D-tryptophyl-L-lysyl-L-threonyl-N-[2-hydroxy-1-(hydroxymethyl)propyl]-, cyclic (2-7)-disulfide, [R-(R*,R*)]- | Formulation, modified-release, >24 hr Somatostatin |
| 150 | enfuvirtide |  | L-Phenylalaninamide, N-acetyl-L-tyrosyl-L-threonyl-L-seryl-L-leucyl-L-isoleucyl-L-histidyl-L-seryl-L-leucyl-L-isoleucyl-L-alpha-glutamyl-L-alpha-glutamyl-L-seryl-L-glutaminyl-L-asparaginyl-L-glutaminyl-L-glutaminyl-L-alpha-glutamyl-L-lysyl-L-asparaginyl-L-alpha-glutamyl-L-glutaminyl-L-alpha-glutamyl-L-leucyl-L-leucyl-L-alpha-glutamyl-L-leucyl-L-alpha-aspartyl-L-lysyl-L-tryptophyl-L-alanyl-L-seryl-L-leucyl-L-tryptophyl-L-asparaginyl-L-tryptophyl- | Formulation, parenteral, needle-free Antiviral, anti-HIV |
| 236 | PR-21 |  | gi\|2213924\|gb\|AAB61615.1\| neural cell adhesion molecule [Homo sapiens] MLQTKDLIWTLFFLGTAVSLQVDIVPSQGEISVGESKF FLCQVAGDAKDKDISWFSPNGEKLTPNQQRIS VVWNDDSSSTLTIYNANIDDAGIYKCVVTGEDGSESE ATVNVKIFQKLMFKNAPTPQEFREGEDAVIVCD VVSSLPPTIIWKHKGRDVILKKDVRFIFLSNNYLPIPGI KKTDEGTYRCEGRILARGEINFNDIQVIVNV PPTIQARQNIVNATANLGQSVTLVCDAEGFPGPTMSW TKDGEQIEQEEHDEKYLFSDDSSHLTIKKVDKN HEAENICIAENKVGEQDATIHLKVFAKPQITYVEDQTA MELAEQVILTVEASGDHIPYITWWTSTWQI | Neurological Cognition enhancer |
| 237 | AC-163794 | GIP | gi\|183221\|gb\|AAA53192.1\| gastric inhibitory polypeptide precursor MVATKTFALLLLSLFLAVGLGEKKEGHFSALPSLPVG SHAKVSSPQPRGPRYAEGTFISDYSIAMDKIHQ QDFVNWLLAQKGKKNDWKHNITQREARALELASQA NRKEEEAVEPQSSPAKNPSDEDLLRDLLIQELLAC LLDQTNLCRLRSR; | Antidiabetic |
| 456 | glucagon |  | Glucagon (1-29); Glukagon; HG Factor; HG-Factor; Hyperglycemic Glycogenolytic Factor; Hyperglycemic-Glycogenolytic Factor; Proglucagon (33-61) | Formulation, transdermal, systemic hypoglycemia |
| 457 | Insulin |  | Insulin (ox), 8A-L-threonine-10A-L-isoleucine-30B-L-threonine- | Formulation, oral, other Formulation, optimized, nanoparticles Antidiabetic |
| 458 | Dekafin-2 |  | DNA Synthesis Factor; Fibroblast Growth Factor; Fibroblast Growth Regulatory Factor; Growth Factor, Fibroblast; Growth Factors, Fibroblast | Anticancer, other |

TABLE 1-continued

This table lists the SEQ ID NOs., names, sequences, and known or suspected therapeutic activities of various peptides described herein. The SEQ ID NOs. 1-301 describe sequences that are required to be provided with the Sequence Listing and are therefore appended with the instant Specification. In some instances, these peptides contain features that are either inconsistent with or not amenable to inclusion in the Sequence Listing. For example, a sequence with less than four-amino acids; a sequence with a D-amino acid; or certain modification that cannot be described in the Sequence Listing presently, and therefore are not provided in the Sequence Listing. However, for the ease of use and description, a SEQ ID NO. has been provided to these peptides (i.e., SEQ ID NOs: 302-469).

| SEQ ID NO: | Name | Family | Sequence and/or other Identifying Information | Therapeutic Activity |
|---|---|---|---|---|
| 238 and 239 | relaxin | | (1) Glu-Leu-Tyr-Ser-Ala-Leu-Ala.Asn-Lys-Cys-Cys-His-Val-Gly-Cys-Thr-Lys-Arg-Ser-Leu-Ala-Arg-Phe-Cys (2) H-Asp-Ser-Trp-Met-Glu-Glu-Val-Ile-Lys-Leu-Cys-Gly-Arg-Glu-Leu-Val-Arg-Ala-Gln-Ile-Ala-Ile-Cys-Gly-Met-Ser-Thr-Ser Cys 11 of each chain form disulfide bond; cys 24 of the first chain forms disulfide bond with cys 23 of chain 2 | Recombinant hormone Hormone Labour inducer Antihypertensive, other |
| 459 | rhNRG-1 | | Differentiation Factor, neu; GGF Protein; Glial Growth Factor; Heregulin; NDF Protein; NRG1 Protein; Neuregulin 1; neu Differentiation Factor | Recombinant, other Cardiostimulant |
| 240 | c-peptide analogue | C-peptide | Glu-Ala-Glu-Asp-Leu-Gln-Val-Gly-Gln-Val-Glu-Leu-Gly-Gly-Gly-Pro-Gly-Ala-Gly-Ser-Leu-Gln-Pro-Leu-Ala-Leu-Glu-Gly-Ser-Leu-Gln | Symptomatic antidiabetic |
| 241 | SB-101 | | gi|30353933|gb|AAH52287.1| CD44 protein [Homo sapiens] MDKFWWHAAWGLCLVPLSLAQIDLNITCRFAGVFHV EKNGRYSISRTEAADLCKAFNSTLPTMAQMEKAL SIGFETCSST | Recombinant, other Anticancer, other |
| 242 | Britistatin | | gi|66270695|gb|AAY43681.1| disintegrin isoform D-1 [Bitis arietans] SPPVCGNKILEQGEDCDCGSPANCQDRCCNAATCKLT PGSQCNYGECCDQCRFKKAGTVCRIARGDWNDDYCT GKSSDCPWNH | Antithrombotic |
| 243 | echistatin | | gi|208338|gb|AAA72777.1| echistatin MECESGPCCRNCKFLKEGTICKRARGDDLDDYCNGK TCDCPRNPHKGPAT | Antithrombotic |
| 244 | gastrin | | gi|4503923: 20-101 gastrin preproprotein [Homo sapiens] EASWKPRSQQPDAPLGTGANRDLELPWLEQQGPASH HRRQLGPQGPPHLVADPSKKQGPWLEEEEEAYGWM DFGRRSAEDEN | diabetes |
| 245 | herpes simplex vaccine | | gi|9629447: 1-23 envelope glycoprotein D [Human herpesvirus 1] MGGAAARLGAVILFVVIVGLHGV | Prophylactic vaccine |
| 246 | neurotensin | | gi|5453816: 152-163 neurotensin/neuromedin N preproprotein [Homo sapiens] LYENKPRRPYIL | Analgesic, other |
| 247 | nociceptin | | gi|5453922|ref|NP_006219.1| prepronociceptin [Homo sapiens] MKVLLCDLLLLSLFSSVFSSCQRDCLTCQEKLHPALDS FDLEVCILECEEKVFPSPLWTPCTKVMARSSWQLSPA APEHVAAALYQPRASEMQHLRRMPRVRSLFQEQEEP EPGMEEAGEMEQKQLQKRFGGFTGARKSARKLANQ KRFSEFMRQYLVLSMQSSQRRRTLHQNGNV | Neurological Cognition enhancer Analgesic, other |
| 248 | oxyntomodulin | | sp|P01275.3|GLUC_HUMAN: 53-89 Glucagon precursor [Contains: Glicentin; Glicentin-related polypeptide (GRPP); Oxyntomodulin (OXY) (OXM)] HSQGTFTSDYSKYLDSRRAQDFVQWLMNTKRNRNNI A | Obesity; Antiulcer |
| 249 | pancreastatin | | gi|164417: 256-304 chromogranin A precursor GWPQAPAMDGAGKTGAEEAQPPEGKGAREHSRQEEE EETAGAPQGLFRG | Antidiabetic |
| 250 | relaxin | Relaxin | gi|5902052|ref|NP_008842.1| relaxin 1 preproprotein [Homo sapiens] MPRLFLFHLLEFCLLLNQFSRAVAAKWKDDVIKLCGR ELVRAQIAICGMSTWSKRSLSQEDAPQTPRPVAEIVPS FINKDTETIIMLEFIANLPPELKAALSERQPSLPELQQY VPALKDSNLSFEEFKKLIRNRQSEAADSNPSELKYLGL DTHSQKKRRPYVALFEKCCLIGCTKRSLAKYC | Recombinant hormone Hormone Labour inducer |
| 251 | secretin | | gi|11345450: 28-54 secretin preproprotein [Homo sapiens] HSDGTFTSELSRLREGARLQRLLQGLV | Haemostatic; diagnostic of pancreatic dysfunction, asthma, COPD, others |
| 252 | TIMP | | MAPFEPLASGILLLLWLIAPSRACTCVPPHPQTAFCNS DLVIRAKFVGTPEVNQTTLYQRYEIKMTKMYKGFQA LGDAADIRFVYTPAMESVCGYFHRSHNRSEEFLIAGK LQDGLLHITTCSFVAPWNSLSLAQRRGFTKTYTVGCE ECTVFPCLSIPCKLQSGTHCLWTDQLLQGSEKGFQSRH LACLPREPGLCTWQSLRSQIA | Recombinant, other Vulnerary Antiarthritic, other Stomatological |
| 252 | TIMP | | MAPFEPLASGILLLLWLIAPSRACTCVPPHPQTAFCNS DLVIRAKFVGTPEVNQTTLYQRYEIKMTKMYKGFQA LGDAADIRFVYTPAMESVCGYFHRSHNRSEEFLIAGK LQDGLLHITTCSFVAPWNSLSLAQRRGFTKTYTVGCE | Recombinant, other Antiarthritic, other Stomatological |

TABLE 1-continued

This table lists the SEQ ID NOs., names, sequences, and known or suspected therapeutic activities of various peptides described herein. The SEQ ID NOs. 1-301 describe sequences that are required to be provided with the Sequence Listing and are therefore appended with the instant Specification. In some instances, these peptides contain features that are either inconsistent with or not amenable to inclusion in the Sequence Listing. For example, a sequence with less than four-amino acids; a sequence with a D-amino acid; or certain modification that cannot be described in the Sequence Listing presently, and therefore are not provided in the Sequence Listing. However, for the ease of use and description, a SEQ ID NO. has been provided to these peptides (i.e., SEQ ID NOs: 302-469).

| SEQ ID NO: | Name | Family | Sequence and/or other Identifying Information | Therapeutic Activity |
|---|---|---|---|---|
| 253 | tendamistat | | ECTVFPCLSIPCKLQSGTHCLWTDQLLQGSEKGFQSRH LACLPREPGLCTWQSLRSQIA Asp-Thr-Thr-Val-Ser-Glu-Pro-Ala-Pro-Ser-Cys-Val-Thr-Leu-Tyr-Gln-Ser-Trp-Arg-Tyr-Ser-Gln-Ala-Asp-Asn-Gly-Cys-Ala-Gln-Thr-Val-Thr-Val-Lys-Val-Val-Tyr-Glu-Asp-Asp-Thr-Glu-Gly-Leu-Cys-Tyr-Ala-Val-Ala-Pro-Gly-Gln-Ile-Thr-Thr-Val-Gly-Asp-Gly-Tyr-Ile-Gly-Ser-His-Gly-His-Ala-Arg-Tyr-Leu-Ala-Arg-Cys-Leu | Antidiabetic |
| 254 | thymosin β4 | | gi\|11056061\|ref\|NP_066932.1\| thymosin, beta 4 [*Homo sapiens*] MSDKPDMAEIEKFDKSKLKKTETQEKNPLPSKETIEQE KQAGES | Vulnerary Ophthalmological Symptomatic antidiabetic Dermatological Cardiovascular Septic shock treatment Antiasthma |
| 255 | urodilatin | | Thr-Ala-Pro-Arg-Ser-Leu-Arg-Arg-Ser-Ser-Cys-Phe-Gly-Gly-Arg-Met-Asp-Arg-Ile-Gly-Ala-Gln-Ser-Gly-Leu-Gly-Cys-Asn-Ser-Phe-Arg-Tyr | Cardiostimulant Urological Antiasthma |
| 256 | Pharmaprojects No. 6236 | | Gly-Ser-Arg-Ala-His-Ser-Ser-His-Leu-Lys | Anticancer, other Antiarrhythmic Antiparkinsonian Cognition enhancer Neuroprotective |
| 257 | ANUP-1 | | Glu-Leu-Lys-Cys-Tyr-Thr-Cys-Lys-Glu-Pro-Met-Thr-Ser-Ala-Ala-Cys | Anticancer, other |
| 258 | DMI-4983 | | Asp-Ala-His-Lys | Cardiovascular |
| 460 | Glypromate | | Gly-Pro-Glu | Neuroprotective |
| 259 | CD-NP | | Lys Met Val Gln Gly Ser Gly Cys Phe Gly Arg Lys Met Asp Ile Ser Ser Ser Ser Gly Leu Gly Cys Pro Ser Leu Arg Asp Pro Arg Pro Asn Ala Pro Ser Thr Ser Ala | Cardiostimulant |
| 260 | Kisspeptin-54 | | GTSLSPPPESSGSPQQPGLSAPHSRQIPAPQGAVLVQRE KDLPNYNWNSFGLRF-NH2 | Cancer metastasis, angiogenesis |
| 261 | Kisspeptin-14 | | DLPNYNWNSFGLRF-NH2 | Cancer metastasis, angiogenesis |
| 262 | Kisspeptin-13 | | LPNYNWNSFGLRF-NH2 | Cancer metastasis, angiogenesis |
| 263 | Kisspeptin-10 | | YNWNSFGLRF-NH2 | Cancer metastasis, angiogenesis |
| 264 | Ziconotide | | CKGKGAKCSRLMYDCCTGSCRSGKC | |
| 461 | Biphalin | | Tyr-D-Ala-Gly-Phe-NH-NH-Phe-Gly-D-Ala-Tyr | |
| 39 | Nesiritide | Brain Netriuritic peptide (BNP) | SPKMVQGSGCFGRKMDRISSSSGLGCKVLRRH | |
| 40 | CD-NP | | GLSKGCFGLKLDRIGSMSGLGCPSLRDPRPNAPSTSA | |
| 265 | Protegrin-1 | Cytolytic | RGGRLCYCRRRFCVCVGR-NH2 | antibiotic |
| 266 | V681 | | Ac-KWKSFLKTFKSAVKTVLHTALKAISS-NH2 | |
| 462 | V681 (V13A_D) | | Ac-KWKSFLKTFKSA(AD)KTVLHTALKAISS-NH2 | '(AD)' discloses the D-configuration of Alanine |
| 267 | V681 des A12 | | KWKSFLKTFKSVKTVLHTALKAISS | |
| 268 | V681 V13K | | KWKSFLKTFKSAKKTVLHTALKAISS | |
| 269 | V681 V13K, T15K | | KWKSFLKTFKSAKKKVLHTALKAISS | |
| 270 | GLP-2 | GLP | HADGSFSDEMNTILDNLAARDFINWLIQTKITD | |
| 271 | GLP-2 (A2G) | GLP | HGDGSFSDEMNTILDNLAARDFINWLIQTKITD | |
| 272 | GLP-2 (A2G/C34) | GLP | HGDGSFSDEMNTILDNLAARDFINWLIQTKITDC | |
| 273 | AOD-9604 | Human Growth Hormone | LRIVQCASVEGSCGFY | Musculoskeletal, COPD, Hypnotic/Sedative, Immunostimulant, Antidiabetic, Anabolic, Symptomatic antidiabetic, Vulnerary |
| 274 | Ac-AOD-9604(S8K) | Human Growth Hormone | Ac-LRIVQCAKVEGSCGFY | Musculoskeletal, COPD, Hypnotic/Sedative, Immunostimulant, Antidiabetic, Anabolic, Symptomatic antidiabetic, Vulnerary |

TABLE 1-continued

This table lists the SEQ ID NOs., names, sequences, and known or suspected therapeutic activities of various peptides described herein. The SEQ ID NOs. 1-301 describe sequences that are required to be provided with the Sequence Listing and are therefore appended with the instant Specification. In some instances, these peptides contain features that are either inconsistent with or not amenable to inclusion in the Sequence Listing. For example, a sequence with less than four-amino acids; a sequence with a D-amino acid; or certain modification that cannot be described in the Sequence Listing presently, and therefore are not provided in the Sequence Listing. However, for the ease of use and description, a SEQ ID NO. has been provided to these peptides (i.e., SEQ ID NOs: 302-469).

| SEQ ID NO: | Name | Family | Sequence and/or other Identifying Information | Therapeutic Activity |
|---|---|---|---|---|
| 275 | Ac-AOD-9604(K17) | Human Growth Hormone | Ac-LRIVQCASVEGSCGFYK | Musculoskeletal, COPD, Hypnotic/Sedative, Immunostimulant, Antidiabetic, Anabolic, Symptomatic antidiabetic, Vulnerary |
| 276 | C-peptide | Insulin | EAEDLQVGQVELGGGPGAGSLQPLALEGSLQ | |
| 463 | CR845 | Opioids | peripherally-selective kappa opioid receptor agonists<br><br>D-Phe-D-Phe-D-Leu-D-Lys-[ω(4-aminopiperidine-4-carboxylic acid)]-OH | acute and chronic pain of visceral, inflammatory and neuropathic origin, and for the treatment of pruritis (itch) |
| 277 | Protegrin-2 | Cytolytic | RGGRLCYCRRRFCICV | antibiotic |
| 278 | Protegrin-3 | Cytolytic | RGGGLCYCRRRFCVCVGRG | antibiotic |
| 279 | Protegrin-4 | Cytolytic | RGGRLCYCRGWICFCVGRG | antibiotic |
| 280 | Protegrin-5 | Cytolytic | RGGRLCYCRPRFCVCVGRG | antibiotic |
| 281 | Preprotegrin | Cytolytic | METQRASLCLGRWSLWLLLLGLVVPSASAQALSYRE AVLRAVDRLNEQSSEANLYRLLELDQPPKADEDPGT PKPVSFTVKETVCPRPTRQPPELCDFKENGRVKQCV GTVTLDQIKDPLDITCNEVQGVRGGRLCYCRPRFCV CVGRG | antibiotic |
| 248 | Oxyntomodulin | | HSQGTFTSDYSKYLDSRRAQDFVQWLMNTKRNRNNI A | |
| 276 | C-peptide | | EAEDLQVGQVELGGGPGAGSLQPLALEGSLQ | |
| 282 | C-peptide mutant | | EGSLC | |
| 283 | Human Opioid Growth Factor | Enkephalin | Tyr-Gly-Gly-Phe-Met | |
| 284 | cholecystokinin | | RDY(SO3-)TGW(Nle)DF | |
| 285 | Dynorphin A (1-13) | | YGGFLRRIRPKLK | |
| 464 | Pralmorelin (GHRFA) | | D-Ala-D-2-Nal-Ala-Trp-D-Phe-Lys-NH$_2$ | |
| 286 | Aniritide | | RSSCFGGRMDRIGAQSGLGCNSFRY | |
| 287 | Vessel dilator proANP31-67 | | EVVPPQVLSDPNEEAGAALSPLPEVPPWTGEVSPAQR | |
| 465 | Peptide G | | Arg-Pro-Lys-Pro-Gln-Arg-D-Trp-MePhe-D-Trp-Leu-Met | |
| 466 | Tiplimotide | | D - Ala - lys - pro - val - val - his - leu - phe - ala - asp - ile - val - thr - pro - arg - thr - pro | |
| 288 | Desirudin (63-desulfohirudin) | | VVYTDCTESGQNLCLCEGSNVCGQGNKCILGSDGEK NQCVTGEGTPKPQSHNDGDFEEIPEEYLQ | |
| 467 | Examorelin | | His-DTrp(2-Me)-Ala-Trp-DPhe-Lys-NH2 | |
| 172 | Terlipressin | Vesopressin | Gly-Gly-Gly-c[Cys-Tyr-Phe-Gln-Asn-Cys]-Pro-Lys-Gly-NH2 | |
| 289 | Osteogenic Growth Factor (WT) | | ALKRQGRTLYGFGG | |
| 290 | Osteogenic Growth Factor (10-14) | | YGFGG | |

TABLE 1-continued

This table lists the SEQ ID NOs., names, sequences, and known or suspected therapeutic activities of various peptides described herein. The SEQ ID NOs. 1-301 describe sequences that are required to be provided with the Sequence Listing and are therefore appended with the instant Specification. In some instances, these peptides contain features that are either inconsistent with or not amenable to inclusion in the Sequence Listing. For example, a sequence with less than four-amino acids; a sequence with a D-amino acid; or certain modification that cannot be described in the Sequence Listing presently, and therefore are not provided in the Sequence Listing. However, for the ease of use and description, a SEQ ID NO. has been provided to these peptides (i.e., SEQ ID NOs: 302-469).

| SEQ ID NO: | Name | Family | Sequence and/or other Identifying Information | Therapeutic Activity |
|---|---|---|---|---|
| 291 | Myelin Basic Protein peptide | | Ac-ASQKRPSQRHG | |
| 292 | Myelin Basic Protein peptide Ac1-11[4Y] | | Ac-ASQYRPSQRHG | |
| 293 | Gonadorelin (24-33) | | pyroGlu-His-Trp-Ser-Tyr-Gly-Leu-Arg-Pro-Gly CONH2 | |
| 468 | Bremelanotide | Alpha-MSH | Ac-Nle-cyclo[Asp-His-D-Phe-Arg-Trp-Lys]-OH | |
| 294 | Islet Neogenesis associated peptide (INGAP) | | GLHDPSHGTLPNGSG | Diabetes |
| 295 | Urocortin II | | IVLSLDVPIGLLQILLEQARARAAREQATTNARILARV GHC | |
| 296 | A6 (anti-angiogenic peptide) | | CH3CO—NH2-KPSSPPEE-CONH2 | |
| 297 | Obestatin | | H-Phe-Asn-Ala-Pro-Phe-Asp-Val-Gly-Ile-Lys-Leu-Ser-Gly-Val-Gln-Tyr-Gln-Gln-His-Ser-Gln-Ala-Leu-NH2 | |
| 298 | ITF-1697 | | Gly-Lys(Et)-Pro-Arg | |
| 299 | CNP (C-type netriuretic peptide | | GLSKGCFGLKLDRIGSMSGLGC | |
| 300 | Osteocalcin | | YLYQWLGAPVPYPDPLEPRREVCELNPDCELADHIG FQEAYRRFYGPV | Diabetes |
| 301 | | | EAEDLQVGQVELGGGPGAGCLQPLALEGSLQ | |
| 469 | D4F-APO1 mimetic peptide | | Ac-D-W-F-K-A-F-Y-D-K-V-A-E-K-F-K-E-A-F-NH$_2$ | |

(—NH$_2$ indicates amidation at the C-terminus; Ac indicates acetylation; other modifications are as described herein and in the specification; SIN indicates Sequence Identification Number)

In other embodiments, the therapeutic peptides are selected from the group consisting of peptide G, OTS-102, Angiocol (antiangiogenic peptide group), ABT-510 (antiangiogenic peptide group), A6 (antiangiogenic peptide group), islet neogenesis gene associated protein (INGAP), tendamistat, recombinant human carperitide (alpha-atrial natriuretic peptide) (natriuretic peptide group), urodilatin (natriuretic peptide group), desirudin, Obestatin, ITF-1697, oxyntomodulin, cholecystokinin, bactericidal permeability increasing (BPI) protein, C-peptide, Prosaptide TX14(A), sermorelin acetate (GHRFA group), pralmorelin (GHRFA group), growth hormone releasing factor (GHRFA group), examorelin (GHRFA group), gonadorelin (LH-related peptide group), corticoliberin, atrial natriuretic peptide (natriuretic peptide group), anergix, somatostatin (GHRFA group), 29-amino-acid peptide growth hormone releasing hormone (GHRH) analogue (GHRFA group), bremelanotide (melanocortin agonist group), melanocortin peptidomimetic compound (melanocortin agonist group), antiprogestogens-GnRH antagonists (LH-related peptide group), recombinant LH (luteinizing hormone) (LH-related peptide group), terlipressin, Ecallantide-60-amino-acid recombinant peptide kallikrein inhibitor, calphobindin I, tiplimotide, osteogenic growth peptide, myelin basic protein, dynorphin A, anaritide (natriuretic peptide group), secretin, GLP-2, and gastrin.

The therapeutic peptides of the invention may comprise any of the 20 natural amino acids, and/or non-natural amino acids, amino acid analogs, and peptidomimetics, in any combination. The peptides may be composed of D-amino acids or L-amino acids, or a combination of both in any proportion. In addition to natural amino acids, the therapeutic peptides may contain, or may be modified to include, 1, 2, 3, 4, 5, 6, 7, 8, 9, 10, 15, 20, 25, or more non-natural amino acids. Exemplary non-natural amino acids and amino acid analogs that can be use with the invention include, but are not limited to, 2-aminobutyric acid, 2-aminoisobutyric acid, 3-(1-naphthyl)alanine, 3-(2-naphthyl)alanine, 3-methylhistidine, 3-pyridylalanine, 4-chlorophenylalanine, 4-fluorophenylalanine, 4-hydroxyproline, 5-hydroxylysine, alloisoleucine, citrulline, dehydroalanine, homoarginine, homocysteine, homoserine, hydroxyproline, N-acetylserine, N-formylmethionine, N-methylglycine, N-methylisoleucine, norleucine, N-α-methylarginine, O-phosphoserine, ornithine, phenylglycine, pipecolinic acid, piperazic acid, pyroglutamine, sarcosine, valanine, β-alanine, and β-cyclohexylalanine.

The therapeutic peptides may be, or may be modified to be, linear, branched, or cyclic, with our without branching.

Additionally, the therapeutic peptides may optionally be modified or protected with a variety of functional groups or protecting groups, including amino terminus protecting groups and/or carboxy terminus protecting groups. Protecting groups, and the manner in which they are introduced and removed are described, for example, in "Protective Groups in Organic Chemistry," Plenum Press, London, N.Y. 1973; and. Greene et al., "PROTECTIVE GROUPS IN ORGANIC SYNTHESIS" 3$^{rd}$ Edition, John Wiley and Sons, Inc., New York, 1999. Numerous protecting groups are known in the art. An illustrative, non-limiting list of protecting groups includes methyl, formyl, ethyl, acetyl, t-butyl, anisyl, benzyl, trifluoroacetyl, N-hydroxysuccinimide, t-butoxycarbonyl, benzoyl, 4-methylbenzyl, thioanizyl, thiocresyl, benzyloxymethyl, 4-nitrophenyl, benzyloxycarbonyl, 2-nitrobenzoyl, 2-nitrophenylsulphenyl, 4-toluenesulphonyl, pentafluorophenyl, diphenylmethyl, 2-chlorobenzyloxycarbonyl, 2,4,5-trichlorophenyl, 2-bromobenzyloxycarbonyl, 9-fluorenylmethyloxycarbonyl, triphenylmethyl, and 2,2,5,7,8-pentamethyl-chroman-6-sulphonyl. For discussions of various different types of amino- and carboxy-protecting groups, see, for example, U.S. Pat. No. 5,221,736 (issued Jun. 22, 1993); U.S. Pat. No. 5,256,549 (issued Oct. 26, 1993); U.S. Pat. No. 5,049,656 (issued Sep. 17, 1991); and U.S. Pat. No. 5,521,184 (issued May 28, 1996).

The therapeutic peptides contain, or may be modified to contain, functional groups to which a water-soluble polymer may be attached, either directly or through a spacer moiety or linker. Functional groups include, but are not limited to, the N-terminus of the therapeutic peptide, the C-terminus of the therapeutic peptide, and any functional groups on the side chain of an amino acid, e.g. lysine, cysteine, histidine, aspartic acid, glutamic acid, tyrosine, arginine, serine, methionine, and threonine, present in the therapeutic peptide.

The therapeutic peptides can be prepared by any means known in the art, including non-recombinant and recombinant methods, or they may, in some instances, be commercially available. Chemical or non-recombinant methods include, but are not limited to, solid phase peptide synthesis (SPPS), solution phase peptide synthesis, native chemical ligation, intein-mediated protein ligation, and chemical ligation, or a combination thereof. In a preferred embodiment, the therapeutic peptides are synthesized using standard SPPS, either manually or by using commercially available automated SPPS synthesizers.

SPPS has been known in the art since the early 1960's (Merrifield, R. B., *J. Am. Chem. Soc.*, 85:2149-2154 (1963)), and is widely employed. (See also, Bodanszky, Principles of Peptide Synthesis, Springer-Verlag, Heidelberg (1984)). There are several known variations on the general approach. (See, for example, "Peptide Synthesis, Structures, and Applications" © 1995 by Academic Press, Chapter 3 and White (2003) *Fmoc Solid Phase Peptide Synthesis, A practical Approach*, Oxford University Press, Oxford). Very briefly, in solid phase peptide synthesis, the desired C-terminal amino acid residue is coupled to a solid support. The subsequent amino acid to be added to the peptide chain is protected on its amino terminus with Boc, Fmoc, or other suitable protecting group, and its carboxy terminus is activated with a standard coupling reagent. The free amino terminus of the support-bound amino acid is allowed to react with the carboxy-terminus of the subsequent amino acid, coupling the two amino acids. The amino terminus of the growing peptide chain is deprotected, and the process is repeated until the desired polypeptide is completed. Side chain protecting groups may be utilized as needed.

Alternatively, the therapeutic peptides may be prepared recombinantly. Exemplary recombinant methods used to prepare therapeutic peptides include the following, among others, as will be apparent to one skilled in the art. Typically, a therapeutic peptide as defined and/or described herein is prepared by constructing the nucleic acid encoding the desired peptide or fragment, cloning the nucleic acid into an expression vector, transforming a host cell (e.g., plant, bacteria such as *Escherichia coli*, yeast such as *Saccharomyces cerevisiae*, or mammalian cell such as Chinese hamster ovary cell or baby hamster kidney cell), and expressing the nucleic acid to produce the desired peptide or fragment. The expression can occur via exogenous expression or via endogenous expression (when the host cell naturally contains the desired genetic coding). Methods for producing and expressing recombinant polypeptides in vitro and in prokaryotic and eukaryotic host cells are known to those of ordinary skill in the art. See, for example, U.S. Pat. No. 4,868,122, and Sambrook et al., Molecular Cloning—A Laboratory Manual, Cold Spring Harbor Laboratory Press (1989).

To facilitate identification and purification of the recombinant peptide, nucleic acid sequences that encode an epitope tag or other affinity binding sequence can be inserted or added in-frame with the coding sequence, thereby producing a fusion peptide comprised of the desired therapeutic peptide and a peptide suited for binding. Fusion peptides can be identified and purified by first running a mixture containing the fusion peptide through an affinity column bearing binding moieties (e.g., antibodies) directed against the epitope tag or other binding sequence in the fusion peptide, thereby binding the fusion peptide within the column. Thereafter, the fusion peptide can be recovered by washing the column with the appropriate solution (e.g., acid) to release the bound fusion peptide. Optionally, the tag may subsequently be removed by techniques known in the art. The recombinant peptide can also be identified and purified by lysing the host cells, separating the peptide, e.g., by size exclusion chromatography, and collecting the peptide. These and other methods for identifying and purifying recombinant peptides are known to those of ordinary skill in the art.

Related Peptides

It will be appreciated and understood by one of skill in the art that certain modifications can be made to the therapeutic peptides defined and/or disclosed herein that do not alter, or only partially abrogate, the properties and activities of these therapeutic peptides. In some instances, modifications may be made that result in an increase in therapeutic activities. Additionally, modifications may be made that increase certain biological and chemical properties of the therapeutic peptides in a beneficial way, e.g. increased in vivo half life, increased stability, decreased susceptibility to proteolytic cleavage, etc. Thus, in the spirit and scope of the invention, the term "therapeutic peptide" is used herein in a manner to include not only the therapeutic peptides defined and/or disclosed herein, but also related peptides, i.e. peptides that contain one or more modifications relative to the therapeutic peptides defined and/or disclosed herein, wherein the modification(s) do not alter, only partially abrogate, or increase the therapeutic activities as compared to the parent peptide.

Related peptides include, but are not limited to, fragments of therapeutic peptides, therapeutic peptide variants, and therapeutic peptide derivatives. Related peptides also include any and all combinations of these modifications. In a non-limiting example, a related peptide may be a fragment of a therapeutic peptide as disclosed herein having one or more amino acid substitutions. Thus it will be understood that any reference to a particular type of related peptide is not limited to a therapeutic peptide having only that particular modification, but rather encompasses a therapeutic peptide having that particular modification and optionally any other modification.

Related peptides may be prepared by action on a parent peptide or a parent protein (e.g. proteolytic digestion to generate fragments) or through de novo preparation (e.g. solid phase synthesis of a peptide having a conservative amino acid substitution relative to the parent peptide). Related peptides may arise by natural processes (e.g. processing and other post-translational modifications) or may be made by chemical modification techniques. Such modifications are well-known to those of skill in the art.

A related peptide may have a single alteration or multiple alterations relative to the parent peptide. Where multiple alterations are present, the alterations may be of the same type or a given related peptide may contain different types of modifications. Furthermore, modifications can occur anywhere in a polypeptide, including the peptide backbone, the amino acid side-chains, and the N- or C-termini.

As previously noted, related peptides include fragments of the therapeutic peptides defined and/or disclosed herein, wherein the fragment retains some of or all of at least one therapeutic activity of the parent peptide. The fragment may also exhibit an increase in at least one therapeutic activity of the parent peptide. In certain embodiments of the invention, therapeutic peptides include related peptides having at least 2, 3, 4, 5, 6, 7, 8, 9, 10, 11, 12, 13, 14, 15, 20, 25, 30, 35, 40, 45, 50, 60, 70, 80, 90, or 100 contiguous amino acid residues, or more than 125 contiguous amino acid residues, of any of the therapeutic peptides disclosed, herein, including in Table 1. In other embodiments of the invention, therapeutic peptides include related peptides having 0, 1, 2, 3, 4, 5, 6, 7, 8, 9, 10, 15, 20, 25, 30, 35, 40, 45, or 50 amino acid residues deleted from the N-terminus and/or having 0, 1, 2, 3, 4, 5, 6, 7, 8, 9, 10, 15, 20, 25, 30, 35, 40, 45, or 50 amino acid residues deleted from the C-terminus of any of the therapeutic peptides disclosed herein, including in Table 1.

Related peptides also include variants of the therapeutic peptides defined and/or disclosed herein, wherein the variant retains some of or all of at least one therapeutic activity of the parent peptide. The variant may also exhibit an increase in at least one therapeutic activity of the parent peptide. In certain embodiments of the invention, therapeutic peptides include variants having 1, 2, 3, 4, 5, 6, 7, 8, 9, 10, 15, 20, 25, 30, 35, 40, 45, or 50 conservative and/or non-conservative amino acid substitutions relative to the therapeutic peptides disclosed herein, including in Table 1. Desired amino acid substitutions, whether conservative or non-conservative, can be determined by those skilled in the art.

In certain embodiments of the invention, therapeutic peptides include variants having conservative amino substitutions; these substitutions will produce a therapeutic peptide having functional and chemical characteristics similar to those of the parent peptide. In other embodiments, therapeutic peptides include variants having non-conservative amino substitutions; these substitutions will produce a therapeutic peptide having functional and chemical characteristics that may differ substantially from those of the parent peptide. In certain embodiments of the invention, therapeutic peptide variants have both conservative and non-conservative amino acid substitutions. In other embodiments, each amino acid residue may be substituted with alanine.

Natural amino acids may be divided into classes based on common side chain properties: nonpolar (Gly, Ala, Val, Leu, Ile, Met); polar neutral (Cys, Ser, Thr, Pro, Asn, Gln); acidic (Asp, Glu); basic (His, Lys, Arg); and aromatic (Trp, Tyr, Phe). By way of example, non-conservative amino acid substitutions may involve the substitution of an amino acid of one class for that of another, and may be introduced in regions of the peptide not critical for therapeutic activity.

Preferably, amino acid substitutions are conservative. Conservative amino acid substitutions may involve the substitution of an amino acid of one class for that of the same class. Conservative amino acid substitutions may also encompass non-natural amino acid residues, including peptidomimetics and other atypical forms of amino acid moieties, and may be incorporated through chemical peptide synthesis.

Amino acid substitutions may be made with consideration to the hydropathic index of amino acids. The importance of the hydropathic amino acid index in conferring interactive biological function on a protein is generally understood in the art (Kyte et al., 1982, *J. Mol. Biol.* 157:105–31). Each amino acid has been assigned a hydropathic index on the basis of its hydrophobicity and charge characteristics. The hydropathic indices are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known that certain amino acids may be substituted for other amino acids having a similar hydropathic index or score and still retain a similar biological activity. In making changes based upon the hydropathic index, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity. The greatest local average hydrophilicity of a protein, as governed by the hydrophilicity of its adjacent amino acids, correlates with its biological properties. According to U.S. Pat. No. 4,554,101, incorporated herein by reference, the following hydrophilicity values have been assigned to these amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); and tryptophan (−3.4). In making changes based upon similar hydrophilicity values, the substitution of amino acids whose hydrophilicity values are within ±2 is preferred, those which are within ±1 are particularly preferred, and those within ±0.5 are even more particularly preferred.

In certain embodiments of the invention, therapeutic peptides include variants having 1, 2, 3, 4, 5, 6, 7, 8, 9, 10, 15, 20, 25, 30, 35, 40, 45, or 50 amino acid deletions relative to the therapeutic peptides disclosed herein, including in Table 1. The deleted amino acid(s) may be at the N- or C-terminus of the peptide, at both termini, at an internal location or locations within the peptide, or both internally and at one or both termini. Where the variant has more than one amino acid deletion, the deletions may be of contiguous amino acids or of amino acids at different locations within the primary amino acid sequence of the parent peptide.

In other embodiments of the invention, therapeutic peptides include variants having 1, 2, 3, 4, 5, 6, 7, 8, 9, 10, 15, 20, 25, 30, 35, 40, 45, or 50 amino acid additions relative to the therapeutic peptides disclosed herein, including in Table 1. The added amino acid(s) may be at the N- or C-terminus of the peptide, at both termini, at an internal location or locations within the peptide, or both internally and at one or both termini. Where the variant has more than one amino acid addition, the amino acids may be added contiguously, or the amino acids may be added at different locations within the primary amino acid sequence of the parent peptide.

Addition variants also include fusion peptides. Fusions can be made either at the N-terminus or at the C-terminus of the therapeutic peptides disclosed herein, including in Table 1. In certain embodiments, the fusion peptides have 1, 2, 3, 4, 5, 6, 7, 8, 9, 10, 15, 20, 25, 30, 35, 40, 45, or 50 amino acid additions relative to the therapeutic peptides disclosed herein, including in Table 1. Fusions may be attached directly to the therapeutic peptide with no connector molecule or may be through a connector molecule. As used in this context, a connector molecule may be an atom or a collection of atoms optionally used to link a therapeutic peptide to another peptide. Alternatively, the connector may be an amino acid sequence designed for cleavage by a protease to allow for the separation of the fused peptides.

The therapeutic peptides of the invention may be fused to peptides designed to improve certain qualities of the therapeutic peptide, such as therapeutic activity, circulation time, or reduced aggregation. Therapeutic peptides may be fused to an immunologically active domain, e.g. an antibody epitope, to facilitate purification of the peptide, or to increase the in vivo half life of the peptide. Additionally, therapeutic peptides may be fused to known functional domains, cellular localization sequences, or peptide permeant motifs known to improve membrane transfer properties.

In certain embodiments of the invention, therapeutic peptides also include variants incorporating one or more non-natural amino acids, amino acid analogs, and peptidomimetics. Thus the present invention encompasses compounds structurally similar to the therapeutic peptides defined and/or disclosed herein, which are formulated to mimic the key portions of the therapeutic peptides of the present invention. Such compounds may be used in the same manner as the therapeutic peptides of the invention. Certain mimetics that mimic elements of protein secondary and tertiary structure have been previously described. Johnson et al., Biotechnology and Pharmacy, Pezzuto et al. (Eds.), Chapman and Hall, NY, 1993. The underlying rationale behind the use of peptide mimetics is that the peptide backbone of proteins exists chiefly to orient amino acid side chains in such a way as to facilitate molecular interactions. A peptide mimetic is thus designed to permit molecular interactions similar to the parent peptide. Mimetics can be constructed to achieve a similar spatial orientation of the essential elements of the amino acid side chains. Methods for generating specific structures have been disclosed in the art. For example, U.S. Pat. Nos. 5,446,128, 5,710,245, 5,840,833, 5,859,184, 5,440,013; 5,618,914, 5,670,155, 5,475,085, 5,929,237, 5,672,681 and 5,674,976, the contents of which are hereby incorporated by reference, all disclose peptidomimetics structures that may have improved properties over the parent peptide, for example they may be conformationally restricted, be more thermally stable, exhibit increased resistance to degradation, etc.

In another embodiment, related peptides comprise or consist of a peptide sequence that is at least 70% identical to any of the therapeutic peptides disclosed herein, including in Table 1. In additional embodiments, related peptides are at least 75% identical, at least 80% identical, at least 85% identical, 90% identical, at least 91% identical, at least 92% identical, 93% identical, at least 94% identical, at least 95% identical, 96% identical, at least 97% identical, at least 98% identical, or at least 99% identical to any of the therapeutic peptides disclosed herein, including in Table 1.

Sequence identity (also known as % homology) of related polypeptides can be readily calculated by known methods. Such methods include, but are not limited to those described in *Computational Molecular Biology* (A. M. Lesk, ed., Oxford University Press 1988); *Biocomputing: Informatics and Genome Projects* (D. W. Smith, ed., Academic Press 1993); *Computer Analysis of Sequence Data* (Part 1, A. M. Griffin and H. G. Griffin, eds., Humana Press 1994); G. von Heinle, *Sequence Analysis in Molecular Biology* (Academic Press 1987); *Sequence Analysis Primer* (M. Gribskov and J. Devereux, eds., M. Stockton Press 1991); and Carillo et al., 1988, *SIAM J. Applied Math.*, 48:1073.

Preferred methods to determine sequence identity and/or similarity are designed to give the largest match between the sequences tested. Methods to determine sequence identity are described in publicly available computer programs. Preferred computer program methods to determine identity and similarity between two sequences include, but are not limited to, the GCG program package, including GAP (Devereux et al., 1984, *Nucleic Acids Res.* 12:387; Genetics Computer Group, University of Wisconsin, Madison, Wis.), BLASTP, BLASTN, and FASTA (Altschul et al., 1990, *J. Mol. Biol.* 215:403-10). The BLASTX program is publicly available from the National Center for Biotechnology Information (NCBI) and other sources (Altschul et al., *BLAST Manual* (NCB NLM NIH, Bethesda, Md.); Altschul et al., 1990, supra). The well-known Smith Waterman algorithm may also be used to determine identity.

For example, using the computer algorithm GAP (Genetics Computer Group, University of Wisconsin, Madison, Wis.), two polypeptides for which the percent sequence identity is to be determined are aligned for optimal matching of their respective amino acids (the "matched span," as determined by the algorithm). A gap opening penalty (which is calculated as 3× the average diagonal; the "average diagonal" is the average of the diagonal of the comparison matrix being used; the "diagonal" is the score or number assigned to each perfect amino acid match by the particular comparison matrix) and a gap extension penalty (which is usually 0.1× the gap opening penalty), as well as a comparison matrix such as PAM 250 or BLOSUM 62 are used in conjunction with the algorithm. A standard comparison matrix is also used by the algorithm (see Dayhoff et al., 5 *Atlas of Protein Sequence and Structure* (Supp. 3 1978) (PAM250 comparison matrix); Henikoff et al., 1992, *Proc. Natl. Acad. Sci USA* 89:10915-19 (BLOSUM 62 comparison matrix)). The particular choices to be made with regard to algorithms, gap opening penalties, gap extension penalties, comparison matrices, and thresholds of similarity will be readily apparent to those of skill in the art and will depend on the specific comparison to be made.

Related peptides also include derivatives of the therapeutic peptides defined and/or disclosed herein, wherein the variant retains some of or all of at least one therapeutic activity of the parent peptide. The derivative may also exhibit an increase in at least one therapeutic activity of the parent peptide. Chemical alterations of therapeutic peptide derivatives include, but are not limited to, acetylation, acylation, ADP-ribosylation, amidation, biotinylation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. (See, for instance, T. E. Creighton, Proteins, Structure and Molecular Properties, 2nd ed., W.H. Freeman and Company, New York (1993); Posttranslational Covalent Modification of Proteins, B. C. Johnson, ed., Academic Press, New York, pgs. 1-12 (1983); Seifter et al., Meth. Enzymol 182:626-46 (1990); Rattan et al., Ann. N.Y. Acad. Sci. 663:48-62, 1992).

Therapeutic peptide derivatives also include molecules formed by the deletion of one or more chemical groups from the parent peptide. Methods for preparing chemically modified derivatives of the therapeutic peptides defined and/or disclosed herein are known to one of skill in the art.

In some embodiments of the invention, the therapeutic peptides may be modified with one or more methyl or other lower alkyl groups at one or more positions of the therapeutic peptide sequence. Examples of such groups include methyl, ethyl, propyl, isopropyl, butyl, isobutyl, pentyl, etc. In certain preferred embodiments, arginine, lysine, and histidine residues of the therapeutic peptides are modified with methyl or other lower alkyl groups.

In other embodiments of the invention, the therapeutic peptides may be modified with one or more glycoside moieties relative to the parent peptide. Although any glycoside can be used, in certain preferred embodiments the therapeutic peptide is modified by introduction of a monosaccharide, a disaccharide, or a trisaccharide or it may contain a glycosylation sequence found in natural peptides or proteins in any mammal. The saccharide may be introduced at any position, and more than one glycoside may be introduced. Glycosylation may occur on a naturally occurring amino acid residue in the therapeutic peptide, or alternatively, an amino acid may be substituted with another for modification with the saccharide.

Glycosylated therapeutic peptides may be prepared using conventional Fmoc chemistry and solid phase peptide synthesis techniques, e.g., on resin, where the desired protected glycoamino acids are prepared prior to peptide synthesis and then introduced into the peptide chain at the desired position during peptide synthesis. Thus, the therapeutic peptide polymer conjugates may be conjugated in vitro. The glycosylation may occur before deprotection. Preparation of aminoacid glycosides is described in U.S. Pat. No. 5,767,254, WO 2005/097158, and Doores, K., et al., Chem. Commun., 1401-1403, 2006, which are incorporated herein by reference in their entireties. For example, alpha and beta selective glycosylations of serine and threonine residues are carried out using the Koenigs-Knorr reaction and Lemieux's in situ anomerization methodology with Schiff base intermediates. Deprotection of the Schiff base glycoside is then carried out using mildly acidic conditions or hydrogenolysis. A composition, comprising a glycosylated therapeutic peptide conjugate made by stepwise solid phase peptide synthesis involving contacting a growing peptide chain with protected amino acids in a stepwise manner, wherein at least one of the protected amino acids is glycosylated, followed by watersoluble polymer conjugation, may have a purity of at least 95%, such as at least 97%, or at least 98%, of a single species of the glycosylated and conjugated therapeutic peptide.

Monosaccharides that may by used for introduction at one or more amino acid residues of the therapeutic peptides defined and/or disclosed herein include glucose (dextrose), fructose, galactose, and ribose. Additional monosaccharides suitable for use include glyceraldehydes, dihydroxyacetone, erythrose, threose, erythrulose, arabinose, lyxose, xylose, ribulose, xylulose, allose, altrose, mannose, N-Acetylneuraminic acid, fucose, N-Acetylgalactosamine, and N-Acetylglucosamine, as well as others. Glycosides, such as mono-, di-, and trisaccharides for use in modifying a therapeutic peptide, may be naturally occurring or may be synthetic. Disaccharides that may by used for introduction at one or more amino acid residues of the therapeutic peptides defined and/or disclosed herein include sucrose, lactose, maltose, trehalose, melibiose, and cellobiose, among others. Trisaccharides include acarbose, raffinose, and melezitose.

In further embodiments of the invention, the therapeutic peptides defined and/or disclosed herein may be chemically coupled to biotin. The biotin/therapeutic peptide molecules can then to bind to avidin.

As previously noted, modifications may be made to the therapeutic peptides defined and/or disclosed herein that do not alter, or only partially abrogate, the properties and activities of these therapeutic peptides. In some instances, modifications may be made that result in an increase in therapeutic activity. Thus, included in the scope of the invention are modifications to the therapeutic peptides disclosed herein, including in Table 1, that retain at least 1%, at least 5%, at least 10%, at least 20%, at least 30%, at least 40%, at least 50%, at least 55%, at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, and any range derivable therein, such as, for example, at least 70% to at least 80%, and more preferably at least 81% to at least 90%; or even more preferably, between at least 91% and at least 99% of the therapeutic activity relative to the unmodified therapeutic peptide. Also included in the scope of the invention are modification to the therapeutic peptides disclosed herein, including in Table 1, that have greater than 100%, greater than 110%, greater than 125%, greater than 150%, greater than 200%, or greater than 300%, or greater than 10-fold or greater than 100-fold, and any range derivable therein, of the therapeutic activity relative to the unmodified therapeutic peptide.

The level of therapeutic activity of a given therapeutic peptide, or a modified therapeutic peptide, may be determined by any suitable in vivo or in vitro assay. For example, therapeutic activity may be assayed in cell culture, or by clinical evaluation, $EC_{50}$ assays, $IC_{50}$ assays, or dose response curves. In vitro or cell culture assays, for example, are commonly available and known to one of skill in the art for many therapeutic peptides as disclosed herein, including in Table 1. It will be understood by one of skill in the art that the percent activity of a modified therapeutic peptide relative to its unmodified parent can be readily ascertained through a comparison of the activity of each as determined through the assays disclosed herein or as known to one of skill in the art.

One of skill in the art will be able to determine appropriate modifications to the therapeutic peptides defined and/or disclosed herein, including those disclosed herein, including in Table 1. For identifying suitable areas of the therapeutic peptides that may be changed without abrogating their therapeutic activities, one of skill in the art may target areas not believed to be essential for activity. For example, when similar peptides with comparable activities exist from the same species or across other species, one of skill in the art may compare those amino acid sequences to identify residues that are conserved among similar peptides. It will be understood that changes in areas of a therapeutic peptide that are not conserved relative to similar peptides would be less likely to adversely affect the therapeutic activity. One skilled in the art would also know that, even in relatively conserved regions, one may substitute chemically similar amino acids while retaining therapeutic activity. Therefore, even areas that may be important for biological activity and/or for structure may be subject to amino acid substitutions without destroying the therapeutic activity or without adversely affecting the peptide structure.

Additionally, as appropriate, one of skill in the art can review structure-function studies identifying residues in similar peptides that are important for activity or structure. In view of such a comparison, one can predict the importance of an amino acid residue in a therapeutic peptide that corresponds to an amino acid residue that is important for activity or structure in similar peptides. One of skill in the art may opt for amino acid substitutions within the same class of amino acids for such predicted important amino acid residues of the therapeutic peptides.

Also, as appropriate, one of skill in the art can also analyze the three-dimensional structure and amino acid sequence in relation to that structure in similar peptides. In view of such information, one of skill in the art may predict the alignment of amino acid residues of a therapeutic peptide with respect to its three dimensional structure. One of skill in the art may choose not to make significant changes to amino acid residues predicted to be on the surface of the peptide, since such residues may be involved in important interactions with other molecules. Moreover, one of skill in the art may generate variants containing a single amino acid substitution at each amino acid residue for test purposes. The variants could be screened using therapeutic activity assays known to those with skill in the art. Such variants could be used to gather information about suitable modifications. For example, where a change to a particular amino acid residue resulted in abrogated, undesirably reduced, or unsuitable activity, variants with such a modification would be avoided. In other words, based on information gathered from routine experimentation, one of skill in the art can readily determine the amino acids where further modifications should be avoided either alone or in combination with other modifications.

One of skill in the art may also select suitable modifications based on secondary structure predication. A number of scientific publications have been devoted to the prediction of secondary structure. See Moult, 1996, *Curr. Opin. Biotechnol.* 7:422-27; Chou et al., 1974, *Biochemistry* 13:222-45; Chou et al., 1974, *Biochemistry* 113:211-22; Chou et al., 1978, Adv. *Enzymol. Relat. Areas Mol. Biol.* 47:45-48; Chou et al., 1978, *Ann. Rev. Biochem.* 47:251-276; and Chou et al., 1979, *Biophys. J.* 26:367-84. Moreover, computer programs are currently available to assist with predicting secondary structure. One method of predicting secondary structure is based upon homology modeling. For example, two peptides or proteins which have a sequence identity of greater than 30%, or similarity greater than 40%, often have similar structural topologies. Recent growth of the protein structural database (PDB, http://www.rcsb.org/pdb/home/home.do) has provided enhanced predictability of secondary, tertiary, and quarternary structure, including the potential number of folds within the structure of a peptide or protein. See Holm et al., 1999, *Nucleic Acids Res.* 27:244-47. It has been suggested that there are a limited number of folds in a given peptide or protein and that once a critical number of structures have been resolved, structural prediction will become dramatically more accurate (Brenner et al., 1997, *Curr. Opin. Struct. Biol.* 7:369-76).

Additional methods of predicting secondary structure include "threading" (Jones, 1997, *Curr. Opin. Struct. Biol.* 7:377-87; Sippl et al., 1996, *Structure* 4:15-19), "profile analysis" (Bowie et al., 1991, *Science*, 253:164-70; Gribskov et al., 1990, *Methods Enzymol.* 183:146-59; Gribskov et al., 1987, *Proc. Nat. Acad. Sci. U.S.A.* 84:4355-58), and "evolutionary linkage" (See Holm et al., supra, and Brenner et al., supra).

Therapeutic Peptide Conjugates

As described above, a conjugate of the invention comprises a water-soluble polymer covalently attached (either directly or through a spacer moiety or linker) to a therapeutic peptide. Typically, for any given conjugate, there will be about one to five water-soluble polymers covalently attached to a therapeutic peptide (wherein for each water-soluble polymer, the water-soluble polymer can be attached either directly to the therapeutic peptide or through a spacer moiety).

To elaborate, a therapeutic peptide conjugate of the invention typically has about 1, 2, 3, or 4 water-soluble polymers individually attached to a therapeutic peptide. That is to say, in certain embodiments, a conjugate of the invention will possess about 4 water-soluble polymers individually attached to a therapeutic peptide, or about 3 water-soluble polymers individually attached to a therapeutic peptide, or about 2 water-soluble polymers individually attached to a therapeutic peptide, or about 1 water-soluble polymer attached to a therapeutic peptide. The structure of each of the water-soluble polymers attached to the therapeutic peptide may be the same or different. One therapeutic peptide conjugate in accordance with the invention is one having a water-soluble polymer releasably attached to the therapeutic peptide, particularly at the N-terminus of the therapeutic peptide. Another therapeutic peptide conjugate in accordance with the invention is one having a water-soluble polymer stably attached to the therapeutic peptide, particularly at the N-terminus of the therapeutic peptide. Another therapeutic peptide conjugate is one having a water-soluble polymer releasably attached to the therapeutic peptide, particularly at the C-terminus of the therapeutic peptide. Another therapeutic peptide conjugate in accordance with the invention is one having a water-soluble polymer stably attached to the therapeutic peptide, particularly at the C-terminus of the therapeutic peptide. Other therapeutic peptide conjugates in accordance with the invention are those having a water-soluble polymer releasably or stably attached to an amino acid within the therapeutic peptide. Additional water-soluble polymers may be releasably or stably attached to other sites on the therapeutic peptide, e.g., such as one or more additional sites. For example, a therapeutic peptide conjugate having a water-soluble polymer releasably attached to the N-terminus may additionally possess a water-soluble polymer stably attached to a lysine residue. In one embodiment, one or more amino acids may be inserted, at the N- or C-terminus, or within the peptide to releasably or stably attach a water soluble polymer. One preferred embodiment of the present invention is a mono-therapeutic peptide polymer conjugate, i.e., a therapeutic peptide having one water-soluble polymer covalently attached thereto. In an even more preferred embodiment, the water-soluble polymer is one that is attached to the therapeutic peptide at its N-terminus.

Preferably, a therapeutic peptide polymer conjugate of the invention is absent a metal ion, i.e., the therapeutic peptide is not chelated to a metal ion.

For the therapeutic peptide polymer conjugates described herein, the therapeutic peptide may optionally possess one or more N-methyl substituents. Alternatively, for the therapeutic peptide polymer conjugates described herein, the therapeutic peptide may be glycosylated, e.g., having a mono- or disaccharide, or naturally-occurring amino acid glycosylation covalently attached to one or more sites thereof.

As discussed herein, the compounds of the present invention may be made by various methods and techniques known and available to those skilled in the art.

The Water-Soluble Polymer

A conjugate of the invention comprises a therapeutic peptide attached, stably or releasably, to a water-soluble polymer. The water-soluble polymer is typically hydrophilic, nonpeptidic, and biocompatible. A substance is considered biocompatible if the beneficial effects associated with use of the substance alone or with another substance (e.g., an active agent such a therapeutic peptide) in connection with living tissues (e.g., administration to a patient) outweighs any deleterious effects as evaluated by a clinician, e.g., a physician. A substance is considered nonimmunogenic if the intended use of the substance in vivo does not produce an undesired immune response (e.g., the formation of antibodies) or, if an immune response is produced, that such a response is not deemed clinically significant or important as evaluated by a clinician. Typically, the water-soluble polymer is hydrophilic, biocompatible and nonimmunogenic.

Further the water-soluble polymer is typically characterized as having from 2 to about 300 termini, preferably from 2 to 100 termini, and more preferably from about 2 to 50 termini. Examples of such polymers include, but are not limited to, poly(alkylene glycols) such as polyethylene glycol (PEG), poly(propylene glycol) ("PPG"), copolymers of ethylene glycol and propylene glycol and the like, poly (oxyethylated polyol), poly(olefinic alcohol), poly(vinylpyrrolidone), poly(hydroxyalkylmethacrylamide), poly(hydroxyalkylmethacrylate), poly(saccharides), poly($\alpha$-hydroxy acid), poly(vinyl alcohol), polyphosphazene, polyoxazoline, poly(N-acryloylmorpholine), and combinations of any of the foregoing, including copolymers and terpolymers thereof.

The water-soluble polymer is not limited to a particular structure and may possess a linear architecture (e.g., alkoxy PEG or bifunctional PEG), or a non-linear architecture, such as branched, forked, multi-armed (e.g., PEGs attached to a polyol core), or dendritic (i.e. having a densely branched structure with numerous end groups). Moreover, the polymer subunits can be organized in any number of different patterns and can be selected, e.g., from homopolymer, alternating copolymer, random copolymer, block copolymer, alternating tripolymer, random tripolymer, and block tripolymer.

One particularly preferred type of water-soluble polymer is a polyalkylene oxide, and in particular, polyethylene glycol (or PEG). Generally, a PEG used to prepare a therapeutic peptide polymer conjugate of the invention is "activated" or reactive. That is to say, the activated PEG (and other activated water-soluble polymers collectively referred to herein as "polymeric reagents") used to form a therapeutic peptide conjugate comprises an activated functional group suitable for coupling to a desired site or sites on the therapeutic peptide. Thus, a polymeric reagent for use in preparing a therapeutic peptide conjugate includes a functional group for reaction with the therapeutic peptide.

Representative polymeric reagents and methods for conjugating such polymers to an active moiety are known in the art, and are, e.g., described in Harris, J. M. and Zalipsky, S., eds, Poly(ethylene glycol), Chemistry and Biological Applications, ACS, Washington, 1997; Veronese, F., and J. M Harris, eds., Peptide and Protein PEGylation, Advanced Drug Delivery Reviews, 54(4); 453-609 (2002); Zalipsky, S., et al., "Use of Functionalized Poly(Ethylene Glycols) for Modification of Polypeptides" in Polyethylene Glycol Chemistry: Biotechnical and Biomedical Applications, J. M. Harris, ed., Plenus Press, New York (1992); Zalipsky (1995) Advanced Drug Reviews 16:157-182, and in Roberts, et al., Adv. Drug Delivery Reviews, 54, 459-476 (2002).

Additional PEG reagents suitable for use in forming a conjugate of the invention, and methods of conjugation are described in the Pasut. G., et al., Expert Opin. Ther. Patents (2004), 14(5). PEG reagents suitable for use in the present invention also include those available from NOF Corporation, as described generally on the NOF website (http://nofamerica.net/store/). Products listed therein and their chemical structures are expressly incorporated herein by reference. Additional PEGs for use in forming a therapeutic peptide conjugate of the invention include those available from Polypure (Norway) and from QuantaBioDesign LTD (Ohio), where the contents of their online catalogs (2006) with respect to available PEG reagents are expressly incorporated herein by reference. In addition, water soluble polymer reagents useful for preparing peptide conjugates of the invention can be prepared synthetically. Descriptions of the water soluble polymer reagent synthesis can be found in, for example, U.S. Pat. Nos. 5,252,714, 5,650,234, 5,739,208, 5,932,462, 5,629,384, 5,672,662, 5,990,237, 6,448,369, 6,362,254, 6,495,659, 6,413,507, 6,376,604, 6,348,558, 6,602,498, and 7,026,440.

Typically, the weight-average molecular weight of the water-soluble polymer in the conjugate is from about 100 Daltons to about 150,000 Daltons. Exemplary ranges include weight-average molecular weights in the range of from about 250 Daltons to about 80,000 Daltons, from 500 Daltons to about 80,000 Daltons, from about 500 Daltons to about 65,000 Daltons, from about 500 Daltons to about 40,000 Daltons, from about 750 Daltons to about 40,000 Daltons, from about 1000 Daltons to about 30,000 Daltons. In a preferred embodiment, the weight average molecular weight of the water-soluble polymer in the conjugate ranges from about 1000 Daltons to about 10,000 Daltons. In certain other preferred embodiments, the range is from about 1000 Daltons to about 5000 Daltons, from about 5000 Daltons to about 10,000 Daltons, from about 2500 Daltons to about 7500 Daltons, from about 1000 Daltons to about 3000 Daltons, from about 3000 Daltons to about 7000 Daltons, or from about 7000 Daltons to about 10,000 Daltons. In a further preferred embodiment, the weight average molecular weight of the water-soluble polymer in the conjugate ranges from about 20,000 Daltons to about 40,000 Daltons. In other preferred embodiments, the range is from about 20,000 Daltons to about 30,000 Daltons, from about 30,000 Daltons to about 40,000 Daltons, from about 25,000 Daltons to about 35,000 Daltons, from about 20,000 Daltons to about 26,000 Daltons, from about 26,000 Daltons to about 34,000 Daltons, or from about 34,000 Daltons to about 40,000 Daltons.

For any given water-soluble polymer, a molecular weight in one or more of these ranges is typical. Generally, a therapeutic peptide conjugate in accordance with the invention, when intended for subcutaneous or intravenous administration, will comprise a PEG or other suitable water-soluble polymer having a weight average molecular weight of about 20,000 Daltons or greater, while a therapeutic peptide conjugate intended for pulmonary administration will generally, although not necessarily, comprise a PEG polymer having a weight average molecular weight of about 20,000 Daltons or less.

Exemplary weight-average molecular weights for the water-soluble polymer include about 100 Daltons, about 200 Daltons, about 300 Daltons, about 400 Daltons, about 500 Daltons, about 600 Daltons, about 700 Daltons, about 750 Daltons, about 800 Daltons, about 900 Daltons, about 1,000 Daltons, about 1,500 Daltons, about 2,000 Daltons, about 2,200 Daltons, about 2,500 Daltons, about 3,000 Daltons, about 4,000 Daltons, about 4,400 Daltons, about 4,500 Daltons, about 5,000 Daltons, about 5,500 Daltons, about 6,000 Daltons, about 7,000 Daltons, about 7,500 Daltons, about 8,000 Daltons, about 9,000 Daltons, about 10,000 Daltons, about 11,000 Daltons, about 12,000 Daltons, about 13,000 Daltons, about 14,000 Daltons, about 15,000 Daltons, about 20,000 Daltons, about 22,500 Daltons, about 25,000 Daltons, about 30,000 Daltons, about 35,000 Daltons, about 40,000 Daltons, about 45,000 Daltons, about 50,000 Daltons, about 55,000 Daltons, about 60,000 Daltons, about 65,000 Daltons, about 70,000 Daltons, and about 75,000 Daltons.

Branched versions of the water-soluble polymer (e.g., a branched 40,000 Dalton water-soluble polymer comprised of two 20,000 Dalton polymers or the like) having a total molecular weight of any of the foregoing can also be used. In one or more particular embodiments, depending upon the other features of the subject therapeutic peptide polymer conjugate, the conjugate is one that does not have one or more attached PEG moieties having a weight-average molecular weight of less than about 6,000 Daltons.

In instances in which the water-soluble polymer is a PEG, the PEG will typically comprise a number of $(OCH_2CH_2)$ monomers. As used herein, the number of repeat units is typically identified by the subscript "n" in, for example, "$(OCH_2CH_2)_n$." Thus, the value of (n) typically falls within one or more of the following ranges: from 2 to about 3400, from about 100 to about 2300, from about 100 to about 2270, from about 136 to about 2050, from about 225 to about 1930, from about 450 to about 1930, from about 1200 to about 1930, from about 568 to about 2727, from about 660 to about 2730, from about 795 to about 2730, from about 795 to about 2730, from about 909 to about 2730, and from about 1,200 to about 1,900. Preferred ranges of n include from about 10 to about 700, and from about 10 to about 1800. For any given polymer in which the molecular weight is known, it is possible to determine the number of repeating units (i.e., "n") by dividing the total weight-average molecular weight of the polymer by the molecular weight of the repeating monomer.

With regard to the molecular weight of the water-soluble polymer, in one or more embodiments of the invention, depending upon the other features of the particular therapeutic peptide conjugate, the conjugate comprises a therapeutic peptide covalently attached to a water-soluble polymer having a molecular weight greater than about 2,000 Daltons.

A polymer for use in the invention may be end-capped, that is, a polymer having at least one terminus capped with a relatively inert group, such as a lower alkoxy group (i.e., a $C_{1-6}$ alkoxy group) or a hydroxyl group. One frequently employed end-capped polymer is methoxy-PEG (commonly referred to as mPEG), wherein one terminus of the polymer is a methoxy (—$OCH_3$) group. The -PEG- symbol used in the foregoing generally represents the following structural unit: —$CH_2CH_2O$—$(CH_2CH_2O)_n$—$CH_2CH_2$—, where (n) generally ranges from about zero to about 4,000.

Multi-armed or branched PEG molecules, such as those described in U.S. Pat. No. 5,932,462, are also suitable for use in the present invention. For example, the PEG may be described generally according to the structure:

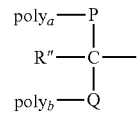

where $poly_a$ and $poly_b$ are PEG backbones (either the same or different), such as methoxy poly(ethylene glycol); R" is a non-reactive moiety, such as H, methyl or a PEG backbone; and P and Q are non-reactive linkages. In one embodiment, the branched PEG molecule is one that includes a lysine residue, such as the following reactive PEG suitable for use in forming a therapeutic peptide conjugate. Although the branched PEG below is shown with a reactive succinimidyl group, this represents only one of a myriad of reactive functional groups suitable for reacting with a therapeutic peptide.

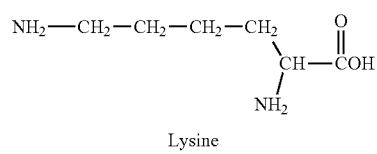

Lysine

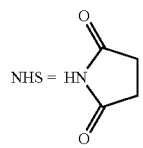

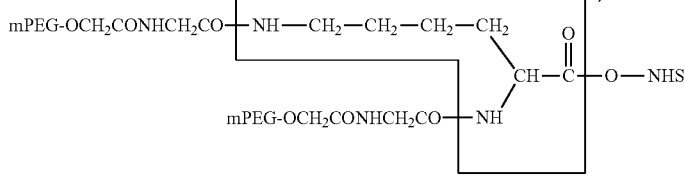

Branched mPEG Succinimidyl Derivative

In some instances, the polymeric reagent (as well as the corresponding conjugate prepared from the polymeric reagent) may lack a lysine residue in which the polymeric portions are connected to amine groups of the lysine via a "—OCH$_2$CONHCH$_2$CO—" group. In still other instances, the polymeric reagent (as well as the corresponding conjugate prepared from the polymeric reagent) may lack a branched water-soluble polymer that includes a lysine residue (wherein the lysine residue is used to effect branching).

Additional branched-PEGs for use in forming a therapeutic peptide conjugate of the present invention include those described in co-owned U.S. Patent Application Publication No. 2005/0009988. Representative branched polymers described therein include those having the following generalized structure:

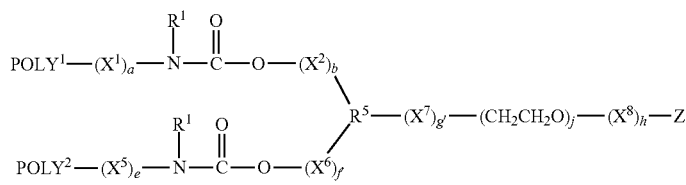

where POLY$^1$ is a water-soluble polymer; POLY$^2$ is a water-soluble polymer; (a) is 0, 1, 2 or 3; (b) is 0, 1, 2 or 3; (e) is 0, 1, 2 or 3; (f') is 0, 1, 2 or 3; (g') is 0, 1, 2 or 3; (h) is 0, 1, 2 or 3; (j) is 0 to 20; each R$^1$ is independently H or an organic radical selected from alkyl, substituted alkyl, alkenyl, substituted alkenyl, alkynyl, substituted alkynyl, aryl and substituted aryl; X$^1$, when present, is a spacer moiety; X$^2$, when present, is a spacer moiety; X$^5$, when present, is a spacer moiety; X$^6$, when present, is a spacer moiety; X$^7$, when present, is a spacer moiety; X$^8$, when present, is a spacer moiety; R$^5$ is a branching moiety; and Z is a reactive group for coupling to a therapeutic peptide, optionally via an intervening spacer. POLY$^1$ and POLY$^2$ in the preceding branched polymer structure may be different or identical, i.e., are of the same polymer type (structure) and molecular weight.

A preferred branched polymer falling into the above classification suitable for use in the present invention is:

with this embodiment of the invention possesses the structure, R(POLY-Z)$_y$, where each Z is independently an end-capping group or a reactive group, e.g., suitable for reaction with a therapeutic peptide. In yet a further embodiment when Z is a reactive group, upon reaction with a therapeutic peptide, the resulting linkage can be hydrolytically stable, or alternatively, may be degradable, i.e., hydrolyzable. Typically, at least one polymer arm possesses a terminal functional group suitable for reaction with, e.g., a therapeutic peptide. Branched PEGs such as those represented generally by the formula, R(PEG)$_y$ above possess 2 polymer arms to about 300 polymer arms (i.e., n ranges from 2 to about 300). Preferably, such branched PEGs typically possess from 2 to about 25 polymer arms, such as from 2 to about 20 polymer arms, from 2 to about 15 polymer arms, or from 3 to about 15 polymer arms. Multi-armed polymers include those having 3, 4, 5, 6, 7 or 8 arms.

Core molecules in branched PEGs as described above include polyols, which are then further functionalized. Such polyols include aliphatic polyols having from 1 to 10 carbon atoms and from 1 to 10 hydroxyl groups, including ethylene glycol, alkane diols, alkyl glycols, alkylidene alkyl diols, alkyl cycloalkane diols, 1,5-decalindiol, 4,8-bis(hydroxymethyl)tricyclodecane, cycloalkylidene diols, dihydroxyalkanes, trihydroxyalkanes, and the like. Cycloaliphatic polyols may also be employed, including straight chained or closed-ring sugars and sugar alcohols, such as mannitol, sorbitol, inositol, xylitol, quebrachitol, threitol, arabitol, erythritol, adonitol, ducitol, facose, ribose, arabinose, xylose, lyxose, rhamnose, galactose, glucose, fructose, sorbose, mannose, pyranose, altrose, talose, tagitose, pyranosides, sucrose, lactose, maltose, and the like. Additional

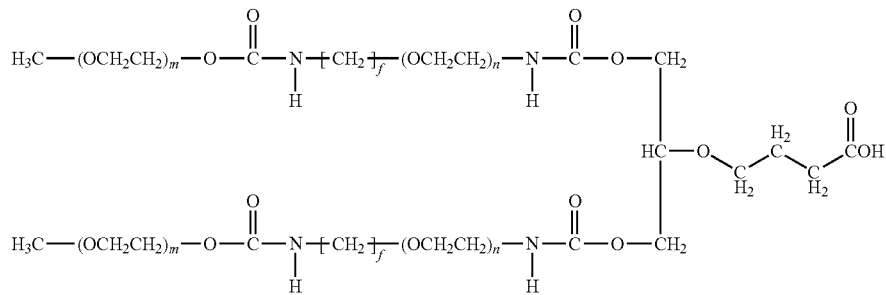

where (m) is 2 to 4000, and (f) is 0 to 6 and (n) is 0 to 20.

Branched polymers suitable for preparing a conjugate of the invention also include those represented more generally by the formula R(POLY)$_y$, where R is a central or core molecule from which extends 2 or more POLY arms such as PEG. The variable y represents the number of POLY arms, where each of the polymer arms can independently be end-capped or alternatively, possess a reactive functional group at its terminus. A more explicit structure in accordance aliphatic polyols include derivatives of glyceraldehyde, glucose, ribose, mannose, galactose, and related stereoisomers. Other core polyols that may be used include crown ether, cyclodextrins, dextrins and other carbohydrates such as starches and amylose. Typical polyols include glycerol, pentaerythritol, sorbitol, and trimethylolpropane.

As will be described in more detail in the linker section below, although any of a number of linkages can be used to covalently attach a polymer to a therapeutic peptide, in certain instances, the linkage is degradable, designated herein as $L_D$, that is to say, contains at least one bond or moiety that hydrolyzes under physiological conditions, e.g., an ester, hydrolyzable carbamate, carbonate, or other such group. In other instances, the linkage is hydrolytically stable.

Illustrative multi-armed PEGs having 3 arms, 4 arms, and 8 arms are known and are available commercially and/or can be prepared following techniques known to those skilled in the art. Multi-armed activated polymers for use in the method of the invention include those corresponding to the following structure, where E represents a reactive group suitable for reaction with a reactive group on the therapeutic peptide. In one or more embodiments, E is an —OH (for reaction with a therapeutic peptide carboxy group or equivalent), a carboxylic acid or equivalaent (such as an active ester), a carbonic acid (for reaction with therapeutic peptide —OH groups), or an amino group.

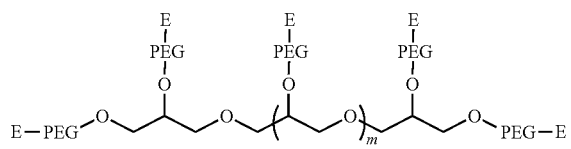

In the structure above, PEG is —(CH$_2$CH$_2$O)$_n$CH$_2$CH$_2$—, and m is selected from 3, 4, 5, 6, 7, and 8. In certain embodiments, typical linkages are ester, carboxyl and hydrolyzable carbamate, such that the polymer-portion of the conjugate is hydrolyzed in vivo to release the therapeutic peptide from the intact polymer conjugate. In such instances, the linker L is designated as $L_D$.

Alternatively, the polymer may possess an overall forked structure as described in U.S. Pat. No. 6,362,254. This type of polymer segment is useful for reaction with two therapeutic peptide moieties, where the two therapeutic peptide moieties are positioned a precise or predetermined distance apart.

In any of the representative structures provided herein, one or more degradable linkages may additionally be contained in the polymer segment, POLY, to allow generation in vivo of a conjugate having a smaller PEG chain than in the initially administered conjugate. Appropriate physiologically cleavable (i.e., releasable) linkages include but are not limited to ester, carbonate ester, carbamate, sulfate, phosphate, acyloxyalkyl ether, acetal, and ketal. Such linkages when contained in a given polymer segment will often be stable upon storage and upon initial administration.

The PEG polymer used to prepare a therapeutic peptide polymer conjugate may comprise a pendant PEG molecule having reactive groups, such as carboxyl or amino, covalently attached along the length of the PEG rather than at the end of the PEG chain(s). The pendant reactive groups can be attached to the PEG directly or through a spacer moiety, such as an alkylene group.

In certain embodiments, a therapeutic peptide polymer conjugate according to one aspect of the invention is one comprising a therapeutic peptide releasably attached, preferably at its N-terminus, to a water-soluble polymer. Hydrolytically degradable linkages, useful not only as a degradable linkage within a polymer backbone, but also, in the case of certain embodiments of the invention, for covalently attaching a water-soluble polymer to a therapeutic peptide, include: carbonate; imine resulting, for example, from reaction of an amine and an aldehyde (see, e.g., Ouchi et al. (1997) *Polymer Preprints* 38(1):582-3); phosphate ester, formed, for example, by reacting an alcohol with a phosphate group; hydrazone, e.g., formed by reaction of a hydrazide and an aldehyde; acetal, e.g., formed by reaction of an aldehyde and an alcohol; orthoester, formed, for example, by reaction between a formate and an alcohol; and esters, and certain urethane (carbamate) linkages.

Illustrative PEG reagents for use in preparing a releasable therapeutic peptide conjugate in accordance with the invention are described in U.S. Pat. Nos. 6,348,558, 5,612,460, 5,840,900, 5,880,131, and 6,376,470.

Additional PEG reagents for use in the invention include hydrolyzable and/or releasable PEGs and linkers such as those described in U.S. Patent Application Publication No. 2006-0293499. In the resulting conjugate, the therapeutic peptide and the polymer are each covalently attached to different positions of the aromatic scaffold, e.g., Fmoc or FMS, structure, and are releasable under physiological conditions. Generalized structures corresponding to the polymers described therein are provided below.

For example, one such polymeric reagent comprises the following structure:

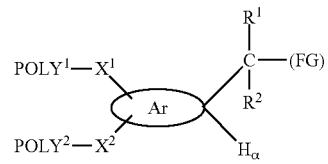

where POLY$^1$ is a first water-soluble polymer; POLY$^2$ is a second water-soluble polymer; X$^1$ is a first spacer moiety; X$^2$ is a second spacer moiety;

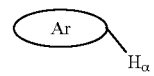

is an aromatic-containing moiety bearing an ionizable hydrogen atom, H$_\alpha$; R$^1$ is H or an organic radical; R$^2$ is H or an organic radical; and (FG) is a functional group capable of reacting with an amino group of an active agent to form a releasable linkage, such as a carbamate linkage (such as N-succinimidyloxy, 1-benzotriazolyloxy, oxycarbonylimidazole, —O—C(O)—Cl, O—C(O)—Br, unsubstituted aromatic carbonate radicals and substituted aromatic carbonate radicals). The polymeric reagent can include one, two, three, four or more electron altering groups attached to the aromatic-containing moiety.

Preferred aromatic-containing moieties are bicyclic and tricyclic aromatic hydrocarbons. Fused bicyclic and tricyclic aromatics include pentalene, indene, naphthalene, azulene, heptalene, biphenylene, as-indacene, s-indacene, acenaphthylene, fluorene, phenalene, phenanthrene, anthracene, and fluoranthene.

A preferred polymer reagent possesses the following structure,

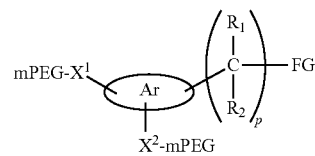

where mPEG corresponds to CH$_3$O—(CH$_2$CH$_2$O)$_n$CH$_2$CH$_2$—, X$^1$ and X$^2$ are each independently a spacer moiety having an atom length of from about 1 to about 18 atoms, n ranges from 10 to 1800, p is an integer ranging from 1 to 8, R$^1$ is H or lower alkyl, R$^2$ is H or lower alkyl, and Ar is an aromatic hydrodrocarbon, preferably a bicyclic or tricyclic aromatic hydrocarbon. FG is as defined above. Preferably, FG corresponds to an activated carbonate ester suitable for reaction with an amino group on therapeutic peptide. Preferred spacer moieties, X$^1$ and X$^2$, include —NH—C(O)—CH$_2$—O—, —NH—C(O)—(CH$_2$)$_q$—O—, —NH—C(O)—(CH$_2$)$_q$—C(O)—NH—, —NH—C(O)—(CH$_2$)$_q$—, and —C(O)—NH—, where q is selected from 2, 3, 4, and 5. Preferably, although not necessarily, the nitrogen in the preceding spacers is proximal to the PEG rather than to the aromatic moiety.

Another such branched (2-armed) polymeric reagent comprised of two electron altering groups comprises the following structure:

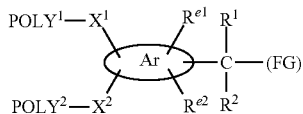

wherein each of POLY$^1$, POLY$^2$, X$^1$, X$^2$, R$^1$, R$^2$,

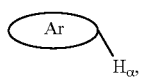

and (FG) is as defined immediately above, and R$^{e1}$ is a first electron altering group; and R$^{e2}$ is a second electron altering group. An electron altering group is a group that is either electron donating (and therefore referred to as an "electron donating group"), or electron withdrawing (and therefore referred to as an "electron withdrawing group"). When attached to the aromatic-containing moiety bearing an ionizable hydrogen atom, an electron donating group is a group having the ability to position electrons away from itself and closer to or within the aromatic-containing moiety. When attached to the aromatic-containing moiety bearing an ionizable hydrogen atom, an electron withdrawing group is a group having the ability to position electrons toward itself and away from the aromatic-containing moiety. Hydrogen is used as the standard for comparison in the determination of whether a given group positions electrons away or toward itself. Preferred electron altering groups include, but are not limited to, —CF$_3$, —CH$_2$CF$_3$, —CH$_2$C$_6$F$_5$, —CN, —NO$_2$, —S(O)R, —S(O)Aryl, —S(O$_2$)R, —S(O$_2$)Aryl, —S(O$_2$)OR, —S(O$_2$)OAryl, —S(O$_2$)NHR, —S(O$_2$)NHAryl, —C(O)R, —C(O)Aryl, —C(O)OR, —C(O)NHR, and the like, wherein R is H or an organic radical.

An additional branched polymeric reagent suitable for use in the present invention comprises the following structure:

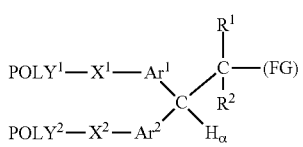

where POLY$^1$ is a first water-soluble polymer; POLY$^2$ is a second water-soluble polymer; X$^1$ is a first spacer moiety; X$^2$ is a second spacer moiety; Ar$^1$ is a first aromatic moiety; Ar$^2$ is a second aromatic moiety; H$_\alpha$ is an ionizable hydrogen atom; R$^1$ is H or an organic radical; R$^2$ is H or an organic radical; and (FG) is a functional group capable of reacting with an amino group of therapeutic peptide to form a releasable linkage, such as carbamate linkage.

Another exemplary polymeric reagent comprises the following structure:

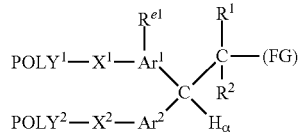

wherein each of POLY$^1$, POLY$^2$, X$^1$, X$^2$, Ar$^1$, Ar$^2$, H$_\alpha$, R$^1$, R$^2$, and (FG) is as previously defined, and R$^{e1}$ is a first electron altering group. While stereochemistry is not specifically shown in any structure provided herein, the provided structures contemplate both enantiomers, as well as compositions comprising mixtures of each enantiomer in equal amounts (i.e., a racemic mixture) and unequal amounts.

Yet an additional polymeric reagent for use in preparing a therapeutic peptide conjugate possesses the following structure:

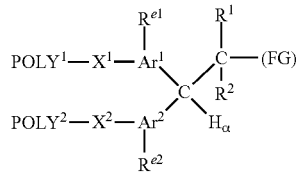

wherein each of POLY$^1$, POLY$^2$, X$^1$, X$^2$, Ar$^1$, Ar$^2$, H$_\alpha$, R$^1$, R$^2$, and (FG) is as previously defined, and R$^{e1}$ is a first electron altering group; and R$^{e2}$ is a second electron altering group.

A preferred polymeric reagent comprises the following structure:

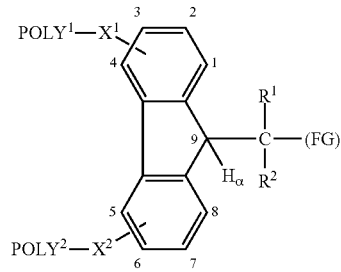

wherein each of POLY$^1$, POLY$^2$, X$^1$, X$^2$, R$^1$, R$^2$, H$_\alpha$ and (FG) is as previously defined, and, as can be seen from the structure above, the aromatic moiety is a fluorene. The POLY arms substituted on the fluorene can be in any position in each of their respective phenyl rings, i.e., POLY$^1$-X$^1$— can be positioned at any one of carbons 1, 2, 3, and 4, and POLY$^2$-X$^2$— can be in any one of positions 5, 6, 7, and 8.

Yet another preferred fluorene-based polymeric reagent comprises the following structure:

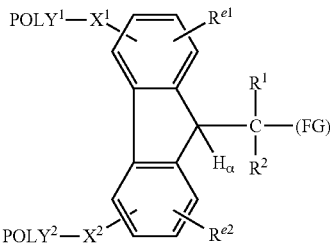

wherein each of POLY$^1$, POLY$^2$, X$^1$, X$^2$, R$^1$, R$^2$, H$_\alpha$ and (FG) is as previously defined, and R$^{e1}$ is a first electron altering group; and R$^{e2}$ is a second electron altering group as described above.

Yet another exemplary polymeric reagent for conjugating to a therapeutic peptide comprises the following fluorene-based structure:

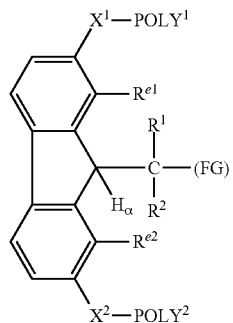

wherein each of POLY$^1$, POLY$^2$, X$^1$, X$^2$, R$^1$, R$^2$, H$_\alpha$ and (FG) is as previously defined, and R$^{e1}$ is a first electron altering group; and R$^{e2}$ is a second electron altering group.

Particular fluorene-based polymeric reagents for forming a releasable therapeutic peptide polymer conjugate in accordance with the invention include the following:

Still another exemplary polymeric reagent comprises the following structure:

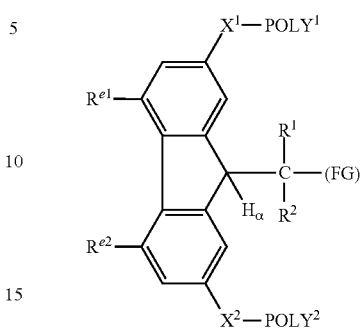

wherein each of POLY$^1$, POLY$^2$, X$^1$, X$^2$, R$^1$, R$^2$, H$_\alpha$ and (FG) is as previously defined, and R$^{e1}$ is a first electron altering group; and R$^{e2}$ is a second electron altering group. Branched reagents suitable for preparing a releasable therapeutic peptide conjugate include N-{di(mPEG(20,000)oxymethylcarbonylamino)fluoren-9-ylmethoxycarbonyloxy}succinimide, N-[2,7 di(4mPEG(10,000)aminocarbonylbutyrylamino)fluoren-9 ylmethoxycarbonyloxy]-succinimide ("G2PEG2Fmoc$_{20k}$-NHS"), and PEG2-CAC-Fmoc$_{4k}$-BTC. Of course, PEGs of any molecular weight as set forth herein may be employed in the above structures, and the particular activating groups described above are not meant to be limiting in any respect, and may be substituted by any other suitable activating group suitable for reaction with a reactive group present on the therapeutic peptide.

Those of ordinary skill in the art will recognize that the foregoing discussion describing water-soluble polymers for use in forming a therapeutic peptide conjugate is by no means exhaustive and is merely illustrative, and that all polymeric materials having the qualities described above are

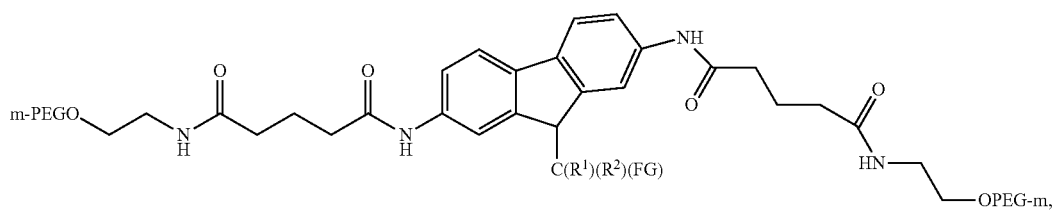

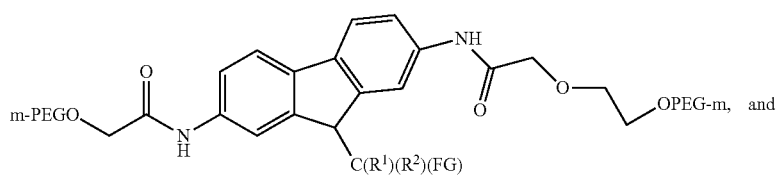

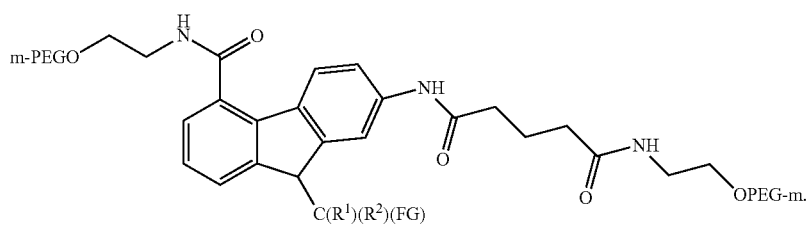

contemplated. As used herein, the term "polymeric reagent" generally refers to an entire molecule, which can comprise a water-soluble polymer segment, as well as additional spacers and functional groups.

The Linkage

The particular linkage between the therapeutic peptide and the water-soluble polymer depends on a number of factors. Such factors include, for example, the particular linkage chemistry employed, the particular spacer moieties utilized, if any, the particular therapeutic peptide, the available functional groups within the therapeutic peptide (either for attachment to a polymer or conversion to a suitable attachment site), and the possible presence of additional reactive functional groups or absence of functional groups within the therapeutic peptide due to modifications made to the peptide such as methylation and/or glycosylation, and the like.

In one or more embodiments of the invention, the linkage between the therapeutic peptide and the water-soluble polymer is a releasable linkage. That is, the water-soluble polymer is cleaved (either through hydrolysis, an enzymatic processes, or otherwise), thereby resulting in an unconjugated therapeutic peptide. Preferably, the releasable linkage is a hydrolytically degradable linkage, where upon hydrolysis, the therapeutic peptide, or a slightly modified version thereof, is released. The releasable linkage may result in the water-soluble polymer (and any spacer moiety) detaching from the therapeutic peptide in vivo (and in vitro) without leaving any fragment of the water-soluble polymer (and/or any spacer moiety or linker) attached to the therapeutic peptide. Exemplary releasable linkages include carbonate, carboxylate ester, phosphate ester, thiolester, anhydrides, acetals, ketals, acyloxyalkyl ether, imines, carbamates, and orthoesters. Such linkages can be readily formed by reaction of the therapeutic peptide and/or the polymeric reagent using coupling methods commonly employed in the art. Hydrolyzable linkages are often readily formed by reaction of a suitably activated polymer with a non-modified functional group contained within the therapeutic peptide. Preferred positions for covalent attachment of a water-soluble polymer incluce the N-terminal, the C-terminal, as well as the internal lysines. Preferred releasable linkages include carbamate and ester.

Generally speaking, a preferred therapeutic peptide conjugate of the invention will possess the following generalized structure:

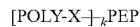

[POLY-X—]$_k$PEP where POLY is a water-soluble polymer such as any of the illustrative polymeric reagents provided in Tables 2-4 herein, X is a linker, and in some embodiments a hydrolyzable linkage ($L_D$), and k is an integer selected from 1, 2, and 3, and in some instances 4, 5, 6, 7, 8, 9 and 10. In the generalized structure above, where X is $L_D$, $L_D$ refers to the hydrolyzable linkage per se (e.g., a carbamate or an ester linkage), while "POLY" is meant to include the polymer repeat units, e.g., $CH_3(OCH_2CH_2)_n$—. In a preferred embodiment of the invention, at least one of the water-soluble polymer molecules is covalently attached to the N-terminus of therapeutic peptide. In one embodiment of the invention, k equals 1 and X is —O—C(O)—NH—, where the —NH— is part of the therapeutic peptide residue and represents an amino group thereof.

Although releasable linkages are exemplary, the linkage between the therapeutic peptide and the water-soluble polymer (or the linker moiety that is attached to the polymer) may be a hydrolytically stable linkage, such as an amide, a urethane (also known as carbamate), amine, thioether (also known as sulfide), or urea (also known as carbamide). One such embodiment of the invention comprises a therapeutic peptide having a water-soluble polymer such as PEG covalently attached at the N-terminus of therapeutic peptide. In such instances, alkylation of the N-terminal residue permits retention of the charge on the N-terminal nitrogen.

With regard to linkages, in one or more embodiments of the invention, a conjugate is provided that comprises a therapeutic peptide covalently attached at an amino acid residue, either directly or through a linker comprised of one or more atoms, to a water-soluble polymer.

The conjugates (as opposed to an unconjugated therapeutic peptide) may or may not possess a measurable degree of therapeutic peptide activity. That is to say, a conjugate in accordance with the invention will typically possess anywhere from about 0% to about 100% or more of the therapeutic activity of the unmodified parent therapeutic peptide. Typically, compounds possessing little or no therapeutic activity contain a releasable linkage connecting the polymer to the therapeutic peptide, so that regardless of the lack of therapeutic activity in the conjugate, the active parent molecule (or a derivative thereof having therapeutic activity) is released by cleavage of the linkage (e.g., hydrolysis upon aqueous-induced cleavage of the linkage). Such activity may be determined using a suitable in vivo or in vitro model, depending upon the known activity of the particular moiety having therapeutic peptide activity employed.

Optimally, cleavage of a linkage is facilitated through the use of hydrolytically cleavable and/or enzymatically cleavable linkages such as urethane, amide, certain carbamate, carbonate or ester-containing linkages. In this way, clearance of the conjugate via cleavage of individual water-soluble polymer(s) can be modulated by selecting the polymer molecular size and the type of functional group for providing the desired clearance properties. In certain instances, a mixture of polymer conjugates is employed where the polymers possess structural or other differences effective to alter the release (e.g., hydrolysis rate) of the therapeutic peptide, such that one can achieve a desired sustained delivery profile.

One of ordinary skill in the art can determine the proper molecular size of the polymer as well as the cleavable functional group, depending upon several factors including the mode of administration. For example, one of ordinary skill in the art, using routine experimentation, can determine a proper molecular size and cleavable functional group by first preparing a variety of polymer-(therapeutic peptide) conjugates with different weight-average molecular weights, degradable functional groups, and chemical structures, and then obtaining the clearance profile for each conjugate by administering the conjugate to a patient and taking periodic blood and/or urine samples. Once a series of clearance profiles has been obtained for each tested conjugate, a conjugate or mixture of conjugates having the desired clearance profile(s) can be determined.

For conjugates possessing a hydrolytically stable linkage that couples the therapeutic peptide to the water-soluble polymer, the conjugate will typically possess a measurable degree of therapeutic activity. For instance, such conjugates are typically characterized as having a therapeutic activity satisfying one or more of the following percentages relative to that of the unconjugated therapeutic peptide: at least 2%, at least 5%, at least 10%, at least 15%, at least 25%, at least 30%, at least 40%, at least 50%, at least 60%, at least 80%, at least 85%, at least 90%, at least 95%, at least 97%, at least 100%, more than 105%, more than 10-fold, or more than 100-fold (when measured in a suitable model, such as those presented here and/or known in the art). Often, conjugates having a hydrolytically stable linkage (e.g., an amide linkage) will possess at least some degree of the therapeutic activity of the unmodified parent therapeutic peptide.

Exemplary conjugates in accordance with the invention will now be described. Amino groups on a therapeutic peptide provide a point of attachment between the therapeutic peptide and the water-soluble polymer. For example, a therapeutic peptide may comprise one or more lysine residues, each lysine residue containing an g-amino group that may be available for conjugation, as well as one amino terminus.

There are a number of examples of suitable water-soluble polymeric reagents useful for forming covalent linkages with available amines of a therapeutic peptide. Certain specific examples, along with the corresponding conjugates, are provided in Table 2 below. In the table, the variable (n) represents the number of repeating monomeric units and "PEP" represents a therapeutic peptide following conjugation to the water-soluble polymer. While each polymeric portion [e.g., $(OCH_2CH_2)_n$ or $(CH_2CH_2O)_n$] presented in Table 2 terminates in a "$CH_3$" group, other groups (such as H and benzyl) can be substituted therefore.

As will be clearly understood by one skilled in the art, for conjugates such as those set forth below resulting from reaction with a therapeutic peptide amino group, the amino group extending from the therapeutic peptide designation "~NH-PEP" represents the residue of the therapeutic peptide itself in which the ~NH— is an amino group of the therapeutic peptide. One preferred site of attachment for the polymeric reagents shown below is the N-terminus. Further, although the conjugates in Tables 2-4 herein illustrate a single water-soluble polymer covalently attached to a therapeutic peptide, it will be understood that the conjugate structures on the right are meant to also encompass conjugates having more than one of such water-soluble polymer molecules covalently attached to therapeutic peptide, e.g., 2, 3, or 4 water-soluble polymer molecules.

TABLE 2

Amine-Specific Polymeric Reagents and the Therapeutic Peptide Conjugates Formed Therefrom

| Polymeric Reagent | Corresponding Conjugate |
|---|---|
| <br>mPEG-Oxycarbonylimidazole Reagent | H$_3$CO—(CH$_2$CH$_2$O)$_n$—C(=O)—NH—PEP<br>Carbamate Linkage |
| 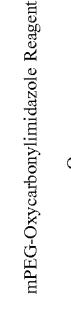<br>mPEG Nitrophenyl Reagent | H$_3$CO—(CH$_2$CH$_2$O)$_n$—C(=O)—NH—PEP<br>Carbamate Linkage |
| 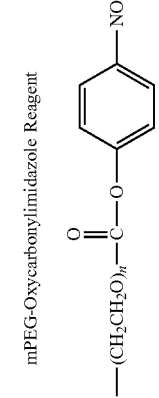<br>mPEG-Trichlorophenyl Carbonate Reagent | H$_3$CO—(CH$_2$CH$_2$O)$_n$—C(=O)—NH—PEP<br>Carbamate Linkage |
| 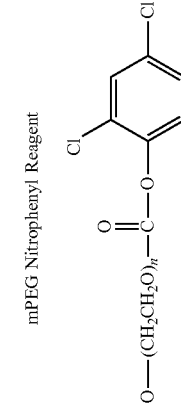<br>Fmoc-NHS Reagent | 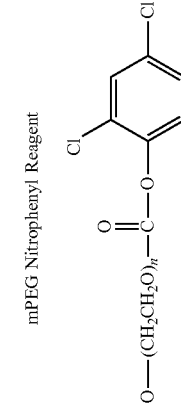<br>Carbamate Linkage |

TABLE 2-continued

Amine-Specific Polymeric Reagents and the Therapeutic Peptide Conjugates Formed Therefrom

| Polymeric Reagent | Corresponding Conjugate |
|---|---|

TABLE 2-continued

Amine-Specific Polymeric Reagents and the Therapeutic Peptide Conjugates Formed Therefrom

| Polymeric Reagent | Corresponding Conjugate |
|---|---|
| 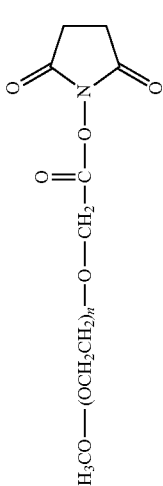<br>mPEG-Succinimidyl Reagent | 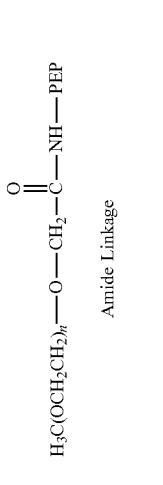<br>Amide Linkage |
| 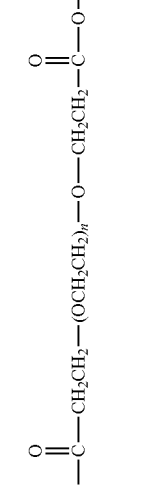<br>Homobifunctional PEG-Succinimidyl Reagent | 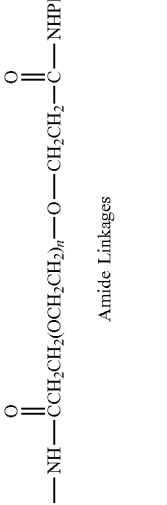<br>Amide Linkages |
| <br>Heterobifunctional PEG-Succinimidyl Reagent | <br>Amide Linkage |
| 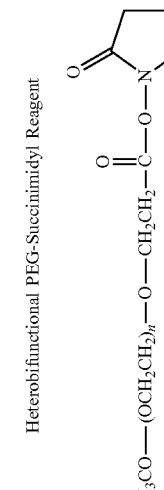<br>mPEG-Succinimidyl Reagent | 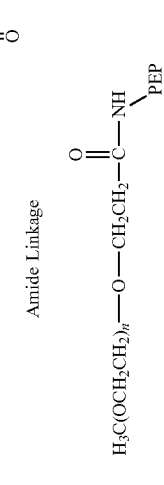<br>Amide Linkage |
| 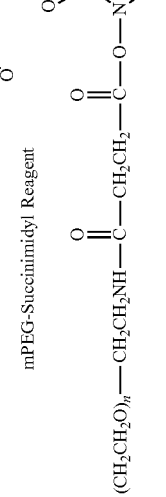 | 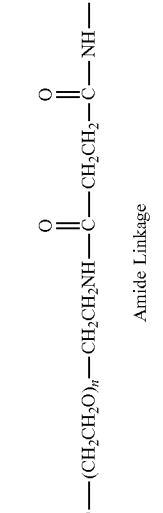<br>Amide Linkage |

TABLE 2-continued

Amine-Specific Polymeric Reagents and the Therapeutic Peptide Conjugates Formed Therefrom

| Polymeric Reagent | Corresponding Conjugate |
|---|---|
| mPEG-Succinimidyl Reagent<br>$H_3CO-(CH_2CH_2O)_n-CH_2CH_2SH-CH_2CH_2-\text{[NHS ester]}$ | $H_3CO-(CH_2CH_2O)_n-CH_2CH_2SH-CH_2CH_2-C(=O)-NH-PEP$<br>Amide Linkage |
| mPEG Succinimidyl Reagent<br>$H_3C-(OCH_2CH_2)_n-O-CH_2CH_2-\text{[NHS ester]}$ | $H_3C-(OCH_2CH_2)_n-O-CH_2CH_2-C(=O)-NH-PEP$<br>Amide Linkage |
| mPEG-Benzotriazole Carbonate Reagent<br>$H_3C-(OCH_2CH_2)_n-O-C(=O)-\text{[OBt]}$ | $H_3C-(OCH_2CH_2)_n-O-C(=O)-NH-PEP$<br>Carbamate Linkage |
| mPEG-Succinimidyl Reagent<br>$H_3C-(OCH_2CH_2)_n-NH-C(=O)-O-C_6H_4-C(=O)-O-\text{[NHS]}$ | $H_3C-(OCH_2CH_2)_n-NH-C(=O)-O-C_6H_4-C(=O)-NH-PEP$<br>Carbamate Linkage |
| mPEG-Succinimidyl Reagent<br>$H_3CO-(CH_2CH_2O)_n-C_6H_4-C(=O)-O-\text{[NHS]}$ | $H_3CO-(CH_2CH_2O)_n-C_6H_4-C(=O)-NH-PEP$<br>Amide Linkage |

TABLE 2-continued

Amine-Specific Polymeric Reagents and the Therapeutic Peptide Conjugates Formed Therefrom

| Polymeric Reagent | Corresponding Conjugate |
|---|---|
| mPEG Succinimidyl Reagent | Amide Linkage |
| Branched mPEG2-N-Hydroxysuccinimide Reagent | Amide Linkage |
| Branched mPEG2-Aldehyde Reagent | Secondary Amine Linkage |
| mPEG-Succinimidyl Reagent | Amide Linkage |

TABLE 2-continued

Amine-Specific Polymeric Reagents and the Therapeutic Peptide Conjugates Formed Therefrom

| Polymeric Reagent | Corresponding Conjugate |
|---|---|
| mPEG-Succinimidyl Reagent | Amide Linkage |
| Homobifunctional PEG-Succinimidyl Reagent | Amide Linkages |
| mPEG-Succinimidyl Reagent | Amide Linkage |
| Homobifunctional PEG-Succinimidyl Propionate Reagent | Amide Linkages |
| mPEG-Succinimidyl Reagent | Amide Linkage |

TABLE 2-continued

Amine-Specific Polymeric Reagents and the Therapeutic Peptide Conjugates Formed Therefrom

| Polymeric Reagent | Corresponding Conjugate |
|---|---|
| $H_3C-(OCH_2CH_2)_n-NH-\overset{O}{\underset{\|}{C}}-O-CH_2$<br>$\quad\quad\quad\quad\quad\quad\quad\quad\quad\quad\quad\quad\quad O\;\;\;\;\;\;\;\;\;\;HC-OCH_2-CH_2-CH-CH_3$<br>$H_3C-(OCH_2CH_2)_n-NH-\overset{\|}{\underset{O}{C}}-O-CH_2$<br>Branched mPEG2-N-Hydroxysuccinimide Reagent | $H_3C-(OCH_2CH_2)_n-NH-\overset{O}{\underset{\|}{C}}-O-CH_2$<br>$\quad\quad\quad\quad\quad\quad\quad\quad\quad\quad\quad\quad\quad O\;\;\;\;\;\;\;\;\;\;HC-OCH_2CH_2CH-\overset{O}{\underset{\|}{C}}-NH-PEP$<br>$\quad\quad\quad\quad\quad\quad\quad\quad\quad\quad\quad\quad\quad\quad\quad\quad\quad\quad\quad\quad\quad\quad\quad\quad CH_3$<br>$H_3C-(OCH_2CH_2)_n-NH-\overset{\|}{\underset{O}{C}}-O-CH_2$<br>Amide Linkage |
| $H_3C-(OCH_2CH_2)_n-NH-\overset{O}{\underset{\|}{C}}-O-CH_2$<br>$\quad\quad\quad\quad\quad\quad\quad\quad\quad\quad\quad\quad\quad O\;\;\;\;\;\;\;\;\;\;HC-OCH_2-CH_2-CH_2-\overset{O}{\underset{\|}{C}}-O-CH_2$<br>$H_3C-(OCH_2CH_2)_n-NH-\overset{\|}{\underset{O}{C}}-O-CH_2$<br>Branched mPEG2-N-Hydroxysuccinimide Reagent | $H_3C-(OCH_2CH_2)_n-NH-\overset{O}{\underset{\|}{C}}-O-CH_2$<br>$\quad\quad\quad\quad\quad\quad\quad\quad\quad\quad\quad\quad\quad O\;\;\;\;\;\;\;\;\;\;HC-OCH_2CH_2CH_2-\overset{O}{\underset{\|}{C}}-NH-PEP$<br>$H_3C-(OCH_2CH_2)_n-NH-\overset{\|}{\underset{O}{C}}-O-CH_2$<br>Amide Linkage |
| $H_3C-(OCH_2CH_2)_n-O-CH_2-CH_2-\overset{O}{\underset{\|}{C}}-S-\underset{\text{(pyridyl)}}{}$<br>mPEG-Thioester Reagent | $H_3C-(OCH_2CH_2)_n-O-CH_2CH_2\overset{O}{\underset{\|}{C}}-NH-PEP$<br>Amide Linkage |
| $\overset{O}{\underset{\|}{HC}}-CH_2CH_2-(OCH_2CH_2)_n-O-CH_2CH_2-\overset{O}{\underset{\|}{CH}}$<br>Homobifunctional PEG Propionaldehyde Reagent | $NH-CH_2CH_2CH_2-(OCH_2CH_2)_n-O-CH_2CH_2-CH_2-NH$<br>$\|\quad\quad\quad\quad\quad\quad\quad\quad\quad\quad\quad\quad\quad\quad\quad\quad\quad\quad\quad\quad\quad\quad\quad\quad\quad\quad\quad\quad\quad\quad\quad\quad\quad\|$<br>PEP$\quad\quad\quad\quad\quad\quad\quad\quad\quad\quad\quad\quad\quad\quad\quad\quad\quad\quad\quad\quad\quad\quad\quad\quad\quad\quad\quad\quad\quad\quad\quad\quad\quad$PEP<br>Secondary Amine Linkages |
| $H_3C-(OCH_2CH_2)_n-O-CH_2CH_2-\overset{O}{\underset{\|}{CH}}$<br>mPEG Propionaldehyde Reagent | $H_3C-(OCH_2CH_2)_n-O-CH_2CH_2-CH_2-NH-PEP$<br>Secondary Amine Linkage |
| $\overset{O}{\underset{\|}{HCCH_2CH_2CH_2}}-(OCH_2CH_2)_n-O-CH_2CH_2CH_2-\overset{O}{\underset{\|}{CH}}$<br>Homobifunctional PEG Butyraldehyde Reagent | $NH-CH_2CH_2CH_2CH_2-(OCH_2CH_2)_n-O-CH_2CH_2CH_2-CH_2-NH$<br>$\|\quad\quad\quad\quad\quad\quad\quad\quad\quad\quad\quad\quad\quad\quad\quad\quad\quad\quad\quad\quad\quad\quad\quad\quad\quad\quad\quad\quad\quad\quad\quad\quad\quad\|$<br>PEP$\quad\quad\quad\quad\quad\quad\quad\quad\quad\quad\quad\quad\quad\quad\quad\quad\quad\quad\quad\quad\quad\quad\quad\quad\quad\quad\quad\quad\quad\quad\quad\quad\quad$PEP<br>Secondary Amine Linkages |
| $H_3C-(OCH_2CH_2)_n-O-CH_2CH_2CH_2-\overset{O}{\underset{\|}{CH}}$ | $H_3C-(OCH_2CH_2)_n-O-CH_2CH_2CH_2-CH_2-NH-PEP$<br>Secondary Amine Linkage |

TABLE 2-continued

Amine-Specific Polymeric Reagents and the Therapeutic Peptide Conjugates Formed Therefrom

| Polymeric Reagent | Corresponding Conjugate |
|---|---|
| mPEG Butyraldehyde Reagent: $H_3C-(OCH_2CH_2)_n-O-\overset{O}{\overset{\|}{C}}-NH-(CH_2CH_2O)_4-CH_2CH_2CH$ | $H_3C-(OCH_2CH_2)_n-O-\overset{O}{\overset{\|}{C}}NH-(CH_2CH_2O)_4-CH_2CH_2CH_2-\underset{PEP}{NH}$ |
| mPEG Butyraldehyde Reagent: $\overset{O}{\overset{\|}{C}}-(OCH_2CH_2)_n-\overset{O}{\overset{\|}{C}}-NH-(CH_2CH_2O)_4-CH_2CH_2CH$<br>$HN$<br>$(CH_2CH_2O)_4-CH_2CH_2CH$<br>Homobifunctional PEG Butyraldehyde Reagent | Secondary Amine Linkage<br><br>$\overset{O}{\overset{\|}{C}}-(OCH_2CH_2)_n-CNH-(CH_2CH_2O)_4-CH_2CH_2CH_2-NH-PEP$<br>$HN$<br>$(CH_2CH_2O)_4-CH_2CH_2CH_2-NH-PEP$<br>Secondary Amine Linkages |
| $H_3C-(OCH_2CH_2)_n-NH-\overset{O}{\overset{\|}{C}}-O-CH_2$<br>$\phantom{H_3C-(OCH_2CH_2)_n-NH-C-O-}CH-C-NH-(CH_2CH_2O)_4-CH_2-CH_2-CH_2$<br>$\phantom{H_3C-(OCH_2CH_2)_n-NH-C-O-CH-C-NH-}\overset{O}{\overset{\|}{C}}$<br>$H_3C-(OCH_2CH_2)_n-NH-\overset{O}{\overset{\|}{C}}-O-\overset{\|}{C}-NH$<br>Branched mPEG2 Butyraldehyde Reagent | $H_3C-(OCH_2CH_2)_n-NH-\overset{O}{\overset{\|}{C}}-O-CH_2$<br>$\phantom{xxx}HC-\overset{O}{\overset{\|}{C}}-NH-(CH_2CH_2O)_4-CH_2CH_2CH_2-NH-PEP$<br>$H_3C-(OCH_2CH_2)_n-NH-\overset{O}{\overset{\|}{C}}-O-CH_2$<br>Secondary Amine Linkage |
| $H_3C-(OCH_2CH_2)_n-NH-\overset{O}{\overset{\|}{C}}-O-CH_2$<br>$\phantom{H_3C-(OCH_2CH_2)_n-NH-C-O-}HC-\overset{O}{\overset{\|}{C}}-NH-(CH_2CH_2O)_4-CH_2CH_2CH$<br>$H_3C-(OCH_2CH_2)_n-NH-\overset{O}{\overset{\|}{C}}-O-CH_2$<br>Branched mPEG2 Butyraldehyde Reagent | $H_3C-(OCH_2CH_2)_n-NH-\overset{O}{\overset{\|}{C}}-O-CH_2$<br>$\phantom{xxx}HC-\overset{O}{\overset{\|}{C}}-NH-(CH_2CH_2O)_4-CH_2CH_2CH_2-NH-PEP$<br>$H_3C-(OCH_2CH_2)_n-NH-\overset{O}{\overset{\|}{C}}-O-CH_2$<br>Secondary Amine Linkage |
| $H_3C-(OCH_2CH_2)_n-O-CH_2-CH\overset{OCH_2CH_3}{\underset{OCH_3}{\diagdown}}$<br>mPEG Acetal Reagent | $H_3C-(OCH_2CH_2)_n-O-CH_2CH_2-NH-PEP$<br>Secondary Amine Linkage |
| $H_3C-(OCH_2CH_2)_n-O-CH_2CH_2-\underset{O}{\overset{\|}{C}}-N\underset{\diagdown}{\diagup}=O$<br>mPEG Piperidone Reagent | $H_3C-(OCH_2CH_2)_n-O-CH_2CH_2-\underset{O}{\overset{\|}{C}}-N\underset{\diagdown}{\diagup}-NH-PEP$<br>Secondary Amine Linkage (to a secondary carbon) |

TABLE 2-continued

Amine-Specific Polymeric Reagents and the Therapeutic Peptide Conjugates Formed Therefrom

| Polymeric Reagent | Corresponding Conjugate |
|---|---|
| $H_3C-(OCH_2CH_2)_n-O-(CH_2)_{2-5}-\overset{O}{\overset{\|}{C}}-CH_3$<br>mPEG Methylketone Reagent | $H_3C-(OCH_2CH_2)_n-O-(CH_2)_{2-5}-\underset{\underset{NH-PEP}{\|}}{CH}-CH_3$<br>secondary amine linkage (to a secondary carbon) |
| $H_3CO-(CH_2CH_2O)_n-\overset{O}{\underset{\underset{O}{\|}}{\overset{\|}{S}}}-CH_2-CF_3$<br>mPEG Tresylate Reagent | $H_3CO-(CH_2CH_2O)_n-CH_2CH_2-NH-PEP$<br>Secondary Amine Linkage |
| <br>mPEG Maleimide Reagent (under certain reaction conditions such as pH > 8) | <br>Secondary Amine Linkage |
| <br>mPEG Maleimide Reagent (under certain reaction conditions such as pH > 8) | <br>Secondary Amine Linkage |
| 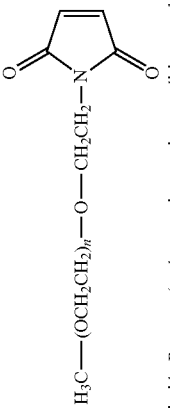<br>mPEG Maleimide Reagent (under certain reaction conditions such as pH > 8) | 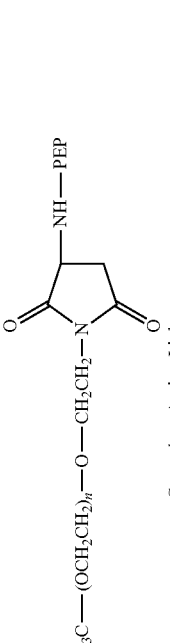<br>Secondary Amine Linkage |

TABLE 2-continued

Amine-Specific Polymeric Reagents and the Therapeutic Peptide Conjugates Formed Therefrom

| Polymeric Reagent | Corresponding Conjugate |
|---|---|
| 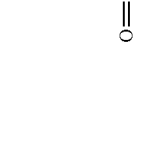<br>mPEG Forked Maleimide Reagent (under certain reaction conditions such as pH > 8) | 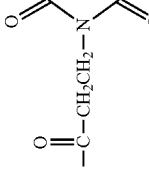<br>Secondary Amine Linkages |
| 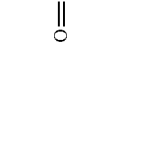<br>Branched mPEG2 Maleimide Reagent (under certain reaction conditions such as pH > 8) | <br>Secondary Amine Linkage |

Amine Conjugation and Resulting Conjugates

Conjugation of a polymeric reagent to an amine group of a therapeutic peptide can be accomplished by a variety of techniques. In one approach, a therapeutic peptide is conjugated to a polymeric reagent functionalized with an active ester such as a succinimidyl derivative (e.g., an N-hydroxysuccinimide ester). In this approach, the polymeric reagent bearing the reactive ester is reacted with the therapeutic peptide in aqueous media under appropriate pH conditions, e.g., from pHs ranging from about 3 to about 8, about 3 to about 7, or about 4 to about 6.5. Most polymer active esters can couple to a target peptide such as therapeutic peptide at physiological pH, e.g., at 7.0. However, less reactive derivatives may require a different pH. Typically, activated PEGs can be attached to a peptide such as therapeutic peptide at pHs from about 7.0 to about 10.0 for covalent attachment to an internal lysine. Typically, lower pHs are used, e.g., 4 to about 5.75, for preferential covalent attachment to the N-terminus. Thus, different reaction conditions (e.g., different pHs or different temperatures) can result in the attachment of a water-soluble polymer such as PEG to different locations on the therapeutic peptide (e.g., internal lysines versus the N-terminus). Coupling reactions can often be carried out at room temperature, although lower temperatures may be required for particularly labile therapeutic peptide moieties. Reaction times are typically on the order of minutes, e.g., 30 minutes, to hours, e.g., from about 1 to about 36 hours), depending upon the pH and temperature of the reaction. N-terminal PEGylation, e.g., with a PEG reagent bearing an aldehyde group, is typically conducted under mild conditions, pHs from about 5-10, for about 6 to 36 hours. Varying ratios of polymeric reagent to therapeutic peptide may be employed, e.g., from an equimolar ratio up to a 10-fold molar excess of polymer reagent. Typically, up to a 5-fold molar excess of polymer reagent will suffice.

In certain instances, it may be preferable to protect certain amino acids from reaction with a particular polymeric reagent if site specific or site selective covalent attachment is desired using commonly employed protection/deprotection methodologies such as those well known in the art.

In an alternative approach to direct coupling reactions, the PEG reagent may be incorporated at a desired position of the therapeutic peptide during peptide synthesis. In this way, site-selective introduction of one or more PEGs can be achieved. See, e.g., International Patent Publication No. WO 95/00162, which describes the site selective synthesis of conjugated peptides.

Exemplary conjugates that can be prepared using, for example, polymeric reagents containing a reactive ester for coupling to an amino group of therapeutic peptide, comprise the following alpha-branched structure:

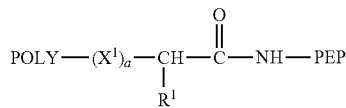

where POLY is a water-soluble polymer, (a) is either zero or one; $X^1$, when present, is a spacer moiety comprised of one or more atoms; $R^1$ is hydrogen an organic radical; and "~NH-PEP" represents a residue of a therapeutic peptide, where the underlined amino group represents an amino group of the therapeutic peptide.

With respect to the structure corresponding to that referred to in the immediately preceding paragraph, any of the water-soluble polymers provided herein can be defined as POLY, any of the spacer moieties provided herein can be defined as $X^1$ (when present), any of the organic radicals provided herein can be defined as $R^1$ (in instances where $R^1$ is not hydrogen), and any of the therapeutic peptides provided herein can be employed. In one or more embodiments corresponding to the structure referred to in the immediately preceding paragraph, POLY is a poly(ethylene glycol) such as $H_3CO(CH_2CH_2O)_n$—, wherein (n) is an integer having a value of from 3 to 4000, more preferably from 10 to about 1800; (a) is one; $X^1$ is a $C_{1-6}$ alkylene, such as one selected from methylene (i.e., —$CH_2$—), ethylene (i.e., —$CH_2$—$CH_2$—) and propylene (i.e., —$CH_2$—$CH_2$—$CH_2$—); $R^1$ is H or lower alkyl such as methyl or ethyl; and PEP corresponds to any therapeutic peptide disclosed herein, including in Table 1.

Typical of another approach for conjugating a therapeutic peptide to a polymeric reagent is reductive amination. Typically, reductive amination is employed to conjugate a primary amine of a therapeutic peptide with a polymeric reagent functionalized with a ketone, aldehyde or a hydrated form thereof (e.g., ketone hydrate and aldehyde hydrate). In this approach, the primary amine from the therapeutic peptide (e.g., the N-terminus) reacts with the carbonyl group of the aldehyde or ketone (or the corresponding hydroxy-containing group of a hydrated aldehyde or ketone), thereby forming a Schiff base. The Schiff base, in turn, is then reductively converted to a stable conjugate through use of a reducing agent such as sodium borohydride or any other suitable reducing agent. Selective reactions (e.g., at the N-terminus) are possible, particularly with a polymer functionalized with a ketone or an alpha-methyl branched aldehyde and/or under specific reaction conditions (e.g., reduced pH).

Exemplary conjugates that can be prepared using, for example, polymeric reagents containing an aldehyde (or aldehyde hydrate) or ketone or (ketone hydrate) possess the following structure:

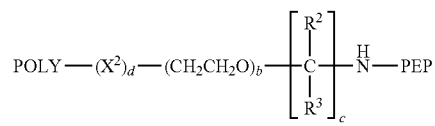

where POLY is a water-soluble polymer; (d) is either zero or one; $X^2$, when present, is a spacer moiety comprised of one or more atoms; (b) is an integer having a value of one through ten; (c) is an integer having a value of one through ten; $R^2$, in each occurrence, is independently H or an organic radical; $R^3$, in each occurrence, is independently H or an organic radical; and "~NH-PEP" represents a residue of a therapeutic peptide, where the underlined amino group represents an amino group of the therapeutic peptide.

Yet another illustrative conjugate of the invention possesses the structure:

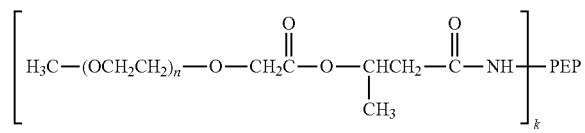

where k ranges from 1 to 3, and n ranges from 10 to about 1800.

With respect to the structure corresponding to that referred to in immediately preceding paragraph, any of the water-soluble polymers provided herein can be defined as POLY, any of the spacer moieties provided herein can be defined as $X^2$ (when present), any of the organic radicals provided herein can be independently defined as $R^2$ and $R^3$ (in instances where $R^2$ and $R^3$ are independently not hydrogen), and any of the PEP moieties provided herein can be defined as a therapeutic peptide. In one or more embodiments of the structure referred to in the immediately preceding paragraph, POLY is a poly(ethylene glycol) such as $H_3CO(CH_2CH_2O)_n$—, wherein (n) is an integer having a value of from 3 to 4000, more preferably from 10 to about 1800; (d) is one; $X^1$ is amide [e.g., —C(O)NH—]; (b) is 2 through 6, such as 4; (c) is 2 through 6, such as 4; each of $R^2$ and $R^3$ are independently H or lower alkyl, such as methyl when lower alkyl; and PEP is therapeutic peptide.

Another example of a therapeutic peptide conjugate in accordance with the invention has the following structure:

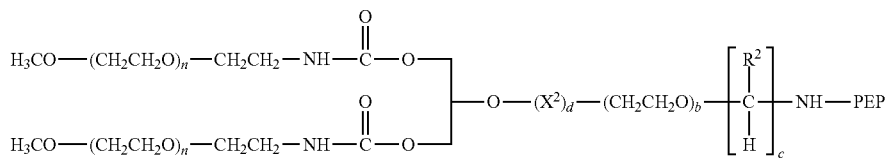

wherein each (n) is independently an integer having a value of from 3 to 4000, preferably from 10 to 1800; $X^2$ is as previously defined; (b) is 2 through 6; (c) is 2 through 6; $R^2$, in each occurrence, is independently H or lower alkyl; and "~NH-PEP" represents a residue of a therapeutic peptide, where the underlined amino group represents an amino group of the therapeutic peptide.

Additional therapeutic peptide polymer conjugates resulting from reaction of a water-soluble polymer with an amino group of therapeutic peptide are provided below. The following conjugate structures are releasable. One such structure corresponds to:

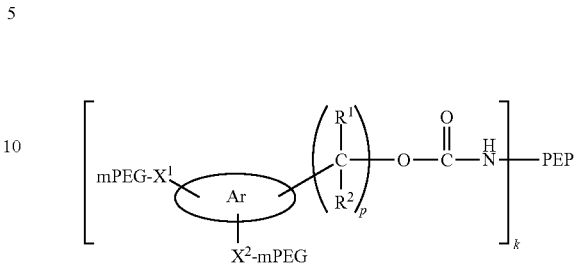

where mPEG is $CH_3O$—$(CH_2CH_2O)_nCH_2CH_2$—, n ranges from 10 to 1800, p is an integer ranging from 1 to 8, $R^1$ is H or lower alkyl, $R^2$ is H or lower alkyl, Ar is an aromatic hydrocarbon, such as a fused bicyclic or tricyclic aromatic hydrocarbon, $X^1$ and $X^2$ are each independently a spacer moiety having an atom length of from about 1 to about 18 atoms, ~NH-PEP is as previously described, and k is an integer selected from 1, 2, and 3. The value of k indicates the number of water-soluble polymer molecules attached to different sites on the therapeutic peptide. In a preferred embodiment, $R^1$ and $R^2$ are both H. The spacer moieties, $X^1$ and $X^2$, preferably each contain one amide bond. In a preferred embodiment, $X^1$ and $X^2$ are the same. Preferred spacers, i.e., $X^1$ and $X^2$, include —NH—C(O)—$CH_2$—O—, —NH—C(O)—$(CH_2)_q$—O—, —NH—C(O)—$(CH_2)_q$—C(O)—NH—, —NH—C(O)—$(CH_2)_q$—, and —C(O)—NH—, where q is selected from 2, 3, 4, and 5. Although the spacers can be in either orientation, preferably, the nitrogen is proximal to the PEG rather than to the aromatic moiety. Illustrative aromatic moieties include pentalene, indene, naphthalene, indacene, acenaphthylene, and fluorene.

Particularly preferred conjugates of this type are provided below.

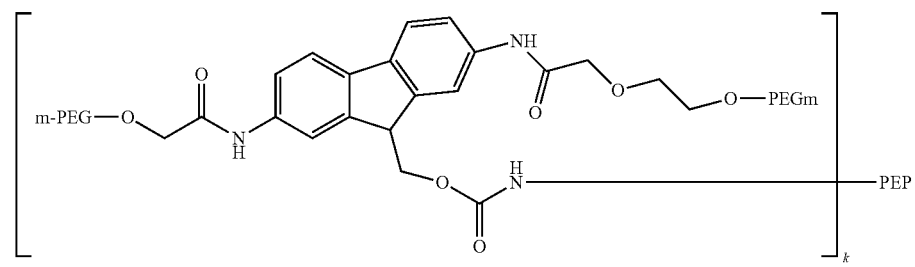

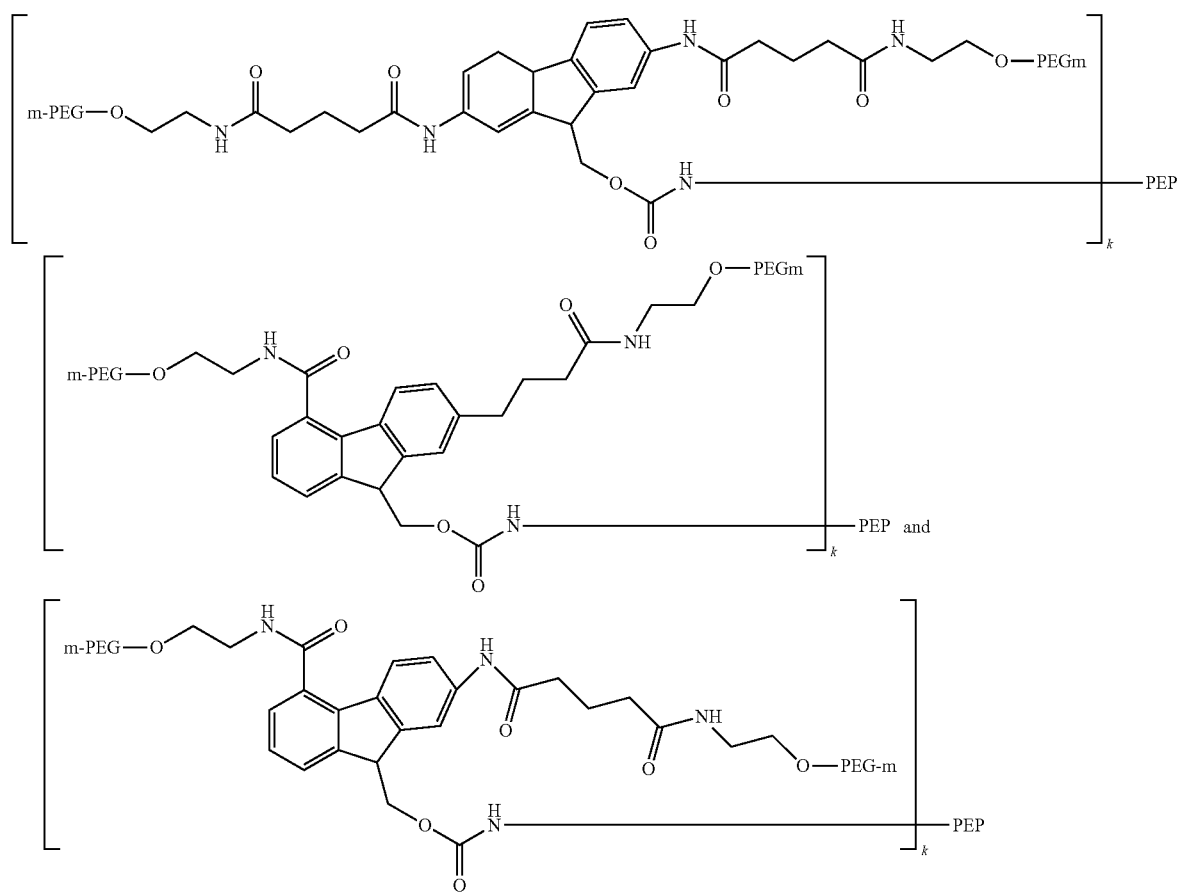

Additional therapeutic peptide conjugates resulting from covalent attachment to amino groups of therapeutic peptide that are also releasable include the following:

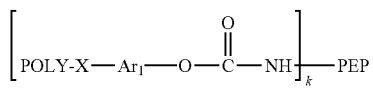

where X is either —O— or —NH—C(O)—, $Ar_1$ is an aromatic group, e.g., ortho, meta, or para-substituted phenyl, and k is an integer selected from 1, 2, and 3. Particular conjugates of this type include:

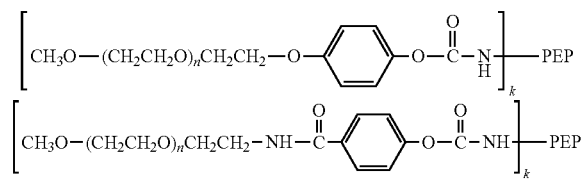

where n ranges from about 10 to about 1800.

Additional releasable conjugates in accordance with the invention are prepared using water-soluble polymer reagents such as those described in U.S. Pat. No. 6,214,966. Such water-soluble polymers result in a releasable linkage following conjugation, and possess at least one releasable ester linkage close to the covalent attachment to the active agent. The polymers generally possess the following structure, PEG-W—$CO_2$—NHS or an equivalent activated ester, where

| W = | —$O_2C$—$(CH_2)_b$—O— | b = 1-5 |
|---|---|---|
| | —O—$(CH_2)_b CO_2$—$(CH_2)_c$— | b = 1-5, c = 2-5 |
| | —O—$(CH_2)_b$—$CO_2$—$(CH_2)_c$—O— | b = 1-5, c = 2-5 | and NHS is N-hydroxysuccinimidyl. Upon hydrolysis, the resulting released active agent, e.g., therapeutic peptide, will possess a short tag resulting from hydrolysis of the ester functionality of the polymer reagent. Illustrative releasable conjugates of this type include: mPEG-O—$(CH_2)_b$—COOCH$_2$C(O)—NH-therapeutic peptide, and mPEG-O—$(CH_2)_b$—COO—CH($CH_3$)—$CH_2$—C(O)—NH-therapeutic peptide, where the number of water-soluble polymers attached to therapeutic peptide can be anywhere from 1 to 4, or more preferably, from 1 to 3.

Carboxyl Coupling and Resulting Conjugates

Carboxyl groups represent another functional group that can serve as a point of attachment to the therapeutic peptide. The conjugate will have the following structure:

PEP-C(O)—X-POLY where PEP-C(O)~corresponds to a residue of a therapeutic peptide where the carbonyl is a carbonyl (derived from the carboxy group) of the therapeutic peptide, X is a spacer moiety, such as a heteroatom selected from O, N(H), and S, and POLY is a water-soluble polymer such as PEG, optionally terminating in an end-capping moiety.

The C(O)—X linkage results from the reaction between a polymeric derivative bearing a terminal functional group and a carboxyl-containing therapeutic peptide. As discussed above, the specific linkage will depend on the type of functional group utilized. If the polymer is end-functionalized or "activated" with a hydroxyl group, the resulting linkage will be a carboxylic acid ester and X will be O. If the polymer backbone is functionalized with a thiol group, the resulting linkage will be a thioester and X will be S. When certain multi-arm, branched or forked polymers are employed, the C(O)X moiety, and in particular the X moiety, may be relatively more complex and may include a longer linker structure.

Polymeric reagents containing a hydrazide moiety are also suitable for conjugation at a carbonyl. To the extent that the therapeutic peptide does not contain a carbonyl moiety, a carbonyl moiety can be introduced by reducing any carboxylic acid functionality (e.g., the C-terminal carboxylic acid). Specific examples of polymeric reagents comprising a hydrazide moiety, along with the corresponding conjugates, are provided in Table 3, below. In addition, any polymeric reagent comprising an activated ester (e.g., a succinimidyl group) can be converted to contain a hydrazide moiety by reacting the polymer activated ester with hydrazine ($NH_2$—$NH_2$) or tert-butyl carbamate [$NH_2NHCO_2C(CH_3)_3$]. In the table, the variable (n) represents the number of repeating monomeric units and "=C-(PEP)" represents a residue of a therapeutic peptide following conjugation to the polymeric reagent were the underlined C is part of the therapeutic peptide. Optionally, the hydrazone linkage can be reduced using a suitable reducing agent. While each polymeric portion [e.g., $(OCH_2CH_2)_n$ or $(CH_2CH_2O)_n$] presented in Table 3 terminates in a "$CH_3$" group, other groups (such as H and benzyl) can be substituted therefor.

TABLE 3

Carboxyl-Specific Polymeric Reagents and the GM-Therapeutic Peptide Conjugates Formed Therefrom

| Polymeric Reagent | Corresponding Conjugate |
|---|---|
| $H_3CO-(CH_2CH_2O)_n CH_2CH_2-\overset{O}{\underset{\|}{C}}-NH-NH_2$ <br> mPEG-Hydrazine Reagent | $H_3CO-(CH_2CH_2O)_n CH_2CH_2-\overset{O}{\underset{\|}{C}}-NH-N=\underline{C}-PEP$ <br> Hydrazone Linkage |
| $H_3CO-(CH_2CH_2O)_n CH_2CH_2-O-CH_2-\overset{O}{\underset{\|}{C}}-NH-NH_2$ <br> mPEG-Hydrazine Reagent | $H_3CO-(CH_2CH_2O)_n CH_2CH_2-O-CH_2-\overset{O}{\underset{\|}{C}}-NH-N=\underline{C}-PEP$ <br> Hydrazone Linkage |
| $H_3CO-(CH_2CH_2O)_n CH_2CH_2-NH-\overset{O}{\underset{\|}{C}}-NH-NH_2$ <br> mPEG-Hydrazine Reagent | $H_3CO-(CH_2CH_2O)_n CH_2CH_2-NH-\overset{O}{\underset{\|}{C}}-NH-N=\underline{C}-PEP$ <br> Hydrazone Linkage |
| $H_3CO-(CH_2CH_2O)_n CH_2CH_2-NH-NH-\overset{O}{\underset{\|}{C}}-NH-NH_2$ <br> mPEG-Hydrazine Reagent | $H_3CO-(CH_2CH_2O)_n CH_2CH_2-\overset{H}{N}-NH-\overset{O}{\underset{\|}{C}}-NH-N=\underline{C}-PEP$ <br> Hydrazone Linkage |
| $H_3CO-(CH_2CH_2O)_n CH_2CH_2-NH-\overset{S}{\underset{\|}{C}}-NH-NH_2$ <br> mPEG-Hydrazine Reagent | $H_3CO-(CH_2CH_2O)_n CH_2CH_2-NH-\overset{S}{\underset{\|}{C}}-NH-N=\underline{C}-PEP$ <br> Hydrazone Linkage |
| $H_3CO-(CH_2CH_2O)_n CH_2CH_2-NH-NH-\overset{S}{\underset{\|}{C}}-NH-NH_2$ <br> mPEG-Hydrazine Reagent | $H_3CO-(CH_2CH_2O)_n CH_2CH_2-\overset{H}{N}-NH-\overset{S}{\underset{\|}{C}}-NH-N=\underline{C}-PEP$ <br> Hydrazone Linkage |
| $H_3CO-(CH_2CH_2O)_n CH_2CH_2-NH-\overset{O}{\underset{\|}{C}}-NH-NH-\overset{O}{\underset{\|}{C}}-NH-NH_2$ <br> mPEG-Hydrazine Reagent | $H_3CO-(CH_2CH_2O)_n CH_2CH_2-NH-\overset{O}{\underset{\|}{C}}-NH-NH-\overset{O}{\underset{\|}{C}}-NH-N=\underline{C}-PEP$ <br> Hydrazone Linkage |
| $H_3CO-(CH_2CH_2O)_n CH_2CH_2-O-\overset{O}{\underset{\|}{C}}-NH-NH_2$ <br> mPEG-Hydrazine Reagent | $H_3CO-(CH_2CH_2O)_n CH_2CH_2-O-\overset{O}{\underset{\|}{C}}-NH-N=\underline{C}-PEP$ <br> Hydrazone Linkage |

Thiol Coupling and Resulting Conjugates

Thiol groups contained within the therapeutic peptide can serve as effective sites of attachment for the water-soluble polymer. The thiol groups contained in cysteine residues of the therapeutic peptide can be reacted with an activated PEG that is specific for reaction with thiol groups, e.g., an N-maleimidyl polymer or other derivative, as described in, for example, U.S. Pat. No. 5,739,208, WO 01/62827, and in Table 4 below. In certain embodiments, cysteine residues may be introduced in the therapeutic peptide and may be used to attach a water-soluble polymer.

Specific examples of the reagents themselves, along with the corresponding conjugates, are provided in Table 4 below. In the table, the variable (n) represents the number of repeating monomeric units and "—S-(PEP)" represents a residue of a therapeutic peptide following conjugation to the water-soluble polymer, where the S represents the residue of a therapeutic peptide thiol group. While each polymeric portion [e.g., $(OCH_2CH_2)_n$ or $(CH_2CH_2O)_n$] presented in Table 4 terminates in a "$CH_3$" group, other end-capping groups (such as H and benzyl) or reactive groups may be used as well.

TABLE 4

Thiol-Specific Polymeric Reagents and the Therapeutic peptide Conjugates Formed Therefrom

| Polymeric Reagent | Corresponding Conjugate |
|---|---|
| H₃C—(OCH₂CH₂)ₙ—O—CH₂CH₂—[maleimide]<br>mPEG Maleimide Reagent | H₃C—(OCH₂CH₂)ₙ—O—CH₂CH₂—[succinimide]—S—PEP<br>Thioether Linkage |
| H₃CO—(CH₂CH₂O)ₙ—CH₂CH₂—[maleimide]<br>mPEG Maleimide Reagent | H₃CO—(CH₂CH₂O)ₙ—CH₂CH₂—[succinimide]—S—PEP<br>Thioether Linkage |
| H₃CO—(CH₂CH₂O)ₙ—C(=O)—NH—CH₂CH₂OCH₂CH₂OCH₂CH₂NH—C(=O)—CH₂CH₂—[maleimide]<br>mPEG Maleimide Reagent | H₃CO—(CH₂CH₂O)ₙ—C(=O)—NH—CH₂CH₂OCH₂CH₂OCH₂CH₂NH—C(=O)—CH₂CH₂—[succinimide]—S—PEP<br>Thioether Linkage |
| [maleimide]—N—(CH₂CH₂O)ₙ—CH₂CH₂—[maleimide]<br>Homobifunctional mPEG Maleimide Reagent | PEP—S—[succinimide]—N—(CH₂CH₂O)ₙ—CH₂CH₂—[succinimide]—S—PEP<br>Thioether Linkages |

TABLE 4-continued
Thiol-Specific Polymeric Reagents and the Therapeutic peptide Conjugates Formed Therefrom
| Polymeric Reagent | Corresponding Conjugate |
|---|---|
| 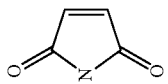 mPEG Maleimide Reagent |  Thioether Linkage |
| 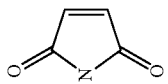 mPEG Maleimide Reagent |  Thioether Linkage |
| 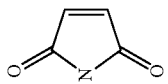 mPEG Forked Maleimide Reagent |  Thioether Linkage |

TABLE 4-continued

Thiol-Specific Polymeric Reagents and the Therapeutic peptide Conjugates Formed Therefrom

| Polymeric Reagent | Corresponding Conjugate |
| --- | --- |
| Branched mPEG2 Maleimide Reagent | Thioether Linkage |
| Branched mPEG2 Maleimide Reagent | Thioether Linkage |
| Branched mPEG2 Forked Maleimide Reagent | Thioether Linkages |

TABLE 4-continued

Thiol-Specific Polymeric Reagents and the Therapeutic peptide Conjugates Formed Therefrom

| Polymeric Reagent | Corresponding Conjugate |
|---|---|
| H₃C—(OCH₂CH₂)ₙ—NH—C(=O)—O—CH₂—CH(—O—C(=O)—NH—CH₂CH₂—(OCH₂CH₂)ₙ—CH₃)—CH₂—O—C(=O)—CH₂—CH₂—N(maleimide)  Branched mPEG2 Forked Maleimide Reagent | H₃C—(OCH₂CH₂)ₙ—NH—C(=O)—O—CH₂—CH(—O—C(=O)—NH—CH₂CH₂—(OCH₂CH₂)ₙ—CH₃)—CH₂—O—C(=O)—CH₂—CH₂—N(succinimide-S-PEP) |
| H₃C—(OCH₂CH₂)ₙ—O—CH₂CH₂—S(=O)₂—CH=CH₂  mPEG Vinyl Sulfone Reagent | H₃C—(OCH₂CH₂)ₙ—O—CH₂CH₂—S(=O)₂—CH₂—CH₂—S—PEP  Thioether Linkages |
| H₃C—(OCH₂CH₂)ₙ—O—CH₂CH₂—C(=O)—NH—CH₂—CH₂—SH  mPEG Thiol Reagent | H₃C—(OCH₂CH₂)ₙ—O—CH₂CH₂—C(=O)—NH—CH₂—CH₂—S—S—PEP  Thioether Linkage |
| HS—CH₂CH₂—NH—C(=O)—CH₂—(OCH₂CH₂)ₙ—C(=O)—NH—CH₂—CH₂—SH  Homobifunctional PEG Thiol Reagent | PEP—S—S—CH₂—CH₂—NH—C(=O)—CH₂—(OCH₂CH₂)ₙ—C(=O)—NHCH₂CH₂—S—S—PEP  Disulfide Linkages |
| H₃CO—(CH₂CH₂O)ₙ—CH₂CH₂CH₂—S—S—(2-pyridyl)  mPEG Disulfide Reagent | H₃CO—(CH₂CH₂O)ₙ—CH₂CH₂CH₂—S—S—PEP  Disulfide Linkage |

TABLE 4-continued

Thiol-Specific Polymeric Reagents and the Therapeutic peptide Conjugates Formed Therefrom

| Polymeric Reagent | Corresponding Conjugate |
|---|---|
| ![pyridyl]—S—S—CH$_2$CH$_2$—(CH$_2$CH$_2$O)$_n$—CH$_2$CH$_2$CH$_2$—S—S—[pyridyl]<br>Homobifunctional PEG Disulfide Reagent | PEP—S—S—CH$_2$CH$_2$—(CH$_2$CH$_2$O)$_n$—CH$_2$CH$_2$CH$_2$—S—S—PEP<br>Disulfide Linkages |

With respect to conjugates formed from water-soluble polymers bearing one or more maleimide functional groups (regardless of whether the maleimide reacts with an amine or thiol group on the therapeutic peptide), the corresponding maleamic acid form(s) of the water-soluble polymer can also react with the therapeutic peptide. Under certain conditions (e.g., a pH of about 7-9 and in the presence of water), the maleimide ring will "open" to form the corresponding maleamic acid. The maleamic acid, in turn, can react with an amine or thiol group of a therapeutic peptide. Exemplary maleamic acid-based reactions are schematically shown below. POLY represents the water-soluble polymer, and ~S-PEP represents a residue of a therapeutic peptide, where the S is derived from a thiol group of the therapeutic peptide.

peptide. The conjugation reaction is allowed to proceed until substantially no further conjugation occurs, which can generally be determined by monitoring the progress of the reaction over time.

Progress of the reaction can be monitored by withdrawing aliquots from the reaction mixture at various time points and analyzing the reaction mixture by SDS-PAGE or MALDI-TOF mass spectrometry or any other suitable analytical method. Once a plateau is reached with respect to the amount of conjugate formed or the amount of unconjugated polymer remaining, the reaction is assumed to be complete. Typically, the conjugation reaction takes anywhere from minutes to several hours (e.g., from 5 minutes to 24 hours or more). The resulting product mixture is preferably, but not

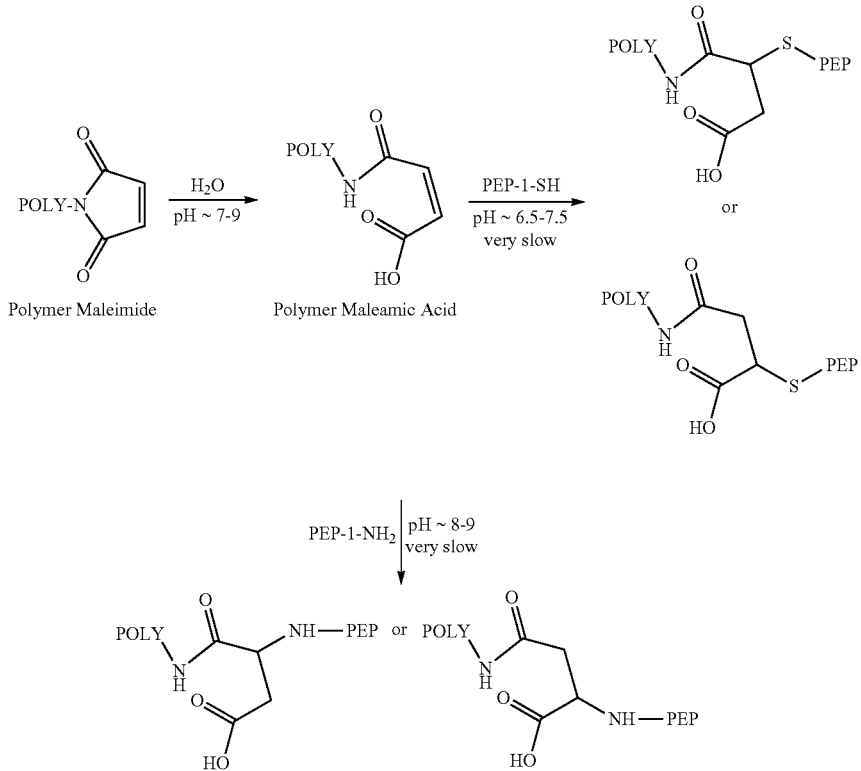

Thiol PEGylation is specific for free thiol groups on the therapeutic peptide. Typically, a polymer maleimide is conjugated to a sulfhydryl-containing therapeutic peptide at pHs ranging from about 6-9 (e.g., at 6, 6.5, 7, 7.5, 8, 8.5, or 9), more preferably at pHs from about 7-9, and even more preferably at pHs from about 7 to 8. Generally, a slight molar excess of polymer maleimide is employed, for example, a 1.5 to 15-fold molar excess, preferably a 2-fold to 10 fold molar excess. Reaction times generally range from about 15 minutes to several hours, e.g., 8 or more hours, at room temperature. For sterically hindered sulfhydryl groups, required reaction times may be significantly longer. Thiol-selective conjugation is preferably conducted at pHs around 7. Temperatures for conjugation reactions are typically, although not necessarily, in the range of from about 0° C. to about 40° C.; conjugation is often carried out at room temperature or less. Conjugation reactions are often carried out in a buffer such as a phosphate or acetate buffer or similar system.

With respect to reagent concentration, an excess of the polymeric reagent is typically combined with the therapeutic necessarily purified, to separate out excess reagents, unconjugated reactants (e.g., therapeutic peptide) undesired multi-conjugated species, and free or unreacted polymer. The resulting conjugates can then be further characterized using analytical methods such as MALDI, capillary electrophoresis, gel electrophoresis, and/or chromatography.

An illustrative therapeutic peptide conjugate formed by reaction with one or more therapeutic peptide thiol groups may possess the following structure:

POLY-X$_{0,1}$—C(O)Z—Y—S—S-(PEP)

where POLY is a water-soluble polymer, X is an optional linker, Z is a heteroatom selected from the group consisting of O, NH, and S, and Y is selected from the group consisting of $C_{2-10}$ alkyl, $C_{2-10}$ substituted alkyl, aryl, and substituted aryl, and —S-PEP is a residue of a therapeutic peptide, where the S represents the residue of a therapeutic peptide thiol group. Such polymeric reagents suitable for reaction with a therapeutic peptide to result in this type of conjugate are described in U.S. Patent Application Publication No. 2005/0014903, which is incorporated herein by reference.

With respect to polymeric reagents suitable for reacting with a therapeutic peptide thiol group, those described here and elsewhere can be obtained from commercial sources. In addition, methods for preparing polymeric reagents are described in the literature.

Additional Conjugates and Features Thereof

As is the case for any therapeutic peptide polymer conjugate of the invention, the attachment between the therapeutic peptide and water-soluble polymer can be direct, wherein no intervening atoms are located between the therapeutic peptide and the polymer, or indirect, wherein one or more atoms are located between the therapeutic peptide and polymer. With respect to the indirect attachment, a "spacer moiety or linker" serves as a link between the therapeutic peptide and the water-soluble polymer. The one or more atoms making up the spacer moiety can include one or more of carbon atoms, nitrogen atoms, sulfur atoms, oxygen atoms, and combinations thereof. The spacer moiety can comprise an amide, secondary amine, carbamate, thioether, and/or disulfide group. Nonlimiting examples of specific spacer moieties (including "X", $X^1$, $X^2$, and $X^3$) include those selected from the group consisting of —O—, —S—, —S—S—, —C(O)—, —C(O)O—, —OC(O)—, —CH$_2$—C(O)O—, —CH$_2$—OC(O)—, —C(O)O—CH$_2$—, —OC(O)—CH$_2$—, —C(O)—NH—, —NH—C(O)—NH—, —O—C(O)—NH—, —C(S)—, —CH$_2$—, —CH$_2$—CH$_2$—, —CH$_2$—CH$_2$—CH$_2$—, —CH$_2$—CH$_2$—CH$_2$—CH$_2$—, —O—CH$_2$—, —CH$_2$—O—, —O—CH$_2$—CH$_2$—, —CH$_2$—O—CH$_2$—, —CH$_2$—CH$_2$—O—, —O—CH$_2$—CH$_2$—CH$_2$—, —CH$_2$—O—CH$_2$—CH$_2$—, —CH$_2$—CH$_2$—O—CH$_2$—, —CH$_2$—CH$_2$—CH$_2$—O—, —O—CH$_2$—CH$_2$—CH$_2$—CH$_2$—, —CH$_2$—O—CH$_2$—CH$_2$—CH$_2$—, —CH$_2$—CH$_2$—O—CH$_2$—CH$_2$—, —CH$_2$—CH$_2$—CH$_2$—O—CH$_2$—, —CH$_2$—CH$_2$—CH$_2$—CH$_2$—O—, —C(O)—NH—CH$_2$—, —C(O)—NH—CH$_2$—CH$_2$—, —CH$_2$—C(O)—NH—CH$_2$—, —CH$_2$—CH$_2$—C(O)—NH—, —C(O)—NH—CH$_2$—CH$_2$—CH$_2$—, —CH$_2$—C(O)—NH—CH$_2$—CH$_2$—, —CH$_2$—CH$_2$—C(O)—NH—CH$_2$—, —CH$_2$—CH$_2$—CH$_2$—C(O)—NH—, —C(O)—NH—CH$_2$—CH$_2$—CH$_2$—CH$_2$—, —CH$_2$—C(O)—NH—CH$_2$—CH$_2$—CH$_2$—, —CH$_2$—CH$_2$—C(O)—NH—CH$_2$—CH$_2$—, —CH$_2$—CH$_2$—CH$_2$—C(O)—NH—CH$_2$—, —CH$_2$—CH$_2$—CH$_2$—CH$_2$—C(O)—NH—, —C(O)—O—CH$_2$—, —CH$_2$—C(O)—O—CH$_2$—, —CH$_2$—CH$_2$—C(O)—O—CH$_2$—, —C(O)—O—CH$_2$—CH$_2$—, —NH—C(O)—CH$_2$—, —CH$_2$—NH—C(O)—CH$_2$—, —CH$_2$—CH$_2$—NH—C(O)—CH$_2$—, —NH—C(O)—CH$_2$—CH$_2$—, —CH$_2$—NH—C(O)—CH$_2$—CH$_2$—, —CH$_2$—CH$_2$—NH—C(O)—CH$_2$—CH$_2$—, —C(O)—NH—CH$_2$—, —C(O)—NH—CH$_2$—CH$_2$—, —O—C(O)—NH—CH$_2$—, —O—C(O)—NH—CH$_2$—CH$_2$—, —NH—CH$_2$—, —NH—CH$_2$—CH$_2$—, —CH$_2$—NH—CH$_2$—, —CH$_2$—CH$_2$—NH—CH$_2$—, —C(O)—CH$_2$—, —C(O)—CH$_2$—CH$_2$—, —CH$_2$—C(O)—CH$_2$—, —CH$_2$—CH$_2$—C(O)—CH$_2$—, —CH$_2$—CH$_2$—C(O)—CH$_2$—CH$_2$—, —CH$_2$—CH$_2$—C(O)—, —CH$_2$—CH$_2$—CH$_2$—C(O)—NH—CH$_2$—CH$_2$—NH—, —CH$_2$—CH$_2$—CH$_2$—C(O)—NH—CH$_2$—CH$_2$—NH—C(O)—, —CH$_2$—CH$_2$—CH$_2$—C(O)—NH—CH$_2$—CH$_2$—NH—C(O)—CH$_2$—, —CH$_2$—CH$_2$—NH—C(O)—CH$_2$—, —CH$_2$—CH$_2$—CH$_2$—C(O)—NH—CH$_2$—CH$_2$—NH—C(O)—CH$_2$—CH$_2$—, —O—C(O)—NH—[CH$_2$]$_h$—(OCH$_2$CH2)$_j$—, bivalent cycloalkyl group, —O—, —S—, an amino acid, —N(R$^6$)—, and combinations of two or more of any of the foregoing, wherein R$^6$ is H or an organic radical selected from the group consisting of alkyl, substituted alkyl, alkenyl, substituted alkenyl, alkynyl, substituted alkynyl, aryl and substituted aryl, (h) is zero to six, and (j) is zero to 20. Other specific spacer moieties have the following structures: —C(O)—NH—(CH$_2$)$_{1-6}$—NH—C(O)—, —NH—C(O)—NH—(CH$_2$)$_{1-6}$—NH—C(O)—, and —O—C(O)—NH—(CH$_2$)$_{1-6}$—NH—C(O)—, wherein the subscript values following each methylene indicate the number of methylenes contained in the structure, e.g., (CH$_2$)$_{1-6}$ means that the structure can contain 1, 2, 3, 4, 5 or 6 methylenes. Additionally, any of the above spacer moieties may further include an ethylene oxide oligomer chain comprising 1 to 20 ethylene oxide monomer units [i.e., —(CH$_2$CH$_2$O)$_{1-20}$]. That is, the ethylene oxide oligomer chain can occur before or after the spacer moiety, and optionally in between any two atoms of a spacer moiety comprised of two or more atoms. Also, the oligomer chain would not be considered part of the spacer moiety if the oligomer is adjacent to a polymer segment and merely represent an extension of the polymer segment.

As indicated above, in some instances the water-soluble polymer-(PEP) conjugate will include a non-linear water-soluble polymer. Such a non-linear water-soluble polymer encompasses a branched water-soluble polymer (although other non linear water-soluble polymers are also contemplated). Thus, in one or more embodiments of the invention, the conjugate comprises a therapeutic peptide covalently attached, either directly or through a spacer moiety comprised of one or more atoms, to a branched water-soluble polymer, at in a non-limiting example, an internal or N-terminal amine. As used herein, an internal amine is an amine that is not part of the N-terminal amino acid (meaning not only the N-terminal amine, but any amine on the side chain of the N-terminal amino acid).

Although such conjugates include a branched water-soluble polymer attached (either directly or through a spacer moiety) to a therapeutic peptide at an internal amino acid of the therapeutic peptide, additional branched water-soluble polymers can also be attached to the same therapeutic peptide at other locations as well. Thus, for example, a conjugate including a branched water-soluble polymer attached (either directly or through a spacer moiety) to a therapeutic peptide at an internal amino acid of the therapeutic peptide, can further include an additional branched water-soluble polymer covalently attached, either directly or through a spacer moiety comprised of one or more atoms, to the N-terminal amino acid residue, such as at the N-terminal amine.

One preferred branched water-soluble polymer comprises the following structure:

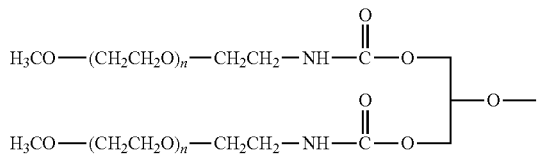

wherein each (n) is independently an integer having a value of from 3 to 4000, or more preferably, from about 10 to 1800.

Also forming part of the invention are multi-armed polymer conjugates comprising a polymer scaffold having 3 or more polymer arms each suitable for capable of covalent attachment of a therapeutic peptide.

Exemplary conjugates in accordance with this embodiment of the invention will generally comprise the following structure:

wherein R is a core molecule as previously described, POLY is a water-soluble polymer, X is a cleavable, e.g., hydrolyzable linkage, and y ranges from about 3 to 15.

More particularly, such a conjugate may comprise the structure:

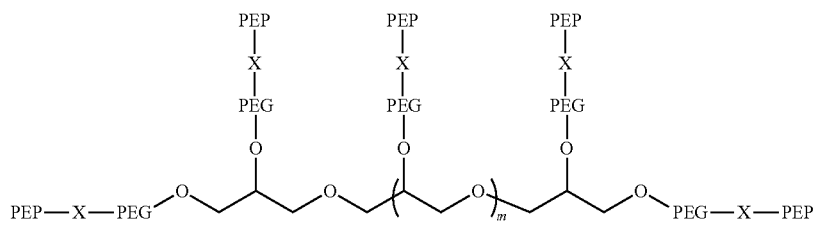

where m is selected from 3, 4, 5, 6, 7, and 8.

In yet a related embodiment, the therapeutic peptide conjugate may correspond to the structure:

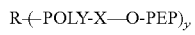

where R is a core molecule as previously described, X is —NH—P—Z—C(O) P is a spacer, Z is —O—, —NH—, or —CH$_2$—, —O-PEP is a hydroxyl residue of a therapeutic peptide, and y is 3 to 15. Preferably, X is a residue of an amino acid.

Purification

The therapeutic peptide polymer conjugates described herein can be purified to obtain/isolate different conjugate species. Specifically, a product mixture can be purified to obtain an average of anywhere from one, two, or three or even more PEGs per therapeutic peptide. In one embodiment of the invention, preferred therapeutic peptide conjugates are mono-conjugates. The strategy for purification of the final conjugate reaction mixture will depend upon a number of factors, including, for example, the molecular weight of the polymeric reagent employed, the therapeutic peptide, and the desired characteristics of the product—e.g., monomer, dimer, particular positional isomers, etc.

If desired, conjugates having different molecular weights can be isolated using gel filtration chromatography and/or ion exchange chromatography. Gel filtration chromatography may be used to fractionate different therapeutic peptide conjugates (e.g., 1-mer, 2-mer, 3-mer, and so forth, wherein "1-mer" indicates one polymer molecule per therapeutic peptide, "2-mer" indicates two polymers attached to therapeutic peptide, and so on) on the basis of their differing molecular weights (where the difference corresponds essentially to the average molecular weight of the water-soluble polymer). While this approach can be used to separate PEG and other therapeutic peptide polymer conjugates having different molecular weights, this approach is generally ineffective for separating positional isomers having different polymer attachment sites within the therapeutic peptide. For example, gel filtration chromatography can be used to separate from each other mixtures of PEG 1-mers, 2-mers, 3-mers, and so forth, although each of the recovered PEG-mer compositions may contain PEGs attached to different reactive amino groups (e.g., lysine residues) or other functional groups of the therapeutic peptide.

Gel filtration columns suitable for carrying out this type of separation include Superdex™ and Sephadex™ columns available from Amersham Biosciences (Piscataway, N.J.). Selection of a particular column will depend upon the desired fractionation range desired. Elution is generally carried out using a suitable buffer, such as phosphate, acetate, or the like. The collected fractions may be analyzed by a number of different methods, for example, (i) optical density (OD) at 280 nm for protein content, (ii) bovine serum albumin (BSA) protein analysis, (iii) iodine testing for PEG content (Sims et al. (1980) *Anal. Biochem,* 107: 60-63), and (iv) sodium dodecyl sulfate polyacrylamide gel electrophoresis (SDS PAGE), followed by staining with barium iodide.

Separation of positional isomers is typically carried out by reverse phase chromatography using a reverse phase-high performance liquid chromatography (RP-HPLC) C18 column (Amersham Biosciences or Vydac) or by ion exchange chromatography using an ion exchange column, e.g., a DEAE- or CM-Sepharose™ ion exchange column available from Amersham Biosciences. Either approach can be used to separate polymer-therapeutic peptide isomers having the same molecular weight (positional isomers).

The resulting purified compositions are preferably substantially free of the non-conjugated therapeutic peptide. In addition, the compositions preferably are substantially free of all other non-covalently attached water-soluble polymers.

Compositions

Compositions of Conjugate Isomers

Also provided herein are compositions comprising any one or more of the therapeutic peptide polymer conjugates described herein. In certain instances, the composition will comprise a plurality of therapeutic peptide polymer conjugates. For instance, such a composition may comprise a mixture of therapeutic peptide polymer conjugates having one, two, three and/or even four water-soluble polymer molecules covalently attached to sites on the therapeutic peptide. That is to say, a composition of the invention may comprise a mixture of monomer, dimer, and possibly even trimer or 4-mer. Alternatively, the composition may possess only mono-conjugates, or only di-conjugates, etc. A mono-conjugate therapeutic peptide composition will typically comprise therapeutic peptide moieties having only a single polymer covalently attached thereto, e.g., preferably releasably attached. A mono-conjugate composition may comprise only a single positional isomer, or may comprise a mixture of different positional isomers having polymer covalently attached to different sites within the therapeutic peptide.

In yet another embodiment, a therapeutic peptide conjugate may possess multiple therapeutic peptides covalently attached to a single multi-armed polymer having 3 or more polymer arms. Typically, the therapeutic peptide moieties are each attached at the same therapeutic peptide amino acid site, e.g., the N-terminus.

With respect to the conjugates in the composition, the composition will typically satisfy one or more of the following characteristics: at least about 85% of the conjugates in the composition will have from one to four polymers attached to the therapeutic peptide; at least about 85% of the conjugates in the composition will have from one to three polymers attached to the therapeutic peptide; at least about 85% of the conjugates in the composition will have from one to two polymers attached to the therapeutic peptide; or at least about 85% of the conjugates in the composition will have one polymer attached to the therapeutic peptide (e.g., be monoPEGylated); at least about 95% of the conjugates in the composition will have from one to four polymers attached to the therapeutic peptide; at least about 95% of the conjugates in the composition will have from one to three polymers attached to the therapeutic peptide; at least about 95% of the conjugates in the composition will have from one to two polymers attached to the therapeutic peptide; at least about 95% of the conjugates in the composition will have one polymers attached to the therapeutic peptide; at least about 99% of the conjugates in the composition will have from one to four polymers attached to the therapeutic peptide; at least about 99% of the conjugates in the composition will have from one to three polymers attached to the therapeutic peptide; at least about 99% of the conjugates in the composition will have from one to two polymers attached to the therapeutic peptide; and at least about 99% of the conjugates in the composition will have one polymer attached to the therapeutic peptide (e.g., be monoPEGylated).

In one or more embodiments, the conjugate-containing composition is free or substantially free of albumin.

In one or more embodiments of the invention, a pharmaceutical composition is provided comprising a conjugate comprising a therapeutic peptide covalently attached, e.g., releasably, to a water-soluble polymer, wherein the water-soluble polymer has a weight-average molecular weight of greater than about 2,000 Daltons; and a pharmaceutically acceptable excipient.

Control of the desired number of polymers for covalent attachment to therapeutic peptide is achieved by selecting the proper polymeric reagent, the ratio of polymeric reagent to the Therapeutic peptide, temperature, pH conditions, and other aspects of the conjugation reaction. In addition, reduction or elimination of the undesired conjugates (e.g., those conjugates having four or more attached polymers) can be achieved through purification mean as previously described.

For example, the water-soluble polymer-(therapeutic peptide) conjugates can be purified to obtain/isolate different conjugated species. Specifically, the product mixture can be purified to obtain an average of anywhere from one, two, three, or four PEGs per therapeutic peptide, typically one, two or three PEGs per therapeutic peptide. In one or more embodiments, the product comprises one PEG per therapeutic peptide, where PEG is releasably (via hydrolysis) attached to PEG polymer, e.g., a branched or straight chain PEG polymer.

Pharmaceutical Compositions

Optionally, a therapeutic peptide conjugate composition of the invention will comprise, in addition to the therapeutic peptide conjugate, a pharmaceutically acceptable excipient. More specifically, the composition may further comprise excipients, solvents, stabilizers, membrane penetration enhancers, etc., depending upon the particular mode of administration and dosage form.

Pharmaceutical compositions of the invention encompass all types of formulations and in particular those that are suited for injection, e.g., powders or lyophilates that can be reconstituted as well as liquids, as well as for inhalation. Examples of suitable diluents for reconstituting solid compositions prior to injection include bacteriostatic endotoxin-free water for injection, dextrose 5% in water, phosphate-buffered saline, Ringer's solution, saline, sterile water, deionized water, and combinations thereof. With respect to liquid pharmaceutical compositions, solutions and suspensions are envisioned.

Exemplary pharmaceutically acceptable excipients include, without limitation, carbohydrates, inorganic salts, antimicrobial agents, antioxidants, surfactants, buffers, acids, bases, and combinations thereof.

Representative carbohydrates for use in the compositions of the present invention include sugars, derivatized sugars such as alditols, aldonic acids, esterified sugars, and sugar polymers. Exemplary carbohydrate excipients suitable for use in the present invention include, for example, monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol), pyranosyl sorbitol, myoinositol and the like. Preferred, in particular for formulations intended for inhalation, are non-reducing sugars, sugars that can form a substantially dry amorphous or glassy phase when combined with the composition of the present invention, and sugars possessing relatively high glass transition temperatures, or Tgs (e.g., Tgs greater than 40° C., or greater than 50° C., or greater than 60° C., or greater than 70° C., or having Tgs of 80° C. and above). Such excipients may be considered glass-forming excipients.

Additional excipients include amino acids, peptides and particularly oligomers comprising 2-9 amino acids, or 2-5 mers, and polypeptides, all of which may be homo or hetero species.

Exemplary protein excipients include albumins such as human serum albumin (HSA), recombinant human albumin (rHA), gelatin, casein, hemoglobin, and the like. The compositions may also include a buffer or a pH-adjusting agent, typically but not necessarily a salt prepared from an organic acid or base. Representative buffers include organic acid salts of citric acid, ascorbic acid, gluconic acid, carbonic acid, tartaric acid, succinic acid, acetic acid, or phthalic acid. Other suitable buffers include Tris, tromethamine hydrochloride, borate, glycerol phosphate, and phosphate. Amino acids such as glycine are also suitable.

The compositions of the present invention may also include one or more additional polymeric excipients/additives, e.g., polyvinylpyrrolidones, derivatized celluloses such as hydroxymethylcellulose, hydroxyethylcellulose, and hydroxypropylmethylcellulose, FICOLLs (a polymeric sugar), hydroxyethylstarch (HES), dextrates (e.g., cyclodextrins, such as 2-hydroxypropyl-β-cyclodextrin and sulfobutylether-β-cyclodextrin), polyethylene glycols, and pectin.

The compositions may further include flavoring agents, taste-masking agents, inorganic salts (e.g., sodium chloride), antimicrobial agents (e.g., benzalkonium chloride), sweeteners, antioxidants, antistatic agents, surfactants (e.g., polysorbates such as "TWEEN 20" and "TWEEN 80," and pluronics such as F68 and F88, available from BASF), sorbitan esters, lipids (e.g., phospholipids such as lecithin and other phosphatidylcholines, phosphatidylethanolamines, although preferably not in liposomal form), fatty acids and fatty esters, steroids (e.g., cholesterol), and chelating agents (e.g., zinc and other such suitable cations). The use of certain di-substituted phosphatidylcholines for producing perforated microstructures (i.e., hollow, porous microspheres) may also be employed.

Other pharmaceutical excipients and/or additives suitable for use in the compositions according to the present invention are listed in "Remington: The Science & Practice of Pharmacy," 21$^{st}$ ed., Williams & Williams, (2005), and in the "Physician's Desk Reference," 60th ed., Medical Economics, Montvale, N.J. (2006).

The amount of the therapeutic peptide conjugate (i.e., the conjugate formed between the active agent and the polymeric reagent) in the composition will vary depending on a number of factors, but will optimally be a therapeutically effective amount when the composition is stored in a unit dose container (e.g., a vial). In addition, a pharmaceutical preparation, if in solution form, can be housed in a syringe. A therapeutically effective amount can be determined experimentally by repeated administration of increasing amounts of the conjugate in order to determine which amount produces a clinically desired endpoint.

The amount of any individual excipient in the composition will vary depending on the activity of the excipient and particular needs of the composition. Typically, the optimal amount of any individual excipient is determined through routine experimentation, i.e., by preparing compositions containing varying amounts of the excipient (ranging from low to high), examining the stability and other parameters, and then determining the range at which optimal performance is attained with no significant adverse effects.

Generally, however, the excipient or excipients will be present in the composition in an amount of about 1% to about 99% by weight, from about 5% to about 98% by weight, from about 15 to about 95% by weight of the excipient, or with concentrations less than 30% by weight. In general, a high concentration of the therapeutic peptide is desired in the final pharmaceutical formulation.

Combination of Actives

A composition of the invention may also comprise a mixture of water-soluble polymer-(therapeutic peptide) conjugates and unconjugated therapeutic peptide, to thereby provide a mixture of fast-acting and long-acting therapeutic peptide.

Additional pharmaceutical compositions in accordance with the invention include those comprising, in addition to an extended-action therapeutic peptide water-soluble polymer conjugate as described herein, a rapid acting therapeutic peptide polymer conjugate where the water-soluble polymer is releasably attached to a suitable location on the therapeutic peptide.

Administration

The therapeutic peptide conjugates of the invention can be administered by any of a number of routes including without limitation, oral, rectal, nasal, topical (including transdermal, aerosol, buccal and sublingual), vaginal, parenteral (including subcutaneous, intramuscular, intravenous and intradermal), intrathecal, and pulmonary. Preferred forms of administration include parenteral and pulmonary. Suitable formulation types for parenteral administration include ready-for-injection solutions, dry powders for combination with a solvent prior to use, suspensions ready for injection, dry insoluble compositions for combination with a vehicle prior to use, and emulsions and liquid concentrates for dilution prior to administration, among others.

In some embodiments of the invention, the compositions comprising the peptide-polymer conjugates may further be incorporated into a suitable delivery vehicle. Such delivery vehicles may provide controlled and/or continuous release of the conjugates and may also serve as a targeting moiety. Non-limiting examples of delivery vehicles include, adjuvants, synthetic adjuvants, microparticles, microcapsules, microparticles, liposomes, and yeast cell wall particles. Yeast cells walls may be variously processed to selectively remove protein component, glucan, or mannan layers, and are referred to as whole glucan particles (WGP), yeast beta-glucan mannan particles (YGMP), yeast glucan particles (YGP), \Rhodotorula yeast cell particles (YCP). Yeast cells such as *S. cerevisiae* and *Rhodotorula* sp. are preferred; however, any yeast cell may be used. These yeast cells exhibit different properties in terms of hydrodynamic volume and also differ in the target organ where they may release their contents. The methods of manufacture and characterization of these particles are described in U.S. Pat. Nos. 5,741,495; 4,810,646; 4,992,540; 5,028,703; 5,607,677, and US Patent Applications Nos. 2005/0281781, and 2008/0044438.

In one or more embodiments of the invention, a method is provided, the method comprising delivering a conjugate to a patient, the method comprising the step of administering to the patient a pharmaceutical composition comprising a therapeutic peptide polymer conjugate as provided herein. Administration can be effected by any of the routes herein described. The method may be used to treat a patient suffering from a condition that is responsive to treatment with therapeutic peptide by administering a therapeutically effective amount of the pharmaceutical composition.

As previously stated, the method of delivering a therapeutic peptide polymer conjugate as provided herein may be used to treat a patient having a condition that can be remedied or prevented by administration of therapeutic peptide.

Certain conjugates of the invention, e.g., releasable conjugates, include those effective to release the therapeutic peptide, e.g., by hydrolysis, over a period of several hours or even days (e.g., 2-7 days, 2-6 days, 3-6 days, 3-4 days) when evaluated in a suitable in-vivo model.

The actual dose of the therapeutic peptide conjugate to be administered will vary depending upon the age, weight, and general condition of the subject as well as the severity of the condition being treated, the judgment of the health care professional, and conjugate being administered. Therapeutically effective amounts are known to those skilled in the art and/or are described in the pertinent reference texts and literature. Generally, a conjugate of the invention will be delivered such that plasma levels of a therapeutic peptide are within a range of about 0.5 picomoles/liter to about 500 picomoles/liter. In certain embodiments the conjugate of the invention will be delivered such that plasma levels of a therapeutic peptide are within a range of about 1 picomoles/liter to about 400 picomoles/liter, a range of about 2.5 picomoles/liter to about 250 picomoles/liter, a range of about 5 picomoles/liter to about 200 picomoles/liter, or a range of about 10 picomoles/liter to about 100 picomoles/liter.

On a weight basis, a therapeutically effective dosage amount of a therapeutic peptide conjugate as described herein will range from about 0.01 mg per day to about 1000 mg per day for an adult. For example, dosages may range from about 0.1 mg per day to about 100 mg per day, or from about 1.0 mg per day to about 10 mg/day. On an activity basis, corresponding doses based on international units of activity can be calculated by one of ordinary skill in the art.

The unit dosage of any given conjugate (again, such as provided as part of a pharmaceutical composition) can be administered in a variety of dosing schedules depending on the judgment of the clinician, needs of the patient, and so forth. The specific dosing schedule will be known by those of ordinary skill in the art or can be determined experimentally using routine methods. Exemplary dosing schedules include, without limitation, administration five times a day, four times a day, three times a day, twice daily, once daily, three times weekly, twice weekly, once weekly, twice monthly, once monthly, and any combination thereof. Once the clinical endpoint has been achieved, dosing of the composition is halted.

It is to be understood that while the invention has been described in conjunction with the preferred specific embodiments thereof, the foregoing description as well as the examples that follow are intended to illustrate and not limit the scope of the invention. Other aspects, advantages and modifications within the scope of the invention will be apparent to those skilled in the art to which the invention pertains.

All articles, books, patents and other publications referenced herein are hereby incorporated by reference in their entireties.

EXPERIMENTAL

The practice of the invention will employ, unless otherwise indicated, conventional techniques of organic synthesis and the like, which are within the skill of the art. Such techniques are fully explained in the literature. Reagents and materials are commercially available unless specifically stated to the contrary. See, for example, J. March, Advanced Organic Chemistry: Reactions Mechanisms and Structure, 4th Ed. (New York: Wiley-Interscience, 1992), supra.

In the following examples, efforts have been made to ensure accuracy with respect to numbers used (e.g., amounts, temperatures, etc.) but some experimental error and deviation should be accounted for. Unless indicated otherwise, temperature is in degrees C. and pressure is at or near atmospheric pressure at sea level.

Although other abbreviations known by one having ordinary skill in the art will be referenced, other reagents and materials will be used, and other methods known by one having ordinary skill in the art will be used, the following list and methods description is provided for the sake of convenience.

Abbreviations
mPEG-SPA mPEG-succinimidyl propionate
mPEG-SBA mPEG-succinimidyl butanoate
mPEG-SPC mPEG-succinimidyl phenyl carbonate
mPEG-OPSS mPEG-orthopyridyl-disulfide
mPEG-MAL mPEG-maleimide, $CH_3O-(CH_2CH_2O)_n-CH_2CH_2-MAL$
mPEG-SMB mPEG-succinimidyl α-methylbutanoate, $CH_3O-(CH_2CH_2O)_n-CH_2CH_2-CH(CH_3)-C(O)-O$-succinimide
mPEG-ButyrALD $H_3O-(CH_2CH_2O)_n-CH_2CH_2-O-C(O)-NH-(CH_2CH_2O)_4-CH_2CH_2CH_2C(O)H$
mPEG-PIP $CH_3O-(CH_2CH_2O)_n-CH_2CH_2-C(O)$-piperidin-4-one
mPEG-CM $CH_3O-(CH_2CH_2O)_n-CH_2CH_2-O-CH_2-C(O)-OH)$
anh. Anhydrous
CV column volume
Fmoc 9-fluorenylmethoxycarbonyl
$NaCNBH_3$ sodium cyanoborohydride
HCl hydrochloric acid
HEPES 4-(2-hydroxyethyl)-1-piperazineethanesulfonic acid
NMR nuclear magnetic resonance
DCC 1,3-dicyclohexylcarbodiimide
DMF dimethylformamide
DMSO dimethyl sulfoxide
DI deionized
MW molecular weight
K or kDa kilodaltons
SEC Size exclusion chromatography
HPLC high performance liquid chromatography
FPLC fast protein liquid chromatography
SDS-PAGE sodium dodecyl sulfate-polyacrylamide gel electrophoresis
MALDI-TOF Matrix Assisted Laser Desorption Ionization Time-of-Flight
TLC Thin Layer Chromatography
THF Tetrahydrofuran
Materials All PEG reagents referred to in the appended examples are commercially available unless otherwise indicated.

mPEG Reagent Preparation

Typically, a water-soluble polymer reagent is used in the preparation of peptide conjugates of the invention. For purposes of the present invention, a water-soluble polymer reagent is a water-soluble polymer-containing compound having at least one functional group that can react with a functional group on a peptide (e.g., the N-terminus, the C-terminus, a functional group associated with the side chain of an amino acid located within the peptide) to create a covalent bond. Taking into account the known reactivity of the functional group(s) associated with the water-soluble polymer reagent, it is possible for one of ordinary skill in the art to determine whether a given water-soluble polymer reagent will form a covalent bond with the functional group(s) of a peptide.

Representative polymeric reagents and methods for conjugating such polymers to an active moiety are known in the art, and are, e.g., described in Harris, J. M. and Zalipsky, S., eds, *Poly(ethylene glycol), Chemistry and Biological Applications*, ACS, Washington, 1997; Veronese, F., and J. M Harris, eds., *Peptide and Protein PEGylation*, Advanced Drug Delivery Reviews, 54(4); 453-609 (2002); Zalipsky, S., et al., "*Use of Functionalized Poly(Ethylene Glycols) for Modification of Polypeptides*" in *Polyethylene Glycol Chemistry: Biotechnical and Biomedical Applications*, J. M. Harris, ed., Plenus Press, New York (1992); Zalipsky (1995) *Advanced Drug Reviews* 16:157-182, and in Roberts, et al., *Adv. Drug Delivery Reviews,* 54, 459-476 (2002).

Additional PEG reagents suitable for use in forming a conjugate of the invention, and methods of conjugation are described in Shearwater Corporation, Catalog 2001; Shearwater Polymers, Inc., Catalogs, 2000 and 1997-1998, and in Pasut. G., et al., *Expert Opin. Ther. Patents* (2004), 14(5). PEG reagents suitable for use in the present invention also include those available from NOF Corporation (Tokyo, Japan), as described generally on the NOF website (2006) under Products, High Purity PEGs and Activated PEGs. Products listed therein and their chemical structures are expressly incorporated herein by reference. Additional PEGs for use in forming a GLP-1 conjugate of the invention include those available from Polypure (Norway) and from QuantaBioDesign LTD (Powell, Ohio), where the contents of their online catalogs (2006) with respect to available PEG reagents are expressly incorporated herein by reference.

In addition, water-soluble polymer reagents useful for preparing peptide conjugates of the invention is prepared synthetically. Descriptions of the water-soluble polymer reagent synthesis can be found in, for example, U.S. Pat. Nos. 5,252,714, 5,650,234, 5,739,208, 5,932,462, 5,629, 384, 5,672,662, 5,990,237, 6,448,369, 6,362,254, 6,495,659, 6,413,507, 6,376,604, 6,348,558, 6,602,498, and 7,026,440.

Example 1

Peptide G-mPEG Conjugates

Peptide G is an amino acid synthetic peptide containing residues 161-189 of the 40 kDa laminin binding domain of 67LR, which has been found to inhibit laminin-coated melanoma cells from attaching to endothelial cells that express the 67 kDa laminin receptor (Gastronovo et al., *J. Biol. Chem.* 1991, 266, 20440-6. The 20 amino acid sequence is Ile-Pro-Cys-Asn-Asn-Lys-Gly-Ala-His-Ser-Val-Gly-Leu-Met-Trp-Trp-Met-Leu-Ala-Arg, has been proposed as potential new antimetastatic agent. (Gastronovo et al., *Cancer Res.* 1991, 51, 5672-8).

a) mPEG-$N^{ter}$-Peptide G Via mPEG-SPC

Peptide G is prepared and purified according to standard automated peptide synthesis or recombinant techniques known to those skilled in the art. An illustrative polymeric reagent, mPEG-SPC reagent,

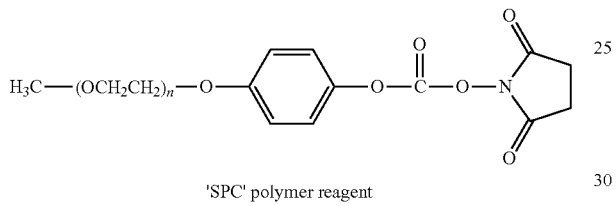

'SPC' polymer reagent is covalently attached to the N-terminus of Peptide G, to provide a $N^{ter}$-conjugate form of the peptide. mPEG-SPC 20 kDa, stored at −20° C. under argon, is warmed to ambient temperature. The reaction is performed at room temperature. About 3-5-fold molar excess of mPEG-SPC 20 kDa reagent is used based upon absolute peptide content. The mPEG-SPC reagent is weighed into a glass vial containing a magnetic stirrer bar. A solution of Peptide G prepared in phosphate buffered saline, PBS, pH 7.4 is added and the mixture is stirred using a magnetic stirrer until the mPEG-SPC is fully dissolved. The stirring speed is reduced and the reaction is allowed to proceed to formation of conjugate product. The reaction is optionally quenched to terminate the reaction. The pH of the conjugate solution at the end of the reaction is measured and further acidified by addition of 0.1M HCl, if necessary, to bring the pH of the final solution to about 5.5. The conjugate solution is then analyzed by SDS-PAGE and RP-HPLC (C18) to determine the extent of mPEG-$N^{ter}$-Peptide G conjugate formation.

Using this same approach, other conjugates are prepared using mPEG derivatives having other weight-average molecular weights that also bear an N-hydroxysuccinimide moiety.

b) Peptide G-$C^{ter}$-mPEG

An illustrative polymeric reagent, mPEG-NH$_2$ reagent is covalently attached to the C-terminus of Peptide G, to provide a $C^{ter}$-conjugate form of the peptide. For coupling to the C-terminus, a protected Peptide G (Prot-Peptide G, e.g, Fmoc-Ile-Pro-Cys(tBu)-Asn-Asn-Lys(Fmoc)-Gly-Ala-His-Ser(Dmab)-Val-Gly-Leu-Met-Trp-Trp-Met-Leu-Ala-Arg (Tos)) is prepared and purified according to standard automated peptide synthesis techniques known to those skilled in the art. mPEG-NH$_2$ 20 kDa, stored at −20° C. under argon, is warmed to ambient temperature. The reaction is performed at room temperature. About 3-5-fold molar excess of mPEG-NH$_2$, PyBOP (benzotriazol-1-yloxy)tripyrrolidinonophosphonium hexafluorophosphate), and 1-hydroxybenzotriazole (HOBt) are used, based upon absolute peptide content. The mPEG-NH$_2$, PyBOP, HOBt are weighed into a glass vial containing a magnetic stirrer bar. A solution of Prot-Peptide G is prepared in N,N-dimethylformamide is added and the mixture is stirred using a magnetic stirrer until the mPEG-NH$_2$ is fully dissolved. The stirring speed is reduced and the reaction is allowed to proceed to formation of conjugate product. The conjugate solution is then analyzed by SDS-PAGE and RP-HPLC (C18) to determine the extent of Prot-Peptide G-$C^{ter}$-mPEG conjugate formation. The remaining protecting groups are removed under standard deprotection conditions to yield the Peptide G-$C^{ter}$-mPEG conjugate.

Using this same approach, other conjugates are prepared using mPEG derivatives having other weight-average molecular weights that also bear an amino moiety.

c) Peptide G-Cys(S-mPEG)

mPEG-Maleimide is obtained having a molecular weight of 5 kDa and having the basic structure shown below:

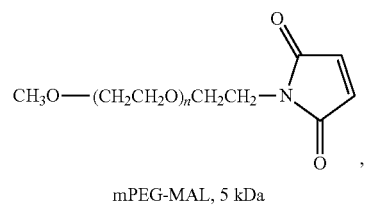

mPEG-MAL, 5 kDa

Peptide G, which has a thiol-containing cysteine residue, is dissolved in buffer. To this peptide solution is added a 3-5 fold molar excess of mPEG-MAL, 5 kDa. The mixture is stirred at room temperature under an inert atmosphere for several hours. Analysis of the reaction mixture reveals successful conjugation of this peptide.

Using this same approach, other conjugates are prepared using mPEG-MAL having other weight average molecular weights.

d) mPEG-$N^{ter}$-Peptide G Via mPEG-SMB

An mPEG-N-Hydroxysuccinimide is obtained having a molecular weight of 5 kDa and having the basic structure shown below:

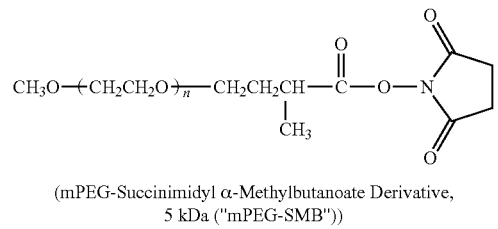

(mPEG-Succinimidyl α-Methylbutanoate Derivative, 5 kDa ("mPEG-SMB"))

mPEG-SMB, 5 kDa, stored at −20° C. under argon, is warmed to ambient temperature. A five-fold excess (relative to the amount of the peptide) of the warmed mPEG-SMB is dissolved in buffer to form a 10% reagent solution. The 10% reagent solution is quickly added to the aliquot of a stock Peptide G solution and mixed well. After the addition of the mPEG-SMB, the pH of the reaction mixture is determined and adjusted to 6.7 to 6.8 using conventional techniques. To allow for coupling of the mPEG-SMB to the peptide via an amide linkage, the reaction solution is stirred for several hours (e.g., 5 hours) at room temperature in the dark or stirred overnight at 3-8° C. in a cold room, thereby resulting in a conjugate solution. The reaction is quenched with a 20-fold molar excess (with respect to the peptide) of Tris buffer.

Using this same approach, other conjugates are prepared using mPEG derivatives having other weight-average molecular weights that also bear an N-hydroxysuccinimide moiety.

Example 2

OTS102-mPEG Conjugates

OTS-102 is an angiogenesis inhibitor for cancer treatment consisting of KDR169, the nine amino acid sequence starting at residue 169 of VEGFR2. KDR169 activates CD8-positive CTL's in an HLA-A2402 dependent manner. Augmented CTL exerts cytotoxicity to tumor-associated neovascular endothelial cells expressing KDR (VEGF receptor), and shows anti-tumor activity (see, U.S. Patent Application No. 2006/216301 A1 and OncoTherapy Sciences, Inc web site, http://www.oncotherapy.co.jp/eng/rd/page3.html). KDR169 has the sequence, Arg-Phe-Val-Pro-Asp-Gly-Asn-Arg-Ile (RFVPDGNRI) (see, Seq. No. 8, in US2006/216301A1).

a) mPEG-N$^{ter}$-OTS102 Via mPEG-SPC

The 9-aa KDR169 peptide is prepared and purified according to standard automated peptide synthesis or recombinant techniques known to those skilled in the art. An illustrative polymeric reagent, mPEG-SPC reagent, is covalently attached to the N-terminus of KDR169, to provide a N$^{ter}$-conjugate form of the peptide. mPEG-SPC 20 kDa, stored at −20° C. under argon, is warmed to ambient temperature. The reaction is performed at room temperature. About 3-5-fold molar excess of mPEG-SPC 20 kDa reagent is used based upon absolute peptide content. The mPEG-SPC reagent is weighed into a glass vial containing a magnetic stirrer bar. A solution of KDR169 prepared in phosphate buffered saline, PBS, pH 7.4 is added and the mixture is stirred using a magnetic stirrer until the mPEG-SPC is fully dissolved. The stirring speed is reduced and the reaction is allowed to proceed to formation of conjugate product. The reaction is optionally quenched to terminate the reaction. The pH of the conjugate solution at the end of the reaction is measured and further acidified by addition of 0.1M HCl, if necessary, to bring the pH of the final solution to about 5.5. The conjugate solution is then analyzed by SDS-PAGE and RP-HPLC (C18) to determine the extent of mPEG-N$^{ter}$-OTS102 conjugate formation.

Using this same approach, other conjugates are prepared using mPEG derivatives having other weight-average molecular weights that also bear an N-hydroxysuccinimide moiety.

b) OTS102-C$^{ter}$-mPEG

An illustrative polymeric reagent, mPEG-NH$_2$ reagent is covalently attached to the C-terminus of KDR169, to provide a C$^{ter}$-conjugate form of the peptide. For coupling to the C-terminus, a protected KDR169 (Prot-KDR169, e.g., Fmoc-Arg(Tos)-Phe-Val-Pro-Asp(OBz)-Gly-Asn-Arg(Tos)-Ile-OH) is prepared and purified according to standard automated peptide synthesis techniques known to those skilled in the art. mPEG-NH$_2$ 20 kDa, stored at −20° C. under argon, is warmed to ambient temperature. The reaction is performed at room temperature. About 3-5-fold molar excess of mPEG-NH$_2$, PyBOP (benzotriazol-1-yloxy)tripyrrolidinonophosphonium hexafluorophosphate), and 1-hydroxybenzotriazole (HOBt) are used, based upon absolute peptide content. The mPEG-NH$_2$, PyBOP, HOBt are weighed into a glass vial containing a magnetic stirrer bar. A solution of Prot-KDR169 is prepared in N,N-dimethylformamide is added and the mixture is stirred using a magnetic stirrer until the mPEG-NH$_2$ is fully dissolved. The stirring speed is reduced and the reaction is allowed to proceed to formation of conjugate product. The conjugate solution is then analyzed by SDS-PAGE and RP-HPLC (C18) to determine the extent of Prot-KDR169-C$^{ter}$-mPEG conjugate formation. The remaining protecting groups are removed under standard deprotection conditions to yield the OTS102-C$^{ter}$-mPEG conjugate.

Using this same approach, other conjugates are prepared using mPEG derivatives having other weight-average molecular weights that also bear an amino moiety.

c) OTS102-Asp(O-mPEG)

An illustrative polymeric reagent, mPEG-NH$_2$ reagent is covalently attached to the Asp residue of KDR169, to provide a Asp-conjugate form of the peptide. For coupling to the Asp residue, a protected KDR169 (Prot2-KDR169, e.g., Fmoc-Arg(Tos)-Phe-Val-Pro-Asp(OBz)-Gly-Asn-Arg(Tos)-Ile-O(tBu)) is prepared and purified according to standard automated peptide synthesis techniques known to those skilled in the art. Deprotection of the Asp(OBz) residue (H$_2$/Pd) yields the free-Asp carboxylate for subsequent coupling (Prot3-KDR169, e.g., Fmoc-Arg(Tos)-Phe-Val-Pro-Asp(OH)-Gly-Asn-Arg(Tos)-Ile-O(tBu)). mPEG-NH$_2$ 20 kDa, stored at −20° C. under argon, is warmed to ambient temperature. The reaction is performed at room temperature. A 5-fold molar excess of mPEG-NH$_2$, PyBOP (benzotriazol-1-yloxy)tripyrrolidinonophosphonium hexafluorophosphate), and 1-hydroxybenzotriazole (HOBt) are used, based upon absolute peptide content. The mPEG-NH$_2$, PyBOP, HOBt are weighed into a glass vial containing a magnetic stirrer bar. A solution of Prot3-KDR169 is prepared in N,N-dimethylformamide is added and the mixture is stirred using a magnetic stirrer until the mPEG-NH$_2$ is fully dissolved. The stirring speed is reduced and the reaction is allowed to proceed to formation of conjugate product. The conjugate solution is then analyzed by SDS-PAGE and RP-HPLC (C18) to determine the extent of Prot3-KDR169-(Asp-O-mPEG) conjugate formation. The remaining protecting groups are removed under standard deprotection conditions to yield the OTS102-Asp(O-mPEG) conjugate.

Using this same approach, other conjugates are prepared using mPEG derivatives having other weight-average molecular weights that also bear an amino moiety.

d) mPEG-N$^{ter}$-OTS102 Via mPEG-SMB mPEG-SMB, 5 kDa, stored at −20° C. under argon, is warmed to ambient temperature. A five-fold excess (relative to the amount of the peptide) of the warmed mPEG-SMB is dissolved in buffer to form a 10% reagent solution. The 10% reagent solution is quickly added to the aliquot of a stock OTS102 solution and mixed well. After the addition of the mPEG-SMB, the pH of the reaction mixture is determined and adjusted to 6.7 to 6.8 using conventional techniques. To allow for coupling of the mPEG-SMB to the peptide via an amide linkage, the reaction solution is stirred for several hours (e.g., 5 hours) at room temperature in the dark or stirred overnight at 3-8° C. in a cold room, thereby resulting in a conjugate solution. The reaction is quenched with a 20-fold molar excess (with respect to the peptide) of Tris buffer.

Using this same approach, other conjugates are prepared using mPEG derivatives having other weight-average molecular weights that also bear an N-hydroxysuccinimide moiety.

Example 3

Angiocol™-mPEG Conjugates

Angiocol™ is a recombinant protein derived from the non-collagenous domain (alpha-2) of type IV collagen, which has been shown in preclinical studies to inhibit macrovascular endothelial cell proliferation (new blood vessel growth), as well as tumour growth, in in vitro and in vivo models by targeting the assembly and organization of the vascular basal lamina. Angiocol™ has been proposed for the treatment of retinal neovascularization (Coleman et al., *Microcirculation* 2004, 11, 530).

a) mPEG-$N^{ter}$-Angiocol Via mPEG-SPC

Angiocol™ is prepared and purified according to standard automated peptide synthesis or recombinant techniques known to those skilled in the art. An illustrative polymeric reagent, mPEG-SPC reagent,

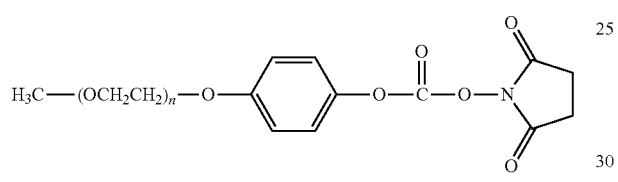

'SPC' polymer reagent is covalently attached to the N-terminus of Angiocol™, to provide a $N^{ter}$-conjugate form of the peptide. mPEG-SPC 20 kDa, stored at −20° C. under argon, is warmed to ambient temperature. The reaction is performed at room temperature. About 3-5-fold molar excess of mPEG-SPC 20 kDa reagent is used based upon absolute peptide content. The mPEG-SPC reagent is weighed into a glass vial containing a magnetic stirrer bar. A solution of Angiocol™ prepared in phosphate buffered saline, PBS, pH 7.4 is added and the mixture is stirred using a magnetic stirrer until the mPEG-SPC is fully dissolved. The stirring speed is reduced and the reaction is allowed to proceed to formation of conjugate product. The reaction is optionally quenched to terminate the reaction. The pH of the conjugate solution at the end of the reaction is measured and further acidified by addition of 0.1M HCl, if necessary, to bring the pH of the final solution to about 5.5. The conjugate solution is then analyzed by SDS-PAGE and RP-HPLC (C18) to determine the extent of mPEG-$N^{ter}$-Angiocol conjugate formation.

Using this same approach, other conjugates are prepared using mPEG derivatives having other weight-average molecular weights that also bear an N-hydroxysuccinimide moiety.

b) Angiocol-$C^{ter}$-mPEG

An illustrative polymeric reagent, mPEG-$NH_2$ reagent is covalently attached to the C-terminus of Angiocol™, to provide a $C^{ter}$-conjugate form of the peptide. For coupling to the C-terminus, a protected Angiocol™ (Prot-Angiocol™) is prepared and purified according to standard automated peptide synthesis techniques known to those skilled in the art. mPEG-$NH_2$ 20 kDa, stored at −20° C. under argon, is warmed to ambient temperature. The reaction is performed at room temperature. About 3-5-fold molar excess of mPEG-$NH_2$, PyBOP (benzotriazol-1-yloxy)tripyrrolidinonophosphonium hexafluorophosphate), and 1-hydroxybenzotriazole (HOBt) are used, based upon absolute peptide content. The mPEG-$NH_2$, PyBOP, HOBt are weighed into a glass vial containing a magnetic stirrer bar. A solution of Prot-Angiocol™ is prepared in N,N-dimethylformamide is added and the mixture is stirred using a magnetic stirrer until the mPEG-$NH_2$ is fully dissolved. The stirring speed is reduced and the reaction is allowed to proceed to formation of conjugate product. The conjugate solution is then analyzed by SDS-PAGE and RP-HPLC (C18) to determine the extent of Prot-Angiocol-$C^{ter}$-mPEG conjugate formation. The remaining protecting groups are removed under standard deprotection conditions to yield the Angiocol-$C^{ter}$-mPEG conjugate.

Using this same approach, other conjugates are prepared using mPEG derivatives having other weight-average molecular weights that also bear an amino moiety.

c) mPEG-$N^{ter}$-Angiocol™ Via mPEG-SMB

An mPEG-N-Hydroxysuccinimide is obtained having a molecular weight of 5 kDa and having the basic structure shown below:

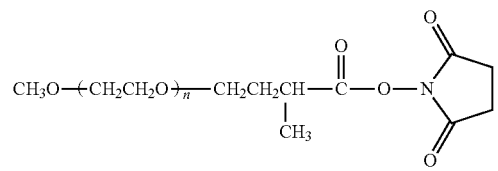

mPEG-Succinimidyl α-Methylbutanoate Derivative, 5 kDa ("mPEG-SMB"))

mPEG-SMB, 5 kDa, stored at −20° C. under argon, is warmed to ambient temperature. A five-fold excess (relative to the amount of the peptide) of the warmed mPEG-SMB is dissolved in buffer to form a 10% reagent solution. The 10% reagent solution is quickly added to the aliquot of a stock Angiocol™ solution and mixed well. After the addition of the mPEG-SMB, the pH of the reaction mixture is determined and adjusted to 6.7 to 6.8 using conventional techniques. To allow for coupling of the mPEG-SMB to the peptide via an amide linkage, the reaction solution is stirred for several hours (e.g., 5 hours) at room temperature in the dark or stirred overnight at 3-8° C. in a cold room, thereby resulting in a conjugate solution. The reaction is quenched with a 20-fold molar excess (with respect to the peptide) of Tris buffer.

Using this same approach, other conjugates are prepared using mPEG derivatives having other weight-average molecular weights that also bear an N-hydroxysuccinimide moiety.

Example 4

ABT-510 (Antiangiogenic Peptide Group)-mPEG Conjugates

ABT-510 is nonapeptide analogue that mimics the antiangiogenic activity of the endogenous protein thrombospondin-1 (TSP-1) which is in development for treatment of advanced malignancies. ABT-510 blocks the actions of multiple pro-angiogenic growth factors known to play a role in cancer related blood vessel growth, such as VEGF, bFGF, HGF, and IL-8 (Haviv et al., *J. Med. Chem.* 2005, 48, 2838; Baker et al., *J. Clin. Oncol.* 2005, 23, 9013). In human studies, ABT-510 was found to be safe and have efficacy in phase I trials in combination regimens (Gietema et al., *Ann. Oncol.* 2006, 17, 1320-7). NAc-Sar-Gly-Val-(d-allo-Ile)-Thr-Nva-Ile-Arg-ProNEt (PubChem Substance ID: 12015488)

a) mPEG-N$^{ter}$-ABT-510 Via mPEG-SPC

ABT-510 is prepared and purified according to standard automated peptide synthesis or recombinant techniques known to those skilled in the art, without the N-terminal acetyl group (NH$_2$-ABT-510). An illustrative polymeric reagent, mPEG-SPC reagent, is covalently attached to the N-terminus of NH$_2$-ABT-510, to provide a N$^{ter}$-conjugate form of the peptide. mPEG-SPC 20 kDa, stored at −20° C. under argon, is warmed to ambient temperature. The reaction is performed at room temperature. About 3-5-fold molar excess of mPEG-SPC 20 kDa reagent is used based upon absolute peptide content. The mPEG-SPC reagent is weighed into a glass vial containing a magnetic stirrer bar. A solution of NH$_2$-ABT-510 prepared in phosphate buffered saline, PBS, pH 7.4 is added and the mixture is stirred using a magnetic stirrer until the mPEG-SPC is fully dissolved. The stirring speed is reduced and the reaction is allowed to proceed to formation of conjugate product. The reaction is optionally quenched to terminate the reaction. The pH of the conjugate solution at the end of the reaction is measured and further acidified by addition of 0.1M HCl, if necessary, to bring the pH of the final solution to about 5.5. The conjugate solution is then analyzed by SDS-PAGE and RP-HPLC (C18) to determine the extent of mPEG-N$^{ter}$-ABT-510 conjugate formation.

Using this same approach, other conjugates are prepared using mPEG derivatives having other weight-average molecular weights that also bear an N-hydroxysuccinimide moiety.

b) ABT-510-C$^{ter}$-mPEG

An illustrative polymeric reagent, mPEG-NH$_2$ reagent is covalently attached to the C-terminus of ABT-510, to provide a C$^{ter}$-conjugate form of the peptide. For coupling to the C-terminus, a protected ABT-510, lacking the C-terminal ethyl amide (Prot-ABT-510, e.g., NAc-Sar(tBu)-Gly-Val-(d-allo-Ile)-Thr(tBu)-Nva-Ile-Arg(Tos)-Pro-OH) is prepared and purified according to standard automated peptide synthesis techniques known to those skilled in the art. mPEG-NH$_2$ 20 kDa, stored at −20° C. under argon, is warmed to ambient temperature. The reaction is performed at room temperature. About 3-5-fold molar excess of mPEG-NH$_2$, PyBOP (benzotriazol-1-yloxy)tripyrrolidinonophosphonium hexafluorophosphate), and 1-hydroxybenzotriazole (HOBt) are used, based upon absolute peptide content. The mPEG-NH$_2$, PyBOP, HOBt are weighed into a glass vial containing a magnetic stirrer bar. A solution of Prot-ABT-510 is prepared in N,N-dimethylformamide is added and the mixture is stirred using a magnetic stirrer until the mPEG-NH$_2$ is fully dissolved. The stirring speed is reduced and the reaction is allowed to proceed to formation of conjugate product. The conjugate solution is then analyzed by SDS-PAGE and RP-HPLC (C18) to determine the extent of Prot-ABT-510-C$^{ter}$-mPEG conjugate formation. The remaining protecting groups are removed under standard deprotection conditions to yield the ABT-510-C$^{ter}$-mPEG conjugate.

Using this same approach, other conjugates are prepared using mPEG derivatives having other weight-average molecular weights that also bear an amino moiety.

c) mPEG-N$^{ter}$-ABT-510 Via mPEG-SMB mPEG-SMB, 5 kDa, stored at −20° C. under argon, is warmed to ambient temperature. A five-fold excess (relative to the amount of the peptide) of the warmed mPEG-SMB is dissolved in buffer to form a 10% reagent solution. The 10% reagent solution is quickly added to the aliquot of a stock NH$_2$-ABT-510 (as in Example 4a) solution and mixed well. After the addition of the mPEG-SMB, the pH of the reaction mixture is determined and adjusted to 6.7 to 6.8 using conventional techniques. To allow for coupling of the mPEG-SMB to the peptide via an amide linkage, the reaction solution is stirred for several hours (e.g., 5 hours) at room temperature in the dark or stirred overnight at 3-8° C. in a cold room, thereby resulting in a conjugate solution. The reaction is quenched with a 20-fold molar excess (with respect to the peptide) of Tris buffer.

Using this same approach, other conjugates are prepared using mPEG derivatives having other weight-average molecular weights that also bear an N-hydroxysuccinimide moiety.

Example 5

A6-mPEG Conjugates

A6 is a urokinase-derived eight amino-acid peptide, NAc-Lys-Pro-Ser-Ser-Pro-Pro-Glu-Glu-NH$_2$, with anti-angiogenic properties which has been shown to suppress metastases and prolong the life span of prostate tumor-bearing mice (Boyd et al., *Am. J. Pathology* 2003, 162. 619).

a) mPEG-N$^{ter}$-A6 Via mPEG-SPC

A6 is prepared and purified according to standard automated peptide synthesis or recombinant techniques known to those skilled in the art, without the N-terminal acetyl group (NH$_2$-A6). An illustrative polymeric reagent, mPEG-SPC reagent, is covalently attached to the N-terminus of NH$_2$-A6, to provide a N$^{ter}$-conjugate form of the peptide. mPEG-SPC 20 kDa, stored at −20° C. under argon, is warmed to ambient temperature. The reaction is performed at room temperature. About 3-5-fold molar excess of mPEG-SPC 20 kDa reagent is used based upon absolute peptide content. The mPEG-SPC reagent is weighed into a glass vial containing a magnetic stirrer bar. A solution of NH$_2$-A6 prepared in phosphate buffered saline, PBS, pH 7.4 is added and the mixture is stirred using a magnetic stirrer until the mPEG-SPC is fully dissolved. The stirring speed is reduced and the reaction is allowed to proceed to formation of conjugate product. The reaction is optionally quenched to terminate the reaction. The pH of the conjugate solution at the end of the reaction is measured and further acidified by addition of 0.1M HCl, if necessary, to bring the pH of the final solution to about 5.5. The conjugate solution is then analyzed by SDS-PAGE and RP-HPLC (C18) to determine the extent of mPEG-N$^{ter}$-A6 conjugate formation.

Using this same approach, other conjugates are prepared using mPEG derivatives having other weight-average molecular weights that also bear an N-hydroxysuccinimide moiety.

b) A6-C$^{ter}$-mPEG

An illustrative polymeric reagent, mPEG-NH$_2$ reagent is covalently attached to the C-terminus of A6, to provide a C$^{ter}$-conjugate form of the peptide. For coupling to the C-terminus, a protected A6, lacking the C-terminal amide (Prot-A6, e.g., NAc-Lys(Fmoc)-Pro-Ser(tBu)-Ser(tBu)-Pro-Pro-Glu(tBu)-Glu(tBu)-OH) is prepared and purified according to standard automated peptide synthesis techniques known to those skilled in the art. mPEG-NH$_2$ 20 kDa, stored at −20° C. under argon, is warmed to ambient temperature. The reaction is performed at room temperature. About 3-5-fold molar excess of mPEG-NH$_2$, PyBOP (benzotriazol-1-yloxy)tripyrrolidinonophosphonium hexafluorophosphate), and 1-hydroxybenzotriazole (HOBt) are used, based upon absolute peptide content. The mPEG-NH$_2$, PyBOP, HOBt are weighed into a glass vial containing a magnetic stirrer bar. A solution of Prot-A6 is prepared in N,N-dimethylformamide is added and the mixture is stirred using a magnetic stirrer until the mPEG-NH$_2$ is fully dissolved. The stirring speed is reduced and the reaction is allowed to proceed to formation of conjugate product. The conjugate solution is then analyzed by SDS-PAGE and RP-HPLC (C18) to determine the extent of Prot-A6-C$^{ter}$-mPEG conjugate formation. The remaining protecting groups are removed under standard deprotection conditions to yield the ABT-510-C$^{ter}$-mPEG conjugate.

Using this same approach, other conjugates are prepared using mPEG derivatives having other weight-average molecular weights that also bear an amino moiety.

c) mPEG-N$^{ter}$-A6 Via mPEG-SMB

An mPEG-N-Hydroxysuccinimide is obtained having a molecular weight of 5 kDa and having the basic structure shown below: mPEG-SMB, 5 kDa, stored at −20° C. under argon, is warmed to ambient temperature. A five-fold excess (relative to the amount of the peptide) of the warmed mPEG-SMB is dissolved in buffer to form a 10% reagent solution. The 10% reagent solution is quickly added to the aliquot of a stock NH$_2$-A6 (as in Example 4a) solution and mixed well. After the addition of the mPEG-SMB, the pH of the reaction mixture is determined and adjusted to 6.7 to 6.8 using conventional techniques. To allow for coupling of the mPEG-SMB to the peptide via an amide linkage, the reaction solution is stirred for several hours (e.g., 5 hours) at room temperature in the dark or stirred overnight at 3-8° C. in a cold room, thereby resulting in a conjugate solution. The reaction is quenched with a 20-fold molar excess (with respect to the peptide) of Tris buffer.

Using this same approach, other conjugates are prepared using mPEG derivatives having other weight-average molecular weights that also bear an N-hydroxysuccinimide moiety.

d) A6-Glu(O-mPEG)

An illustrative polymeric reagent, mPEG-NH$_2$ reagent is covalently attached to the Glu residue of A6, to provide a Glu-conjugate form of the peptide. For coupling to the Glu residue, a protected A6 (Prot2-A6, e.g., NAc-Lys(Fmoc)-Pro-Ser(tBu)-Ser(tBu)-Pro-Pro-Glu(OBz)-Glu(tBu)-O(tBu)) is prepared and purified according to standard automated peptide synthesis techniques known to those skilled in the art. Deprotection of the Glu(OBz) residue (H$_2$/Pd) yields the free-Glu carboxylate for subsequent coupling (Prot3-A6, e.g., NAc-Lys(Fmoc)-Pro-Ser(tBu)-Ser(tBu)-Pro-Pro-Glu-Glu(tBu)-O(tBu)) mPEG-NH$_2$ 20 kDa, stored at −20° C. under argon, is warmed to ambient temperature. The reaction is performed at room temperature. A 5-fold molar excess of mPEG-NH$_2$, PyBOP (benzotriazol-1-yloxy)tripyrrolidinonophosphonium hexafluorophosphate), and 1-hydroxybenzotriazole (HOBt) are used, based upon absolute peptide content. The mPEG-NH$_2$, PyBOP, HOBt are weighed into a glass vial containing a magnetic stirrer bar. A solution of Prot3-A6 is prepared in N,N-dimethylformamide is added and the mixture is stirred using a magnetic stirrer until the mPEG-NH$_2$ is fully dissolved. The stirring speed is reduced and the reaction is allowed to proceed to formation of conjugate product. The conjugate solution is then analyzed by SDS-PAGE and RP-HPLC (C18) to determine the extent of Prot3-A6-(Glu-O-mPEG) conjugate formation. The remaining protecting groups are removed under standard deprotection conditions to yield the A6-Glu(O-mPEG) conjugate.

Using this same approach, other conjugates are prepared using mPEG derivatives having other weight-average molecular weights that also bear an amino moiety.

Example 6

Islet Neogenesis Gene Associated Protein (INGAP)-mPEG Conjugates

Islet Neogenesis-Associated Protein (INGAP) is a member of the Reg family of proteins implicated in various settings of endogenous pancreatic regeneration. The expression of INGAP and other RegIII proteins has also been linked with the induction of islet neogenesis in animal models of disease and regeneration. Administration of a peptide fragment of INGAP (INGAP peptide) has been demonstrated to reverse chemically induced diabetes as well as improve glycemic control and survival in an animal model of type 1 diabetes. (Lipsett et al., *Cell Biochem. Biophys.* 2007, 48, 127). INGAP peptide (INGAPP) is a 15 amino acid sequence contained within the 175 amino acid INGAP (see, amino acids 103-117 of SEQ ID. NO: 2 of U.S. Pat. No. 5,834,590): Ile-Gly-Leu-His-Asp-Pro-Ser-His-Gly-Thr-Leu-Pro-Asn-Gly-Ser.

a) mPEG-N$^{ter}$-INGAPP Via mPEG-SPC

INGAPP is prepared and purified according to standard automated peptide synthesis or recombinant techniques known to those skilled in the art. An illustrative polymeric reagent, mPEG-SPC reagent, is covalently attached to the N-terminus of INGAPP, to provide a N$^{ter}$-conjugate form of the peptide. mPEG-SPC 20 kDa, stored at −20° C. under argon, is warmed to ambient temperature. The reaction is performed at room temperature. About 3-5-fold molar excess of mPEG-SPC 20 kDa reagent is used based upon absolute peptide content. The mPEG-SPC reagent is weighed into a glass vial containing a magnetic stirrer bar. A solution of INGAPP prepared in phosphate buffered saline, PBS, pH 7.4 is added and the mixture is stirred using a magnetic stirrer until the mPEG-SPC is fully dissolved. The stirring speed is reduced and the reaction is allowed to proceed to formation of conjugate product. The reaction is optionally quenched to terminate the reaction. The pH of the conjugate solution at the end of the reaction is measured and further acidified by addition of 0.1M HCl, if necessary, to bring the pH of the final solution to about 5.5. The conjugate solution is then analyzed by SDS-PAGE and RP-HPLC (C18) to determine the extent of mPEG-N$^{ter}$-INGAPP conjugate formation.

Using this same approach, other conjugates are prepared using mPEG derivatives having other weight-average molecular weights that also bear an N-hydroxysuccinimide moiety.

b) INGAPP-C$^{ter}$-mPEG

An illustrative polymeric reagent, mPEG-NH$_2$ reagent is covalently attached to the C-terminus of INGAPP, to provide a C$^{ter}$-conjugate form of the peptide. For coupling to the C-terminus, a protected INGAPP (Prot-INGAPP, e.g Fmoc-Ile-Gly-Leu-His-Asp(tBu)-Pro-Ser(tBu)-His-Gly-Thr(tBu)-Leu-Pro-Asn-Gly-Ser(tBu)-OH) is prepared and purified according to standard automated peptide synthesis techniques known to those skilled in the art. mPEG-NH$_2$ 20 kDa, stored at −20° C. under argon, is warmed to ambient temperature. The reaction is performed at room temperature. About 3-5-fold molar excess of mPEG-NH$_2$, PyBOP (benzotriazol-1-yloxy)tripyrrolidinonophosphonium hexafluorophosphate), and 1-hydroxybenzotriazole (HOBt) are used, based upon absolute peptide content. The mPEG-NH$_2$, PyBOP, HOBt are weighed into a glass vial containing a magnetic stirrer bar. A solution of Prot-INGAPP is prepared in N,N-dimethylformamide is added and the mixture is stirred using a magnetic stirrer until the mPEG-NH$_2$ is fully dissolved. The stirring speed is reduced and the reaction is allowed to proceed to formation of conjugate product. The conjugate solution is then analyzed by SDS-PAGE and RP-HPLC (C18) to determine the extent of Prot-INGAPP-C$^{ter}$-mPEG conjugate formation. The remaining protecting groups are removed under standard deprotection conditions to yield the INGAPP-C$^{ter}$-mPEG conjugate.

Using this same approach, other conjugates are prepared using mPEG derivatives having other weight-average molecular weights that also bear an amino moiety.

c) mPEG-N$^{ter}$-INGAPP Via mPEG-SMB

An mPEG-N-Hydroxysuccinimide is obtained having a molecular weight of 5,000 Daltons and having the basic structure shown below: mPEG-SMB, 5 kDa, stored at −20° C. under argon, is warmed to ambient temperature. A five-fold excess (relative to the amount of the peptide) of the warmed mPEG-SMB is dissolved in buffer to form a 10% reagent solution. The 10% reagent solution is quickly added to the aliquot of a stock INGAPP solution and mixed well. After the addition of the mPEG-SMB, the pH of the reaction mixture is determined and adjusted to 6.7 to 6.8 using conventional techniques. To allow for coupling of the mPEG-SMB to the peptide via an amide linkage, the reaction solution is stirred for several hours (e.g., 5 hours) at room temperature in the dark or stirred overnight at 3-8° C. in a cold room, thereby resulting in a conjugate solution. The reaction is quenched with a 20-fold molar excess (with respect to the peptide) of Tris buffer.

Using this same approach, other conjugates are prepared using mPEG derivatives having other weight-average molecular weights that also bear an N-hydroxysuccinimide moiety.

d) INGAPP-Asp(O-mPEG)

An illustrative polymeric reagent, mPEG-NH$_2$ reagent is covalently attached to the Asp residue of INGAPP, to provide a Asp-conjugate form of the peptide. For coupling to the Asp residue, a protected INGAPP (Prot2-INGAPP, e.g., Fmoc-Ile-Gly-Leu-His-Asp(OBz)-Pro-Ser(tBu)-His-Gly-Thr(tBu)-Leu-Pro-Asn-Gly-Ser(tBu)-O(tBu)) is prepared and purified according to standard automated peptide synthesis techniques known to those skilled in the art. Deprotection of the Asp(OBz) residue (H$_2$/Pd) yields the free-Asp carboxylate for subsequent coupling (Prot3-INGAPP, e.g., Fmoc-Ile-Gly-Leu-His-Asp(OBz)-Pro-Ser(tBu)-His-Gly-Thr(tBu)-Leu-Pro-Asn-Gly-Ser(tBu)-O(tBu)). mPEG-NH$_2$ 20 kDa, stored at −20° C. under argon, is warmed to ambient temperature. The reaction is performed at room temperature. A 5-fold molar excess of mPEG-NH$_2$, PyBOP (benzotriazol-1-yloxy)tripyrrolidinonophosphonium hexafluorophosphate), and 1-hydroxybenzotriazole (HOBt) are used, based upon absolute peptide content. The mPEG-NH$_2$, PyBOP, HOBt are weighed into a glass vial containing a magnetic stirrer bar. A solution of Prot3-INGAPP is prepared in N,N-dimethylformamide is added and the mixture is stirred using a magnetic stirrer until the mPEG-NH$_2$ is fully dissolved. The stirring speed is reduced and the reaction is allowed to proceed to formation of conjugate product. The conjugate solution is then analyzed by SDS-PAGE and RP-HPLC (C18) to determine the extent of Prot3-INGAPP-(Asp-O-mPEG) conjugate formation. The remaining protecting groups are removed under standard deprotection conditions to yield the INGAPP-Asp (O-mPEG) conjugate.

Using this same approach, other conjugates are prepared using mPEG derivatives having other weight-average molecular weights that also bear an amino moiety.

Example 7

Tendamistat-mPEG Conjugates

Tendamistat (HOE 467) is 74 residue alpha-amylase inactivator which effectively attenuates starch digestion (Meyer et al., *S. Afr. Med. J.* 1984, 66, 222), having the sequence, Asp-Thr-Thr-Val-Ser-Glu-Pro-Ala-Pro-Ser-Cys-Val-Thr-Leu-Tyr-Gln-Ser-Trp-Arg-Tyr-Ser-Gln-Ala-Asp-Asp-Gly-Cys-Ala-Glu-Thr-Val-Thr-Val-Lys-Val-Val-Tyr-Glu-Asp-Asp-Thr-Glu-Gly-Leu-Cys-Tyr-Ala-Val-Ala-Pro-Gly- Gln-Ile-Thr-Thr-Val-Gly-Asp-Gly-Tyr-Ile-Gly-Ser-His-Gly-His-Ala-Arg-Tyr-Leu-Ala-Arg-Cys-Leu (DTTVSEPAPS CVTLYQSWRY SQADNGCAET VTVK-VVYEDD TEGLCYAVAP GQITTVGDGY IGSH-GHARYL ARCL) (PubChem Protein Accession No. CAA00655)

a) mPEG-N$^{ter}$-Tendamistat-Via mPEG-SPC

Tendamistat is prepared and purified according to standard automated peptide synthesis or recombinant techniques known to those skilled in the art. An illustrative polymeric reagent, mPEG-SPC reagent, is covalently attached to the N-terminus of Tendamistat, to provide a N$^{ter}$-conjugate form of the peptide. mPEG-SPC 20 kDa, stored at −20° C. under argon, is warmed to ambient temperature. The reaction is performed at room temperature. About 3-5-fold molar excess of mPEG-SPC 20 kDa reagent is used based upon absolute peptide content. The mPEG-SPC reagent is weighed into a glass vial containing a magnetic stirrer bar. A solution of Tendamistat prepared in phosphate buffered saline, PBS, pH 7.4 is added and the mixture is stirred using a magnetic stirrer until the mPEG-SPC is fully dissolved. The stirring speed is reduced and the reaction is allowed to proceed to formation of conjugate product. The reaction is optionally quenched to terminate the reaction. The pH of the conjugate solution at the end of the reaction is measured and further acidified by addition of 0.1M HCl, if necessary, to bring the pH of the final solution to about 5.5. The conjugate solution is then analyzed by SDS-PAGE and RP-HPLC (C18) to determine the extent of mPEG-N$^{ter}$-Tendamistat conjugate formation.

Using this same approach, other conjugates are prepared using mPEG derivatives having other weight-average molecular weights that also bear an N-hydroxysuccinimide moiety.

b) Tendamistat-C$^{ter}$-mPEG

An illustrative polymeric reagent, mPEG-NH$_2$ reagent is covalently attached to the C-terminus of Tendamistat, to provide a C$^{ter}$-conjugate form of the peptide. For coupling to the C-terminus, a protected Tendamistat (Prot-Tendamistat, e.g., Fmoc-Asp(tBu)-Thr(tBu)-Thr(tBu)-Val-Ser(tBu)-Glu (tBu)-Pro-Ala-Pro-Ser(tBu)-Cys(tBu)-Val-Thr(tBu)-Leu-Tyr(tBu)-Gln-Ser(tBu)-Trp-Arg(Tos)-Tyr- Ser(tBu)-Gln-Ala-Asp(tBu)-Asp(tBu)-Gly-Cys(tBu)-Ala-Glu(tBu)-Thr (tBu)-Val-Thr(tBu)-Val-Lys(Fmoc)-Val-Val-Tyr(tBu)-Glu (tBu)-Asp(tBu)-Asp(tBu)-Thr(tBu)-Glu(tBu)-Gly-Leu-Cys (tBu)-Tyr(tBu)-Ala-Val-Ala-Pro-Gly- Gln-Ile-Thr(tBu)-Thr (tBu)-Val-Gly-Asp(tBu)-Gly-Tyr(tBu)-Ile-Gly-Ser(tBu)-His-Gly-His-Ala-Arg(Tos)-Tyr(tBu)-Leu-Ala-Arg(Tos)-Cys(tBu)-Leu) is prepared and purified according to standard automated peptide synthesis techniques known to those skilled in the art. mPEG-NH$_2$ 20 kDa, stored at −20° C. under argon, is warmed to ambient temperature. The reaction is performed at room temperature. About 3-5-fold molar excess of mPEG-NH$_2$, PyBOP (benzotriazol-1-yloxy)tripyrrolidinonophosphonium hexafluorophosphate), and 1-hydroxybenzotriazole (HOBt) are used, based upon absolute peptide content. The mPEG-NH$_2$, PyBOP, HOBt are weighed into a glass vial containing a magnetic stirrer bar. A solution of Prot-Tendamistat is prepared in N,N-dimethylformamide is added and the mixture is stirred using a magnetic stirrer until the mPEG-NH$_2$ is fully dissolved. The stirring speed is reduced and the reaction is allowed to proceed to formation of conjugate product. The conjugate solution is then analyzed by SDS-PAGE and RP-HPLC (C18) to determine the extent of Prot-Tendamistat-C$^{ter}$-mPEG conjugate formation. The remaining protecting groups are removed under standard deprotection conditions to yield the Tendamistat-C$^{ter}$-mPEG conjugate.

Using this same approach, other conjugates are prepared using mPEG derivatives having other weight-average molecular weights that also bear an amino moiety.

c) Tendamistat-Cys(S-mPEG)

Tendamistat, which has a thiol-containing cysteine residue, is dissolved in buffer. To this peptide solution is added a 3-5 fold molar excess of mPEG-MAL, 5 kDa. The mixture is stirred at room temperature under an inert atmosphere for several hours. Analysis of the reaction mixture reveals successful conjugation of this peptide.

Using this same approach, other conjugates are prepared using mPEG-MAL having other weight average molecular weights.

d) mPEG-N$^{ter}$-Tendamistat Via mPEG-SMB mPEG-SMB, 5 kDa, stored at −20° C. under argon, is warmed to ambient temperature. A five-fold excess (relative to the amount of the peptide) of the warmed mPEG-SMB is dissolved in buffer to form a 10% reagent solution. The 10% reagent solution is quickly added to the aliquot of a stock Tendamistat solution and mixed well. After the addition of the mPEG-SMB, the pH of the reaction mixture is determined and adjusted to 6.7 to 6.8 using conventional techniques. To allow for coupling of the mPEG-SMB to the peptide via an amide linkage, the reaction solution is stirred for several hours (e.g., 5 hours) at room temperature in the dark or stirred overnight at 3-8° C. in a cold room, thereby resulting in a conjugate solution. The reaction is quenched with a 20-fold molar excess (with respect to the peptide) of Tris buffer.

Using this same approach, other conjugates are prepared using mPEG derivatives having other weight-average molecular weights that also bear an N-hydroxysuccinimide moiety.

e) Tendamistat-Glu(O-mPEG)

An illustrative polymeric reagent, mPEG-NH$_2$ reagent is covalently attached to the Glu residue of Tendamistat, to provide a Glu-conjugate form of the peptide. For coupling to the Glu residue, a protected Tendamistat (Prot2-Tendamistat, e.g., Fmoc-Asp(tBu)-Thr(tBu)-Thr(tBu)-Val-Ser(tBu)-Glu(OBz)-Pro-Ala-Pro-Ser(tBu)-Cys(tBu)-Val-Thr(tBu)-Leu-Tyr(tBu)-Gln-Ser(tBu)-Trp- Arg(Tos)-Tyr-Ser(tBu)-Gln-Ala-Asp(tBu)-Asp(tBu)-Gly-Cys(tBu)-Ala-Glu(tBu)-Thr(tBu)-Val-Thr(tBu)-Val-Lys(Fmoc)-Val-Val-Tyr(tBu)-Glu(tBu)-Asp(tBu)-Asp(tBu)-Thr(tBu)-Glu(tBu)-Gly-Leu-Cys(tBu)-Tyr(tBu)-Ala- Val-Ala-Pro-Gly-Gln-Ile-Thr(tBu)-Thr(tBu)-Val-Gly-Asp(tBu)-Gly-Tyr(tBu)-Ile-Gly-Ser(tBu)-His-Gly-His-Ala-Arg(Tos)-Tyr(tBu)-Leu-Ala-Arg(Tos)-Cys(tBu)-Leu(OtBu)) is prepared and purified according to standard automated peptide synthesis techniques known to those skilled in the art. Deprotection of the Glu(OBz) residue (H$_2$/Pd) yields the free-Glu carboxylate for subsequent coupling (Prot3-Tendamistat, e.g., Fmoc-Asp(tBu)-Thr(tBu)-Thr(tBu)-Val-Ser(tBu)-Glu-Pro-Ala-Pro-Ser(tBu)-Cys(tBu)-Val-Thr(tBu)-Leu-Tyr(tBu)-Gln-Ser(tBu)-Trp-Arg(Tos)-Tyr-Ser(tBu)-Gln-Ala-Asp(tBu)- Asp(tBu)-Gly-Cys(tBu)-Ala-Glu(tBu)-Thr(tBu)-Val-Thr(tBu)-Val-Lys(Fmoc)-Val-Val-Tyr(tBu)-Glu(tBu)-Asp(tBu)-Asp(tBu)-Thr(tBu)-Glu(tBu)-Gly-Leu-Cys(tBu)-Tyr(tBu)-Ala-Val-Ala-Pro-Gly-Gln-Ile-Thr(tBu)-Thr(tBu)- Val-Gly-Asp(tBu)-Gly-Tyr(tBu)-Ile-Gly-Ser(tBu)-His-Gly-His-Ala-Arg(Tos)-Tyr(tBu)-Leu-Ala-Arg(Tos)-Cys(tBu)-Leu(OtBu)) mPEG-NH$_2$ 20 kDa, stored at −20° C. under argon, is warmed to ambient temperature. The reaction is performed at room temperature. A 5-fold molar excess of mPEG-NH$_2$, PyBOP (benzotriazol-1-yloxy)tripyrrolidinonophosphonium hexafluorophosphate), and 1-hydroxybenzotriazole (HOBt) are used, based upon absolute peptide content. The mPEG-NH$_2$, PyBOP, HOBt are weighed into a glass vial containing a magnetic stirrer bar. A solution of Prot3-Tendamistat is prepared in N,N-dimethylformamide is added and the mixture is stirred using a magnetic stirrer until the mPEG-NH$_2$ is fully dissolved. The stirring speed is reduced and the reaction is allowed to proceed to formation of conjugate product. The conjugate solution is then analyzed by SDS-PAGE and RP-HPLC (C18) to determine the extent of Prot3-Tendamistat-(Glu-O-mPEG) conjugate formation. The remaining protecting groups are removed under standard deprotection conditions to yield the Tendamistat-Glu(O-mPEG) conjugate.

Using this same approach, other conjugates are prepared using mPEG derivatives having other weight-average molecular weights that also bear an amino moiety.

Example 8

Recombinant Human Carperitide-mPEG Conjugates

Carperitide (α-atriopeptin) is secreted by the heart, is a member of the natriuretic peptide family which is comprised of peptides secreted by various organs. Carperitide is has been proposed for the treatment of acute heart failure and shown therapeutic potential to treat peripheral arterial diseases refractory to conventional therapies (Park et al., *Endocrinology* 2008, 149, 483). Carperitide has the amino acid sequence Ser-Leu-Arg-Arg-Ser-Ser-Cys-Phe-Gly-Gly-Arg-Met-Asp-Arg-Ile-Gly-Ala-Gln-Ser-Gly-Leu-Gly-Cys-Asn-Ser-Phe-Arg-Tyr (SLRRSSCFGGRMDRIGAQSGLGCNSFRY).

a) mPEG-N$^{ter}$-Carperitide-Via mPEG-SPC

Carperitide can be prepared and purified according to standard automated peptide synthesis or recombinant techniques known to those skilled in the art. An illustrative polymeric reagent, mPEG-SPC reagent, is covalently attached to the N-terminus of Carperitide, to provide a N$^{ter}$-conjugate form of the peptide. mPEG-SPC 20 kDa, stored at −20° C. under argon, is warmed to ambient temperature. The reaction is performed at room temperature. About 3-5-fold molar excess of mPEG-SPC 20 kDa reagent is used, based upon absolute peptide content. The mPEG-SPC reagent is weighed into a glass vial containing a magnetic stirrer bar. A solution of Carperitide prepared in phosphate buffered saline, PBS, pH 7.4 is added and the mixture is rapidly stirred using a magnetic stirrer until the mPEG-SPC is fully dissolved. The stirring speed is reduced and the reaction is allowed to proceed to formation of conjugate product. The reaction is optionally quenched to terminate the reaction. The pH of the conjugate solution at the end of the reaction is measured and further acidified by addition of 0.1M HCl, if necessary, to bring the pH of the final solution to about 5.5. The conjugate solution is then analyzed by SDS-PAGE and RP-HPLC (C18) to determine the extent of mPEG-N$^{ter}$-Carperitide conjugate formation.

Using this same approach, other conjugates can be prepared using mPEG derivatives having other weight-average molecular weights that also bear an N-hydroxysuccinimide moiety.

b) Carperitide-C$^{ter}$-mPEG

An illustrative polymeric reagent, mPEG-NH$_2$ reagent is covalently attached to the C-terminus of Carperitide, to provide a C$^{ter}$-conjugate form of the peptide. For coupling to the C-terminus, a protected Carperitide (Prot-Carperitide, e.g., Fmoc-Ser(tBu)-Leu-Arg(Tos)-Arg(Tos)-Ser(tBu)-Ser(tBu)-Cys(tBu)-Phe-Gly-Gly-Arg(Tos)-Met-Asp(tBu)-Arg(Tos)-Ile-Gly-Ala-Gln-Ser(tBu)-Gly-Leu-Gly-Cys(tBu)-Asn-Ser(tBu)-Phe-Arg(Tos)-Tyr(tBu)-OH) can be prepared and purified according to standard automated peptide synthesis or recombinant techniques known to those skilled in the art. mPEG-NH$_2$ 20 kDa, stored at −20° C. under argon, is warmed to ambient temperature. The reaction is performed at room temperature. About 3-5-fold molar excess of mPEG-NH$_2$, PyBOP (benzotriazol-1-yloxy)tripyrrolidinonophosphonium hexafluorophosphate), and 1-hydroxybenzotriazole (HOBt) are used, based upon absolute peptide content. The mPEG-NH$_2$, PyBOP, HOBt are weighed into a glass vial containing a magnetic stirrer bar. A solution of Prot-Carperitide is prepared in N,N-dimethylformamide is added and the mixture is rapidly stirred using a magnetic stirrer until the mPEG-NH$_2$ is fully dissolved. The stirring speed is reduced and the reaction is allowed to proceed to formation of conjugate product. The conjugate solution is then analyzed by SDS-PAGE and RP-HPLC (C18) to determine the extent of Prot-Carperitide-C$^{ter}$-mPEG conjugate formation. The remaining protecting groups are removed under standard deprotection conditions to yield the Carperitide-C$^{ter}$-mPEG conjugate.

Using this same approach, other conjugates can be prepared using mPEG derivatives having other weight-average molecular weights that also bear an amino moiety.

c) Carperitide-Cys (S-mPEG)

Carperitide, which has a thiol-containing cysteine residue, is dissolved in buffer. To this peptide solution is added a 3-5 fold molar excess of mPEG-MAL, 5 kDa. The mixture is stirred at room temperature under an inert atmosphere for several hours. Analysis of the reaction mixture reveals successful conjugation of this peptide.

Using this same approach, other conjugates can be prepared using mPEG-MAL having other weight average molecular weights.

d) mPEG-N$^{ter}$-Carperitide Via mPEG-SMB mPEG-SMB, 5 kDa, stored at −20° C. under argon, is warmed to ambient temperature. A five-fold excess (relative to the amount of the peptide) of the warmed mPEG-SMB is dissolved in buffer to form a 10% reagent solution. The 10% reagent solution is quickly added to the aliquot of a stock Carperitide solution and mixed well. After the addition of the mPEG-SMB, the pH of the reaction mixture is determined and adjusted to 6.7 to 6.8 using conventional techniques. To allow for coupling of the mPEG-SMB to the peptide via an amide linkage, the reaction solution is stirred for several hours (e.g., 5 hours) at room temperature in the dark or stirred overnight at 3-8° C. in a cold room, thereby resulting in a conjugate solution. The reaction is quenched with a 20-fold molar excess (with respect to the peptide) of Tris buffer.

Using this same approach, other conjugates can be prepared using mPEG derivatives having other weight-average molecular weights that also bear an N-hydroxysuccinimide moiety.

e) Carperitide-Asp(O-mPEG)

An illustrative polymeric reagent, mPEG-NH$_2$ reagent is covalently attached to the Asp residue of Carperitide, to provide a Asp-conjugate form of the peptide. For coupling to the Asp residue, a protected Carperitide (Prot2-Carperitide, e.g., Fmoc-Ser(tBu)-Leu-Arg(Tos)-Arg(Tos)-Ser(tBu)-Ser(tBu)-Cys(tBu)-Phe-Gly-Gly-Arg(Tos)-Met-Asp(OBz)-Arg(Tos)-Ile-Gly-Ala-Gln-Ser(tBu)- Gly-Leu-Gly-Cys(tBu)-Asn-Ser(tBu)-Phe-Arg(Tos)-Tyr(tBu)-O(tBu)) is prepared and purified according to standard automated peptide synthesis techniques known to those skilled in the art. Deprotection of the Asp(OBz) residue (H$_2$/Pd) yields the free-Asp carboxylate for subsequent coupling (Prot3-Carperitide, e.g., Fmoc-Ser(tBu)-Leu-Arg(Tos)-Arg(Tos)-Ser(tBu)-Ser(tBu)-Cys(tBu)-Phe-Gly-Gly-Arg(Tos)-Met-Asp-Arg(Tos)-Ile-Gly-Ala-Gln-Ser(tBu)-Gly-Leu- Gly-Cys(tBu)-Asn-Ser(tBu)-Phe-Arg(Tos)-Tyr(tBu)-O(tBu)).

mPEG-NH$_2$ 20 kDa, stored at −20° C. under argon, is warmed to ambient temperature. The reaction is performed at room temperature. A 5-fold molar excess of mPEG-NH$_2$, PyBOP (benzotriazol-1-yloxy)tripyrrolidinonophosphonium hexafluorophosphate), and 1-hydroxybenzotriazole (HOBt) are used, based upon absolute peptide content. The mPEG-NH$_2$, PyBOP, HOBt are weighed into a glass vial containing a magnetic stirrer bar. A solution of Prot3-Carperitide is prepared in N,N-dimethylformamide is added and the mixture is rapidly stirred using a magnetic stirrer until the mPEG-NH$_2$ is fully dissolved. The stirring speed is reduced and the reaction is allowed to proceed to formation of conjugate product. The conjugate solution is then analyzed by SDS-PAGE and RP-HPLC (C18) to determine the extent of Prot3-Carperitide-(Asp-O-mPEG) conjugate formation. The remaining protecting groups are removed under standard deprotection conditions to yield the Carperitide-Asp(O-mPEG) conjugate.

Using this same approach, other conjugates is prepared using mPEG derivatives having other weight-average molecular weights that also bear an amino moiety.

Example 9

Urodilatin-mPEG Conjugates

Urodilatin is a member of the natriuretic peptide family which is comprised of peptides secreted by various organs, has been studied for use in treating various conditions, including renal failure or congestive heart failure (see, e.g., U.S. Pat. Nos. 5,571,789 and 6,831,064; Kentsch et al., *Eur. J. Clin. Invest.* 1992, 22, 662; Kentsch et al., *Eur. J. Clin. Invest.* 1995, 25, 281; Elsner et al., *Am. Heart J.* 1995, 129, 766; Forssmann et al., *Clinical Pharmacology and Therapeutics* 1998, 64, 322; and US Patent Application Publication No. 2006/0264376A1). Urodilatin has the amino acid sequence set forth in GenBank Accession No. 1506430A; Thr-Ala-Pro-Arg-Ser-Leu-Arg-Arg-Ser-Ser-Cys-Phe-Gly-Gly-Arg-Met-Asp-Arg-Ile-Gly-Ala-Gln-Ser-Gly-Leu-Gly-Cys-Asn- Ser-Phe-Arg-Tyr (TAPRSLRRSS CFGGRM-DRIG AQSGLGCNSF RY). Urodilatin is also the 95-126 fragment [ANP(95-126)] of atrial natriuretic peptide (ANP).

a) mPEG-N$^{ter}$-Urodilatin-Via mPEG-SPC

Urodilatin is prepared and purified according to standard automated peptide synthesis or recombinant techniques known to those skilled in the art. An illustrative polymeric reagent, mPEG-SPC reagent, is covalently attached to the N-terminus of Urodilatin, to provide a N$^{ter}$-conjugate form of the peptide. mPEG-SPC 20 kDa, stored at −20° C. under argon, is warmed to ambient temperature. The reaction is performed at room temperature. About 3-5-fold molar excess of mPEG-SPC 20 kDa reagent is used based upon absolute peptide content. The mPEG-SPC reagent is weighed into a glass vial containing a magnetic stirrer bar. A solution of Urodilatin prepared in phosphate buffered saline, PBS, pH 7.4 is added and the mixture is stirred using a magnetic stirrer until the mPEG-SPC is fully dissolved. The stirring speed is reduced and the reaction is allowed to proceed to formation of conjugate product. The reaction is optionally quenched to terminate the reaction. The pH of the conjugate solution at the end of the reaction is measured and further acidified by addition of 0.1M HCl, if necessary, to bring the pH of the final solution to about 5.5. The conjugate solution is then analyzed by SDS-PAGE and RP-HPLC (C18) to determine the extent of mPEG-N$^{ter}$-Urodilatin conjugate formation.

Using this same approach, other conjugates are prepared using mPEG derivatives having other weight-average molecular weights that also bear an N-hydroxysuccinimide moiety.

b) Urodilatin-C$^{ter}$-mPEG

An illustrative polymeric reagent, mPEG-NH$_2$ reagent is covalently attached to the C-terminus of Urodilatin, to provide a C$^{ter}$-conjugate form of the peptide. For coupling to the C-terminus, a protected Urodilatin (Prot-Urodilatin, e.g., Fmoc-Thr(tBu)-Ala-Pro-Arg(Tos)-Ser(tBu)-Leu-Arg(Tos)-Arg(Tos)-Ser(tBu)-Ser(tBu)-Cys(tBu)-Phe-Gly-Gly-Arg(Tos)-Met-Asp(tBu)-Arg(Tos)-Ile-Gly-Ala- Gln-Ser(tBu)-Gly-Leu-Gly-Cys(tBu)-Asn-Ser(tBu)-Phe-Arg(Tos)-Tyr(tBu)-OH) is prepared and purified according to standard automated peptide synthesis techniques known to those skilled in the art. mPEG-NH$_2$ 20 kDa, stored at −20° C. under argon, is warmed to ambient temperature. The reaction is performed at room temperature. About 3-5-fold molar excess of mPEG-NH$_2$, PyBOP (benzotriazol-1-yloxy)tripyrrolidinonophosphonium hexafluorophosphate), and 1-hydroxybenzotriazole (HOBt) are used, based upon absolute peptide content. The mPEG-NH$_2$, PyBOP, HOBt are weighed into a glass vial containing a magnetic stirrer bar. A solution of Prot-Urodilatin is prepared in N,N-dimethylformamide is added and the mixture is stirred using a magnetic stirrer until the mPEG-NH$_2$ is fully dissolved. The stirring speed is reduced and the reaction is allowed to proceed to formation of conjugate product. The conjugate solution is then analyzed by SDS-PAGE and RP-HPLC (C18) to determine the extent of Prot-Urodilatin-C$^{ter}$-mPEG conjugate formation. The remaining protecting groups are removed under standard deprotection conditions to yield the Urodilatin-C$^{ter}$-mPEG conjugate.

Using this same approach, other conjugates are prepared using mPEG derivatives having other weight-average molecular weights that also bear an amino moiety.

c) Urodilatin-Cys(S-mPEG)

Urodilatin, which has a thiol-containing cysteine residue, is dissolved in buffer. To this peptide solution is added a 3-5 fold molar excess of mPEG-MAL, 5 kDa. The mixture is stirred at room temperature under an inert atmosphere for several hours. Analysis of the reaction mixture reveals successful conjugation of this peptide.

Using this same approach, other conjugates are prepared using mPEG-MAL having other weight average molecular weights.

d) mPEG-N$^{ter}$-Urodilatin Via mPEG-SMB mPEG-SMB, 5 kDa, stored at −20° C. under argon, is warmed to ambient temperature. A five-fold excess (relative to the amount of the peptide) of the warmed mPEG-SMB is dissolved in buffer to form a 10% reagent solution. The 10% reagent solution is quickly added to the aliquot of a stock Urodilatin solution and mixed well. After the addition of the mPEG-SMB, the pH of the reaction mixture is determined and adjusted to 6.7 to 6.8 using conventional techniques. To allow for coupling of the mPEG-SMB to the peptide via an amide linkage, the reaction solution is stirred for several hours (e.g., 5 hours) at room temperature in the dark or stirred overnight at 3-8° C. in a cold room, thereby resulting in a conjugate solution. The reaction is quenched with a 20-fold molar excess (with respect to the peptide) of Tris buffer.

Using this same approach, other conjugates are prepared using mPEG derivatives having other weight-average molecular weights that also bear an N-hydroxysuccinimide moiety.

e) Urodilatin-Asp(O-mPEG)

An illustrative polymeric reagent, mPEG-NH$_2$ reagent is covalently attached to the Asp residue of Urodilatin, to provide a Asp-conjugate form of the peptide. For coupling to the Asp residue, a protected Urodilatin (Prot2-Urodilatin, e.g., Fmoc-Thr(tBu)-Ala-Pro-Arg(Tos)-Ser(tBu)-Leu-Arg(Tos)-Arg(Tos)-Ser(tBu)-Ser(tBu)-Cys(tBu)-Phe-Gly-Gly-Arg(Tos)-Met-Asp(OBz)-Arg(Tos)- Ile-Gly-Ala-Gln-Ser(tBu)-Gly-Leu-Gly-Cys(tBu)-Asn-Ser(tBu)-Phe-Arg(Tos)-Tyr(tBu)-NH$_2$) is prepared and purified according to standard automated peptide synthesis techniques known to those skilled in the art. Deprotection of the Asp(OBz) residue (H$_2$/Pd) yields the free-Asp carboxylate for subsequent coupling (Prot3-Urodilatin, e.g. Fmoc-Thr(tBu)-Ala-Pro-Arg(Tos)-Ser(tBu)-Leu-Arg(Tos)-Arg(Tos)-Ser(tBu)-Ser(tBu)-Cys(tBu)-Phe-Gly-Gly- Arg(Tos)-Met-Asp-Arg(Tos)-Ile-Gly-Ala-Gln-Ser(tBu)-Gly-Leu-Gly-Cys(tBu)-Asn-Ser(tBu)-Phe-Arg(Tos)-Tyr(tBu)-NH$_2$). mPEG-NH$_2$ 20 kDa, stored at −20° C. under argon, is warmed to ambient temperature. The reaction is performed at room temperature. A 5-fold molar excess of mPEG-NH$_2$, PyBOP (benzotriazol-1-yloxy)tripyrrolidinonophosphonium hexafluorophosphate), and 1-hydroxybenzotriazole (HOBt) are used, based upon absolute peptide content. The mPEG-NH$_2$, PyBOP, HOBt are weighed into a glass vial containing a magnetic stirrer bar. A solution of Prot3-Urodilatin is prepared in N,N-dimethylformamide is added and the mixture is stirred using a magnetic stirrer until the mPEG-NH$_2$ is fully dissolved. The stirring speed is reduced and the reaction is allowed to proceed to formation of conjugate product. The conjugate solution is then analyzed by SDS-PAGE and RP-HPLC (C18) to determine the extent of Prot3-Urodilatin-(Asp-O-mPEG) conjugate formation. The remaining protecting groups are removed under standard deprotection conditions to yield the Urodilatin-Asp(O-mPEG) conjugate.

Using this same approach, other conjugates are prepared using mPEG derivatives having other weight-average molecular weights that also bear an amino moiety.

Example 10

Desirudin-mPEG Conjugates

Desirudin, a recombinant hirudin, is a member of a class of anticoagulants that act by directly inhibiting thrombin. Desirudin acts via a bivalent binding arrangement with both the active site and fibrinogen-binding site (exosite 1) of thombin, and has been shown to be useful in the prevention and management of thromboembolic disease, reducing the incidence of deep vein thrombosis (DVT) in patients undergoing elective hip replacement, preventing restenosis after coronary angioplasty for unstable angina, and in the treatment of acute coronary syndromes for patients in whom heparin therapy is not a viable option (Matheson and Goa, *Drugs* 2000, 60, 679). Desirudin has the primary sequence Val-Val-Tyr-Thr-Asp-Cys-Thr-Glu-Ser-Gly-Gln-Asn-Leu-Cys-Leu-Cys-Glu-Gly-Ser-Asn-Val-Cys-Gly-Gln-Gly-Asn-Lys-Cys-Ile-Leu-Gly-Ser-Asp-Gly-Glu-Lys-Asn-Gln-Cys-Val- Thr-Gly-Glu-Gly-Thr-Pro-Lys-Pro-Gln-Ser-His-Asn-Asp-Gly-Asp-Phe-Glu-Glu-Ile-Pro-Glu-Glu-Tyr-Leu-Gln.

a) mPEG-N$^{ter}$-Desirudin Via mPEG-SPC

Desirudin is prepared and purified according to standard automated peptide synthesis or recombinant techniques known to those skilled in the art. An illustrative polymeric reagent, mPEG-SPC reagent,

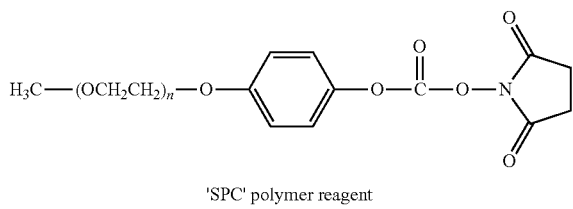

'SPC' polymer reagent is covalently attached to the N-terminus of Desirudin, to provide a N$^{ter}$-conjugate form of the peptide. mPEG-SPC 20 kDa, stored at −20° C. under argon, is warmed to ambient temperature. The reaction is performed at room temperature. About 3-5-fold molar excess of mPEG-SPC 20 kDa reagent is used based upon absolute peptide content. The mPEG-SPC reagent is weighed into a glass vial containing a magnetic stirrer bar. A solution of Desirudin prepared in phosphate buffered saline, PBS, pH 7.4 is added and the mixture is stirred using a magnetic stirrer until the mPEG-SPC is fully dissolved. The stirring speed is reduced and the reaction is allowed to proceed to formation of conjugate product. The reaction is optionally quenched to terminate the reaction. The pH of the conjugate solution at the end of the reaction is measured and further acidified by addition of 0.1M HCl, if necessary, to bring the pH of the final solution to about 5.5. The conjugate solution is then analyzed by SDS-PAGE and RP-HPLC (C18) to determine the extent of mPEG-N$^{ter}$-Desirudin conjugate formation.

Using this same approach, other conjugates are prepared using mPEG derivatives having other weight-average molecular weights that also bear an N-hydroxysuccinimide moiety.

b) Desirudin-C$^{ter}$-mPEG

An illustrative polymeric reagent, mPEG-NH$_2$ reagent is covalently attached to the C-terminus of Desirudin, to provide a C$^{ter}$-conjugate form of the peptide. For coupling to the C-terminus, a protected Desirudin (Prot-Val-Val-Tyr(tBu)-Thr(tBu)-Asp(tBu)-Cys(tBu)-Thr(tBu)-Glu(tBu)-Ser(tBu)-Gly-Gln-Asn-Leu-Cys(tBu)-Leu-Cys-Glu(tBu)-Gly-Ser (tBu)-Asn-Val-Cys(tBu)-Gly-Gln-Gly-Asn- Lys(Fmoc)-Cys (tBu)-Ile-Leu-Gly-Ser(tBu)-Asp(tBu)-Gly-Glu(tBu)-Lys (Fmoc)-Asn-Gln-Cys(tBu)-Val-Thr(tBu)-Gly-Glu(tBu)-Gly-Thr(tBu)-Pro-Lys(Fmoc)-Pro-Gln-Ser(tBu)-His-Asn-Asp(tBu)-Gly-Asp(tBu)-Phe-Glu(tBu)- Glu(tBu)-Ile-Pro-Glu(tBu)-Glu(tBu)-Tyr(tBu)-Leu-Gln-OH) is prepared and purified according to standard automated peptide synthesis techniques known to those skilled in the art. mPEG-NH$_2$ 20 kDa, stored at −20° C. under argon, is warmed to ambient temperature. The reaction is performed at room temperature. About 3-5-fold molar excess of mPEG-NH$_2$, PyBOP (benzotriazol-1-yloxy)tripyrrolidinonophosphonium hexafluorophosphate), and 1-hydroxybenzotriazole (HOBt) are used, based upon absolute peptide content. The mPEG-NH$_2$, PyBOP, HOBt are weighed into a glass vial containing a magnetic stirrer bar. A solution of Prot-Desirudin is prepared in N,N-dimethylformamide is added and the mixture is stirred using a magnetic stirrer until the mPEG-NH$_2$ is fully dissolved. The stirring speed is reduced and the reaction is allowed to proceed to formation of conjugate product. The conjugate solution is then analyzed by SDS-PAGE and RP-HPLC (C18) to determine the extent of Prot-Desirudin-C$^{ter}$-mPEG conjugate formation. The remaining protecting groups are removed under standard deprotection conditions to yield the Desirudin-C$^{ter}$-mPEG conjugate.

Using this same approach, other conjugates are prepared using mPEG derivatives having other weight-average molecular weights that also bear an amino moiety.

c) Desirudin-Cys(S-mPEG)

Desirudin, which has a thiol-containing cysteine residue, is dissolved in buffer. To this peptide solution is added a 3-5 fold molar excess of mPEG-MAL, 5 kDa. The mixture is stirred at room temperature under an inert atmosphere for several hours. Analysis of the reaction mixture reveals successful conjugation of this peptide.

Using this same approach, other conjugates are prepared using mPEG-MAL having other weight average molecular weights.

d) mPEG-N$^{ter}$-Desirudin Via mPEG-SMB

An mPEG-N-Hydroxysuccinimide is obtained having a molecular weight of 5 kDa and having the basic structure shown below:

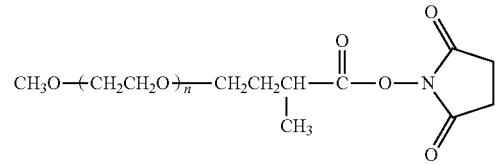

(mPEG-Succinimidyl α-Methylbutanoate Derivative, 5 kDa ("mPEG-SMB"))

mPEG-SMB, 5 kDa, stored at −20° C. under argon, is warmed to ambient temperature. A five-fold excess (relative to the amount of the peptide) of the warmed mPEG-SMB is dissolved in buffer to form a 10% reagent solution. The 10% reagent solution is quickly added to the aliquot of a stock Desirudin solution and mixed well. After the addition of the mPEG-SMB, the pH of the reaction mixture is determined and adjusted to 6.7 to 6.8 using conventional techniques. To allow for coupling of the mPEG-SMB to the peptide via an amide linkage, the reaction solution is stirred for several hours (e.g., 5 hours) at room temperature in the dark or stirred overnight at 3-8° C. in a cold room, thereby resulting in a conjugate solution. The reaction is quenched with a 20-fold molar excess (with respect to the peptide) of Tris buffer.

Using this same approach, other conjugates are prepared using mPEG derivatives having other weight-average molecular weights that also bear an N-hydroxysuccinimide moiety.

e) Desirudin-Asp(O-mPEG)

An illustrative polymeric reagent, mPEG-NH$_2$ reagent is covalently attached to the Asp residue of Desirudin, to provide a Asp-conjugate form of the peptide. For coupling to the Asp residue, a protected Desirudin (Prot2-Desirudin, e.g. Fmoc-Val-Val-Tyr(tBu)-Thr(tBu)-Asp(OBz)-Cys(tBu)-Thr(tBu)-Glu(tBu)-Ser(tBu)-Gly-Gln-Asn-Leu-Cys(tBu)-Leu-Cys-Glu(tBu)-Gly-Ser(tBu)-Asn- Val-Cys(tBu)-Gly-Gln-Gly-Asn-Lys(Fmoc)-Cys(tBu)-Ile-Leu-Gly-Ser(tBu)-Asp(tBu)-Gly-Glu(tBu)-Lys(Fmoc)-Asn-Gln-Cys(tBu)-Val-Thr(tBu)-Gly-Glu(tBu)-Gly-Thr(tBu)-Pro-Lys(Fmoc)-Pro-Gln-Ser(tBu)-His-Asn-Asp(tBu)- Gly-Asp(tBu)-Phe-Glu(tBu)-Glu(tBu)-Ile-Pro-Glu(tBu)-Glu(tBu)-Tyr(tBu)-Leu-Gln-NH$_2$) is prepared and purified according to standard automated peptide synthesis techniques known to those skilled in the art. Deprotection of the Asp(OBz) residue (H$_2$/Pd) yields the free-Asp carboxylate for subsequent coupling (Prot3-Desirudin, e.g. Fmoc-Val-Val-Tyr(tBu)-Thr(tBu)-Asp-Cys(tBu)-Thr(tBu)-Glu(tBu)-Ser(tBu)-Gly-Gln-Asn-Leu-Cys(tBu)-Leu-Cys-Glu(tBu)-Gly-Ser(tBu)-Asn-Val-Cys(tBu)-Gly-Gln-Gly-Asn- Lys(Fmoc)-Cys(tBu)-Ile-Leu-Gly-Ser(tBu)-Asp(tBu)-Gly-Glu(tBu)-Lys(Fmoc)-Asn-Gln-Cys(tBu)-Val-Thr(tBu)-Gly-Glu(tBu)-Gly-Thr(tBu)-Pro-Lys(Fmoc)-Pro-Gln-Ser(tBu)-His-Asn-Asp(tBu)-Gly-Asp(tBu)-Phe-Glu(tBu)- Glu(tBu)-Ile-Pro-Glu(tBu)-Glu(tBu)-Tyr(tBu)-Leu-Gln-NH$_2$). mPEG-NH$_2$ 20 kDa, stored at −20° C. under argon, is warmed to ambient temperature. The reaction is performed at room temperature. A 5-fold molar excess of mPEG-NH$_2$, PyBOP (benzotriazol-1-yloxy)tripyrrolidinonophosphonium hexafluorophosphate), and 1-hydroxybenzotriazole (HOBt) are used, based upon absolute peptide content. The mPEG-NH$_2$, PyBOP, HOBt are weighed into a glass vial containing a magnetic stirrer bar. A solution of Prot3-Desirudin is prepared in N,N-dimethylformamide is added and the mixture is stirred using a magnetic stirrer until the mPEG-NH$_2$ is fully dissolved. The stirring speed is reduced and the reaction is allowed to proceed to formation of conjugate product. The conjugate solution is then analyzed by SDS-PAGE and RP-HPLC (C18) to determine the extent of Prot3-Desirudin-(Asp-O-mPEG) conjugate formation. The remaining protecting groups are removed under standard deprotection conditions to yield the Desirudin-Asp(O-mPEG) conjugate.

Example 11

Obestatin-mPEG Conjugates

Obestatin is 28-amino acid, acylated, orexigenic peptide that is a ligand for growth hormone secretagogue receptors and is encoded by the same gene that also encodes ghrelin, a peptide hormone that increases appetite. Treatment of rats with obestatin suppressed food intake, inhibited jejunal contraction, and decreased body-weight gain (Zhang et al., Science 2005, 310, 996). Synthetic human obestatin is available from California Peptide Research, Inc (Napa, Calif.), having the sequence, Phe-Asn-Ala-Pro-Phe-Asp-Val-Gly-Ile-Lys-Leu-Ser-Gly-Val-Gln-Tyr-Gln-Gln-His-Ser-Gln-Ala-Leu-NH$_2$ (PubChem Substance ID: 47205412).

a) mPEG-N$^{ter}$-Obestatin Via mPEG-SPC

An illustrative polymeric reagent, mPEG-SPC reagent, is covalently attached to the N-terminus of Obestatin, to provide a N$^{ter}$-conjugate form of the peptide. mPEG-SPC 20 kDa, stored at −20° C. under argon, is warmed to ambient temperature. The reaction is performed at room temperature. About 3-5-fold molar excess of mPEG-SPC 20 kDa reagent is used based upon absolute peptide content. The mPEG-SPC reagent is weighed into a glass vial containing a magnetic stirrer bar. A solution of Obestatin prepared in phosphate buffered saline, PBS, pH 7.4 is added and the mixture is stirred using a magnetic stirrer until the mPEG-SPC is fully dissolved. The stirring speed is reduced and the reaction is allowed to proceed to formation of conjugate product. The reaction is optionally quenched to terminate the reaction. The pH of the conjugate solution at the end of the reaction is measured and further acidified by addition of 0.1M HCl, if necessary, to bring the pH of the final solution to about 5.5. The conjugate solution is then analyzed by SDS-PAGE and RP-HPLC (C18) to determine the extent of mPEG-N$^{ter}$-Obestatin conjugate formation.

Using this same approach, other conjugates are prepared using mPEG derivatives having other weight-average molecular weights that also bear an N-hydroxysuccinimide moiety.

b) Obestatin-C$^{ter}$-mPEG

An illustrative polymeric reagent, mPEG-NH$_2$ reagent is covalently attached to the C-terminus of Obestatin, to provide a C$^{ter}$-conjugate form of the peptide. For coupling to the C-terminus, a protected Obestatin lacking the C-terminus amide (Prot-Obestatin, e.g., Fmoc-Phe-Asn-Ala-Pro-Phe-Asp(tBu)-Val-Gly-Ile-Lys(Fmoc)-Leu-Ser(tBu)-Gly-Val-Gln-Tyr(tBu)-Gln-Gln-His-Ser(tBu)-Gln-Ala- Leu-OH) is prepared and purified according to standard automated peptide synthesis techniques known to those skilled in the art. mPEG-NH$_2$ 20 kDa, stored at −20° C. under argon, is warmed to ambient temperature. The reaction is performed at room temperature. About 3-5-fold molar excess of mPEG-NH$_2$, PyBOP (benzotriazol-1-yloxy)tripyrrolidinonophosphonium hexafluorophosphate), and 1-hydroxybenzotriazole (HOBt) are used, based upon absolute peptide content. The mPEG-NH$_2$, PyBOP, HOBt are weighed into a glass vial containing a magnetic stirrer bar. A solution of Prot-Obestatin is prepared in N,N-dimethylformamide is added and the mixture is stirred using a magnetic stirrer until the mPEG-NH$_2$ is fully dissolved. The stirring speed is reduced and the reaction is allowed to proceed to formation of conjugate product. The conjugate solution is then analyzed by SDS-PAGE and RP-HPLC (C18) to determine the extent of Prot-Obestatin-C$^{ter}$-mPEG conjugate formation. The remaining protecting groups are removed under standard deprotection conditions to yield the Obestatin-C$^{ter}$-mPEG conjugate.

Using this same approach, other conjugates are prepared using mPEG derivatives having other weight-average molecular weights that also bear an amino moiety.

c) Obestatin-Cys(S-mPEG)

Obestatin, which has a thiol-containing cysteine residue, is dissolved in buffer. To this peptide solution is added a 3-5 fold molar excess of mPEG-MAL, 5 kDa. The mixture is stirred at room temperature under an inert atmosphere for several hours. Analysis of the reaction mixture reveals successful conjugation of this peptide.

Using this same approach, other conjugates are prepared using mPEG-MAL having other weight average molecular weights.

d) mPEG-N$^{ter}$-Obestatin Via mPEG-SMB mPEG-SMB, 5 kDa, stored at −20° C. under argon, is warmed to ambient temperature. A five-fold excess (relative to the amount of the peptide) of the warmed mPEG-SMB is dissolved in buffer to form a 10% reagent solution. The 10% reagent solution is quickly added to the aliquot of a stock Obestatin solution and mixed well. After the addition of the mPEG-SMB, the pH of the reaction mixture is determined and adjusted to 6.7 to 6.8 using conventional techniques. To allow for coupling of the mPEG-SMB to the peptide via an amide linkage, the reaction solution is stirred for several hours (e.g., 5 hours) at room temperature in the dark or stirred overnight at 3-8° C. in a cold room, thereby resulting in a conjugate solution. The reaction is quenched with a 20-fold molar excess (with respect to the peptide) of Tris buffer.

Using this same approach, other conjugates are prepared using mPEG derivatives having other weight-average molecular weights that also bear an N-hydroxysuccinimide moiety.

e) Obestatin-Lys-mPEG

PEG-SMB, 5 kDa, stored at −20° C. under argon, is warmed to ambient temperature. A five-fold excess (relative to the amount of the peptide) of the warmed mPEG-SMB is dissolved in buffer to form a 10% reagent solution. The 10% reagent solution is quickly added to the aliquot of a stock protected Obestatin (e.g., Fmoc-Phe-Asn-Ala-Pro-Phe-Asp(tBu)-Val-Gly-Ile-Lys-Leu-Ser(tBu)-Gly-Val-Gln-Tyr(tBu)-Gln-Gln-His-Ser(tBu)-Gln-Ala-Leu-$NH_2$) solution and mixed well. After the addition of the mPEG-SMB, the pH of the reaction mixture is determined and adjusted to 6.7 to 6.8 using conventional techniques. To allow for coupling of the mPEG-SMB to the peptide via an amide linkage, the reaction solution is stirred for several hours (e.g., 5 hours) at room temperature in the dark or stirred overnight at 3-8° C. in a cold room, thereby resulting in a conjugate solution. The reaction is quenched with a 20-fold molar excess (with respect to the peptide) of Tris buffer. The remaining protecting groups are removed under standard deprotection conditions to yield the Obestatin-Lys(O-mPEG) conjugate.

Using this same approach, other conjugates are prepared using mPEG derivatives having other weight-average molecular weights that also bear an N-hydroxysuccinimide moiety.

Example 12

ITF-1697(Icrocaptide)-mPEG Conjugates

ITF-1697 is a tetrapeptide, Gly-(N-Et)Lys-Pro-Arg (PubChem Compound ID: 216295), which reduces mortality and tissue damage in lipopolysaccharide (LPS)-induced systemic endotoxemia and coronary ischemia and ischemia/reperfusion (see, International Patent Application Publication WO 1995/10531.). A randomized, double-blind study in patients with acute myocardial infarction undergoing coronary revascularisation demonstrated reduce infarct size by radionuclide imaging (Syeda et al., *Drugs R & D* 2004, 5, 141).

a) mPEG-$N^{ter}$-ITF-1697-Via mPEG-SPC

ITF-1697 is prepared and purified according to standard automated peptide synthesis or recombinant techniques known to those skilled in the art. An illustrative polymeric reagent, mPEG-SPC reagent, is covalently attached to the N-terminus of ITF-1697, to provide a $N^{ter}$-conjugate form of the peptide. mPEG-SPC 20 kDa, stored at −20° C. under argon, is warmed to ambient temperature. The reaction is performed at room temperature. About 3-5-fold molar excess of mPEG-SPC 20 kDa reagent is used based upon absolute peptide content. The mPEG-SPC reagent is weighed into a glass vial containing a magnetic stirrer bar. A solution of ITF-1697 prepared in phosphate buffered saline, PBS, pH 7.4 is added and the mixture is stirred using a magnetic stirrer until the mPEG-SPC is fully dissolved. The stirring speed is reduced and the reaction is allowed to proceed to formation of conjugate product. The reaction is optionally quenched to terminate the reaction. The pH of the conjugate solution at the end of the reaction is measured and further acidified by addition of 0.1M HCl, if necessary, to bring the pH of the final solution to about 5.5. The conjugate solution is then analyzed by SDS-PAGE and RP-HPLC (C18) to determine the extent of mPEG-$N^{ter}$-ITF-1697 conjugate formation.

Using this same approach, other conjugates are prepared using mPEG derivatives having other weight-average molecular weights that also bear an N-hydroxysuccinimide moiety.

b) ITF-1697-$C^{ter}$-mPEG

An illustrative polymeric reagent, mPEG-$NH_2$ reagent is covalently attached to the C-terminus of ITF-1697, to provide a $C^{ter}$-conjugate form of the peptide. For coupling to the C-terminus, a protected ITF-1697 (Prot-ITF-1697, e.g., Fmoc-Gly-(N-Et)Lys(Fmoc)-Pro-Arg(Tos)-OH) is prepared and purified according to standard automated peptide synthesis techniques known to those skilled in the art. mPEG-$NH_2$ 20 kDa, stored at −20° C. under argon, is warmed to ambient temperature. The reaction is performed at room temperature. About 3-5-fold molar excess of mPEG-$NH_2$, PyBOP (benzotriazol-1-yloxy)tripyrrolidinonophosphonium hexafluorophosphate), and 1-hydroxybenzotriazole (HOBt) are used, based upon absolute peptide content. The mPEG-$NH_2$, PyBOP, HOBt are weighed into a glass vial containing a magnetic stirrer bar. A solution of Prot-ITF-1697 is prepared in N,N-dimethylformamide is added and the mixture is stirred using a magnetic stirrer until the mPEG-$NH_2$ is fully dissolved. The stirring speed is reduced and the reaction is allowed to proceed to formation of conjugate product. The conjugate solution is then analyzed by SDS-PAGE and RP-HPLC (C18) to determine the extent of Prot-ITF-1697-$C^{ter}$-mPEG conjugate formation. The remaining protecting groups are removed under standard deprotection conditions to yield the ITF-1697-$C^{ter}$-mPEG conjugate.

Using this same approach, other conjugates are prepared using mPEG derivatives having other weight-average molecular weights that also bear an amino moiety.

c) mPEG-$N^{ter}$-ITF-1697 Via mPEG-SMB mPEG-SMB, 5 kDa, stored at −20° C. under argon, is warmed to ambient temperature. A five-fold excess (relative to the amount of the peptide) of the warmed mPEG-SMB is dissolved in buffer to form a 10% reagent solution. The 10% reagent solution is quickly added to the aliquot of a stock ITF-1697 solution and mixed well. After the addition of the mPEG-SMB, the pH of the reaction mixture is determined and adjusted to 6.7 to 6.8 using conventional techniques. To allow for coupling of the mPEG-SMB to the peptide via an amide linkage, the reaction solution is stirred for several hours (e.g., 5 hours) at room temperature in the dark or stirred overnight at 3-8° C. in a cold room, thereby resulting in a conjugate solution. The reaction is quenched with a 20-fold molar excess (with respect to the peptide) of Tris buffer.

Using this same approach, other conjugates are prepared using mPEG derivatives having other weight-average molecular weights that also bear an N-hydroxysuccinimide moiety.

d) ITF-1697-Lys-mPEG

PEG-SMB, 5 kDa, stored at −20° C. under argon, is warmed to ambient temperature. A five-fold excess (relative to the amount of the peptide) of the warmed mPEG-SMB is dissolved in buffer to form a 10% reagent solution. The 10% reagent solution is quickly added to the aliquot of a stock protected ITF-1697 (e.g., Fmoc-Gly-(N-Et)Lys-Pro-Arg(Tos)-O(tBu)) solution and mixed well. After the addition of the mPEG-SMB, the pH of the reaction mixture is determined and adjusted to 6.7 to 6.8 using conventional techniques. To allow for coupling of the mPEG-SMB to the peptide via an amide linkage, the reaction solution is stirred for several hours (e.g., 5 hours) at room temperature in the dark or stirred overnight at 3-8° C. in a cold room, thereby resulting in a conjugate solution. The reaction is quenched with a 20-fold molar excess (with respect to the peptide) of Tris buffer. The remaining protecting groups are removed under standard deprotection conditions to yield the ITF-1697-Lys(O-mPEG) conjugate.

Using this same approach, other conjugates are prepared using mPEG derivatives having other weight-average molecular weights that also bear an N-hydroxysuccinimide moiety.

Example 13

Oxyntomodulin-mPEG Conjugates

Oxyntomodulin (Amylin) is a 37-amino acid peptide derived from proglucagon found in the colon, produced by the oxyntic (fundic) cells of the oxyntic mucosa and is known to bind both the Glucagon-like peptide-1 (GLP-1) and the glucagon receptors. A randomized, double-blind, placebo-controlled, cross-over study in humans has shown Oxyntomodulin suppresses appetite and food intake (Cohen et al., J. Clin. Endocrin. Met. 2003, 88, 4696). Oxyntomodulin is commercially available from GenScript Corporation (Piscataway, N.J.; Cat. No. RP11278) with the sequence, Lys-Cys-Asn-Thr-Ala-Thr-Cys-Ala-Thr-Gln-Arg-Leu-Ala-Asn-Phe-Leu-Val-His-Ser-Ser-Asn-Asn-Phe-Gly-Ala-Ile-Leu-Ser-Ser-Thr-Asn-Val-Gly-Ser-Asn-Thr-Tyr-$NH_2$ (KCNTATCATQ RLANFLVHSS NNFGAILSST NVG-SNTY-$NH_2$).

a) mPEG-$N^{ter}$-Oxyntomodulin-Via mPEG-SPC

An illustrative polymeric reagent, mPEG-SPC reagent, is covalently attached to the N-terminus of Oxyntomodulin, to provide a $N^{ter}$-conjugate form of the peptide. mPEG-SPC 20 kDa, stored at −20° C. under argon, is warmed to ambient temperature. The reaction is performed at room temperature. About 3-5-fold molar excess of mPEG-SPC 20 kDa reagent is used based upon absolute peptide content. The mPEG-SPC reagent is weighed into a glass vial containing a magnetic stirrer bar. A solution of Oxyntomodulin prepared in phosphate buffered saline, PBS, pH 7.4 is added and the mixture is stirred using a magnetic stirrer until the mPEG-SPC is fully dissolved. The stirring speed is reduced and the reaction is allowed to proceed to formation of conjugate product. The reaction is optionally quenched to terminate the reaction. The pH of the conjugate solution at the end of the reaction is measured and further acidified by addition of 0.1M HCl, if necessary, to bring the pH of the final solution to about 5.5. The conjugate solution is then analyzed by SDS-PAGE and RP-HPLC (C18) to determine the extent of mPEG-$N^{ter}$-Oxyntomodulin conjugate formation.

Using this same approach, other conjugates are prepared using mPEG derivatives having other weight-average molecular weights that also bear an N-hydroxysuccinimide moiety.

b) Oxyntomodulin-$C^{ter}$-mPEG

An illustrative polymeric reagent, mPEG-$NH_2$ reagent is covalently attached to the C-terminus of Oxyntomodulin, to provide a $C^{ter}$-conjugate form of the peptide. For coupling to the C-terminus, a protected Oxyntomodulin lacking the C-terminus amide (Prot-Oxyntomodulin, e.g., Fmoc-Lys(Fmoc)-Cys(tBu)-Asn-Thr(tBu)-Ala-Thr(tBu)-Cys(tBu)-Ala-Thr(tBu)-Gln-Arg(Tos)-Leu-Ala-Asn-Phe-Leu-Val-His-Ser(tBu)-Ser(tBu)-Asn-Asn-Phe-Gly-Ala-Ile-Leu-Ser(tBu)-Ser(tBu)-Thr(tBu)-Asn-Val-Gly- Ser(tBu)-Asn-Thr(tBu)-Tyr(tBu)-OH) is prepared and purified according to standard automated peptide synthesis techniques known to those skilled in the art. mPEG-$NH_2$ 20 kDa, stored at −20° C. under argon, is warmed to ambient temperature. The reaction is performed at room temperature. About 3-5-fold molar excess of mPEG-$NH_2$, PyBOP (benzotriazol-1-yloxy) tripyrrolidinonophosphonium hexafluorophosphate), and 1-hydroxybenzotriazole (HOBt) are used, based upon absolute peptide content. The mPEG-$NH_2$, PyBOP, HOBt are weighed into a glass vial containing a magnetic stirrer bar. A solution of Prot-Oxyntomodulin is prepared in N,N-dimethylformamide is added and the mixture is stirred using a magnetic stirrer until the mPEG-$NH_2$ is fully dissolved. The stirring speed is reduced and the reaction is allowed to proceed to formation of conjugate product. The conjugate solution is then analyzed by SDS-PAGE and RP-HPLC (C18) to determine the extent of Prot-Oxyntomodulin-$C^{ter}$-mPEG conjugate formation. The remaining protecting groups are removed under standard deprotection conditions to yield the Oxyntomodulin-$C^{ter}$-mPEG conjugate.

Using this same approach, other conjugates are prepared using mPEG derivatives having other weight-average molecular weights that also bear an amino moiety.

c) Oxyntomodulin-Cys(S-mPEG)

Oxyntomodulin, which has a thiol-containing cysteine residue, is dissolved in buffer. To this peptide solution is added a 3-5 fold molar excess of mPEG-MAL, 5 kDa. The mixture is stirred at room temperature under an inert atmosphere for several hours. Analysis of the reaction mixture reveals successful conjugation of this peptide.

Using this same approach, other conjugates are prepared using mPEG-MAL having other weight average molecular weights.

d) mPEG-$N^{ter}$-Oxyntomodulin Via mPEG-SMB mPEG-SMB, 5 kDa, stored at −20° C. under argon, is warmed to ambient temperature. A five-fold excess (relative to the amount of the peptide) of the warmed mPEG-SMB is dissolved in buffer to form a 10% reagent solution. The 10% reagent solution is quickly added to the aliquot of a stock Oxyntomodulin solution and mixed well. After the addition of the mPEG-SMB, the pH of the reaction mixture is determined and adjusted to 6.7 to 6.8 using conventional techniques. To allow for coupling of the mPEG-SMB to the peptide via an amide linkage, the reaction solution is stirred for several hours (e.g., 5 hours) at room temperature in the dark or stirred overnight at 3-8° C. in a cold room, thereby resulting in a conjugate solution. The reaction is quenched with a 20-fold molar excess (with respect to the peptide) of Tris buffer.

Using this same approach, other conjugates are prepared using mPEG derivatives having other weight-average molecular weights that also bear an N-hydroxysuccinimide moiety.

e) Oxyntomodulin-Lys-mPEG

PEG-SMB, 5 kDa, stored at −20° C. under argon, is warmed to ambient temperature. A five-fold excess (relative to the amount of the peptide) of the warmed mPEG-SMB is dissolved in buffer to form a 10% reagent solution. The 10% reagent solution is quickly added to the aliquot of a stock protected Oxyntomodulin (e.g., Fmoc-Lys-Cys(tBu)-Asn-Thr(tBu)-Ala-Thr(tBu)-Cys(tBu)-Ala-Thr(tBu)-Gln-Arg(Tos)-Leu-Ala-Asn-Phe-Leu-Val-His-Ser(tBu)-Ser(tBu)-Asn-Asn- Phe-Gly-Ala-Ile-Leu-Ser(tBu)-Ser(tBu)-Thr(tBu)-Asn-Val-Gly-Ser(tBu)-Asn-Thr(tBu)-Tyr(tBu)-O(tBu)) solution and mixed well. After the addition of the mPEG-SMB, the pH of the reaction mixture is determined and adjusted to 6.7 to 6.8 using conventional techniques. To allow for coupling of the mPEG-SMB to the peptide via an amide linkage, the reaction solution is stirred for several hours (e.g., 5 hours) at room temperature in the dark or stirred overnight at 3-8° C. in a cold room, thereby resulting in a conjugate solution. The reaction is quenched with a 20-fold molar excess (with respect to the peptide) of Tris buffer. The remaining protecting groups are removed under standard deprotection conditions to yield the Oxyntomodulin-Lys(O-mPEG) conjugate.

Using this same approach, other conjugates are prepared using mPEG derivatives having other weight-average molecular weights that also bear an N-hydroxysuccinimide moiety.

Example 14

Cholecystokinin-mPEG Conjugates

Cholecystokinin is a peptide hormone secreted by the upper intestinal mucosa which increases gallbladder contraction, release of pancreatic exocrine (or digestive) enzymes, and is responsible for stimulating the digestion of fat and proteins. Cholecystokinin has also been shown to be a physiologic regulator of gastric emptying in humans (Liddle et al., *J. Clin. Invest.* 1986, 77, 992). Cholecystokinin has the sequence, Met-Asn-Ser-Gly-Val-Cys-Leu-Cys-Val-Leu-Met-Ala-Val-Leu-Ala-Ala-Gly-Ala-Leu-Thr-Gln-Pro-Val-Pro-Pro-Ala-Asp-Pro-Ala-Gly-Ser-Gly-Leu-Gln-Arg-Ala-Glu- Glu-Ala-Pro-Arg-Arg-Gln-Leu-Arg-Val-Ser-Gln-Arg-Thr-Asp-Gly-Glu-Ser-Arg-Ala-His-Leu-Gly-Ala-Leu-Leu-Ala-Arg-Tyr-Ile-Gln-Gln-Ala-Arg-Lys-Ala-Pro-Ser-Gly-Arg-Met-Ser-Ile-Val-Lys-Asn-Leu-Gln-Asn-Leu-Asp-Pro- Ser-His-Arg-Ile-Ser-Asp-Arg-Asp-Tyr-Met-Gly-Trp-Met-Asp-Phe-Gly-Arg-Arg-Ser-Ala-Glu-Glu-Tyr-Glu-Tyr-Pro-Ser (MNSGVCLCVL MAVLAAGALT QPVPPADPAG SGLQRAEEAP RRQLRVSQRT DGES-RAHLGA LLARYIQQAR KAPSGRMSIV KNLQN-LDPSH RISDRDYMGW MDFGRRSAEE YEYPS; PubChem Protein Accession No. AAA53094; Takahashi et al., *Gene*, 1986, 50, 353).

a) mPEG-N$^{ter}$-Cholecystokinin-Via mPEG-SPC

Cholecystokinin is prepared and purified according to standard automated peptide synthesis or recombinant techniques known to those skilled in the art. An illustrative polymeric reagent, mPEG-SPC reagent, is covalently attached to the N-terminus of Cholecystokinin, to provide a N$^{ter}$-conjugate form of the peptide. mPEG-SPC 20 kDa, stored at −20° C. under argon, is warmed to ambient temperature. The reaction is performed at room temperature. About 3-5-fold molar excess of mPEG-SPC 20 kDa reagent is used based upon absolute peptide content. The mPEG-SPC reagent is weighed into a glass vial containing a magnetic stirrer bar. A solution of Cholecystokinin prepared in phosphate buffered saline, PBS, pH 7.4 is added and the mixture is stirred using a magnetic stirrer until the mPEG-SPC is fully dissolved. The stirring speed is reduced and the reaction is allowed to proceed to formation of conjugate product. The reaction is optionally quenched to terminate the reaction. The pH of the conjugate solution at the end of the reaction is measured and further acidified by addition of 0.1M HCl, if necessary, to bring the pH of the final solution to about 5.5. The conjugate solution is then analyzed by SDS-PAGE and RP-HPLC (C18) to determine the extent of mPEG-N$^{ter}$-Cholecystokinin conjugate formation.

Using this same approach, other conjugates are prepared using mPEG derivatives having other weight-average molecular weights that also bear an N-hydroxysuccinimide moiety.

b) Cholecystokinin-C$^{ter}$-mPEG

An illustrative polymeric reagent, mPEG-NH$_2$ reagent is covalently attached to the C-terminus of Cholecystokinin, to provide a C$^{ter}$-conjugate form of the peptide. For coupling to the C-terminus, a protected Cholecystokinin (Prot-Cholecystokinin, e.g., Fmoc-Met-Asn-Ser(tBu)-Gly-Val-Cys(tBu)-Leu-Cys(tBu)-Val-Leu-Met-Ala-Val-Leu-Ala-Ala-Gly-Ala-Leu-Thr(tBu)-Gln-Pro-Val-Pro-Pro-Ala- Asp(tBu)-Pro-Ala-Gly-Ser(tBu)-Gly-Leu-Gln-Arg(Tos)-Ala-Glu(tBu)-Glu(tBu)-Ala-Pro-Arg(Tos)-Arg(Tos)-Gln-Leu-Arg(Tos)-Val-Ser(tBu)-Gln-Arg(Tos)-Thr(tBu)-Asp(tBu)-Gly-Glu(tBu)-Ser(tBu)-Arg(Tos)-Ala-His-Leu- Gly-Ala-Leu-Leu-Ala-Arg(Tos)-Tyr(tBu)-Ile-Gln-Gln-Ala-Arg (Tos)-Lys(Fmoc)-Ala-Pro-Ser(tBu)-Gly-Arg(Tos)-Met-Ser (tBu)-Ile-Val-Lys(Fmoc)-Asn-Leu-Gln-Asn-Leu-Asp(tBu)-Pro-Ser(tBu)-His-Arg(Tos)-Ile-S er(tBu)-Asp(tBu)-Arg (Tos)-Asp(tBu)-Tyr(tBu)-Met-Gly-Trp-Met-Asp(tBu)-Phe-Gly-Arg(Tos)-Arg(Tos)-Ser(tBu)-Ala-Glu(tBu)-Glu(tBu)-Tyr(tBu)-Glu(tBu)-Tyr(tBu)-Pro-Ser(tBu)) is prepared and purified according to standard automated peptide synthesis techniques known to those skilled in the art. mPEG-NH$_2$ 20 kDa, stored at −20° C. under argon, is warmed to ambient temperature. The reaction is performed at room temperature. About 3-5-fold molar excess of mPEG-NH$_2$, PyBOP (benzotriazol-1-yloxy)tripyrrolidinonophosphonium hexafluorophosphate), and 1-hydroxybenzotriazole (HOBt) are used, based upon absolute peptide content. The mPEG-NH$_2$, PyBOP, HOBt are weighed into a glass vial containing a magnetic stirrer bar. A solution of Prot-Cholecystokinin is prepared in N,N-dimethylformamide is added and the mixture is stirred using a magnetic stirrer until the mPEG-NH$_2$ is fully dissolved. The stirring speed is reduced and the reaction is allowed to proceed to formation of conjugate product. The conjugate solution is then analyzed by SDS-PAGE and RP-HPLC (C18) to determine the extent of Prot-Cholecystokinin-C$^{ter}$-mPEG conjugate formation. The remaining protecting groups are removed under standard deprotection conditions to yield the Cholecystokinin-C$^{ter}$-mPEG conjugate.

Using this same approach, other conjugates are prepared using mPEG derivatives having other weight-average molecular weights that also bear an amino moiety.

c) Cholecystokinin-Cys(S-mPEG)

Cholecystokinin, which has a thiol-containing cysteine residue, is dissolved in buffer. To this peptide solution is added a 3-5 fold molar excess of mPEG-MAL, 5 kDa. The mixture is stirred at room temperature under an inert atmosphere for several hours. Analysis of the reaction mixture reveals successful conjugation of this peptide.

Using this same approach, other conjugates are prepared using mPEG-MAL having other weight average molecular weights.

d) mPEG-N$^{ter}$-Cholecystokinin Via mPEG-SMB mPEG-SMB, 5 kDa, stored at −20° C. under argon, is warmed to ambient temperature. A five-fold excess (relative to the amount of the peptide) of the warmed mPEG-SMB is dissolved in buffer to form a 10% reagent solution. The 10% reagent solution is quickly added to the aliquot of a stock Cholecystokinin solution and mixed well. After the addition of the mPEG-SMB, the pH of the reaction mixture is determined and adjusted to 6.7 to 6.8 using conventional techniques. To allow for coupling of the mPEG-SMB to the peptide via an amide linkage, the reaction solution is stirred for several hours (e.g., 5 hours) at room temperature in the dark or stirred overnight at 3-8° C. in a cold room, thereby resulting in a conjugate solution. The reaction is quenched with a 20-fold molar excess (with respect to the peptide) of Tris buffer.

Using this same approach, other conjugates are prepared using mPEG derivatives having other weight-average molecular weights that also bear an N-hydroxysuccinimide moiety.

e) Cholecystokinin-Glu(O-mPEG)

An illustrative polymeric reagent, mPEG-NH$_2$ reagent is covalently attached to the Glu residue of Cholecystokinin, to provide a Glu-conjugate form of the peptide. For coupling to the Glu residue, a protected Cholecystokinin (Prot2-Cholecystokinin, e.g., Fmoc-Met-Asn-Ser(tBu)-Gly-Val-Cys(tBu)-Leu-Cys(tBu)-Val-Leu-Met-Ala-Val-Leu-Ala-Ala-Gly-Ala-Leu-Thr(tBu)-Gln-Pro-Val-Pro-Pro-Ala-Asp(tBu)-Pro-Ala-Gly-Ser(tBu)-Gly-Leu-Gln-Arg(Tos)-Ala-Glu(OBz)-Glu(tBu)-Ala-Pro-Arg(Tos)-Arg(Tos)-Gln-Leu-Arg(Tos)-Val-Ser(tBu)-Gln-Arg(Tos)-Thr(tBu)-Asp(tBu)-Gly-Glu(tBu)-Ser(tBu)-Arg(Tos)-Ala-His-Leu-Gly-Ala-Leu-Leu-Ala-Arg(Tos)-Tyr(tBu)-Ile-Gln-Gln-Ala-Arg(Tos)-Lys(Fmoc)-Ala-Pro-Ser(tBu)-Gly-Arg(Tos)-Met-Ser(tBu)-Ile-Val-Lys(Fmoc)-Asn-Leu-Gln-Asn-Leu-Asp(tBu)-Pro-Ser(tBu)-His-Arg(Tos)-Ile-Ser(tBu)-Asp(tBu)-Arg(Tos)-Asp(tBu)-Tyr(tBu)-Met-Gly-Trp-Met-Asp(tBu)-Phe-Gly-Arg(Tos)-Arg(Tos)-Ser(tBu)-Ala-Glu(tBu)-Glu(tBu)-Tyr(tBu)-Glu(tBu)-Tyr(tBu)-Pro-Ser(tBu)-O(tBu)) is prepared and purified according to standard automated peptide synthesis techniques known to those skilled in the art. Deprotection of the Glu(OBz) residue (H$_2$/Pd) yields the free-Glu carboxylate for subsequent coupling (Prot3-Cholecystokinin, e.g., Fmoc-Met-Asn-Ser(tBu)-Gly-Val-Cys(tBu)-Leu-Cys(tBu)-Val-Leu-Met-Ala-Val-Leu-Ala-Ala-Gly-Ala-Leu-Thr(tBu)-Gln-Pro-Val-Pro-Pro-Ala-Asp(tBu)-Pro-Ala-Gly-Ser(tBu)-Gly-Leu-Gln-Arg(Tos)-Ala-Glu-Glu(tBu)-Ala-Pro-Arg(Tos)-Arg(Tos)-Gln-Leu-Arg(Tos)-Val-Ser(tBu)-Gln-Arg(Tos)-Thr(tBu)-Asp(tBu)-Gly-Glu(tBu)-Ser(tBu)-Arg(Tos)-Ala-His-Leu-Gly-Ala-Leu-Leu-Ala-Arg(Tos)-Tyr(tBu)-Ile-Gln-Gln-Ala-Arg(Tos)-Lys(Fmoc)-Ala-Pro-Ser(tBu)-Gly-Arg(Tos)-Met-Ser(tBu)-Ile-Val-Lys(Fmoc)-Asn-Leu-Gln-Asn-Leu-Asp(tBu)-Pro-Ser(tBu)-His-Arg(Tos)-Ile-Ser(tBu)-Asp(tBu)-Arg(Tos)-Asp(tBu)-Tyr(tBu)-Met-Gly-Trp-Met-Asp(tBu)-Phe-Gly-Arg(Tos)-Arg(Tos)-Ser(tBu)-Ala-Glu(tBu)-Glu(tBu)-Tyr(tBu)-Glu(tBu)-Tyr(tBu)-Pro-Ser(tBu)-O(tBu)) mPEG-NH$_2$ 20 kDa, stored at −20° C. under argon, is warmed to ambient temperature. The reaction is performed at room temperature. A 5-fold molar excess of mPEG-NH$_2$, PyBOP (benzotriazol-1-yloxy)tripyrrolidinonophosphonium hexafluorophosphate), and 1-hydroxybenzotriazole (HOBt) are used, based upon absolute peptide content. The mPEG-NH$_2$, PyBOP, HOBt are weighed into a glass vial containing a magnetic stirrer bar. A solution of Prot3-Cholecystokinin is prepared in N,N-dimethylformamide is added and the mixture is stirred using a magnetic stirrer until the mPEG-NH$_2$ is fully dissolved. The stirring speed is reduced and the reaction is allowed to proceed to formation of conjugate product. The conjugate solution is then analyzed by SDS-PAGE and RP-HPLC (C18) to determine the extent of Prot3-Cholecystokinin-(Glu-O-mPEG) conjugate formation. The remaining protecting groups are removed under standard deprotection conditions to yield the Cholecystokinin-Glu(O-mPEG) conjugate.

Using this same approach, other conjugates are prepared using mPEG derivatives having other weight-average molecular weights that also bear an amino moiety.

Example 15

Bactericidal Permeability Increasing (BPI) Protein-mPEG Conjugates

Bactericidal permeability increasing protein (BPI) is a 487 residue (~50 kDa) protein which is part of the innate immune system and which displays selective cytotoxicity toward gram-negative bacteria through binding to lipopolysaccharides produced by the bacteria. BPI has the sequence, MRENMARGPC NAPRWVSLMV LVAIGTAVTA AVN-PGVVVRI SQKGLDYASQ QGTAALQKEL KRIKIP-DYSD SFKIKHLGKG HYSFYSMDIR EFQLPSSQIS MVPNVGLKFS ISNANIKISG KWKAQKRFLK MSGNFDLSIE GMSISADLKL GSNPTSGKPT ITCSSC-SSHI NSVHVHISKS KVGWLIQLFH KKIESALRNK MNSQVCEKVT NSVSSKLQPY FQTLPVMTKI DSVAGINYGL VAPPATTAET LDVQMKGEFY SENHH-NPPPF APPVMEFPAA HDRMVYLGLS DYFFNTAGLV YQEAGVLKMT LRDDMIPKES KFRLTTKFFG TFLPE-VAKKF PNMKIQIHVS ASTPPHLSVQ PTGLTFYPAV DVQAFAVLPN SSLASLFLIG MHTTGSMEVS AESN-RLVGEL KLDRLLLELK HSNIGPFPVE LLQDIMNYIV PILVLPRVNE KLQKGFPLPT PARVQLYNVV LQPHQN-FLLF GADVVYK (PubChem Protein Accession No. AAA51841; Gray et al., *J. Biol. Chem.* 1989, 264, 9505).

a) mPEG-N$^{ter}$-BPI-Via mPEG-SPC

BPI is prepared and purified according to standard recombinant techniques known to those skilled in the art. An illustrative polymeric reagent, mPEG-SPC reagent, is covalently attached to the N-terminus of BPI, to provide a N$^{ter}$-conjugate form of the peptide. mPEG-SPC 20 kDa, stored at −20° C. under argon, is warmed to ambient temperature. The reaction is performed at room temperature. About 3-5-fold molar excess of mPEG-SPC 20 kDa reagent is used based upon absolute peptide content. The mPEG-SPC reagent is weighed into a glass vial containing a magnetic stirrer bar. A solution of BPI prepared in phosphate buffered saline, PBS, pH 7.4 is added and the mixture is stirred using a magnetic stirrer until the mPEG-SPC is fully dissolved. The stirring speed is reduced and the reaction is allowed to proceed to formation of conjugate product. The reaction is optionally quenched to terminate the reaction. The pH of the conjugate solution at the end of the reaction is measured and further acidified by addition of 0.1M HCl, if necessary, to bring the pH of the final solution to about 5.5. The conjugate solution is then analyzed by SDS-PAGE and RP-HPLC (C18) to determine the extent of mPEG-N$^{ter}$-BPI conjugate formation.

Using this same approach, other conjugates are prepared using mPEG derivatives having other weight-average molecular weights that also bear an N-hydroxysuccinimide moiety.

b) BPI-C$^{ter}$-mPEG

An illustrative polymeric reagent, mPEG-NH$_2$ reagent is covalently attached to the C-terminus of BPI, to provide a C$^{ter}$-conjugate form of the peptide. mPEG-NH$_2$ 20 kDa, stored at −20° C. under argon, is warmed to ambient temperature. The reaction is performed at room temperature. About 3-5-fold molar excess of mPEG-NH$_2$, PyBOP (benzotriazol-1-yloxy)tripyrrolidinonophosphonium hexafluorophosphate), and 1-hydroxybenzotriazole (HOBt) are used, based upon absolute peptide content. The mPEG-NH$_2$, PyBOP, HOBt are weighed into a glass vial containing a magnetic stirrer bar. A solution of BPI is prepared in N,N-dimethylformamide is added and the mixture is stirred using a magnetic stirrer until the mPEG-NH$_2$ is fully dissolved. The stirring speed is reduced and the reaction is allowed to proceed to formation of conjugate product. The conjugate solution is then analyzed by SDS-PAGE and RP-HPLC (C18) to determine the extent of BPI-$C^{ter}$-mPEG conjugate formation. The $C^{ter}$ conjugate is isolated and purified according the general procedure outlined above.

Using this same approach, other conjugates are prepared using mPEG derivatives having other weight-average molecular weights that also bear an amino moiety.

c) BPI-Cys(S-mPEG)

BPI, which has a thiol-containing cysteine residue, is dissolved in buffer. To this peptide solution is added a 3-5 fold molar excess of mPEG-MAL, 5 kDa. The mixture is stirred at room temperature under an inert atmosphere for several hours. Analysis of the reaction mixture reveals successful conjugation of this peptide.

Using this same approach, other conjugates are prepared using mPEG-MAL having other weight average molecular weights.

d) mPEG-$N^{ter}$-BPI Via mPEG-SMB mPEG-SMB, 5 kDa, stored at −20° C. under argon, is warmed to ambient temperature. A five-fold excess (relative to the amount of the peptide) of the warmed mPEG-SMB is dissolved in buffer to form a 10% reagent solution. The 10% reagent solution is quickly added to the aliquot of a stock BPI solution and mixed well. After the addition of the mPEG-SMB, the pH of the reaction mixture is determined and adjusted to 6.7 to 6.8 using conventional techniques. To allow for coupling of the mPEG-SMB to the peptide via an amide linkage, the reaction solution is stirred for several hours (e.g., 5 hours) at room temperature in the dark or stirred overnight at 3-8° C. in a cold room, thereby resulting in a conjugate solution. The reaction is quenched with a 20-fold molar excess (with respect to the peptide) of Tris buffer. The $N^{ter}$ conjugate is isolated and purified according the general procedure outlined above.

Using this same approach, other conjugates are prepared using mPEG derivatives having other weight-average molecular weights that also bear an N-hydroxysuccinimide moiety.

e) BPI-Lys-mPEG

PEG-SMB, 5 kDa, stored at −20° C. under argon, is warmed to ambient temperature. A five-fold excess (relative to the amount of the peptide) of the warmed mPEG-SMB is dissolved in buffer to form a 10% reagent solution. The 10% reagent solution is quickly added to the aliquot of a stock BPI solution and mixed well. After the addition of the mPEG-SMB, the pH of the reaction mixture is determined and adjusted to 6.7 to 6.8 using conventional techniques. To allow for coupling of the mPEG-SMB to the peptide via an amide linkage, the reaction solution is stirred for several hours (e.g., 5 hours) at room temperature in the dark or stirred overnight at 3-8° C. in a cold room, thereby resulting in a conjugate solution. The reaction is quenched with a 20-fold molar excess (with respect to the peptide) of Tris buffer. The Lys conjugate is isolated and purified according the general procedure outlined above to yield the BPI-Lys-mPEG conjugate.

Using this same approach, other conjugates are prepared using mPEG derivatives having other weight-average molecular weights that also bear an N-hydroxysuccinimide moiety.

Example 16

C-Peptide-mPEG Conjugates

C-peptide is a product of the cleavage of proinsulin, consisting of the B and A chains of insulin linked together via a connecting C-peptide, produced when proinsulin is released into the blood stream in response to a rise in serum glucose. C-peptide has the sequence, Glu-Ala-Glu-Asp-Leu-Gln-Val-Gly-Gln-Val-Glu-Leu-Gly-Gly-Gly-Pro-Gly-Ala-Gly-Ser-Leu-Gln-Pro-Leu-Ala-Leu-Glu-Gly-Ser-Leu-Gln (U.S. Pat. No. 6,610,649). C-peptide alone has been proposed for the treatment of diabetes (EP 132 769); insulin in combination with C-peptide can be administered for the prevention of diabetic complications (SE 460334).

a) mPEG-$N^{ter}$-C-Peptide-Via mPEG-SPC

C-peptide is prepared and purified according to standard automated peptide synthesis or recombinant techniques known to those skilled in the art. An illustrative polymeric reagent, mPEG-SPC reagent, is covalently attached to the N-terminus of C-peptide, to provide a $N^{ter}$-conjugate form of the peptide. mPEG-SPC 20 kDa, stored at −20° C. under argon, is warmed to ambient temperature. The reaction is performed at room temperature. About 3-5-fold molar excess of mPEG-SPC 20 kDa reagent is used based upon absolute peptide content. The mPEG-SPC reagent is weighed into a glass vial containing a magnetic stirrer bar. A solution of C-peptide prepared in phosphate buffered saline, PBS, pH 7.4 is added and the mixture is stirred using a magnetic stirrer until the mPEG-SPC is fully dissolved. The stirring speed is reduced and the reaction is allowed to proceed to formation of conjugate product. The reaction is optionally quenched to terminate the reaction. The pH of the conjugate solution at the end of the reaction is measured and further acidified by addition of 0.1M HCl, if necessary, to bring the pH of the final solution to about 5.5. The conjugate solution is then analyzed by SDS-PAGE and RP-HPLC (C18) to determine the extent of mPEG-$N^{ter}$-C-peptide conjugate formation.

Using this same approach, other conjugates are prepared using mPEG derivatives having other weight-average molecular weights that also bear an N-hydroxysuccinimide moiety.

b) C-Peptide-$C^{ter}$-mPEG

An illustrative polymeric reagent, mPEG-NH$_2$ reagent is covalently attached to the C-terminus of C-peptide, to provide a $C^{ter}$-conjugate form of the peptide. For coupling to the C-terminus, a protected C-peptide (Prot-C-peptide, e.g., Fmoc-Glu(tBu)-Ala-Glu(tBu)-Asp(tBu)-Leu-Gln-Val-Gly-Gln-Val-Glu(tBu)-Leu-Gly-Gly-Gly-Pro-Gly-Ala-Gly-Ser (tBu)-Leu-Gln-Pro-Leu-Ala-Leu-Glu(tBu)-Gly- Ser(tBu)-Leu-Gln) is prepared and purified according to standard automated peptide synthesis techniques known to those skilled in the art. mPEG-NH$_2$ 20 kDa, stored at −20° C. under argon, is warmed to ambient temperature. The reaction is performed at room temperature. About 3-5-fold molar excess of mPEG-NH$_2$, PyBOP (benzotriazol-1-yloxy)tripyrrolidinonophosphonium hexafluorophosphate), and 1-hydroxybenzotriazole (HOBt) are used, based upon absolute peptide content. The mPEG-NH$_2$, PyBOP, HOBt are weighed into a glass vial containing a magnetic stirrer bar. A solution of Prot-C-peptide is prepared in N,N-dimethylformamide is added and the mixture is stirred using a magnetic stirrer until the mPEG-NH$_2$ is fully dissolved. The stirring speed is reduced and the reaction is allowed to proceed to formation of conjugate product. The conjugate solution is then analyzed by SDS-PAGE and RP-HPLC (C18) to determine the extent of Prot-C-peptide-$C^{ter}$-mPEG conjugate formation. The remaining protecting groups are removed under standard deprotection conditions to yield the C-peptide-$C^{ter}$-mPEG conjugate.

Using this same approach, other conjugates are prepared using mPEG derivatives having other weight-average molecular weights that also bear an amino moiety.

c) mPEG-N$^{ter}$-C-Peptide Via mPEG-SMB mPEG-SMB, 5 kDa, stored at −20° C. under argon, is warmed to ambient temperature. A five-fold excess (relative to the amount of the peptide) of the warmed mPEG-SMB is dissolved in buffer to form a 10% reagent solution. The 10% reagent solution is quickly added to the aliquot of a stock C-peptide solution and mixed well. After the addition of the mPEG-SMB, the pH of the reaction mixture is determined and adjusted to 6.7 to 6.8 using conventional techniques. To allow for coupling of the mPEG-SMB to the peptide via an amide linkage, the reaction solution is stirred for several hours (e.g., 5 hours) at room temperature in the dark or stirred overnight at 3-8° C. in a cold room, thereby resulting in a conjugate solution. The reaction is quenched with a 20-fold molar excess (with respect to the peptide) of Tris buffer.

Using this same approach, other conjugates are prepared using mPEG derivatives having other weight-average molecular weights that also bear an N-hydroxysuccinimide moiety.

d) C-Peptide-Glu(O-mPEG)

An illustrative polymeric reagent, mPEG-NH$_2$ reagent is covalently attached to the Glu residue of C-peptide, to provide a Glu-conjugate form of the peptide. For coupling to the Glu residue, a protected C-peptide (Prot2 C-peptide, e.g., Fmoc-Glu(tBu)-Ala-Glu(tBu)-Asp(tBu)-Leu-Gln-Val-Gly-Gln-Val-Glu(OBz)-Leu-Gly-Gly-Gly-Pro-Gly-Ala-Gly-Ser(tBu)-Leu-Gln-Pro-Leu-Ala-Leu- Glu(tBu)-Gly-Ser(tBu)-Leu-Gln)-O(tBu)) is prepared and purified according to standard automated peptide synthesis techniques known to those skilled in the art. Deprotection of the Glu(OBz) residue (H$_2$/Pd) yields the free-Glu carboxylate for subsequent coupling (Prot3-C-peptide, e.g., Fmoc-Glu(tBu)-Ala-Glu(tBu)-Asp(tBu)-Leu-Gln-Val-Gly-Gln-Val-Glu-Leu-Gly-Gly-Gly-Pro-Gly-Ala-Gly-Ser(tBu)-Leu-Gln-Pro-Leu-Ala-Leu-Glu(tBu)-Gly-Ser(tBu)-Leu-Gln)- O(tBu)) mPEG-NH$_2$ 20 kDa, stored at −20° C. under argon, is warmed to ambient temperature. The reaction is performed at room temperature. A 5-fold molar excess of mPEG-NH$_2$, PyBOP (benzotriazol-1-yloxy)tripyrrolidinonophosphonium hexafluorophosphate), and 1-hydroxybenzotriazole (HOBt) are used, based upon absolute peptide content. The mPEG-NH$_2$, PyBOP, HOBt are weighed into a glass vial containing a magnetic stirrer bar. A solution of Prot3-C-peptide is prepared in N,N-dimethylformamide is added and the mixture is stirred using a magnetic stirrer until the mPEG-NH$_2$ is fully dissolved. The stirring speed is reduced and the reaction is allowed to proceed to formation of conjugate product. The conjugate solution is then analyzed by SDS-PAGE and RP-HPLC (C18) to determine the extent of Prot3-C-peptide-(Glu-O-mPEG) conjugate formation. The remaining protecting groups are removed under standard deprotection conditions to yield the C-peptide-Glu(O-mPEG) conjugate.

Using this same approach, other conjugates are prepared using mPEG derivatives having other weight-average molecular weights that also bear an amino moiety.

Example 17

Prosaptide™ TX14(A)-mPEG Conjugates

Prosaptide TX14(A) is a 14-mer amino acid sequence derived from the active neurotrophic region in the amino-terminal portion of the saposin C domain. Prosaptides are active on a variety of neuronal cells, stimulating sulfatide synthesis and increasing sulfatide concentration in Schwann cells and oligodendrocytes. This indicates that prosaposin and prosaptides are trophic factors for myelin formation. Prosaptide TX14(A) may have potential for therapeutic use in neuropathic pain syndromes in humans (Otero et al. *Neurosci. Lett.* 1999, 270, 29). Prosaptide TX14(A) is commercially available from AnaSpec (San Jose, Calif.) with the sequence, Thr-(D-Ala)-Leu-Ile-Asp-Asn-Asn-Ala-Thr-Glu-Glu-Ile-Leu-Tyr.

a) mPEG-N$^{ter}$-Prosaptide TX14(A)-Via mPEG-SPC

An illustrative polymeric reagent, mPEG-SPC reagent, is covalently attached to the N-terminus of Prosaptide TX14 (A), to provide a N$^{ter}$-conjugate form of the peptide. mPEG-SPC 20 kDa, stored at −20° C. under argon, is warmed to ambient temperature. The reaction is performed at room temperature. About 3-5-fold molar excess of mPEG-SPC 20 kDa reagent is used based upon absolute peptide content. The mPEG-SPC reagent is weighed into a glass vial containing a magnetic stirrer bar. A solution of Prosaptide TX14(A) prepared in phosphate buffered saline, PBS, pH 7.4 is added and the mixture is stirred using a magnetic stirrer until the mPEG-SPC is fully dissolved. The stirring speed is reduced and the reaction is allowed to proceed to formation of conjugate product. The reaction is optionally quenched to terminate the reaction. The pH of the conjugate solution at the end of the reaction is measured and further acidified by addition of 0.1M HCl, if necessary, to bring the pH of the final solution to about 5.5. The conjugate solution is then analyzed by SDS-PAGE and RP-HPLC (C18) to determine the extent of mPEG-N$^{ter}$-Prosaptide TX14(A) conjugate formation.

Using this same approach, other conjugates are prepared using mPEG derivatives having other weight-average molecular weights that also bear an N-hydroxysuccinimide moiety.

b) Prosaptide TX14(A)-C$^{ter}$-mPEG

An illustrative polymeric reagent, mPEG-NH$_2$ reagent is covalently attached to the C-terminus of Prosaptide TX14 (A), to provide a C$^{ter}$-conjugate form of the peptide. For coupling to the C-terminus, a protected Prosaptide TX14(A) (Prot-Prosaptide TX14(A), e.g., Fmoc-Thr(tBu)-(D-Ala)-Leu-Ile-Asp(tBu)-Asn-Asn-Ala-Thr(tBu)-Glu(tBu)-Glu(tBu)-Ile-Leu-Tyr(tBu) is prepared and purified according to standard automated peptide synthesis techniques known to those skilled in the art. mPEG-NH$_2$ 20 kDa, stored at −20° C. under argon, is warmed to ambient temperature. The reaction is performed at room temperature. About 3-5-fold molar excess of mPEG-NH$_2$, PyBOP (benzotriazol-1-yloxy) tripyrrolidinonophosphonium hexafluorophosphate), and 1-hydroxybenzotriazole (HOBt) are used, based upon absolute peptide content. The mPEG-NH$_2$, PyBOP, HOBt are weighed into a glass vial containing a magnetic stirrer bar. A solution of Prot-Prosaptide TX14(A) is prepared in N,N-dimethylformamide is added and the mixture is stirred using a magnetic stirrer until the mPEG-NH$_2$ is fully dissolved. The stirring speed is reduced and the reaction is allowed to proceed to formation of conjugate product. The conjugate solution is then analyzed by SDS-PAGE and RP-HPLC (C18) to determine the extent of Prot-Prosaptide TX14(A)-C$^{ter}$-mPEG conjugate formation. The remaining protecting groups are removed under standard deprotection conditions to yield the Prosaptide TX14(A)-C$^{ter}$-mPEG conjugate.

Using this same approach, other conjugates are prepared using mPEG derivatives having other weight-average molecular weights that also bear an amino moiety.

c) mPEG-N$^{ter}$-Prosaptide TX14(A) Via mPEG-SMB mPEG-SMB, 5 kDa, stored at −20° C. under argon, is warmed to ambient temperature. A five-fold excess (relative to the amount of the peptide) of the warmed mPEG-SMB is dissolved in buffer to form a 10% reagent solution. The 10% reagent solution is quickly added to the aliquot of a stock Prosaptide TX14(A) solution and mixed well. After the addition of the mPEG-SMB, the pH of the reaction mixture is determined and adjusted to 6.7 to 6.8 using conventional techniques. To allow for coupling of the mPEG-SMB to the peptide via an amide linkage, the reaction solution is stirred for several hours (e.g., 5 hours) at room temperature in the dark or stirred overnight at 3-8° C. in a cold room, thereby resulting in a conjugate solution. The reaction is quenched with a 20-fold molar excess (with respect to the peptide) of Tris buffer.

Using this same approach, other conjugates are prepared using mPEG derivatives having other weight-average molecular weights that also bear an N-hydroxysuccinimide moiety.

d) Prosaptide TX14(A)-Glu(O-mPEG)

An illustrative polymeric reagent, mPEG-NH$_2$ reagent is covalently attached to the Glu residue of Prosaptide TX14 (A), to provide a Glu-conjugate form of the peptide. For coupling to the Glu residue, a protected Prosaptide TX14(A) (Prot2-Prosaptide TX14(A), e.g., Fmoc-Thr(tBu)-(D-Ala)-Leu-Ile-Asp(tBu)-Asn-Asn-Ala-Thr(tBu)-Glu(OBz)-Glu(tBu)-Ile-Leu-Tyr(tBu)-O(tBu)) is prepared and purified according to standard automated peptide synthesis techniques known to those skilled in the art. Deprotection of the Glu(OBz) residue (H$_2$/Pd) yields the free-Glu carboxylate for subsequent coupling (Prot3-Prosaptide TX14(A), e.g., Fmoc-Thr(tBu)-(D-Ala)-Leu-Ile-Asp(tBu)-Asn-Asn-Ala-Thr(tBu)-Glu-Glu(tBu)-Ile-Leu-Tyr(tBu)-O(tBu)) mPEG-NH$_2$ 20 kDa, stored at −20° C. under argon, is warmed to ambient temperature. The reaction is performed at room temperature. A 5-fold molar excess of mPEG-NH$_2$, PyBOP (benzotriazol-1-yloxy)tripyrrolidinonophosphonium hexafluorophosphate), and 1-hydroxybenzotriazole (HOBt) are used, based upon absolute peptide content. The mPEG-NH$_2$, PyBOP, HOBt are weighed into a glass vial containing a magnetic stirrer bar. A solution of Prot3-Prosaptide TX14 (A) is prepared in N,N-dimethylformamide is added and the mixture is stirred using a magnetic stirrer until the mPEG-NH$_2$ is fully dissolved. The stirring speed is reduced and the reaction is allowed to proceed to formation of conjugate product. The conjugate solution is then analyzed by SDS-PAGE and RP-HPLC (C18) to determine the extent of Prot3-Prosaptide TX14(A-(Glu-O-mPEG) conjugate formation. The remaining protecting groups are removed under standard deprotection conditions to yield the Prosaptide TX14(A)-Glu(O-mPEG) conjugate.

Using this same approach, other conjugates are prepared using mPEG derivatives having other weight-average molecular weights that also bear an amino moiety.

Example 18

Sermorelin Acetate (GHRFA Group)-mPEG Conjugates

Sermorelin is the biologically active fragment of human growth hormone-releasing factor, consisting of GHRH (1-29)-amide, which can be used as a provocative test of growth hormone deficiency (Prakash and Goa, *Biodrugs* 1999, 12, 139). Sermoline may also increase IGF-1 levels and improve body composition (increased lean mass and reduced truncal and visceral fat) in patients with HIV (Koutkia et al, *JAMA* 2004, 292, 210). Synthetic sermorelin acetate is commercially available from Gelacs Innovation (Hangzhou, China) with the sequence, Tyr-Ala-Asp-Ala-Ile-Phe-Thr-Asn-Ser-Tyr-Arg-Lys-Val-Leu-Gly-Gln-Leu-Ser-Ala-Arg-Lys-Leu-Leu-Gln-Asp-Ile-Met-Ser-Arg-NH$_2$ a) mPEG-N$^{ter}$-Sermorelin-Via mPEG-SPC An illustrative polymeric reagent, mPEG-SPC reagent, is covalently attached to the N-terminus of Sermorelin, to provide a N$^{ter}$-conjugate form of the peptide. mPEG-SPC 20 kDa, stored at −20° C. under argon, is warmed to ambient temperature. The reaction is performed at room temperature. About 3-5-fold molar excess of mPEG-SPC 20 kDa reagent is used based upon absolute peptide content. The mPEG-SPC reagent is weighed into a glass vial containing a magnetic stirrer bar. A solution of Sermorelin prepared in phosphate buffered saline, PBS, pH 7.4 is added and the mixture is stirred using a magnetic stirrer until the mPEG-SPC is fully dissolved. The stirring speed is reduced and the reaction is allowed to proceed to formation of conjugate product. The reaction is optionally quenched to terminate the reaction. The pH of the conjugate solution at the end of the reaction is measured and further acidified by addition of 0.1M HCl, if necessary, to bring the pH of the final solution to about 5.5. The conjugate solution is then analyzed by SDS-PAGE and RP-HPLC (C18) to determine the extent of mPEG-N$^{ter}$-Sermorelin conjugate formation.

Using this same approach, other conjugates are prepared using mPEG derivatives having other weight-average molecular weights that also bear an N-hydroxysuccinimide moiety.

b) Sermorelin-C$^{ter}$-mPEG

An illustrative polymeric reagent, mPEG-NH$_2$ reagent is covalently attached to the C-terminus of Sermorelin, to provide a C$^{ter}$-conjugate form of the peptide. For coupling to the C-terminus, a protected Sermorelin lacking the C-terminus amide (Prot-Sermorelin, e.g., Fmoc-Tyr-Ala-Asp(tBu)-Ala-Ile-Phe-Thr-Asn-Ser(tBu)-Tyr(tBu)-Arg(Tos)-Lys-Val-Leu-Gly-Gln-Leu-Ser(tBu)-Ala-Arg(Tos)-Lys(Fmoc)-Leu-Leu-Gln-Asp(tBu)-Ile-Met-Ser(tBu)-Arg(Tos)-OH) is prepared and purified according to standard automated peptide synthesis techniques known to those skilled in the art. mPEG-NH$_2$ 20 kDa, stored at −20° C. under argon, is warmed to ambient temperature. The reaction is performed at room temperature. About 3-5-fold molar excess of mPEG-NH$_2$, PyBOP (benzotriazol-1-yloxy)tripyrrolidinonophosphonium hexafluorophosphate), and 1-hydroxybenzotriazole (HOBt) are used, based upon absolute peptide content. The mPEG-NH$_2$, PyBOP, HOBt are weighed into a glass vial containing a magnetic stirrer bar. A solution of Prot-Sermorelin is prepared in N,N-dimethylformamide is added and the mixture is stirred using a magnetic stirrer until the mPEG-NH$_2$ is fully dissolved. The stirring speed is reduced and the reaction is allowed to proceed to formation of conjugate product. The conjugate solution is then analyzed by SDS-PAGE and RP-HPLC (C18) to determine the extent of Prot-Sermorelin-C$^{ter}$-mPEG conjugate formation. The remaining protecting groups are removed under standard deprotection conditions to yield the Sermorelin-C$^{ter}$-mPEG conjugate.

Using this same approach, other conjugates are prepared using mPEG derivatives having other weight-average molecular weights that also bear an amino moiety.

c) mPEG-N$^{ter}$-Sermorelin Via mPEG-SMB mPEG-SMB, 5 kDa, stored at −20° C. under argon, is warmed to ambient temperature. A five-fold excess (relative to the amount of the peptide) of the warmed mPEG-SMB is dissolved in buffer to form a 10% reagent solution. The 10% reagent solution is quickly added to the aliquot of a stock Sermorelin solution and mixed well. After the addition of the mPEG-SMB, the pH of the reaction mixture is determined and adjusted to 6.7 to 6.8 using conventional techniques. To allow for coupling of the mPEG-SMB to the peptide via an amide linkage, the reaction solution is stirred for several hours (e.g., 5 hours) at room temperature in the dark or stirred overnight at 3-8° C. in a cold room, thereby resulting in a conjugate solution. The reaction is quenched with a 20-fold molar excess (with respect to the peptide) of Tris buffer.

Using this same approach, other conjugates are prepared using mPEG derivatives having other weight-average molecular weights that also bear an N-hydroxysuccinimide moiety.

d) Sermorelin-Lys-mPEG

PEG-SMB, 5 kDa, stored at −20° C. under argon, is warmed to ambient temperature. A five-fold excess (relative to the amount of the peptide) of the warmed mPEG-SMB is dissolved in buffer to form a 10% reagent solution. The 10% reagent solution is quickly added to the aliquot of a stock protected Sermorelin (e.g., Fmoc-Tyr-Ala-Asp(tBu)-Ala-Ile-Phe-Thr-Asn-Ser(tBu)-Tyr(tBu)-Arg(Tos)-Lys-Val-Leu-Gly-Gln-Leu-Ser(tBu)-Ala-Arg(Tos)-Lys-Leu-Leu-Gln-Asp(tBu)-Ile-Met-Ser(tBu)-Arg(Tos)-NH$_2$) solution and mixed well. After the addition of the mPEG-SMB, the pH of the reaction mixture is determined and adjusted to 6.7 to 6.8 using conventional techniques. To allow for coupling of the mPEG-SMB to the peptide via an amide linkage, the reaction solution is stirred for several hours (e.g., 5 hours) at room temperature in the dark or stirred overnight at 3-8° C. in a cold room, thereby resulting in a conjugate solution. The reaction is quenched with a 20-fold molar excess (with respect to the peptide) of Tris buffer. The remaining protecting groups are removed under standard deprotection conditions to yield the Sermorelin-Lys(O-mPEG) conjugate.

Using this same approach, other conjugates are prepared using mPEG derivatives having other weight-average molecular weights that also bear an N-hydroxysuccinimide moiety.

Example 19

Pralmorelin-mPEG Conjugates

Pralmorelin (GHRP-2) is a growth-hormone releasing peptide having the composition, D-Ala-([3-(naphthalen-2-yl)]-D-Ala)-Ala-Trp-(D-Phe)-Lys-NH$_2$. Pralmorelin has been proposed for the diagnosis of serious growth hormone deficiency and for treatment of short stature (Furata et al. *Arz.-Forsch.* 2004, 54, 868), and for treating acute heart failure, chronic heart failure at a phase of acute exacerbation, and heart failure at a phase of transition to chronic heart failure (U.S. Pat. No. 6,878,689).

a) mPEG-N$^{ter}$-Pralmorelin-Via mPEG-SPC

Pralmorelin is prepared and purified according to standard automated peptide synthesis or recombinant techniques known to those skilled in the art. An illustrative polymeric reagent, mPEG-SPC reagent, is covalently attached to the N-terminus of Pralmorelin, to provide a N$^{ter}$-conjugate form of the peptide. mPEG-SPC 20 kDa, stored at −20° C. under argon, is warmed to ambient temperature. The reaction is performed at room temperature. About 3-5-fold molar excess of mPEG-SPC 20 kDa reagent is used based upon absolute peptide content. The mPEG-SPC reagent is weighed into a glass vial containing a magnetic stirrer bar. A solution of Pralmorelin prepared in phosphate buffered saline, PBS, pH 7.4 is added and the mixture is stirred using a magnetic stirrer until the mPEG-SPC is fully dissolved. The stirring speed is reduced and the reaction is allowed to proceed to formation of conjugate product. The reaction is optionally quenched to terminate the reaction. The pH of the conjugate solution at the end of the reaction is measured and further acidified by addition of 0.1M HCl, if necessary, to bring the pH of the final solution to about 5.5. The conjugate solution is then analyzed by SDS-PAGE and RP-HPLC (C18) to determine the extent of mPEG-N$^{ter}$-Pralmorelin conjugate formation.

Using this same approach, other conjugates are prepared using mPEG derivatives having other weight-average molecular weights that also bear an N-hydroxysuccinimide moiety.

b) Pralmorelin-C$^{ter}$-mPEG

An illustrative polymeric reagent, mPEG-NH$_2$ reagent is covalently attached to the C-terminus of Pralmorelin, to provide a C$^{ter}$-conjugate form of the peptide. For coupling to the C-terminus, a protected Pralmorelin lacking the C-terminus amide (Prot-Pralmorelin, e.g., Fmoc-D-Ala-([3-(naphthalen-2-yl)]-D-Ala)-Ala-Trp-(D-Phe)-Lys(Fmoc)-OH) is prepared and purified according to standard automated peptide synthesis techniques known to those skilled in the art. mPEG-NH$_2$ 20 kDa, stored at −20° C. under argon, is warmed to ambient temperature. The reaction is performed at room temperature. About 3-5-fold molar excess of mPEG-NH$_2$, PyBOP (benzotriazol-1-yloxy)tripyrrolidinonophosphonium hexafluorophosphate), and 1-hydroxybenzotriazole (HOBt) are used, based upon absolute peptide content. The mPEG-NH$_2$, PyBOP, HOBt are weighed into a glass vial containing a magnetic stirrer bar. A solution of Prot-Pralmorelin is prepared in N,N-dimethylformamide is added and the mixture is stirred using a magnetic stirrer until the mPEG-NH$_2$ is fully dissolved. The stirring speed is reduced and the reaction is allowed to proceed to formation of conjugate product. The conjugate solution is then analyzed by SDS-PAGE and RP-HPLC (C18) to determine the extent of Prot-Pralmorelin-C$^{ter}$-mPEG conjugate formation. The remaining protecting groups are removed under standard deprotection conditions to yield the Pralmorelin-C$^{ter}$-mPEG conjugate.

Using this same approach, other conjugates are prepared using mPEG derivatives having other weight-average molecular weights that also bear an amino moiety.

c) mPEG-N$^{ter}$-Pralmorelin Via mPEG-SMB mPEG-SMB, 5 kDa, stored at −20° C. under argon, is warmed to ambient temperature. A five-fold excess (relative to the amount of the peptide) of the warmed mPEG-SMB is dissolved in buffer to form a 10% reagent solution. The 10% reagent solution is quickly added to the aliquot of a stock Pralmorelin solution and mixed well. After the addition of the mPEG-SMB, the pH of the reaction mixture is determined and adjusted to 6.7 to 6.8 using conventional techniques. To allow for coupling of the mPEG-SMB to the peptide via an amide linkage, the reaction solution is stirred for several hours (e.g., 5 hours) at room temperature in the dark or stirred overnight at 3-8° C. in a cold room, thereby resulting in a conjugate solution. The reaction is quenched with a 20-fold molar excess (with respect to the peptide) of Tris buffer.

Using this same approach, other conjugates are prepared using mPEG derivatives having other weight-average molecular weights that also bear an N-hydroxysuccinimide moiety.

d) Pralmorelin-Lys-mPEG

PEG-SMB, 5 kDa, stored at −20° C. under argon, is warmed to ambient temperature. A five-fold excess (relative to the amount of the peptide) of the warmed mPEG-SMB is dissolved in buffer to form a 10% reagent solution. The 10% reagent solution is quickly added to the aliquot of a stock protected Pralmorelin (e.g., Fmoc-D-Ala-([3-(naphthalen-2-yl)]-D-Ala)-Ala-Trp-(D-Phe)-Lys-NH$_2$) solution and mixed well. After the addition of the mPEG-SMB, the pH of the reaction mixture is determined and adjusted to 6.7 to 6.8 using conventional techniques. To allow for coupling of the mPEG-SMB to the peptide via an amide linkage, the reaction solution is stirred for several hours (e.g., 5 hours) at room temperature in the dark or stirred overnight at 3-8° C. in a cold room, thereby resulting in a conjugate solution. The reaction is quenched with a 20-fold molar excess (with respect to the peptide) of Tris buffer. The remaining protecting groups are removed under standard deprotection conditions to yield the Pralmorelin-Lys(O-mPEG) conjugate.

Using this same approach, other conjugates are prepared using mPEG derivatives having other weight-average molecular weights that also bear an N-hydroxysuccinimide moiety.

Example 20

Growth Hormone Releasing Factor (GHRFA Group)-mPEG Conjugates

Growth hormone-releasing factor (GHRF) is a hypothalamic peptide which positively regulates the synthesis and secretion of growth hormone in the anterior pituitary. Growth hormone releasing factor is commercially available from GenScript Corporation (Piscataway, N.J.; Cat. No. RP10734) with the sequence, Tyr-Ala-Asp-Ala-Ile-Phe-Thr-Asn-Ser-Tyr-Arg-Lys-Val-Leu-Gly-Gln-Leu-Ser-Ala-Arg-Lys-Leu-Leu-Gln-Asp-Ile-Met-Ser-Arg-Gln-Gln-Gly-Glu-Ser-Asn- Gln-Glu-Arg-Gly-Ala-Arg-Ala-Arg-Leu-NH$_2$ (YADAIFTNSY RKVLGQLSAR KLLQDIMSRQ QGESNQERGA RARL-NH$_2$)

a) mPEG-N$^{ter}$-GHRF-Via mPEG-SPC

An illustrative polymeric reagent, mPEG-SPC reagent, is covalently attached to the N-terminus of GHRF, to provide a N$^{ter}$-conjugate form of the peptide. mPEG-SPC 20 kDa, stored at −20° C. under argon, is warmed to ambient temperature. The reaction is performed at room temperature. About 3-5-fold molar excess of mPEG-SPC 20 kDa reagent is used based upon absolute peptide content. The mPEG-SPC reagent is weighed into a glass vial containing a magnetic stirrer bar. A solution of GHRF prepared in phosphate buffered saline, PBS, pH 7.4 is added and the mixture is stirred using a magnetic stirrer until the mPEG-SPC is fully dissolved. The stirring speed is reduced and the reaction is allowed to proceed to formation of conjugate product. The reaction is optionally quenched to terminate the reaction. The pH of the conjugate solution at the end of the reaction is measured and further acidified by addition of 0.1M HCl, if necessary, to bring the pH of the final solution to about 5.5. The conjugate solution is then analyzed by SDS-PAGE and RP-HPLC (C18) to determine the extent of mPEG-N$^{ter}$-GHRF conjugate formation.

Using this same approach, other conjugates are prepared using mPEG derivatives having other weight-average molecular weights that also bear an N-hydroxysuccinimide moiety.

b) GHRF-C$^{ter}$-mPEG

An illustrative polymeric reagent, mPEG-NH$_2$ reagent is covalently attached to the C-terminus of GHRF, to provide a C$^{ter}$-conjugate form of the peptide. For coupling to the C-terminus, a protected GHRF lacking the C-terminus amide (Prot-GHRF, e.g., Fmoc-Tyr(tBu)-Ala-Asp(tBu)-Ala-Ile-Phe-Thr(tBu)-Asn-Ser(tBu)-Tyr(tBu)-Arg(Tos)-Lys (Fmoc)-Val-Leu-Gly-Gln-Leu-Ser(tBu)-Ala-Arg(Tos)-Lys (Fmoc)- Leu-Leu-Gln-Asp(tBu)-Ile-Met-Ser(tBu)-Arg (Tos)-Gln-Gln-Gly-Glu(tBu)-Ser(tBu)-Asn-Gln-Glu(tBu)-Arg(Tos)-Gly-Ala-Arg(Tos)-Ala-Arg(Tos)-Leu-OH) is prepared and purified according to standard automated peptide synthesis techniques known to those skilled in the art. mPEG-NH$_2$ 20 kDa, stored at −20° C. under argon, is warmed to ambient temperature. The reaction is performed at room temperature. About 3-5-fold molar excess of mPEG-NH$_2$, PyBOP (benzotriazol-1-yloxy)tripyrrolidinonophosphonium hexafluorophosphate), and 1-hydroxybenzotriazole (HOBt) are used, based upon absolute peptide content. The mPEG-NH$_2$, PyBOP, HOBt are weighed into a glass vial containing a magnetic stirrer bar. A solution of Prot-GHRF is prepared in N,N-dimethylformamide is added and the mixture is stirred using a magnetic stirrer until the mPEG-NH$_2$ is fully dissolved. The stirring speed is reduced and the reaction is allowed to proceed to formation of conjugate product. The conjugate solution is then analyzed by SDS-PAGE and RP-HPLC (C18) to determine the extent of Prot-GHRF-C$^{ter}$-mPEG conjugate formation. The remaining protecting groups are removed under standard deprotection conditions to yield the GHRF-C$^{ter}$-mPEG conjugate.

Using this same approach, other conjugates are prepared using mPEG derivatives having other weight-average molecular weights that also bear an amino moiety.

c) mPEG-N$^{ter}$-GHRF Via mPEG-SMB

PEG-SMB, 5 kDa, stored at −20° C. under argon, is warmed to ambient temperature. A five-fold excess (relative to the amount of the peptide) of the warmed mPEG-SMB is dissolved in buffer to form a 10% reagent solution. The 10% reagent solution is quickly added to the aliquot of a stock GHRF solution and mixed well. After the addition of the mPEG-SMB, the pH of the reaction mixture is determined and adjusted to 6.7 to 6.8 using conventional techniques. To allow for coupling of the mPEG-SMB to the peptide via an amide linkage, the reaction solution is stirred for several hours (e.g., 5 hours) at room temperature in the dark or stirred overnight at 3-8° C. in a cold room, thereby resulting in a conjugate solution. The reaction is quenched with a 20-fold molar excess (with respect to the peptide) of Tris buffer.

Using this same approach, other conjugates are prepared using mPEG derivatives having other weight-average molecular weights that also bear an N-hydroxysuccinimide moiety.

d) GHRF-Lys-mPEG

PEG-SMB, 5 kDa, stored at −20° C. under argon, is warmed to ambient temperature. A five-fold excess (relative to the amount of the peptide) of the warmed mPEG-SMB is dissolved in buffer to form a 10% reagent solution. The 10% reagent solution is quickly added to the aliquot of a stock protected GHRF (e.g., Fmoc-Tyr(tBu)-Ala-Asp(tBu)-Ala-Ile-Phe-Thr(tBu)-Asn-Ser(tBu)-Tyr(tBu)-Arg(Tos)-Lys (Fmoc)-Val-Leu-Gly-Gln-Leu-Ser(tBu)-Ala-Arg(Tos)-Lys-Leu-Leu- Gln-Asp(tBu)-Ile-Met-Ser(tBu)-Arg(Tos)-Gln-Gln-Gly-Glu(tBu)-Ser(tBu)-Asn-Gln-Glu(tBu)-Arg(Tos)-Gly-Ala-Arg(Tos)-Ala-Arg(Tos)-Leu-NH$_2$) solution and mixed well. After the addition of the mPEG-SMB, the pH of the reaction mixture is determined and adjusted to 6.7 to 6.8 using conventional techniques. To allow for coupling of the mPEG-SMB to the peptide via an amide linkage, the reaction solution is stirred for several hours (e.g., 5 hours) at room temperature in the dark or stirred overnight at 3-8° C. in a cold room, thereby resulting in a conjugate solution. The reaction is quenched with a 20-fold molar excess (with respect to the peptide) of Tris buffer. The remaining protecting groups are removed under standard deprotection conditions to yield the GHRF-Lys(O-mPEG) conjugate.

Using this same approach, other conjugates are prepared using mPEG derivatives having other weight-average molecular weights that also bear an N-hydroxysuccinimide moiety.

Example 21

Examorelin (GHRFA Group)-mPEG Conjugates

Examorelin is a synthetic growth hormone releasing peptide; which has been found to reverse the worsening of cardiac dysfunction in growth hormone deficient rats (Colonna et al., *Eur. J. Pharmacol.* 1997, 334, 201), and has been suggested for the normalization of cardiac pressure and treating heart disease in humans (U.S. Pat. No. 5,932,548). The sequence of Examorelin is His-(D-2-methyl-Trp)-Ala-Trp-(D-Phe)-Lys-$NH_2$.

a) mPEG-$N^{ter}$-Examorelin-Via mPEG-SPC

Examorelin is prepared and purified according to standard automated peptide synthesis or recombinant techniques known to those skilled in the art. An illustrative polymeric reagent, mPEG-SPC reagent, is covalently attached to the N-terminus of Examorelin, to provide a $N^{ter}$-conjugate form of the peptide. mPEG-SPC 20 kDa, stored at −20° C. under argon, is warmed to ambient temperature. The reaction is performed at room temperature. About 3-5-fold molar excess of mPEG-SPC 20 kDa reagent is used based upon absolute peptide content. The mPEG-SPC reagent is weighed into a glass vial containing a magnetic stirrer bar. A solution of Examorelin prepared in phosphate buffered saline, PBS, pH 7.4 is added and the mixture is stirred using a magnetic stirrer until the mPEG-SPC is fully dissolved. The stirring speed is reduced and the reaction is allowed to proceed to formation of conjugate product. The reaction is optionally quenched to terminate the reaction. The pH of the conjugate solution at the end of the reaction is measured and further acidified by addition of 0.1M HCl, if necessary, to bring the pH of the final solution to about 5.5. The conjugate solution is then analyzed by SDS-PAGE and RP-HPLC (C18) to determine the extent of mPEG-$N^{ter}$-Examorelin conjugate formation.

Using this same approach, other conjugates are prepared using mPEG derivatives having other weight-average molecular weights that also bear an N-hydroxysuccinimide moiety.

b) Examorelin-$C^{ter}$-mPEG

An illustrative polymeric reagent, mPEG-$NH_2$ reagent is covalently attached to the C-terminus of Examorelin, to provide a $C^{ter}$-conjugate form of the peptide. For coupling to the C-terminus, a protected Examorelin lacking the C-terminus amide (Prot-Examorelin, e.g., Fmoc-His-(D-2-methyl-Trp)-Ala-Trp-(D-Phe)-Lys(Fmoc)-OH) is prepared and purified according to standard automated peptide synthesis techniques known to those skilled in the art. mPEG-$NH_2$ 20 kDa, stored at −20° C. under argon, is warmed to ambient temperature. The reaction is performed at room temperature. About 3-5-fold molar excess of mPEG-$NH_2$, PyBOP (benzotriazol-1-yloxy)tripyrrolidinonophosphonium hexafluorophosphate), and 1-hydroxybenzotriazole (HOBt) are used, based upon absolute peptide content. The mPEG-$NH_2$, PyBOP, HOBt are weighed into a glass vial containing a magnetic stirrer bar. A solution of Prot-Examorelin is prepared in N,N-dimethylformamide is added and the mixture is stirred using a magnetic stirrer until the mPEG-$NH_2$ is fully dissolved. The stirring speed is reduced and the reaction is allowed to proceed to formation of conjugate product. The conjugate solution is then analyzed by SDS-PAGE and RP-HPLC (C18) to determine the extent of Prot-Examorelin-$C^{ter}$-mPEG conjugate formation. The remaining protecting groups are removed under standard deprotection conditions to yield the Examorelin-$C^{ter}$-mPEG conjugate.

Using this same approach, other conjugates are prepared using mPEG derivatives having other weight-average molecular weights that also bear an amino moiety.

c) mPEG-$N^{ter}$-Examorelin Via mPEG-SMB mPEG-SMB, 5 kDa, stored at −20° C. under argon, is warmed to ambient temperature. A five-fold excess (relative to the amount of the peptide) of the warmed mPEG-SMB is dissolved in buffer to form a 10% reagent solution. The 10% reagent solution is quickly added to the aliquot of a stock Examorelin solution and mixed well. After the addition of the mPEG-SMB, the pH of the reaction mixture is determined and adjusted to 6.7 to 6.8 using conventional techniques. To allow for coupling of the mPEG-SMB to the peptide via an amide linkage, the reaction solution is stirred for several hours (e.g., 5 hours) at room temperature in the dark or stirred overnight at 3-8° C. in a cold room, thereby resulting in a conjugate solution. The reaction is quenched with a 20-fold molar excess (with respect to the peptide) of Tris buffer.

Using this same approach, other conjugates are prepared using mPEG derivatives having other weight-average molecular weights that also bear an N-hydroxysuccinimide moiety.

d) Examorelin-Lys-mPEG

PEG-SMB, 5 kDa, stored at −20° C. under argon, is warmed to ambient temperature. A five-fold excess (relative to the amount of the peptide) of the warmed mPEG-SMB is dissolved in buffer to form a 10% reagent solution. The 10% reagent solution is quickly added to the aliquot of a stock protected Examorelin (e.g., Fmoc-His-(D-2-methyl-Trp)-Ala-Trp-(D-Phe)-Lys-$NH_2$) solution and mixed well. After the addition of the mPEG-SMB, the pH of the reaction mixture is determined and adjusted to 6.7 to 6.8 using conventional techniques. To allow for coupling of the mPEG-SMB to the peptide via an amide linkage, the reaction solution is stirred for several hours (e.g., 5 hours) at room temperature in the dark or stirred overnight at 3-8° C. in a cold room, thereby resulting in a conjugate solution. The reaction is quenched with a 20-fold molar excess (with respect to the peptide) of Tris buffer. The remaining protecting groups are removed under standard deprotection conditions to yield the Examorelin-Lys(O-mPEG) conjugate.

Using this same approach, other conjugates are prepared using mPEG derivatives having other weight-average molecular weights that also bear an N-hydroxysuccinimide moiety.

Example 22

Gonadorelin (LH-Relatedpeptide Group)-mPEG Conjugates

Gonadorelin (GnRH) is a decapeptide that stimulates the synthesis and secretion of both pituitary gonadotropins, luteinizing hormone and follicle stimulating hormone. GnRH is produced by neurons in the septum preoptic area of the hypothalamus and released into the pituitary portal blood, leading to stimulation of gonadotrophs in the anterior pituitary gland. Gonadorelin has been proposed for treating benign prostatic hyperplasia (U.S. Pat. No. 4,321,260), prostatic hypertrophy (U.S. Pat. No. 5,610,136), treating malignant neoplasia and acquired immune deficiency syndrome (U.S. Pat. No. 4,966,753), management of prostate and breast carcinoma, endometriosis and uterine leiomyomata, precocious puberty and nontumorous ovarian hyperandrogenic syndromes (Pace et al., *Am. Fam. Physician* 1991, 44, 1777). Synthetic gonadorelin is commercially available from Gelacs Innovation (Hangzhou, China) with the sequence, Glp-His-Trp-Ser-Tyr-Gly-Leu-Arg-Pro-Gly-NH$_2$.

a) GnRH-C$^{ter}$-mPEG

An illustrative polymeric reagent, mPEG-NH$_2$ reagent is covalently attached to the C-terminus of GnRH, to provide a C$^{ter}$-conjugate form of the peptide. For coupling to the C-terminus, a protected GnRH lacking the C-terminus amide (Prot-GnRH, e.g., Glp-His-Trp-Ser(tBu)-Tyr(tBu)-Gly-Leu-Arg(Tos)-Pro-Gly-OH) is prepared and purified according to standard automated peptide synthesis or recombinant techniques known to those skilled in the art. mPEG-NH$_2$ 20 kDa, stored at −20° C. under argon, is warmed to ambient temperature. The reaction is performed at room temperature. About 3-5-fold molar excess of mPEG-NH$_2$, PyBOP (benzotriazol-1-yloxy)tripyrrolidinonophosphonium hexafluorophosphate), and 1-hydroxybenzotriazole (HOBt) are used, based upon absolute peptide content. The mPEG-NH$_2$, PyBOP, HOBt are weighed into a glass vial containing a magnetic stirrer bar. A solution of Prot-GnRH is prepared in N,N-dimethylformamide is added and the mixture is stirred using a magnetic stirrer until the mPEG-NH$_2$ is fully dissolved. The stirring speed is reduced and the reaction is allowed to proceed to formation of conjugate product. The conjugate solution is then analyzed by SDS-PAGE and RP-HPLC (C18) to determine the extent of Prot-GnRH-C$^{ter}$-mPEG conjugate formation. The remaining protecting groups are removed under standard deprotection conditions to yield the GnRH-C$^{ter}$-mPEG conjugate.

Using this same approach, other conjugates are prepared using mPEG derivatives having other weight-average molecular weights that also bear an amino moiety.

Example 23

Corticoliberin-mPEG Conjugates

Corticoliberin is a 41-amino acid peptide hormone and neurotransmitter involved in the stress response having the sequence, Ser-Gln-Glu-Pro-Pro-Ile-Ser-Leu-Asp-Leu-Thr-Phe-His-Leu-Leu-Arg-Glu-Val-Leu-Glu-Met-Thr-Lys-Ala-Asp-Gln-Leu-Ala-Gln-Gln-Ala-His-Ser-Asn-Arg-Lys-Leu-Leu-Asp-Ile- Ala (Vale et al., *Science* 1981, 4514, 1394). In humans, CRH regulates, via release of proopiomelanocortin, ACTH secretion from the anterior pituitary and has several direct actions on central and peripheral tissues. Corticoliberin has also been found to have direct anti-inflammatory properties. Thus, corticoliberin has found therapeutic uses inhibiting inflammatory response (U.S. Pat. No. 4,801, 612), and reduction of edema for brain and musculature injury (U.S. Pat. No. 5,137,871), i.e., the use of CRH to decrease the leakage of blood components into tissues produced by various adverse medical conditions, and thus to treat a patient for injury to or disease of the brain, central nervous system or musculature in which edema is a factor.

a) mPEG-N$^{ter}$ Corticoliberin-Via mPEG-SPC

Corticoliberin is prepared and purified according to standard automated peptide synthesis or recombinant techniques known to those skilled in the art. An illustrative polymeric reagent, mPEG-SPC reagent, is covalently attached to the N-terminus of Corticoliberin, to provide a N$^{ter}$-conjugate form of the peptide. mPEG-SPC 20 kDa, stored at −20° C. under argon, is warmed to ambient temperature. The reaction is performed at room temperature. About 3-5-fold molar excess of mPEG-SPC 20 kDa reagent is used based upon absolute peptide content. The mPEG-SPC reagent is weighed into a glass vial containing a magnetic stirrer bar. A solution of Corticoliberin prepared in phosphate buffered saline, PBS, pH 7.4 is added and the mixture is stirred using a magnetic stirrer until the mPEG-SPC is fully dissolved. The stirring speed is reduced and the reaction is allowed to proceed to formation of conjugate product. The reaction is optionally quenched to terminate the reaction. The pH of the conjugate solution at the end of the reaction is measured and further acidified by addition of 0.1M HCl, if necessary, to bring the pH of the final solution to about 5.5. The conjugate solution is then analyzed by SDS-PAGE and RP-HPLC (C18) to determine the extent of mPEG-N$^{ter}$-Corticoliberin conjugate formation.

Using this same approach, other conjugates are prepared using mPEG derivatives having other weight-average molecular weights that also bear an N-hydroxysuccinimide moiety.

b) Corticoliberin-C$^{ter}$-mPEG

An illustrative polymeric reagent, mPEG-NH$_2$ reagent is covalently attached to the C-terminus of Corticoliberin, to provide a C$^{ter}$-conjugate form of the peptide. For coupling to the C-terminus, a protected Corticoliberin (Prot-Corticoliberin, e.g., Fmoc-Ser(tBu)-Gln-Glu(tBu)-Pro-Pro-Ile-Ser(tBu)-Leu-Asp(tBu)-Leu-Thr(tBu)-Phe-His-Leu-Leu-Arg(Tos)-Glu(tBu)-Val-Leu-Glu(tBu)-Met- Thr(tBu)-Lys (Fmoc)-Ala-Asp(tBu)-Gln-Leu-Ala-Gln-Gln-Ala-His-Ser (tBu)-Asn-Arg(Tos)-Lys(Fmoc)-Leu-Leu-Asp(tBu)-Ile-Ala) is prepared and purified according to standard automated peptide synthesis techniques known to those skilled in the art. mPEG-NH$_2$ 20 kDa, stored at −20° C. under argon, is warmed to ambient temperature. The reaction is performed at room temperature. About 3-5-fold molar excess of mPEG-NH$_2$, PyBOP (benzotriazol-1-yloxy)tripyrrolidinonophosphonium hexafluorophosphate), and 1-hydroxybenzotriazole (HOBt) are used, based upon absolute peptide content. The mPEG-NH$_2$, PyBOP, HOBt are weighed into a glass vial containing a magnetic stirrer bar. A solution of Prot-Corticoliberin is prepared in N,N-dimethylformamide is added and the mixture is stirred using a magnetic stirrer until the mPEG-NH$_2$ is fully dissolved. The stirring speed is reduced and the reaction is allowed to proceed to formation of conjugate product. The conjugate solution is then analyzed by SDS-PAGE and RP-HPLC (C18) to determine the extent of Prot-Corticoliberin-C$^{ter}$-mPEG conjugate formation. The remaining protecting groups are removed under standard deprotection conditions to yield the Corticoliberin-C$^{ter}$-mPEG conjugate.

Using this same approach, other conjugates are prepared using mPEG derivatives having other weight-average molecular weights that also bear an amino moiety.

c) mPEG-N$^{ter}$-Corticoliberin Via mPEG-SMB mPEG-SMB, 5 kDa, stored at −20° C. under argon, is warmed to ambient temperature. A five-fold excess (relative to the amount of the peptide) of the warmed mPEG-SMB is dissolved in buffer to form a 10% reagent solution. The 10% reagent solution is quickly added to the aliquot of a stock Corticoliberin solution and mixed well. After the addition of the mPEG-SMB, the pH of the reaction mixture is determined and adjusted to 6.7 to 6.8 using conventional techniques. To allow for coupling of the mPEG-SMB to the peptide via an amide linkage, the reaction solution is stirred for several hours (e.g., 5 hours) at room temperature in the dark or stirred overnight at 3-8° C. in a cold room, thereby resulting in a conjugate solution. The reaction is quenched with a 20-fold molar excess (with respect to the peptide) of Tris buffer.

Using this same approach, other conjugates are prepared using mPEG derivatives having other weight-average molecular weights that also bear an N-hydroxysuccinimide moiety.

d) Corticoliberin-Lys-mPEG

PEG-SMB, 5 kDa, stored at −20° C. under argon, is warmed to ambient temperature. A five-fold excess (relative to the amount of the peptide) of the warmed mPEG-SMB is dissolved in buffer to form a 10% reagent solution. The 10% reagent solution is quickly added to the aliquot of a stock protected Corticoliberin (e.g., Fmoc-Ser(tBu)-Gln-Glu (tBu)-Pro-Pro-Ile-Ser(tBu)-Leu-Asp(tBu)-Leu-Thr(tBu)-Phe-His-Leu-Leu-Arg(Tos)-Glu(tBu)-Val-Leu-Glu(tBu)-Met- Thr(tBu)-Lys-Ala-Asp(tBu)-Gln-Leu-Ala-Gln-Gln-Ala-His-Ser(tBu)-Asn-Arg(Tos)-Lys(Fmoc)-Leu-Leu-Asp (tBu)-Ile-Ala-O(tBu)) solution and mixed well. After the addition of the mPEG-SMB, the pH of the reaction mixture is determined and adjusted to 6.7 to 6.8 using conventional techniques. To allow for coupling of the mPEG-SMB to the peptide via an amide linkage, the reaction solution is stirred for several hours (e.g., 5 hours) at room temperature in the dark or stirred overnight at 3-8° C. in a cold room, thereby resulting in a conjugate solution. The reaction is quenched with a 20-fold molar excess (with respect to the peptide) of Tris buffer. The remaining protecting groups are removed under standard deprotection conditions to yield the Corticoliberin-Lys(O-mPEG) conjugate.

Using this same approach, other conjugates are prepared using mPEG derivatives having other weight-average molecular weights that also bear an N-hydroxysuccinimide moiety.

Example 24

Atrial Natriuretic Peptide (Atriopeptin)-mPEG Conjugates

Atrial natriuretic peptide (ANP; atriopeptin) is a peptide hormone secreted by muscle cells in the upper atria of the heart, in response to high blood pressure. It is involved in the homeostatic control of body water, sodium, potassium and adiposity. ANP acts to reduce the water, sodium and adipose loads on the circulatory system, thereby reducing blood pressure (Needleman and Greenwald, *N. Engl. J. Med.* 1986, 314, 828). Human atrial natriuretic peptide is commercially available from GenScript Corporation (Piscataway, N.J.; Cat. No. RP11927) with the sequence, Ser-Leu-Arg-Arg-Ser-Ser-Cys-Phe-Gly-Gly-Arg-Met-Asp-Arg-Ile-Gly-Ala-Gln-Ser-Gly-Leu-Gly-Cys-Asn-Ser-Phe-Arg-Tyr (SL-RRSSCFGG RMDRIGAQSG LGCNSFRY).

a) mPEG-N$^{ter}$-ANP-Via mPEG-SPC

An illustrative polymeric reagent, mPEG-SPC reagent, is covalently attached to the N-terminus of ANP, to provide a N$^{ter}$-conjugate form of the peptide. mPEG-SPC 20 kDa, stored at −20° C. under argon, is warmed to ambient temperature. The reaction is performed at room temperature. About 3-5-fold molar excess of mPEG-SPC 20 kDa reagent is used based upon absolute peptide content. The mPEG-SPC reagent is weighed into a glass vial containing a magnetic stirrer bar. A solution of ANP prepared in phosphate buffered saline, PBS, pH 7.4 is added and the mixture is stirred using a magnetic stirrer until the mPEG-SPC is fully dissolved. The stirring speed is reduced and the reaction is allowed to proceed to formation of conjugate product. The reaction is optionally quenched to terminate the reaction. The pH of the conjugate solution at the end of the reaction is measured and further acidified by addition of 0.1M HCl, if necessary, to bring the pH of the final solution to about 5.5. The conjugate solution is then analyzed by SDS-PAGE and RP-HPLC (C18) to determine the extent of mPEG-N$^e$-ANP conjugate formation.

Using this same approach, other conjugates are prepared using mPEG derivatives having other weight-average molecular weights that also bear an N-hydroxysuccinimide moiety.

b) ANP-C$^{ter}$-mPEG

An illustrative polymeric reagent, mPEG-NH$_2$ reagent is covalently attached to the C-terminus of ANP, to provide a C$^{ter}$-conjugate form of the peptide. For coupling to the C-terminus, a protected ANP (Prot-ANP, e.g., Fmoc-Ser(tBu)-Leu-Arg(Tos)-Arg(Tos)-Ser(tBu)-Ser(tBu)-Cys(tBu)-Phe-Gly-Gly-Arg(Tos)-Met-Asp(tBu)-Arg(Tos)-Ile-Gly-Ala-Gln-Ser(tBu)-Gly-Leu-Gly-Cys(tBu)-Asn-Ser(tBu)-Phe- Arg(Tos)-Tyr(tBu)-OH) is prepared and purified according to standard automated peptide synthesis techniques known to those skilled in the art. mPEG-NH$_2$ 20 kDa, stored at −20° C. under argon, is warmed to ambient temperature. The reaction is performed at room temperature. About 3-5-fold molar excess of mPEG-NH$_2$, PyBOP (benzotriazol-1-yloxy)tripyrrolidinonophosphonium hexafluorophosphate), and 1-hydroxybenzotriazole (HOBt) are used, based upon absolute peptide content. The mPEG-NH$_2$, PyBOP, HOBt are weighed into a glass vial containing a magnetic stirrer bar. A solution of Prot-ANP is prepared in N,N-dimethylformamide is added and the mixture is stirred using a magnetic stirrer until the mPEG-NH$_2$ is fully dissolved. The stirring speed is reduced and the reaction is allowed to proceed to formation of conjugate product. The conjugate solution is then analyzed by SDS-PAGE and RP-HPLC (C18) to determine the extent of Prot-ANP-C$^{ter}$-mPEG conjugate formation. The remaining protecting groups are removed under standard deprotection conditions to yield the ANP-C$^{ter}$-mPEG conjugate.

Using this same approach, other conjugates are prepared using mPEG derivatives having other weight-average molecular weights that also bear an amino moiety.

c) ANP-Cys(S-mPEG)

ANP, which has a thiol-containing cysteine residue, is dissolved in buffer. To this peptide solution is added a 3-5 fold molar excess of mPEG-MAL, 5 kDa. The mixture is stirred at room temperature under an inert atmosphere for several hours. Analysis of the reaction mixture reveals successful conjugation of this peptide.

Using this same approach, other conjugates are prepared using mPEG-MAL having other weight average molecular weights.

d) mPEG-N$^{ter}$-ANP Via mPEG-SMB mPEG-SMB, 5 kDa, stored at −20° C. under argon, is warmed to ambient temperature. A five-fold excess (relative to the amount of the peptide) of the warmed mPEG-SMB is dissolved in buffer to form a 10% reagent solution. The 10% reagent solution is quickly added to the aliquot of a stock ANP solution and mixed well. After the addition of the mPEG-SMB, the pH of the reaction mixture is determined and adjusted to 6.7 to 6.8 using conventional techniques. To allow for coupling of the mPEG-SMB to the peptide via an amide linkage, the reaction solution is stirred for several hours (e.g., 5 hours) at room temperature in the dark or stirred overnight at 3-8° C. in a cold room, thereby resulting in a conjugate solution. The reaction is quenched with a 20-fold molar excess (with respect to the peptide) of Tris buffer.

Using this same approach, other conjugates are prepared using mPEG derivatives having other weight-average molecular weights that also bear an N-hydroxysuccinimide moiety.

e) ANP-Asp(O-mPEG)

An illustrative polymeric reagent, mPEG-NH$_2$ reagent is covalently attached to the Asp residue of ANP, to provide a Asp-conjugate form of the peptide. For coupling to the Asp residue, a protected ANP (Prot2-ANP, e.g., Fmoc-Ser(tBu)-Leu-Arg(Tos)-Arg(Tos)-Ser(tBu)-Ser(tBu)-Cys(tBu)-Phe-Gly-Gly-Arg(Tos)-Met-Asp(OBz)-Arg(Tos)-Ile-Gly-Ala-Gln-Ser(tBu)-Gly-Leu-Gly-Cys(tBu)-Asn- Ser(tBu)-Phe-Arg(Tos)-Tyr(tBu)-O(tBu)) is prepared and purified according to standard automated peptide synthesis techniques known to those skilled in the art. Deprotection of the Asp(OBz) residue (H$_2$/Pd) yields the free-Asp carboxylate for subsequent coupling (Prot3-ANP, e.g., Fmoc-Ser(tBu)-Leu-Arg(Tos)-Arg(Tos)-Ser(tBu)-Ser(tBu)-Cys(tBu)-Phe-Gly-Gly-Arg(Tos)-Met-Asp-Arg(Tos)-Ile-Gly-Ala-Gln-Ser(tBu)-Gly-Leu-Gly-Cys(tBu)-Asn-Ser(tBu)-Phe- Arg(Tos)-Tyr(tBu)-O(tBu)). mPEG-NH$_2$ 20 kDa, stored at −20° C. under argon, is warmed to ambient temperature. The reaction is performed at room temperature. A 5-fold molar excess of mPEG-NH$_2$, PyBOP (benzotriazol-1-yloxy)tripyrrolidinonophosphonium hexafluorophosphate), and 1-hydroxybenzotriazole (HOBt) are used, based upon absolute peptide content. The mPEG-NH$_2$, PyBOP, HOBt are weighed into a glass vial containing a magnetic stirrer bar. A solution of Prot3-ANP is prepared in N,N-dimethylformamide is added and the mixture is stirred using a magnetic stirrer until the mPEG-NH$_2$ is fully dissolved. The stirring speed is reduced and the reaction is allowed to proceed to formation of conjugate product. The conjugate solution is then analyzed by SDS-PAGE and RP-HPLC (C18) to determine the extent of Prot3-ANP-(Asp-O-mPEG) conjugate formation. The remaining protecting groups are removed under standard deprotection conditions to yield the ANP-Asp(O-mPEG) conjugate.

Using this same approach, other conjugates are prepared using mPEG derivatives having other weight-average molecular weights that also bear an amino moiety.

Example 25

AnergiX-mPEG Conjugates

AnergiX is a T cell inhibitor which has been proposed for the treatment of rheumatoid arthritis comprising soluble Major Histocompatibility Complex (MHC) molecules linked to antigenic peptides recognized by specific subsets of T cells (U.S. Pat. No. 5,468,481).

a) mPEG-N$^{ter}$-AnergiX Via mPEG-SPC

AnergiX is prepared and purified according to standard automated peptide synthesis or recombinant techniques known to those skilled in the art. An illustrative polymeric reagent, mPEG-SPC reagent, is covalently attached to the N-terminus of AnergiX, to provide a N$^{ter}$-conjugate form of the peptide. mPEG-SPC 20 kDa, stored at −20° C. under argon, is warmed to ambient temperature. The reaction is performed at room temperature. About 3-5-fold molar excess of mPEG-SPC 20 kDa reagent is used based upon absolute peptide content. The mPEG-SPC reagent is weighed into a glass vial containing a magnetic stirrer bar. A solution of AnergiX prepared in phosphate buffered saline, PBS, pH 7.4 is added and the mixture is stirred using a magnetic stirrer until the mPEG-SPC is fully dissolved. The stirring speed is reduced and the reaction is allowed to proceed to formation of conjugate product. The reaction is optionally quenched to terminate the reaction. The pH of the conjugate solution at the end of the reaction is measured and further acidified by addition of 0.1M HCl, if necessary, to bring the pH of the final solution to about 5.5. The conjugate solution is then analyzed by SDS-PAGE and RP-HPLC (C18) to determine the extent of mPEG-N$^{ter}$-AnergiX conjugate formation.

Using this same approach, other conjugates are prepared using mPEG derivatives having other weight-average molecular weights that also bear an N-hydroxysuccinimide moiety.

b) AnergiX-C$^{Ter-mPEG}$

An illustrative polymeric reagent, mPEG-NH$_2$ reagent is covalently attached to the C-terminus of AnergiX, to provide a C$^{ter}$-conjugate form of the peptide. For coupling to the C-terminus, a protected AnergiX (Prot-AnergiX) is prepared and purified according to standard automated peptide synthesis techniques known to those skilled in the art. mPEG-NH$_2$ 20 kDa, stored at −20° C. under argon, is warmed to ambient temperature. The reaction is performed at room temperature. About 3-5-fold molar excess of mPEG-NH$_2$, PyBOP (benzotriazol-1-yloxy)tripyrrolidinonophosphonium hexafluorophosphate), and 1-hydroxybenzotriazole (HOBt) are used, based upon absolute peptide content. The mPEG-NH$_2$, PyBOP, HOBt are weighed into a glass vial containing a magnetic stirrer bar. A solution of Prot-AnergiX is prepared in N,N-dimethylformamide is added and the mixture is stirred using a magnetic stirrer until the mPEG-NH$_2$ is fully dissolved. The stirring speed is reduced and the reaction is allowed to proceed to formation of conjugate product. The conjugate solution is then analyzed by SDS-PAGE and RP-HPLC (C18) to determine the extent of Prot-AnergiX-C$^{ter}$-mPEG conjugate formation. The remaining protecting groups are removed under standard deprotection conditions to yield the AnergiX-C$^{ter}$-mPEG conjugate.

Using this same approach, other conjugates are prepared using mPEG derivatives having other weight-average molecular weights that also bear an amino moiety.

c) mPEG-N$^{ter}$-AnergiX Via mPEG-SMB

An mPEG-N-Hydroxysuccinimide is obtained having a molecular weight of 5 kDa and having the basic structure shown below:

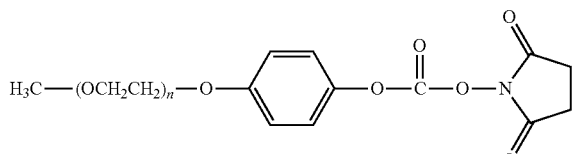

'SPC' polymer reagent

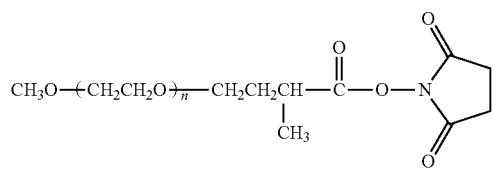

(mPEG-Succinimidyl α-Methylbutanoate Derivative, 5 kDa ("mPEG-SMB"))

mPEG-SMB, 5 kDa, stored at −20° C. under argon, is warmed to ambient temperature. A five-fold excess (relative to the amount of the peptide) of the warmed mPEG-SMB is dissolved in buffer to form a 10% reagent solution. The 10% reagent solution is quickly added to the aliquot of a stock AnergiX solution and mixed well. After the addition of the mPEG-SMB, the pH of the reaction mixture is determined and adjusted to 6.7 to 6.8 using conventional techniques. To allow for coupling of the mPEG-SMB to the peptide via an amide linkage, the reaction solution is stirred for several hours (e.g., 5 hours) at room temperature in the dark or stirred overnight at 3-8° C. in a cold room, thereby resulting in a conjugate solution. The reaction is quenched with a 20-fold molar excess (with respect to the peptide) of Tris buffer.

Using this same approach, other conjugates are prepared using mPEG derivatives having other weight-average molecular weights that also bear an N-hydroxysuccinimide moiety.

Example 26

Somatostatin-mPEG Conjugates

Somatostatin is a peptide hormone that regulates the endocrine system and affects neurotransmission and cell proliferation via interaction with G-protein-coupled somatostatin receptors (of which five different subtypes have been characterized) and inhibition of the release of numerous secondary hormones. Binding to the different types of somatostatin subtypes have been associated with the treatment of various conditions and/or diseases. (Raynor et al., *Molecular Pharmacol.* 1993, 43, 838; Lloyd, et al., *Am. J. Physiol.* 1995, 268, G102) Indications associated with activation of the somatostatin receptor subtypes are inhibition of insulin and/or glucagon for treating diabetes mellitus, angiopathy, proliferative retinopathy, dawn phenomenon and nephropathy; inhibition of gastric acid secretion and more particularly peptic ulcers, enterocutaneous and pancreaticocutaneous fistula, irritable bowel syndrome, Dumping syndrome, watery diarrhea syndrome, AIDS related diarrhea, chemotherapy-induced diarrhea, acute or chronic pancreatitis and gastrointestinal hormone secreting tumors; treatment of cancer such as hepatoma; inhibition of angiogenesis, treatment of inflammatory disorders such as arthritis; retinopathy; chronic allograft rejection; angioplasty; preventing graft vessel and gastrointestinal bleeding. Somatostatin is commercially available from Gelacs Innovation (Hangzhou, China)) with the sequence, His-Ser-Asp-Gly-Thr-Phe-Thr-Ser-Glu-Leu-Ser-Arg-Leu-Arg-Asp-Ser-Ala-Arg-Leu-Gln-Arg-Leu-Leu-Gln-Gly-Leu-Val-NH$_2$ a) mPEG-N$^{ter}$-Somatostatin-Via mPEG-SPC An illustrative polymeric reagent, mPEG-SPC reagent, is covalently attached to the N-terminus of Somatostatin, to provide a N$^{ter}$-conjugate form of the peptide. mPEG-SPC 20 kDa, stored at −20° C. under argon, is warmed to ambient temperature. The reaction is performed at room temperature. About 3-5-fold molar excess of mPEG-SPC 20 kDa reagent is used based upon absolute peptide content. The mPEG-SPC reagent is weighed into a glass vial containing a magnetic stirrer bar. A solution of Somatostatin prepared in phosphate buffered saline, PBS, pH 7.4 is added and the mixture is stirred using a magnetic stirrer until the mPEG-SPC is fully dissolved. The stirring speed is reduced and the reaction is allowed to proceed to formation of conjugate product. The reaction is optionally quenched to terminate the reaction. The pH of the conjugate solution at the end of the reaction is measured and further acidified by addition of 0.1M HCl, if necessary, to bring the pH of the final solution to about 5.5. The conjugate solution is then analyzed by SDS-PAGE and RP-HPLC (C18) to determine the extent of mPEG-N$^{ter}$-Somatostatin conjugate formation.

Using this same approach, other conjugates are prepared using mPEG derivatives having other weight-average molecular weights that also bear an N-hydroxysuccinimide moiety.

b) Somatostatin-C$^{ter}$-mPEG

An illustrative polymeric reagent, mPEG-NH$_2$ reagent is covalently attached to the C-terminus of Somatostatin, to provide a C$^{ter}$-conjugate form of the peptide. For coupling to the C-terminus, a protected Somatostatin lacking the C-terminus amide(Prot-Somatostatin, e.g., Fmoc-His-Ser(tBu)-Asp(tBu)-Gly-Thr(tBu)-Phe-Thr(tBu)-Ser(tBu)-Glu(tBu)-Leu-Ser(tBu)-Arg(Tos)-Leu-Arg(Tos)-Asp(tBu)-Ser(tBu)-Ala-Arg(Tos)-Leu-Gln-Arg(Tos)-Leu-Leu-Gln-Gly-Leu-Val-OH) is prepared and purified according to standard automated peptide synthesis techniques known to those skilled in the art. mPEG-NH$_2$ 20 kDa, stored at −20° C. under argon, is warmed to ambient temperature. The reaction is performed at room temperature. About 3-5-fold molar excess of mPEG-NH$_2$, PyBOP (benzotriazol-1-yloxy)tripyrrolidinonophosphonium hexafluorophosphate), and 1-hydroxybenzotriazole (HOBt) are used, based upon absolute peptide content. The mPEG-NH$_2$, PyBOP, HOBt are weighed into a glass vial containing a magnetic stirrer bar. A solution of Prot-Somatostatin is prepared in N,N-dimethylformamide is added and the mixture is stirred using a magnetic stirrer until the mPEG-NH$_2$ is fully dissolved. The stirring speed is reduced and the reaction is allowed to proceed to formation of conjugate product. The conjugate solution is then analyzed by SDS-PAGE and RP-HPLC (C18) to determine the extent of Prot-Somatostatin-C$^{ter}$-mPEG conjugate formation. The remaining protecting groups are removed under standard deprotection conditions to yield the Somatostatin-CtY-mPEG conjugate.

Using this same approach, other conjugates are prepared using mPEG derivatives having other weight-average molecular weights that also bear an amino moiety.

c) mPEG-N$^{ter}$-Somatostatin Via mPEG-SMB mPEG-SMB, 5 kDa, stored at −20° C. under argon, is warmed to ambient temperature. A five-fold excess (relative to the amount of the peptide) of the warmed mPEG-SMB is dissolved in buffer to form a 10% reagent solution. The 10% reagent solution is quickly added to the aliquot of a stock Somatostatin solution and mixed well. After the addition of the mPEG-SMB, the pH of the reaction mixture is determined and adjusted to 6.7 to 6.8 using conventional techniques. To allow for coupling of the mPEG-SMB to the peptide via an amide linkage, the reaction solution is stirred for several hours (e.g., 5 hours) at room temperature in the dark or stirred overnight at 3-8° C. in a cold room, thereby resulting in a conjugate solution. The reaction is quenched with a 20-fold molar excess (with respect to the peptide) of Tris buffer.

Using this same approach, other conjugates are prepared using mPEG derivatives having other weight-average molecular weights that also bear an N-hydroxysuccinimide moiety.

d) Somatostatin-Asp(O-mPEG)

An illustrative polymeric reagent, mPEG-NH$_2$ reagent is covalently attached to the Asp residue of Somatostatin, to provide a Asp-conjugate form of the peptide. For coupling to the Asp residue, a protected Somatostatin (Prot2-Somatostatin, e.g., Fmoc-His-Ser(tBu)-Asp(OBz)-Gly-Thr(tBu)-Phe-Thr(tBu)-Ser(tBu)-Glu(tBu)-Leu-Ser(tBu)-Arg(Tos)-

Leu-Arg(Tos)-Asp(tBu)-Ser(tBu)-Ala- Arg(Tos)-Leu-Gln-Arg(Tos)-Leu-Leu-Gln-Gly-Leu-Val-NH$_2$) is prepared and purified according to standard automated peptide synthesis techniques known to those skilled in the art. Deprotection of the Asp(OBz) residue (H$_2$/Pd) yields the free-Asp carboxylate for subsequent coupling (Prot3-Somatostatin, e.g., Fmoc-His-Ser(tBu)-Asp-Gly-Thr(tBu)-Phe-Thr(tBu)-Ser(tBu)-Glu(tBu)-Leu-Ser(tBu)-Arg(Tos)-Leu-Arg(Tos)-Asp(tBu)-Ser(tBu)-Ala-Arg(Tos)-Leu- Gln-Arg(Tos)-Leu-Leu-Gln-Gly-Leu-Val-$_{NH2}$). mPEG-NH$_2$ 20 kDa, stored at −20° C. under argon, is warmed to ambient temperature. The reaction is performed at room temperature. A 5-fold molar excess of mPEG-NH$_2$, PyBOP (benzotriazol-1-yloxy)tripyrrolidinonophosphonium hexafluorophosphate), and 1-hydroxybenzotriazole (HOBt) are used, based upon absolute peptide content. The mPEG-NH$_2$, PyBOP, HOBt are weighed into a glass vial containing a magnetic stirrer bar. A solution of Prot3-Somatostatin is prepared in N, N-dimethylformamide is added and the mixture is stirred using a magnetic stirrer until the mPEG-NH$_2$ is fully dissolved. The stirring speed is reduced and the reaction is allowed to proceed to formation of conjugate product. The conjugate solution is then analyzed by SDS-PAGE and RP-HPLC (C18) to determine the extent of Prot3-Somatostatin-(Asp-O-mPEG) conjugate formation. The remaining protecting groups are removed under standard deprotection conditions to yield the Somatostatin-Asp(O-mPEG) conjugate.

Using this same approach, other conjugates are prepared using mPEG derivatives having other weight-average molecular weights that also bear an amino moiety.

Example 27

29-Amino-Acid Peptide Growth Hormone Releasing Hormone (GHRH) Analogue-mPEG Conjugates GHRH stimulates growth hormone secretion from the anterior pituitary gland. GHRH can increase the height velocity in children with growth disorders (idiopathic growth hormone deficiency). In addition, GHRH can help production of muscle mass and stimulate fat breakdown by stimulating indirectly the production of IGF-1 via inducing the release of growth hormone. Most patients with idiopathic growth hormone deficiency have a deficit in hypothalamic GHRH synthesis or release rather than in growth hormone itself, so treatment with GHRH is considered a logical approach in the management of these patients. GHRH has a very short half-life (10-20 min) due to rapid proteolysis and glomerular filtration. The 29-amino acid peptide of GHRH ("GHRH-29") has the sequence Tyr-Ala-Asp-Ala-Ile-Phe-Thr-Asn-Ser-Tyr-Arg-Lys-Val-Leu-Gly-Glu-Leu-Ser-Ala-Arg-Lys-Leu-Leu-Gln-Asp-Ile-Met-Ser-Arg.

a) mPEG-N$^{ter}$-GHRH-29 Via mPEG-SPC

GHRH-29 is prepared and purified according to standard automated peptide synthesis or recombinant techniques known to those skilled in the art. An illustrative polymeric reagent, mPEG-SPC reagent, is covalently attached to the N-terminus of GHRH-29, to provide a N$^{ter}$-conjugate form of the peptide. mPEG-SPC 20 kDa, stored at −20° C. under argon, is warmed to ambient temperature. The reaction is performed at room temperature. About 3-5-fold molar excess of mPEG-SPC 20 kDa reagent is used based upon absolute peptide content. The mPEG-SPC reagent is weighed into a glass vial containing a magnetic stirrer bar. A solution of GHRH-29 prepared in phosphate buffered saline, PBS, pH 7.4 is added and the mixture is stirred using a magnetic stirrer until the mPEG-SPC is fully dissolved. The stirring speed is reduced and the reaction is allowed to proceed to formation of conjugate product. The reaction is optionally quenched to terminate the reaction. The pH of the conjugate solution at the end of the reaction is measured and further acidified by addition of 0.1M HCl, if necessary, to bring the pH of the final solution to about 5.5. The conjugate solution is then analyzed by SDS-PAGE and RP-HPLC (C18) to determine the extent of mPEG-N$^{ter}$-GHRH-29 conjugate formation.

Using this same approach, other conjugates are prepared using mPEG derivatives having other weight-average molecular weights that also bear an N-hydroxysuccinimide moiety.

b) GHRH-29-C$^{ter}$-mPEG

An illustrative polymeric reagent, mPEG-NH$_2$ reagent is covalently attached to the C-terminus of GHRH-29, to provide a C$^{ter}$-conjugate form of the peptide. For coupling to the C-terminus, a protected GHRH-29 (Prot-GHRH-29) is prepared and purified according to standard automated peptide synthesis techniques known to those skilled in the art. mPEG-NH$_2$ 20 kDa, stored at −20° C. under argon, is warmed to ambient temperature. The reaction is performed at room temperature. About 3-5-fold molar excess of mPEG-NH$_2$, PyBOP (benzotriazol-1-yloxy)tripyrrolidinonophosphonium hexafluorophosphate), and 1-hydroxybenzotriazole (HOBt) are used, based upon absolute peptide content. The mPEG-NH$_2$, PyBOP, HOBt are weighed into a glass vial containing a magnetic stirrer bar. A solution of Prot-GHRH-29 is prepared in N,N-dimethylformamide is added and the mixture is stirred using a magnetic stirrer until the mPEG-NH$_2$ is fully dissolved. The stirring speed is reduced and the reaction is allowed to proceed to formation of conjugate product. The conjugate solution is then analyzed by SDS-PAGE and RP-HPLC (C18) to determine the extent of Prot-GHRH-29-C$^{ter}$-mPEG conjugate formation. The remaining protecting groups are removed under standard deprotection conditions to yield the GHRH-29-C$^{ter}$-mPEG conjugate.

Using this same approach, other conjugates are prepared using mPEG derivatives having other weight-average molecular weights that also bear an amino moiety.

c) mPEG-N$^{ter}$-GHRH-29 Via mPEG-SMB

An mPEG-N-Hydroxysuccinimide is obtained having a molecular weight of 5 kDa and having the basic structure shown below:

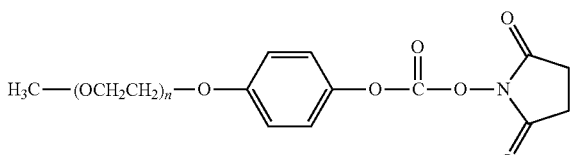

'SPC' polymer reagent

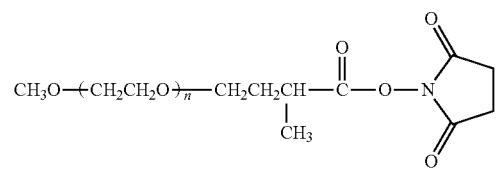

(mPEG-Succinimidyl α-Methylbutanoate Derivative, 5 kDa ("mPEG-SMB"))

mPEG-SMB, 5 kDa, stored at −20° C. under argon, is warmed to ambient temperature. A five-fold excess (relative to the amount of the peptide) of the warmed mPEG-SMB is dissolved in buffer to form a 10% reagent solution. The 10% reagent solution is quickly added to the aliquot of a stock GHRH-29 solution and mixed well. After the addition of the mPEG-SMB, the pH of the reaction mixture is determined and adjusted to 6.7 to 6.8 using conventional techniques. To allow for coupling of the mPEG-SMB to the peptide via an amide linkage, the reaction solution is stirred for several hours (e.g., 5 hours) at room temperature in the dark or stirred overnight at 3-8° C. in a cold room, thereby resulting in a conjugate solution. The reaction is quenched with a 20-fold molar excess (with respect to the peptide) of Tris buffer.

Using this same approach, other conjugates are prepared using mPEG derivatives having other weight-average molecular weights that also bear an N-hydroxysuccinimide moiety.

Example 28

Bremelanotide (Melanocortin Agonist Group)-mPEG Conjugates

Bremelanotide is a cyclic hepta-peptide lactam analog of alpha-melanocyte-stimulating hormone (alpha-MSH) that activates the melanocortin receptors MC3-R and MC4-R in the central nervous system. It has been proposed for use in treating sexual dysfunction in men (erectile dysfunction or impotence) as well as sexual dysfunction in women (sexual arousal disorder). Bremelanotide has the sequence (NAc-Nle)-cyclo[Asp-His-(D-Phe)-Arg-Trp-Lys]-OH (U.S. Pat. Nos. 6,579,968 and 6,794,489).

a) mPEG-$N^{ter}$-Bremelanotide-Via mPEG-SPC

Bremelanotide lacking the N-terminus acetyl group ($NH_2$—Bremelanotide) is prepared and purified according to standard automated peptide synthesis or recombinant techniques known to those skilled in the art. An illustrative polymeric reagent, mPEG-SPC reagent, is covalently attached to the N-terminus of Bremelanotide, to provide a $N^{ter}$-conjugate form of the peptide. mPEG-SPC 20 kDa, stored at −20° C. under argon, is warmed to ambient temperature. The reaction is performed at room temperature. About 3-5-fold molar excess of mPEG-SPC 20 kDa reagent is used based upon absolute peptide content. The mPEG-SPC reagent is weighed into a glass vial containing a magnetic stirrer bar. A solution of $NH_2$-Bremelanotide prepared in phosphate buffered saline, PBS, pH 7.4 is added and the mixture is stirred using a magnetic stirrer until the mPEG-SPC is fully dissolved. The stirring speed is reduced and the reaction is allowed to proceed to formation of conjugate product. The reaction is optionally quenched to terminate the reaction. The pH of the conjugate solution at the end of the reaction is measured and further acidified by addition of 0.1M HCl, if necessary, to bring the pH of the final solution to about 5.5. The conjugate solution is then analyzed by SDS-PAGE and RP-HPLC (C18) to determine the extent of mPEG-$N^{ter}$-Bremelanotide conjugate formation.

Using this same approach, other conjugates are prepared using mPEG derivatives having other weight-average molecular weights that also bear an N-hydroxysuccinimide moiety.

b) Bremelanotide-$C^{ter}$-mPEG

An illustrative polymeric reagent, mPEG-$NH_2$ reagent is covalently attached to the C-terminus of Bremelanotide, to provide a $C^{ter}$-conjugate form of the peptide. For coupling to the C-terminus, a protected Bremelanotide (Prot-Bremelanotide, e.g., sequence (NAc-Nle)-cyclo[Asp-His-(D-Phe)-Arg(Tos)-Trp-Lys]-OH) is prepared and purified according to standard automated peptide synthesis techniques known to those skilled in the art. mPEG-$NH_2$ 20 kDa, stored at −20° C. under argon, is warmed to ambient temperature. The reaction is performed at room temperature. About 3-5-fold molar excess of mPEG-$NH_2$, PyBOP (benzotriazol-1-yloxy) tripyrrolidinonophosphonium hexafluorophosphate), and 1-hydroxybenzotriazole (HOBt) are used, based upon absolute peptide content. The mPEG-$NH_2$, PyBOP, HOBt are weighed into a glass vial containing a magnetic stirrer bar. A solution of Prot-Bremelanotide is prepared in N, N-dimethylformamide is added and the mixture is stirred using a magnetic stirrer until the mPEG-$NH_2$ is fully dissolved. The stirring speed is reduced and the reaction is allowed to proceed to formation of conjugate product. The conjugate solution is then analyzed by SDS-PAGE and RP-HPLC (C18) to determine the extent of Prot-Bremelanotide-$C^{ter}$-mPEG conjugate formation. The remaining protecting groups are removed under standard deprotection conditions to yield the Bremelanotide-$C^{ter}$-mPEG conjugate.

Using this same approach, other conjugates are prepared using mPEG derivatives having other weight-average molecular weights that also bear an amino moiety.

c) mPEG-$N^{ter}$-Bremelanotide Via mPEG-SMB mPEG-SMB, 5 kDa, stored at −20° C. under argon, is warmed to ambient temperature. A five-fold excess (relative to the amount of the peptide) of the warmed mPEG-SMB is dissolved in buffer to form a 10% reagent solution. The 10% reagent solution is quickly added to the aliquot of a stock Bremelanotide solution and mixed well. After the addition of the mPEG-SMB, the pH of the reaction mixture is determined and adjusted to 6.7 to 6.8 using conventional techniques. To allow for coupling of the mPEG-SMB to the peptide via an amide linkage, the reaction solution is stirred for several hours (e.g., 5 hours) at room temperature in the dark or stirred overnight at 3-8° C. in a cold room, thereby resulting in a conjugate solution. The reaction is quenched with a 20-fold molar excess (with respect to the peptide) of Tris buffer.

Using this same approach, other conjugates are prepared using mPEG derivatives having other weight-average molecular weights that also bear an N-hydroxysuccinimide moiety.

Example 29

Melanocortin Peptidomimetic Compound (Melanocortin Agonist Group)-mPEG Conjugates Melanocortins are a group of pituitary peptide hormones that include adrenocortinotropin (ACTH) and the alpha, beta and gamma melanocyte-stimulating hormones (MSH) that derive from the prohormone proopiomelanocortin. Melanocortins act through several melanocortin receptors designated MC-1 through MC5. Several synthetic melanocortins are in development including Palatin Technologies' bremelanotide for erectile dysfunction and sexual arousal disorder. Bremelanotide is a cyclic hepta-peptide lactam analog of alpha-melanocyte-stimulating hormone that activates MC-3 and MC-4. Bremelanotide acts within the central nervous system rather than the vascular system (blood flow) to elicit arousal. The peptide has the amino acid sequence Ac-Nle-cyclo[Asp-His-D-Phe-Arg-Trp-Lys]-OH.

a) mPEG-N$^{ter}$-Bremelanotide Via mPEG-SPC

Bremelanotide is prepared and purified according to standard automated peptide synthesis or recombinant techniques known to those skilled in the art. An illustrative polymeric reagent, mPEG-SPC reagent,

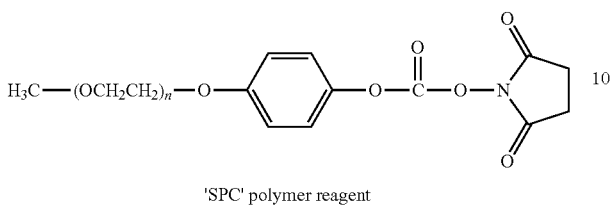

'SPC' polymer reagent is covalently attached to the N-terminus of Bremelanotide, to provide a N$^{ter}$-conjugate form of the peptide. mPEG-SPC 20 kDa, stored at −20° C. under argon, is warmed to ambient temperature. The reaction is performed at room temperature. About 3-5-fold molar excess of mPEG-SPC 20 kDa reagent is used based upon absolute peptide content. The mPEG-SPC reagent is weighed into a glass vial containing a magnetic stirrer bar. A solution of Bremelanotide prepared in phosphate buffered saline, PBS, pH 7.4 is added and the mixture is stirred using a magnetic stirrer until the mPEG-SPC is fully dissolved. The stirring speed is reduced and the reaction is allowed to proceed to formation of conjugate product. The reaction is optionally quenched to terminate the reaction. The pH of the conjugate solution at the end of the reaction is measured and further acidified by addition of 0.1M HCl, if necessary, to bring the pH of the final solution to about 5.5. The conjugate solution is then analyzed by SDS-PAGE and RP-HPLC (C18) to determine the extent of mPEG-N$^{ter}$-Bremelanotide conjugate formation.

Using this same approach, other conjugates are prepared using mPEG derivatives having other weight-average molecular weights that also bear an N-hydroxysuccinimide moiety.

b) Bremelanotide-C$^{ter}$-mPEG

An illustrative polymeric reagent, mPEG-NH$_2$ reagent is covalently attached to the C-terminus of Bremelanotide, to provide a C$^{ter}$-conjugate form of the peptide. For coupling to the C-terminus, a protected Bremelanotide (Prot-Bremelanotide) is prepared and purified according to standard automated peptide synthesis techniques known to those skilled in the art. mPEG-NH$_2$ 20 kDa, stored at −20° C. under argon, is warmed to ambient temperature. The reaction is performed at room temperature. About 3-5-fold molar excess of mPEG-NH$_2$, PyBOP (benzotriazol-1-yloxy)tripyrrolidinonophosphonium hexafluorophosphate), and 1-hydroxybenzotriazole (HOBt) are used, based upon absolute peptide content. The mPEG-NH$_2$, PyBOP, HOBt are weighed into a glass vial containing a magnetic stirrer bar. A solution of Prot-Bremelanotide is prepared in N,N-dimethylformamide is added and the mixture is stirred using a magnetic stirrer until the mPEG-NH$_2$ is fully dissolved. The stirring speed is reduced and the reaction is allowed to proceed to formation of conjugate product. The conjugate solution is then analyzed by SDS-PAGE and RP-HPLC (C18) to determine the extent of Prot-Bremelanotide-C$^{ter}$-mPEG conjugate formation. The remaining protecting groups are removed under standard deprotection conditions to yield the Bremelanotide-C$^{ter}$-mPEG conjugate.

Using this same approach, other conjugates are prepared using mPEG derivatives having other weight-average molecular weights that also bear an amino moiety.

c) mPEG-N$^{ter}$-Bremelanotide Via mPEG-SMB

An mPEG-N-Hydroxysuccinimide is obtained having a molecular weight of 5 kDa and having the basic structure shown below:

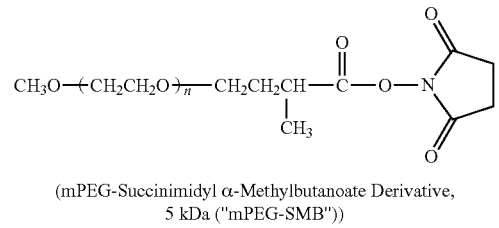

(mPEG-Succinimidyl α-Methylbutanoate Derivative, 5 kDa ("mPEG-SMB"))

mPEG-SMB, 5 kDa, stored at −20° C. under argon, is warmed to ambient temperature. A five-fold excess (relative to the amount of the peptide) of the warmed mPEG-SMB is dissolved in buffer to form a 10% reagent solution. The 10% reagent solution is quickly added to the aliquot of a stock Bremelanotide solution and mixed well. After the addition of the mPEG-SMB, the pH of the reaction mixture is determined and adjusted to 6.7 to 6.8 using conventional techniques. To allow for coupling of the mPEG-SMB to the peptide via an amide linkage, the reaction solution is stirred for several hours (e.g., 5 hours) at room temperature in the dark or stirred overnight at 3-8° C. in a cold room, thereby resulting in a conjugate solution. The reaction is quenched with a 20-fold molar excess (with respect to the peptide) of Tris buffer.

Using this same approach, other conjugates are prepared using mPEG derivatives having other weight-average molecular weights that also bear an N-hydroxysuccinimide moiety.

Example 30

Recombinant LH (Luteinizing Hormone) (LH-Related Peptide Group)-mPEG Conjugates

LH appears to play an important role in both male and female reproduction. In females, an LH surge is associated with ovulation and with the initiation of the conversion of the residual follicle into a corpus luteum that, in turn, produces progesterone to prepare the endometrium for a possible implantation. In males, through the Leydig cell of the testes, LH is responsible for the production of testosterone. LH is a glycoprotein composed of two subunits attached via two disulfide bonds. The two subunits are comprised of 92 and 121 amino acids.

a) mPEG-N$^{ter}$-LH Via mPEG-SPC

LH is prepared and purified according to standard automated peptide synthesis or recombinant techniques known to those skilled in the art. An illustrative polymeric reagent, mPEG-SPC reagent,

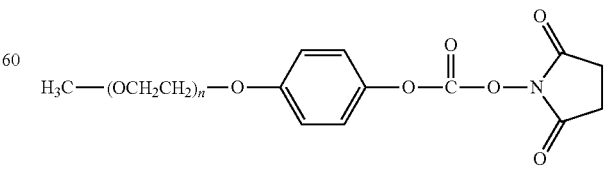

'SPC' polymer reagent is covalently attached to the N-terminus of LH, to provide a $N^{ter}$-conjugate form of the peptide. mPEG-SPC 20 kDa, stored at −20° C. under argon, is warmed to ambient temperature. The reaction is performed at room temperature. About 3-5-fold molar excess of mPEG-SPC 20 kDa reagent is used based upon absolute peptide content. The mPEG-SPC reagent is weighed into a glass vial containing a magnetic stirrer bar. A solution of LH prepared in phosphate buffered saline, PBS, pH 7.4 is added and the mixture is stirred using a magnetic stirrer until the mPEG-SPC is fully dissolved. The stirring speed is reduced and the reaction is allowed to proceed to formation of conjugate product. The reaction is optionally quenched to terminate the reaction. The pH of the conjugate solution at the end of the reaction is measured and further acidified by addition of 0.1M HCl, if necessary, to bring the pH of the final solution to about 5.5. The conjugate solution is then analyzed by SDS-PAGE and RP-HPLC (C18) to determine the extent of mPEG-$N^{ter}$-LH conjugate formation.

Using this same approach, other conjugates are prepared using mPEG derivatives having other weight-average molecular weights that also bear an N-hydroxysuccinimide moiety.

b) LH-$C^{ter}$-mPEG

An illustrative polymeric reagent, mPEG-NH$_2$ reagent is covalently attached to the C-terminus of LH, to provide a $C^{ter}$-conjugate form of the peptide. For coupling to the C-terminus, a protected LH (Prot-LH) is prepared and purified according to standard automated peptide synthesis techniques known to those skilled in the art. mPEG-NH$_2$ 20 kDa, stored at −20° C. under argon, is warmed to ambient temperature. The reaction is performed at room temperature. About 3-5-fold molar excess of mPEG-NH$_2$, PyBOP (benzotriazol-1-yloxy)tripyrrolidinonophosphonium hexafluorophosphate), and 1-hydroxybenzotriazole (HOBt) are used, based upon absolute peptide content. The mPEG-NH$_2$, PyBOP, HOBt are weighed into a glass vial containing a magnetic stirrer bar. A solution of Prot-LH is prepared in N,N-dimethylformamide is added and the mixture is stirred using a magnetic stirrer until the mPEG-NH$_2$ is fully dissolved. The stirring speed is reduced and the reaction is allowed to proceed to formation of conjugate product. The conjugate solution is then analyzed by SDS-PAGE and RP-HPLC (C18) to determine the extent of Prot-LH-$C^{ter}$-mPEG conjugate formation. The remaining protecting groups are removed under standard deprotection conditions to yield the LH-$C^{ter}$-mPEG conjugate.

Using this same approach, other conjugates are prepared using mPEG derivatives having other weight-average molecular weights that also bear an amino moiety.

c) mPEG-$N^{ter}$-LH Via mPEG-SMB

An mPEG-N-Hydroxysuccinimide is obtained having a molecular weight of 5 kDa and having the basic structure shown below:

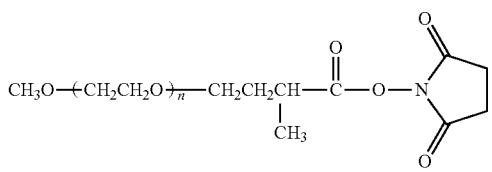

(mPEG-Succinimidyl α-Methylbutanoate Derivative, 5 kDa ("mPEG-SMB"))

mPEG-SMB, 5 kDa, stored at −20° C. under argon, is warmed to ambient temperature. A five-fold excess (relative to the amount of the peptide) of the warmed mPEG-SMB is dissolved in buffer to form a 10% reagent solution. The 10% reagent solution is quickly added to the aliquot of a stock LH solution and mixed well. After the addition of the mPEG-SMB, the pH of the reaction mixture is determined and adjusted to 6.7 to 6.8 using conventional techniques. To allow for coupling of the mPEG-SMB to the peptide via an amide linkage, the reaction solution is stirred for several hours (e.g., 5 hours) at room temperature in the dark or stirred overnight at 3-8° C. in a cold room, thereby resulting in a conjugate solution. The reaction is quenched with a 20-fold molar excess (with respect to the peptide) of Tris buffer.

Using this same approach, other conjugates are prepared using mPEG derivatives having other weight-average molecular weights that also bear an N-hydroxysuccinimide moiety.

Example 31

Terlipressin-mPEG Conjugates

Terlipressin is an analogue of vasopressin used as a vasoactive drug in the management of hypotension. It has been found to be effective when norepinephrine does not help. Indications for use include norepinephrine-resistant septic shock (O'Brien et al., *Lancet*, 2002, 359, 1209), hepatorenal syndrome (Gluud et al., *Cochrane Database of Systematic Reviews* 2006, Issue 3. Art. No.: CD005162. DOI: 10.1002/14651858.CD005162.pub2) and bleeding esophageal varices (Ioannou et al., *Cochrane Database of Systematic Reviews* 2003, Issue 1. Art. No.: CD002147. DOI: 10.1002/14651858.CD002147). Terlipressin has the sequence, Gly-Gly-Gly-cyclo-[Cys-Tyr-Phe-Gln-Asp-Cys]-Pro-Lys-GlyNH$_2$.

a) mPEG-$N^{ter}$-Terlipressin-Via mPEG-SPC

Terlipressin is prepared and purified according to standard automated peptide synthesis or recombinant techniques known to those skilled in the art. An illustrative polymeric reagent, mPEG-SPC reagent, is covalently attached to the N-terminus of Terlipressin, to provide a $N^{ter}$-conjugate form of the peptide. mPEG-SPC 20 kDa, stored at −20° C. under argon, is warmed to ambient temperature. The reaction is performed at room temperature. About 3-5-fold molar excess of mPEG-SPC 20 kDa reagent is used based upon absolute peptide content. The mPEG-SPC reagent is weighed into a glass vial containing a magnetic stirrer bar. A solution of Terlipressin prepared in phosphate buffered saline, PBS, pH 7.4 is added and the mixture is stirred using a magnetic stirrer until the mPEG-SPC is fully dissolved. The stirring speed is reduced and the reaction is allowed to proceed to formation of conjugate product. The reaction is optionally quenched to terminate the reaction. The pH of the conjugate solution at the end of the reaction is measured and further acidified by addition of 0.1M HCl, if necessary, to bring the pH of the final solution to about 5.5. The conjugate solution is then analyzed by SDS-PAGE and RP-HPLC (C18) to determine the extent of mPEG-$N^{ter}$-Terlipressin conjugate formation.

Using this same approach, other conjugates are prepared using mPEG derivatives having other weight-average molecular weights that also bear an N-hydroxysuccinimide moiety.

b) Terlipressin-$C^{ter}$-mPEG

An illustrative polymeric reagent, mPEG-NH$_2$ reagent is covalently attached to the C-terminus of Terlipressin, to provide a $C^{ter}$-conjugate form of the peptide. For coupling to the C-terminus, a protected Terlipressin lacking the C-terminus amide (Prot-Terlipressin, e.g., Fmoc-Gly-Gly-Gly-Cys(tBu)-Tyr(tBu)-Phe-Gln-Asp(tBu)-Cys(tBu)-Pro-Lys (Fmoc)-Gly-OH) is prepared and purified according to standard automated peptide synthesis techniques known to those skilled in the art. mPEG-NH$_2$ 20 kDa, stored at −20° C. under argon, is warmed to ambient temperature. The reaction is performed at room temperature. About 3-5-fold molar excess of mPEG-NH$_2$, PyBOP (benzotriazol-1-yloxy) tripyrrolidinonophosphonium hexafluorophosphate), and 1-hydroxybenzotriazole (HOBt) are used, based upon absolute peptide content. The mPEG-NH$_2$, PyBOP, HOBt are weighed into a glass vial containing a magnetic stirrer bar. A solution of Prot-Terlipressin is prepared in N,N-dimethylformamide is added and the mixture is stirred using a magnetic stirrer until the mPEG-NH$_2$ is fully dissolved. The stirring speed is reduced and the reaction is allowed to proceed to formation of conjugate product. The conjugate solution is then analyzed by SDS-PAGE and RP-HPLC (C18) to determine the extent of Prot-Terlipressin-$C^{ter}$-mPEG conjugate formation. The remaining protecting groups are removed under standard deprotection conditions to yield the Terlipressin-$C^{ter}$-mPEG conjugate.

Using this same approach, other conjugates are prepared using mPEG derivatives having other weight-average molecular weights that also bear an amino moiety.

c) Terlipressin-Cys(S-mPEG)

Terlipressin, which has a thiol-containing cysteine residue, is dissolved in buffer. To this peptide solution is added a 3-5 fold molar excess of mPEG-MAL, 5 kDa. The mixture is stirred at room temperature under an inert atmosphere for several hours. Analysis of the reaction mixture reveals successful conjugation of this peptide.

Using this same approach, other conjugates are prepared using mPEG-MAL having other weight average molecular weights.

d) mPEG-N$^{ter}$-Terlipressin Via mPEG-SMB mPEG-SMB, 5 kDa, stored at −20° C. under argon, is warmed to ambient temperature. A five-fold excess (relative to the amount of the peptide) of the warmed mPEG-SMB is dissolved in buffer to form a 10% reagent solution. The 10% reagent solution is quickly added to the aliquot of a stock Terlipressin solution and mixed well. After the addition of the mPEG-SMB, the pH of the reaction mixture is determined and adjusted to 6.7 to 6.8 using conventional techniques. To allow for coupling of the mPEG-SMB to the peptide via an amide linkage, the reaction solution is stirred for several hours (e.g., 5 hours) at room temperature in the dark or stirred overnight at 3-8° C. in a cold room, thereby resulting in a conjugate solution. The reaction is quenched with a 20-fold molar excess (with respect to the peptide) of Tris buffer.

Using this same approach, other conjugates are prepared using mPEG derivatives having other weight-average molecular weights that also bear an N-hydroxysuccinimide moiety.

e) Terlipressin-Lys-mPEG

PEG-SMB, 5 kDa, stored at −20° C. under argon, is warmed to ambient temperature. A five-fold excess (relative to the amount of the peptide) of the warmed mPEG-SMB is dissolved in buffer to form a 10% reagent solution. The 10% reagent solution is quickly added to the aliquot of a stock protected Terlipressin (e.g., Fmoc-Gly-Gly-Gly-Cys(tBu)-Tyr(tBu)-Phe-Gln-Asp(tBu)-Cys(tBu)-Pro-Lys-Gly-NH$_2$) solution and mixed well. After the addition of the mPEG-SMB, the pH of the reaction mixture is determined and adjusted to 6.7 to 6.8 using conventional techniques. To allow for coupling of the mPEG-SMB to the peptide via an amide linkage, the reaction solution is stirred for several hours (e.g., 5 hours) at room temperature in the dark or stirred overnight at 3-8° C. in a cold room, thereby resulting in a conjugate solution. The reaction is quenched with a 20-fold molar excess (with respect to the peptide) of Tris buffer. The remaining protecting groups are removed under standard deprotection conditions to yield the Terlipressin-Lys(O-mPEG) conjugate.

Using this same approach, other conjugates are prepared using mPEG derivatives having other weight-average molecular weights that also bear an N-hydroxysuccinimide moiety.

Example 32

Ecallantide-mPEG Conjugates

Ecallantide is a 60-amino acid peptide which is an inhibitor of the protein kallikrein used for hereditary angioedema and in the prevention of blood loss in cardiothoracic surgery (Lehmann, *Expert Opin. Biol. Ther.* 2008, 8, 1187). It has been shown to inhibit kallikrein in a laboratory investigation known as phage display (Lehmann, 2008). Ecallantide has the sequence Glu-Ala-Met-His-Ser-Phe-Cys-Ala-Phe-Lys-Ala-Asp-Asp-Gly-Pro-Cys-Arg-Ala-Ala-His-Pro-Arg-Trp-Phe-Phe-Asn-Ile-Phe-Thr-Arg-Gln-Cys-Glu-Glu-Phe-Ile-Tyr-Gly-Gly-Cys-Glu-Gly-Asn-Gln-Asn-Arg-Phe- Glu-Ser-Leu-Glu-Glu-Cys-Lys-Lys-Met-Cys-Thr-Arg-Asp (U.S. Pat. Appl. Pub. No. 20070213275).

a) mPEG-N$^{ter}$-Ecallantide-Via mPEG-SPC

Ecallantide is prepared and purified according to standard automated peptide synthesis or recombinant techniques known to those skilled in the art. An illustrative polymeric reagent, mPEG-SPC reagent, is covalently attached to the N-terminus of Ecallantide, to provide a N$^{ter}$-conjugate form of the peptide. mPEG-SPC 20 kDa, stored at −20° C. under argon, is warmed to ambient temperature. The reaction is performed at room temperature. About 3-5-fold molar excess of mPEG-SPC 20 kDa reagent is used based upon absolute peptide content. The mPEG-SPC reagent is weighed into a glass vial containing a magnetic stirrer bar. A solution of Ecallantide prepared in phosphate buffered saline, PBS, pH 7.4 is added and the mixture is stirred using a magnetic stirrer until the mPEG-SPC is fully dissolved. The stirring speed is reduced and the reaction is allowed to proceed to formation of conjugate product. The reaction is optionally quenched to terminate the reaction. The pH of the conjugate solution at the end of the reaction is measured and further acidified by addition of 0.1M HCl, if necessary, to bring the pH of the final solution to about 5.5. The conjugate solution is then analyzed by SDS-PAGE and RP-HPLC (C18) to determine the extent of mPEG-N$^{ter}$-Ecallantide conjugate formation.

Using this same approach, other conjugates are prepared using mPEG derivatives having other weight-average molecular weights that also bear an N-hydroxysuccinimide moiety.

b) Ecallantide-$C^{ter}$-mPEG

An illustrative polymeric reagent, mPEG-NH$_2$ reagent is covalently attached to the C-terminus of Ecallantide, to provide a $C^{ter}$-conjugate form of the peptide. For coupling to the C-terminus, a protected Ecallantide (Prot-Ecallantide, e.g., Fmoc-Glu(tBu)-Ala-Met-His-Ser(tBu)-Phe-Cys(tBu)-Ala-Phe-Lys(Fmoc)-Ala-Asp(tBu)-Asp(tBu)-Gly-Pro-Cys (tBu)-Arg(Tos)-Ala-Ala-His-Pro-Arg(Tos)- Trp-Phe-Phe-Asn-Ile-Phe-Thr(tBu)-Arg(Tos)-Gln-Cys(tBu)-Glu(tBu)-

Glu(tBu)-Phe-Ile-Tyr(tBu)-Gly-Gly-Cys(tBu)-Glu(tBu)-Gly-Asn-Gln-Asn-Arg(Tos)-Phe-Glu(tBu)-Ser(tBu)-Leu-Glu(tBu)-Glu(tBu)-Cys(tBu)-Lys(Fmoc)- Lys(Fmoc)-Met-Cys (tBu)-Thr(tBu)-Arg(Tos)-Asp(tBu)-OH) is prepared and purified according to standard automated peptide synthesis techniques known to those skilled in the art. mPEG-NH$_2$ 20 kDa, stored at −20° C. under argon, is warmed to ambient temperature. The reaction is performed at room temperature. About 3-5-fold molar excess of mPEG-NH$_2$, PyBOP (benzotriazol-1-yloxy)tripyrrolidinonophosphonium hexafluorophosphate), and 1-hydroxybenzotriazole (HOBt) are used, based upon absolute peptide content. The mPEG-NH$_2$, PyBOP, HOBt are weighed into a glass vial containing a magnetic stirrer bar. A solution of Prot-Ecallantide is prepared in N,N-dimethylformamide is added and the mixture is stirred using a magnetic stirrer until the mPEG-NH$_2$ is fully dissolved. The stirring speed is reduced and the reaction is allowed to proceed to formation of conjugate product. The conjugate solution is then analyzed by SDS-PAGE and RP-HPLC (C18) to determine the extent of Prot-Ecallantide-C$^{ter}$-mPEG conjugate formation. The remaining protecting groups are removed under standard deprotection conditions to yield the Ecallantide-C$^{ter}$-mPEG conjugate.

Using this same approach, other conjugates are prepared using mPEG derivatives having other weight-average molecular weights that also bear an amino moiety.

c) Ecallantide-Cys(S-mPEG)

Ecallantide, which has a thiol-containing cysteine residue, is dissolved in buffer. To this peptide solution is added a 3-5 fold molar excess of mPEG-MAL, 5 kDa. The mixture is stirred at room temperature under an inert atmosphere for several hours. Analysis of the reaction mixture reveals successful conjugation of this peptide.

Using this same approach, other conjugates are prepared using mPEG-MAL having other weight average molecular weights.

d) mPEG-$N^{ter}$-Ecallantide Via mPEG-SMB mPEG-SMB, 5 kDa, stored at −20° C. under argon, is warmed to ambient temperature. A five-fold excess (relative to the amount of the peptide) of the warmed mPEG-SMB is dissolved in buffer to form a 10% reagent solution. The 10% reagent solution is quickly added to the aliquot of a stock Ecallantide solution and mixed well. After the addition of the mPEG-SMB, the pH of the reaction mixture is determined and adjusted to 6.7 to 6.8 using conventional techniques. To allow for coupling of the mPEG-SMB to the peptide via an amide linkage, the reaction solution is stirred for several hours (e.g., 5 hours) at room temperature in the dark or stirred overnight at 3-8° C. in a cold room, thereby resulting in a conjugate solution. The reaction is quenched with a 20-fold molar excess (with respect to the peptide) of Tris buffer.

Using this same approach, other conjugates are prepared using mPEG derivatives having other weight-average molecular weights that also bear an N-hydroxysuccinimide moiety.

e) Ecallantide-Lys-mPEG

PEG-SMB, 5 kDa, stored at −20° C. under argon, is warmed to ambient temperature. A five-fold excess (relative to the amount of the peptide) of the warmed mPEG-SMB is dissolved in buffer to form a 10% reagent solution. The 10% reagent solution is quickly added to the aliquot of a stock protected Ecallantide (e.g., Fmoc-Glu(tBu)-Ala-Met-His-Ser(tBu)-Phe-Cys(tBu)-Ala-Phe-Lys-Ala-Asp(tBu)-Asp (tBu)-Gly-Pro-Cys(tBu)-Arg(Tos)-Ala-Ala-His-Pro-Arg (Tos)- Trp-Phe-Phe-Asn-Ile-Phe-Thr(tBu)-Arg(Tos)-Gln-Cys(tBu)-Glu(tBu)-Glu(tBu)-Phe-Ile-Tyr(tBu)-Gly-Gly-Cys(tBu)-Glu(tBu)-Gly-Asn-Gln-Asn-Arg(Tos)-Phe-Glu (tBu)-Ser(tBu)-Leu-Glu(tBu)-Glu(tBu)-Cys(tBu)-Lys (Fmoc)- Lys(Fmoc)-Met-Cys(tBu)-Thr(tBu)-Arg(Tos)-Asp (tBu)-$NH_2$) solution and mixed well. After the addition of the mPEG-SMB, the pH of the reaction mixture is determined and adjusted to 6.7 to 6.8 using conventional techniques. To allow for coupling of the mPEG-SMB to the peptide via an amide linkage, the reaction solution is stirred for several hours (e.g., 5 hours) at room temperature in the dark or stirred overnight at 3-8° C. in a cold room, thereby resulting in a conjugate solution. The reaction is quenched with a 20-fold molar excess (with respect to the peptide) of Tris buffer. The remaining protecting groups are removed under standard deprotection conditions to yield the Ecallantide-Lys(O-mPEG) conjugate.

Using this same approach, other conjugates are prepared using mPEG derivatives having other weight-average molecular weights that also bear an N-hydroxysuccinimide moiety.

Example 33

Calphobindin I-mPEG Conjugates

Calphobindin I (CPB-I, annexin V) is an anticoagulant protein purified from human placenta; it is a member of the annexin family that binds phospholipids in a calcium-dependent manner. CPB-I helps reepithelialization through the promotion of both uPA synthesis and migration of keratinocytes without stimulating their proliferation (Nakao et al., Eur. J. Biochem. 2005, 223, 901). Calphobindin I has the sequence, Ala Gln Val Leu Arg Gly Thr Val Thr Asp Phe Pro Gly Phe Asp Glu Arg Ala Asp Ala Glu Thr Leu Arg Lys Ala Met Lys Gly Leu Gly Thr Asp Glu Glu Ser Ile Leu Thr Leu Leu Thr Ser Arg Ser Asn Ala Gln Arg Gln Glu Ile Ser Ala Ala Phe Lys Thr Leu Phe Gly Arg Asp Leu Leu Asp Asp Leu Lys Ser Glu Leu Thr Gly Lys Phe Glu Lys Leu Ile Val Ala Leu Met Lys Pro Ser Arg Leu Tyr Asp Ala Tyr Glu Leu Lys His Ala Leu Lys Gly Ala Gly Thr Asn Glu Lys Val Leu Thr Glu Ile Ile Ala Ser Arg Thr Pro Glu Glu Leu Arg Ala Ile Lys Gln Val Tyr Glu Glu Glu Tyr Gly Ser Ser Leu Glu Asp Asp Val Val Gly Asp Thr Ser Gly Tyr Tyr Gln Arg Met Leu Val Val Leu Leu Gln Ala Asn Arg Asp Pro Asp Ala Gly Ile Asp Glu Ala Gln Val Glu Gln Asp Ala Gln Ala Leu Phe Gln Ala Gly Glu Leu Lys Trp Gly Thr Asp Glu Glu Lys Phe Ile Thr Ile Phe Gly Thr Arg Ser Val Ser His Leu Arg Lys Val Phe Asp Lys Tyr Met Thr Ile Ser Gly Phe Gln Ile Glu Glu Thr Ile Asp Arg Glu Thr Ser Gly Asn Leu Glu Gln Leu Leu Leu Ala Val Val Lys Ser Ile Arg Ser Ile Pro Ala Tyr Leu Ala Glu Thr Leu Tyr Tyr Ala Met Lys Gly Ala Gly Thr Asp Asp His Thr Leu Ile Arg Val Met Val Ser Arg Ser Glu Ile Asp Leu Phe Asn Ile Arg Lys Glu Phe Arg Lys Asn Phe Ala Thr Ser Leu Tyr Ser Met Ile Lys Gly Asp Thr Ser Gly Asp Tyr Lys Lys Ala Leu Leu Leu Leu Cys Gly Glu Asp Asp (U.S. Pat. No. 7,393, 833).

a) mPEG-$N^{ter}$-CPB-I-Via mPEG-SPC

CPB-I is prepared and purified according to standard recombinant techniques known to those skilled in the art. An illustrative polymeric reagent, mPEG-SPC reagent, is covalently attached to the N-terminus of CPB-I, to provide a $N^{ter}$-conjugate form of the peptide. mPEG-SPC 20 kDa, stored at −20° C. under argon, is warmed to ambient temperature. The reaction is performed at room temperature. About 3-5-fold molar excess of mPEG-SPC 20 kDa reagent is used based upon absolute peptide content. The mPEG-SPC reagent is weighed into a glass vial containing a magnetic stirrer bar. A solution of CPB-I prepared in phosphate buffered saline, PBS, pH 7.4 is added and the mixture is stirred using a magnetic stirrer until the mPEG-SPC is fully dissolved. The stirring speed is reduced and the reaction is allowed to proceed to formation of conjugate product. The reaction is optionally quenched to terminate the reaction. The pH of the conjugate solution at the end of the reaction is measured and further acidified by addition of 0.1M HCl, if necessary, to bring the pH of the final solution to about 5.5. The conjugate solution is then analyzed by SDS-PAGE and RP-HPLC (C18) to determine the extent of mPEG-$N^{ter}$-CPB-I conjugate formation.

Using this same approach, other conjugates are prepared using mPEG derivatives having other weight-average molecular weights that also bear an N-hydroxysuccinimide moiety.

b) CPB-I-$C^{ter}$-mPEG

An illustrative polymeric reagent, mPEG-$NH_2$ reagent is covalently attached to the C-terminus of CPB-I, to provide a $C^{ter}$-conjugate form of the peptide. mPEG-$NH_2$ 20 kDa, stored at −20° C. under argon, is warmed to ambient temperature. The reaction is performed at room temperature. About 3-5-fold molar excess of mPEG-$NH_2$, PyBOP (benzotriazol-1-yloxy)tripyrrolidinonophosphonium hexafluorophosphate), and 1-hydroxybenzotriazole (HOBt) are used, based upon absolute peptide content. The mPEG-$NH_2$, PyBOP, HOBt are weighed into a glass vial containing a magnetic stirrer bar. A solution of CPB-I is prepared in N,N-dimethylformamide is added and the mixture is stirred using a magnetic stirrer until the mPEG-$NH_2$ is fully dissolved. The stirring speed is reduced and the reaction is allowed to proceed to formation of conjugate product. The conjugate solution is then analyzed by SDS-PAGE and RP-HPLC (C18) to determine the extent of CPB-I-$C^{ter}$-mPEG conjugate formation. The $C^{ter}$ conjugate is isolated and purified according the general procedure outlined above.

Using this same approach, other conjugates are prepared using mPEG derivatives having other weight-average molecular weights that also bear an amino moiety.

c) CPB-I-Cys(S-mPEG)

CPB-I, which has a thiol-containing cysteine residue, is dissolved in buffer. To this peptide solution is added a 3-5 fold molar excess of mPEG-MAL, 5 kDa. The mixture is stirred at room temperature under an inert atmosphere for several hours. Analysis of the reaction mixture reveals successful conjugation of this peptide.

Using this same approach, other conjugates are prepared using mPEG-MAL having other weight average molecular weights.

d) mPEG-$N^{ter}$-CPB-I Via mPEG-SMB mPEG-SMB, 5 kDa, stored at −20° C. under argon, is warmed to ambient temperature. A five-fold excess (relative to the amount of the peptide) of the warmed mPEG-SMB is dissolved in buffer to form a 10% reagent solution. The 10% reagent solution is quickly added to the aliquot of a stock CPB-I solution and mixed well. After the addition of the mPEG-SMB, the pH of the reaction mixture is determined and adjusted to 6.7 to 6.8 using conventional techniques. To allow for coupling of the mPEG-SMB to the peptide via an amide linkage, the reaction solution is stirred for several hours (e.g., 5 hours) at room temperature in the dark or stirred overnight at 3-8° C. in a cold room, thereby resulting in a conjugate solution. The reaction is quenched with a 20-fold molar excess (with respect to the peptide) of Tris buffer.

Using this same approach, other conjugates are prepared using mPEG derivatives having other weight-average molecular weights that also bear an N-hydroxysuccinimide moiety.

e) CPB-I-Lys-mPEG

PEG-SMB, 5 kDa, stored at −20° C. under argon, is warmed to ambient temperature. A five-fold excess (relative to the amount of the peptide) of the warmed mPEG-SMB is dissolved in buffer to form a 10% reagent solution. The 10% reagent solution is quickly added to the aliquot of a stock CPB-I solution and mixed well. After the addition of the mPEG-SMB, the pH of the reaction mixture is determined and adjusted to 6.7 to 6.8 using conventional techniques. To allow for coupling of the mPEG-SMB to the peptide via an amide linkage, the reaction solution is stirred for several hours (e.g., 5 hours) at room temperature in the dark or stirred overnight at 3-8° C. in a cold room, thereby resulting in a conjugate solution. The reaction is quenched with a 20-fold molar excess (with respect to the peptide) of Tris buffer. The Lys conjugate is isolated and purified according the general procedure outlined above to yield the CPB-I-Lys-mPEG conjugate.

Using this same approach, other conjugates are prepared using mPEG derivatives having other weight-average molecular weights that also bear an N-hydroxysuccinimide moiety.

Example 34

Tiplimotide-mPEG Conjugates

Tiplimotide is the myelin basic protein peptide, amino acid sequence 83-99, D-Ala-Lys-Pro-Val-Val-His-Leu-Phe-Ala-Asn-Ile-Val-Thr-Pro-Arg-Thr-Pro, (U.S. Pat. No. 6,379,670). Subcutaneous administration of tiplimotide in multiple sclerosis patients can induce an APL-reactive immune response in which T lymphocytes cross-reactive with the immunodominant neuroantigen MBP secrete anti-inflammatory cytokines (Crowe et al., Ann. Neurol. 2000, 48, 758).

a) mPEG-$N^{ter}$-Tiplimotide-Via mPEG-SPC

Tiplimotide is prepared and purified according to standard automated peptide synthesis or recombinant techniques known to those skilled in the art. An illustrative polymeric reagent, mPEG-SPC reagent, is covalently attached to the N-terminus of Tiplimotide, to provide a $N^{ter}$-conjugate form of the peptide. mPEG-SPC 20 kDa, stored at −20° C. under argon, is warmed to ambient temperature. The reaction is performed at room temperature. About 3-5-fold molar excess of mPEG-SPC 20 kDa reagent is used based upon absolute peptide content. The mPEG-SPC reagent is weighed into a glass vial containing a magnetic stirrer bar. A solution of Tiplimotide prepared in phosphate buffered saline, PBS, pH 7.4 is added and the mixture is stirred using a magnetic stirrer until the mPEG-SPC is fully dissolved. The stirring speed is reduced and the reaction is allowed to proceed to formation of conjugate product. The reaction is optionally quenched to terminate the reaction. The pH of the conjugate solution at the end of the reaction is measured and further acidified by addition of 0.1M HCl, if necessary, to bring the pH of the final solution to about 5.5. The conjugate solution is then analyzed by SDS-PAGE and RP-HPLC (C18) to determine the extent of mPEG-$N^{ter}$-Tiplimotide conjugate formation.

Using this same approach, other conjugates are prepared using mPEG derivatives having other weight-average molecular weights that also bear an N-hydroxysuccinimide moiety.

b) Tiplimotide-$C^{ter}$-mPEG

An illustrative polymeric reagent, mPEG-NH$_2$ reagent is covalently attached to the C-terminus of Tiplimotide, to provide a $C^{ter}$-conjugate form of the peptide. For coupling to the C-terminus, a protected Tiplimotide (Prot-Tiplimotide, e.g., Fmoc-D-Ala-Lys(Fmoc)-Pro-Val-Val-His-Leu-Phe-Ala-Asn-Ile-Val-Thr(tBu)-Pro-Arg(Tos)-Thr(tBu)-Pro) is prepared and purified according to standard automated peptide synthesis techniques known to those skilled in the art. mPEG-NH$_2$ 20 kDa, stored at −20° C. under argon, is warmed to ambient temperature. The reaction is performed at room temperature. About 3-5-fold molar excess of mPEG-NH$_2$, PyBOP (benzotriazol-1-yloxy)tripyrrolidinonophosphonium hexafluorophosphate), and 1-hydroxybenzotriazole (HOBt) are used, based upon absolute peptide content. The mPEG-NH$_2$, PyBOP, HOBt are weighed into a glass vial containing a magnetic stirrer bar. A solution of Prot-Tiplimotide is prepared in N,N-dimethylformamide is added and the mixture is stirred using a magnetic stirrer until the mPEG-NH$_2$ is fully dissolved. The stirring speed is reduced and the reaction is allowed to proceed to formation of conjugate product. The conjugate solution is then analyzed by SDS-PAGE and RP-HPLC (C18) to determine the extent of Prot-Tiplimotide-$C^{ter}$-mPEG conjugate formation. The remaining protecting groups are removed under standard deprotection conditions to yield the Tiplimotide-$C^{ter}$-mPEG conjugate.

Using this same approach, other conjugates are prepared using mPEG derivatives having other weight-average molecular weights that also bear an amino moiety.

c) mPEG-$N^{ter}$-Tiplimotide Via mPEG-SMB mPEG-SMB, 5 kDa, stored at −20° C. under argon, is warmed to ambient temperature. A five-fold excess (relative to the amount of the peptide) of the warmed mPEG-SMB is dissolved in buffer to form a 10% reagent solution. The 10% reagent solution is quickly added to the aliquot of a stock Tiplimotide solution and mixed well. After the addition of the mPEG-SMB, the pH of the reaction mixture is determined and adjusted to 6.7 to 6.8 using conventional techniques. To allow for coupling of the mPEG-SMB to the peptide via an amide linkage, the reaction solution is stirred for several hours (e.g., 5 hours) at room temperature in the dark or stirred overnight at 3-8° C. in a cold room, thereby resulting in a conjugate solution. The reaction is quenched with a 20-fold molar excess (with respect to the peptide) of Tris buffer.

Using this same approach, other conjugates are prepared using mPEG derivatives having other weight-average molecular weights that also bear an N-hydroxysuccinimide moiety.

d) Tiplimotide-Lys-mPEG

PEG-SMB, 5 kDa, stored at −20° C. under argon, is warmed to ambient temperature. A five-fold excess (relative to the amount of the peptide) of the warmed mPEG-SMB is dissolved in buffer to form a 10% reagent solution. The 10% reagent solution is quickly added to the aliquot of a stock protected Tiplimotide (e.g., Fmoc-D-Ala-Lys-Pro-Val-Val-His-Leu-Phe-Ala-Asn-Ile-Val-Thr(tBu)-Pro-Arg(Tos)-Thr(tBu)-Pro-O(tBu)) solution and mixed well. After the addition of the mPEG-SMB, the pH of the reaction mixture is determined and adjusted to 6.7 to 6.8 using conventional techniques. To allow for coupling of the mPEG-SMB to the peptide via an amide linkage, the reaction solution is stirred for several hours (e.g., 5 hours) at room temperature in the dark or stirred overnight at 3-8° C. in a cold room, thereby resulting in a conjugate solution. The reaction is quenched with a 20-fold molar excess (with respect to the peptide) of Tris buffer. The remaining protecting groups are removed under standard deprotection conditions to yield the Tiplimotide-Lys(O-mPEG) conjugate.

Using this same approach, other conjugates are prepared using mPEG derivatives having other weight-average molecular weights that also bear an N-hydroxysuccinimide moiety.

Example 35

Osteogenic Growth Peptide-mPEG Conjugates

Osteogenic growth peptide (OGP) is a circulating stimulator of osteoblastic activity; identical to the C-terminus of histone H4 having the sequence, Ala-Leu-Lys-Arg-Gln-Gly-Arg-Thr-Leu-Tyr-Gly-Phe-Gly-Gly (PubChem Compound ID: 16132186). In particular, osteogenic growth peptide has been shown to have a regulatory role in bone formation and hemopoiesis (Bab and Chorev, *Biopolymers* 2002, 66, 33).

a) mPEG-$N^{ter}$-OGP-Via mPEG-SPC

OGP is prepared and purified according to standard automated peptide synthesis or recombinant techniques known to those skilled in the art. An illustrative polymeric reagent, mPEG-SPC reagent, is covalently attached to the N-terminus of OGP, to provide a $N^{ter}$-conjugate form of the peptide. mPEG-SPC 20 kDa, stored at −20° C. under argon, is warmed to ambient temperature. The reaction is performed at room temperature. About 3-5-fold molar excess of mPEG-SPC 20 kDa reagent is used based upon absolute peptide content. The mPEG-SPC reagent is weighed into a glass vial containing a magnetic stirrer bar. A solution of OGP prepared in phosphate buffered saline, PBS, pH 7.4 is added and the mixture is stirred using a magnetic stirrer until the mPEG-SPC is fully dissolved. The stirring speed is reduced and the reaction is allowed to proceed to formation of conjugate product. The reaction is optionally quenched to terminate the reaction. The pH of the conjugate solution at the end of the reaction is measured and further acidified by addition of 0.1M HCl, if necessary, to bring the pH of the final solution to about 5.5. The conjugate solution is then analyzed by SDS-PAGE and RP-HPLC (C18) to determine the extent of mPEG-$N^{ter}$-OGP conjugate formation.

Using this same approach, other conjugates are prepared using mPEG derivatives having other weight-average molecular weights that also bear an N-hydroxysuccinimide moiety.

b) OGP-$C^{ter}$-mPEG

An illustrative polymeric reagent, mPEG-NH$_2$ reagent is covalently attached to the C-terminus of OGP, to provide a $C^{ter}$-conjugate form of the peptide. For coupling to the C-terminus, a protected OGP (Prot-OGP, e.g., Fmoc-Ala-Leu-Lys(Fmoc)-Arg(Tos)-Gln-Gly-Arg(Boc)-Thr(tBu)-Leu-Tyr(tBu)-Gly-Phe-Gly-Gly) is prepared and purified according to standard automated peptide synthesis techniques known to those skilled in the art. mPEG-NH$_2$ 20 kDa, stored at −20° C. under argon, is warmed to ambient temperature. The reaction is performed at room temperature. About 3-5-fold molar excess of mPEG-NH$_2$, PyBOP (benzotriazol-1-yloxy)tripyrrolidinonophosphonium hexafluorophosphate), and 1-hydroxybenzotriazole (HOBt) are used, based upon absolute peptide content. The mPEG-NH$_2$, PyBOP, HOBt are weighed into a glass vial containing a magnetic stirrer bar. A solution of Prot-OGP is prepared in N,N-dimethylformamide is added and the mixture is stirred using a magnetic stirrer until the mPEG-NH$_2$ is fully dissolved. The stirring speed is reduced and the reaction is allowed to proceed to formation of conjugate product. The conjugate solution is then analyzed by SDS-PAGE and RP-HPLC (C18) to determine the extent of Prot-OGP-C$^{ter}$-mPEG conjugate formation. The remaining protecting groups are removed under standard deprotection conditions to yield the OGP-C$^{ter}$-mPEG conjugate.

Using this same approach, other conjugates are prepared using mPEG derivatives having other weight-average molecular weights that also bear an amino moiety.

c) mPEG-N$^{ter}$-OGP Via mPEG-SMB mPEG-SMB, 5 kDa, stored at −20° C. under argon, is warmed to ambient temperature. A five-fold excess (relative to the amount of the peptide) of the warmed mPEG-SMB is dissolved in buffer to form a 10% reagent solution. The 10% reagent solution is quickly added to the aliquot of a stock OGP solution and mixed well. After the addition of the mPEG-SMB, the pH of the reaction mixture is determined and adjusted to 6.7 to 6.8 using conventional techniques. To allow for coupling of the mPEG-SMB to the peptide via an amide linkage, the reaction solution is stirred for several hours (e.g., 5 hours) at room temperature in the dark or stirred overnight at 3-8° C. in a cold room, thereby resulting in a conjugate solution. The reaction is quenched with a 20-fold molar excess (with respect to the peptide) of Tris buffer.

Using this same approach, other conjugates are prepared using mPEG derivatives having other weight-average molecular weights that also bear an N-hydroxysuccinimide moiety.

d) OGP-Lys-mPEG

PEG-SMB, 5 kDa, stored at −20° C. under argon, is warmed to ambient temperature. A five-fold excess (relative to the amount of the peptide) of the warmed mPEG-SMB is dissolved in buffer to form a 10% reagent solution. The 10% reagent solution is quickly added to the aliquot of a stock protected OGP (e.g., Fmoc-Ala-Leu-Lys-Arg(Tos)-Gln-Gly-Arg(Boc)-Thr(tBu)-Leu-Tyr(tBu)-Gly-Phe-Gly-Gly-O(tBu)) solution and mixed well. After the addition of the mPEG-SMB, the pH of the reaction mixture is determined and adjusted to 6.7 to 6.8 using conventional techniques. To allow for coupling of the mPEG-SMB to the peptide via an amide linkage, the reaction solution is stirred for several hours (e.g., 5 hours) at room temperature in the dark or stirred overnight at 3-8° C. in a cold room, thereby resulting in a conjugate solution. The reaction is quenched with a 20-fold molar excess (with respect to the peptide) of Tris buffer. The remaining protecting groups are removed under standard deprotection conditions to yield the OGP-Lys(O-mPEG) conjugate.

Using this same approach, other conjugates are prepared using mPEG derivatives having other weight-average molecular weights that also bear an N-hydroxysuccinimide moiety.

Example 36

Myelin Basic Protein-mPEG Conjugates

Myelin basic protein (MBP) is believed to be important in the process of myelination of nerves in the central nervous system. Myelin basic protein (MBP) binds to the cytosolic surface of oligodendrocyte membranes via negatively charged lipids and is responsible for adhesion of these surfaces in the multilayered myelin sheath (Musse and Harauz, *Int. Rev. Neurobiol.* 2007, 79, 149). Human myelin basic protein has the sequence, MASQKRPSQR HGSKY-LATAS TMDHARHGFL PRHRDTGILD SIGRFFGGDR GAPKRGSGKV PWLKPGRSPL PSHARSQPGL CNMYKDSHHP ARTAHYGSLP QKSHGRTQDE NPV-VHFFKNI VTPRTPPPSQ GKGRGLSLSR FSWGAE-GQRP GFGYGGRASD YKSAHKGFKG VDAQGTLSKI FKLGGRDSRS GSPMARR (PubChem Protein Accession No. CAA351749; Streicher and Stoffel, *Biol. Chem. Hoppe-Seyler* 1989, 370 (5), 503).

a) mPEG-N$^{ter}$-MBP-Via mPEG-SPC

MBP is prepared and purified according to standard recombinant techniques known to those skilled in the art. An illustrative polymeric reagent, mPEG-SPC reagent, is covalently attached to the N-terminus of MBP, to provide a N$^{ter}$-conjugate form of the peptide. mPEG-SPC 20 kDa, stored at −20° C. under argon, is warmed to ambient temperature. The reaction is performed at room temperature. About 3-5-fold molar excess of mPEG-SPC 20 kDa reagent is used based upon absolute peptide content. The mPEG-SPC reagent is weighed into a glass vial containing a magnetic stirrer bar. A solution of MBP prepared in phosphate buffered saline, PBS, pH 7.4 is added and the mixture is stirred using a magnetic stirrer until the mPEG-SPC is fully dissolved. The stirring speed is reduced and the reaction is allowed to proceed to formation of conjugate product. The reaction is optionally quenched to terminate the reaction. The pH of the conjugate solution at the end of the reaction is measured and further acidified by addition of 0.1M HCl, if necessary, to bring the pH of the final solution to about 5.5. The conjugate solution is then analyzed by SDS-PAGE and RP-HPLC (C18) to determine the extent of mPEG-N$^{ter}$-MBP conjugate formation.

Using this same approach, other conjugates are prepared using mPEG derivatives having other weight-average molecular weights that also bear an N-hydroxysuccinimide moiety.

b) MBP-C$^{ter}$-mPEG

An illustrative polymeric reagent, mPEG-NH$_2$ reagent is covalently attached to the C-terminus of MBP, to provide a C$^{ter}$-conjugate form of the peptide. For coupling to the C-terminus, mPEG-NH$_2$ 20 kDa, stored at −20° C. under argon, is warmed to ambient temperature. The reaction is performed at room temperature. About 3-5-fold molar excess of mPEG-NH$_2$, PyBOP (benzotriazol-1-yloxy)tripyrrolidinonophosphonium hexafluorophosphate), and 1-hydroxybenzotriazole (HOBt) are used, based upon absolute peptide content. The mPEG-NH$_2$, PyBOP, HOBt are weighed into a glass vial containing a magnetic stirrer bar. A solution of MBP is prepared in N,N-dimethylformamide is added and the mixture is stirred using a magnetic stirrer until the mPEG-NH$_2$ is fully dissolved. The stirring speed is reduced and the reaction is allowed to proceed to formation of conjugate product. The conjugate solution is then analyzed by SDS-PAGE and RP-HPLC (C18) to determine the extent of MBP-C$^{ter}$-mPEG conjugate formation. The C$^{ter}$ conjugate is isolated and purified according the general procedure outlined above.

Using this same approach, other conjugates are prepared using mPEG derivatives having other weight-average molecular weights that also bear an amino moiety.

c) MBP-Cys(S-mPEG)

MBP, which has a thiol-containing cysteine residue, is dissolved in buffer. To this peptide solution is added a 3-5 fold molar excess of mPEG-MAL, 5 kDa. The mixture is stirred at room temperature under an inert atmosphere for several hours. Analysis of the reaction mixture reveals successful conjugation of this peptide.

Using this same approach, other conjugates are prepared using mPEG-MAL having other weight average molecular weights.

d) mPEG-N$^{ter}$-MBP Via mPEG-SMB mPEG-SMB, 5 kDa, stored at −20° C. under argon, is warmed to ambient temperature. A five-fold excess (relative to the amount of the peptide) of the warmed mPEG-SMB is dissolved in buffer to form a 10% reagent solution. The 10% reagent solution is quickly added to the aliquot of a stock MBP solution and mixed well. After the addition of the mPEG-SMB, the pH of the reaction mixture is determined and adjusted to 6.7 to 6.8 using conventional techniques. To allow for coupling of the mPEG-SMB to the peptide via an amide linkage, the reaction solution is stirred for several hours (e.g., 5 hours) at room temperature in the dark or stirred overnight at 3-8° C. in a cold room, thereby resulting in a conjugate solution. The reaction is quenched with a 20-fold molar excess (with respect to the peptide) of Tris buffer.

Using this same approach, other conjugates are prepared using mPEG derivatives having other weight-average molecular weights that also bear an N-hydroxysuccinimide moiety.

e) MBP-Lys-mPEG

PEG-SMB, 5 kDa, stored at −20° C. under argon, is warmed to ambient temperature. A five-fold excess (relative to the amount of the peptide) of the warmed mPEG-SMB is dissolved in buffer to form a 10% reagent solution. The 10% reagent solution is quickly added to the aliquot of a stock MBP solution and mixed well. After the addition of the mPEG-SMB, the pH of the reaction mixture is determined and adjusted to 6.7 to 6.8 using conventional techniques. To allow for coupling of the mPEG-SMB to the peptide via an amide linkage, the reaction solution is stirred for several hours (e.g., 5 hours) at room temperature in the dark or stirred overnight at 3-8° C. in a cold room, thereby resulting in a conjugate solution. The reaction is quenched with a 20-fold molar excess (with respect to the peptide) of Tris buffer. The Lys conjugate is isolated and purified according the general procedure outlined above to yield the MBP-Lys-mPEG conjugate.

Using this same approach, other conjugates are prepared using mPEG derivatives having other weight-average molecular weights that also bear an N-hydroxysuccinimide moiety.

Example 37

Dynorphin A-mPEG Conjugates

Dynorphin A is a member of a class of opiod peptides that arise from cleavage of a precursor protein, prodynorphin and is a 17 amino acid peptide having the sequence, Tyr-Gly-Gly-Phe-Leu-Arg-Arg-Ile-Arg-Pro-Lys-Leu-Lys-Trp-Asp-Asn-Gln (PubChem Substance ID No. 4731). Dynorphins primarily exert their effects through the κ-opioid receptor (KOR), a G-protein coupled receptor and have been shown to play a role as central nervous system transmitters. Dynorphin A has been proposed for uses including the suppression of the cytotoxic activity of mammalian Natural Killer (NK) cells in recipients of transplanted tissue and individuals suffering from autoimmune diseases (U.S. Pat. No. 5,817,628).

a) mPEG-N$^{ter}$-Dynorphin A-Via mPEG-SPC

Dynorphin A is prepared and purified according to standard automated peptide synthesis or recombinant techniques known to those skilled in the art. An illustrative polymeric reagent, mPEG-SPC reagent, is covalently attached to the N-terminus of Dynorphin A, to provide a N$^{ter}$-conjugate form of the peptide. mPEG-SPC 20 kDa, stored at −20° C. under argon, is warmed to ambient temperature. The reaction is performed at room temperature. About 3-5-fold molar excess of mPEG-SPC 20 kDa reagent is used based upon absolute peptide content. The mPEG-SPC reagent is weighed into a glass vial containing a magnetic stirrer bar. A solution of Dynorphin A prepared in phosphate buffered saline, PBS, pH 7.4 is added and the mixture is stirred using a magnetic stirrer until the mPEG-SPC is fully dissolved. The stirring speed is reduced and the reaction is allowed to proceed to formation of conjugate product. The reaction is optionally quenched to terminate the reaction. The pH of the conjugate solution at the end of the reaction is measured and further acidified by addition of 0.1M HCl, if necessary, to bring the pH of the final solution to about 5.5. The conjugate solution is then analyzed by SDS-PAGE and RP-HPLC (C18) to determine the extent of mPEG-N$^{ter}$-Dynorphin A conjugate formation.

Using this same approach, other conjugates are prepared using mPEG derivatives having other weight-average molecular weights that also bear an N-hydroxysuccinimide moiety.

b) Dynorphin A-C$^{ter}$-mPEG

An illustrative polymeric reagent, mPEG-NH$_2$ reagent is covalently attached to the C-terminus of Dynorphin A, to provide a C$^{ter}$-conjugate form of the peptide. For coupling to the C-terminus, a protected Dynorphin A (Prot-Dynorphin A, e.g., Fmoc-Tyr(tBu)-Gly-Gly-Phe-Leu-Arg(Tos)-Arg(Tos)-Ile-Arg(Tos)-Pro-Lys(Fmoc)-Leu-Lys(Fmoc)-Trp-Asp(tBu)-Asn-Gln) is prepared and purified according to standard automated peptide synthesis techniques known to those skilled in the art. mPEG-NH$_2$ 20 kDa, stored at −20° C. under argon, is warmed to ambient temperature. The reaction is performed at room temperature. About 3-5-fold molar excess of mPEG-NH$_2$, PyBOP (benzotriazol-1-yloxy) tripyrrolidinonophosphonium hexafluorophosphate), and 1-hydroxybenzotriazole (HOBt) are used, based upon absolute peptide content. The mPEG-NH$_2$, PyBOP, HOBt are weighed into a glass vial containing a magnetic stirrer bar. A solution of Prot-Dynorphin A is prepared in N,N-dimethylformamide is added and the mixture is stirred using a magnetic stirrer until the mPEG-NH$_2$ is fully dissolved. The stirring speed is reduced and the reaction is allowed to proceed to formation of conjugate product. The conjugate solution is then analyzed by SDS-PAGE and RP-HPLC (C18) to determine the extent of Prot-Dynorphin A-C$^{ter}$-mPEG conjugate formation. The remaining protecting groups are removed under standard deprotection conditions to yield the Dynorphin A-C$^{ter}$-mPEG conjugate.

Using this same approach, other conjugates are prepared using mPEG derivatives having other weight-average molecular weights that also bear an amino moiety.

c) mPEG-N$^{ter}$-Dynorphin a Via mPEG-SMB mPEG-SMB, 5 kDa, stored at −20° C. under argon, is warmed to ambient temperature. A five-fold excess (relative to the amount of the peptide) of the warmed mPEG-SMB is dissolved in buffer to form a 10% reagent solution. The 10% reagent solution is quickly added to the aliquot of a stock Dynorphin A solution and mixed well. After the addition of the mPEG-SMB, the pH of the reaction mixture is determined and adjusted to 6.7 to 6.8 using conventional techniques. To allow for coupling of the mPEG-SMB to the peptide via an amide linkage, the reaction solution is stirred for several hours (e.g., 5 hours) at room temperature in the dark or stirred overnight at 3-8° C. in a cold room, thereby resulting in a conjugate solution. The reaction is quenched with a 20-fold molar excess (with respect to the peptide) of Tris buffer.

Using this same approach, other conjugates are prepared using mPEG derivatives having other weight-average molecular weights that also bear an N-hydroxysuccinimide moiety.

d) Dynorphin A-Lys-mPEG

PEG-SMB, 5 kDa, stored at −20° C. under argon, is warmed to ambient temperature. A five-fold excess (relative to the amount of the peptide) of the warmed mPEG-SMB is dissolved in buffer to form a 10% reagent solution. The 10% reagent solution is quickly added to the aliquot of a stock protected Dynorphin A (e.g., Fmoc-Tyr(tBu)-Gly-Gly-Phe-Leu-Arg(Tos)-Arg(Tos)-Ile-Arg(Tos)-Pro-Lys-Leu-Lys (Fmoc)-Trp-Asp(tBu)-Asn-Gln-O(tBu)) solution and mixed well. After the addition of the mPEG-SMB, the pH of the reaction mixture is determined and adjusted to 6.7 to 6.8 using conventional techniques. To allow for coupling of the mPEG-SMB to the peptide via an amide linkage, the reaction solution is stirred for several hours (e.g., 5 hours) at room temperature in the dark or stirred overnight at 3-8° C. in a cold room, thereby resulting in a conjugate solution. The reaction is quenched with a 20-fold molar excess (with respect to the peptide) of Tris buffer. The remaining protecting groups are removed under standard deprotection conditions to yield the Dynorphin A-Lys(O-mPEG) conjugate.

Using this same approach, other conjugates are prepared using mPEG derivatives having other weight-average molecular weights that also bear an N-hydroxysuccinimide moiety.

Example 38

Anaritide (Natriuretic Peptide Group)-mPEG Conjugates

Anaritide is an antihypertensive 25-amino-acid synthetic form of atrial natriuretic peptide used in the treatment of oliguric acute renal failure having the sequence, Arg-Ser-Ser-cyclo-(Cys-Phe-Gly-Gly-Arg-Met-Asp-Arg-Ile-Gly-Ala-Gln-Ser-Gly-Leu-Gly-Cys)-Asn-Ser-Phe-Arg-Tyr.

a) mPEG-$N^{ter}$-Anaritide-Via mPEG-SPC

Anaritide is prepared and purified according to standard automated peptide synthesis or recombinant techniques known to those skilled in the art. An illustrative polymeric reagent, mPEG-SPC reagent, is covalently attached to the N-terminus of Anaritide, to provide a $N^{ter}$-conjugate form of the peptide. mPEG-SPC 20 kDa, stored at −20° C. under argon, is warmed to ambient temperature. The reaction is performed at room temperature. About 3-5-fold molar excess of mPEG-SPC 20 kDa reagent is used based upon absolute peptide content. The mPEG-SPC reagent is weighed into a glass vial containing a magnetic stirrer bar. A solution of Anaritide prepared in phosphate buffered saline, PBS, pH 7.4 is added and the mixture is stirred using a magnetic stirrer until the mPEG-SPC is fully dissolved. The stirring speed is reduced and the reaction is allowed to proceed to formation of conjugate product. The reaction is optionally quenched to terminate the reaction. The pH of the conjugate solution at the end of the reaction is measured and further acidified by addition of 0.1M HCl, if necessary, to bring the pH of the final solution to about 5.5. The conjugate solution is then analyzed by SDS-PAGE and RP-HPLC (C18) to determine the extent of mPEG-$N^{ter}$-Anaritide conjugate formation.

Using this same approach, other conjugates are prepared using mPEG derivatives having other weight-average molecular weights that also bear an N-hydroxysuccinimide moiety.

b) Anaritide-$C^{ter}$-mPEG

An illustrative polymeric reagent, mPEG-$NH_2$ reagent is covalently attached to the C-terminus of Anaritide, to provide a $C^{ter}$-conjugate form of the peptide. For coupling to the C-terminus, a protected Anaritide (Prot-Anaritide, e.g., Fmoc-Arg(Tos)-Ser(tBu)-Ser(tBu)-Cys(tBu)-Phe-Gly-Gly-Arg(Tos)-Met-Asp(tBu)-Arg(Tos)-Ile-Gly-Ala-Gln-Ser(tBu)-Gly-Leu-Gly-Cys(tBu)-Asn-Ser(tBu)-Phe- Arg(Tos)-Tyr(tBu)-OH) is prepared and purified according to standard automated peptide synthesis techniques known to those skilled in the art. mPEG-$NH_2$ 20 kDa, stored at −20° C. under argon, is warmed to ambient temperature. The reaction is performed at room temperature. About 3-5-fold molar excess of mPEG-$NH_2$, PyBOP (benzotriazol-1-yloxy)tripyr-rolidinonophosphonium hexafluorophosphate), and 1-hydroxybenzotriazole (HOBt) are used, based upon absolute peptide content. The mPEG-$NH_2$, PyBOP, HOBt are weighed into a glass vial containing a magnetic stirrer bar. A solution of Prot-Anaritide is prepared in N,N-dimethylformamide is added and the mixture is stirred using a magnetic stirrer until the mPEG-$NH_2$ is fully dissolved. The stirring speed is reduced and the reaction is allowed to proceed to formation of conjugate product. The conjugate solution is then analyzed by SDS-PAGE and RP-HPLC (C18) to determine the extent of Prot-Anaritide-$C^{ter}$-mPEG conjugate formation. The remaining protecting groups are removed under standard deprotection conditions to yield the Anaritide-$C^{ter}$-mPEG conjugate.

Using this same approach, other conjugates are prepared using mPEG derivatives having other weight-average molecular weights that also bear an amino moiety.

c) Anaritide-Cys(S-mPEG)

Anaritide, which has a thiol-containing cysteine residue, is dissolved in buffer. To this peptide solution is added a 3-5 fold molar excess of mPEG-MAL, 5 kDa. The mixture is stirred at room temperature under an inert atmosphere for several hours. Analysis of the reaction mixture reveals successful conjugation of this peptide.

Using this same approach, other conjugates are prepared using mPEG-MAL having other weight average molecular weights.

d) mPEG-$N^{ter}$-Anaritide Via mPEG-SMB mPEG-SMB, 5 kDa, stored at −20° C. under argon, is warmed to ambient temperature. A five-fold excess (relative to the amount of the peptide) of the warmed mPEG-SMB is dissolved in buffer to form a 10% reagent solution. The 10% reagent solution is quickly added to the aliquot of a stock Anaritide solution and mixed well. After the addition of the mPEG-SMB, the pH of the reaction mixture is determined and adjusted to 6.7 to 6.8 using conventional techniques. To allow for coupling of the mPEG-SMB to the peptide via an amide linkage, the reaction solution is stirred for several hours (e.g., 5 hours) at room temperature in the dark or stirred overnight at 3-8° C. in a cold room, thereby resulting in a conjugate solution. The reaction is quenched with a 20-fold molar excess (with respect to the peptide) of Tris buffer.

Using this same approach, other conjugates are prepared using mPEG derivatives having other weight-average molecular weights that also bear an N-hydroxysuccinimide moiety.

e) Anaritide-Asp(O-mPEG)

An illustrative polymeric reagent, mPEG-$NH_2$ reagent is covalently attached to the Asp residue of Anaritide, to provide an Asp-conjugate form of the peptide. For coupling to the Asp residue, a protected Anaritide (Prot2-Anaritide, e.g., Fmoc-Arg(Tos)-Ser(tBu)-Ser(tBu)-Cys(tBu)-Phe-Gly- Gly-Arg(Tos)-Met-Asp(OBz)-Arg(Tos)-Ile-Gly-Ala-Gln-Ser(tBu)-Gly-Leu-Gly-Cys(tBu)-Asn-Ser(tBu)-Phe-Arg(Tos)-Tyr(tBu)-O(tBu)) is prepared and purified according to standard automated peptide synthesis techniques known to those skilled in the art. Deprotection of the Asp(OBz) residue ($H_2$/Pd) yields the free-Asp carboxylate for subsequent coupling (Prot3-Anaritide, e.g., Fmoc-Arg(Tos)-Ser(tBu)-Ser(tBu)-Cys(tBu)-Phe-Gly-Gly-Arg(Tos)-Met-Asp-Arg(Tos)-Ile-Gly-Ala-Gln-Ser(tBu)-Gly-Leu-Gly-Cys(tBu)-Asn-Ser(tBu)-Phe-Arg(Tos)-Tyr(tBu)- O(tBu)). mPEG-$NH_2$ 20 kDa, stored at −20° C. under argon, is warmed to ambient temperature. The reaction is performed at room temperature. A 5-fold molar excess of mPEG-$NH_2$, PyBOP (benzotriazol-1-yloxy)tripyrrolidinonophosphonium hexafluorophosphate), and 1-hydroxybenzotriazole (HOBt) are used, based upon absolute peptide content. The mPEG-$NH_2$, PyBOP, HOBt are weighed into a glass vial containing a magnetic stirrer bar. A solution of Prot3-Anaritide is prepared in N,N-dimethylformamide is added and the mixture is stirred using a magnetic stirrer until the mPEG-$NH_2$ is fully dissolved. The stirring speed is reduced and the reaction is allowed to proceed to formation of conjugate product. The conjugate solution is then analyzed by SDS-PAGE and RP-HPLC (C18) to determine the extent of Prot3-Anaritide-(Asp-O-mPEG) conjugate formation. The remaining protecting groups are removed under standard deprotection conditions to yield the Anaritide-Asp(O-mPEG) conjugate.

Using this same approach, other conjugates are prepared using mPEG derivatives having other weight-average molecular weights that also bear an amino moiety Example 39

Secretin-mPEG Conjugates

Secretin a 27 amino acid peptide hormone produced in the S cells of the duodenum in the crypts of Lieberkühn to primarily regulate the pH of the duodenal contents via the control of gastric acid secretion and buffering with bicarbonate. Secretin is commercially available from Gelacs Innovation (Hangzhou, China) with the sequence, His-Ser-Asp-Gly-Thr-Phe-Thr-Ser-Glu-Leu-Ser-Arg-Leu-Arg-Asp-Ser-Ala-Arg-Leu-Gln-Arg-Leu-Leu-Gln-Gly-Leu-Val-$NH_2$.

a) mPEG-$N^{ter}$-Secretin-Via mPEG-SPC

Secretin is prepared and purified according to standard automated peptide synthesis or recombinant techniques known to those skilled in the art. An illustrative polymeric reagent, mPEG-SPC reagent, is covalently attached to the N-terminus of Secretin, to provide a $N^{ter}$-conjugate form of the peptide. mPEG-SPC 20 kDa, stored at −20° C. under argon, is warmed to ambient temperature. The reaction is performed at room temperature. About 3-5-fold molar excess of mPEG-SPC 20 kDa reagent is used based upon absolute peptide content. The mPEG-SPC reagent is weighed into a glass vial containing a magnetic stirrer bar. A solution of Secretin prepared in phosphate buffered saline, PBS, pH 7.4 is added and the mixture is stirred using a magnetic stirrer until the mPEG-SPC is fully dissolved. The stirring speed is reduced and the reaction is allowed to proceed to formation of conjugate product. The reaction is optionally quenched to terminate the reaction. The pH of the conjugate solution at the end of the reaction is measured and further acidified by addition of 0.1M HCl, if necessary, to bring the pH of the final solution to about 5.5. The conjugate solution is then analyzed by SDS-PAGE and RP-HPLC (C18) to determine the extent of mPEG-$N^{ter}$-Secretin conjugate formation.

Using this same approach, other conjugates are prepared using mPEG derivatives having other weight-average molecular weights that also bear an N-hydroxysuccinimide moiety.

b) Secretin-$C^{ter}$-mPEG

An illustrative polymeric reagent, mPEG-$NH_2$ reagent is covalently attached to the C-terminus of Secretin, to provide a $C^{ter}$-conjugate form of the peptide. For coupling to the C-terminus, a protected Secretin (Prot-Secretin, e.g., Fmoc-His-Ser(tBu)-Asp(tBu)-Gly-Thr(tBu)-Phe-Thr(tBu)-Ser(tBu)-Glu(tBu)-Leu-Ser(tBu)-Arg(Tos)-Leu-Arg(Tos)-Asp(tBu)-Ser(tBu)-Ala-Arg(Tos)-Leu-Gln- Arg(Tos)-Leu-Leu-Gln-Gly-Leu-Val-OH) is prepared and purified according to standard automated peptide synthesis or recombinant techniques known to those skilled in the art. mPEG-$NH_2$ 20 kDa, stored at −20° C. under argon, is warmed to ambient temperature. The reaction is performed at room temperature. About 3-5-fold molar excess of mPEG-$NH_2$, PyBOP (benzotriazol-1-yloxy)tripyrrolidinonophosphonium hexafluorophosphate), and 1-hydroxybenzotriazole (HOBt) are used, based upon absolute peptide content. The mPEG-$NH_2$, PyBOP, HOBt are weighed into a glass vial containing a magnetic stirrer bar. A solution of Prot-Secretin is prepared in N,N-dimethylformamide is added and the mixture is stirred using a magnetic stirrer until the mPEG-$NH_2$ is fully dissolved. The stirring speed is reduced and the reaction is allowed to proceed to formation of conjugate product. The conjugate solution is then analyzed by SDS-PAGE and RP-HPLC (C18) to determine the extent of Prot-Secretin-$C^{ter}$ mPEG conjugate formation. The remaining protecting groups are removed under standard deprotection conditions to yield the Secretin-$C^{ter}$-mPEG conjugate.

Using this same approach, other conjugates are prepared using mPEG derivatives having other weight-average molecular weights that also bear an amino moiety.

c) mPEG-$N^{ter}$-Secretin Via mPEG-SMB mPEG-SMB, 5 kDa, stored at −20° C. under argon, is warmed to ambient temperature. A five-fold excess (relative to the amount of the peptide) of the warmed mPEG-SMB is dissolved in buffer to form a 10% reagent solution. The 10% reagent solution is quickly added to the aliquot of a stock Secretin solution and mixed well. After the addition of the mPEG-SMB, the pH of the reaction mixture is determined and adjusted to 6.7 to 6.8 using conventional techniques. To allow for coupling of the mPEG-SMB to the peptide via an amide linkage, the reaction solution is stirred for several hours (e.g., 5 hours) at room temperature in the dark or stirred overnight at 3-8° C. in a cold room, thereby resulting in a conjugate solution. The reaction is quenched with a 20-fold molar excess (with respect to the peptide) of Tris buffer.

Using this same approach, other conjugates are prepared using mPEG derivatives having other weight-average molecular weights that also bear an N-hydroxysuccinimide moiety.

d) Secretin-Asp(O-mPEG)

An illustrative polymeric reagent, mPEG-$NH_2$ reagent is covalently attached to the Asp residue of Secretin to provide a Asp-conjugate form of the peptide. For coupling to the Asp residue, a protected Secretin (Prot2-Secretin, e.g., Fmoc-His-Ser(tBu)-Asp(OBz)-Gly-Thr(tBu)-Phe-Thr(tBu)-Ser(tBu)-Glu(tBu)-Leu-Ser(tBu)-Arg(Tos)-Leu-Arg(Tos)-Asp(tBu)-Ser(tBu)-Ala-Arg(Tos)-Leu- Gln-Arg(Tos)-Leu-Leu-Gln-Gly-Leu-Val-$NH_2$) is prepared and purified according to standard automated peptide synthesis techniques known to those skilled in the art. Deprotection of the Asp(OBz) residue ($H_2$/Pd) yields the free-Asp carboxylate for subsequent coupling (Prot3-Secretin, e.g., Fmoc-His-Ser(tBu)-Asp-Gly-Thr(tBu)-Phe-Thr(tBu)-Ser(tBu)-Glu(tBu)-Leu-Ser(tBu)-Arg(Tos)-Leu-Arg(Tos)-Asp(tBu)-Ser(tBu)-Ala-Arg(Tos)-Leu-Gln-Arg(Tos)-Leu- Leu-Gln-Gly-LeuVal-NH$_2$). mPEG-NH$_2$ 20 kDa, stored at −20° C. under argon, is warmed to ambient temperature. The reaction is performed at room temperature. A 5-fold molar excess of mPEG-NH$_2$, PyBOP (benzotriazol-1-yloxy)tripyrrolidinonophosphonium hexafluorophosphate), and 1-hydroxybenzotriazole (HOBt) are used, based upon absolute peptide content. The mPEG-NH$_2$, PyBOP, HOBt are weighed into a glass vial containing a magnetic stirrer bar. A solution of Prot3-Secretin is prepared in N,N-dimethylformamide is added and the mixture is stirred using a magnetic stirrer until the mPEG-NH$_2$ is fully dissolved. The stirring speed is reduced and the reaction is allowed to proceed to formation of conjugate product. The conjugate solution is then analyzed by SDS-PAGE and RP-HPLC (C18) to determine the extent of Prot3-Secretin-(Asp-O-mPEG) conjugate formation. The remaining protecting groups are removed under standard deprotection conditions to yield the Secretin-Asp(O-mPEG) conjugate.

Using this same approach, other conjugates are prepared using mPEG derivatives having other weight-average molecular weights that also bear an amino moiety.

Example 40

GLP-2-mPEG Conjugates

GLP-2 is a 33 amino acid peptide with the sequence His-Ala-Asp-Gly-Ser-Phe-Ser-Asp-Glu-Met-Asn-Thr-Ile-Leu-Asp-Asn-Leu-Ala-Ala-Arg-Asp-Phe-Ile-Asn-Trp-Leu-Ile-Gln-Thr-Lys-Ile-Tyr-Asp (HADGSFSDEM NTILDN-LAAR DFINWLIQTK ITDR, available from GenScript Corporation, Piscataway, N.J.; Cat. No. RP10774) which is produced by the post-translational cleavage or proglucagon in the intestinal endocrine L cells and neurons of the central nervous system. GLP-2 has been proposed for treatments for short bowel syndrome (Jeppesen et al., *Gastroenterology* 2001, 120, 806), Crohn's disease (Peyrin-Biroulet et al., *Lancet* 2008, 372, 67) and osteroporosis (U.S. Pat. No. 6,943,151).

a) mPEG-N$^{ter}$-GLP-2-Via mPEG-SPC

GLP-2 is prepared and purified according to standard automated peptide synthesis or recombinant techniques known to those skilled in the art. An illustrative polymeric reagent, mPEG-SPC reagent, is covalently attached to the N-terminus of GLP-2, to provide a N$^{ter}$-conjugate form of the peptide. mPEG-SPC 20 kDa, stored at −20° C. under argon, is warmed to ambient temperature. The reaction is performed at room temperature. About 3-5-fold molar excess of mPEG-SPC 20 kDa reagent is used based upon absolute peptide content. The mPEG-SPC reagent is weighed into a glass vial containing a magnetic stirrer bar. A solution of GLP-2 prepared in phosphate buffered saline, PBS, pH 7.4 is added and the mixture is stirred using a magnetic stirrer until the mPEG-SPC is fully dissolved. The stirring speed is reduced and the reaction is allowed to proceed to formation of conjugate product. The reaction is optionally quenched to terminate the reaction. The pH of the conjugate solution at the end of the reaction is measured and further acidified by addition of 0.1M HCl, if necessary, to bring the pH of the final solution to about 5.5. The conjugate solution is then analyzed by SDS-PAGE and RP-HPLC (C18) to determine the extent of mPEG-N$^{ter}$-GLP-2 conjugate formation.

Using this same approach, other conjugates are prepared using mPEG derivatives having other weight-average molecular weights that also bear an N-hydroxysuccinimide moiety.

b) GLP-2-C$^{ter}$-mPEG

An illustrative polymeric reagent, mPEG-NH$_2$ reagent is covalently attached to the C-terminus of GLP-2, to provide a C$^{ter}$-conjugate form of the peptide. For coupling to the C-terminus, a protected GLP-2 (Prot-GLP-2, e.g., Fmoc-His-Ala-Asp(tBu)-Gly-Ser(tBu)-Phe-Ser(tBu)-Asp(tBu)-Glu(tBu)-Met-Asn-Thr(tBu)-Ile-Leu-Asp(tBu)-Asn-Leu-Ala-Ala-Arg(Tos)-Asp(tBu)-Phe-Ile-Asn-Trp-Leu- Ile-Gln-Thr(tBu)-Lys(Fmoc)-Ile-Tyr(tBu)-Asp(tBu)-OH) is prepared and purified according to standard automated peptide synthesis techniques known to those skilled in the art. mPEG-NH$_2$ 20 kDa, stored at −20° C. under argon, is warmed to ambient temperature. The reaction is performed at room temperature. About 3-5-fold molar excess of mPEG-NH$_2$, PyBOP (benzotriazol-1-yloxy)tripyrrolidinonophosphonium hexafluorophosphate), and 1-hydroxybenzotriazole (HOBt) are used, based upon absolute peptide content. The mPEG-NH$_2$, PyBOP, HOBt are weighed into a glass vial containing a magnetic stirrer bar. A solution of Prot-GLP-2 is prepared in N,N-dimethylformamide is added and the mixture is stirred using a magnetic stirrer until the mPEG-NH$_2$ is fully dissolved. The stirring speed is reduced and the reaction is allowed to proceed to formation of conjugate product. The conjugate solution is then analyzed by SDS-PAGE and RP-HPLC (C18) to determine the extent of Prot-GLP-2-C$^{ter}$-mPEG conjugate formation. The remaining protecting groups are removed under standard deprotection conditions to yield the GLP-2-C$^{ter}$-mPEG conjugate.

Using this same approach, other conjugates are prepared using mPEG derivatives having other weight-average molecular weights that also bear an amino moiety.

c) mPEG-N$^{ter}$-GLP-2 Via mPEG-SMB mPEG-SMB, 5 kDa, stored at −20° C. under argon, is warmed to ambient temperature. A five-fold excess (relative to the amount of the peptide) of the warmed mPEG-SMB is dissolved in buffer to form a 10% reagent solution. The 10% reagent solution is quickly added to the aliquot of a stock GLP-2 solution and mixed well. After the addition of the mPEG-SMB, the pH of the reaction mixture is determined and adjusted to 6.7 to 6.8 using conventional techniques. To allow for coupling of the mPEG-SMB to the peptide via an amide linkage, the reaction solution is stirred for several hours (e.g., 5 hours) at room temperature in the dark or stirred overnight at 3-8° C. in a cold room, thereby resulting in a conjugate solution. The reaction is quenched with a 20-fold molar excess (with respect to the peptide) of Tris buffer.

Using this same approach, other conjugates are prepared using mPEG derivatives having other weight-average molecular weights that also bear an N-hydroxysuccinimide moiety.

d) GLP-2-Glu(O-mPEG)

An illustrative polymeric reagent, mPEG-NH$_2$ reagent is covalently attached to the Glu residue of GLP-2, to provide a Glu-conjugate form of the peptide. For coupling to the Glu residue, a protected GLP-2 (Prot2-GLP-2, e.g., Fmoc-His-Ala-Asp(tBu)-Gly-Ser(tBu)-Phe-Ser(tBu)-Asp(tBu)-Glu (OBz)-Met-Asn-Thr(tBu)-Ile-Leu-Asp(tBu)-Asn-Leu-Ala-Ala-Arg(Tos)-Asp(tBu)- Phe-Ile-Asn-Trp-Leu-Ile-Gln-Thr(tBu)-Lys(Fmoc)-Ile-Tyr(tBu)-Asp(tBu)-O(tBu)) is prepared and purified according to standard automated peptide synthesis techniques known to those skilled in the art.

Deprotection of the Glu(OBz) residue ($H_2$/Pd) yields the free-Glu carboxylate for subsequent coupling (Prot3-GLP-2, e.g., Fmoc-His-Ala-Asp(tBu)-Gly-Ser(tBu)-Phe-Ser(tBu)-Asp(tBu)-Glu-Met-Asn-Thr(tBu)-Ile-Leu-Asp(tBu)-Asn-Leu-Ala-Ala-Arg(Tos)-Asp(tBu)-Phe-Ile-Asn-Trp-Leu-Ile-Gln-Thr(tBu)-Lys(Fmoc)-Ile-Tyr(tBu)-Asp(tBu)-O(tBu)) mPEG-$NH_2$ 20 kDa, stored at −20° C. under argon, is warmed to ambient temperature. The reaction is performed at room temperature. A 5-fold molar excess of mPEG-$NH_2$, PyBOP (benzotriazol-1-yloxy)tripyrrolidinonophosphonium hexafluorophosphate), and 1-hydroxybenzotriazole (HOBt) are used, based upon absolute peptide content. The mPEG-$NH_2$, PyBOP, HOBt are weighed into a glass vial containing a magnetic stirrer bar. A solution of Prot3-GLP-2 is prepared in N,N-dimethylformamide is added and the mixture is stirred using a magnetic stirrer until the mPEG-$NH_2$ is fully dissolved. The stirring speed is reduced and the reaction is allowed to proceed to formation of conjugate product. The conjugate solution is then analyzed by SDS-PAGE and RP-HPLC (C18) to determine the extent of Prot3-GLP-2-(Glu-O-mPEG) conjugate formation. The remaining protecting groups are removed under standard deprotection conditions to yield the GLP-2-Glu(O-mPEG) conjugate.

Using this same approach, other conjugates are prepared using mPEG derivatives having other weight-average molecular weights that also bear an amino moiety.

Example 41

Gastrin-mPEG Conjugates

Gastrin is a hormone secreted by the G cells of the duodenum and in the pyloric antrum of the stomach which stimulate the secretion of gastric acid by the parietal cells of the stomach in response to stomach distension, vagal stimulation, partially digested proteins, and hypercalcemia. Gastrin is a heptadecapeptide of the sequence, pGlu-Gly-Pro-Trp-Leu-Glu-Glu-Glu-Glu-Glu-Ala-Tyr-Gly-Trp-Met-Asp-Phe-$NH_2$ (PyrGPWLEEEEEA YGWMDF-$NH_2$, available from GenScript Corporation, Piscataway, N.J.; Cat. No. RP12740)

a) mPEG-$N_{ter}$-Gastrin-Via mPEG-SPC

Gastrin is prepared and purified according to standard automated peptide synthesis techniques known to those skilled in the art. An illustrative polymeric reagent, mPEG-SPC reagent, is covalently attached to the N-terminus of Gastrin, to provide a $N^{ter}$-conjugate form of the peptide. mPEG-SPC 20 kDa, stored at −20° C. under argon, is warmed to ambient temperature. The reaction is performed at room temperature. About 3-5-fold molar excess of mPEG-SPC 20 kDa reagent is used based upon absolute peptide content. The mPEG-SPC reagent is weighed into a glass vial containing a magnetic stirrer bar. A solution of Gastrin prepared in phosphate buffered saline, PBS, pH 7.4 is added and the mixture is stirred using a magnetic stirrer until the mPEG-SPC is fully dissolved. The stirring speed is reduced and the reaction is allowed to proceed to formation of conjugate product. The reaction is optionally quenched to terminate the reaction. The pH of the conjugate solution at the end of the reaction is measured and further acidified by addition of 0.1M HCl, if necessary, to bring the pH of the final solution to about 5.5. The conjugate solution is then analyzed by SDS-PAGE and RP-HPLC (C18) to determine the extent of mPEG-$N^{ter}$-Gastrin conjugate formation.

Using this same approach, other conjugates are prepared using mPEG derivatives having other weight-average molecular weights that also bear an N-hydroxysuccinimide moiety.

b) Gastrin-$C^{ter}$-mPEG

An illustrative polymeric reagent, mPEG-$NH_2$ reagent is covalently attached to the C-terminus of Gastrin, to provide a $C^{ter}$-conjugate form of the peptide. For coupling to the C-terminus, a protected Gastrin (Prot-Gastrin, e.g., Fmoc-Glu(tBu)-Gly-Pro-Trp-Leu-Glu(tBu)-Glu(tBu)-Glu(tBu)-Glu(tBu)-Glu(tBu)-Ala-Tyr(tBu)-Gly-Trp-Met-Asp(tBu)-Phe-OH) is prepared and purified according to standard automated peptide synthesis or recombinant techniques known to those skilled in the art. mPEG-$NH_2$ 20 kDa, stored at −20° C. under argon, is warmed to ambient temperature. The reaction is performed at room temperature. About 3-5-fold molar excess of mPEG-$NH_2$, PyBOP (benzotriazol-1-yloxy)tripyrrolidinonophosphonium hexafluorophosphate), and 1-hydroxybenzotriazole (HOBt) are used, based upon absolute peptide content. The mPEG-$NH_2$, PyBOP, HOBt are weighed into a glass vial containing a magnetic stirrer bar. A solution of Prot-Gastrin is prepared in N,N-dimethylformamide is added and the mixture is stirred using a magnetic stirrer until the mPEG-$NH_2$ is fully dissolved. The stirring speed is reduced and the reaction is allowed to proceed to formation of conjugate product. The conjugate solution is then analyzed by SDS-PAGE and RP-HPLC (C18) to determine the extent of Prot-Gastrin-$C^{ter}$-mPEG conjugate formation. The remaining protecting groups are removed under standard deprotection conditions to yield the Gastrin-$C^{ter}$-mPEG conjugate.

Using this same approach, other conjugates are prepared using mPEG derivatives having other weight-average molecular weights that also bear an amino moiety.

c) mPEG-$N^{ter}$-Gastrin Via mPEG-SMB mPEG-SMB, 5 kDa, stored at −20° C. under argon, is warmed to ambient temperature. A five-fold excess (relative to the amount of the peptide) of the warmed mPEG-SMB is dissolved in buffer to form a 10% reagent solution. The 10% reagent solution is quickly added to the aliquot of a stock Gastrin solution and mixed well. After the addition of the mPEG-SMB, the pH of the reaction mixture is determined and adjusted to 6.7 to 6.8 using conventional techniques. To allow for coupling of the mPEG-SMB to the peptide via an amide linkage, the reaction solution is stirred for several hours (e.g., 5 hours) at room temperature in the dark or stirred overnight at 3-8° C. in a cold room, thereby resulting in a conjugate solution. The reaction is quenched with a 20-fold molar excess (with respect to the peptide) of Tris buffer.

Using this same approach, other conjugates are prepared using mPEG derivatives having other weight-average molecular weights that also bear an N-hydroxysuccinimide moiety.

d) Gastrin-Glu(O-mPEG)

An illustrative polymeric reagent, mPEG-$NH_2$ reagent is covalently attached to the Glu residue of Gastrin, to provide a Glu-conjugate form of the peptide. For coupling to the Glu residue, a protected Gastrin (Prot2-Gastrin, e.g., Fmoc-Glu(OBz)-Gly-Pro-Trp-Leu-Glu(tBu)-Glu(tBu)-Glu(tBu)-Glu(tBu)-Glu(tBu)-Ala-Tyr(tBu)-Gly-Trp-Met-Asp(tBu)-Phe-$NH_2$) is prepared and purified according to standard automated peptide synthesis techniques known to those skilled in the art. Deprotection of the Glu(OBz) residue ($H_2$/Pd) yields the free-Glu carboxylate for subsequent coupling (Prot3-Gastrin, e.g., Fmoc-Glu-Gly-Pro-Trp-Leu-Glu(tBu)-Glu(tBu)-Glu(tBu)-Glu(tBu)-Glu(tBu)-Ala-Tyr(tBu)-

Gly-Trp-Met-Asp(tBu)-Phe-NH$_2$) mPEG-NH$_2$ 20 kDa, stored at −20° C. under argon, is warmed to ambient temperature. The reaction is performed at room temperature. A 5-fold molar excess of mPEG-NH$_2$, PyBOP (benzotriazol-1-yloxy)tripyrrolidinonophosphonium hexafluorophosphate), and 1-hydroxybenzotriazole (HOBt) are used, based upon absolute peptide content. The mPEG-NH$_2$, PyBOP, HOBt are weighed into a glass vial containing a magnetic stirrer bar. A solution of Prot3-Gastrin is prepared in N,N-dimethylformamide is added and the mixture is stirred using a magnetic stirrer until the mPEG-NH$_2$ is fully dissolved. The stirring speed is reduced and the reaction is allowed to proceed to formation of conjugate product. The conjugate solution is then analyzed by SDS-PAGE and RP-HPLC (C18) to determine the extent of Prot3-Gastrin-(Glu-O-mPEG) conjugate formation. The remaining protecting groups are removed under standard deprotection conditions to yield the Gastrin-Glu(O-mPEG) conjugate.

Using this same approach, other conjugates are prepared using mPEG derivatives having other weight-average molecular weights that also bear an amino moiety.

Example KISS1

PEGylation of Kisspeptin-13 with mPEG-ButyrALD-30K (Linear)

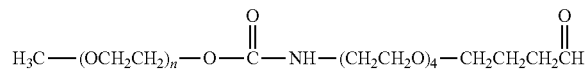

Figure 1:
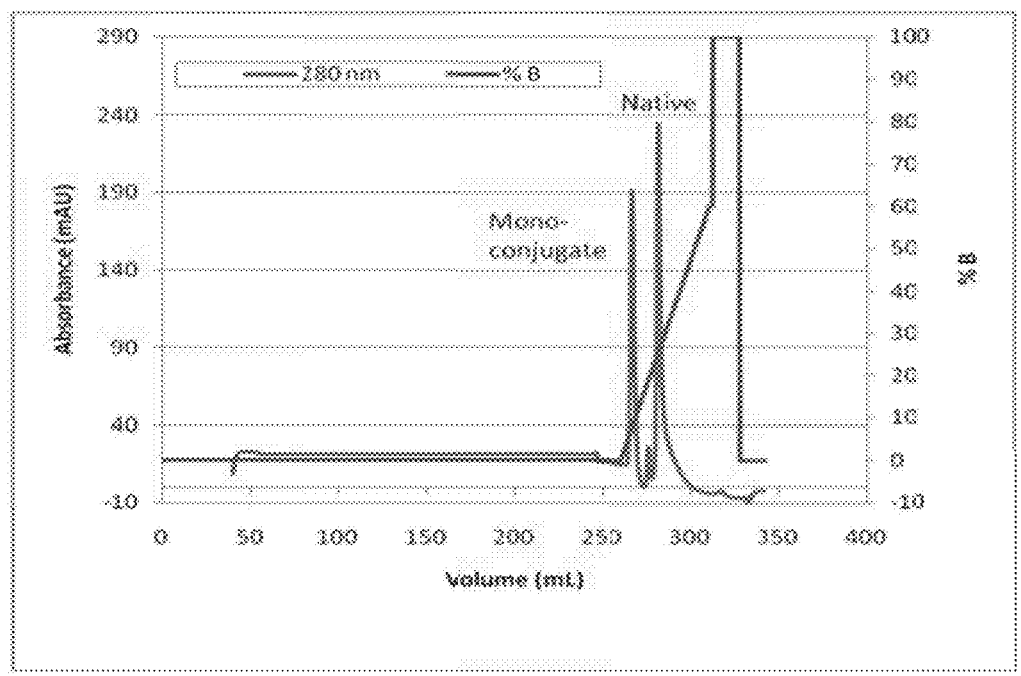
FIG. 1: Cation exchange purification of the PEGylation reaction mixture.
Figure 2:
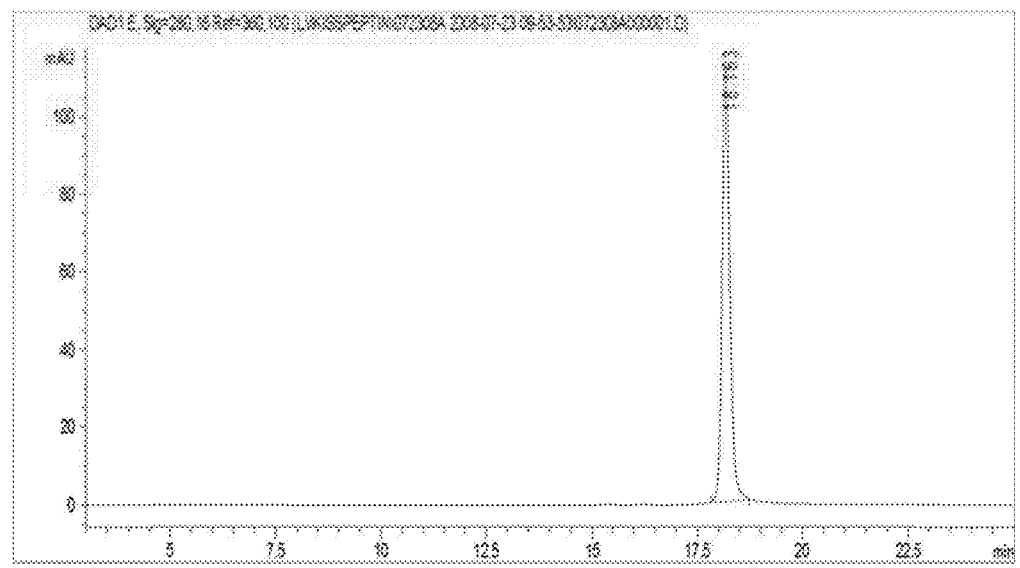
FIG. 2: RP-HPLC analysis of purified [mono]-[mPEG-ButyrALD-30K]-[Kisspeptin-13].

Kisspeptin-13 stock solution (KP-13; 0.454 mL of a 26.4 mg/mL stock solution) in 50 mM sodium acetate, pH 4.0, and 2.907 mL of 50 mM sodium acetate, pH 4.0, were mixed in a 50 mL polypropylene low endotoxin conical tube. PEG solution (three mol equivalents to the amount of peptide) was freshly prepared by dissolving 880 mg of linear mPEG-ButyrALD-30K PEG in 8.8 mL 50 mM sodium acetate, pH 4.0. After vigorous vortexing and 0.22 µm filtration, 8.292 mL of PEG solution was added drop-wise within 30 seconds to the peptide solution while stirring. After 15 minutes, a freshly prepared solution of sodium cyanoborohydride (0.347 mL of 50 mg/mL sodium cyanoborohydride in Milli-Q H$_2$O) was added (ten mol equivalents to PEG). The reaction mixture was allowed to gently stir at room temperature for 17 hours. The reaction was diluted 1:5 with 10 mM sodium acetate, pH 4.0, and purified by cation exchange chromatography (HiTrap SP SEPHAROSE HP; 2×5 mL columns connected in series). Multiple loadings were necessary for purification as the resin had a low binding capacity for the PEGylated peptide. A linear gradient (FIG. 1) separated the mono-conjugate from the non-conjugated peptide. Purification buffers were as follows: A: 10 mM sodium acetate, pH 4.0, and B: 10 mM sodium acetate, 1.0 M sodium chloride, pH 4.0. The diluted reaction mixture was loaded at 1 mL/min with a two column volume wash after the load. The linear gradient consisted of 0 to 60% B over ten column volumes at an elution flow rate of 1 mL/min. The purified mono-conjugate was determined to be 100% pure by reversed phase HPLC (FIG. 2 and Table KISS1.1). MALDI-TOF analysis (FIG. 3), indicated the expected mass (34,017 Da) for Kisspeptin-13 mono-PEGylated with a 30 kD PEG. Final conjugate concentration was determined to be 5.17 mg/mL using a standard curve of Kisspeptin-13 with analytical RP-HPLC.

| TIME (min) | % B | Flow rate (mL/min) |
|---|---|---|
| 0.0 | 25 | 0.4 |
| 3.0 | 25 | 0.4 |
| 28.0 | 70 | 0.4 |
| 28.01 | 100 | 0.4 |
| 31.00 | 100 | 0.4 |
| 31.01 | 25 | 1.0 |
| 35.00 | 25 | 1.0 |

Table KISS1.1: Analytical RP-HPLC method. Symmetry C18, 3.5 µm, 3.6×75 mm. Mobile Phase A: 0.08% TFA/H$_2$O and B: 0.07% TFA/CH$_3$CN.

Example KISS2

PEGylation of Kisspeptin-10 (KP-10) with [mPEG-Butyr-Aldehyde-10K]

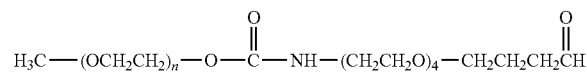

Stock solutions of 2.0 mg/mL KP-10 and 200 mg/mL mPEG-ButyrALD10K were prepared in 2 mM HCl. To initiate a reaction, the two stock solutions and a 1 M sodium acetate, pH 4.0, stock solution were brought to 25° C., and the three stock solutions were mixed (PEG reagent added last) to give final concentrations of 1.0 mg/mL KP-10 (0.75 mM), 50 mM sodium acetate and a 6-fold molar excess of mPEG-ButyrALD10K over KP-10. After 15 minutes reaction, a 10-fold molar excess of NaBH$_3$CN over PEG was added and the reaction was allowed to continue for an additional 16 hours at 25° C. After 16 hr 50 min total reaction time, the reaction was quenched with 100 mM glycine in 100 mM HCl (10 mM final glycine concentration) for 1 hour, after which glacial acetic acid was added to a final concentration of 5% (v/v).

The mono-PEGylated conjugate was purified from the reaction mixture by reversed phase chromatography using a column packed with CG71S media (Rohm Haas) on an AKTA Explorer 100 system (GE Healthcare). Buffer A was 5% acetic acid/20% acetonitrile/75% H$_2$O (v/v), and Buffer B was 5% acetic acid/95% acetonitrile (v/v). The AKTA Explorer plumbing system and the CG 71S resin were sanitized with 1 M HCl and 1 M NaOH and the resin was equilibrated with 10 column volumes Buffer A prior to sample loading. After loading, the resin was washed with 6 CV of buffer A, and the PEGylated and nonPEGylated peptides were eluted using a linear gradient from 100% A/0% B to 0% A/100% B over 15 column volume with a linear flow rate of 90 cm/hour.

Fractions collected during reversed phase chromatography with the CG71S resin were analyzed using analytical reversed-phase HPLC, The mobile phases were: A, 0.08% TFA in water, and B, 0.05% TFA in acetonitrile. A Waters Symmetry C18 column (4.6 mm×75 mm) was used with a flow rate of 0.5 ml/min and a column temperature of 60° C. Detection was carried out at 280 nm. The column was equilibrated in 25% B and conjugate separation was achieved using the gradient timetable shown in Table KISS2.1.

| Step | Time (min) | % Mobile phase B |
|---|---|---|
| 1 | 0.00 | 25.0 |
| 2 | 3.00 | 25.0 |
| 3 | 21.50 | 60.0 |
| 4 | 21.60 | 100.0 |
| 5 | 24.60 | 100.0 |
| 6 | 24.70 | 25.0 |

Fractions containing pure [mono]-[mPEG-ButyAldehyde-10K]-[Kisspeptin-10] as determined by analytical RP-HPLC were pooled, lyophilized and stored at −80° C. A typical reversed phase CG71S chromatogram is shown in FIG. 2.1. RP-HPLC analysis of the purified conjugate is shown in FIG. 2.2, and MALDI-TOF analysis of the purified conjugate is shown in FIG. 2.3. The purity of the mono-PEG-conjugate was 98% by RP-HPLC analysis. The mass as determined by MALDI-TOF was within the expected range.

Example KISS3

PEGylation of Kisspeptin-10 (KP-10) with [mPEG-Butyr-Aldehyde-30K]

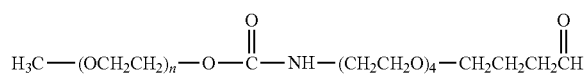

Stock solutions of 2.0 mg/mL KP-10 and 200 mg/mL mPEG-butyrALD30K were prepared in 2 mM HCl. To initiate a reaction, the two stock solutions and a 1 M sodium acetate, pH 4.0, stock solution were brought to 25° C., and the three stock solutions were mixed (PEG reagent added last) to give final concentrations of 1.0 mg/mL KP-10 (0.75 mM), 50 mM sodium acetate and a 6-fold molar excess of mPEG-butyrALD30K over KP-10. After 15 min reaction, a 10-fold molar excess of NaBH$_3$CN over PEG was added and the reaction was allowed to continue for an additional 16 hours at 25° C. After 16 hr 50 min total reaction time, the reaction was quenched with 100 mM glycine in 100 mM HCl (10 mM final glycine concentration) for 1 hour, after which glacial acetic acid was added to a final concentration of 5% (v/v).

The mono-PEGylated conjugate was purified from the reaction mixture by reversed phase chromatography using a column packed with CG71S media (Rohm Haas) on an AKTA Explorer 100 system (GE Healthcare). Buffer A was 5% acetic acid/95% H$_2$O (v/v), and Buffer B was 5% acetic acid/95% acetonitrile (v/v). The AKTA Explorer plumbing system and the CG71S resin were sanitized with 1 M HCl and 1 M NaOH and the resin was equilibrated with 10 column volumes Buffer A prior to sample loading. After loading, the resin was washed with 6 CV of 80% Buffer A/20% Buffer B and the PEGylated and nonPEGylated peptides were eluted using a linear gradient from 80% A/20% B to 40% A/60% B over 15 column volume with a linear flow rate of 90 cm/hour.

Fractions collected during reversed phase chromatography with the CG71S resin were analyzed using reversed-phase HPLC. The mobile phases were: A, 0.08% TFA in water, and B, 0.05% TFA in acetonitrile. A Waters Symmetry C18 column (4.6 mm×75 mm) was used with a flow rate of 0.5 ml/min and a column temperature of 60° C. Detection was carried out at 280 nm. The column was equilibrated in 25% B and conjugate separation was achieved using the gradient timetable shown in Table KISS3.1

| Step | Time (min) | % Mobile phase B |
|---|---|---|
| 1 | 0.00 | 25.0 |
| 2 | 3.00 | 25.0 |
| 3 | 21.50 | 60.0 |
| 4 | 21.60 | 100.0 |
| 5 | 24.60 | 100.0 |
| 6 | 24.70 | 25.0 |

Figure 7:
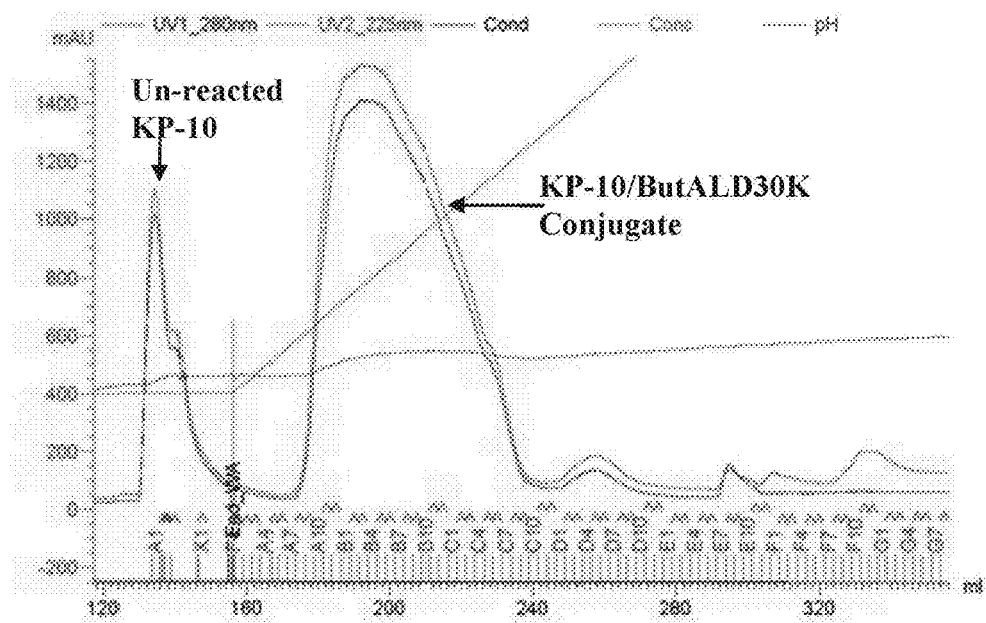
FIG. 7. Typical reversed phase purification profile of [mono]-[mPEG-ButyAldehyde-30K]-[Kisspeptin-10].
Figure 8:
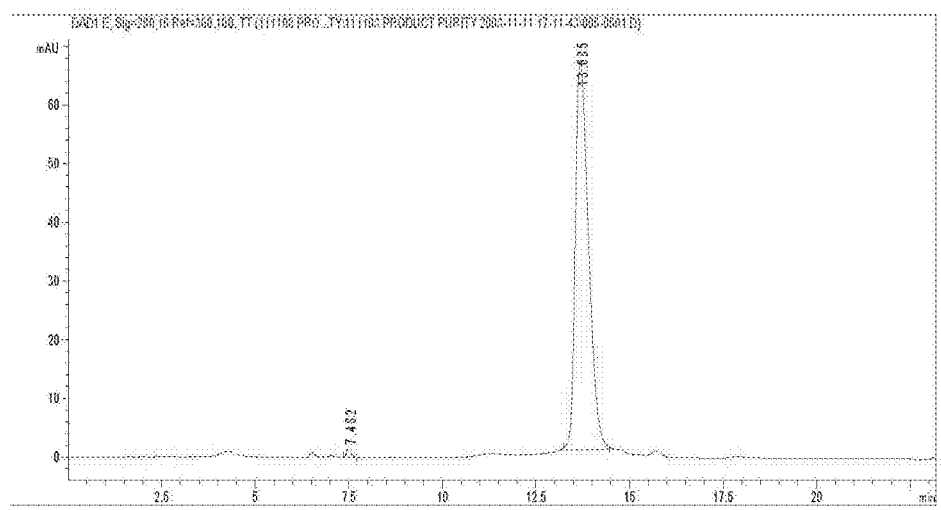
FIG. 8. Purity analysis of mono-[ButyrAldehyde-30K]-[Kisspeptin-1] by Reversed Phase HPLC.
Figure 9:
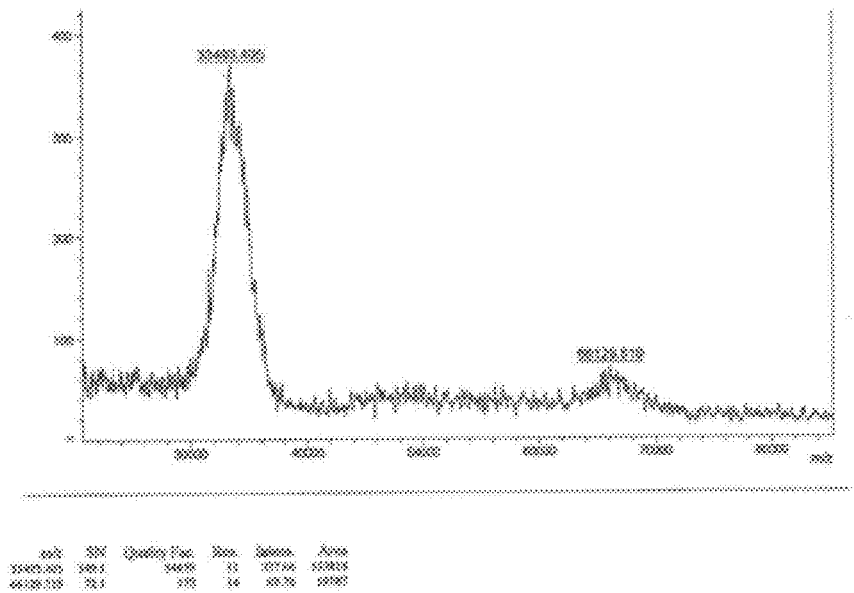
FIG. 9. MALDI-TOF spectrum of purified mono-[mPEG-Butyraldehyde-30K]-[Kisspeptin-10].

Fractions containing pure [mono]-[mPEG-ButyAldehyde30K]-[Kisspeptin-10] as determined by analytical RP-HPLC were pooled, lyophilized and stored at −80° C. A typical reversed phase CG71S chromatogram is shown in FIG. 7. RP-HPLC analysis of the purified conjugate is shown in FIG. 8, and MALDI-TOF analysis of the purified conjugate is shown in FIG. 9. The purity of the mono-PEG-conjugate was 99.2% by RP-HPLC analysis. The mass as determined by MALDI-TOF was within the expected range. The peak at 33.5 kDa is within the expected range for the molecular weight of the mono-PEG-conjugate. The peak at 66.1 kDa may represent the single charged mono-[mPEG-Butyraldehyde-30K]-[Kisspeptin-10] dimer formed during MALDI-TOF analysis.

Example KISS4

PEGylation of Kisspeptin-10 (KP-10) with [mPEG2-CAC-FMOC-NHS-40K]

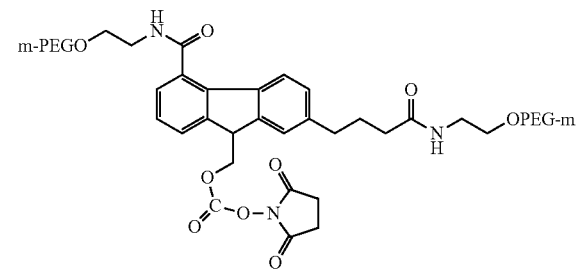

Stock solutions of 2.0 mg/mL KP-10 and 200 mg/mL mPEG2-CAC-FMOC-NHS-40K were prepared in 2 mM HCl. To initiate a reaction, the two stock solutions and a 1 M MES, pH 6.0, stock solution were brought to 25° C., and the three stock solutions were mixed (PEG reagent added last) to give final concentrations of 1.0 mg/mL KP-10 (0.75 mM), 50 mM MES and a 6-fold molar excess of mPEG-butyrALD30K over KP-10. The reaction was allowed to proceed for 2.5 hours at 25° C. After 2.5 hr, the reaction was quenched with 100 mM glycine in 100 mM HCl (10 mM final glycine concentration) for 10 minutes, after which glacial acetic acid was added to a final concentration of 5% (v/v).

The mono-PEGylated conjugate was purified from the reaction mixture by reversed phase chromatography using a column packed with CG71S media (Roam Haas) on an AKTA Explorer 100 system (GE Healthcare). Buffer A was 5% acetic acid/95% H$_2$O (v/v), Buffer B1 was 5% acetic acid/95% ethanol (v/v), and Buffer B2 was 5% acetic acid/95% acetonitrile (v/v). The AKTA Explorer plumbing system and CG71S were sanitized with 1 M HCl and 1 M NaOH and the resin was equilibrated with 10 column volumes Buffer A prior to sample loading. After loading, unreacted PEG reagent was eluted with a linear gradient from 100% A/0% B1 to 0% A/100% B1 over 10 column volumes with a linear flow rate of 90 cm/hour, followed by a 100% Buffer A wash over 4 column volumes. The PEGylated and nonPEGylated peptides were eluted using a linear gradient from 100% A/0% B2 to 40% A/60% B2 over 15 column volumes with a linear flow rate of 90 cm/hour.

Fractions collected during reversed phase chromatography with the CG71S resin were analyzed using analytical reversed-phase HPLC. The mobile phases were: A, 0.08% TFA in water, and B, 0.05% TFA in acetonitrile. A Waters Symmetry C18 column (4.6 mm×75 mm) was used with a flow rate of 0.5 ml/min and a column temperature of 60° C. Detection was carried out at 280 nm. The column was equilibrated in 25% B and conjugate separation was achieved using the gradient timetable shown in Table KISS4.1.

| Step | Time (min) | % Mobile phase B |
|---|---|---|
| 1 | 0.00 | 25.0 |
| 2 | 3.00 | 25.0 |
| 3 | 21.50 | 60.0 |
| 4 | 21.60 | 100.0 |
| 5 | 24.60 | 100.0 |
| 6 | 24.70 | 25.0 |

Fractions containing pure mono-[mPEG2-CAC-FMOC-40K]-[Kisspeptin-10] as determined by RP-HPLC were pooled, lyophilized and stored at −80° C.

Figure 10:
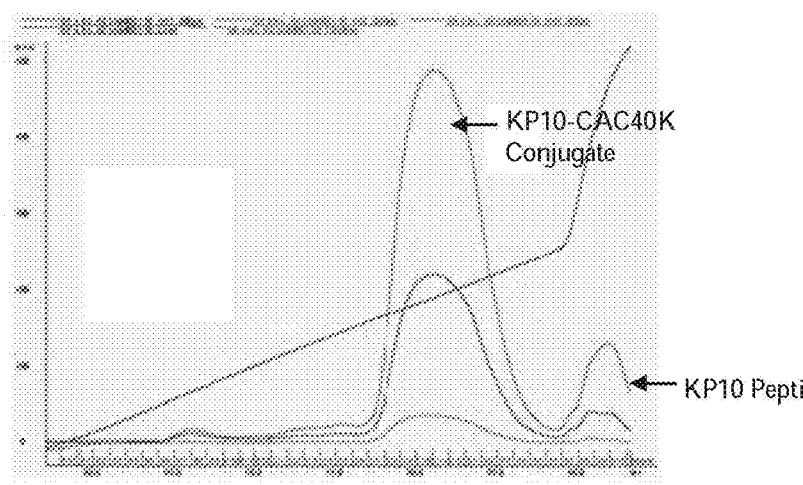
FIG. 10. Typical reversed phase purification profile of mono-[mPEG2-CAC-FMOC-40K]-[Kisspeptin-10].
Figure 11:
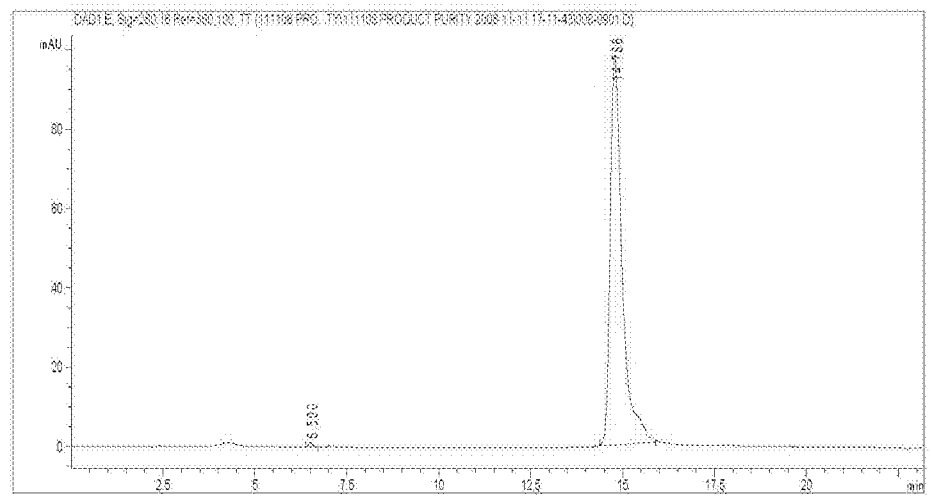
FIG. 11. Purity analysis of [mono]-[CAC-PEG2-FOMC-40K]-[Kisspeptin-10] by Reversed Phase HPLC.
Figure 12:
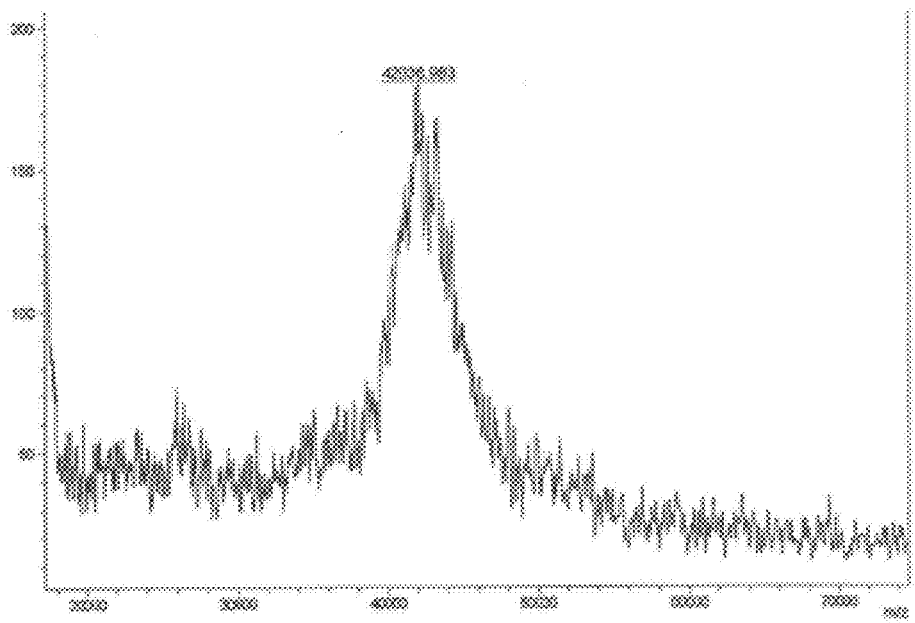
FIG. 12. MALDI-TOF spectrum of purified mono-[CAC-PEG2-FMOC-40K]-[Kisspeptin-10].

A typical reversed phase CG71S chromatogram is shown in FIG. 10. RP-HPLC analysis of the purified conjugate is shown in FIG. 12, and MALDI-TOF analysis of the purified conjugate is shown in FIG. 12. The purity of the mono-PEG-conjugate was 99.6% by RP-HPLC analysis. The mass as determined by MALDI-TOF was within the expected range.

Example KISS5

PEGylation of Kisspeptin-10 (KP-10) with N-m-PEG-Benzamide-p-Succinimidyl Carbonate (SBC)-30K A stock solution of 2.0 mg/mL KP-10 was prepared in 2 mM HCl. To initiate a reaction, the KP-10 stock solution was brought to 25° C., a 15-fold molar excess of SBC-30K lyophilized powder was added with stirring followed immediately with the addition of 1 M MES, pH 6, to give final concentrations of 1.0 mg/mL KP10 (0.75 mM) and 50 mM MES. The reaction was allowed to proceed for 20 minutes at 25° C. After 20 min, the reaction was quenched with 100 mM glycine in 100 mM HCl (10 mM final glycine concentration) for 10 minutes, after which glacial acetic acid was added to a final concentration of 5% (v/v).

The mono-PEGylated conjugate was purified from the reaction mixture by reversed phase chromatography using a column packed with CG71S media (Rohm Haas) on an AKTA Explorer 100 system (GE Healthcare). Buffer A was 5% acetic acid/95% H$_2$O (v/v), Buffer B1 was 5% acetic acid/95% ethanol (v/v), and Buffer B2 was 5% acetic acid/95% acetonitrile (v/v). The AKTA Explorer plumbing system and the CG71S resin were sanitized with 1 M HCl and 1 M NaOH and the resin was equilibrated with 10 column volumes Buffer A prior to sample loading. After loading, unreacted PEG reagent was eluted with a linear gradient from 100% A/0% B1 to 0% A/100% B1 over 10 column volumes with a linear flow rate of 90 cm/hour, followed by a 100% A wash over 4 column volumes. The PEGylated and nonPEGylated peptides were eluted using a linear gradient from 100% A/0% B2 to 40% A/60% B2 over 15 column volumes with a linear flow rate of 90 cm/hour.

Fractions collected during reversed phase chromatography with the CG71S resin were analyzed using analytical reversed-phase HPLC. The mobile phases were: A, 0.08% TFA in water, and B, 0.05% TFA in acetonitrile. A Waters Symmetry C18 column (4.6 mm×75 mm) was used with a flow rate of 0.5 ml/min and a column temperature of 60° C. Detection was carried out at 280 nm. The column was equilibrated in 25% B and conjugate separation was achieved using the gradient timetable shown in Table KISS5.1.

| Step | Time (min) | % Mobile phase B |
|---|---|---|
| 1 | 0.00 | 25.0 |
| 2 | 3.00 | 25.0 |
| 3 | 21.50 | 60.0 |
| 4 | 21.60 | 100.0 |
| 5 | 24.60 | 100.0 |
| 6 | 24.70 | 25.0 |

Figure 13:
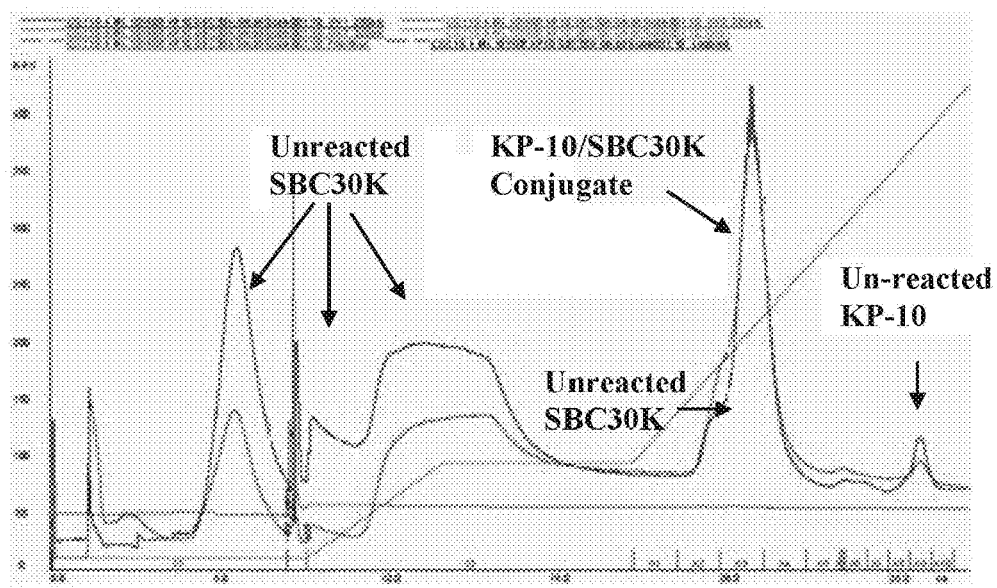
FIG. 13. Typical reversed phase purification profile of mono-[mPEG-SBC-30K]-[Kisspeptin-10].
Figure 14:
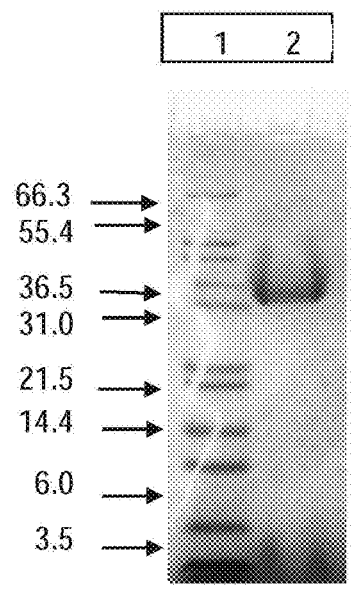
FIG. 14. SDS-PAGE, with Coomassie blue staining) of purified mono-[mPEG-SBC-30K]-[Kisspeptin-10].
Figure 15:
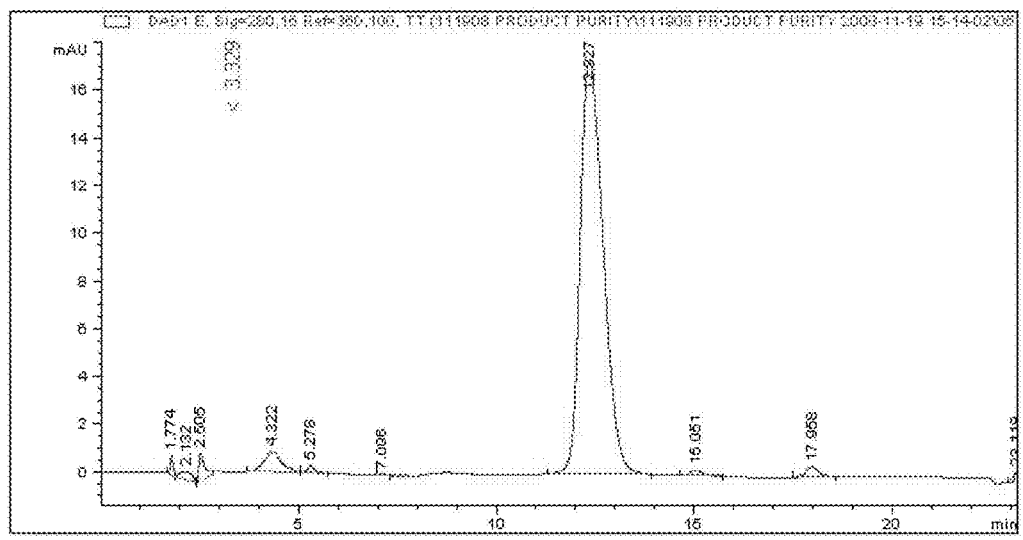
FIG. 15. Purity analysis of mono-[mPEG-SBC-30K]-[Kisspeptin-10] by Reversed Phase HPLC.
Figure 16:
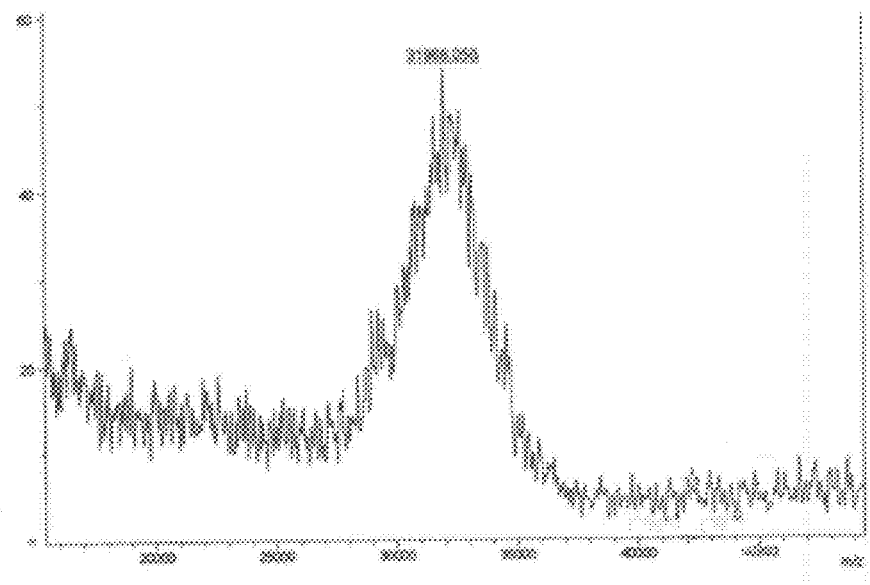
FIG. 16. MALDI-TOF spectrum of purified mono-[mPEG-SBC-30k]-[Kisspeptin-10].

Fractions containing pure mono-[mPEG-SBC-30K]-[Kisspeptin-10] as determined by RP-HPLC were pooled, lyophilized and stored at −80° C. A typical reversed phase CG71S chromatogram is shown in FIG. 13. SDS-PAGE analysis of purified mono-[mPEG-SBC-30K]-[Kisspeptin-10] is shown in FIG. 14. RP-HPLC analysis of the purified conjugate is shown in 15, and MALDI-TOF analysis of the purified conjugate is shown in FIG. 16. The purity of the

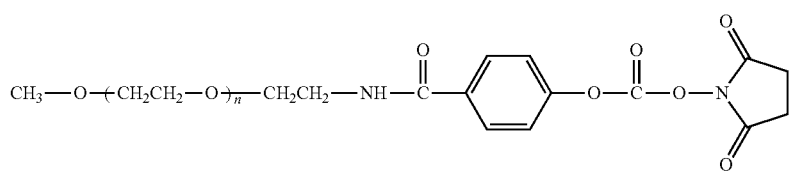

mono-PEG-conjugate was >95% by SDS-PAGE and 95.4% by RP-HPLC analysis. The mass as determined by MALDI-TOF was within the expected range.

Example KISS6

PEGylation of Kisspeptin-54 (KP-54) with mPEG2-Butyr-Aldehyde-40K

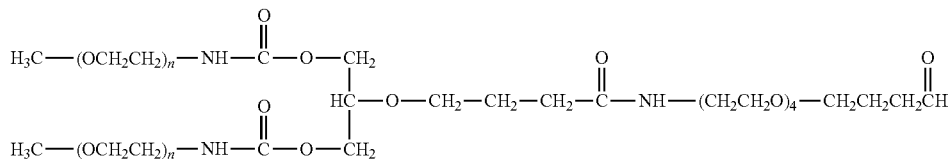

Stock solutions of 2.0 mg/mL KP-54 and 200 mg/mL mPEG-butyrALD40K were prepared in 2 mM HCl. To initiate a reaction, the two stock solutions and a 1 M MES, pH 6.0, stock solution were brought to 25° C., and the three stock solutions were mixed (PEG reagent added last) to give final concentrations of 1.0 mg/mL KP-54 (0.15 mM), 50 mM MES and a 6-fold molar excess of mPEG-butyrALD40K over KP-54. After 15 min reaction, a 10-fold molar excess of NaBH$_3$CN over PEG was added and the reaction was allowed to continue for an additional 16 hours at 25° C. After 16 hr 15 min total reaction time, the reaction was quenched with 100 mM glycine in 100 mM HCl (10 mM final glycine concentration) for 10 minutes. The reaction mixture was diluted with sterile deionized H$_2$O until the conductivity was below 1.0 mS/cm and the pH was then adjusted to 6.0 with 1 M Na$_2$CO$_3$/NaHCO$_3$, pH 10.0.

The mono-PEGylated conjugate was purified from the reaction mixture by cation exchange chromatography using SPHP media (GE Healthcare) on an AKTA Explorer 100 system (GE Healthcare). Buffer A was 20 mM MES, pH 6.0, Buffer B was 20 mM MES and 1 M NaCl, pH 6.0. The AKTA Explorer plumbing system and SPHP resin were sanitized with 1 M HCl and 1 M NaOH and the SPHP resin was equilibrated with 10 column volumes Buffer A prior to sample loading. After loading and a column wash with 5 column volumes Buffer A, the PEGylated and nonPEGy-lated peptides were eluted using a linear gradient from 100% A/0% B to 0% A/100% B over 15 column volumes with a linear flow rate of 90 cm/hour.

Fractions collected during cation exchange chromatography were analyzed using analytical reversed-phase HPLC. The mobile phases were: A, 0.08% TFA in water, and B, 0.05% TFA in acetonitrile. A Waters Symmetry C18 column (4.6 mm×75 mm) was used with a flow rate of 0.5 ml/min and a column temperature of 60° C. Detection was carried out at 280 nm. The column was equilibrated in 25% B and conjugate separation was achieved using the gradient timetable shown in Table KISS6.1.

| Step | Time (min) | % Mobile phase B |
|---|---|---|
| 1 | 0.00 | 25.0 |
| 2 | 3.00 | 25.0 |
| 3 | 21.50 | 60.0 |
| 4 | 21.60 | 100.0 |
| 5 | 24.60 | 100.0 |
| 6 | 24.70 | 25.0 |

Fractions containing pure mono-[mPEG2-ButyrAlde-hyde-40K]-[Kisspeptin-54] as determined by RP-HPLC were pooled and concentrated over a reversed phase CG71S column. The column was washed with 5% acetic acid in acetonitrile and equilibrated with 5% acetic acid prior to loading. After loading, the column was washed with 5% acetic acid and the PEGylated peptide was eluted with a linear gradient from 5% acetic acid to 5% acetic acid/95% acetonitrile (v/v) over 5 column volumes. Fractions containing the conjugate were pooled, lyophilized and stored at −80° C.

Figure 17:
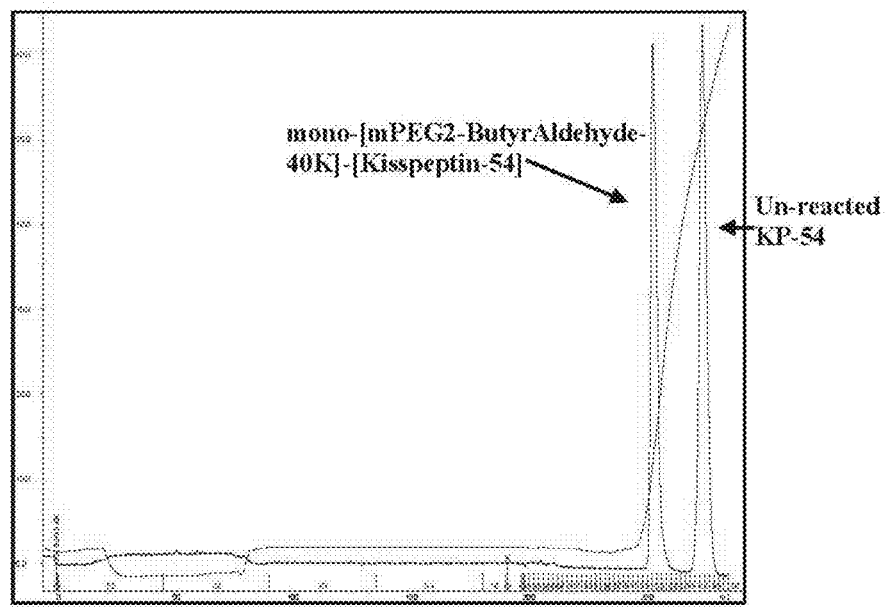
FIG. 17 Typical cation exchange purification profile of mono-[mPEG2-ButyrAldehyde-40K]-[Kisspeptin-54].
Figure 18:
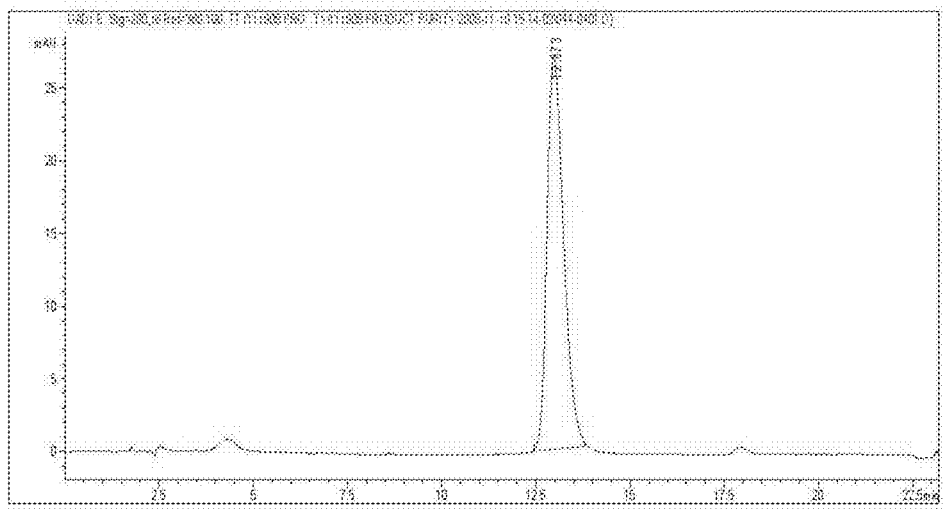
FIG. 18. Purity analysis of [mono]-[mPEG2-ButyrAldehyde-40K]-[Kisspeptin-54] conjugate by Reversed Phase HPLC.
Figure 19:
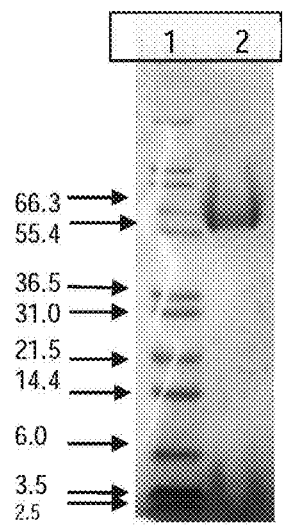
FIG. 19. SDS-PAGE with Coomassie staining of purified [mono]-[mPEG2-ButyrAldehyde-40K]-[Kisspeptin-54].
Figure 20:
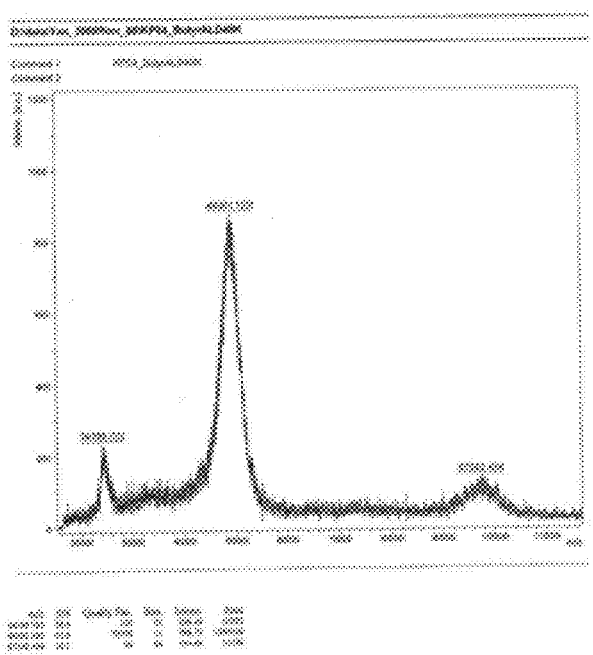
FIG. 20. MALDI-TOF spectrum of purified [mono]-[mPEG2-ButyrAldehyde-40K]-[Kisspeptin-54].

A typical cation exchange SPHP chromatogram is shown in FIG. 17. SDS-PAGE analysis of purified mono-[mPEG2-ButyrAldehyde-40K]-[Kisspeptin-54] is shown in FIG. 18. RP-HPLC analysis of the purified conjugate is shown in FIG. 19, and MALDI-TOF analysis of the purified conjugate is shown in FIG. 20. The purity of the mono-PEG-conjugate was >95% by SDS-PAGE and 100% by RP-HPLC analysis. The mass as determined by MALDI-TOF was within the expected range. The major peak at 49 kDa is within the expected range for the molecular weight of [mono]-[mPEG2-ButyrAldehyde-40K]-[Kisspeptin-54]. The peak at 24 kDa represents the double charged conjugate and the peak at 97 kDa may represent the single charged conjugate dimer formed during MALDI-TOF analysis.

Example KISS7 a) mPEG-N$^{ter}$-KISS1 Via mPEG-SPC

KISS1 is prepared and purified according to standard automated peptide synthesis or recombinant techniques known to those skilled in the art. An illustrative polymeric reagent, mPEG-SPC reagent,

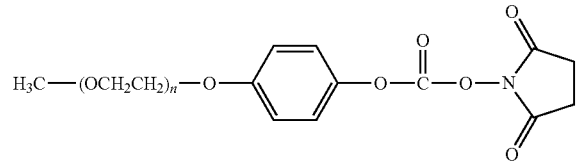

'SPC' polymer reagent is covalently attached to the N-terminus of KISS1, to provide a N$^{ter}$-conjugate form of the peptide. mPEG-SPC 20 kDa, stored at −20° C. under argon, is warmed to ambient temperature. The reaction is performed at room temperature. An X-fold molar excess of mPEG-SPC 20 kDa reagent is used based upon absolute peptide content. The mPEG-SPC reagent is weighed into a glass vial containing a magnetic stirrer bar. A solution of KISS1 prepared in phosphate buffered saline, PBS, pH 7.4 is added and the mixture is stirred using a magnetic stirrer until the mPEG-SPC is fully dissolved. The stirring speed is reduced and the reaction is allowed to proceed to formation of conjugate product. The reaction is optionally quenched to terminate the reaction.

The pH of the conjugate solution at the end of the reaction is measured and further acidified by addition of 0.1M HCl, if necessary, to bring the pH of the final solution to about 5.5. The conjugate solution is then analyzed by SDS-PAGE and RP-HPLC (C18) to determine the extent of mPEG-N$^{ter}$-KISS1 conjugate formation.

Using this same approach, other conjugates are prepared using mPEG derivatives having other weight-average molecular weights that also bear an N-hydroxysuccinimide moiety.

b) KISS1-C$^{ter}$-mPEG

An illustrative polymeric reagent, mPEG-NH$_2$ reagent is covalently attached to the C-terminus of KISS1, to provide a C$^{ter}$-conjugate form of the peptide. For coupling to the C-terminus, a protected KISS1 (Prot-KISS1, e.g, Fmoc-Ile-Pro-Cys(tBu)-Asn-Asn-Lys(Fmoc)-Gly-Ala-His-Ser (Dmab)-Val-Gly-Leu-Met-Trp-Trp-Met-Leu-Ala-Arg(Tos)) is prepared and purified according to standard automated peptide synthesis techniques known to those skilled in the art. mPEG-NH$_2$ 20 kDa, stored at −20° C. under argon, is warmed to ambient temperature. The reaction is performed at room temperature. A X-fold molar excess of mPEG-NH$_2$, PyBOP (benzotriazol-1-yloxy)tripyrrolidinonophosphonium hexafluorophosphate), and 1-hydroxybenzotriazole (HOBt) are used, based upon absolute peptide content. The mPEG-NH$_2$, PyBOP, HOBt are weighed into a glass vial containing a magnetic stirrer bar. A solution of Prot-KISS1 is prepared in N,N-dimethylformamide is added and the mixture is stirred using a magnetic stirrer until the mPEG-NH$_2$ is fully dissolved. The stirring speed is reduced and the reaction is allowed to proceed to formation of conjugate product. The conjugate solution is then analyzed by SDS-PAGE and RP-HPLC (C18) to determine the extent of Prot-KISS1-C$^{ter}$-mPEG conjugate formation. The remaining protecting groups are removed under standard deprotection conditions to yield the KISS1-C$^{ter}$-mPEG conjugate.

Using this same approach, other conjugates are prepared using mPEG derivatives having other weight-average molecular weights that also bear an amino moiety.

c) KISS1-Cys(S-mPEG)

mPEG-Maleimide is obtained having a molecular weight of 5 kDa and having the basic structure shown below:

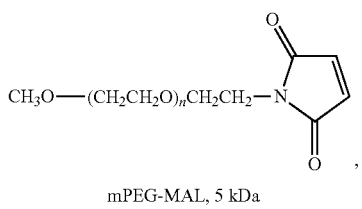

mPEG-MAL, 5 kDa

KISS1, which has a thiol-containing cysteine residue, is dissolved in buffer. To this peptide solution is added a 3-5 fold molar excess of mPEG-MAL, 5 kDa. The mixture is stirred at room temperature under an inert atmosphere for several hours. Analysis of the reaction mixture reveals successful conjugation of this peptide.

Using this same approach, other conjugates are prepared using mPEG-MAL having other weight average molecular weights.

d) mPEG-N$^{ter}$-KISS1 Via mPEG-SMB

An mPEG-N-Hydroxysuccinimide is obtained having a molecular weight of 5 kDa and having the basic structure shown below:

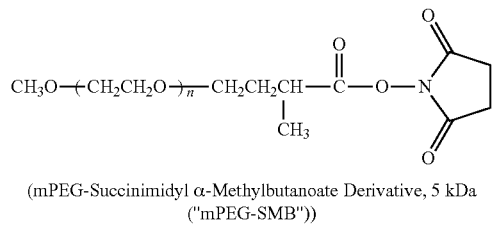

(mPEG-Succinimidyl α-Methylbutanoate Derivative, 5 kDa ("mPEG-SMB"))

mPEG-SMB, 5 kDa, stored at −20° C. under argon, is warmed to ambient temperature. A five-fold excess (relative to the amount of the peptide) of the warmed mPEG-SMB is dissolved in buffer to form a 10% reagent solution. The 10% reagent solution is quickly added to the aliquot of a stock KISS1 solution and mixed well. After the addition of the mPEG-SMB, the pH of the reaction mixture is determined and adjusted to 6.7 to 6.8 using conventional techniques. To allow for coupling of the mPEG-SMB to the peptide via an amide linkage, the reaction solution is stirred for several hours (e.g., 5 hours) at room temperature in the dark or stirred overnight at 3-8° C. in a cold room, thereby resulting in a conjugate solution. The reaction is quenched with a 20-fold molar excess (with respect to the peptide) of Tris buffer.

Using this same approach, other conjugates are prepared using mPEG derivatives having other weight-average molecular weights that also bear an N-hydroxysuccinimide moiety.

d) KISS1-Glu(O-mPEG)

An illustrative polymeric reagent, mPEG-NH$_2$ reagent is covalently attached to the Glu residue of KISS1, to provide a Glu-conjugate form of the peptide. For coupling to the Glu residue, a protected KISS1 (Prot2-KISS1) is prepared and purified according to standard automated peptide synthesis techniques known to those skilled in the art. Deprotection of the Glu(OBz) residue (H$_2$/Pd) yields the free-Glu carboxylate for subsequent coupling (Prot3-KISS1) mPEG-NH$_2$ 20 kDa, stored at −20° C. under argon, is warmed to ambient temperature. The reaction is performed at room temperature. A 5-fold molar excess of mPEG-NH$_2$, PyBOP (benzotriazol-1-yloxy)tripyrrolidinonophosphonium hexafluorophosphate), and 1-hydroxybenzotriazole (HOBt) are used, based upon absolute peptide content. The mPEG-NH$_2$, PyBOP, HOBt are weighed into a glass vial containing a magnetic stirrer bar. A solution of Prot3-KISS1 is prepared in N,N-dimethylformamide is added and the mixture is stirred using a magnetic stirrer until the mPEG-NH$_2$ is fully dissolved. The stirring speed is reduced and the reaction is allowed to proceed to formation of conjugate product. The conjugate solution is then analyzed by SDS-PAGE and RP-HPLC (C18) to determine the extent of Prot3-KISS1-(Glu-O-mPEG) conjugate formation. The remaining protecting groups are removed under standard deprotection conditions to yield the KISS1-Glu(O-mPEG) conjugate.

Using this same approach, other conjugates are prepared using mPEG derivatives having other weight-average molecular weights that also bear an amino moiety.

Example KISS8

A FLIPR assay was conducted to screen Kisspeptin and PEG-Kisspeptin peptides for dose-dependent agonist activities on the GPR54 G-Protein coupled receptor. EC$_{50}$ potency values were determined for each compound on the GPR54 GPCR, and Metastin 45-54 (Kisspeptin 10) was used as the reference agonist.

Sample preparation: Sample compounds are listed in Table KISS8.1. Prior to assay, CAC-PEG2-FMOC-NHS-40K-Kisspeptin 10 and mono-mPEG-SBC-30K-Kisspeptin 10 (provided in 2 mM HCl) were diluted 1:1 in 200 mM or 10 mM HEPES buffer, pH 7, respectively, and incubated at 37° C. for 0, 24, 48, and 96 h for CAC-PEG2-FMOC-NHS-40 K-Kisspeptin 10; 0, and 2 h for mono-mPEG-SBC-30 K-Kisspeptin 10). All compounds were diluted in their storage solvents to produce 250X (of the top dose listed below) master stock solutions. Compounds were then transferred from their master stock solutions into a daughter plate that was used in the assay. Each 250X solution was diluted into assay buffer (1×HBSS with 20 mM HEPES and 2.5 mM Probenecid) to obtain the final top test concentration.

Figure 22:
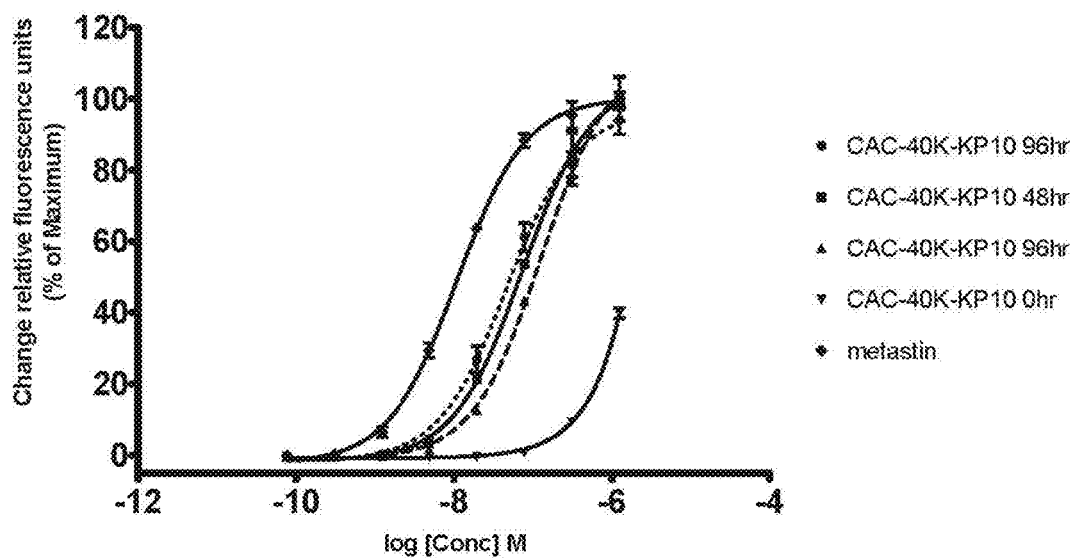
FIG. 22. Agonist activity at GPR54 for releasable PEG conjugate of Kisspeptin 10.
Figure 23:
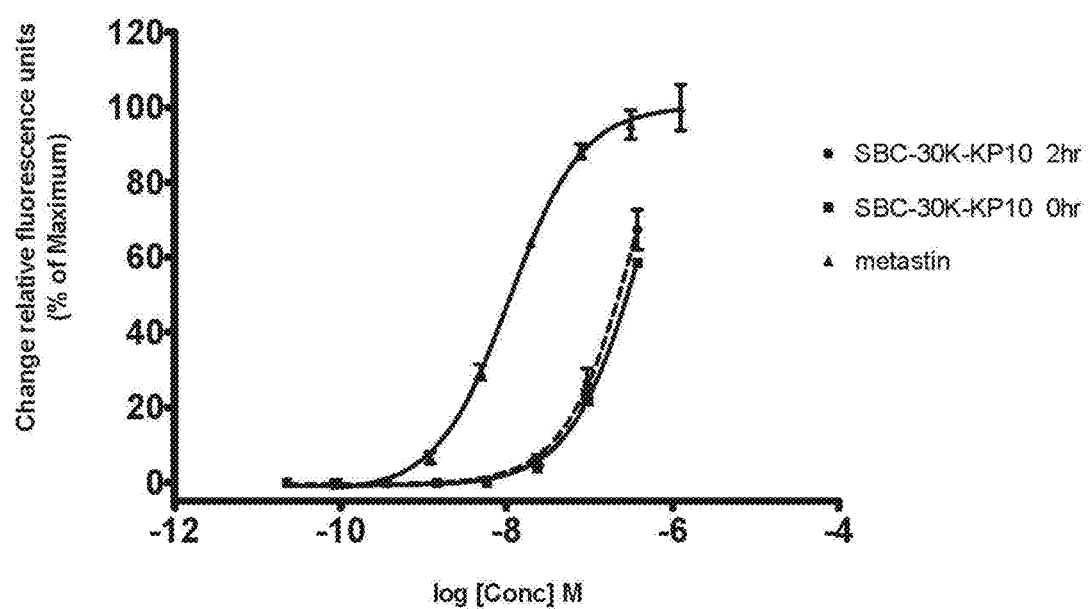
FIG. 23. Agonist activity at GPR54 for releasable PEG conjugate of Kisspeptin 10.

Calcium flux agonist assay: Chemicon's cloned human GPR54-expressing cell line is made in the Chem-1 host, which supports high levels of recombinant GPR54 expression on the cell surface and contains high levels of the promiscuous G protein Gα15 to couple the receptor to the calcium signaling pathway. Sample compounds were plated in an eight-point, four-fold serial dilution series with a top concentration of 0.375 µM (except for CAC-PEG2-FMOC-NHS-40K-Kisspeptin 10, top concentration of 1.25 µM). Reference agonist was handled as mentioned above, serving as assay control. Assay was read for 180 seconds using the FLIPR$^{TETRA}$. All plates were subjected to appropriate baseline corrections. Once baseline corrections were processed, maximum fluorescence values were exported and data manipulated to calculate percentage activation and Z'. Dose response curves were generated using GraphPad Prism. The curves were fit by utilizing sigmoidal dose response (variable slope) fitting with the bottom parameter fixed at 0 (FIGS. 21-23).

TABLE KISS8.1

| stable | releasable | half-life of release | Dose response top dose |
|---|---|---|---|
| KP10 | | n/a | 0.375 µM |
| mPEG-ALD10K-KP10 | | n/a | 0.375 µM |
| mPEG-ALD30K-KP10 | | n/a | 0.375 µM |
| | CAC-PEG2-Fmoc-NHS-40K-KP10 | 32 h | 1.25 µM |
| | mPEG-SBC30K-KP10 | 27 min | 0.375 µM |
| KP13 | | n/a | 0.375 µM |
| mPEG-ALD30K-KP13 | | n/a | 0.375 µM |
| KP54 | | n/a | 0.375 µM |
| mPEG-ALD40K-KP54 | | n/a | 0.375 µM |

Figure 21:
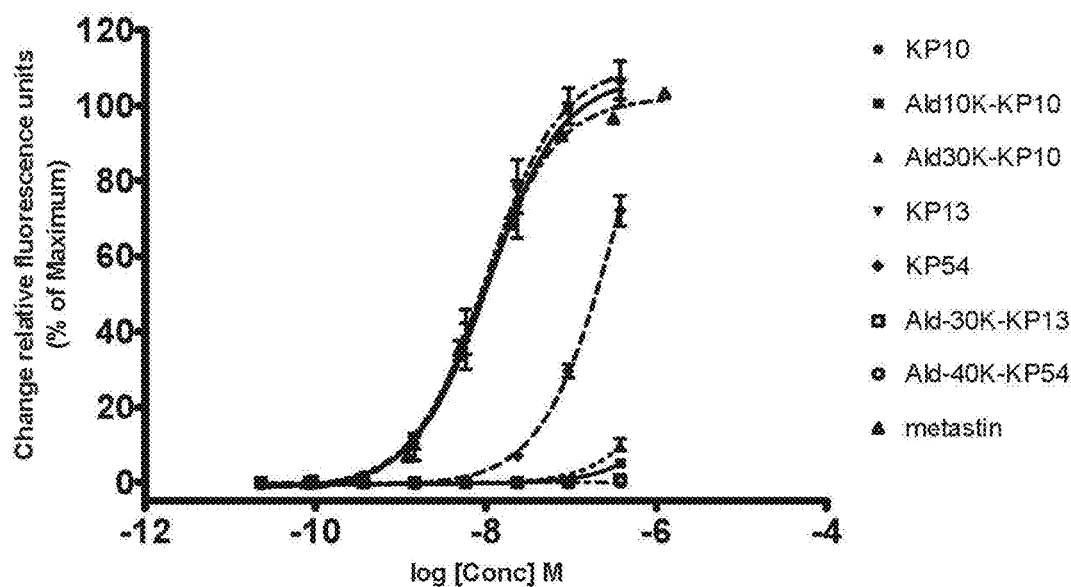
FIG. 21. Agonist activity at GPR54 for stable PEG conjugates of Kisspeptin 10, Kisspeptin 13, and Kisspeptin 54.

FIG. 21. Agonist activity at GPR54 for stable PEG conjugates of Kisspeptin 10, Kisspeptin 13, and Kisspeptin 54.
FIG. 22. Agonist activity at GPR54 for releasable PEG conjugate of Kisspeptin 10.
FIG. 23. Agonist activity at GPR54 for releasable PEG conjugate of Kisspeptin 10.

TABLE KISS8.2

Summary of $EC_{50}$ values of agonist activation at GPR54.

| compound | Time of release | $EC_{50}$ (nM) | Fold change compared to metastin |
|---|---|---|---|
| KP10 | n/a | 10 | 1 |
| Ald10K-KP10 | | No activity | — |
| Ald30K-KP10 | | No activity | — |
| SBC-30K-KP10 | 0 h | 280 | 23 |
| SBC-30K-KP10 | 2 h | 200 | 17 |
| CAC-40K-KP10 | 0 h | 1700 | 155 |
| CAC-40K-KP10 | 24 h | 120 | 9 |
| CAC-40K-KP10 | 48 h | 74 | 6 |
| CAC-40K-KP10 | 96 h | 47 | 4 |
| KP13 | n/a | 11 | 1 |
| Ald30K-KP13 | | No activity | — |
| KP54 | | 190 | 16 |
| Ald40K-KP54 | | No activity | — |
| Metastin (cntl) | | 10-14* | — |

*varied depending on the individual test plate (samples received in different buffers were tested against metastin control in the same buffer)

Stable PEG conjugates of Kisspeptin 10, Kisspeptin 13, and Kisspeptin 54 do not retain agonist activity at the GPR54 receptor, whereas both Kisspeptin 10 releasable conjugates show partial activity after release in buffer at pH 7.0 (Table KISS8.2). The SBC-30K Kisspeptin 10 conjugate has a half-life release rate of 27 minutes, and the activity at 0 h and after 2 h of release were similar, $EC_{50}$=280 and 200 nM, respectively, about 23- and 17-fold less than the metastin control. The activity exhibited by SBC-30K Kisspeptin 10 (0 hr) is believed to be due to release of the peptide from the conjugate prior to assay. The CAC-40K Kisspeptin 10 conjugate, with a half-life of release of 32 h, had $EC_{50}$ values of 1600, 120, 74, and 47 nM after 0, 24, 48, and 96 h release, and showed 155-fold, 9-fold, 6-fold, and 4-fold less activity compared to metastin after 0, 24, 48, and 96 h release, respectively. We did not test the activity of Kisspeptin 10 (metastin) after incubation at 37° C. for an equivalent time.

Example ZIC1

Ziconotide Conjutgate Strategy: The N-terminal amine and four ε-amine groups on lysine residues are the targeted positions for PEGylation. The chemistry of ziconotide PEGylation with the non-releasable mSBA-30K PEG reagent is illustrated.

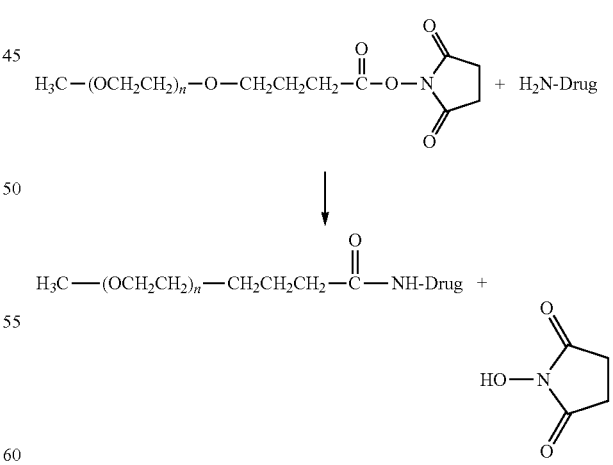

PEGylation of a Drug with a mSBA-NHS Reagent.

PEGylation with releasable PEG reagents such as phenyl carbamate are also performed. Figure shows the PEGylation of ziconotide with a releasable mSBC-30K PEG reagent and the potential pathway to regenerate the parent drug from the conjugate.

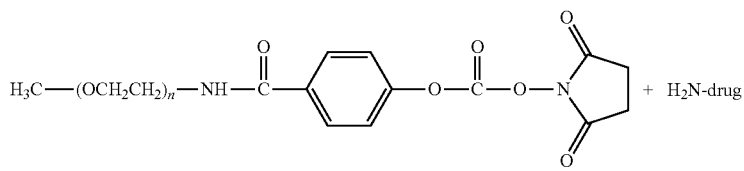

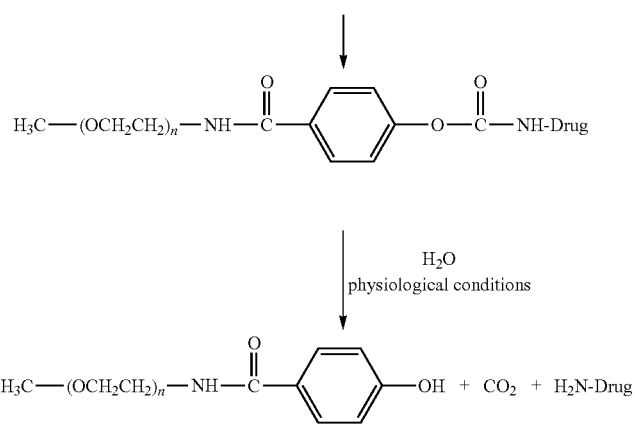

Example of the formation of a carbamate PEG drug conjugate and a possible pathway of regenerating the parent drug under physiological conditions.

PEGylation with releasable PEG reagents such as fluorenylmethyl chloroformate (FMOC) are also performed. Figure below shows the PEGylations of zinconotide with releasable C2-20K-FMOC and CAC-40K-FMOC PEG reagents and the potential pathways to regenerate the parent drug from the conjugates. By fine tuning the PEG reagent structures, the PEG release rate from the conjugate parent drug can be altered.

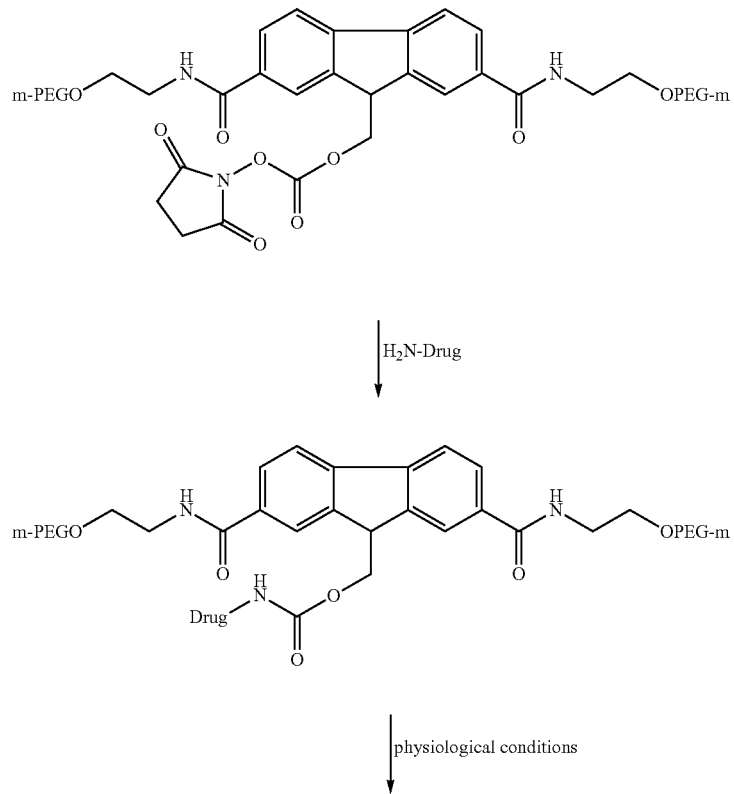

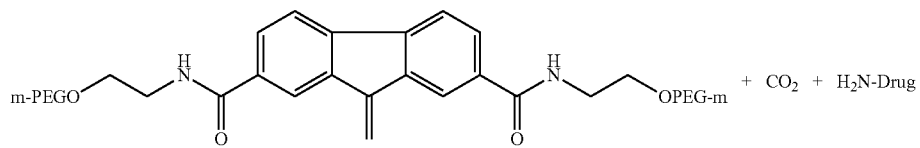
Example of the formation of a C2-FMOC-PEG drug conjugate and a possible pathway of regenerating the parent drug under physiological conditions.
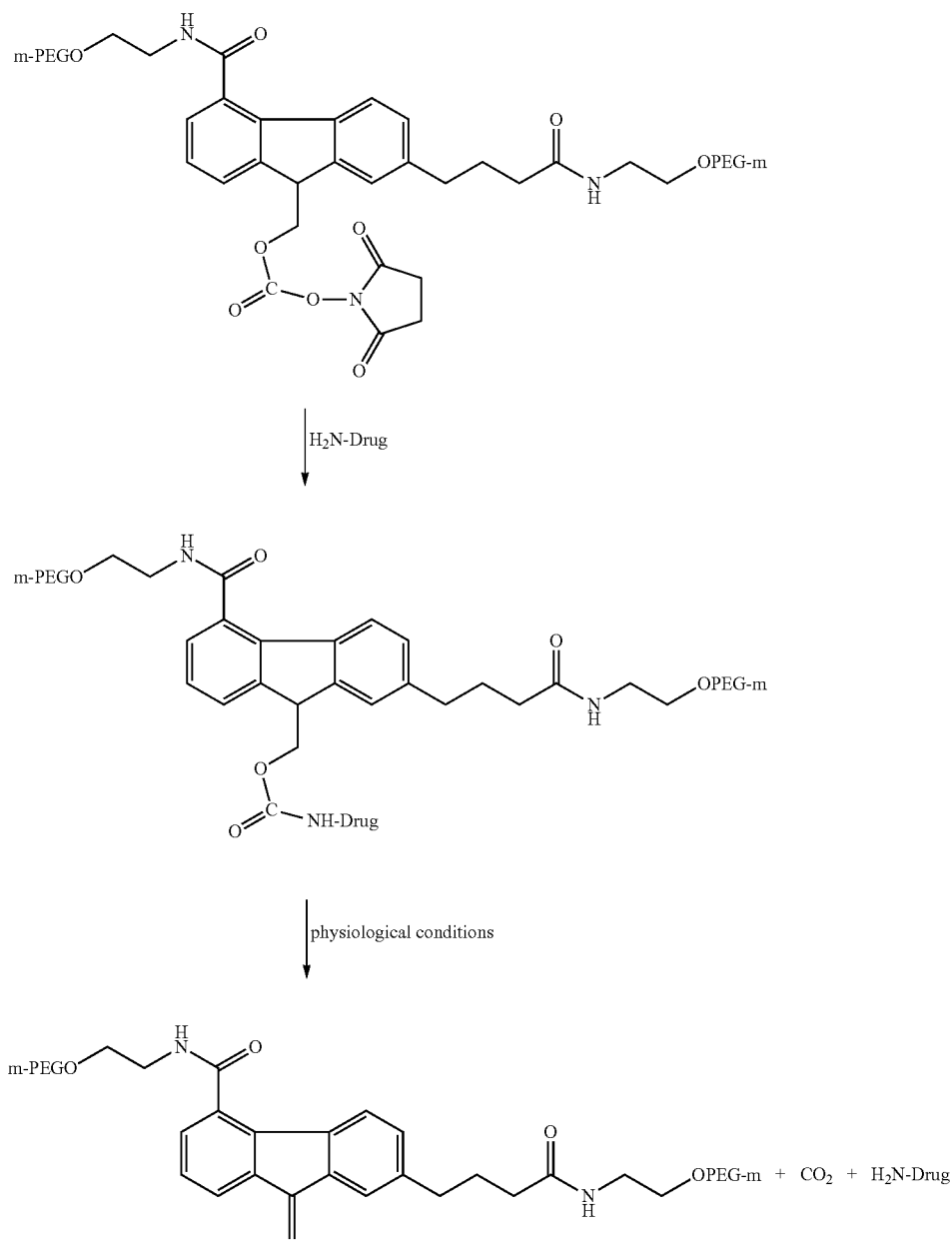

Example of the formation of a CAC-FMOC-PEG drug conjugate and a possible pathway of regenerating the parent drug under physiological conditions.

Example ZIC2

PEGylation of Ziconotide with mPEG-C2-FMOC-20K-NHS

Figure 24:
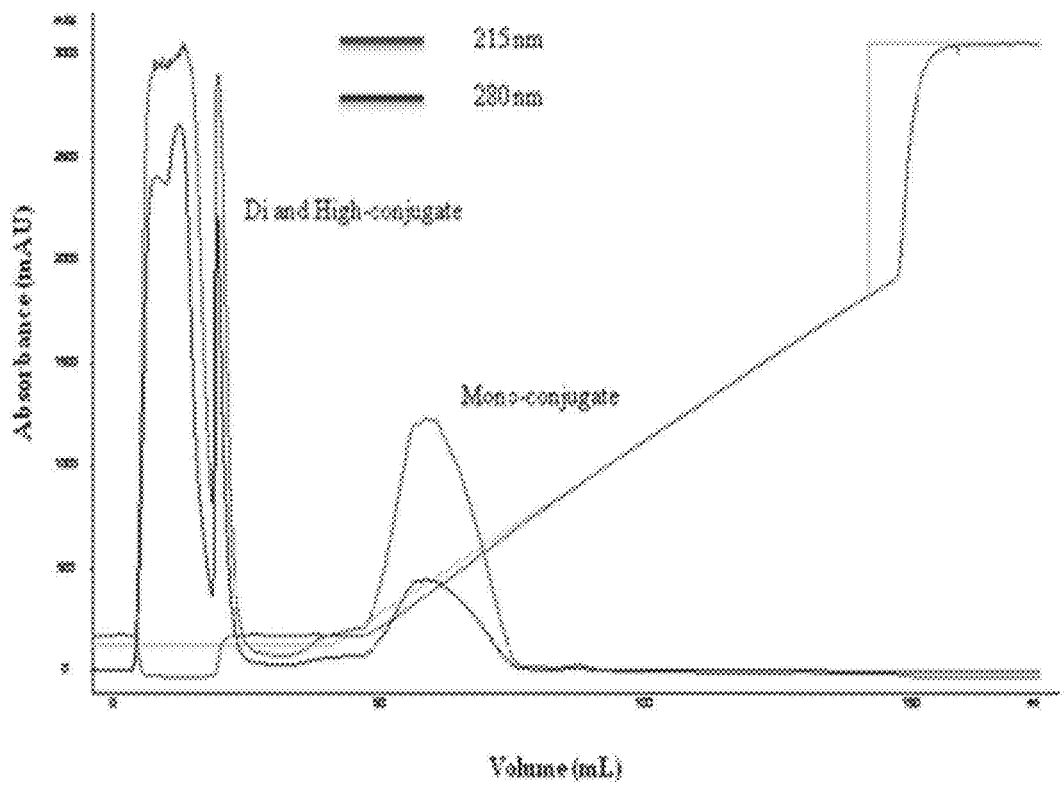
FIG. 24: Cation exchange purification of mono-mPEG-C2-FMOC-20K-ziconotide from the PEGylation reaction mixture.
Figure 25:
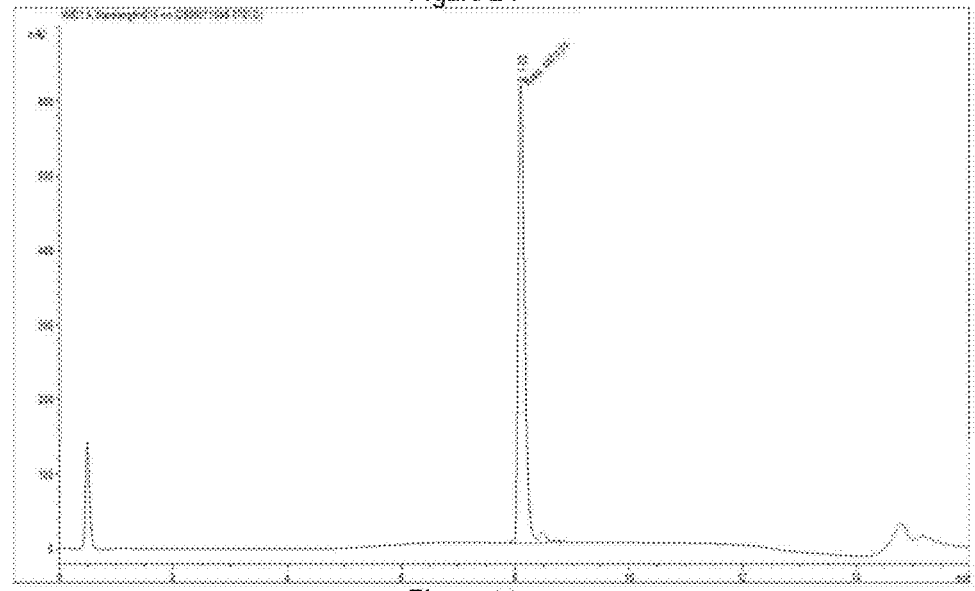
FIG. 25: RP-HPLC analysis of purified mono-mPEG-C2-FMOC-20K-ziconotide.
Figure 26:
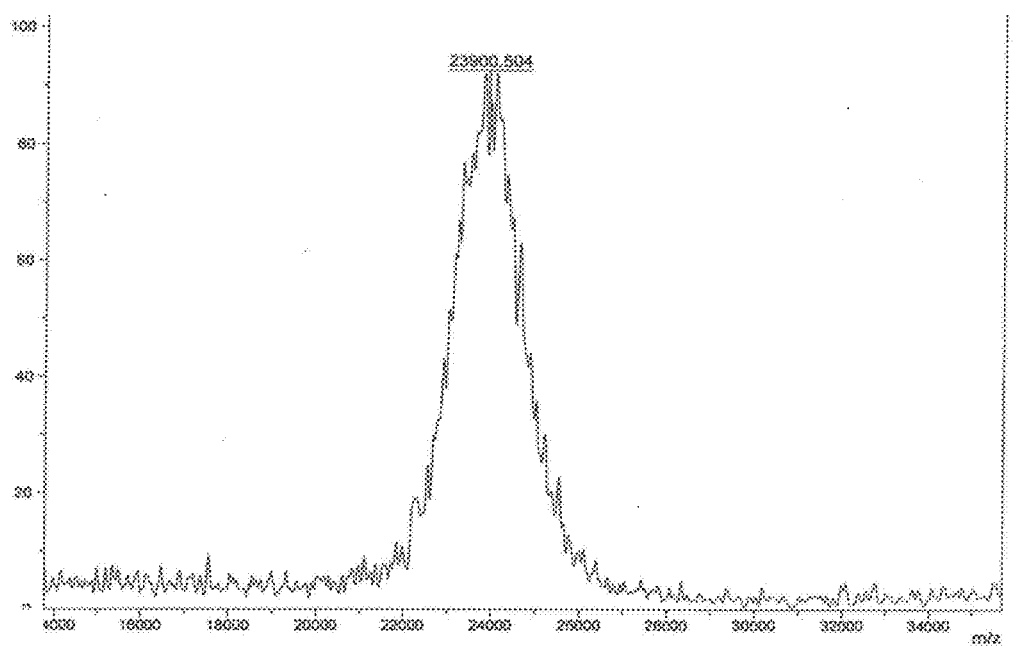
FIG. 26: MALDI-TOF analysis of purified mono-mPEG-C2-FMOC-20K-ziconotide.

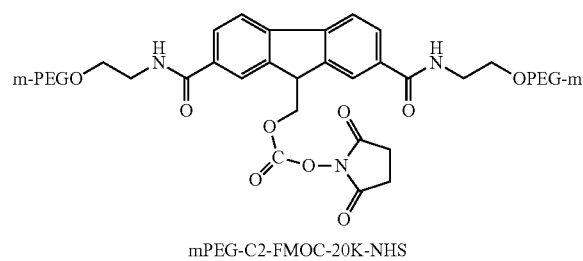

mPEG-C2-FMOC-20K-NHS mono-mPEG-C2-FMOC-20K-ziconotide was produced in a 2.4-mL reaction mixture consisting of 0.44 mL water, 0.096 mL 0.5 M HEPES, pH 7.4, 0.12 mL of 100 mg/ml ziconotide and 2.14 ml of 100 mg/mL mPEG-C2-FMOC-20K. The molar ratio between ziconotide and PEG reagent was 1:2 after the correction of purity of the PEG reagent. mPEG-C2-FMOC-20K, the last reagent added to the mixture, was dissolved in 2 mM HCl to a final concentration of 100 mg/mL immediately before addition. The dissolved PEG reagent was added to the reaction mixture with stirring. The reaction mixture was incubated at 25° C. with stirring for 45 minutes. After 45 minutes, 0.126 mL 0.2 M glycine (unbuffered) was added into the reaction mixture to quench the unreacted PEG reagent. After an additional 30 minutes of stirring at 25° C., the pH of the reaction mixture was adjusted to 5.0 at room temperature with acetic acid. The reaction mixture was diluted 1:10 with 20 mM sodium acetate, pH 5.0, and purified by cation exchange chromatography (HiTrap SP Sepharose HP; 5 mL). A linear salt gradient (FIG. 24) separated the mono-conjugate from the di- and high PEGylated products and unrereacted peptide. Purification buffers were as follows: A: 20 mM sodium acetate, pH 5.0, and B: 20 mM sodium acetate, 1.0 M sodium chloride, pH 5.0. The diluted reaction mixture was loaded at 0.4 mL/min with a two column volume wash after the load. The linear gradient consisted of 0 to 60% B over twenty column volumes at an elution flow rate of 0.4 mL/min. The purified mono-conjugate was determined to be 98% pure by reversed phase HPLC (FIG. 25 and Table ZIC2.1). MALDI-TOF analysis indicated the expected mass (23.9 kDa) for ziconotide mono-PEGylated with a 20 kDa PEG (FIG. 26). The final conjugate concentration was determined to be 0.21 mg/mL using a standard curve of ziconotide with the BCA assay.

TABLE ZIC2.1

Analytical RP-HPLC method: Poroshell, 5 μm, 2.1 × 75 mm. Mobile Phase A: 0.1% TFA/H$_2$O and B: 0.1% TFA/CH$_3$CN

| TIME (min) | % B | Flow rate (mL/min) |
| --- | --- | --- |
| 0.0 | 0 | 0.5 |
| 1.0 | 0 | 0.5 |
| 10 | 80 | 0.5 |
| 10.1 | 95 | 0.5 |
| 12.1 | 95 | 0.5 |

TABLE ZIC2.1-continued

Analytical RP-HPLC method: Poroshell, 5 μm, 2.1 × 75 mm. Mobile Phase A: 0.1% TFA/H$_2$O and B: 0.1% TFA/CH$_3$CN

| TIME (min) | % B | Flow rate (mL/min) |
| --- | --- | --- |
| 12.2 | 0 | 0.5 |
| 16.0 | 0 | 0.5 |

Example ZIC3

PEGylation of Ziconotide with mPEG-CAC-FMOC-40K-NHS

Figure 27:
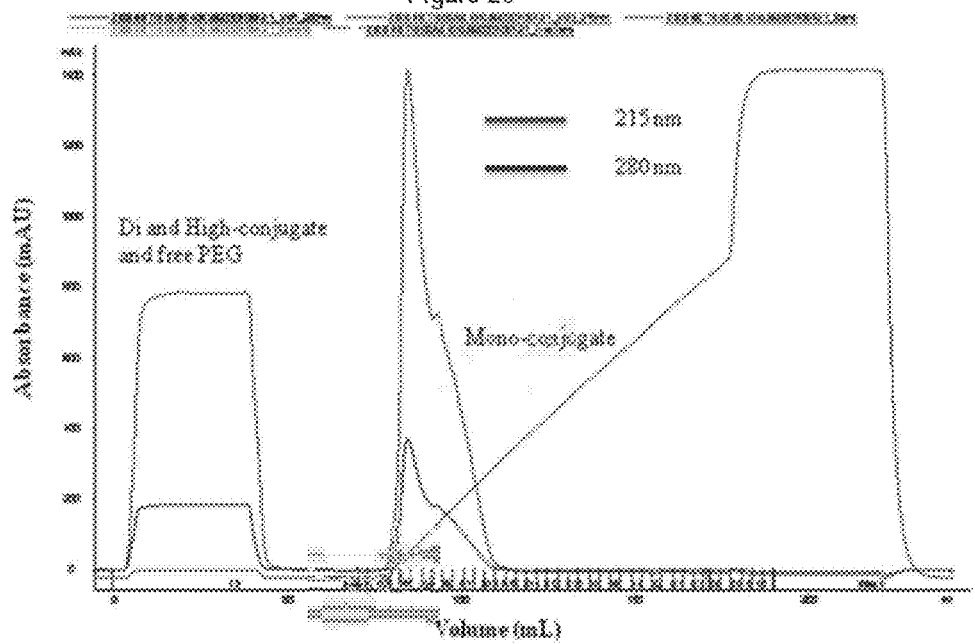
FIG. 27: Cation exchange purification of mono-mPEG-CAC-FMOC-40K-ziconotide from the PEGylation reaction mixture.
Figure 28:
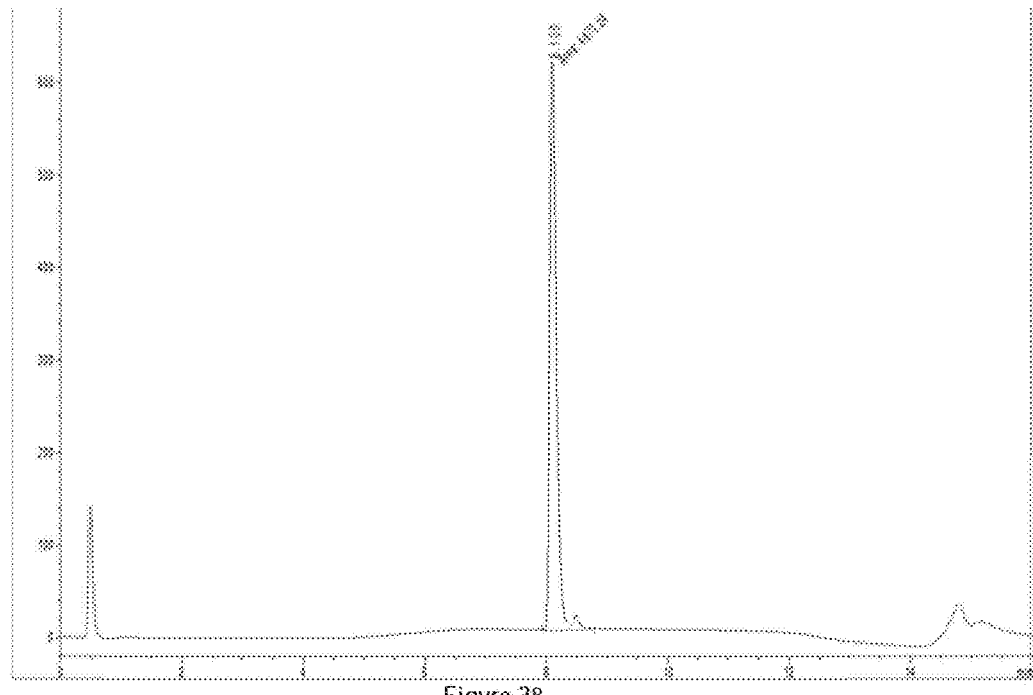
FIG. 28: RP-HPLC analysis of purified mono-mPEG-CAC-FMOC-40K-ziconotide.
Figure 29:
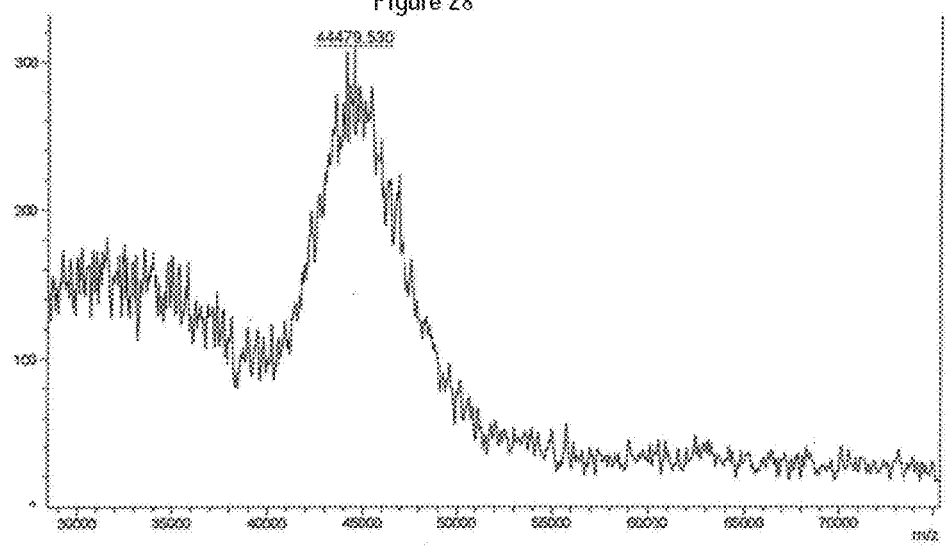
FIG. 29: MALDI-TOF analysis of purified mono-mPEG-CAC-FMOC-40K-ziconotide.

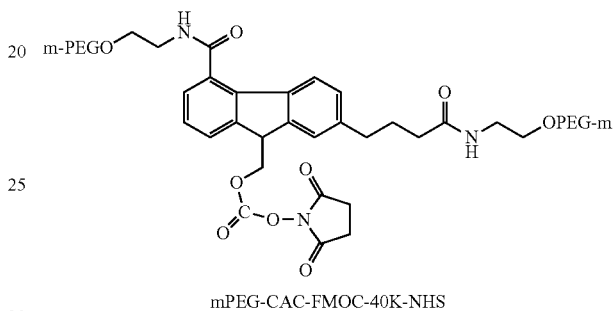

mPEG-CAC-FMOC-40K-NHS mono-mPEG-CAC-FMOC-40K-ziconotide was produced in a 4.8-mL reaction mixture consisting of 2.32 mL water, 0.192 mL 0.5 M HEPES, pH 7.4, 0.12 mL of 100 mg/ml ziconotide and 2.16 ml of 100 mg/mL mPEG-CAC-FMOC-40K. The molar ratio between ziconotide and PEG reagent was 1:1 after the correction of purity of the PEG reagent. mPEG-CAC-FMOC-40K, the last reagent added to the mixture, was dissolved in 2 mM HCl to a final concentration of 100 mg/mL immediately before addition. The dissolved PEG reagent was added to the reaction mixture with stirring. The reaction mixture was incubated at 25° C. with stirring for one hour. After one hour, 0.252 mL 0.2 M glycine (unbuffered) was added into the reaction mixture to quench the unreacted PEG reagent. After an additional 30 minutes of stirring at 25° C., the pH of the reaction mixture was adjusted to 5.0 at room temperature with acetic acid. The reaction mixture was diluted 1:10 with 10 mM sodium acetate, pH 5.0, and purified by cation exchange chromatography (HiTrap SP Sepharose HP; 5 mL). A linear salt gradient (FIG. 27) separated the mono-conjugate from the di- and high PEGylated products and unrereacted peptide. Purification buffers were as follows: A: 10 mM sodium acetate, pH 5.0, and B: 10 mM sodium acetate, 1.0 M sodium chloride, pH 5.0. The diluted reaction mixture was loaded at 0.4 mL/min with a five column volume wash after the load. The linear gradient consisted of 0 to 60% B over twenty column volumes at an elution flow rate of 0.4 mL/min. The purified mono-conjugate was determined to be 93% pure by reversed phase HPLC (FIG. 28 and Table ZIC3.1). MALDI-TOF analysis indicated the expected mass (44.5 kDa) for ziconotide mono-PEGylated with a 40 kDa PEG (FIG. 29). Final conjugate concentration was determined to be 0.17 mg/mL using a standard curve of ziconotide with the BCA assay.

Example ZIC4

PEGylation of Ziconotide with mPEG-SBA-30K-NHS

Figure 30:
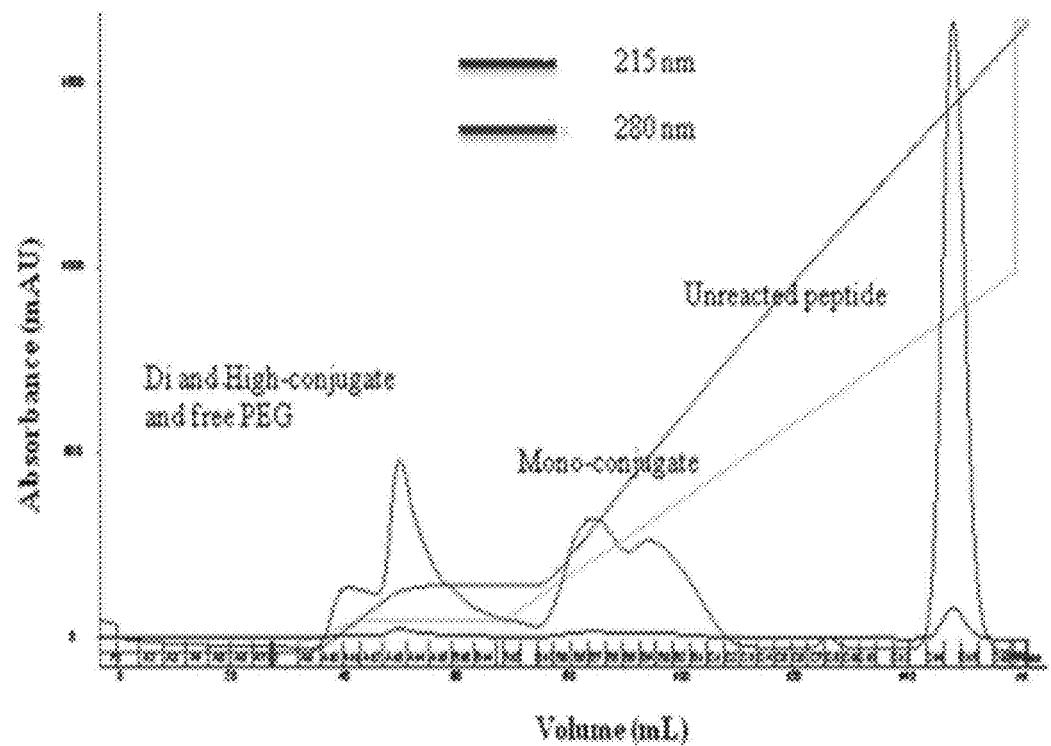
FIG. 30: Cation exchange purification of mono-mPEG-SBA-30K-ziconotide from the PEGylation reaction mixture.
Figure 31:
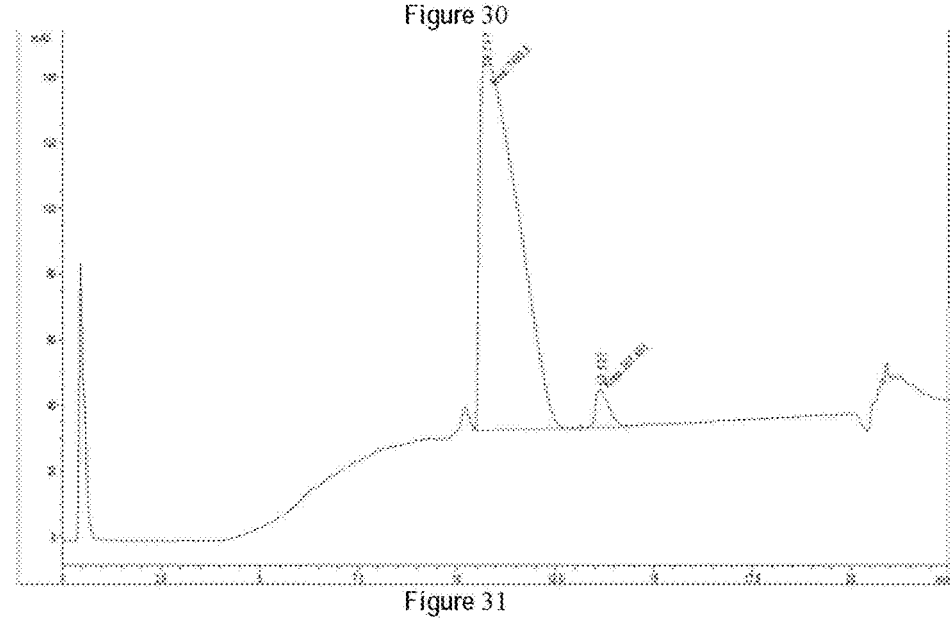
FIG. 31: RP-HPLC analysis of purified mono-mPEG-SBA-30K-ziconotide.
Figure 32:
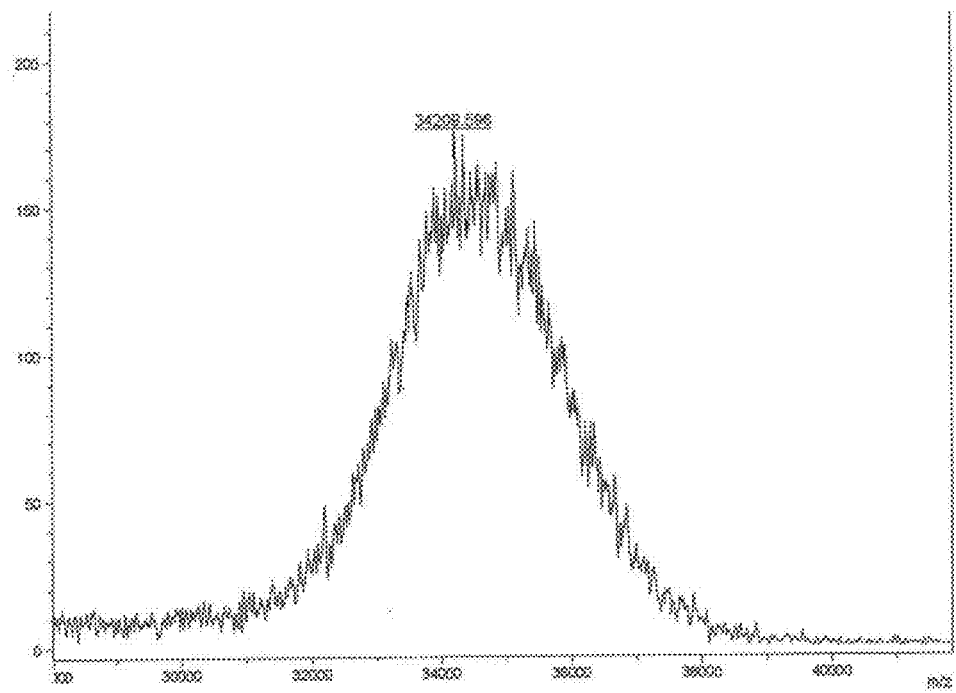
FIG. 32: MALDI-TOF analysis of purified mono-mPEG-SBA-30K-ziconotide.

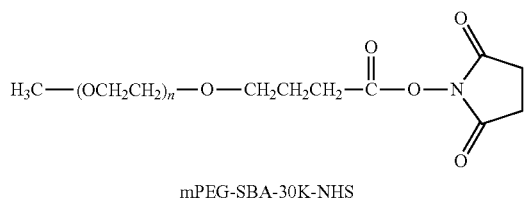

mPEG-SBA-30K-NHS mono-mPEG-C2-FMOC-20K-ziconotide was produced in a 6.0-mL reaction mixture consisting of 4.27 mL water, 0.24 mL 0.5 M HEPES, pH 7.4, 0.12 mL of 100 mg/ml ziconotide and 1.36 ml of 100 mg/mL mPEG-SBA-30K. The molar ratio between ziconotide and PEG reagent was 1:2 after the correction of purity of the PEG reagent. mPEG-SBA-30K, the last reagent added to the mixture, was dissolved in 2 mM HCl to a final concentration of 100 mg/mL immediately before addition. The dissolved PEG reagent was added to the reaction mixture with stirring. The reaction mixture was incubated at 25° C. with stirring for one hour. After one hour, 0.315 mL 0.2 M glycine (unbuffered) was added into the reaction mixture to quench the unreacted PEG reagent. After an additional 30 minutes of stirring at 25° C., the pH of the reaction mixture was adjusted to 5.0 at room temperature with acetic acid. The reaction mixture was diluted 1:10 with 10 mM sodium acetate, pH 5.0, and purified by cation exchange chromatography (HiTrap SP Sepharose HP; 5 mL). A linear salt gradient (FIG. 30) separated the mono-conjugate from the di- and high PEGylated products and unrereacted peptide. Purification buffers were as follows: A: 10 mM sodium acetate, pH 5.0, and B: 10 mM sodium acetate, 1.0 M sodium chloride, pH 5.0. The diluted reaction mixture was loaded at 0.4 mL/min with a five column volume wash after the load. The linear gradient consisted of 0 to 60% B over twenty column volumes at an elution flow rate of 0.4 mL/min. The purified mono-conjugate was determined to be 97% pure by reversed phase HPLC (FIG. 31 and Table ZIC4.1). MALDI-TOF analysis indicated the expected mass (34.2 kDa) for ziconotide mono-PEGylated with a 30 kDa PEG (FIG. 32). Final conjugate concentration was determined to be 0.13 mg/mL using a standard curve of ziconotide with the BCA assay.

Example ZIC5

PEGylation of Ziconotide with mPEG-SBC-30K-NHS

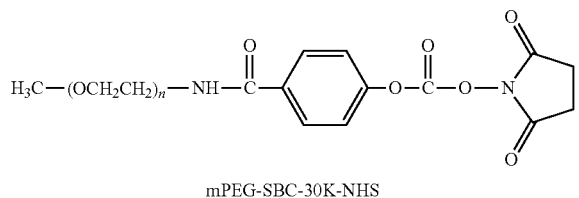

mPEG-SBC-30K-NHS mono-mPEG-SBC-30K-ziconotide was produced in a 0.5-mL reaction mixture consisting of 0.47 mL water, 0.02 mL 0.5 M HEPES, pH 7.4, and 0.01 mL of 100 mg/ml ziconotide. With stirring, 23.6 mg of solid mPEG-SBC-30K-NHS was added. 10 minutes after addition of the PEG reagent, the pH of the reaction mixture was adjusted to 5.0 with 6.2 µL of 1M acetic acid. The reaction mixture was diluted 1:10 with 10 mM sodium acetate, pH 5.0, and purified by cation exchange chromatography (HiTrap SP Sepharose HP; 1 mL). A linear salt gradient (FIG. 33) separated the mono-conjugate from the di- and high PEGylated products and unreacted peptide. Purification buffers were as follows: A: 10 mM sodium acetate, pH 5.0, and B: 10 mM sodium acetate, 1.0 M sodium chloride, pH 5.0. The diluted reaction mixture was loaded at 0.4 mL/min with a two column volume wash after the load. The linear gradient consisted of 0 to 100% B over twenty column volumes at an elution flow rate of 0.4 mL/min.

Figure 33:
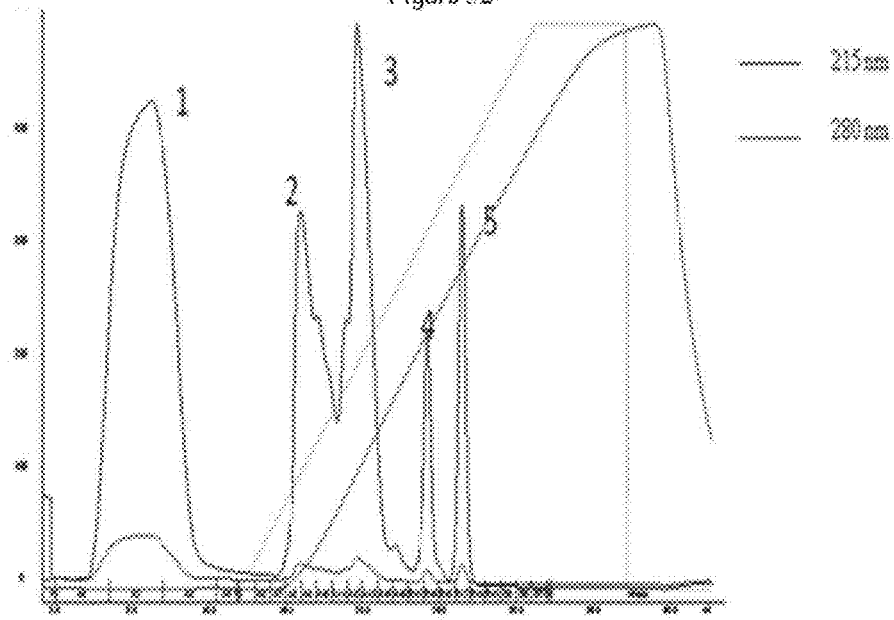
FIG. 33: Cation exchange FPLC chromatography of the PEGylation reaction mixture between ziconotide and mPEG-SBC-30K-NHS.

Five peaks were observed in the cation exchange chromatogram (FIG. 33). Based on SDS-PAGE analysis of aliquots collected from peaks 1 and 5, peak 1 corresponds to the unreacted PEG reagent and highly PEGylated ziconotide and peak 5 corresponds to unreacted ziconotide. Based on the peak retention times during FPLC chromatography, we speculate that peaks 2 and 3 correspond to different positional isomers of mono-PEGylated-ziconotide and peak 4 corresponds to tagged ziconotide in which the PEG group(s) have been released from the peptide. The FPLC and subsequent analytical results strongly suggest that the SBC-ziconotide conjugate is very unstable.

Example ZIC6

N-Type Calcium Channel Binding Assay

Competition binding experiments are conducted by incubating membranes with 0.01 nM of radioligand, [$^{125}$I]ω-conotoxin GVIA, in the presence of variable concentrations (0.3 pM to 30 nM) of test compounds. The reaction is carried out in 50 mM HEPES (pH 7.4) containing 0.2% BSA at 25° C. for 1 hour. Following incubations, the membranes are washed, and the bound radioactivity is measured. Non-specific binding is measured in the presence of 0.1 µM ω-conotoxin GVIA as the cold ligand; this value is subtracted from the total binding to yield the specific binding at each test compound concentration.

Figure 34:
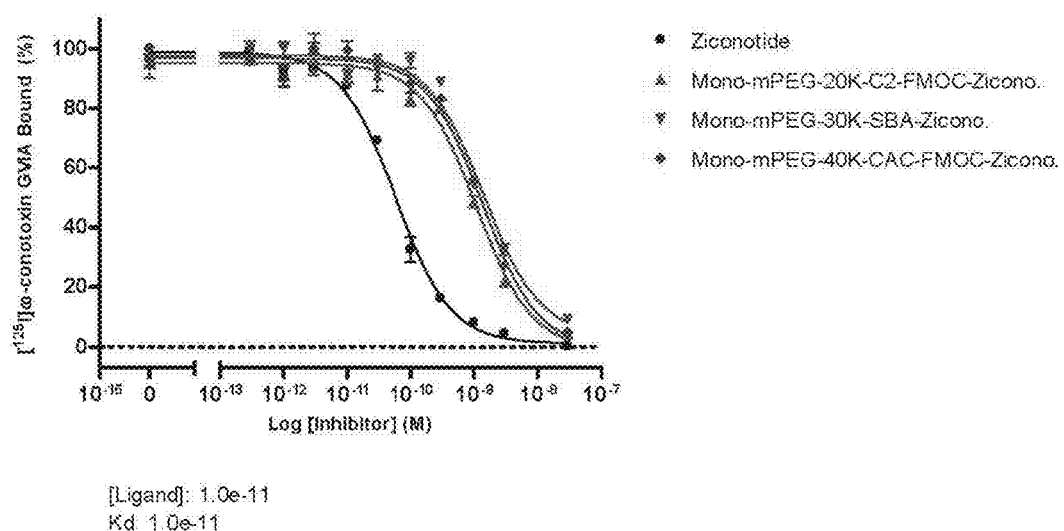
FIG. 34. Mean (±SEM) percent specific binding of ziconotide conjugates to calcium channel, N-type, in rat cortical membranes.

$IC_{50}$ values are obtained from non-linear regression analysis of dose-response curves (FIG. 34) and are calculated for those compounds that showed >50% inhibition of binding at the highest concentration tested. $K_i$ is obtained using the Cheng Prusoff correction using experimental $K_d$ values that are previously determined under these assay conditions.

TABLE ZIC6.1

Summary of binding affinity.

| Compound | MW (Da) | Ki (nM) | Fold Change Relative to Parent |
|---|---|---|---|
| Ziconotide | 2,639 | 0.029 | 1 |
| Mono-mPEG-20K-C2-FMOC-Ziconotide | 23,900 | 0.543 | 19 |
| Mono-mPEG-30K-SBA-Ziconotide | 34,200 | 0.707 | 24 |
| Mono-mPEG-40K-CAC-FMOC-Ziconotide | 44,500 | 0.676 | 23 |

TABLE 2

Compounds.

| Compound | PEG | Stock concentration based on peptide (mg/mL) | Storage buffer | PEG Release rate (if applicable) |
| --- | --- | --- | --- | --- |
| Ziconotide | — | 100 | Water | — |
| Mono-mPEG-20K-C2-FMOC-Ziconotide | Releasable | 0.21 | Na-acetate: 20 mM, NaCl: 150 mM, pH 5.0 | 55% after 24 h and 85% after 42 h @ 37° C. in PBS at pH 7.38 |
| Mono-mPEG-30K-SBA-Ziconotide | Stable | 0.13 | Na-acetate: 10 mM, NaCl: 150 mM, pH 5.0 | — |
| Mono-mPEG-40K-CAC-FMOC-Ziconotide | Releasable | 0.17 | Na-acetate: 10 mM, NaCl: 150 mM, pH 5.0 | 15% after 24.5 h and 22% after 42.5 h @ 37° C. in PBS at pH 7.38 |

Example BIP1

Biphalin-mPEG Conjugates a) mPEG-N$^{ter}$-Biphalin Via mPEG-SPC

Biphalin is prepared and purified according to standard automated peptide synthesis or recombinant techniques known to those skilled in the art. An illustrative polymeric reagent, mPEG-SPC reagent,

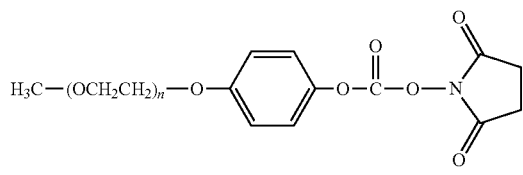

'SPC' polymer reagent is covalently attached to the N-terminus of biphalin, to provide a N$^{ter}$-conjugate form of the peptide. mPEG-SPC 20 kDa, stored at −20° C. under argon, is warmed to ambient temperature. The reaction is performed at room temperature. About 5-fold molar excess of mPEG-SPC 20 kDa reagent is used based upon absolute peptide content. The mPEG-SPC reagent is weighed into a glass vial containing a magnetic stirrer bar. A solution of biphalin prepared in phosphate buffered saline, PBS, pH 7.4 is added and the mixture is stirred using a magnetic stirrer until the mPEG-SPC is fully dissolved. The stirring speed is reduced and the reaction is allowed to proceed to formation of conjugate product. The reaction is optionally quenched to terminate the reaction. The pH of the conjugate solution at the end of the reaction is measured and further acidified by addition of 0.1M HCl, if necessary, to bring the pH of the final solution to about 5.5. The conjugate solution is then analyzed by SDS-PAGE and RP-HPLC (C18) to determine the extent of mPEG-N$^{ter}$-biphalin conjugate formation.

Using this same approach, other conjugates are prepared using mPEG derivatives having other weight-average molecular weights that also bear an N-hydroxysuccinimide moiety.

b) Biphalin-Cys(S-mPEG)

mPEG-Maleimide is obtained having a molecular weight of 5 kDa and having the basic structure shown below:

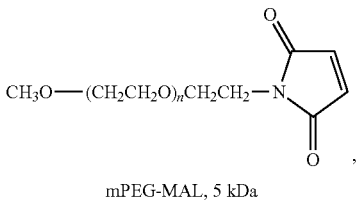

mPEG-MAL, 5 kDa

Biphalin, which is modified to contain a thiol-containing cysteine residue, is dissolved in buffer. To this peptide solution is added a 3-5 fold molar excess of mPEG-MAL, 5 kDa. The mixture is stirred at room temperature under an inert atmosphere for several hours. Analysis of the reaction mixture reveals successful conjugation of this peptide.

Using this same approach, other conjugates are prepared using mPEG-MAL having other weight average molecular weights.

c) mPEG-N$^{ter}$-Biphalin Via mPEG-SMB

An mPEG-N-Hydroxysuccinimide is obtained having a molecular weight of 5 kDa and having the basic structure shown below:

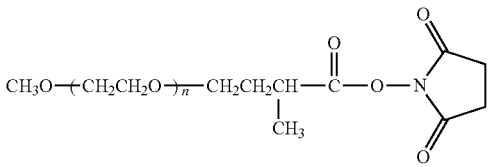

(mPEG-Succinimidyl α-Methylbutanoate Derivative, 5 kDa ("mPEG-SMB"))

mPEG-SMB, 5 kDa, stored at −20° C. under argon, is warmed to ambient temperature. A five-fold excess (relative to the amount of the peptide) of the warmed mPEG-SMB is dissolved in buffer to form a 10% reagent solution. The 10% reagent solution is quickly added to the aliquot of a stock biphalin solution and mixed well. After the addition of the mPEG-SMB, the pH of the reaction mixture is determined and adjusted to 6.7 to 6.8 using conventional techniques. To allow for coupling of the mPEG-SMB to the peptide via an amide linkage, the reaction solution is stirred for several hours (e.g., 5 hours) at room temperature in the dark or stirred overnight at 3-8° C. in a cold room, thereby resulting in a conjugate solution. The reaction is quenched with a 20-fold molar excess (with respect to the peptide) of Tris buffer.

Using this same approach, other conjugates are prepared using mPEG derivatives having other weight-average molecular weights that also bear an N-hydroxysuccinimide moiety.

Example BIP2

PEGylation of Biphalin with mPEG-SPA-2K

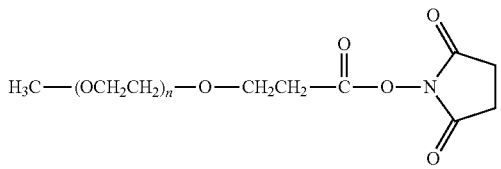

The conjugation reaction took place in acetonitrile. 10.7 mg biphalin was first dissolved into 7.6 mL acetonitrile followed by the addition of 8.1 μL triethylamine. 154 mg SPA-2K was dissolved into 7.6 mL acetonitrile. To start the conjugation reaction, 2.53 mL SPA-2K solution was added to 7.6 mL biphalin solution drop by drop under rapid stirring. The SPA-2K to biphalin molar ratio was 2.4 with SPA-2K in excess. The reaction was allowed to proceed for 66 h at 21° C. for completion. The formation of (SPA-2K)$_2$-biphalin was confirmed by analytical RP-HPLC (Table BIP2).

TABLE BIP 2.1

| Analytical RP-HPLC method. Column: Waters Xbridge C18 5 μm 4.6 × 160 mm. Mobile Phase A: 0.1% TFA/H$_2$O and B: 0.1% TFA/CH$_3$CN. Column temperature: 40° C. UV$_{280\ nm}$ is used to follow the elution. | | |
|---|---|---|
| TIME (min) | % B | Flow rate (mL/min) |
| 0.0 | 20 | 1 |
| 5 | 30 | 1 |
| 35 | 60 | 1 |
| 40 | 80 | 1 |
| 41 | 20 | 1 |

The (SPA-2K)$_2$-biphalin was purified by a CG-71S reverse phase resin using an AKTA Basic System. The reaction mixture was first diluted 5 fold with solvent A [0.1% TFA in water] to reduce sample viscosity. The diluted sample mixture was then loaded onto the CG-71S column at a flow rate of 10 mL/min. After sample loading, the column was first washed with 2 CV solvent A. This was followed by 2 CV 30% solvent B [Solvent B=0.1% TFA in acetonitrile] wash. A gradient elution was next applied from 30 to 45% solvent B in 15 CV. The (SPA-2K)$_2$-biphalin was eluted in this step. The column was finally washed with 1 CV 80% solvent B. The flow rate was constant at 10.25 ml/min throughout the purification process. The chromatogram of the loading and elution is shown in FIG. 36.

FIG. 36: (SPA-2K)$_2$-biphalin purification with CG-71S resin. The UV$_{280\ nm}$ absorption curve and the solvent B percentage are shown.

Figure 37:
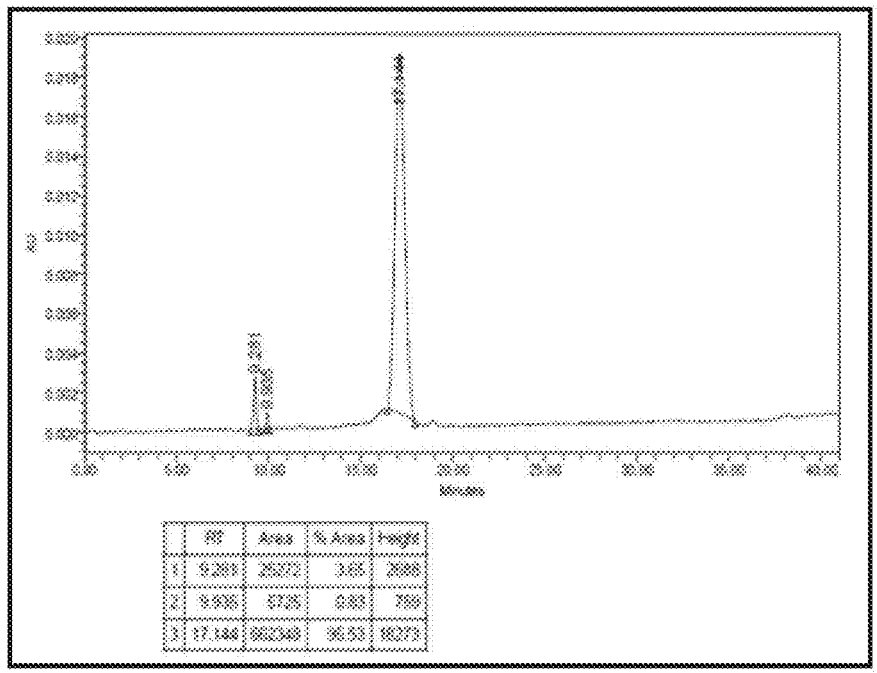
FIG. 37: RP-HPLC analysis of reconstituted (SPA-2K)2-biphalin.

The CG-71S column peak fractions were analyzed by the analytical RP-HPLC method (FIG. 37). Based on their high purities, fractions 32 to 40 (across the whole (SPA-2K)$_2$-biphalin peak) were pooled.

Figure 38:
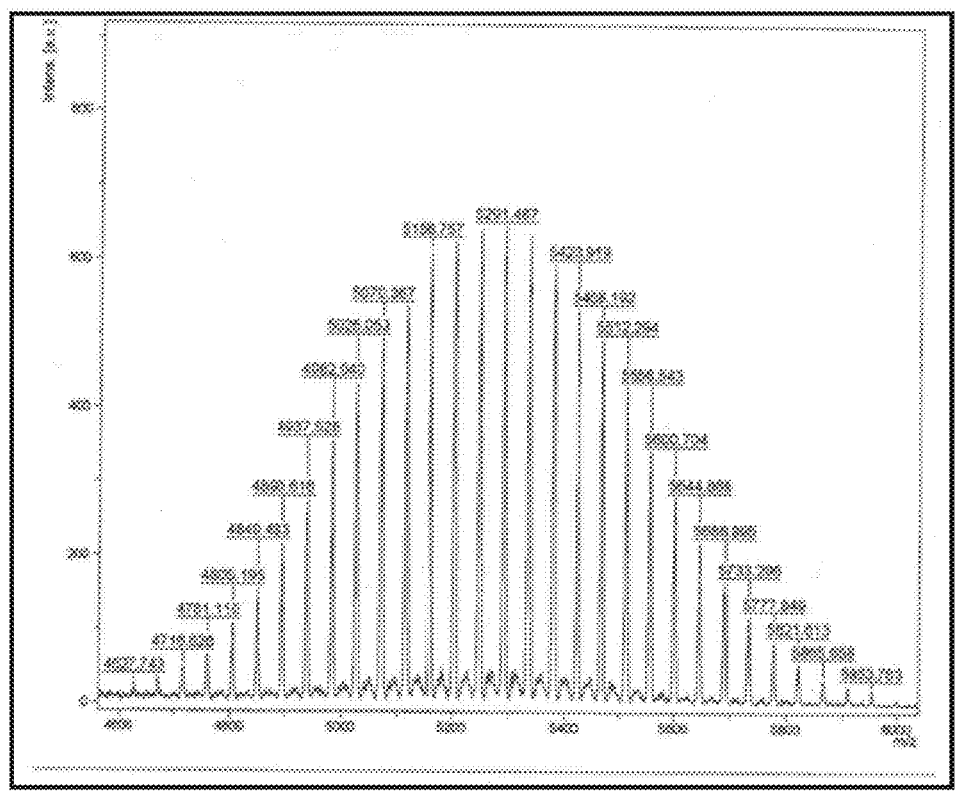
FIG. 38. MALDI TOF MS analysis of reconstituted (SPA-2K)2-biphalin.

This purified (SPA-2K)$_2$-biphalin pool was lyophilized to remove acetonitrile. The lyophilized pellet was reconstituted into 4 mL 20 mM acetate buffer, pH 4.0. The biphalin concentration in the reconstituted (SPA-2K)$_2$-biphalin was measured to be 0.92 mg/mL by BCA. The purity was determined at 95.5% by RP-HPLC (FIG. 37). The number-average molecular weight was calculated to be 5279.15 Da by MALDI-TOF MS (FIG. 38). A final yield of 2.8 mg purified (SPA-2K)$_2$-biphalin was obtained.

Example BIP3

PEGylation of Biphalin with 2,7-C2-PEG2-FMOC-NHS-20K

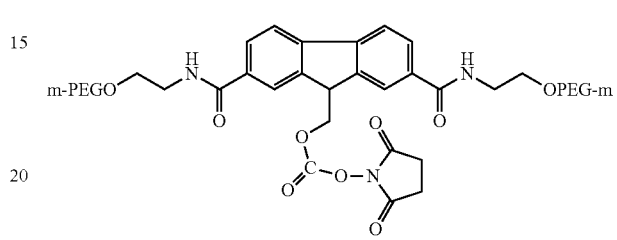

The conjugation reaction took place in an aqueous environment. 18 mg biphalin was first dissolved into 10 mL PBS buffer to make a 1.8 mg/mL stock solution. 800 mg C2-20K was dissolved into 8 mL 2 mM HCl to make a 100 mg/mL stock solution. To initiate the conjugation, 7.5 mL C2-20K stock solution was slowly mixed into 8.9 mL biphalin stock solution drop by drop under rapid stirring. 8.9 mL 10×PBS buffer was added into the reaction mixture to maintain a relatively neutral pH during the reaction (measured at 6.8). The C2-20K to biphalin molar ratio was 3.0 with C2-20K in excess. The reaction was allowed to proceed for 180 min at 21° C. The formation of (C2-20K)$_2$-biphalin was confirmed by analytical RP-HPLC. Table BIP3.1: Analytical RP-HPLC method used to monitor (C2-20K)$_2$-biphalin production. Column: Waters Xbridge C18 5 μm 4.6×160 mm. Mobile Phase A: 0.1% TFA/H$_2$O and B: 0.1% TFA/CH$_3$CN. Column temperature: 40° C. UV$_{280nm}$ was used to follow the elution.

| TIME (min) | % Mobile phase B | Flow rate (mL/min) |
|---|---|---|
| 0.0 | 20 | 1.0 |
| 5 | 30 | 1.0 |
| 35 | 60 | 1.0 |
| 40 | 80 | 1.0 |
| 41 | 20 | 1.0 |

Figure 39:
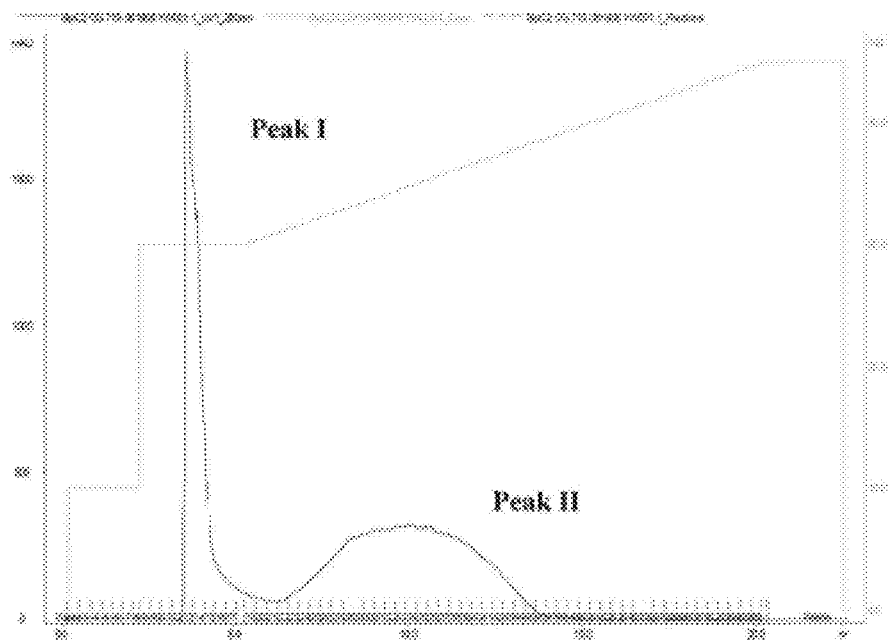
FIG. 39: (C2-20K)$_2$-biphalin purification with CG-71S resin.

The (C2-20K)$_2$-biphalin was purified by a CG-71S reverse phase resin using an AKTA Basic System. The reaction mixture was first diluted 5 fold with solvent A [0.1% TFA in water] to reduce sample viscosity. The diluted sample mixture was loaded onto the CG-71S column at 10 mL/min. After sample loading, the column was first washed with 2 CV 10% solvent B. This was followed by 3 CV 30% solvent B washing. Peaks I was eluted in this step. A linear gradient elution of 30 to 45% solvent B was next applied within 15 CV. Peak II was eluted in this step. The flow rate was constant at 10.25 ml/min throughout the purification process. The chromatogram of the loading and elution is shown in FIG. 39.

The CG-71S column peak I and II fractions were analyzed by the analytical RP-HPLC method. The RP-HPLC data indicated that most contaminants (free PEG and (C2-20K)$_1$-biphalin) were washed off in peak I. The desired (C2-20K)$_2$- biphalin was eluted in peak II. Based on their purities, fractions 28 to 44 in peak II were pooled.

Figure 40:
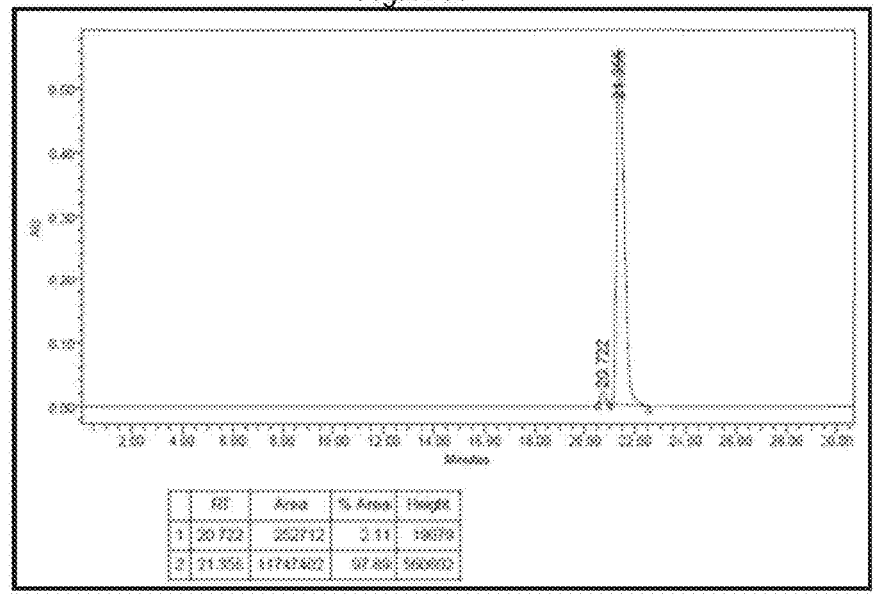
FIG. 40: RP-HPLC analysis of reconstituted (C2-20K)$_2$-biphalin.
Figure 41:
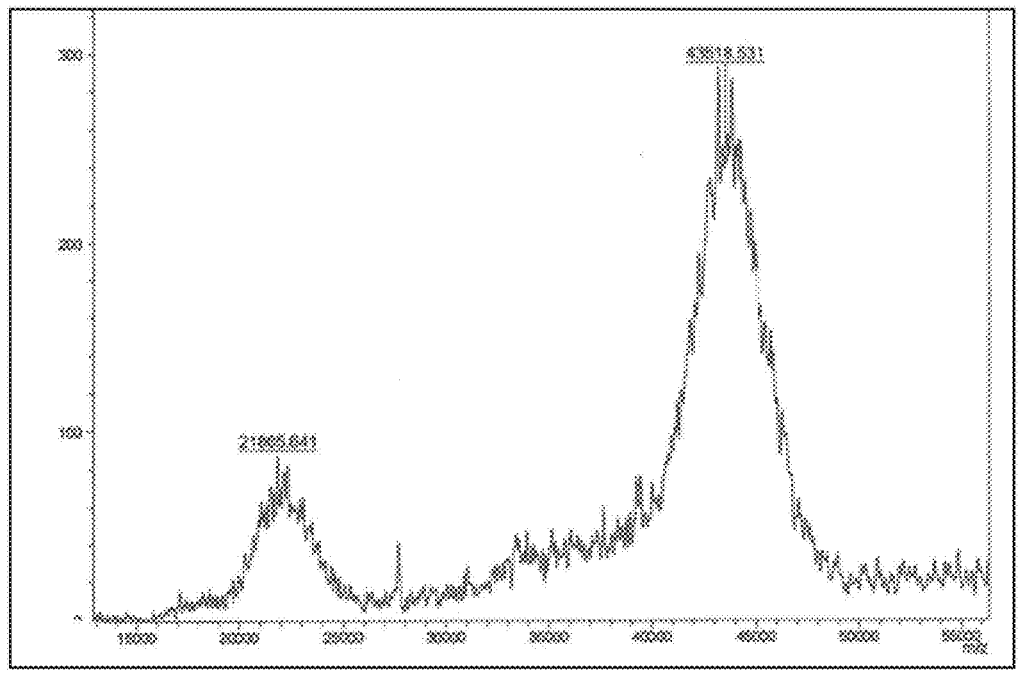
FIG. 41 MALDI-TOF analysis of reconstituted (C2-20K)$_2$-biphalin.

The purified $(C2\text{-}20K)_2$-biphalin pool was lyophilized to remove acetonitrile. The lyophilized pellet was reconstituted into 8 mL 20 mM acetate buffer, pH 4.0. The biphalin concentration in the reconstituted $(C2\text{-}20K)_2$-biphalin was measured to be 0.99 mg/mL by BCA. The purity was determined at 97.9% by RP-HPLC (FIG. 40). The number-average molecular weight was calculated to be 42055.99 Da by MALDI-TOF (FIG. 41). A final yield of 7.43 mg purified $(C2\text{-}20K)_2$-biphalin was obtained.

Example BIP4

PEGylation of Biphalin with 4,7-CAC-PEG2-FMOC-NHS-20K

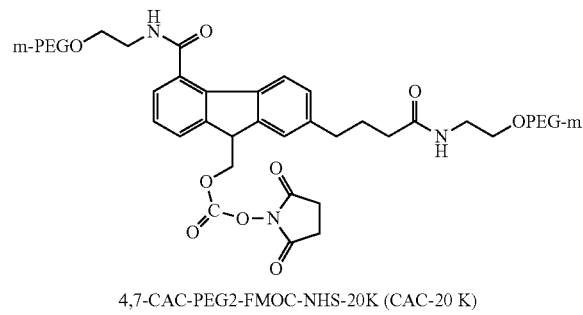

4,7-CAC-PEG2-FMOC-NHS-20K (CAC-20 K)

The conjugation reaction took place in an aqueous environment. 8 mg biphalin was first dissolved into 4.4 mL PBS buffer to make a 1.8 mg/mL stock solution. 650 mg CAC-20K was dissolved into 6.5 mL 2 mM HCl to make a 100 mg/mL stock solution. To initiate the conjugation, 5.28 mL CAC-20K stock solution was slowly mixed into 4.4 mL biphalin stock solution drop by drop under rapid stirring. 4.4 mL 10×PBS buffer was added into the reaction mixture to maintain a relatively neutral pH during the reaction (measured at 6.8). The CAC-20K to biphalin molar ratio was 3.0 with CAC-20K in excess. The reaction was allowed to proceed for 360 min at 21° C. and 12 h at 4° C. for completion. The formation of $(CAC\text{-}20K)_2$-biphalin was confirmed by analytical RP-HPLC. Table BIP4.1: Analytical RP-HPLC method used to monitor $(CAC\text{-}20K)_2$-biphalin production. Column: Waters Xbridge C18 5 μm 4.6×160 mm. Mobile Phase A: 0.1% TFA/$H_2O$ and B: 0.1% TFA/$CH_3CN$. Column temperature: 40° C. $UV_{280nm}$ was used to follow the elution.

| TIME (min) | % Mobile phase B | Flow rate (mL/min) |
|---|---|---|
| 0.0 | 20 | 1.0 |
| 5 | 30 | 1.0 |
| 35 | 60 | 1.0 |
| 40 | 80 | 1.0 |
| 41 | 20 | 1.0 |

Figure 42:
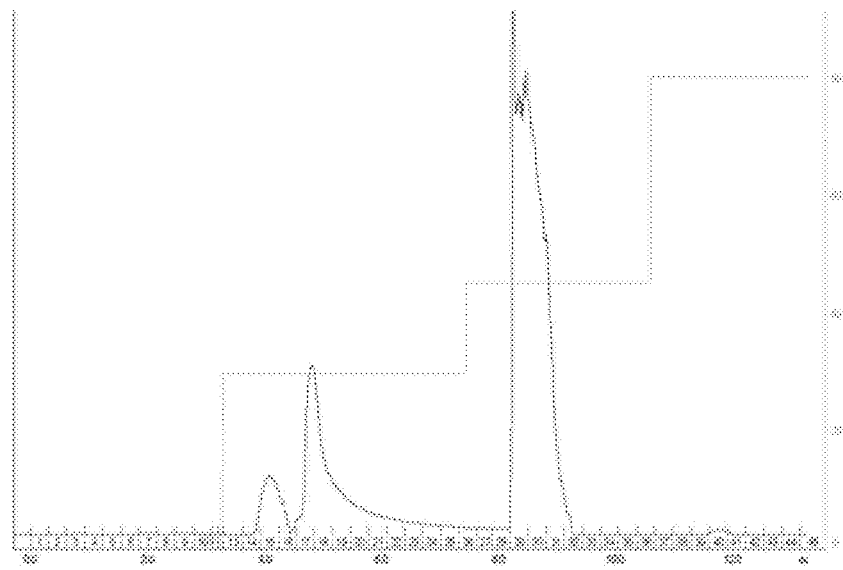
FIG. 42: (CAC-20K)$_2$-biphalin purification with CG-71S resin.

The $(CAC\text{-}20K)_2$-biphalin was purified by a CG-71S reverse phase resin using an AKTA Basic System. The reaction mixture was first diluted 5 fold with solvent A [0.1% TFA in water] to reduce sample viscosity. The diluted sample mixture was loaded onto the CG-71S column at 10 mL/min. After sample loading, the column was first washed with 1 CV solvent A. This was followed by a 30% solvent B [0.1% TFA in acetonitrile] wash until the $UV_{280nm}$ absorbance remained constant with time. Two peaks, I and II, were eluted during this step. The column was further washed with 45% solvent B until $UV_{280nm}$ became constant with time. Peak III was eluted in this step. The column was finally washed with 80% solvent B. The flow rate was constant at 10.25 ml/min throughout the purification process. The chromatogram of the loading and elution is shown in FIG. 42.

Figure 43:
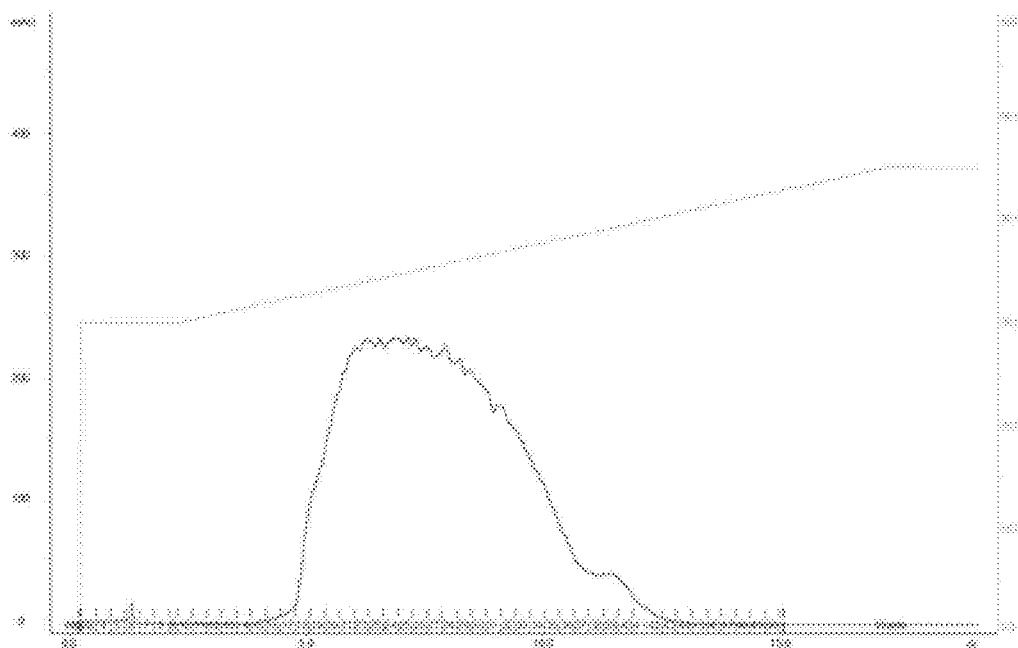
FIG. 43: (CAC-20K)$_2$-biphalin re-purification with CG-71S resin.

The CG-71S column fractions in peaks I, II and III were analyzed by the analytical RP-HPLC method (Table 1). Unexpectedly, peak I comprised highly pure $(CAC\text{-}20K)_2$-biphalin. Most of the free PEG and $(CAC\text{-}20K)_1$-biphalin was washed off in peak II. Although the $(CAC\text{-}20K)_2$-biphalin was the major component in peak III, there was a significant amount of contamination by free PEG and $(CAC\text{-}20K)_1$-biphalin. The average $(CAC\text{-}20K)_2$-biphalin purity in the fractions comprising peak III was estimated at ~80% by RP-HPLC. To achieve a higher $(CAC\text{-}20K)_2$-biphalin purity, the peak III fractions were reloaded onto the CG-71S column and a linear gradient elution was used for a better separation. The peak III fractions (28 to 31) were pooled and diluted 5 fold with solvent A. The diluted sample mixture was loaded onto the CG-71S column at 10 mL/min. After sample loading, the column was first washed with 1 CV solvent A. A gradient elution of 30 to 45% solvent B was next applied within 15 CV. The flow rate was constant at 10.25 ml/min throughout the purification process. The chromatogram of the loading and elution is shown in FIG. 43.

Figure 44:
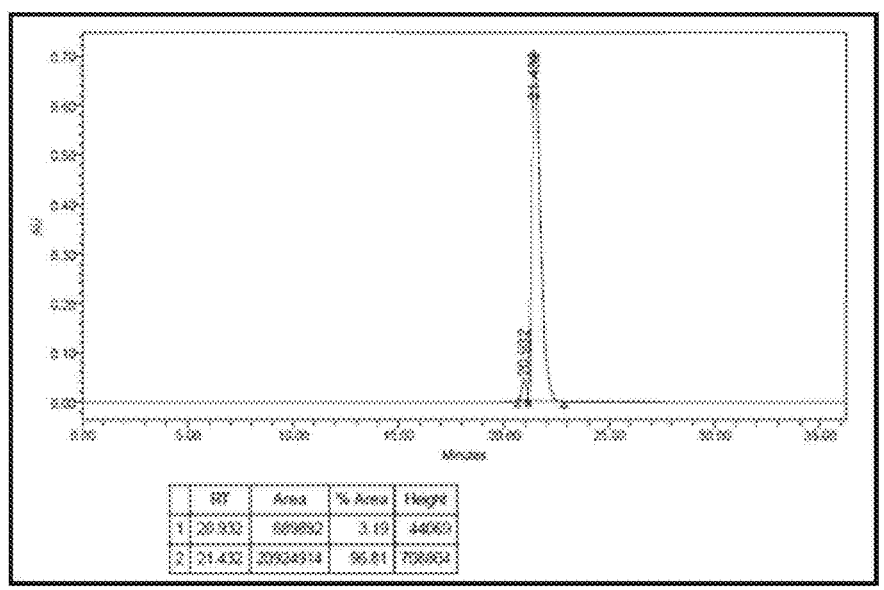
FIG. 44: RP-HPLC analysis of reconstituted (CAC-20K)$_2$-biphalin.
Figure 45:
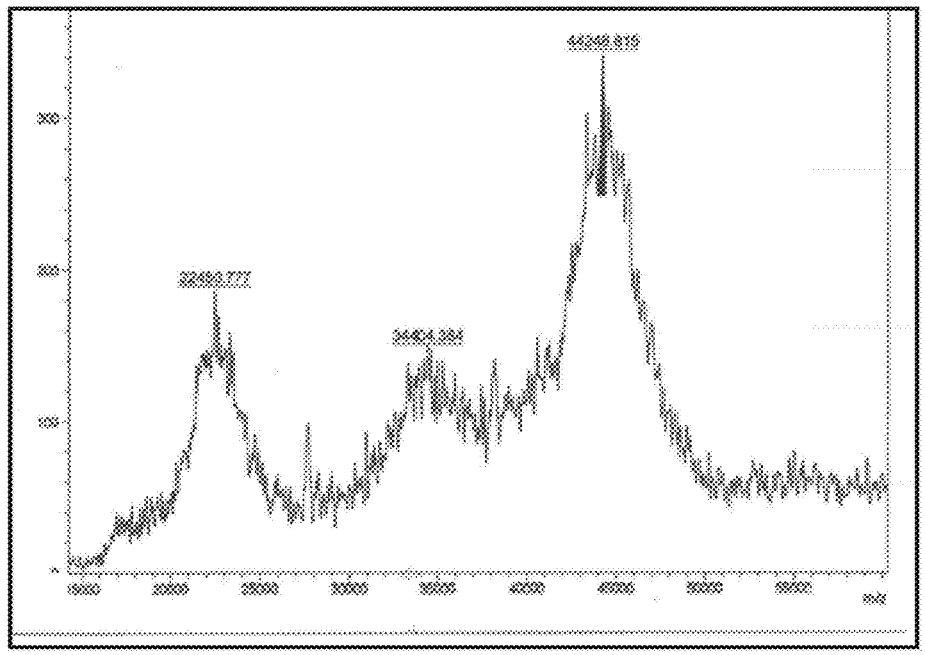
FIG. 45: MALDI-TOF analysis of reconstituted (CAC-20K)$_2$-biphalin.

The CG-71S column fractions were analyzed by the analytical RP-HPLC method (Table). Based on their purities, fractions 23 to 35 were pooled. The purified $(CAC\text{-}20K)_2$-biphalin pool was lyophilized to remove acetonitrile. The lyophilized pellet was reconstituted into 4 mL 20 mM acetate buffer, pH 4.0. The biphalin concentration in the reconstituted $(CAC\text{-}20K)_2$-biphalin was measured to be 0.93 mg/mL by BCA. The purity was determined at 96.8% by RP-HPLC (FIG. 44). The number-average molecular weight was calculated to be 40952.9 Da by MALDI-TOF (FIG. 45). A final yield of 3.1 mg purified $(CAC\text{-}20K)_2$-biphalin was obtained.

FIG. 45: MALDITOF analysis of reconstituted $(CAC\text{-}20K)_2$-biphalin. The peak at ~43 kDa is the expected mass for diPEGylated biphalin. The peak at ~22 kDa is the expected peak for doubly charged diPEGylated biphalin. The ~34 KDa MALDI possibly corresponds to diPEGylated biphalin in which one CAC FMOC group has a single PEG chain.

Example BIP5

Figure 46:
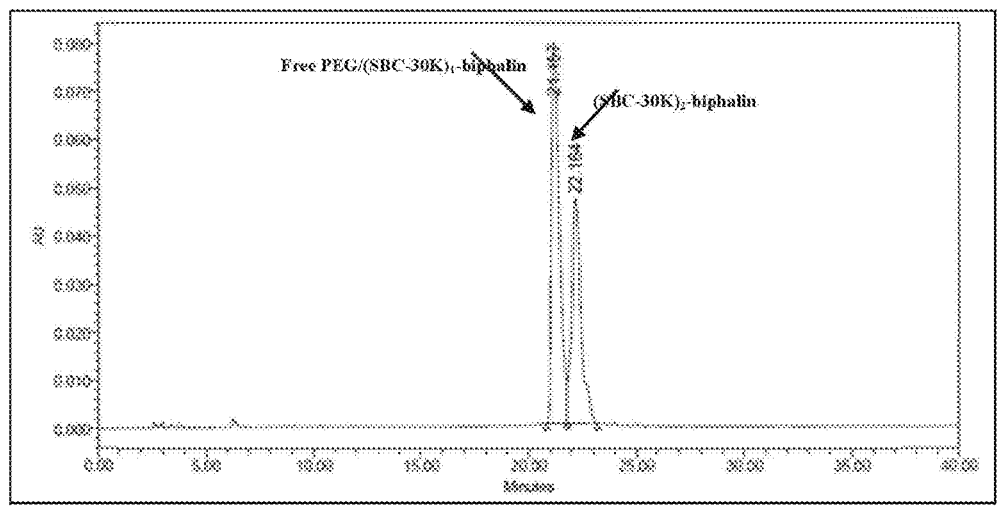
FIG. 46: RP-HPLC analysis of SBC-30K and biphalin conjugation reaction mixture.

PEGylation of Biphalin with N-m-PEG-Benzamide-p-Succinimidyl Carbonate (m-PEG-SBC-30K The conjugation reaction took place in an aqueous environment. 0.84 mg biphalin was first dissolved into 0.47 mL PBS buffer to make a 1.8 mg/mL biphalin solution. To initiate the conjugation, 83.2 mg SBC-30K powder was directly added into 0.47 mL biphalin solution under rapid stirring. The SBC-30K to biphalin molar ratio was 3:0 with SBC-30K in excess. The reaction was allowed to proceed for 20 min at 21° C. After 20 minutes, 0.47 mL 200 mM sodium acetate pH 4.5 buffer was added to stabilize the di-conjugate. The formation of $(SBC-30K)_2$-biphalin was confirmed using an analytical RP-HPLC method (Table 1). The RP-HPLC elution profile is shown in FIG. 46.

Table BIP5.1: Analytical RP-HPLC method used to monitor $(SBC-30K)_2$-biphalin production. Column: Agilent 300 Extend-C18 5 μm 4.6×250 mm. Mobile Phase A: 0.1% $TFA/H_2O$ and B: 0.1% $TFA/CH_3CN$. Column temperature: 40° C. $UV_{280nm}$ was used to follow the elution.

| TIME (min) | % Mobile phase B | Flow rate (mL/min) |
|---|---|---|
| 0.0 | 20 | 1.0 |
| 5 | 30 | 1.0 |
| 35 | 60 | 1.0 |
| 40 | 80 | 1.0 |
| 41 | 20 | 1.0 |

Figure 47:
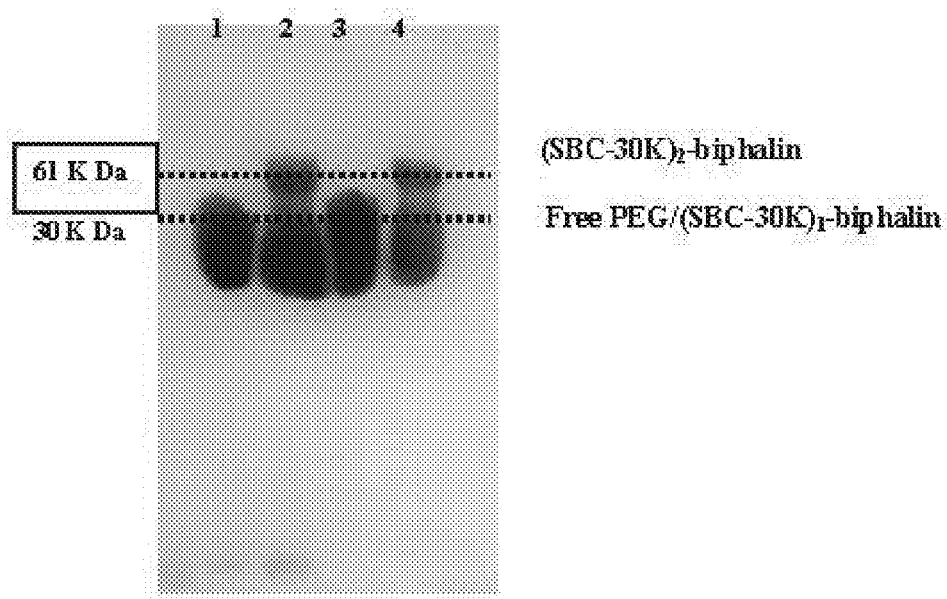
FIG. 47. The purification of (SBC-30K)$_2$-biphalin from the reaction mixture.

FIG. 47. The formation of $(SBC-30K)_2$-biphalin was also confirmed by SDS-PAGE: SDS-PAGE analysis of SBC-30K and biphalin conjugation reaction mixture. The purification of $(SBC-30K)_2$-biphalin from the reaction mixture was not successful due to the instability of the conjugate, even at acidic pH values.

Example BIP6

Radioligand Binding Assay for Biphalin Series at Delta, Mu, and Kappa Opioid Receptors The binding affinities of biphalin (control) and PEG-biphalin releasable and stable conjugates were evaluated using radioligand binding assays in membranes prepared from cells expressing recombinant human μ or δ opioid receptors.

Competition binding experiments were conducted by incubating membrane protein to equilibrium in triplicate in the presence of a fixed concentration of radioligand and increasing concentrations (0.1 nM to 10 μM) of test compound in 100 μL final volume. The radioligands used were specific for each receptor type, and the assay conditions are described in Table BIP6.3. Following incubations, the membranes were rapidly filtered through GF/B filter plate (pre-soaked with 0.5% polyethyleneimine), washed four times with cold 50 mM Tris-HCl, pH 7.5, and the bound radioactivity was then measured. Non-specific binding was measured in the presence of excess naloxone (100 μM); this value was subtracted from the total binding to yield the specific binding at each test concentration.

For all releasable PEG-biphalin conjugates, except di-mPEG-SBC-30K-biphalin, the receptor-binding activity of both released biphalin and PEG-biphalin (unreleased) conjugates were tested. The test compounds were stored under acidic condition to stabilize the PEG conjugation. To test the activity of PEG-biphalin conjugates, the sample was diluted on the day of the assay. To test the activity of released biphalin, the sample was diluted 10-fold in assay buffer prior to the assay and pre-incubated under physiological-like conditions for a period until ~50% of biphalin was estimated to be released, based on pre-determined release rates (refer to Table BIP6.4).

$IC_{50}$ (concentration of test compound required to inhibit 50% of specific binding) values were obtained from non-linear regression analysis of dose-response curves, using GraphPad's Prism 5.01 software, and were calculated for those compounds that showed >50% inhibition of specific binding at the highest concentration tested. $K_i$ (affinity of test compound) was obtained using the Cheng Prusoff correction using experimental $K_d$ (affinity of radioligand) values that were previously determined under these assay conditions. The binding affinities of biphalin and PEG-biphalin conjugates are shown in Tables BIP6.1 and BIP6.2. Biphalin displayed similar, high affinity (3.1-6.5 nM) for human μ and δ opioid receptors, and results were comparable to data published in literature.

Since the releasable conjugates were pre-incubated in assay buffer, pH 7.5 at 37° C., biphalin was also pre-incubated for the maximum time to test the activity of the peptide during treatment under physiological-like conditions. Biphalin remained stable following 72 hour incubation as shown in FIG. 1. Pre-incubated biphalin displayed similar, high affinity for μ and δ opioid receptors when compared to the control prepared on the day of the assay (Table BIP6.1).

Following pre-incubation of di-CAC-PEG2-20K-biphalin for 72 hours and di-C2-PEG2-20K-biphalin for 20 hours, affinity for μ and δ opioid receptors was increased (compared to PEG-biphalin conjugates prepared on the day of the assay) and regained (FIGS. 48 and 49); biphalin released from these conjugates retained receptor binding activity as shown by only <4-fold loss in affinity relative to biphalin. Because di-mPEG-SBC-30K-biphalin was known to dissociate rapidly, only the sample pre-incubated for 20 hours was tested. Biphalin released from the SBC linker displayed a 16-fold loss in affinity for μ opioid receptor relative to biphalin; this reduction in affinity may be attributed to the "tag" contained at the PEG conjugation site of biphalin following its release. Affinity was not obtained for the δ opioid receptor as >50% inhibition of specific binding was not achieved at the highest test concentration (1 μM).

The di-CAC-PEG2-20K-biphalin conjugate displayed much lower affinity for both receptors; reduction in affinity was 324 to 649-folds less relative to biphalin. The di-C2-PEG2-20K-biphalin conjugate displayed a 5-fold reduction in affinity at the μ opioid receptor and 41-fold reduction at the δ opioid receptor; this moderate reduction in affinity suggests that the di-C2-PEG2-20K linker may have been unstable in the assay buffer and resulted in faster release of biphalin. Furthermore, the di-C2-PEG2-20K-biphalin conjugate seemed to be more selective for μ opioid receptor compared to δ opioid receptor. The receptor selectivity may have been due to the rate at which each C2-PEG2-20K linker was being released. One hypothesis is that the C2-PEG2-20K conjugated on residue 8 was released faster (creating the mono-PEG species conjugated on residue 1) thereby exposing biphalin's structure to specifically interact with the μ opioid receptor site.

As for the stable di-mPEG-SPA-2K conjugate, the loss in affinity for μ and δ opioid receptors was significantly greater as shown in FIGS. 49A and 49B. Binding affinity could not be determined because no measurable inhibition of specific binding was detected at the highest test concentration (10 μM).

FIG. 48. Competition binding assay of biphalin and di-CAC-20K-biphalin (released and unreleased) conjugate at human (A) μ opioid and (B) δ opioid receptors. Data presented as mean (±SEM) percent specific binding. FIG. 49. Competition binding assay of biphalin and di-C2-20K-biphalin (released and unreleased), di-SBC-30K-biphalin (released), and di-SPA-2K-biphalin (stable) conjugate at human (A) μ opioid and (B) δ opioid receptors. Data presented as mean (±SEM) percent specific binding.

TABLE BIP6.1

Summary of binding affinity for di-CAC-20K-biphalin conjugate.

| | μ Opioid Receptor | | δ Opioid Receptor | |
|---|---|---|---|---|
| Test Compound | $K_i$ (nM) | Fold Change Relative to Biphalin | $K_i$ (nM) | Fold Change Relative to Biphalin |
| Biphalin | 3.4 | 1.0 | 6.4 | 1.0 |
| Biphalin (Pre-incubated) | 3.1 | 0.9 | 6.5 | 1.0 |
| Di-CAC-PEG2-FMOC-NHS-20K-biphalin | 1117.0 | 324.1 | 4177.0 | 648.5 |
| Di-CAC-PEG2-FMOC-NHS-20K-biphalin (Pre-incubated) | 13.7 | 4.0 | 16.8 | 2.6 |

TABLE BIP6.2

Summary of binding affinity for di-C2-20K-biphalin, di-SPA-2K-biphalin, and di-SBC-30K-biphalin conjugates.

| | μ Opioid Receptor | | δ Opioid Receptor | |
|---|---|---|---|---|
| Test Compound | $K_i$ (nM) | Fold Change Relative to Biphalin | $K_i$ (nM) | Fold Change Relative to Biphalin |
| Biphalin | 4.7 | 1.0 | 5.8 | 1.0 |
| Di-C2-PEG2-FMOC-NHS-20K-biphalin | 21.7 | 4.6 | 234.9 | 40.7 |
| Di-C2-PEG2-FMOC-NHS-20K-biphalin (Pre-incubated) | 10.1 | 2.1 | 21.1 | 3.7 |
| Di-mPEG-SBC-30K-biphalin (Pre-incubated) | 77.7 | 16.4 | Not obtained | Not obtained |
| Di-mPEG-SPA-2K-biphalin | Not obtained | Not obtained | Not obtained | Not obtained |

Not obtained = $K_i$ values could not be determined since >50% inhibition of specific binding was not achieved at the highest concentration tested.

TABLE BIP6.3

Assay conditions.

| Receptor | Receptor Source | Membrane Protein | Radioligand | $K_d$ | Non-specific binding | Methods |
|---|---|---|---|---|---|---|
| μ Opioid | Human recombinant CHO-K1 cells | 5 μg/well | [³H] Naloxone (5 nM) | 4.0 nM | Naloxone (100 μM) | Reaction in 50 mM Tris-HCl (pH 7.5) at 25° C. for 1 h on plate shaker |
| δ Opioid | Human recombinant CHO-K1 cells | 15 μg/well | [³H] DPDPE (5 nM) | 3.9 nM | Naloxone (100 μM) | Reaction in 50 mM Tris-HCl (pH 7.5), 5 mM MgCl₂, 0.1% BSA at 25° C. for 1 h on plate shaker |

TABLE BIP6.4

Test compounds.

| Test Compound | MW (Da) | Stock concentration based on peptide (mg/mL) | Storage buffer | PEG Release rate (if applicable) | Pre-incubation condition (if applicable) |
|---|---|---|---|---|---|
| Biphalin | 909 | 5.0 | PBS, pH 7.4 | — | 72 h in 50 mM Tris-HCl, 5 mM MgCl2, 0.1% BSA, pH 7.5 at 37° C. |
| Di-CAC-PEG2-FMOC-NHS-20K-biphalin Releasable | 40,952 | 0.93 | 20 mM acetate, pH 4.0 | 15% after 23 h at 37° C. in PBS, pH 7.2 | 72 h in 50 mM Tris-HCl, 5 mM MgCl2, 0.1% BSA, pH 7.5 at 37° C. |
| Di-C2-PEG2-FMOC-NHS-20K-biphalin Releasable | 42,055 | 0.99 | 20 mM acetate, pH 4.0 | 50% after 4 h at 37° C. in PBS, pH 7.2 | 20 h in 50 mM Tris-HCl, 5 mM MgCl2, 0.1% BSA, pH 7.5 at 37° C. |
| Di-mPEG-SBC-30K-biphalin | 63,920 | 2.7 | 20 mM acetate, pH 4.0 | 55% after 50 min at 37° C. in 200 mM Na- | 20 h in 50 mM Tris-HCl, 5 mM MgCl2, |

TABLE BIP6.4-continued

| Test Compound | MW (Da) | Stock concentration based on peptide (mg/mL) | Storage buffer | PEG Release rate (if applicable) | Pre-incubation condition (if applicable) |
| --- | --- | --- | --- | --- | --- |
| Releasable | | | | phosphate, pH 7.4 | 0.1% BSA, pH 7.5 at 37° C. |
| Di-mPEG-SPA-2K-biphalin Stable | 5,394 | 7.92 | 20 mM acetate, pH 4.0 | — | — |

Example BNP1

BNP-mPEG Conjugates a) mPEG-N$^{ter}$-eBNP Via mPEG-SPC

BNP is prepared and purified according to standard automated peptide synthesis or recombinant techniques known to those skilled in the art. An illustrative polymeric reagent, mPEG-SPC reagent,

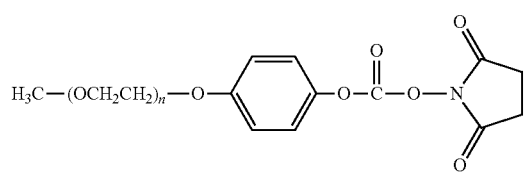

'SPC' polymer reagent is covalently attached to the N-terminus of BNP, to provide a N$^{ter}$-conjugate form of the peptide. mPEG-SPC 20 kDa, stored at −20° C. under argon, is warmed to ambient temperature. The reaction is performed at room temperature. About 3-5-fold molar excess of mPEG-SPC 20 kDa reagent is used based upon absolute peptide content. The mPEG-SPC reagent is weighed into a glass vial containing a magnetic stirrer bar. A solution of BNP prepared in phosphate buffered saline, PBS, pH 7.4 is added and the mixture is stirred using a magnetic stirrer until the mPEG-SPC is fully dissolved. The stirring speed is reduced and the reaction is allowed to proceed to formation of conjugate product. The reaction is optionally quenched to terminate the reaction. The pH of the conjugate solution at the end of the reaction is measured and further acidified by addition of 0.1M HCl, if necessary, to bring the pH of the final solution to about 5.5. The conjugate solution is then analyzed by SDS-PAGE and RP-HPLC (C18) to determine the extent of mPEG-N$^{ter}$-BNP conjugate formation.

Using this same approach, other conjugates are prepared using mPEG derivatives having other weight-average molecular weights that also bear an N-hydroxysuccinimide moiety.

b) BNP-C$^{ter}$-mPEG

An illustrative polymeric reagent, mPEG-NH$_2$ reagent is covalently attached to the C-terminus of BNP, to provide a C$^{ter}$-conjugate form of the peptide. For coupling to the C-terminus, a protected BNP (Prot-BNP) is prepared and purified according to standard automated peptide synthesis techniques known to those skilled in the art. mPEG-NH$_2$ 20 kDa, stored at −20° C. under argon, is warmed to ambient temperature. The reaction is performed at room temperature. About 5-fold molar excess of mPEG-NH$_2$, PyBOP (benzotriazol-1-yloxy)tripyrrolidinonophosphonium hexafluorophosphate), and 1-hydroxybenzotriazole (HOBt) are used, based upon absolute peptide content. The mPEG-NH$_2$, PyBOP, HOBt are weighed into a glass vial containing a magnetic stirrer bar. A solution of Prot-BNP is prepared in N,N-dimethylformamide is added and the mixture is stirred using a magnetic stirrer until the mPEG-NH$_2$ is fully dissolved. The stirring speed is reduced and the reaction is allowed to proceed to formation of conjugate product. The conjugate solution is then analyzed by SDS-PAGE and RP-HPLC (C18) to determine the extent of Prot-BNP-C$^{ter}$-mPEG conjugate formation. The remaining protecting groups are removed under standard deprotection conditions to yield the BNP-C$^{ter}$-mPEG conjugate.

Using this same approach, other conjugates are prepared using mPEG derivatives having other weight-average molecular weights that also bear an amino moiety.

c) BNP-Cys(S-mPEG)

mPEG-Maleimide is obtained having a molecular weight of 5 kDa and having the basic structure shown below:

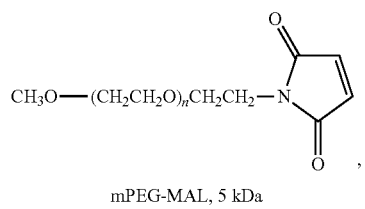

mPEG-MAL, 5 kDa

BNP, which has a thiol-containing cysteine residue, is dissolved in buffer. To this peptide solution is added a 3-5 fold molar excess of mPEG-MAL, 5 kDa. The mixture is stirred at room temperature under an inert atmosphere for several hours. Analysis of the reaction mixture reveals successful conjugation of this peptide.

Using this same approach, other conjugates are prepared using mPEG-MAL having other weight average molecular weights.

d) mPEG-N$^{ter}$-BNP Via mPEG-SMB

An mPEG-N-Hydroxysuccinimide is obtained having a molecular weight of 5 kDa and having the basic structure shown below:

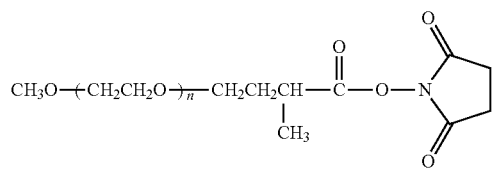

(mPEG-Succinimidyl α-Methylbutanoate Derivative, 5 kDa ("mPEG-SMB"))

mPEG-SMB, 5 kDa, stored at −20° C. under argon, is warmed to ambient temperature. A five-fold excess (relative to the amount of the peptide) of the warmed mPEG-SMB is dissolved in buffer to form a 10% reagent solution. The 10% reagent solution is quickly added to the aliquot of a stock BNP solution and mixed well. After the addition of the mPEG-SMB, the pH of the reaction mixture is determined and adjusted to 6.7 to 6.8 using conventional techniques. To allow for coupling of the mPEG-SMB to the peptide via an amide linkage, the reaction solution is stirred for several hours (e.g., 5 hours) at room temperature in the dark or stirred overnight at 3-8° C. in a cold room, thereby resulting in a conjugate solution. The reaction is quenched with a 20-fold molar excess (with respect to the peptide) of Tris buffer.

Using this same approach, other conjugates are prepared using mPEG derivatives having other weight-average molecular weights that also bear an N-hydroxysuccinimide moiety.

e) BNP-Glu(O-mPEG)

An illustrative polymeric reagent, mPEG-NH$_2$ reagent is covalently attached to the Glu residue of BNP, to provide a Glu-conjugate form of the peptide. For coupling to the Glu residue, a protected BNP (Prot-BNP) is prepared and purified according to standard automated peptide synthesis techniques known to those skilled in the art. Deprotection of the Glu(OBz) residue (H$_2$/Pd) yields the free-Glu carboxylate for subsequent coupling. mPEG-NH$_2$ 20 kDa, stored at −20° C. under argon, is warmed to ambient temperature. The reaction is performed at room temperature. A 5-fold molar excess of mPEG-NH$_2$, PyBOP (benzotriazol-1-yloxy)tripyrrolidinonophosphonium hexafluorophosphate), and 1-hydroxybenzotriazole (HOBt) are used, based upon absolute peptide content. The mPEG-NH$_2$, PyBOP, HOBt are weighed into a glass vial containing a magnetic stirrer bar. A solution of Prot-BNP is prepared in N,N-dimethylformamide is added and the mixture is stirred using a magnetic stirrer until the mPEG-NH$_2$ is fully dissolved. The stirring speed is reduced and the reaction is allowed to proceed to formation of conjugate product. The conjugate solution is then analyzed by SDS-PAGE and RP-HPLC (C18) to determine the extent of Prot-BNP-(Glu-O-mPEG) conjugate formation. The remaining protecting groups are removed under standard deprotection conditions to yield the BNP-Glu(O-mPEG) conjugate.

Using this same approach, other conjugates are prepared using mPEG derivatives having other weight-average molecular weights that also bear an amino moiety.

Example BNP2

PEGylation of BNP-32 with mPEG2-Butyr-ALD-40K

Figure 50:
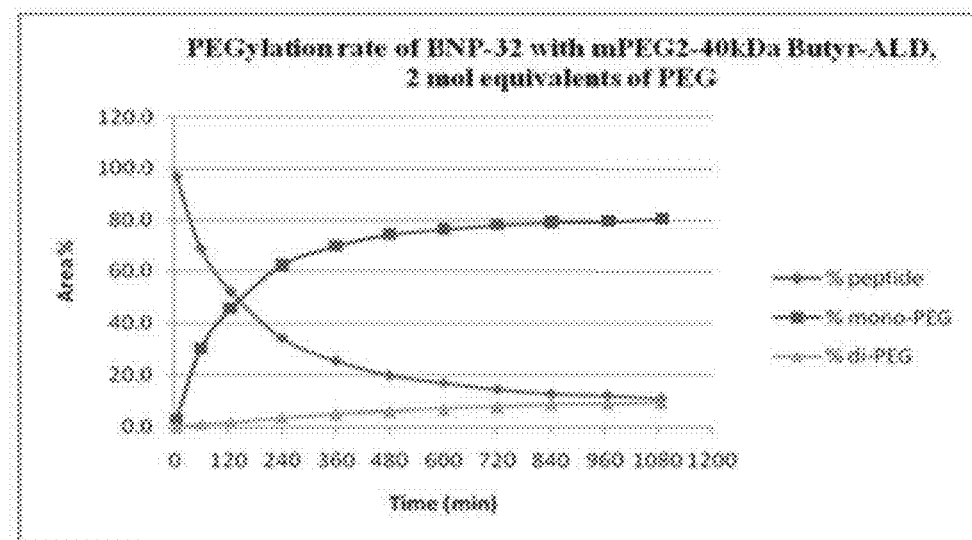
FIG. 50. PEGylation rate of BNP-32 with mPEG2-40kDa Butyr-ALD.

A BNP-32 stock solution of 4 mg/mL peptide content was made in 20 mM Na-citrate buffer pH 4.5 in a sterile low-endotoxin polypropylene tube. This solution could be stored aseptically for at least 1 week at 4° C. Immediately before a PEGylation reaction was performed, a 100 mg/mL stock solution of mPEG-Butyr-ALD-40K was made in the same buffer. A 50 mg/mL solution of sodium-cyanoborohydride (Na-CNHBr) reducing reagent in Milli-Q water was also made immediately before use. A typical PEGylation reaction was carried out as follows: Peptide stock solution (3 mL) was transferred to an appropriate tube containing a magnetic stir-bar and 5.208 mL of the same buffer was added. While stirring, 3.672 mL of a 100 mg/mL solution of mPEG-Butyr-ALD 40K was added dropwise within 1 minute. The reaction was allowed to stir for 15 min after which 0.12 mL of a 50 mg/mL Na-CNHBr solution was added, and the reaction mixture allowed to stir overnight (16-18 h) at room temperature. The resultant reaction mixture contained 1 mg/mL peptide, 2.0 mol equivalents of PEG (with respect to peptide) and 10 mol equivalents of NaCNBr (with respect to PEG). The reaction rate analysis is shown in FIG. 50. The reaction yields were determined by reversed phase HPLC to be 80.4% mono-PEG conjugate (N-terminus directed), 8.9% di-PEG conjugate and 10.7% non-conjugated peptide.

The mono-PEGylated conjugate was purified from the reaction mixture by cation exchange chromatography using a Hi Trap SP Sepharose HP media (GE Healthcare). The linear flow rate of the column was 150 cm/h and the sample loading was 2.0 mg/mL of column bed volume (CV) with a column bed height of 10 cm. The buffers used for purification were: Buffer A: 10 mM NaPO$_4$, pH 7.0 and Buffer B: Buffer A+0.5 M NaCl.

Figure 51:
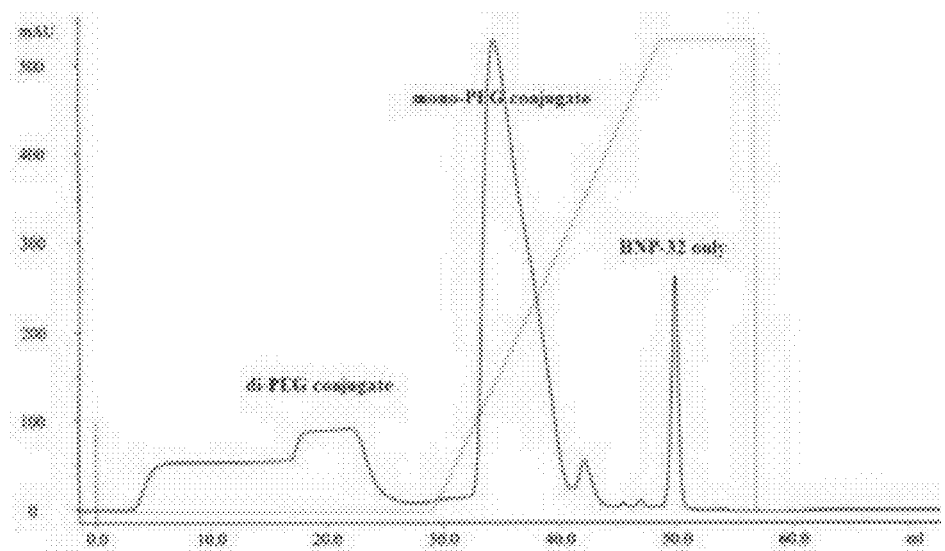
FIG. 51. Typical purification profile for the 40 kDa mPEG2-Butyr-ALD mono-PEG conjugate of BNP-32.

The PEGylation reaction mixture was diluted with 4 volumes of buffer A and the pH adjusted to 8.0. The column was equilibrated in buffer A. The diluted reaction mixture was loaded onto the column and unbound substances washed off the column with 3 column volumes of buffer A. The conjugated peptide was eluted from the column using a linear gradient of 0-100% B over 10 CV. A typical chromatogram is shown in FIG. 51. The purity of the conjugate was 99.5% (by RP-HPLC analysis, FIG. 52) and the mass (as determined by MALDI-TOF, FIG. 53) was within the expected range. The detection wavelength for preparative and analytical chromatography was 225 nm.

Samples were analyzed using reversed-phase HPLC. The mobile phases were A, 0.1% TFA in water and B, 0.05% TFA in acetonitrile. An Agilent Poroshell 300-SB-C8 (P/N 660750-906) column was used with a flow of 0.5 ml/min and column temperature of 50° C. The column was equilibrated in 10% B and conjugate separation was achieved using the gradient timetable shown in Table BNP2.1 below.

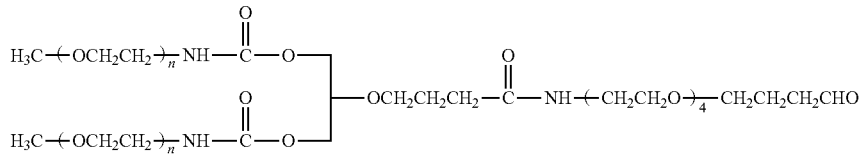

| Time (min) | % B |
|---|---|
| 0 | 10 |
| 2 | 10 |
| 5.5 | 45 |
| 10.5 | 65 |
| 10.6 | 95 |
| 13.6 | 95 |
| 13.7 | 10 |
| Post run | 5 min |

FIG. 50. PEGylation rate of BNP-32 with mPEG2-40 kDa Butyr-ALD. The reaction yields were 80.4% mono-PEG conjugate, 8.9% di-PEG conjugate and 10.7% remaining non-PEGylated peptide after 18 h reaction time. Yields were determined by RP-HPLC.

FIG. 51. Typical purification profile for the 40 kDa mPEG2-Butyr-ALD mono-PEG conjugate of BNP-32. The mono-PEGylated conjugate is indicated. The di-PEG conjugate eluted during the loading step.

Figure 52:
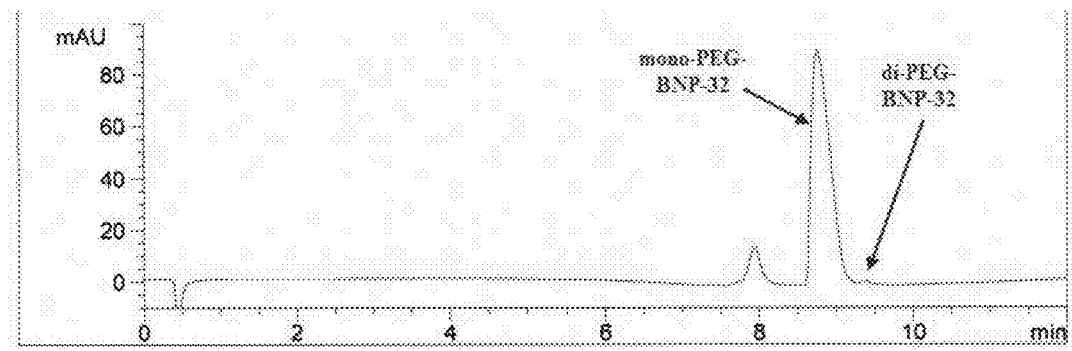
FIG. 52. HPLC analysis of the 40 kDa mPEG2-Butyr-ALD mono-PEG conjugate of BNP-32.

FIG. 52. HPLC analysis of the 40 kDa mPEG2-Butyr-ALD mono-PEG conjugate of BNP-32. The mono- and di-PEGylated forms of BNP-32 are indicated. The peak at 8 min retention time was instrument related and not any product of interest.

Figure 53:
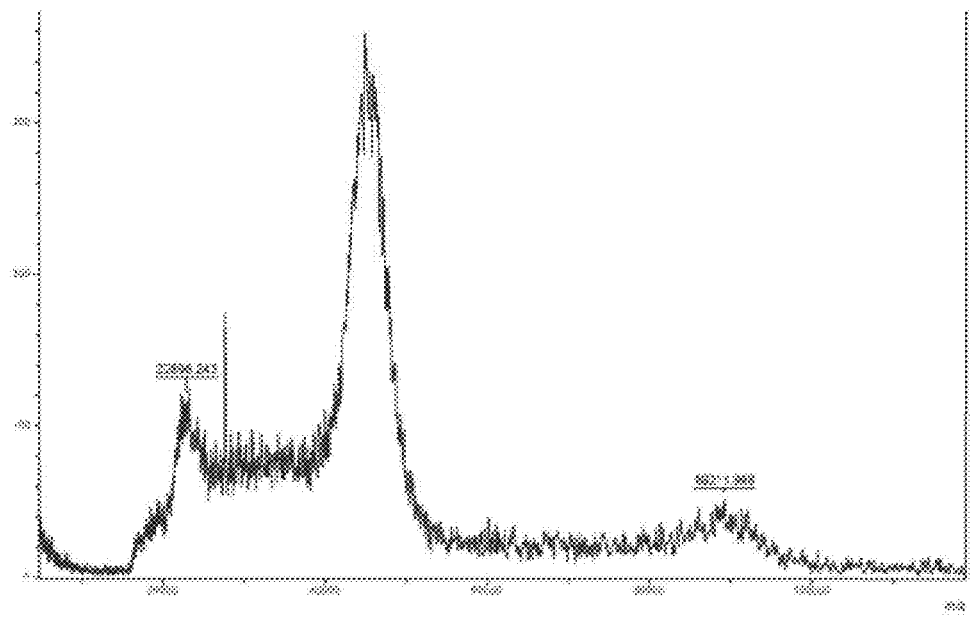
FIG. 53. MALDI-TOF analysis of the 40 kDa mPEG2-Butyr-ALD mono-PEG conjugate of BNP-32.

FIG. 53. MALDI-TOF analysis of the 40 kDa mPEG2-Butyr-ALD mono-PEG conjugate of BNP-32. The detected mass of the major peak was 45138 Da, which was within the expected range for the mono-conjugate.

Figure 54:
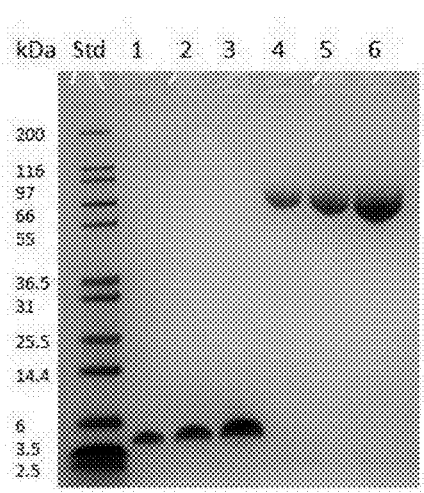
FIG. 54. SDS-PAGE (4-12% Bis-Tris-Nu-PAGE, Invitrogen) analysis of BNP-32 and purified [mono]-[mPEG2-Butyr-ALD-40K]-[BNP-32] conjugate.

FIG. 54. SDS-PAGE (4-12% Bis-Tris-Nu-PAGE, Invitrogen) analysis of BNP-32 and purified [mono]-[mPEG2-Butyr-ALD-40K]-[BNP-32] conjugate. Lanes 1, 2 and 3 are 0.5, 1.0 and 2.0 µg of the non-PEGylated peptide respectively. Lanes 4, 5 and 6 are 0.5, 1.0 and 2.0 µg of the purified mono-PEG-conjugate, respectively.

Example BNP3

Site Specific Acetylation of Brain Natriuretic Peptide (BNP-32)

Specific amine sites can be blocked by acetylation leaving other sites open for PEGylation. BNP-32 is composed of 32 amino acids with a single disulfide bond. The peptide contains 3 lysine residues and an N-terminus containing a free amine group. Previous PEGylation studies with BNP-32 indicate that all four amine groups are sterically accessible for reaction with PEG reagents. (Miller et al., Bioconjugate Chemistry 2006 March-April; 17(2):267-74). In the current study, the pKa difference between the N-terminal amine and the epsilon amines of the lysine residues was used to specifically acetylate the N-terminus, leaving the lysine amines available for PEGylation.

One milligram of BNP-32 was combined with 2 mol equivalents of acetic acid-NHS (previously dissolved in 2 mM HCl) in a total volume of 1 mL in 20 mM MES buffer at pH 6.0 and incubated at room temperature for 2 h. At this pH, one predominant acetylated product was formed based on RP-HPLC analysis. Based on accepted chemical principles known to those skilled in the art, at pH 6.0 the N-terminal amine group is more reactive than the epsilon amines and acetylation would occur predominantly at this position. Also, at lower pH, all amines are less reactive while at higher pH all amines are more reactive. The reaction above was also performed at other pH levels: At pH 4.5 (20 mM citrate buffer) there was significantly lower acetylation for all amine groups, while at pH 7.5 (20 mM HEPES buffer) and pH 9.0 (20 mM boric acid buffer), all amine groups were more reactive and significant acetylation occurred at all four sites as assed by RP-HPLC. Site specificity of the purified reaction products may also be confirmed using methods known to the art such as peptide mapping.

The predominant acetylated product from the reaction performed at pH 6.0 can be purified by standard chromatographic methods. The acetylated peptide can then be PEGylated using any of the reagents that are specific for amine reactive groups and standard methods known to the art, again followed by standard chromatographic methods to purify the conjugate of interest.

Example BNP4

PEGylation of BNP-32 with [mPEG-Butyr-ALD-10K]

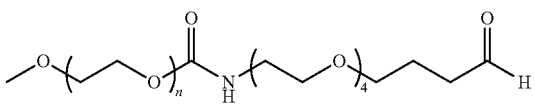

A BNP-32 stock solution of 4 mg/mL peptide content was made in 20 mM sodium-citrate buffer pH 4.5 in a sterile low-endotoxin polypropylene tube. This solution could be stored aseptically for at least 1 week at 4° C. Immediately before a PEGylation reaction was performed, a 100 mg/mL stock solution of [mPEG-Butyr-ALD-10K] was made in the same buffer used to dissolve the peptide. A 50 mg/mL solution of sodium-cyanoborohydride (Na-CNHBr) reducing reagent in Milli-Q water was also made immediately before use. A typical PEGylation reaction was carried out as follows: Peptide stock solution (3 mL, 12 mg) was transferred to an appropriate tube containing a magnetic stir-bar and 8.11 mL of 20 mM sodium-citrate buffer pH 4.5 was added. While stirring, 0.77 mL of a 100 mg/mL solution of mPEG-Butyr-ALD 10K was added drop wise within 1 minute. The reaction was allowed to stir for 15 min after which 0.12 mL of a 50 mg/mL Na-CNHBr solution was added, and the reaction mixture allowed to stir overnight (16-18 h) at room temperature. The resultant reaction mixture contained 1 mg/mL peptide, 2.0 mol equivalents of PEG (with respect to peptide) and 10 mol equivalents of NaCNBr (with respect to PEG). The reaction yields were determined by reversed phase HPLC to be 76% mono-PEG conjugate (N-terminus directed), 10.6% di- and tri-PEG conjugate and 13.4% non-conjugated peptide. This PEG reagent forms stable bonds with amine groups.

The mono-PEGylated conjugate was purified from the reaction mixture by cation exchange chromatography using Hi Trap SP Sepharose HP media (GE Healthcare). The linear flow rate of the column was 150 cm/h and the sample loading was 2.0 mg/mL of column bed volume (CV) with a column bed height of 10 cm. The buffers used for purification were: Buffer A: 10 mM $NaPO_4$, pH 7.0 and Buffer B: Buffer A+0.5 M NaCl. The PEGylation reaction mixture was diluted with 4 volumes of buffer A and the pH adjusted to 8.0 with 0.1 M sodium hydroxide. The column was equilibrated in buffer A. The diluted reaction mixture was loaded onto the column and unbound substances washed off the column with 3 column volumes of buffer A. The conjugated peptide was eluted from the column using a linear gradient of 0-100% B over 10 CV. The detection wavelength for preparative and analytical chromatography was 225 nm.

Fractions collected during cation exchange chromatography were analyzed using reversed-phase HPLC. The mobile phases were: A, 0.1% TFA in water and B, 0.05% TFA in acetonitrile. An Agilent Poroshell 300-SB-C8 (P/N 660750-906) column was used with a flow of 0.5 ml/min and column temperature of 50° C. The column was equilibrated in 10% B and conjugate separation was achieved using the gradient timetable shown in Table 2.1.

| Time (min) | % B |
|---|---|
| 0 | 10 |
| 2 | 10 |
| 5.5 | 45 |
| 10.5 | 65 |
| 10.6 | 95 |
| 13.6 | 95 |
| 13.7 | 10 |
| Post run | 5 min |

Fractions containing pure [mono]-[mPEG-Butyr-ALD-10K]-[BNP-32] as determined by RP-HPLC were pooled and stored in aliquots at −80° C. as the purified conjugate.

Figure 55:
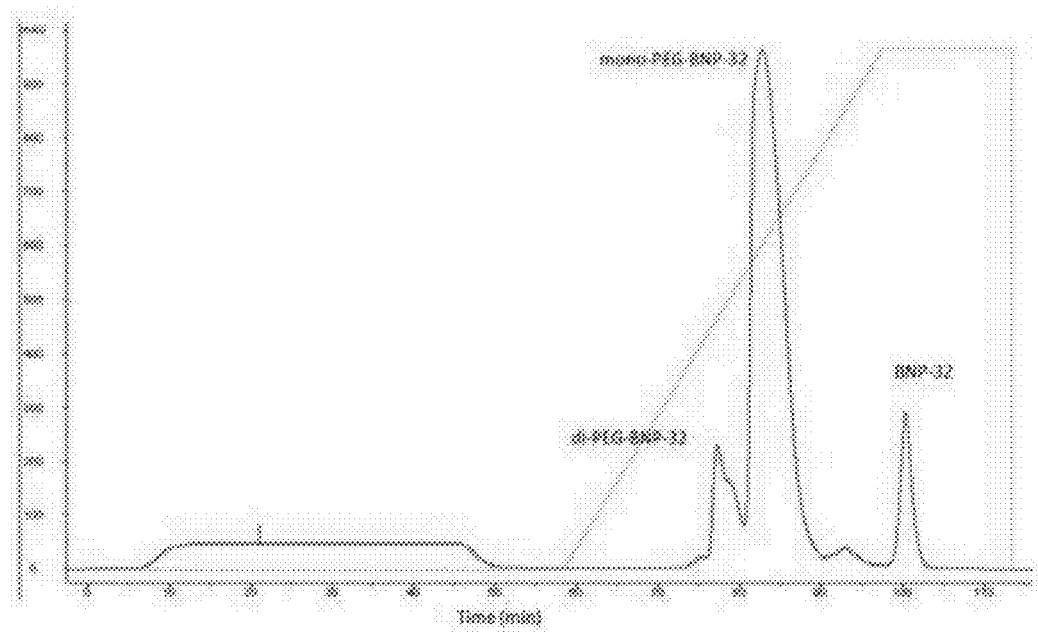
FIG. 55. Typical cation-exchange purification profile of [mono]-[mPEG-Butyr-ALD-10K]-[BNP-32].
Figure 56:
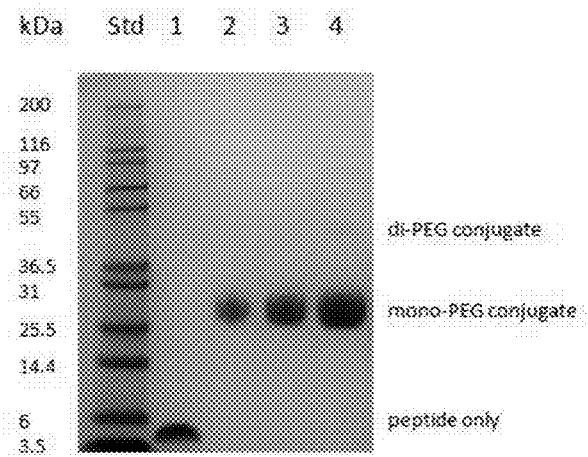
FIG. 56. SDS-PAGE analysis of BNP-32 and the purified [mono]-[mPEG2-Butyr-ALD-40K]-[BNP-32] conjugate.
Figure 57:
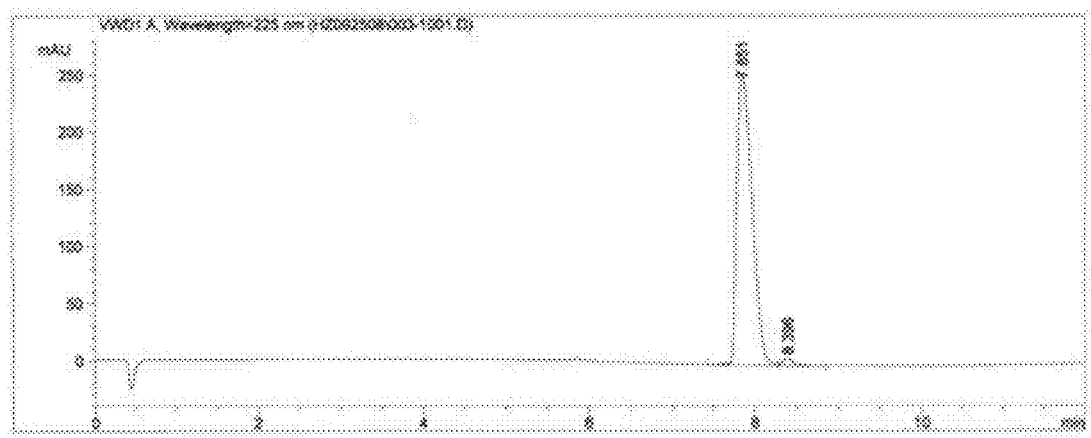
FIG. 57. RP-HPLC analysis of the purified [mono]-[mPEG-Butyr-ALD-10K]-[BNP-32] conjugate.
Figure 58:
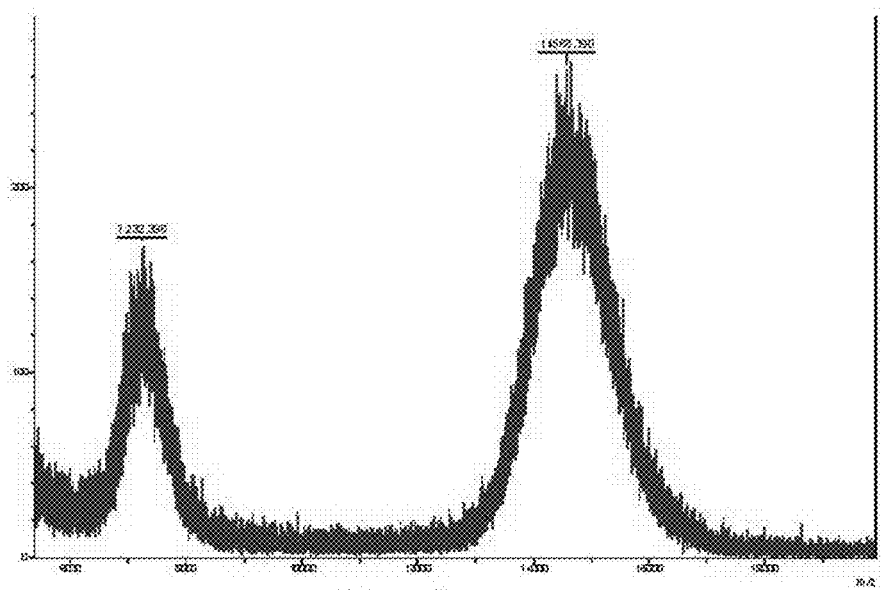
FIG. 58. MALDI-TOF analysis of the purified [mono]-[mPEG-Butyr-ALD-10K]-[BNP-32] conjugate.

A typical cation-exchange chromatogram is shown in FIG. 55. SDS-PAGE analysis of BNP-32 and purified [mono]-[mPEG2-Butyr-ALD-10K]-[BNP-32] conjugate is shown in FIG. 56. RP-HPLC analysis of the purified conjugate is shown in FIG. 57, and MALDI-TOF analysis of the purified conjugate is shown in FIG. 58. The purity of the mono-PEG-conjugate was 98% by SDS-PAGE analysis and 98.4% by RP-HPLC analysis with 1.6% of di-PEG-conjugate. The mass as determined by MALDI-TOF was within the expected range.

FIG. 55. Typical cation-exchange purification profile of [mono]-[mPEG-Butyr-ALD-10K]-[BNP-32]. The PEGylated conjugates and the free peptide peaks are indicated.

FIG. 56. SDS-PAGE (4-12% Bis-Tris-Nu-PAGE, Invitrogen) analysis of BNP-32 and the purified [mono]-[mPEG2-Butyr-ALD-40K]-[BNP-32] conjugate. Lane 1: BNP-32 peptide only (1 µg); Lanes 2, 3 and 4 are 0.5, 1.0 and 2.0 µg of the purified mono-PEG-conjugate, respectively.

FIG. 57. RP-HPLC analysis of the purified [mono]-[mPEG-Butyr-ALD-10K]-[BNP-32] conjugate. The peaks at 7.851 and 8.396 min contain the mono-PEG and di-PEG conjugates, respectively.

FIG. 58. MALDI-TOF analysis of the purified [mono]-[mPEG-Butyr-ALD-10K]-[BNP-32] conjugate. The detected mass of the major peak was 14568 Da, which was within the expected range for the mono-PEG conjugate. The peak at 7232 Da represents the doubly charged conjugate.

Example BNP5

PEGylation of BNP-32 with Releasable [mPEG-SBC-30K]

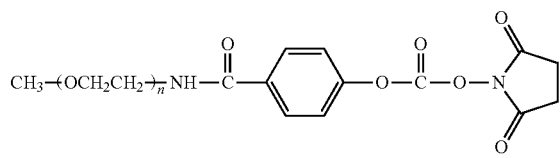

A BNP-32 stock solution of 4 mg/mL peptide content was made in 20 mM MES buffer pH 6.0 in a sterile low-endotoxin polypropylene tube. This solution could be stored aseptically for at least 1 week at 4° C.

A typical PEGylation reaction was carried out as follows: [mPEG-SBC-30K] PEG reagent (1220 mg) was weighed-out in an appropriate tube and dissolved with stirring in 9 ml of the same buffer used to dissolve the peptide. After the PEG had dissolved and with stirring, 3.0 mL of the peptide solution was added. The reaction was allowed to stir for 10 min at room temperature. The resultant reaction mixture contained 1 mg/mL peptide and 8.0 mol equivalents of PEG. After the incubation period, ⅕ volume of a 1 M glycine solution (in the same buffer) was added to quench the reaction. After a further 60 min of stirring at room temperature, 1 volume of 0.2 M acetic acid was added to stabilize the conjugate and the reaction mixture was stored at −20° C. The reaction yielded >80% mono-PEG conjugate. The mPEG SBC reagent forms hydrolysable bonds with amine groups and upon hydrolysis, leaves the peptide modified (tagged).

The mono-PEGylated conjugate was purified from the reaction mixture by cation exchange chromatography using Hi Trap SP Sepharose HP media (GE Healthcare). The linear flow rate of the column was 150 cm/h and the sample loading was 2.0 mg/mL of column bed volume (CV) with a column bed height of 10 cm. The buffers used for purification were: Buffer A: 10 mM NaPO$_4$, pH 7.0 and Buffer B: Buffer A+0.5 M NaCl. The PEGylation reaction mixture was diluted with 4 volumes of buffer A and the pH adjusted to 8.0 with 0.1 M sodium hydroxide. The column was equilibrated in buffer A. The diluted reaction mixture was loaded onto the column and unbound substances washed off the column with 3 column volumes of buffer A. The conjugated peptide was eluted from the column using a linear gradient of 0-100% B over 10 CV. The pooled mono-PEGylated fraction was diluted with 4 volumes of buffer A and the purification step repeated. The detection wavelength for preparative and analytical chromatography was 225 nm.

Fractions collected during cation exchange chromatography were analyzed using reversed-phase HPLC. The mobile phases were A, 0.1% TFA in water and B, 0.05% TFA in acetonitrile. An Agilent Zorbax 5 µm 300-SB-C18, 4.5×50 mm (P/N 860950-902) column was used with a flow of 1.0 ml/min and column temperature of 60° C. The column was equilibrated in 10% B and conjugate separation was achieved using the gradient timetable shown in Table BNP5.1 below.

| Time (min) | % B |
|---|---|
| 0 | 10 |
| 2 | 10 |
| 4 | 30 |
| 8 | 34 |
| 10.2 | 56 |
| 16.2 | 62 |
| 16.3 | 90 |
| 17.0 | 90 |
| 17.01 | 10 |
| Post run | 5 min |

Fractions containing pure [mono]-[mPEG-SBC-30K]-[BNP-32] from the repeat cation-eschange chromatography as determined by RP-HPLC were pooled and stored in aliquots at −80° C. as the purified conjugate.

Figure 59:
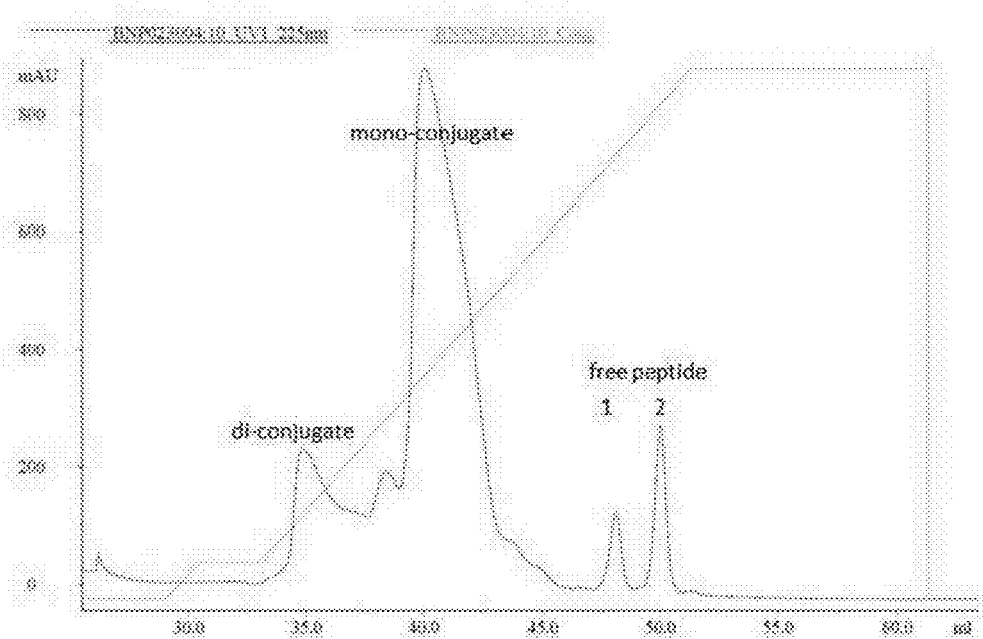
FIG. 59. Typical first cation-exchange purification profile for [mono]-[mPEG-SBC-30K]-[BNP-32].
Figure 60:
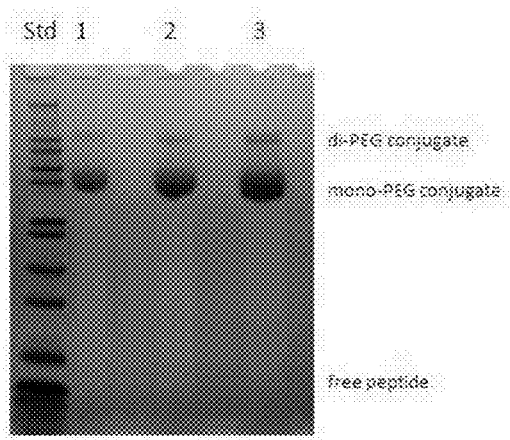
FIG. 60. SDS-PAGE analysis of the purified [mono]-[mPEG-SBC-30K]-[BNP-32] conjugate.
Figure 61:
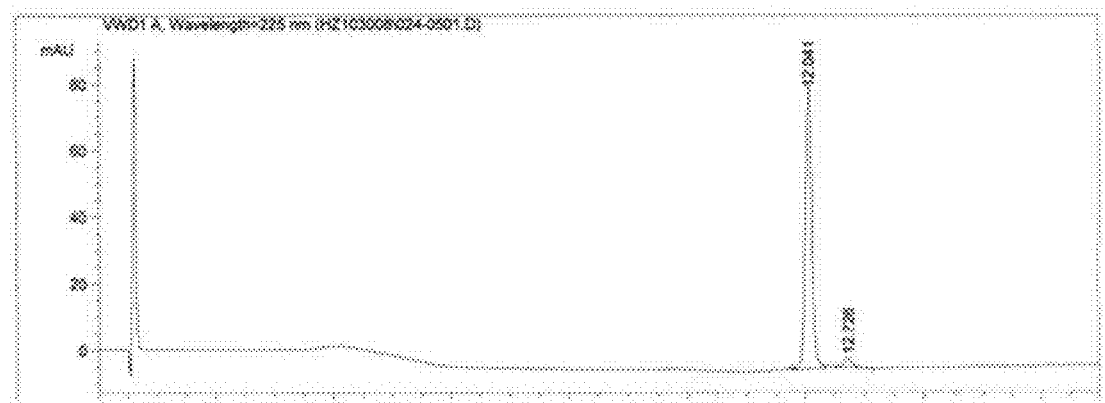
FIG. 61. RP-HPLC analysis of the purified [mono]-[mPEG-SBC-30K]-[BNP-32] conjugate.
Figure 62:
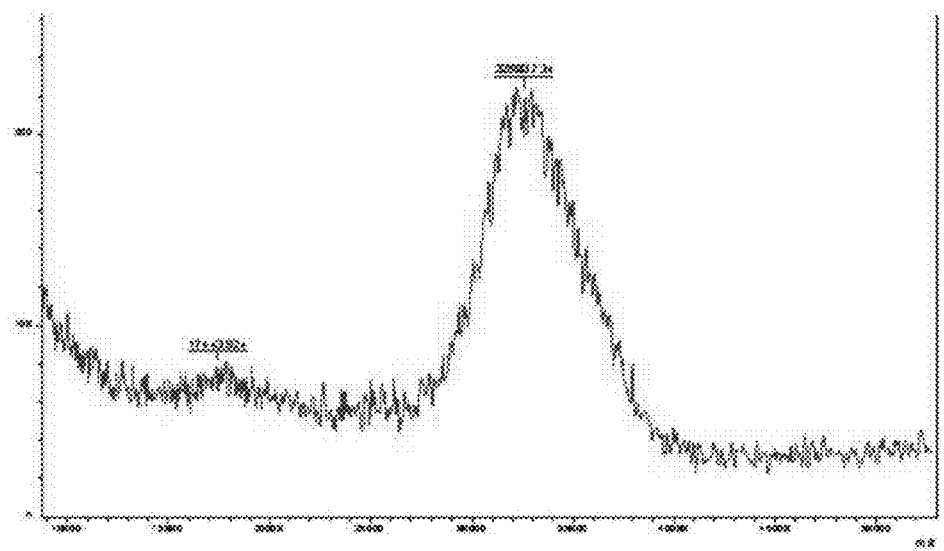
FIG. 62. MALDI-TOF analysis of the purified [mono]-[mPEG-SBC-30K]-[BNP-32] conjugate.

A typical cation-exchange purification chromatogram is shown in FIG. 59. SDS-PAGE analysis of purified [mono]-[mPEG-SBC-30K]-[BNP-32] is shown in FIG. 60. RP-HPLC analysis of the purified conjugate is shown in FIG. 61, and MALDI-TOF analysis of the purified product is shown in FIG. 62. The purity of the mono-PEG-conjugate was 95.8% by RP-HPLC analysis with 4.2% di-PEG conjugate also present. The mass as determined by MALDI-TOF was within the expected range.

FIG. 59. Typical first cation-exchange purification profile for [mono]-[mPEG-SBC-30K]-[BNP-32]. The mono- and di-PEGylated conjugates are indicated. The free peptide eluted in two peaks. On release, this PEG reagent leaves a modified (tagged) peptide. Peak 1 and peak 2 contain modified and unmodified peptide, respectively.

FIG. 60. SDS-PAGE (4-12% Bis-Tris-Nu-PAGE, Invitrogen) analysis of the purified [mono]-[mPEG-SBC-30K]-[BNP-32] conjugate. Lanes 1, 2 and 3 are 0.7, 1.4 and 2.1 µg of the PEGylated peptide, respectively.

FIG. 61. RP-HPLC analysis of the purified [mono]-[mPEG-SBC-30K]-[BNP-32] conjugate. The peaks at 12.041 min and 12.726 retention times contain the mono-PEG and di-PEG conjugates, respectively.

FIG. 62. MALDI-TOF analysis of the purified [mono]-[mPEG-SBC-30K]-[BNP-32] conjugate. The detected mass of the major peak was 32580 Da, which was within the expected range for the mono-PEG-conjugate. The peak at 17444 Da represents the doubly charged conjugate.

Example BNP6

PEGylation of BNP-32 with [mPEG2-C2-Fmoc-NHS-40K]

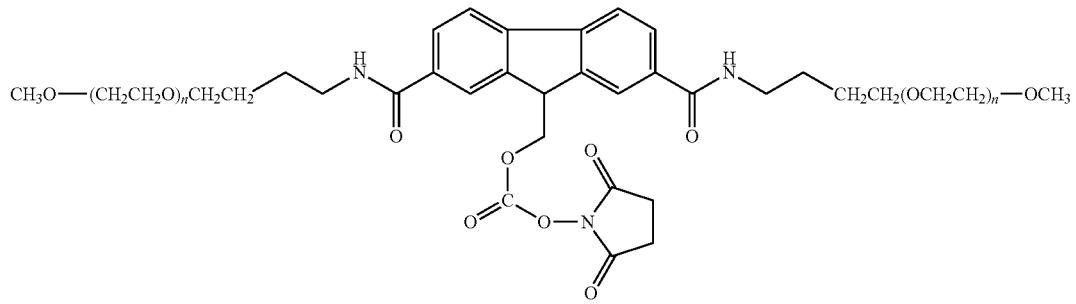

A BNP-32 stock solution of 4 mg/mL peptide content was made in 20 mM MES buffer pH 5.8 in a sterile low-endotoxin polypropylene tube. This solution could be stored aseptically for at least 1 week at 4° C.

Immediately before a PEGylation reaction was performed, a 100 mg/mL stock solution of [mPEG2-C2-fmoc-NHS-40K] PEG reagent was made in the same buffer used to dissolve the peptide. A typical PEGylation reaction was carried out as follows: Peptide stock solution (6 mL, 24 mg) was transferred to an appropriate tube containing a magnetic stir-bar and 10.16 mL of 20 mM MES buffer pH 5.8 was added. While stirring, 7.84 mL of a 100 mg/mL PEG reagent solution was added. The resultant reaction mixture contained 1 mg/mL peptide and 2 mol equivalents of PEG. The reaction was allowed to stir for 90 min at room temperature after which a ⅕ volume of 0.2 M glycine solution (in 20 mM MES buffer pH 5.8) was added and the reaction mixture stirred for another 60 min to quench the reaction. These reaction conditions yielded approximately 60% mono-PEGylated peptide. This PEG reagent forms hydrolysable bonds with amine groups and upon hydrolysis, an unmodified peptide is generated. The reaction mixture was stored at 4° C.

The mono-PEGylated conjugate was purified from the reaction mixture by cation exchange chromatography using Hi Trap SP Sepharose HP media (GE Healthcare). The linear flow rate of the column was 150 cm/h and the sample loading was 1.0 mg/mL of column bed volume (CV) with a column bed height of 11 cm. The buffers used for purification were: Buffer A: 10 sodium-citrate, pH 4.0 and Buffer B: Buffer A+0.8 M NaCl. The PEGylation reaction mixture was diluted with 4 volumes of buffer A. The column was equilibrated in buffer A. The diluted reaction mixture was loaded onto the column and unbound substances washed off the column with 3 column volumes of buffer A. The conjugated peptides were eluted from the column using the following elution steps: (a) linear gradient of 0-4% B over 1 CV followed by a hold at 4% B for 4 CV; (b) linear gradient of 4-50% B over 5 CV followed by a hold at 50% B for 1 CV; (c) step gradient to 80% B followed by a hold at 80% B for 2 CV. The pooled mono-PEGylated fraction was diluted with 4 volumes of buffer A and the purification step repeated. The detection wavelength for preparative and analytical chromatography was 225 nm.

Fractions collected during cation exchange chromatography were analyzed using reversed-phase HPLC. The mobile phases were A, 0.1% TFA in water and B, 0.05% TFA in acetonitrile. An Agilent Zorbax XDB-C8, 5 µm, 4.5×150 mm (P/N 993967-906) column was used with a flow of 0.5 ml/min and column temperature of 60° C. The column was equilibrated in 10% B and conjugate separation was achieved using the gradient timetable shown in Table BNP6.1 below.

| Time (min) | % B |
| --- | --- |
| 0 | 10 |
| 4 | 10 |
| 9 | 35 |
| 10.5 | 50 |
| 23 | 75 |
| 24 | 95 |
| 25 | 95 |
| 25.2 | 10 |
| Post run | 6 min |

Fractions containing pure [mono]-[mPEG2-C2-fmoc-NHS-40K]-[BNP-32] from the repeat cation-eschange chromatography as determined by RP-HPLC were pooled and stored in aliquots at −80° C. as the purified conjugate.

Figure 63:
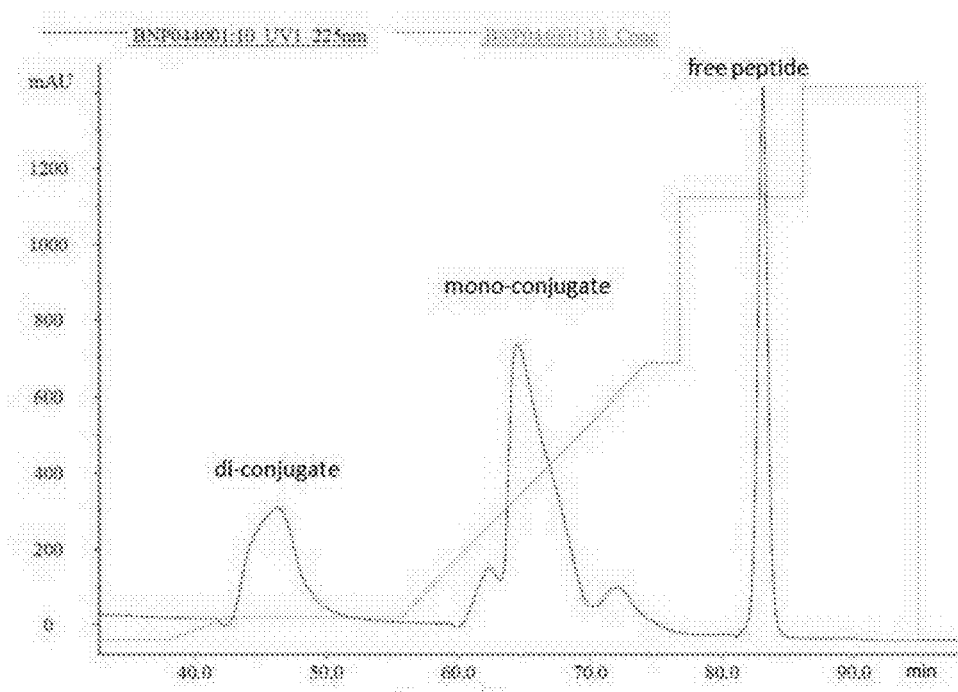
FIG. 63. Typical first cation-exchange purification profile of [mPEG2-C2-fmoc-NHS-40K].
Figure 64:
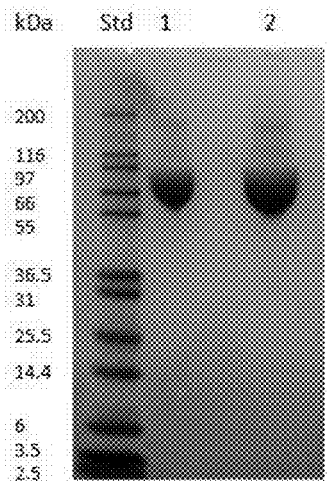
FIG. 64. SDS-PAGE analysis of the purified [mPEG2-C2-fmoc-NHS-40K]-[BNP-32] conjugate.
Figure 65:
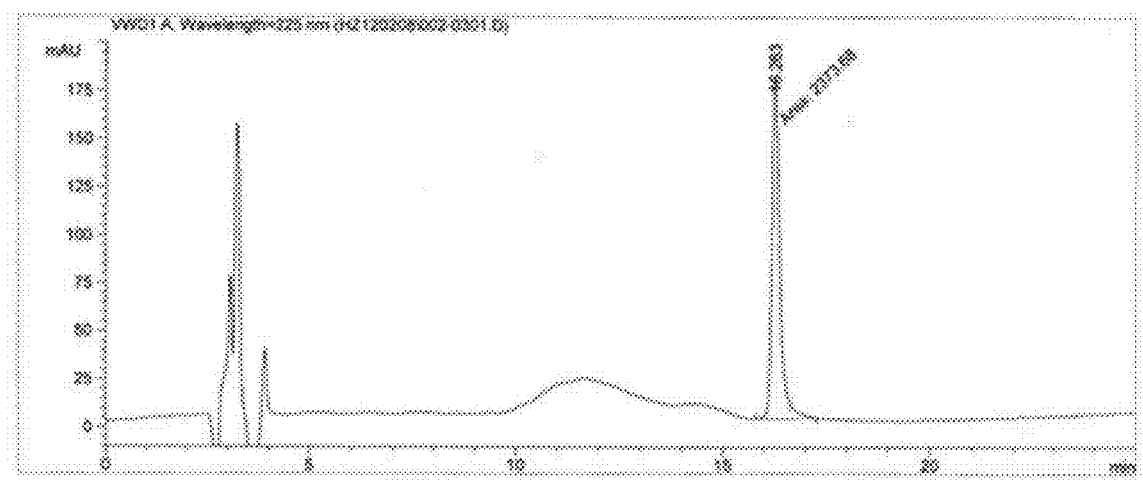
FIG. 65. RP-HPLC analysis of the purified [mPEG2-C2-fmoc-NHS-40K]-[BNP-32] conjugate.
Figure 66:
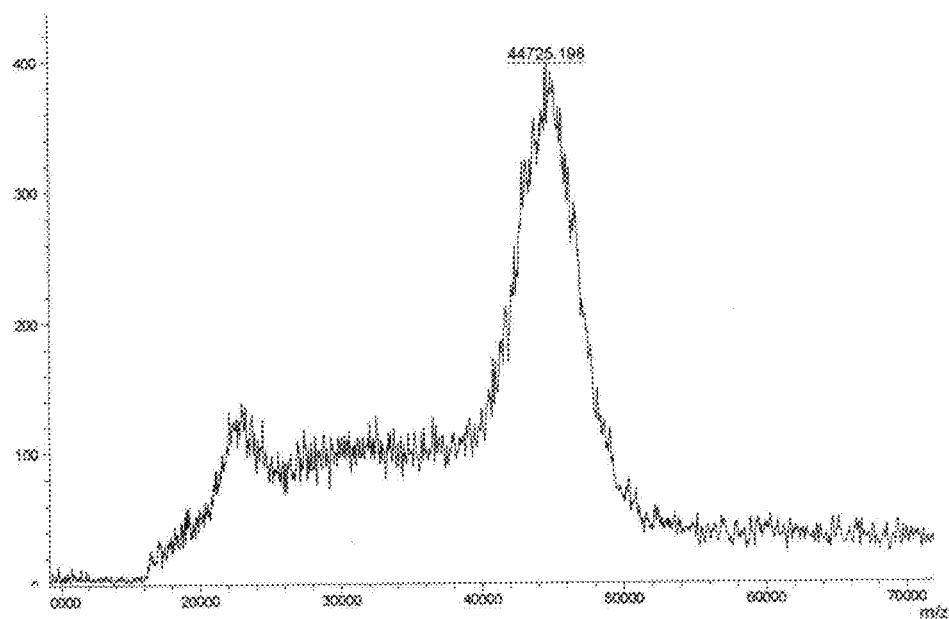
FIG. 66. MALDI-TOF analysis of the purified [mPEG2-C2-fmoc-NHS-40K]-[BNP-32] conjugate.

A typical first cation-exchange purification chromatogram is shown in FIG. 63. SDS-PAGE analysis of purified [mono]-[mPEG2-C2-fmoc-NHS-40K]-[BNP-32] is shown in FIG. 64. RP-HPLC analysis of the purified conjugate is shown in FIG. 65, and MALDI-TOF analysis of the purified conjugate is shown in FIG. 66. The purity of the mono-PEG-conjugate was 100% by RP-HPLC analysis and >95% (by SDS-PAGE). The mass as determined by MALDI-TOF was within the expected range.

FIG. 63. Typical first cation-exchange purification profile of [mPEG2-C2-fmoc-NHS-40K]. The mono-, di- and non-PEGylated (free peptide) elution peaks are indicated.

FIG. 64. SDS-PAGE (4-12% Bis-Tris-Nu-PAGE, Invitrogen) analysis of the purified [mPEG2-C2-fmoc-NHS-40K]-[BNP-32] conjugate. Lanes 1 and 2 are 1.0 and 2.0 g of the PEGylated peptide, respectively. Low levels of hi-PEGylated forms are also visible.

FIG. 65. RP-HPLC analysis of the purified [mPEG2-C2-fmoc-NHS-40K]-[BNP-32] conjugate. FIG. 66. MALDI-TOF analysis of the purified [mPEG2-C2-fmoc-NHS-40K]-[BNP-32] conjugate.

FIG. 66. MALDI-TOF analysis of the purified [mPEG2-C2-fmoc-NHS-40K]-[BNP-32] conjugate. The detected mass of the major peak was 44725 Da, which was within the expected range for the mono-PEG-conjugate.

Example BNP7

Pharmacokinetic Studies

Thirty one (31) adult male Sprague-Dawley rats with indwelling jugular vein and carotid artery catheters (JVC/CAC) (Charles River Labs, Hollister, Calif.) were utilized for this study. The weight range of the animals was 315-358 grams. All animals were food fasted overnight. Prior to dosing, the rats were weighed, the tails and cage cards were labeled for identification and the doses were calculated. Anesthesia was induced and maintained with 3.0-5.0% isoflurane. The JVC and CAC were externalized and flushed with HEP/saline (10 IU/mL HEP/mL saline). The predose sample was collected from the JVC and the catheters were plugged, and labeled to identify the jugular vein and carotid artery. When all of the animals had recovered from anesthesia and the predose samples were processed, the animals were dosed, intravenously (IV) via the JVC using a 1 mL syringe containing the appropriate test article and the dead volume of the catheter was flushed with 0.9% saline to ensure the animals received the correct dose.

Following a single IV dose, blood samples were collected from groups 1A, 2A, 3A and 4A, at 0 (pre-dose collected as described above), 0.03, 0.33, 2.0, 6.0, 12.0 and 72.0 hours and from Groups 1B, 2B, 3B and 4B at 0 (pre-dose collected as described above), 0.17, 1.0, 4.0, 8.0, 24.0 and 48.0 hours via the carotid artery catheter and processed as stated in the protocol. Following the last collection point, the animals were euthanized.

Figure 67:
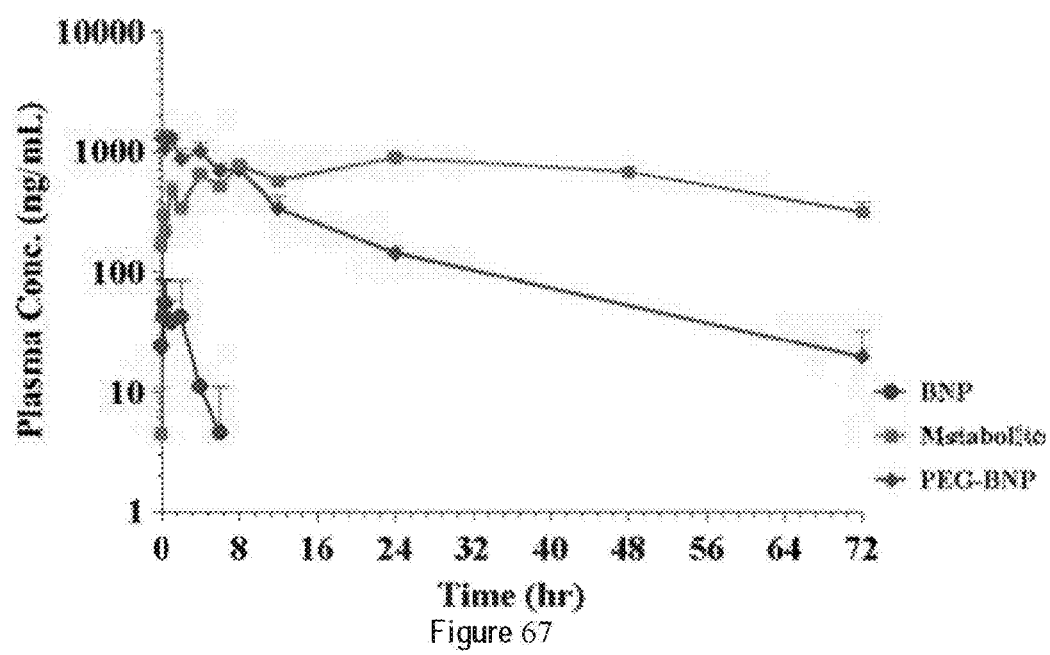
FIG. 67 shows the mean plasma concentration-time profiles of for C2-FMOC-PEG2-40K-BNP, its corresponding metabolite and released BNP.

Pharmacokinetic Analyses: Noncompartmental PK data analysis and report preparation was completed by Research Biology at Nektar Therapeutics (India) Pvt. Ltd. Hyderabad, A.P., India. Individual plasma concentration data are listed and summarized in Appendix A1.1-1.3. PK analysis was performed using WinNonlin (Version 5.2, Mountain View, Calif.-94014). Concentrations in plasma that were below LLOQ were replaced with zeros prior to generating Tables and PK analysis. In the event that more than half (>50%) of the data points were below zero, mean concentration will not be shown in the figures or used in PK parameters estimation. The following PK parameters were estimated using plasma concentration-time profile of each animal:

C0 Extrapolated concentration to time "zero"
Cmax Maximum (peak) concentration
AUCall Area under the concentration-time from zero to time of last concentration value
T1/2(Z) Terminal elimination half-life
AUCinf Area under the concentration-time from zero to time infinity
Tmax Time to reach maximum or peak concentration following administration
CL Total body clearance
Vz Volume of distribution based on terminal phase
Vss Volume of distribution at steady state
MRTlast Mean residence time to last observable concentration
Releasable-PEG:

FIG. 67 shows the mean plasma concentration-time profiles of for C2-FMOC-PEG2-40K-BNP, its corresponding metabolite and released BNP. No measurable plasma concentrations observed after BNP administration and hence the data is not shown in FIG. 67. At first time point collection which was at 0.03 hr, concentration was <20 ng/mL in all the animals. Table BNP7.1 summarizes the PK parameters of BNP following equivalent protein mass of 0.459 mg/kg administered intravenously into rats via C2-FMOC-PEG2-40K-BNP or BNP.

TABLE 1

Comparative PK Parameters of BNP Released from C2-FMOC-PEG2-40K-BNP in BNP Given as Non-Conjugated Native Protein

| Test Article | Cmax (ng/mL) | T½ (hr) | AUCINF (ng · hr/mL) | Tmax (hr) | MRTlast (hr) |
|---|---|---|---|---|---|
| BNP | 0.00 | NC | NC | NC | NC |
| C2-FMOC-PEG2-40K-BNP | 55.4 | 1.25 | 162 | 0.33 | 1.84 |

NC—Cannot be calculated.

Figure 68:
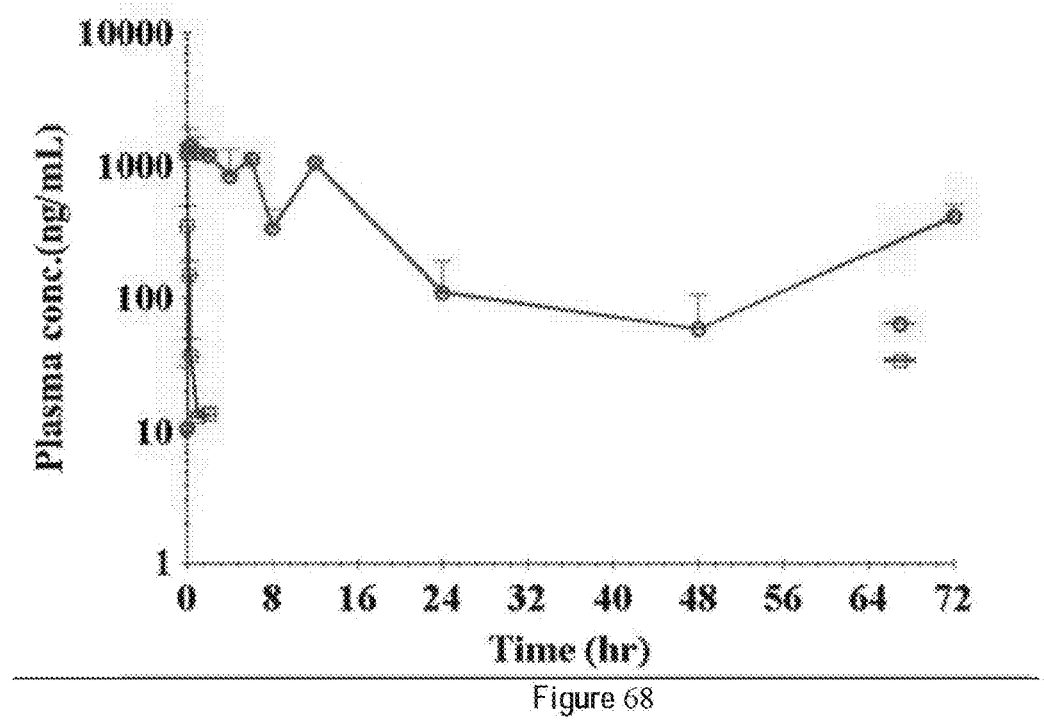
FIG. 68 shows the non-released PEG-BNP levels after the administration of the two non-releasable PEG constructs (ButyrALD-40K-BNP, ButyrALD-10K-BNP).

FIG. 68 shows the non-released PEG-BNP levels after the administration of the two non-releasable PEG constructs (ButyrALD-40K-BNP, ButyrALD-10K-BNP). Table BNP7.2 summarizes the PK parameters of following equivalent protein mass of 0.459 mg/kg administered intravenously into rats.

TABLE BNP7.2

Comparative PK Parameters of Test Articles (Non-Releasable-PEG Conjugates) versus Native BNP Following Equivalent Protein Mass Intravenous Administration to Sprague Dawley rats (Mean ± SD)

| Test Compound | Cmax (ng/mL) | T½ (hr) | AUCINF (ng · hr/mL) | MRTlast (hr) | CL (mL/hr/kg) | Vss (mL/kg) |
|---|---|---|---|---|---|---|
| BNP | 0.00 | NC | NC | NC | NC | NC |
| ButyrALD-40K-BNP | 1410 | 26.1 | 41300 | 24.0 | 11.1 | 631 |
| ButyrALD-10K-BNP | 355 | 0.272 | 96.6 | 0.368 | 4750 | 2270 |

NC—Cannot be calculated, there were no measurable plasma concentrations.

BNP concentrations were <LLOQ (LLOQ: 20 ng/mL) and therefore, no PK Parameters were reported.

BNP released from C2-FMOC-PEG2-40K-BNP reached peak concentrations of 55.4 ng/mL at 0.3 h and stayed above 20 ng/mL for 8 hr following C2-FMOC-PEG2-40K-BNP dosing. Half-life value for released BNP is 1.25 h following C2-FMOC-PEG2-40K-BNP IV bolus administration. Peak concentrations of 1300 ng/mL, a half-life of 15.0 hr and with plasma C2-FMOC-PEG2-40K-BNP concentrations remained above 100 ng/mL up to 24 h supported the prolonged release of BNP in plasma. The observed release of BNP from releasable-PEG C2-FMOC-PEG2-40K-BNP is consistent with the appearance of free PEG-metabolite (PEG-fulvene) which was also released from the conjugate. Binding to cell surface clearance receptors with internalization and degradation, proteolytic cleavage and renal filtration are the possible route of elimination for releasable C2-FMOC-PEG2-40K-BNP.

For the non-releasable PEG-constructs, ButyrALD-40K-BNP was observed to have longer half-life, lower clearance and higher exposure than ButyrALD-10K-BNP, probably due to increased PEG-length of the conjugate. No BNP was measurable in plasma following parent BNP administration.

Due to staggered sample collection, two very distinct concentration-time profiles were observed for two subgroups received ButyrALD-40K-BNP treatment. Therefore, the PK parameters estimated from the pooled data from the two subgroups to be interpreted with caution. ButyrALD-40K-BNP showed higher peak plasma concentration, approximately higher exposure and longer half-life than ButyrALD-10K-BNP when compared using pooled data.

Example PRO1

Protegrin-mPEG Conjugates
a) mPEG-N$^{ter}$-Protegrin Via mPEG-SPC

Protegrin is prepared and purified according to standard automated peptide synthesis or recombinant techniques known to those skilled in the art. An illustrative polymeric reagent, mPEG-SPC reagent,

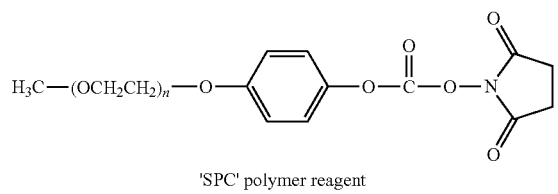

'SPC' polymer reagent is covalently attached to the N-terminus of protegrin, to provide a N$^{ter}$-conjugate form of the peptide. mPEG-SPC 20 kDa, stored at −20° C. under argon, is warmed to ambient temperature. The reaction is performed at room temperature. An X-fold molar excess of mPEG-SPC 20 kDa reagent is used based upon absolute peptide content. The mPEG-SPC reagent is weighed into a glass vial containing a magnetic stirrer bar. A solution of Protegrin prepared in phosphate buffered saline, PBS, pH 7.4 is added and the mixture is stirred using a magnetic stirrer until the mPEG-SPC is fully dissolved. The stirring speed is reduced and the reaction is allowed to proceed to formation of conjugate product. The reaction is optionally quenched to terminate the reaction. The pH of the conjugate solution at the end of the reaction is measured and further acidified by addition of 0.1M HCl, if necessary, to bring the pH of the final solution to about 5.5. The conjugate solution is then analyzed by SDS-PAGE and RP-HPLC (C18) to determine the extent of mPEG-N$^{ter}$-Protegrin conjugate formation.

Using this same approach, other conjugates are prepared using mPEG derivatives having other weight-average molecular weights that also bear an N-hydroxysuccinimide moiety.

b) Protegrin-C$^{ter}$-mPEG

An illustrative polymeric reagent, mPEG-NH$_2$ reagent is covalently attached to the C-terminus of protegrin, to provide a C$^{ter}$-conjugate form of the peptide. For coupling to the C-terminus, a protected Protegrin (Prot-protegrin) is prepared and purified according to standard automated peptide synthesis techniques known to those skilled in the art. mPEG-NH$_2$ 20 kDa, stored at −20° C. under argon, is warmed to ambient temperature. The reaction is performed at room temperature. A X-fold molar excess of mPEG-NH$_2$, PyBOP (benzotriazol-1-yloxy)tripyrrolidinonophosphonium hexafluorophosphate), and 1-hydroxybenzotriazole (HOBt) are used, based upon absolute peptide content. The mPEG-NH$_2$, PyBOP, HOBt are weighed into a glass vial containing a magnetic stirrer bar. A solution of Prot-protegrin is prepared in N,N-dimethylformamide is added and the mixture is stirred using a magnetic stirrer until the mPEG-NH$_2$ is fully dissolved. The stirring speed is reduced and the reaction is allowed to proceed to formation of conjugate product. The conjugate solution is then analyzed by SDS-PAGE and RP-HPLC (C18) to determine the extent of Prot-Protegrin-C$^{ter}$-mPEG conjugate formation. The remaining protecting groups are removed under standard deprotection conditions to yield the protegrin-C$^{ter}$-mPEG conjugate.

Using this same approach, other conjugates are prepared using mPEG derivatives having other weight-average molecular weights that also bear an amino moiety.

c) Protegrin-Cys(S-mPEG)

mPEG-Maleimide is obtained having a molecular weight of 5 kDa and having the basic structure shown below:

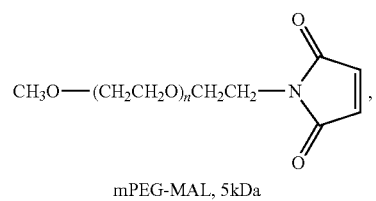

mPEG-MAL, 5kDa

Protegrin, which has a thiol-containing cysteine residue, is dissolved in buffer. To this peptide solution is added a 3-5 fold molar excess of mPEG-MAL, 5 kDa. The mixture is stirred at room temperature under an inert atmosphere for several hours. Analysis of the reaction mixture reveals successful conjugation of this peptide.

Using this same approach, other conjugates are prepared using mPEG-MAL having other weight average molecular weights.

d) mPEG-N$^{ter}$-Protegrin Via mPEG-SMB

An mPEG-N-Hydroxysuccinimide is obtained having a molecular weight of 5 kDa and having the basic structure shown below:

281

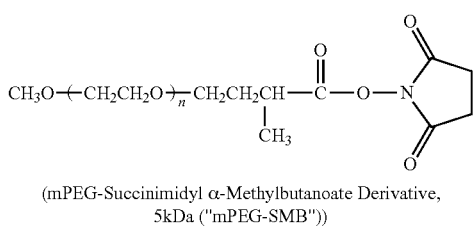

(mPEG-Succinimidyl α-Methylbutanoate Derivative, 5kDa ("mPEG-SMB"))

mPEG-SMB, 5 kDa, stored at −20° C. under argon, is warmed to ambient temperature. A five-fold excess (relative to the amount of the peptide) of the warmed mPEG-SMB is dissolved in buffer to form a 10% reagent solution. The 10% reagent solution is quickly added to the aliquot of a stock protegrin solution and mixed well. After the addition of the mPEG-SMB, the pH of the reaction mixture is determined and adjusted to 6.7 to 6.8 using conventional techniques. To allow for coupling of the mPEG-SMB to the peptide via an amide linkage, the reaction solution is stirred for several hours (e.g., 5 hours) at room temperature in the dark or stirred overnight at 3-8° C. in a cold room, thereby resulting in a conjugate solution. The reaction is quenched with a 20-fold molar excess (with respect to the peptide) of Tris buffer.

Using this same approach, other conjugates are prepared using mPEG derivatives having other weight-average molecular weights that also bear an N-hydroxysuccinimide moiety.

e) Protegrin-Glu(O-mPEG)

An illustrative polymeric reagent, mPEG-NH$_2$ reagent is covalently attached to the Glu residue of Protegrin, to provide a Glu-conjugate form of the peptide. For coupling to the Glu residue, a protected Protegrin (Prot2-Protegrin) is prepared and purified according to standard automated peptide synthesis techniques known to those skilled in the art. Deprotection of the Glu(OBz) residue (H$_2$/Pd) yields the free-Glu carboxylate for subsequent coupling. mPEG-NH$_2$ 20 kDa, stored at −20° C. under argon, is warmed to ambient temperature. The reaction is performed at room temperature. A 5-fold molar excess of mPEG-NH$_2$, PyBOP (benzotriazol-1-yloxy)tripyrrolidinonophosphonium hexafluorophosphate), and 1-hydroxybenzotriazole (HOBt) are used, based upon absolute peptide content. The mPEG-NH$_2$, PyBOP, HOBt are weighed into a glass vial containing a magnetic stirrer bar. A solution of Prot3-Protegrin is prepared in N,N-dimethylformamide is added and the mixture is stirred using a magnetic stirrer until the mPEG-NH$_2$ is fully dissolved. The stirring speed is reduced and the reaction is allowed to proceed to formation of conjugate product. The conjugate solution is then analyzed by SDS-PAGE and RP-HPLC (C18) to determine the extent of Prot3-Protegrin-(Glu-O-mPEG) conjugate formation. The remaining protecting groups are removed under standard deprotection conditions to yield the Protegrin-Glu(O-mPEG) conjugate.

Using this same approach, other conjugates are prepared using mPEG derivatives having other weight-average molecular weights that also bear an amino moiety.

Example PRO2

PEGylation of Protegrin-1 (PG-1) with [mPEG2-CAC-FMOC-NHS-40K]

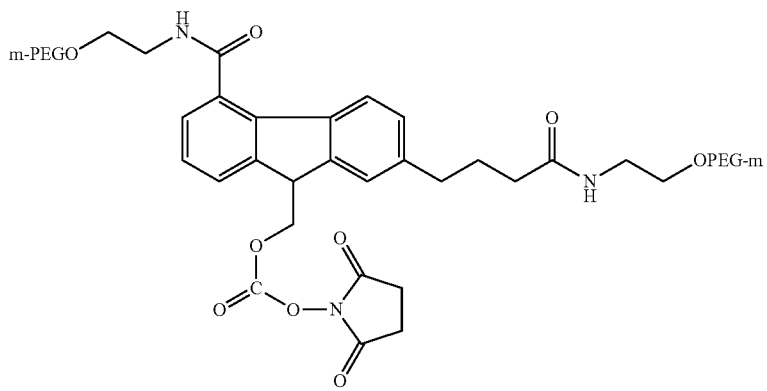

Stock solutions of 5.0 mg/mL PG-1 and 200 mG/mL mPEG2-CAC-FMOC-NHS-40K were prepared in 2 mM HCl. To initiate a reaction, the two stock solutions and a 0.5 M MES, pH 6.0, stock solution were brought to 25° C. and the three stock solutions were mixed (PEG reagent added last) to give final concentrations of 1.0 mg/mLPG-1, 50 mM MES and a 5-fold molar excess of mPEG2-CAC-FMOC-NHS-40K over PG-1. After 3.5 hours at 25° C. the reaction was quenched with 100 mM glycine in 100 mM HCl (10 mM final glycine concentration) for 1 hour. The reaction mixture was then diluted with deionized sterile water until the conductivity was below 1.0 mS/cm and the pH was adjusted to 6.0 with 1 M Na$_2$CO$_3$/NaHCO$_3$, pH 10.0.

The mono-PEGylated conjugate was purified from the reaction mixture by cation exchange chromatography using a column packed with SPHP media (GE Healthcare) on an AKTA Explorer 100 system (GE Healthcare). Buffer A was 20 mM MES, pH 6.0; Buffer B was 20 mM MES and 1 M NaCl, pH 6.0. The AKTA Explorer plumbing system and SPHP column were sanitized with 1 M HCl and 1 M NaOH and the resin was equilibrated with 10 column volumes Buffer A prior to sample loading. After loading, the column was washed with 10 column volumes 80% A/20% B to remove un-reacted PEG reagent. PEGylated and nonPEGylated peptides were eluted using a linear gradient from 80% A/20% B to 0% A/100% B over 20 column volumes with a linear flow rate of 90 cm/hour.

Fractions collected during cation exchange chromatography were analyzed using analytical reversed-phase HPLC. The mobile phases were: A, 0.1% TFA in water, and B, 0.05% TFA in acetonitrile. A Waters Symmetry C18 column (4.6 mm×75 mm) was used with a flow rate of 1.0 ml/min and a column temperature of 50° C. Detection was carried out at 280 nm. The column was equilibrated in 20% B and conjugate separation was achieved using the gradient timetable shown in Table PRO2.1.

| Step | Time (min) | % Mobile phase B |
| --- | --- | --- |
| 1 | 0.00 | 20.0 |
| 2 | 2.00 | 30.0 |
| 3 | 5.00 | 45.0 |
| 4 | 6.00 | 45.0 |
| 5 | 18.00 | 80.0 |
| 6 | 18.10 | 100.0 |
| 7 | 20.10 | 100.0 |
| 8 | 20.20 | 10.0 |

Fractions containing pure mono-[mPEG2-CAC-FMOC-40K]-[PG-1] as determined by RP-HPLC were pooled. Glacial acetic acid was added to the pooled fractions to a final concentration of 5% (v/v) and loaded onto a CG71S column (Rohm Haas) for Endotoxin removal and buffer exchange. Prior to sample loading, the column had been washed with 5% acetic acid in acetonitrile and equilibrated with 5% acetic acid in water (v/v). After sample loading, the column was washed with 10 column volumes of 5% acetic acid and mono-[mPEG2-CAC-FMOC-40K]-[PG-1] was eluted with a linear 0-100% gradient from 5% acetic acid to 5% acetic acid/95% Acetonitrile (v/v) over 10 column volumes. Fractions containing the conjugate as determined by analytical reversed phase HPLC, were pooled, lyophilized and stored at −80° C.

Figure 69:
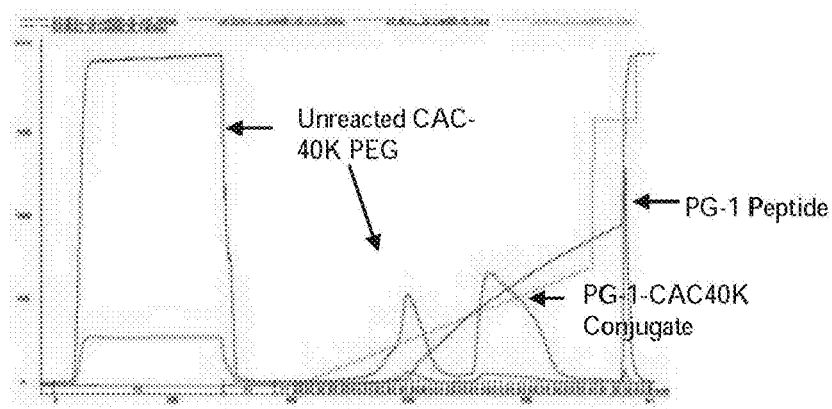
FIG. 69. Typical cation exchange purification profile of mono-[mPEG2-CAC-FMOC-40K]-[PG-1].
Figure 70:
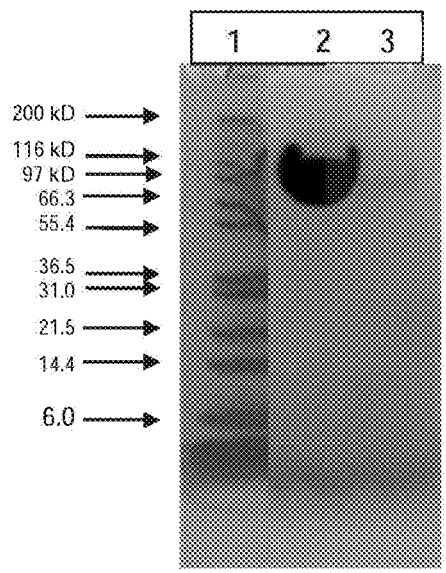
FIG. 70. SDS-PAGE of purified [mono]-[CAC-PEG2-FOMC-NHS-40K]-[Protegrin-1].
Figure 71:
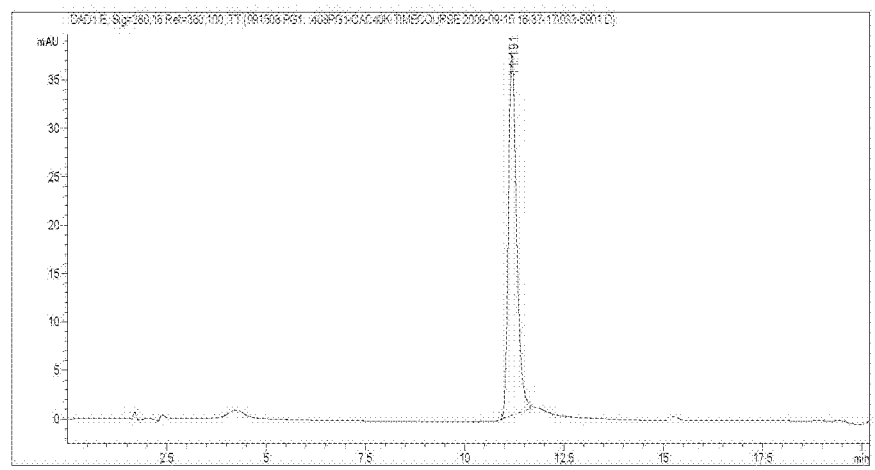
FIG. 71. Purity analysis of [mono]-[CAC-PEG2-FOMC-40K]-[Protegrin-1] by RP-HPLC.
Figure 72:
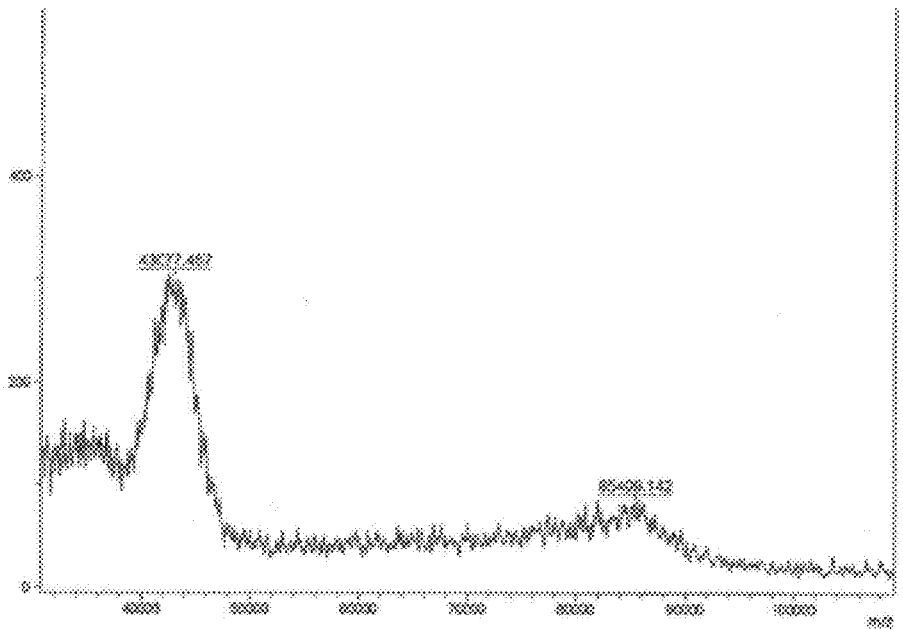
FIG. 72. MALDI-TOF spectrum of purified mono-[CAC-PEG2-FMOC-40K]-[Protegrin-1].

A typical SPHP cation exchange chromatogram is shown in FIG. 69. SDS-PAGE analysis of purified mono-[mPEG2-CAC-FMOC-40K]-[PG-1] is shown in FIG. 70. RP-HPLC analysis of the purified conjugate is shown in FIG. 71, and MALDI-TOF analysis of the purified conjugate is shown in FIG. 72.

The purity of the mono-PEG-conjugate was >95% by SDS-PAGE and 100% by RP-HPLC analysis. The mass as determined by MALDI-TOF was within the expected range.

FIG. 69. Typical cation exchange purification profile of mono-[mPEG2-CAC-FMOC-40K]-[PG-1]. The mono-PEGylated conjugate, unreacted peptide and PEG are indicated. The blue line represents absorbance at 280 nm and the red line represents absorbance at 225 nm.

FIG. 70. SDS-PAGE, with Coomassie Blue staining) of purified [mono]-[CAC-PEG2-FOMC-NHS-40K]-[Protegrin-1]. Lane 1, Mark12 MW markers; Lane 2, purified [mono]-[CAC-PEG2-FOMC-NHS-40K]-[Protegrin-1]. Lane 3, smaller quantity of purified [mono]-[CAC-PEG2-FOMC-NHS-40K]-[Protegrin-1]. The apparent large molecular weight of the conjugate, about 95 kDa, is due to a slow mobility of the monomeric conjugate in the gel due to a high degree of PEG hydration. Impurities were not detected in Lane 2.

FIG. 71. Purity analysis of [mono]-[CAC-PEG2-FOMC-40K]-[Protegrin-1] by Reversed Phase HPLC. The purity of the purified conjugate is 100% % at 280 nm. The peak at 4.5 minutes is a column-derived species and is not included in the sample.

FIG. 72. MALDI-TOF spectrum of purified mono-[CAC-PEG2-FMOC-40K]-[Protegrin-1]. The major peak at 43.1 kDa is within the expected range for the molecular weight of the mono-PEG-conjugate. The peak at 85.4 kDa may represent the single charged conjugate dimer formed during MALDI-TOF analysis.

Example PRO3

PEGylation of Protegrin-1 (PG-1) with N-m-PEG-Benzamide-p-Succinimidyl Carbonate (SBC)-30K

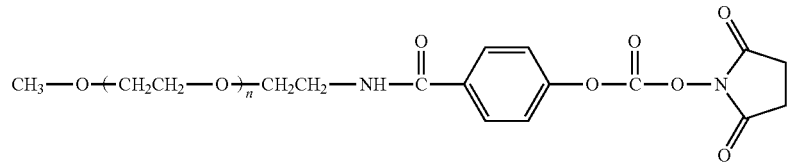

A stock solution of 1.2 mg/mL PG-1 was prepared in 2 mM HCl. To initiate a reaction, the PG-1 stock solution was brought to 25° C., a 15-fold molar excess of SBC-30K lyophilized powder was with stirring followed immediately with the addition of 1 M MES, pH 6, to give final concentrations of 1.0 mG/mL PG-1 (0.46 mM) and 50 mM MES. The reaction was allowed to proceed for 20 minutes at 25° C. After 20 min, the reaction was quenched with 100 mM glycine in 100 mM HCl (10 mM final glycine concentration) for 10 minutes. The reaction mixture was then diluted with deionized sterile water until the conductivity was below 1.0 mS/cm and the pH was adjusted to 4.0 with 1 M sodium acetate, pH 4.5. diluted.

The mono-PEGylated conjugate was purified from the reaction mixture by cation exchange chromatography using a column packed with SPHP media (GE Healthcare) on an AKTA Explorer 100 system (GE Healthcare). Buffer A was 20 mM sodium acetate, pH 4.0, Buffer B was 20 mM sodium acetate and 1 M NaCl, pH 4.0. The AKTA Explorer plumbing system and SPHP column were sanitized with 1 M HCl and 1 M NaOH and the resin was equilibrated with 10 column volumes Buffer A prior to sample loading. After loading, the column was washed with 5 column volumes 100% A/0% B to remove un-reacted PEG reagent. PEGylated and nonPEGylated peptides were eluted using a linear gradient from 80% A/20% B to 0% A/100% B over 20 column volumes with a linear flow rate of 90 cm/hour.

Fractions collected during cation exchange chromatography were analyzed using analytical reversed-phase HPLC. The mobile phases were: A, 0.1% TFA in water, and B, 0.05% TFA in acetonitrile. A Waters Symmetry C18 column (4.6 mm×75 mm) was used with a flow rate of 1.0 ml/min and a column temperature of 50° C. Detection was carried out at 280 nm. The column was equilibrated in 0% B and conjugate separation was achieved using the gradient timetable shown in Table PRO3.1.

| Step | Time (min) | % Mobile phase B |
| --- | --- | --- |
| 1 | 0.00 | 20.0 |
| 2 | 2.00 | 30.0 |
| 3 | 5.00 | 45.0 |

-continued

| Step | Time (min) | % Mobile phase B |
|---|---|---|
| 4 | 6.00 | 45.0 |
| 5 | 18.00 | 80.0 |
| 6 | 18.10 | 100.0 |
| 7 | 20.10 | 100.0 |
| 8 | 20.20 | 10.0 |

Fractions containing pure mono-[mPEG-SBC-30K]-[PG-1] as determined by RP-HPLC were pooled. Glacial acetic acid was added to the pooled fractions to a final concentration of 5% (v/v) and loaded onto a CG71S column (Rohm Haas) for Endotoxin removal and buffer exchange. Prior to sample loading, the column had been washed with 5% acetic acid in acetonitrile and equilibrated with 5% acetic acid in water (v/v). After sample loading, the column was washed with 10 column volumes of 5% acetic acid and mono-[mPEG-SBC-30K]-[PG-1] was eluted with a linear 0-100% gradient from 5% acetic acid to 5% acetic acid/95% Acetonitrile (v/v) over 10 column volumes. Fractions containing the conjugate as determined by analytical reversed phase HPLC, were pooled, lyophilized and stored at −80° C.

Figure 73:
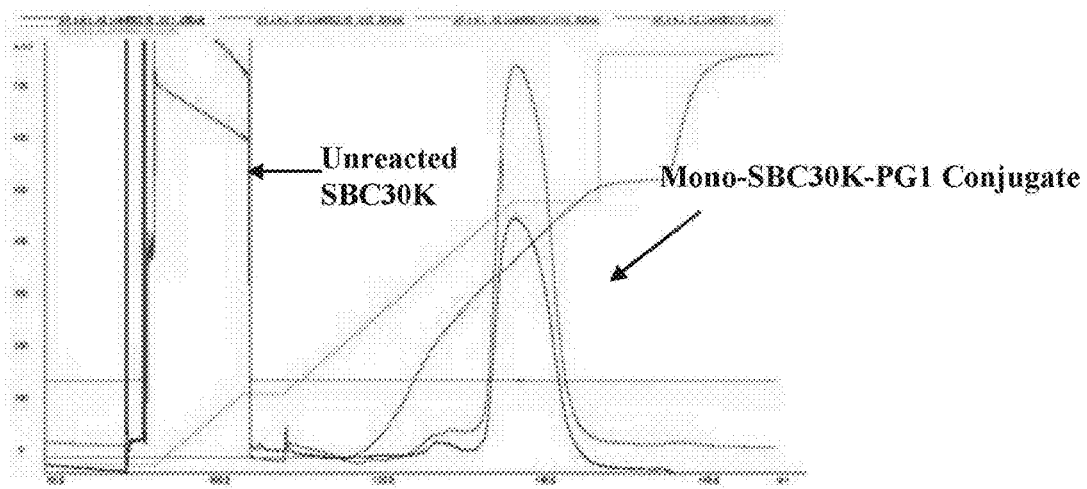
FIG. 73 Typical cation exchange purification profile of mono-[mPEG-SBC-30K]-[PG-1].
Figure 74:
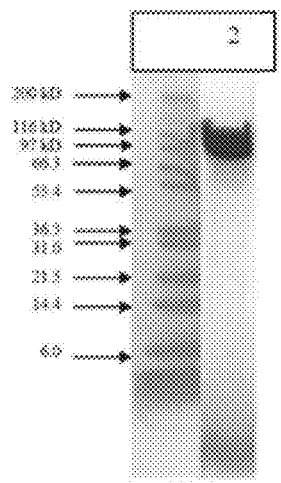
FIG. 74. SDS-PAGE of purified [mono]-[mPEG-SBC-30K-]-[Protegrin-1].
Figure 75:
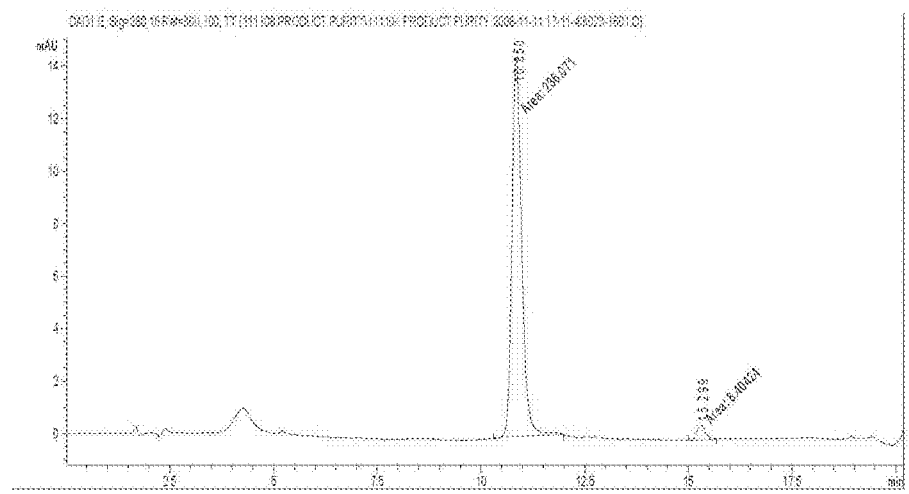
FIG. 75. Purity analysis of [mono]-[mPEG-SBC-30K-]-[Protegrin-1] by RP-HPLC.
Figure 76:
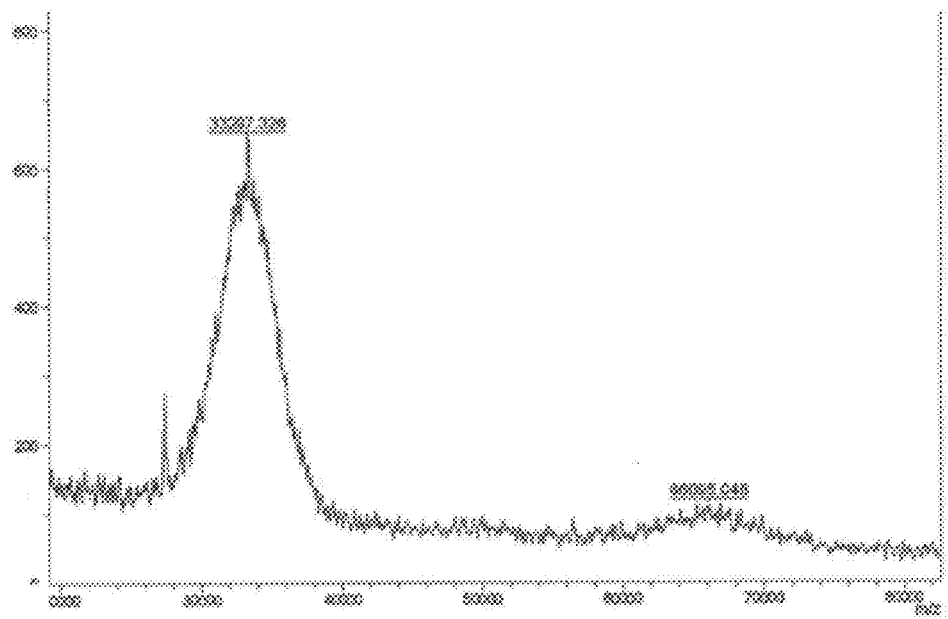
FIG. 76. MALDI-TOF spectrum of purified [mono]-[mPEG-SBC-30K-]-[Protegrin-1].

A typical cation exchange SP-HP chromatogram is shown in FIG. 73. SDS-PAGE analysis of purified mono-[mPEG-SBC-30K]-[PG-1] is shown in FIG. 74. RP-HPLC analysis of the purified conjugate is shown in FIG. 75, and MALDI-TOF analysis of the purified conjugate is shown in FIG. 76.

The purity of the mono-PEG-conjugate was >95% by SDS-PAGE and 96.6% by RP-HPLC analysis. The mass as determined by MALDI-TOF was within the expected range.

FIG. 73 Typical cation exchange purification profile of mono-[mPEG-SBC-30K]-[PG-1]. The mono-PEGylated conjugate and unreacted PEG are indicated. The blue line represents absorbance at 280 nm and the red line represents absorbance at 225 nm.

FIG. 74. SDS-PAGE (4-12% NuPage Bis-Tris, Invitrogen, with Coomassie Blue staining) of purified [mono]-[mPEG-SBC-30K-]-[Protegrin-1]. Lane 1, Mark12 MW markers; Lane 2, purified [mono]-[mPEG-SBC-30K-]-[Protegrin-1]. The apparent large molecular weight of the conjugate, about 97 kDa, is due to a slow mobility of the monomeric conjugate in the gel due to a high degree of PEG hydration. Impurities were not detected in Lane 2.

FIG. 75. Purity analysis of [mono]-[mPEG-SBC-30K-]-[Protegrin-1] by reversed phase HPLC. The purity of the purified conjugate is 96.6% % at 280 nm. The peak with retention time at 15.3 min, is the SBC-30K PEG reagent and constitutes 3.4% of the sample. The peak at 4.5 minutes is a column-derived species and is not included in the sample.

FIG. 76. MALDI-TOF spectrum of purified [mono]-[mPEG-SBC-30K-]-[Protegrin-1]. The major peak at 33.3 kDa is within the expected range for the molecular weight of [mono]-[mPEG-SBC-30K-]-[Protegrin-1]. The peak at 66.1 kDa, may represent the singly charged conjugate dimer formed during MALDI-TOF analysis.

Example PRO4

PEGylation of Protegrin-1 (PG-1) with PEG-diButyrAldehyde-5K OHCCH$_2$CH$_2$CH$_2$—(OCH$_2$CH$_2$)$_4$—NH—COO—PEG-O—CO—NH—(OCH$_2$CH$_2$)$_4$—CH$_2$CH$_2$CH$_2$—CHO Stock solutions of 8.0 mg/mL PG-1 and 200 mG/mL PEG-ButyAldehyde-5000 were prepared in 2 mM HCl. To initiate a reaction, the two stock solutions and a 1 M HEPES, pH 7.0, stock solution were brought to 25° C. and the three stock solutions were mixed (PEG reagent added last) to give final concentrations of 2.0 mg/mLPG-1, 50 mM HEPES and a 5-fold molar excess of PEG-diButyrAldehyde-5K over PG-1, After 15 minute reaction, a 20-fold molar excess of NaBH$_3$CN over PEG was added and the reaction was allowed to continue for an additional 16 hours at 25° C. After 16 hr, 15 min total reaction time, the reaction was quenched with 100 mM glycine in 100 mM HCl (10 mM final glycine concentration) for 1 hour, after which glacial acetic acid was added to a final concentration of 5% (v/v).

The PEGylated conjugate was purified from the reaction mixture by reversed phase chromatography using a column packed with CG71S media (Rohm Haas) on an AKTA Explorer 100 system (GE Healthcare). Buffer A was 5% acetic acid/95% H$_2$O (v/v), and Buffer B was 5% acetic acid/95% acetonitrile (v/v). The AKTA Explorer plumbing system and the CG71S column were sanitized with 1 M HCl and 1 M NaOH and the resin was equilibrated with 10 column volumes Buffer A prior to sample loading. After loading, the column was washed with 6 CV of 80% Buffer A/20% Buffer B and the PEGylated and nonPEGylated peptides were eluted using a linear gradient from 80% A/20% B to 0% A/100% B over 15 column volume with a linear flow rate of 90 cm/hour.

Fractions collected during CG71S reversed phase chromatography were analyzed using analytical reversed-phase HPLC. The mobile phases were: A, 0.1% TFA in water, and B, 0.05% TFA in acetonitrile. A Waters Symmetry C18 column (4.6 mm×75 mm) was used with a flow rate of 1.0 ml/min and a column temperature of 50° C. Detection was carried out at 280 nm. The column was equilibrated in 20% B and conjugate separation was achieved using the gradient timetable shown in Table PRO4.1.

| Step | Time (min) | % Mobile phase B |
|---|---|---|
| 1 | 0.00 | 20.0 |
| 2 | 2.00 | 30.0 |
| 3 | 5.00 | 45.0 |
| 4 | 6.00 | 45.0 |
| 5 | 18.00 | 80.0 |
| 6 | 18.10 | 100.0 |
| 7 | 20.10 | 100.0 |
| 8 | 20.20 | 10.0 |

Figure 77:
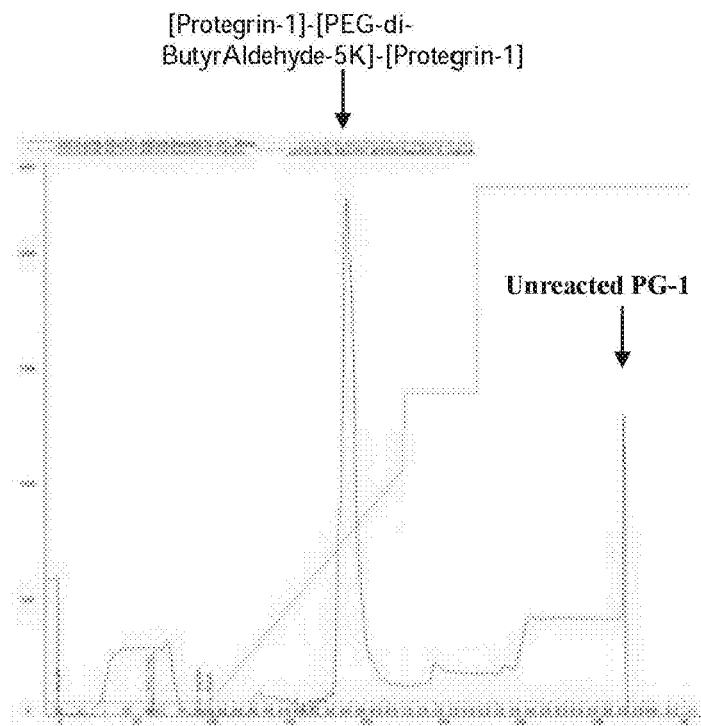
FIG. 77 Typical reversed phase purification profile of [Protegrin-1]-[PEG-di-ButyrAldehyde-5K]-[Protegrin-1].
Figure 78:
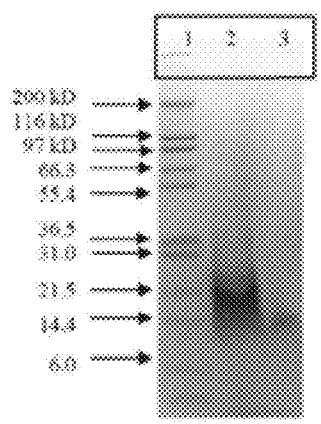
FIG. 78. SDS-PAGE of purified [Protegrin-1]-[PEG-di-butyraldehyde-5K]-[Protegrin-1].
Figure 79:
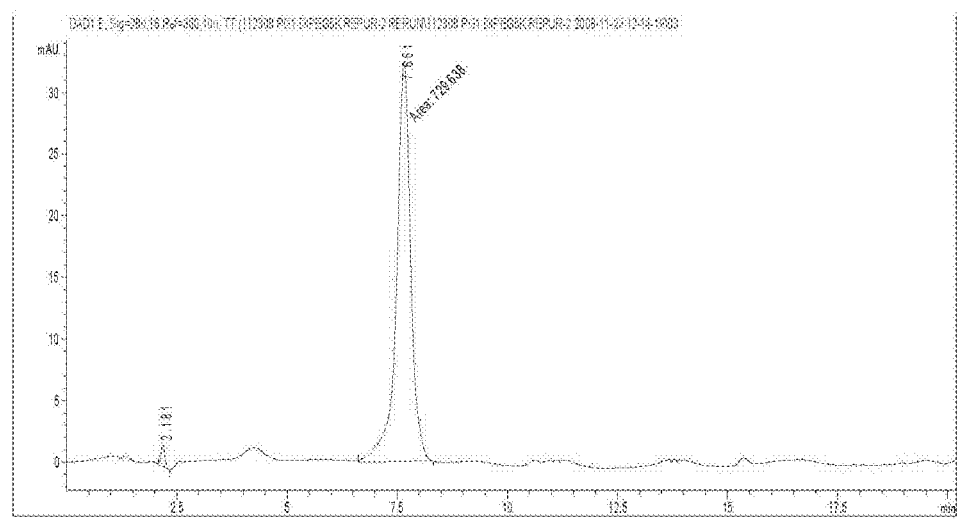
FIG. 79. Purity analysis of [Protegrin-1]-[PEG-di-butyraldehyde-5K]-[Protegrin-1] by reversed phase HPLC.
Figure 80:
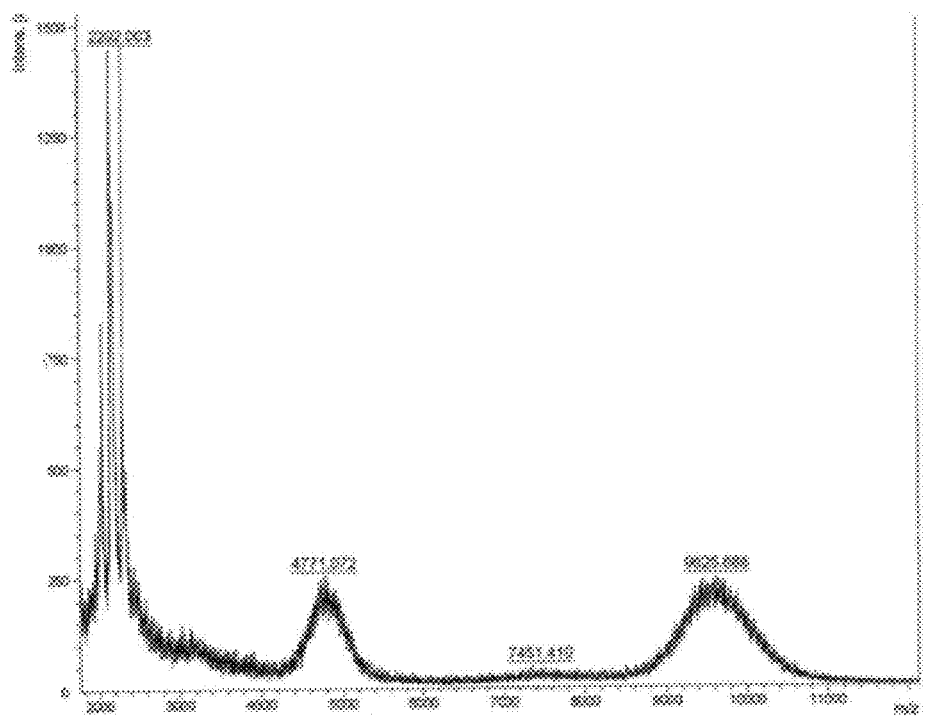
FIG. 80. MALDI-TOF spectrum of [Protegrin-1]-[PEG-di-butyraldehyde-5K]-[Protegrin-1].

Fractions containing pure [Protegrin-1]-[PEG-di-ButyrAldehyde-5K]-[Protegrin-1] as determined by RP-HPLC were pooled, lyophilized and stored at −80° C. A typical reverse phase CG71S chromatogram is shown in FIG. 77. SDS-PAGE analysis of purified [Protegrin-1]-[PEG-di-ButyAldehyde-5K]-[Protegrin-1] is shown in FIG. 78. RP-HPLC analysis of the purified conjugate is shown in FIG. 79, and MALDI-TOF analysis of the purified conjugate is shown in FIG. 80.

The purity of the [Protegrin-1]-[PEG-di-ButyrAldehyde-5K]-[Protegrin-1] conjugate was >95% by SDS-PAGE analysis and 98.7% by RP-HPLC analysis. The mass as determined by MALDI-TOF was within the expected range.

FIG. 77 Typical reversed phase purification profile of [Protegrin-1]-[PEG-di-ButyrAldehyde-5K]-[Protegrin-1]. The conjugate and unreacted peptide are indicated. The blue line represents absorbance at 280 nm.

FIG. 78. SDS-PAGE (12% NuPage Bis-Tris, Invitrogen, with Coomassie Blue staining) of purified [Protegrin-1]-[PEG-di-butyraldehyde-5K]-[Protegrin-1]. Lane 1, Mark12 MW markers; Lane 2, 17 uG of purified [Protegrin-1]-[PEG-di-butyraldehyde-5K]-[Protegrin-1], and Lane 3, 4 uG of purified [Protegrin-1]-[PEG-butyraldehyde-5K]-[Protegrin-1]. The conjugate in Lane 2 migrates with a higher apparent molecular weight than the conjugate in Lane 3, which may be a result of conjugate oligomer formation at higher concentrations. Impurities were not detected (Lane 3).

FIG. 79. Purity analysis of [Protegrin-1]-[PEG-di-butyraldehyde-5K]-[Protegrin-1] by reversed phase HPLC. The purity of the purified conjugate is determined to be 98.7% at 280 nm. The peaks at 2.2 and 4.5 min are column or solvent derived species and are not included in the sample.

FIG. 80. MALDI-TOF spectrum of [Protegrin-1]-[PEG-di-butyraldehyde-5K]-[Protegrin-1]. The peak at 9.6 kDa is within the expected range for the molecular weight of the conjugate. The peak at 4.8 kDa may represent the molecular weight of the doubly charged conjugate, and the peak at 7.5 kDa may represent a conjugate containing a single peptide. The peaks at 2292 Da and 2147 Da are due to an instrument filter effect.

Example PRO5

Conjugation of Protegrin-1 with Dextran Tetra Ethylene Glycol-Butyraldehyde 40K

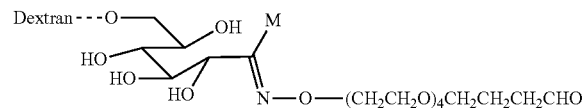

Stock solutions of 0.3 mg/mL protegrin-1 and 55 mg/mL dextran tetra ethylene glycol (TEG)-butyraldehyde 40K, both in 50 mM HEPES, pH 7.0, were prepared. To initiate a reaction, both stock solutions were brought to 25° C. and then mixed in equal volumes. The reaction mixture was stirred at 25° C. After 1 hour reaction, 100 µM sodium cyanoborohydride (final concentration) was added and the reaction was allowed to proceed for an additional 4 hours.

The dextran-protegrin-1 conjugate was purified from the reaction mixture by cation-exchange chromatography using CM Sepharose (GE Healthcare). Upon completion of the conjugation reaction, the reaction mixture was diluted 10-fold with water and loaded onto a column packed with CM Sepharose resin. Buffer A was 10 mM HEPES, pH 7, and buffer B was 10 mM HEPES, pH 7, 1M NaCl. The resin was washed with buffer B and equilibrated with buffer A prior to sample loading. After loading, the column was washed with 2 column volumes buffer A. Conjugated and nonconjugated peptides were eluted in a linear gradient of 0-100% buffer B in 10 column volumes at a flow rate of 7 mL/min (FIG. 1).

Figure 81:
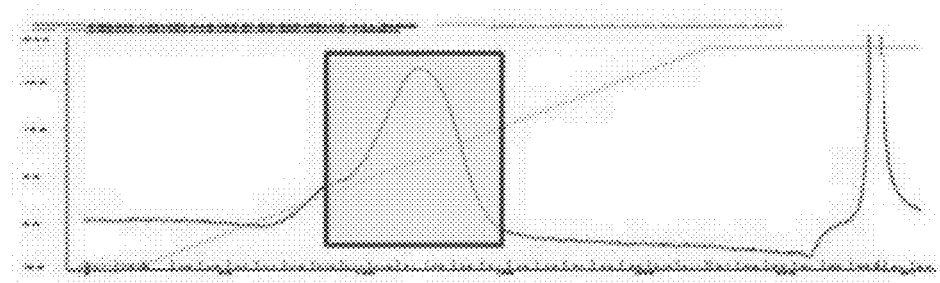
FIG. 81. Typical cation-exchange chromatography profile of dextran-butryaldehyde-40K-protegrin-1.

FIG. 81. Typical cation-exchange chromatography profile of dextran-butyraldehyde-40K-protegrin-1. Fractions containing the conjugate are indicated in the box. The line represents absorbance at 280 nm. Fractions containing dextran-butyraldehyde-40K-protegrin-1 were pooled, dialyzed against water, lyophilized and stored at −80° C.

Figure 82:
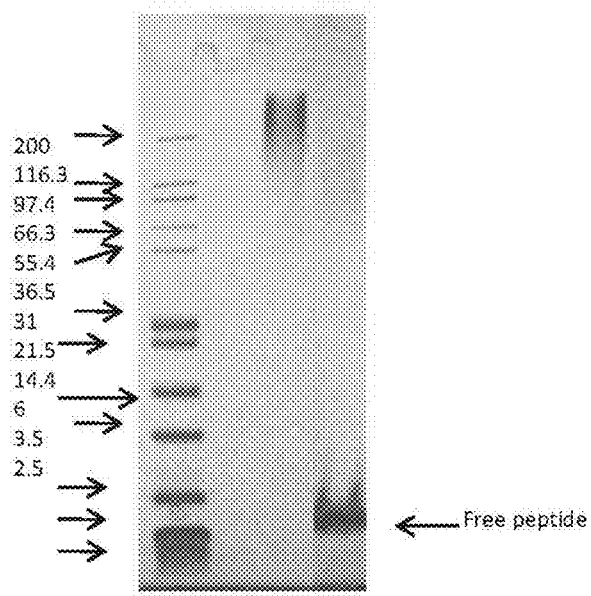
FIG. 82. SDS-PAGE analysis (4-12% gel) of purified dextran-butryraldehyde-40K-protegrin-1.

FIG. 82. SDS-PAGE analysis (4-12% gel) of purified dextran-butyraldehyde-40K-protegrin-1. Dextran perturbs the gel migration of the dextran-peptide conjugate and the conjugate's band location is not indicative of its size. The marker (M) molecular weight unit is kDa.

Example PRO6

The conjugation reaction took place in an aqueous environment. 45.5 mg PG-1 was first dissolved into 9.1 mL PBS buffer to make a 5 mg/mL stock solution. 100 mg $(ALD)_2 2K$ was then dissolved into 1 mL PBS to make a 100 mg/mL stock solution. To initiate the conjugation, 0.867 mL $(ALD)_2 2K$ stock solution was slowly mixed into 9.7 mL PG-1 stock solution drop by drop under rapid stirring. 135 µl of 50 mg/mL sodium cyanoborohydride ($BaBH_3CN$) was added into the reaction mixture 30 min later to facilitate the stable secondary amine linkage formation through reductive amination. The $BaBH_3CN$ to $(ALD)_2 2K$ molar ratio was set at 5 with $BaBH_3CN$ in excess. The final net $(ALD)_2 2K$ (93% substitution) to PG-1 molar ratio was at 2 with $(ALD)_2 2K$ in excess. The formation of PG-1-ButyrALD-2K-PG-1 was confirmed by analytical RP-HPLC (Table PRO6.1).

Table PRO6.1: Analytical RP-HPLC method used to monitor PG-1-ButyrALD-2K-PG-1 production. Column: Waters Xbridge C18 5 µm 4.6×160 mm. Mobile Phase A: 0.1% $TFA/H_2O$ and B: 0.1% $TFA/CH_3CN$. Column temperature: 40° C. $UV_{280nm}$ was used to follow the elution.

| TIME (min) | % Mobile phase B | Flow rate (mL/min) |
|---|---|---|
| 0.0 | 10 | 1.0 |
| 5 | 20 | 1.0 |
| 24 | 70 | 1.0 |
| 25 | 10 | 1.0 |

The $(PG-1)-(ALD)_2 2K-(PG-1)$ was purified by weak cation exchange chromatography using an AKTA Basic System. The reaction mixture was first diluted 5 fold with buffer A [20 mM acetate, pH 4.0] to reduce sample viscosity. The pH of the diluted sample was measured to be 4.0 and the conductivity to be 4.8 mS/cm. The diluted sample mixture was loaded onto a CM Sepharose FF column at 5 mL/min. After sample loading, the column was washed with 2CV 20% buffer B [20 mM acetate, 2 M NaCl, pH 4.0]. The loading and washing steps were done manually. The resin was washed until a flat $UV_{280nm}$ absorption line was observed. A linear gradient elution was applied next from 20% to 60% buffer B within 10 CV. The flow rate was held constant at 5 ml/min during the whole process. The chromatogram of the elution step is shown in FIG. 83.

Figure 83:
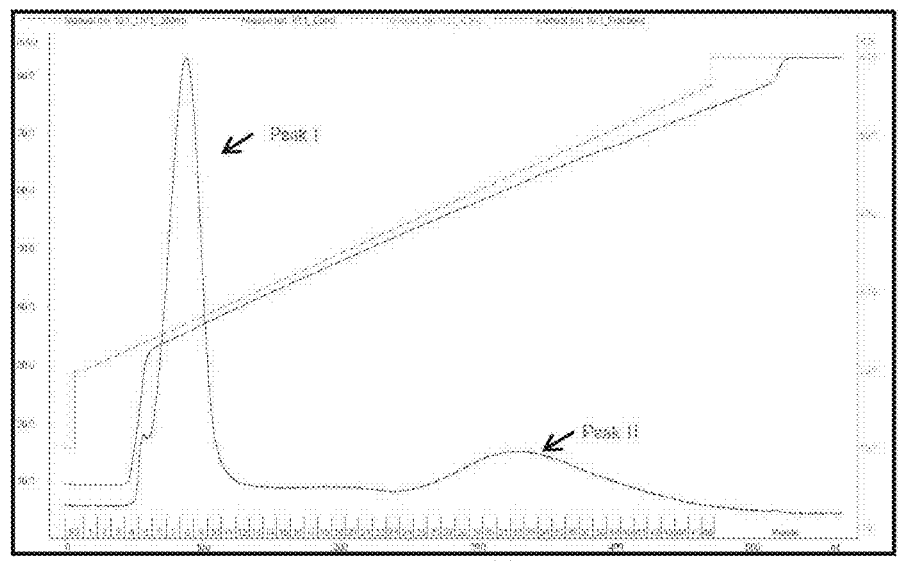
FIG. 83: PG-1 and (ALD)$_2$2K conjugates purification with CM Sepharose FF resin.

FIG. 83: PG-1 and $(ALD)_2 2K$ conjugates purification with CM Sepharose FF resin. The $UV_{280nm}$ absorption curve is shown in blue and buffer B percentage is shown in green. The conductivity is shown in gray. Peak I contains mono-conjugate and peak II contains the desired di-conjugate.

The peak I and II fractions were analyzed by RP-HPLC (Table PRO6.1). The desired product was found in peak II. Based on their high purities, peak II fractions 18 to 33 were pooled. The 210 mL purified $(PG-1)-(ALD)_2 2K-(PG-1)$ fraction pool was first centrifuged with a MWCO 10,000 Centricon to a final volume of 20 mL. The NaCl concentration was then lowered to less than 50 mM by dilution with 20 mM acetate, pH 4.0 buffer (final conductivity 3.8 mS/cm). The volume was reduced to less than 10 mL with a second centrifugation using a MWCO 10,000 Centricon.

The net peptide concentration in the concentrated (PG-1)-$(ALD)_2 2K$-(PG-1) sample was measured to be 0.88 mg/mL by BCA. The conjugate's purity was determined at 96.2% by RP-HPLC. The number-average molecular weight

Figure 84:
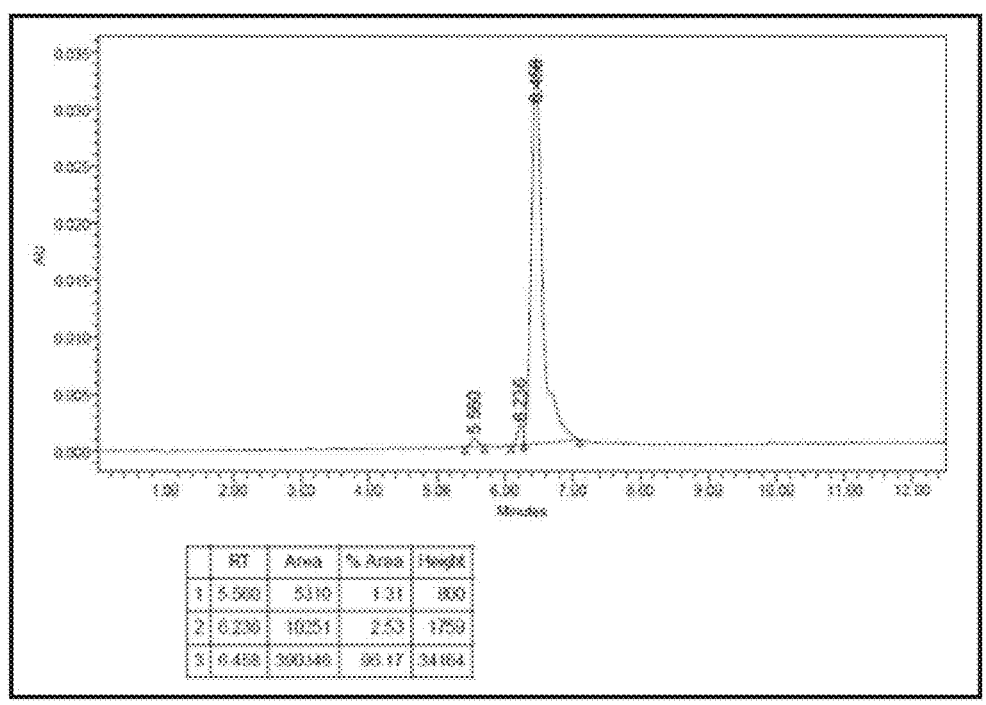
FIG. 84: RP-HPLC analysis of (PG-1)-(ALD)$_2$2K-(PG-1).
Figure 85:
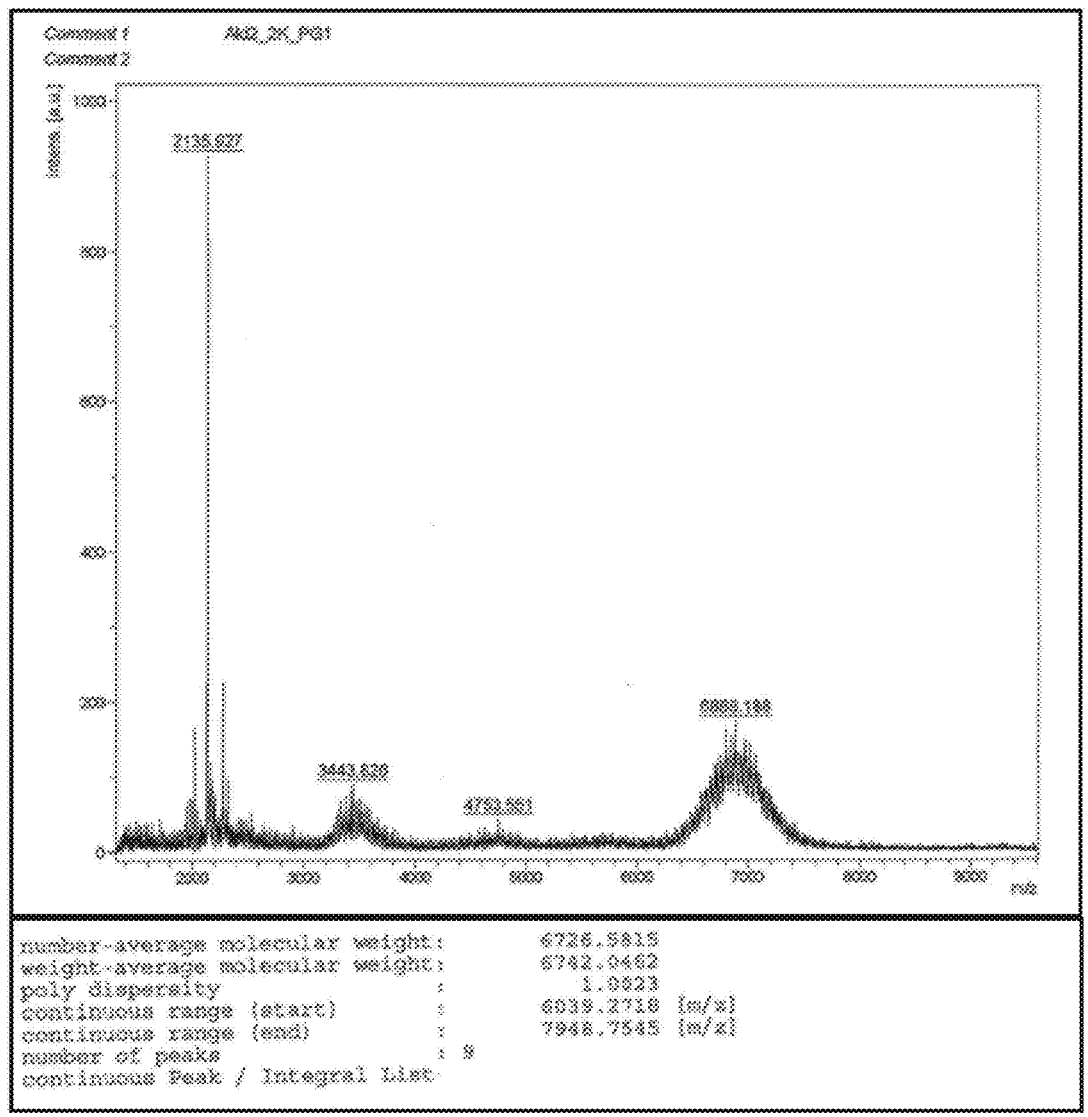
FIG. 85: MALDI analysis of (PG-1)-(ALD)$_2$2K-(PG-1).

was calculated to be 6888.2 Da by MALDI-TOF which is the expected mass of the di-conjugate. A final yield of 6.6 mg purified (PG-1)-(ALD)$_2$K-(PG-1) was obtained. FIG. 84: RP-HPLC analysis of (PG-1)-(ALD)$_2$K-(PG-1) FIG. 85: MALDI analysis of (PG-1)-(ALD)$_2$K-(PG-1). The 4753.6 Da peak might be the residual mono-conjugate contaminant. The 2136 Da peak represents the free peptide. The peak areas do not correspond to the relative amounts of the species in the sample.

Example PRO7

PEGylation of Protegrin-1 with mPEG2-Butaraldehyde-40K

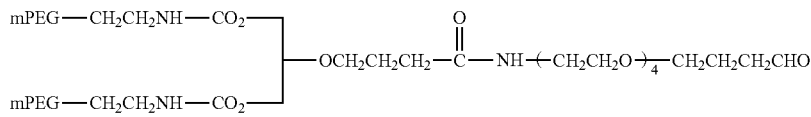

The conjugation reaction took place in an aqueous environment. 12 mg protegrin-1 (PG-1) was first dissolved into 1.2 mL PBS buffer to make a 10 mg/mL stock solution. 1500 mg ALD-40K was dissolved into 15 mL 2 mM HCl to make a 100 mg/mL stock solution. To initiate the conjugation, 11.4 mL ALD-40K stock solution was slowly mixed into 1.2 mL PG-1 stock solution drop by drop under rapid stirring. 360 µL of 50 mg/mL sodium cyanoborohydride (BaBH$_3$CN) was added into the reaction mixture immediately following PEG addition to facilitate the stable secondary amine linkage formation through reductive amination. The BaBH$_3$CN to ALD-40K molar ration was 10 with BaBH$_3$CN in excess. The net ALD-40K (99.5% purity) to PG-1 molar ratio was 5 with ALD-40K in excess. The reaction was allowed to proceed for 46 h at 22° C. for completion. The formation of ALD40K-PG-1 was confirmed by analytical RP-HPLC using the method described in Table PRO7.1.

Table PRO7.2: Analytical RP-HPLC method used to monitor ALD40K-PG-1 production. Column: Waters Xbridge C18 5 µm 4.6×160 mm. Mobile Phase A: 0.1% TFA/H$_2$O and B: 0.1% TFA/CH$_3$CN. Column temperature: 40° C. UV$_{280nm}$ was used to follow the elution.

| TIME (min) | % Mobile phase B | Flow rate (mL/min) |
|---|---|---|
| 0.0 | 10 | 1.0 |
| 5 | 20 | 1.0 |
| 24 | 70 | 1.0 |
| 25 | 10 | 1.0 |

The ALD40K-PG-1 was purified by SP Sepharose HP resin using an AKTA Basic System. The reaction mixture was first diluted 5 fold with buffer A [20 mM MES, pH 6.0] to reduce sample viscosity. The pH of the diluted sample was measured to be 6.0 and the conductivity to be 5.2 mS/cm. The diluted sample mixture was loaded onto an SP Sepharose HP column at 5 mL/min. After sample loading, the column was washed with 100% buffer A. The column was then sequentially washed with a six step gradient (50, 100, 150, 200, 250 and 300 mM NaCl in 20 mM MES, pH 6.0 buffer]. Each wash step was controlled manually and was started only when the UV$_{280nm}$ absorbance was completely flat from the previous wash. The flow rate was constant at 5 ml/min during the whole process. The ALD40K-PG-1, peak II, was eluted at 300 mM NaCl. The chromatogram of the loading and elution is shown in FIG. PRO7.1.

Figure 86:
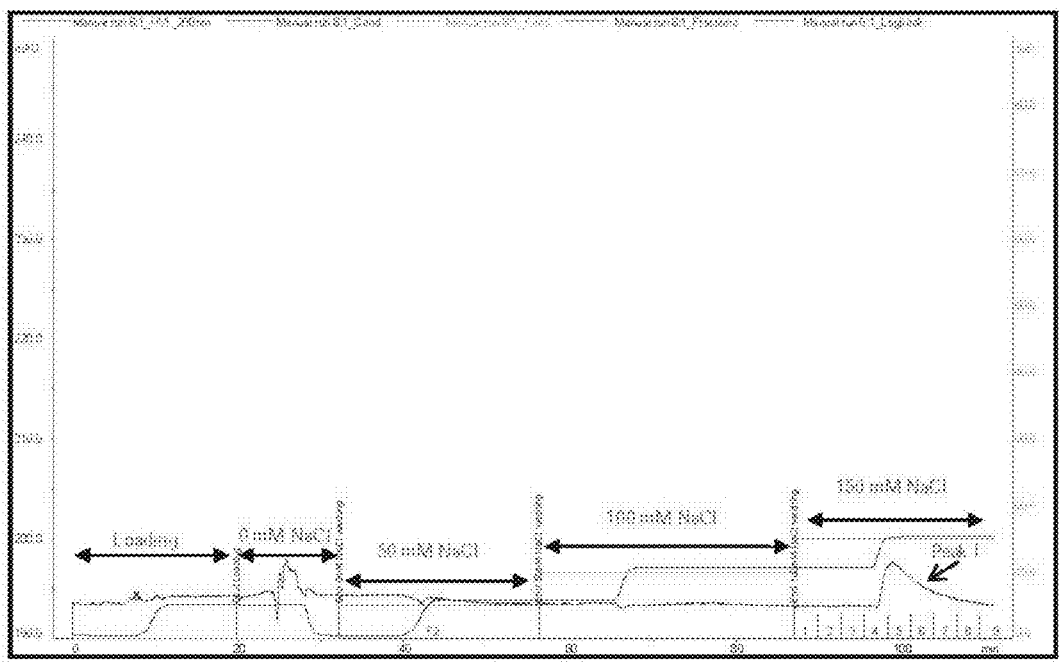
FIGS. 86 and 87: ALD40K-PG-1 purification with SP Sepharose HP resin.
Figure 87:
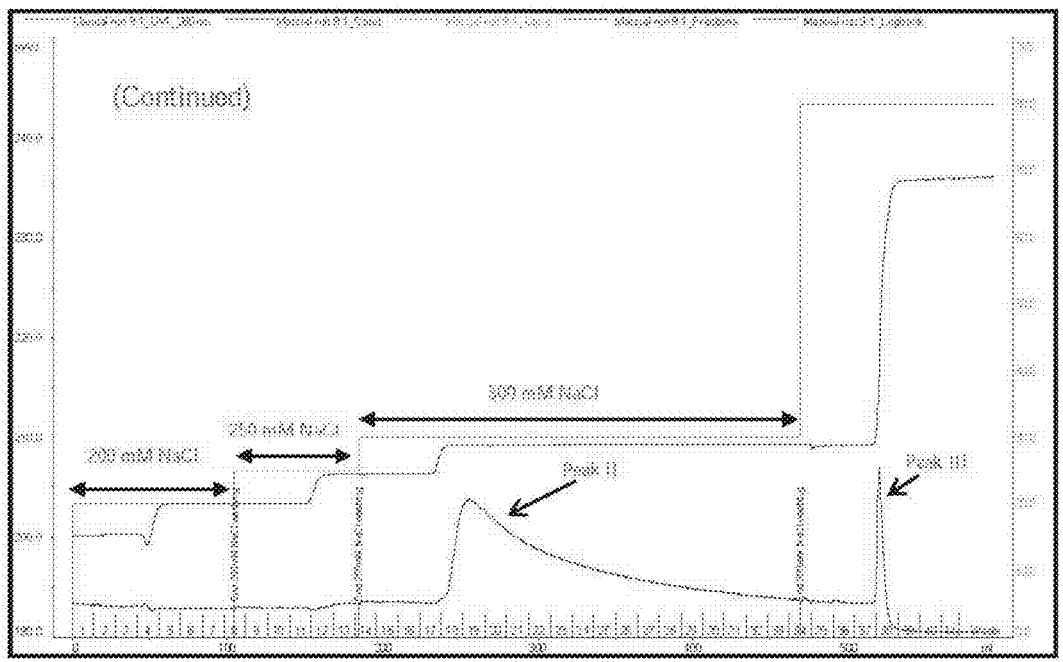

FIGS. 86 and 87: ALD40K-PG-1 purification with SP Sepharose HP resin. The UV$_{280nm}$ absorption curve is shown and buffer B percentage is shown. The conductivity is shown. The NaCl concentration in washing and eluting steps are labeled. The ALD40K-PG-1, peak II, was eluted at 300 mM NaCl.

Figure 88:
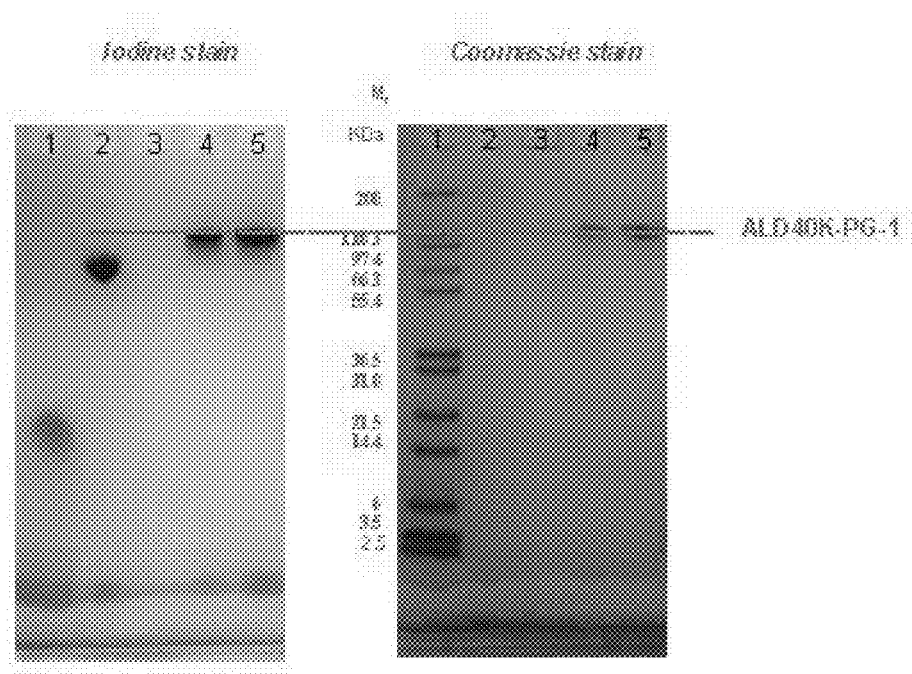
FIG. 88. SDS-PAGE of the purified and concentrated ALD40K-PG-1.

The eluted peaks were analyzed by analytical RP-HPLC (Table PRO7.1) and SDS-PAGE (FIG. 88). The desired product, ALD40K-PG-1, was eluted in peak II. Based on their high purities, peak II fractions 18 to 33 were pooled.

Figure 89:
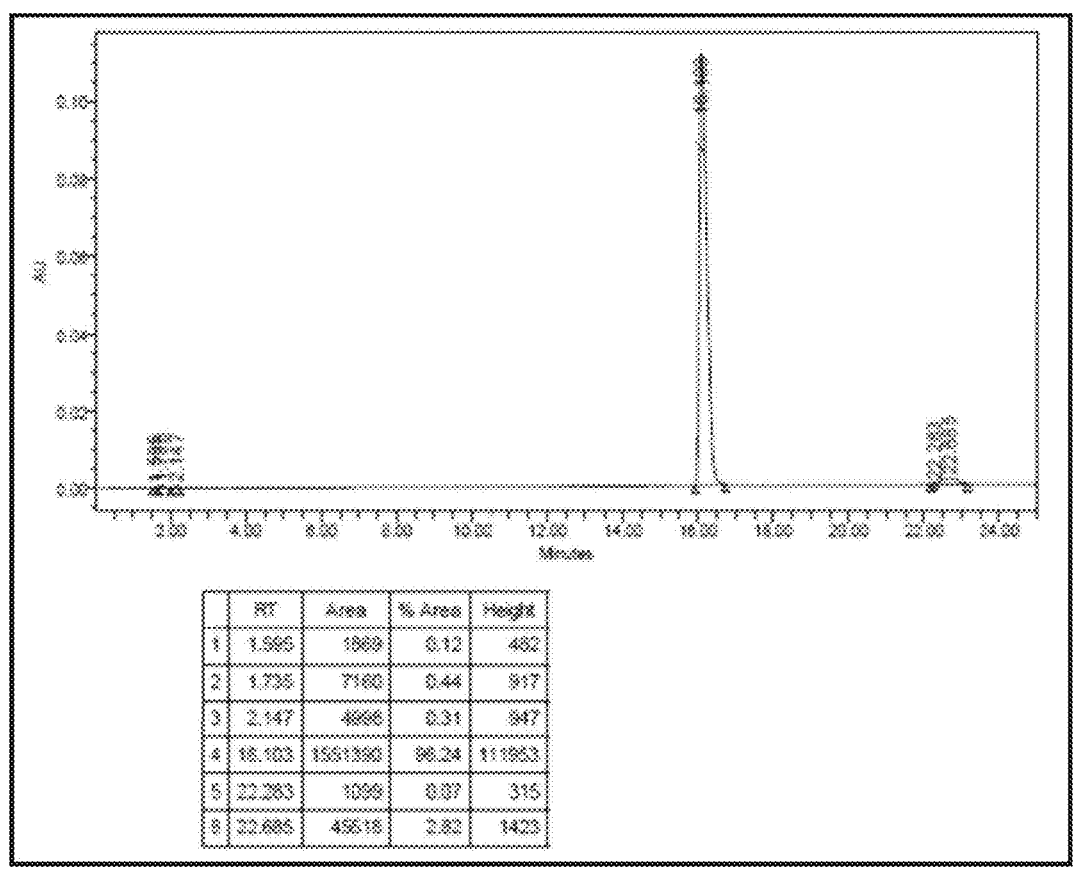
FIG. 89: RP-HPLC analysis of ALD40K-PG-1 (lot #YW-pgALD40K-01).
Figure 90:
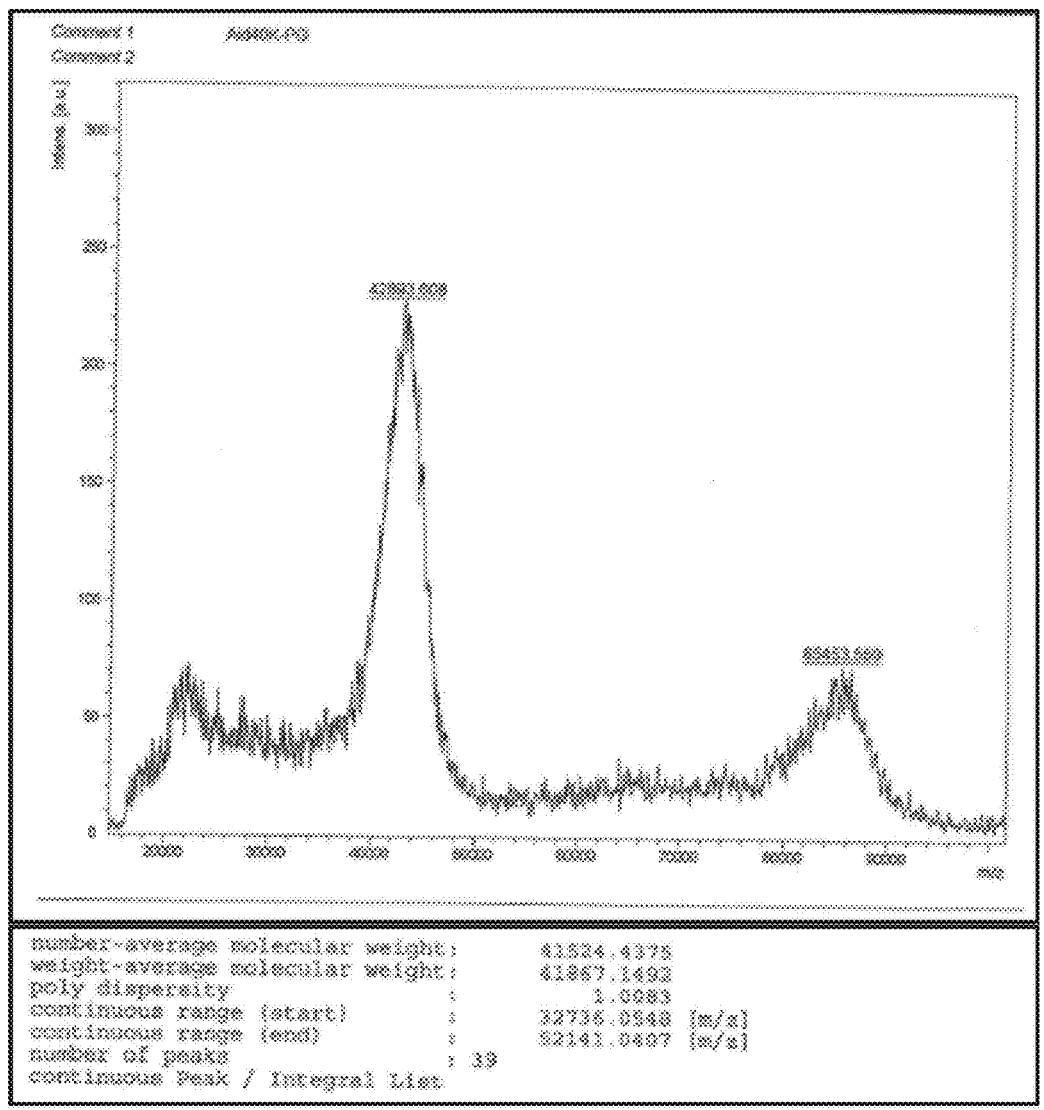
FIG. 90: MALDI analysis of ALD40K-PG-1 (lot #YW-pgALD40K-01).

The purified ALD40K-PG-1 pool was concentrated with a MWCO 10,000 Centricon. The final NaCl concentration was also lowered to 150 mM with 20 mM MES, pH 6.0 buffer dilution. SDS-PAGE of the purified and concentrated ALD40K-PG-1 is shown in FIG. 88. The net peptide concentration in the final ALD40K-PG-1 preparation was measured to be 0.8 mg/mL by BCA. The purity was determined at 96.2% by RP-HPLC (Table PRO7.1 and FIG. 89). The number-average molecular weight was calculated to be 41524 Da by MALDI-TOF, which corresponds to the expected mass of the conjugate (FIG. 90). A final yield of 7.6 mg purified ALD40K-PG-1 was obtained. FIG. 89: RP-HPLC analysis of ALD40K-PG-1 (lot #YW-pgALD40K-01). FIG. 90: MALDI analysis of ALD40K-PG-1 (lot #YW-pgALD40K-01). The ~85 KDa peak is believed to represent the ALD40K-PG-1 conjugate dimer formed as an artifact during MALDI analysis. The dimer is not detected by SDS-PAGE.

Example PRO8

[Mono]-[4,7-CG-PEG2-FMOC-NHS-40K]-[Protegrin-1]-175 PEGylation of Protegrin-1 with 4,7-CG-PEG2-FMOC-NHS-40K

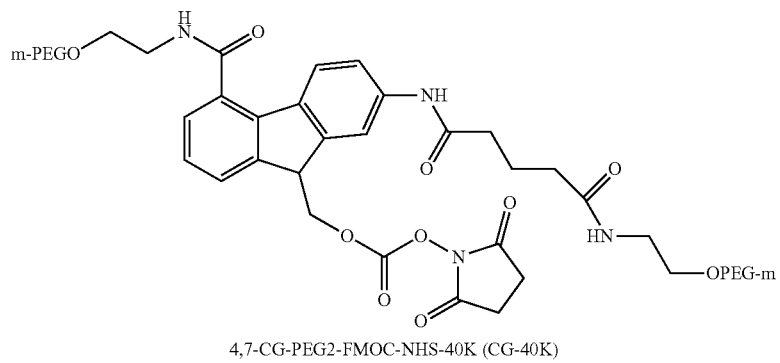

4,7-CG-PEG2-FMOC-NHS-40K (CG-40K)

The conjugation reaction took place in an aqueous environment. 12 mg protegrin-1 (PG-1) was first dissolved into 1.2 mL PBS buffer to make a 10 mg/mL stock solution. 550 mg CG-40K was dissolved into 5.5 mL 2 mM HCl to make a 100 mg/mL stock solution. To initiate the conjugation, 5.0 mL CG-40K stock solution was slowly mixed into 1.2 mL PG-1 stock solution drop by drop under rapid stirring. 5.0 mL 10×PBS buffer was added into the reaction mixture to maintain a relatively neutral pH during the reaction (measured at 6.8). The net active CG-40K (95% purity, 77.8% substitution percentage) to PG-1 molar ratio was 1.7 with CG-40K in excess. The reaction was allowed to proceed for 330 min at 22° C. and 12 h at 4° C. for completion. The formation of CG40K-PG was confirmed by analytical RP-HPLC (Table 1).

Table PRO8.3: Analytical RP-HPLC method used to monitor CG40K-PG production. Column: Waters Xbridge C18 5 µm 4.6×160 mm. Mobile Phase A: 0.1% TFA/H$_2$O and B: 0.1% TFA/CH$_3$CN. Column temperature: 40° C. UV$_{280nm}$ was used to follow the elution.

| TIME (min) | % Mobile phase B | Flow rate (mL/min) |
|---|---|---|
| 0.0 | 10 | 1.0 |
| 5 | 20 | 1.0 |
| 24 | 70 | 1.0 |
| 25 | 10 | 1.0 |

The CG40K-PG-1 was purified by SP Sepharose HP resin using an AKTA Basic System. The reaction mixture was first diluted 5 fold with buffer A [20 mM acetate, pH 4.0] to reduce sample viscosity. The diluted sample mixture was loaded onto an SP HP column at 5 mL/min. After sample loading, the column was washed with 100% buffer A until the UV$_{280nm}$ absorbance was flat. The conjugate was then eluted with a linear gradient of 0 to 80% buffer B [20 mM acetate, 1 M NaCl, pH 4.0] within 10 CV. The flow rate was constant at 5 ml/min during the whole process. The chromatogram of the loading and elution is shown in FIG. 91.

Figure 91:
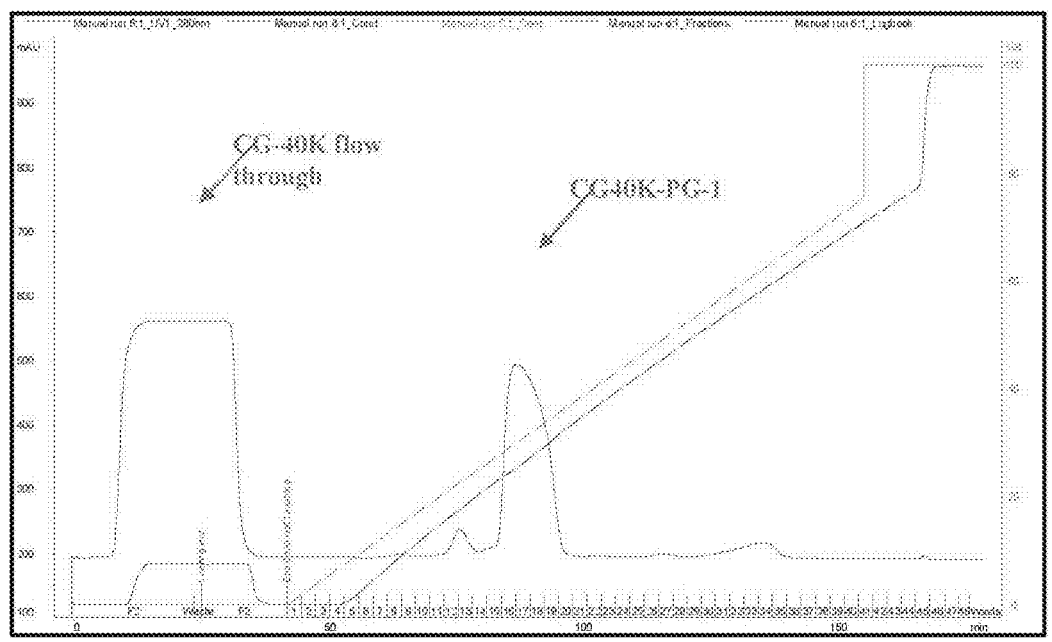
FIG. 91: CG40K-PG-1 purification with SP Sepharose HP resin.

FIG. 91: CG40K-PG-1 purification with SP Sepharose HP resin. The UV$_{280nm}$ absorption curve is shown in blue and buffer B percentage is shown in green. The conductivity is shown in gray.

The CG40K-PG-1 fractions were analyzed by analytical RP-HPLC (Table PRO8.1). Based on their high purities, fractions 16 to 19 were pooled. The purified CG40K-PG-1 pool was concentrated with a MWCO 10,000 Centricon. The final NaCl concentration was also lowered to 150 mM with 20 mM acetate, pH 4.0 buffer dilution.

The net peptide concentration in the final CG40K-PG-1 preparation was measured to be 1.33 mg/mL by BCA. The purity was determined at 99.8% by RP-HPLC (Table PRO8.1 and FIG. 92). The number-average molecular weight was calculated to be 44033 Da by MALDI-TOF (FIG. 93). A final yield of 11.97 mg purified CG40K-PG-1 was obtained.

Figure 92:
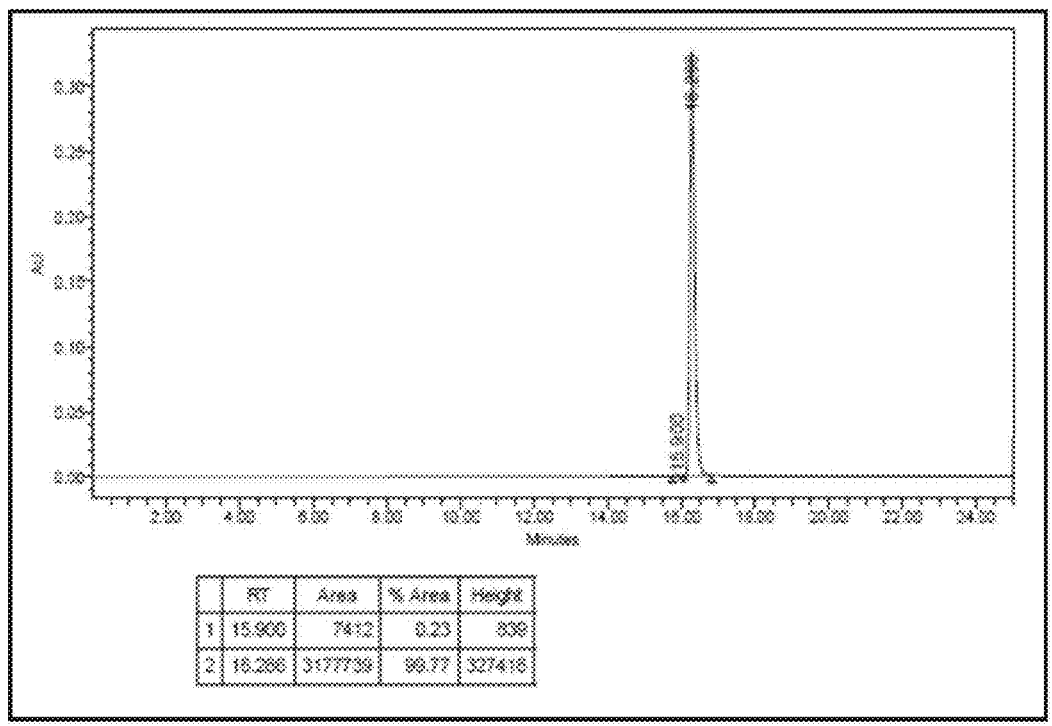
FIG. 92: RP-HPLC analysis of purified CG40K-PG-1.
Figure 93:
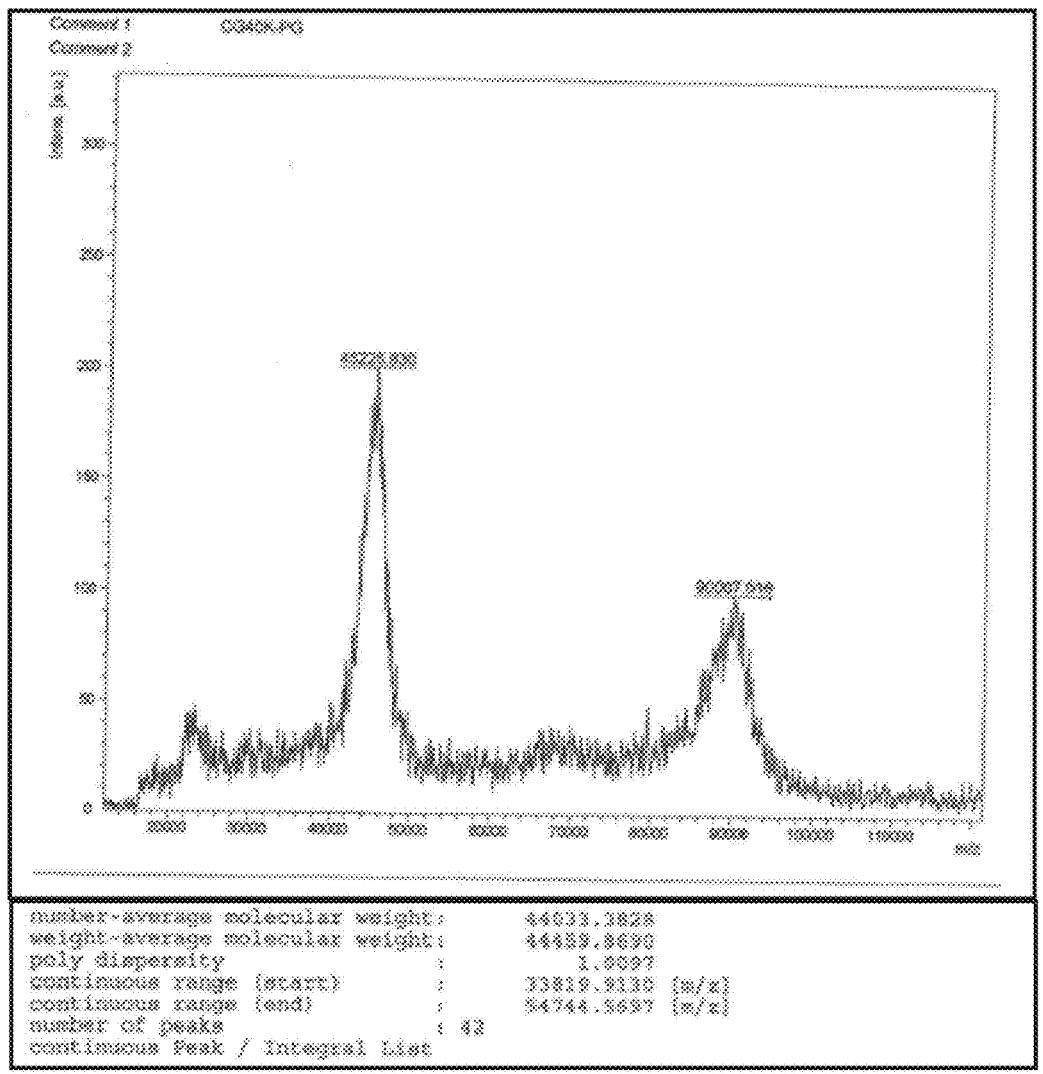
FIG. 93: MALDI-TOF analysis of purified CG40K-PG-1.

FIG. 92: RP-HPLC analysis of purified CG40K-PG-1. Analysis conditions are described in Table PRO8.1.

Figure 94:
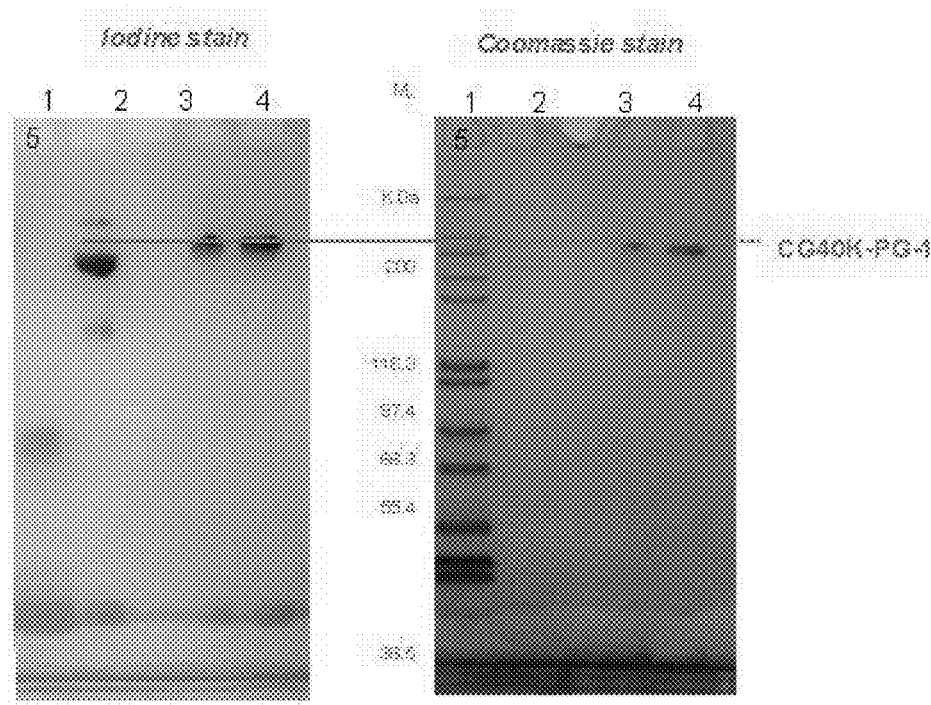
FIG. 94. SDS-PAGE of CG40K-PG-1.

FIG. 93: MALDI-TOF analysis of purified CG40K-PG-1. The ~90 KDa peak is believed to represent the CG40K-PG-1 conjugate dimer formed as an artifact during MALDI analysis. The dimer is not detected by SDS-PAGE (FIG. 94).

Example PRO9

Hemolysis assay. Approximately 10 mL of blood was drawn from one adult rat into Na Heparin tube and kept in ice until use. Red blood cells were washed three times with 10 mL of cold DPBS ((−) CaCl$_2$ and (−) MgCl$_2$) and collected by sequential centrifugation at 3,000 g for 5 min at 4° C. Pellets of red blood cells were resuspended with DPBS ((−) CaCl$_2$ and (−) MgCl$_2$) and the total volume was brought up to initial volume of blood drawn. One mL of resuspended red blood cells was resuspended with 49 mL of DPBS ((−) CaCl$_2$ and (−) MgCl$_2$). Incubation mixture was prepared by 400 fold dilution of stock solution of test compounds with final volume of 800 µl. Final concentration of test compounds was equimolar to that of respective unconjugated compounds. Hemolysis incubation was done at 37° C. with mild agitation. For releasable conjugates, test compounds were preincubated in 1×PBS at 37° C. prior to hemolysis assay. Incubation mixture was centrifuged at 3,000 g for 5 min at 4° C., and the absorbance at 550 nm was read from supernatant. The percent of hemolysis was calculated relative to the 100% hemolysis produced by 0.25% Triton X-100.

| Compounds | Description | Note |
|---|---|---|
| PG1 | Protegrin 1 (PG1) | Samples were preincubated in 1XPBS at 37° C. prior to hemolysis assay. |
| CAC40K-40K-PG1 | PG1 conjugate with a releasable linker (release t$_{1/2}$ in 1XPBS at 37° C. = ~19.6 hr) | |
| CAC40K-fulvene | PEG moiety of CAC40K-PG1 | |
| PG1-ButyrALD-PG1 | PG1 conjugate with a stable linker | |
| Dextran-PG1 | PG1 conjugate with a stable linker | |
| 2 mM HCl | | Buffer control |
| Matrix control | | Matrix control |
| TritonX-100 | Detergent | Positive control |

Figure 95:
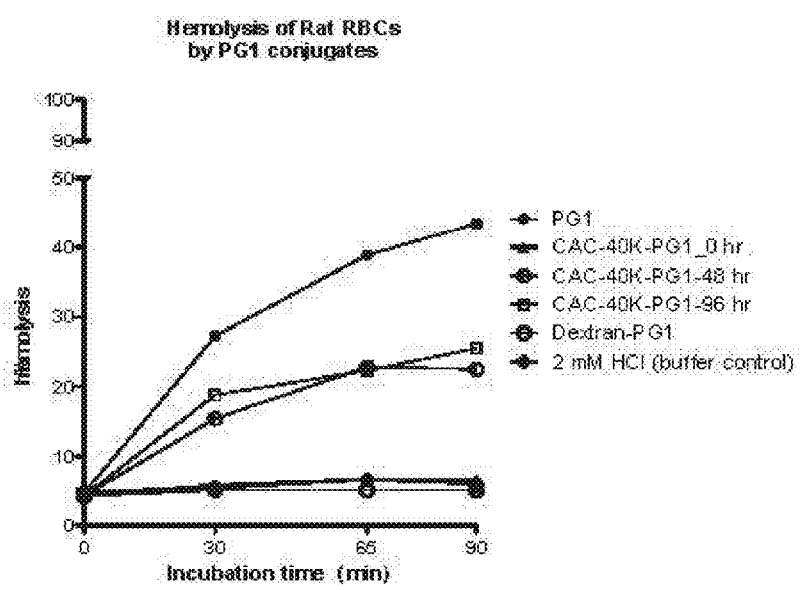
FIG. 95. Hemolysis relative to the 100% hemolysis produced by 0.25% Triton X-100.
Figure 96:
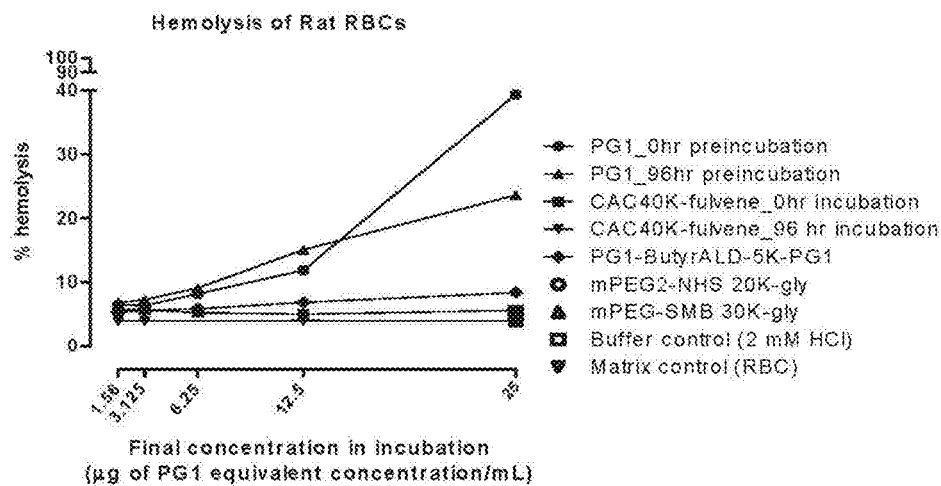
FIG. 96. Hemolysis by PEG reagent controls.
Figure 97:
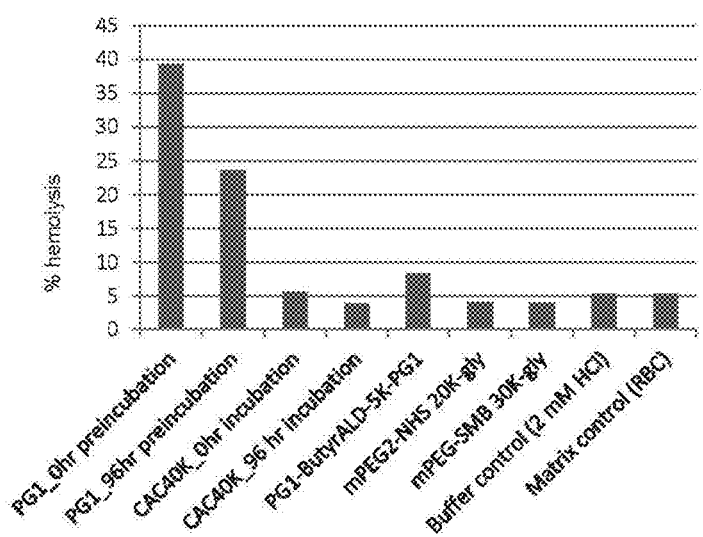
FIG. 97. Hemolysis at the maximum concentration.
Figure 98:
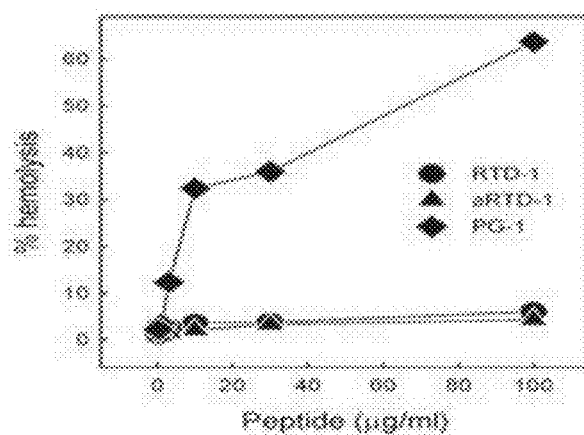
FIG. 98. Hemolytic activities of PG

For PG1, hemolytic effects were almost eliminated by PEG conjugation with a stable linker (PG1-ButyrALD-PG1, Dextran-PG1), (FIG. 95). Percent hemolysis of rat red blood cells by PG1 was comparable to literature data obtained from human red blood cell assay (FIG. 96). PG1-ButyrALD-5K-PG1 appeared to have little hemolytic activity. However, its hemolytic activity was significantly less than PG1. PG1 released from CAC-40K-PG1 exhibited hemolytic activity, however, hemolytic effects from CAC-40K-PG1 that had been preincubated for 96 hr (=5 times of its release t$_{1/2}$, ~19.6 hr) was 60-70% of that from PG1. This loss of activity appears to be mostly due to the degradation of PG1 during preincubation period since PG1 preincubated for 96 hr retained about 60% hemolytic activity compared to that from PG1 preincubated for 0 hr. PEG moiety itself (CAC40K-fulvene, mPEG2-NHS 20K-gly, and mPEG-SMB 30K-gly) did not cause hemolysis. FIG. 95. Hemolysis relative to the 100% hemolysis produced by 0.25% Triton X-100. FIG. 95. Hemolysis by PEG reagent controls. FIG. 97. Hemolysis at the maximum concentration FIG. 98. Hemolytic activities of PG-1: Human red blood cells were incubated with 0 to 100 µg/ml of PG-1 in PBS for 1 h at 37° C. (Tran D et al (2008) *Antimicrob. Agents Chemother* 52:944-953)

Example PRO10

Pharmacokinetic Studies of the Protegrin Conjugates

Twenty one (21) adult male Sprague-Dawley rats with indwelling jugular vein and carotid artery catheters (JVC/CAC) (Charles River Labs, Hollister, Calif.) were utilized for this study. The weight range of the animals was 313-346 grams. All animals were food fasted overnight. Prior to dosing the rats were weighed, the tails and cage cards were labeled for identification and the doses were calculated. Anesthesia was induced and maintained with 3.0-5.0% isoflurane. The JVC and CAC were externalized, flushed with HEP/saline (10 IU/mL HEP/mL saline), plugged, and labeled to identify the jugular vein and carotid artery the predose sample was collected from the JVC. When all of the animals had recovered from anesthesia and the predose samples were processed, the animals were dosed, intravenously (IV) via the JVC using a 1 mL syringe containing the appropriate test article, the dead volume of the catheter was flushed with 0.9% saline to ensure the animals received the correct dose.

Following a single IV dose, blood samples were collected at 0 (pre-dose collected as described above), 2, 10, 30, 60, 120, 240, 360 minutes for NKT-10503 (parent protegrin-1) group and 0 (pre-dose collected as described above), 2, 10, 30, 120, 240, 480, 1440 (24 hrs) minutes for the other groups via the carotid artery catheter and processed as stated in the protocol. Following the last collection point, the animals were euthanized. Bioanalytical analysis: analysis of the plasma samples was conducted using non-validated LC-MS/MS methods.

Pharmacokinetic Analyses: Noncompartmental PK data analysis and report preparation was completed. PK analysis was performed using WinNonlin (Version 5.2, Mountain View, Calif.-94014). Concentrations in plasma that were below LLOQ were replaced with zeros prior to generating Tables and PK analysis. The following PK parameters were estimated using plasma concentration-time profile of each animal:

| | |
|---|---|
| $C_0$ | Extrapolated concentration to time "zero" |
| $C_{max}$ | Maximum (peak) concentration |
| $AUC_{all}$ | Area under the concentration-time from zero to time of last concentration value |
| $T_{1/2(Z)}$ | Terminal elimination half-life |
| $AUC_{inf}$ | Area under the concentration-time from zero to time infinity |
| $T_{max}$ | Time to reach maximum or peak concentration following administration |
| CL | Total body clearance |
| $V_z$ | Volume of distribution based on terminal phase |
| $V_{ss}$ | Volume of distribution at steady state |
| $MRT_{last}$ | Mean residence time to last observable concentration |

Figure 99:
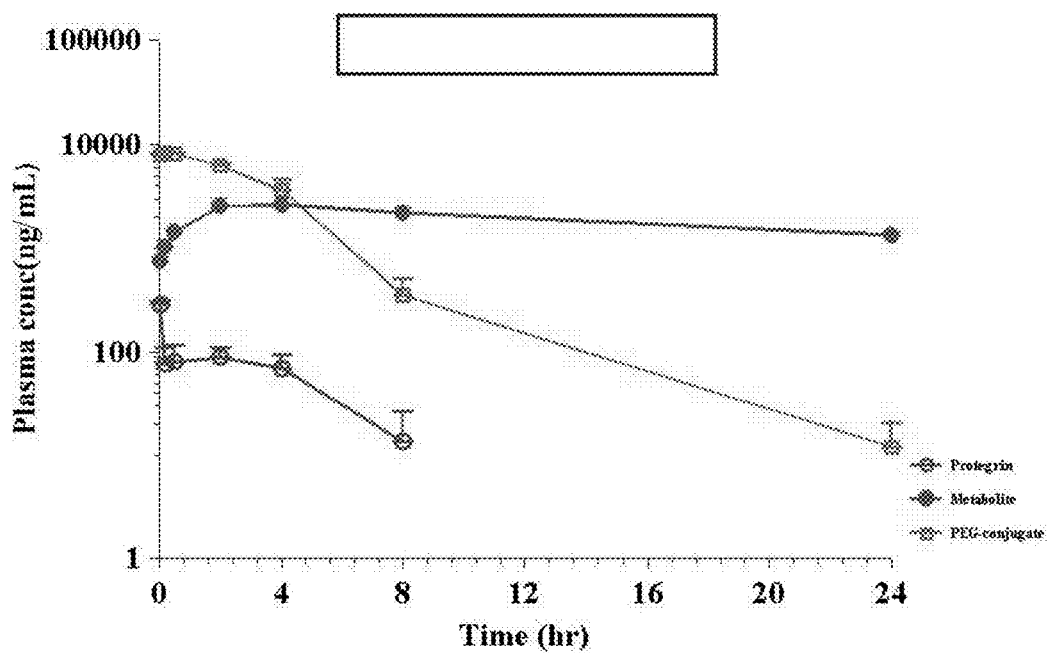
Figure 100:
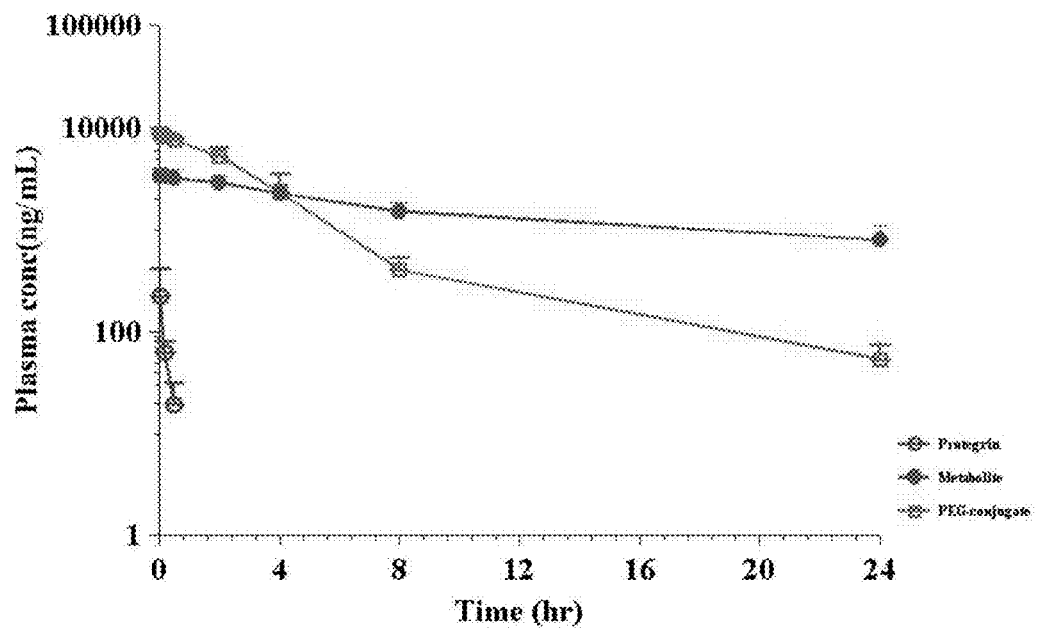
Figure 101:
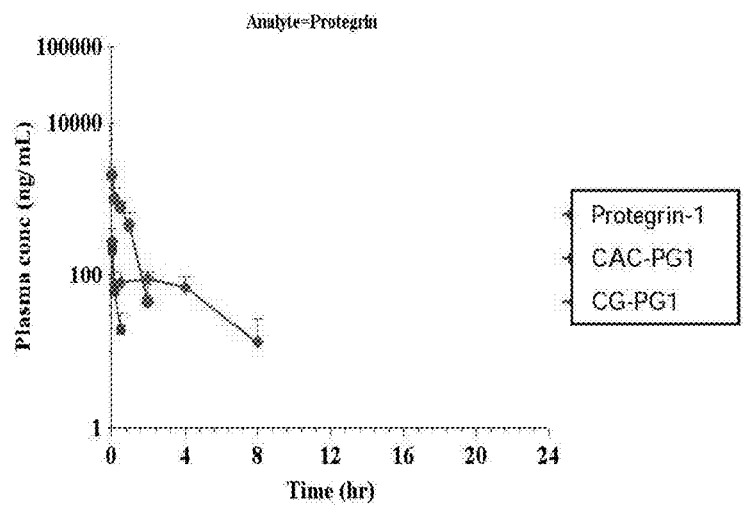
FIG. 101. shows the released Protegrin-1 levels after the administration of the two releasable PEG constructs versus the level of Protegrin-1 given as native protein at the same dose (mg/kg).

Releasable-PEG: FIG. 99 and 100 show the mean plasma concentration-time profiles for CG-PEG$_2$-FMOC-40K-PG-1 and CAC-PEG$_2$-FMOC-40K-PG-1, their corresponding PEG-metabolite and released Protegrin-1. FIG. 101 shows the released Protegrin-1 levels after the administration of the two releasable PEG constructs versus the level of Protegrin-1 given as native protein at the same dose (mg/kg). Table PRO10.1 summarizes the PK parameters of protegrin-1 following equivalent protein mass of 1.6 mg/kg administered intravenously into rats via, CG-PEG$_2$-FMOC-40K-PG-1, CAC-PEG$_2$-FMOC-40K-PG-1 or native protegrin-1.

TABLE PRO10.1

Comparative PK Parameters of Protegrin-1 and PEG conjugates

| Test Compound | $C_{max}$ (ng/mL) | $T_{1/2}$ (hr) | $AUC_{INF}$ (ng · hr/mL) | $T_{max}$ (hr) | $MRT_{last}$ (hr) |
|---|---|---|---|---|---|
| Protegrin-1 | 2050 ± 601 | 0.35 ± 0.10 | 1160 ± 351 | 0.03 | 0.52 ± 0.05 |
| CAC-PEG$_2$-FMOC-40K-PG-1 | 222 ± 189 | 0.13* | 31.0* | 0.03 | 0.13 ± 0.02 |
| CG-PEG$_2$-FMOC-40K-PG-1 | 285 ± 30.0 | 1.95* | 655* | 0.03 | 2.53 ± 0.60 |

*n-2

Figure 102:
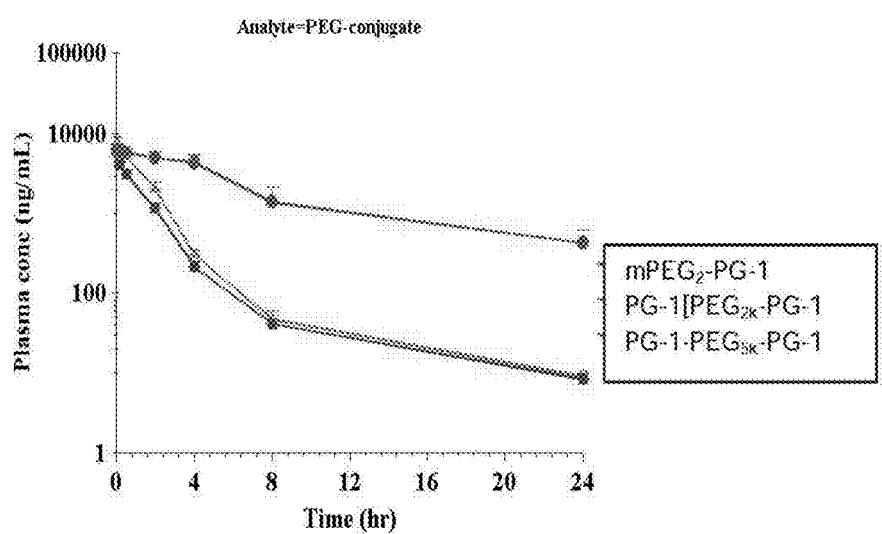
FIG. 102 shows the mean plasma concentration-time profiles for mPEG$_2$-PG-1, PG-1[PEG$_2$k-PG-1, PG-1-PEG$_{5k}$-PG-1.
Figure 103:
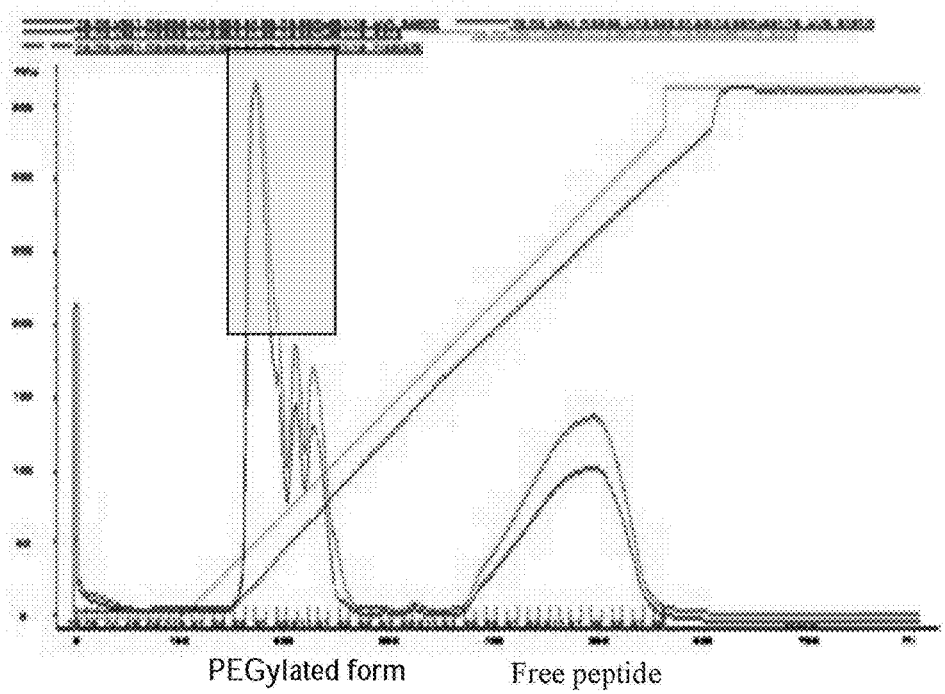
FIG. 103. Typical cation-exchange purification profile of [mPEG2-NHS-20K]-[V681(V13AD)].
Figure 104:
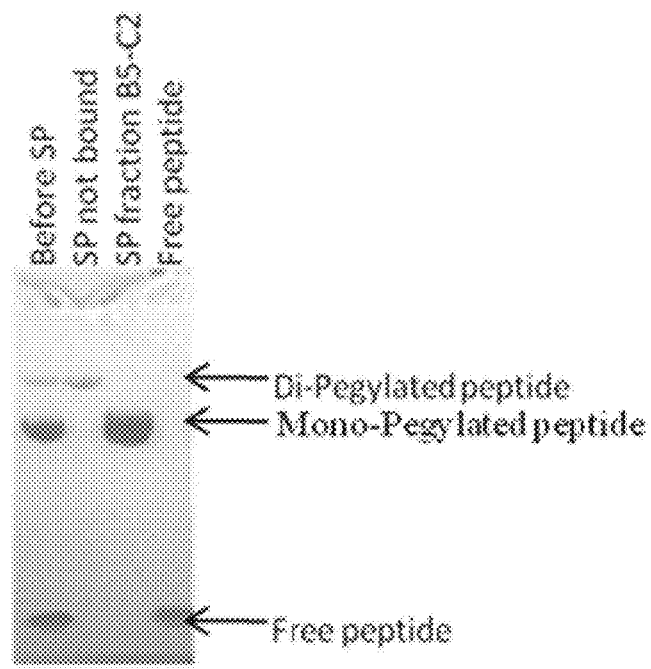
FIG. 104. SDS-PAGE analysis of V681(V13AD) PEGylation.
Figure 105:
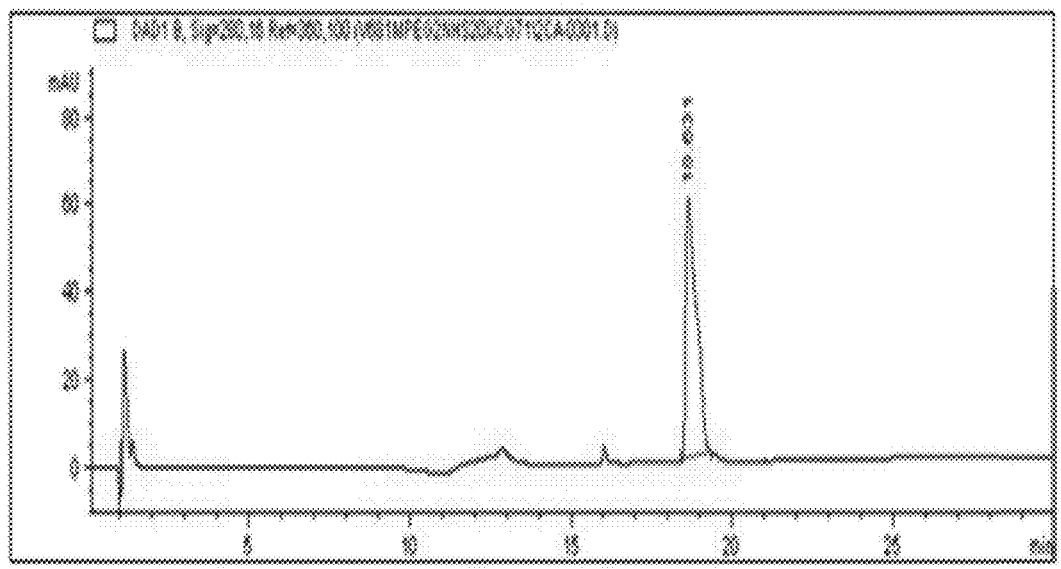
FIG. 105. Purity analysis of [mono]-[mPEG2-NHS 20K]-[V681(V13AD)] conjugate by reverse phase HPLC.
Figure 106:
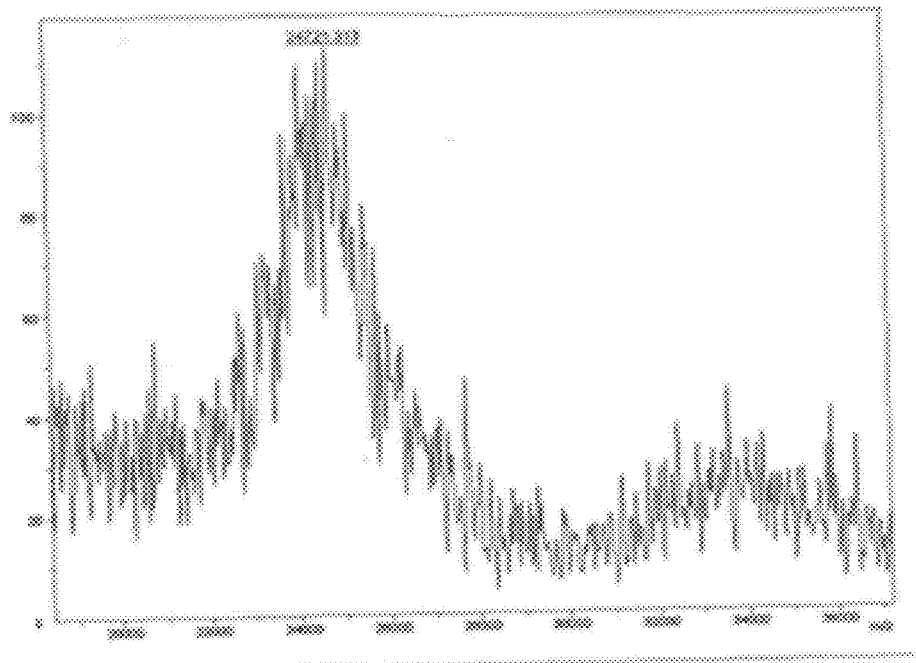
FIG. 106. MALDI-TOF spectra for [mono]-[mPEG2-NHS 20K]-[V681(V13AD)].

Non-Releasable-PEG:

FIG. 102 shows the mean plasma concentration-time profiles for NKT-10502, NKT-10519 and NKT-531 observed in this study. Table 2 summarizes the PK parameters of NKT-10502, NKT-10519 and NKT-531 following equivalent protein mass of 1.6 mg/kg administered intravenously into rats. Based on the observed data, NKT-10502 appeared to be declined slower than NKT-10519 and NKT-531.

TABLE PRO10.2

Comparative PK Parameters of Non-Releasable-PEG Protegrin-1 Conjugates Following Equivalent Protein Mass Intravenous Administration to Sprague Dawley rats (Mean ± SD)

| Test Compound | $C_{max}$ (ng/mL) | $T_{1/2}$ (hr) | $AUC_{INF}$ (ug · hr/mL) | $MRT_{last}$ (hr) | CL (mL/hr/kg) | $V_{ss}$ (mL/kg) |
|---|---|---|---|---|---|---|
| Protegrin-1 | 2050 ± 601 | 0.35 ± 0.10 | 1.16 ± 0.351 | 0.52 ± 0.05 | 1470 ± 434 | 848 ± 360 |
| mPEG$_2$-40K-PG-1 | 6110 ± 664 | 10.8 ± 3.0 | 52.7 ± 16.3 | 5.6 ± 0.83 | 32.9 ± 12.4 | 320 ± 131 |
| PG-1-PEG-2K-PG-1 | 6520 ± 679 | 7.3 ± 1.1 | 7.7 ± 1.09 | 1.7 ± 0.14 | 209 ± 27.3 | 432 ± 40.5 |
| PG-1-PEG-5K-PG-1 | 7550 ± 1680 | 6.8 ± 0.65 | 11.9 ± 0.866 | 1.6 ± 0.16 | 135 ± 9.22 | 248 ± 22.1 |

Example V1

V681-mPEG Conjugates (V681 Herein Refers to all V681-Like Peptides)

a) mPEG-N$^{ter}$-V681 Via mPEG-SPC

V681 peptide is prepared and purified according to standard automated peptide synthesis or recombinant techniques known to those skilled in the art. An illustrative polymeric reagent, mPEG-SPC reagent,

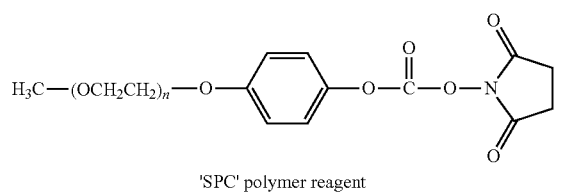

'SPC' polymer reagent is covalently attached to the N-terminus of V681, to provide a N$^{ter}$-conjugate form of the peptide. mPEG-SPC 20 kDa, stored at −20° C. under argon, is warmed to ambient temperature. The reaction is performed at room temperature. About 3-5-fold molar excess of mPEG-SPC 20 kDa reagent is used based upon absolute peptide content. The mPEG-SPC reagent is weighed into a glass vial containing a magnetic stirrer bar. A solution of V681 prepared in phosphate buffered saline, PBS, pH 7.4 is added and the mixture is stirred using a magnetic stirrer until the mPEG-SPC is fully dissolved. The stirring speed is reduced and the reaction is allowed to proceed to formation of conjugate product. The reaction is optionally quenched to terminate the reaction. The pH of the conjugate solution at the end of the reaction is measured and further acidified by addition of 0.1M HCl, if necessary, to bring the pH of the final solution to about 5.5. The conjugate solution is then analyzed by SDS-PAGE and RP-HPLC (C18) to determine the extent of mPEG-N$^{ter}$-V681 conjugate formation.

Using this same approach, other conjugates are prepared using mPEG derivatives having other weight-average molecular weights that also bear an N-hydroxysuccinimide moiety.

b) V681-C$^{ter}$-mPEG

An illustrative polymeric reagent, mPEG-$NH_2$ reagent is covalently attached to the C-terminus of V681, to provide a C$^{ter}$-conjugate form of the peptide. For coupling to the C-terminus, a protected V681 peptide is prepared and purified according to standard automated peptide synthesis techniques known to those skilled in the art. mPEG-$NH_2$ 20 kDa, stored at −20° C. under argon, is warmed to ambient temperature. The reaction is performed at room temperature. About 5-fold molar excess of mPEG-$NH_2$, PyBOP (benzotriazol-1-yloxy)tripyrrolidinonophosphonium hexafluorophosphate), and 1-hydroxybenzotriazole (HOBt) are used, based upon absolute peptide content. The mPEG-$NH_2$, PyBOP, HOBt are weighed into a glass vial containing a magnetic stirrer bar. A solution of Prot-V681 peptide is prepared in N, N-dimethylformamide is added and the mixture is stirred using a magnetic stirrer until the mPEG-$NH_2$ is fully dissolved. The stirring speed is reduced and the reaction is allowed to proceed to formation of conjugate product. The conjugate solution is then analyzed by SDS-PAGE and RP-HPLC (C18) to determine the extent of Prot-V681-C$^{ter}$-mPEG conjugate formation. The remaining protecting groups are removed under standard deprotection conditions to yield the V681-C$^{ter}$-mPEG conjugate.

Using this same approach, other conjugates are prepared using mPEG derivatives having other weight-average molecular weights that also bear an amino moiety.

c) V681-Cys(S-mPEG)

mPEG-Maleimide is obtained having a molecular weight of 5 kDa and having the basic structure shown below:

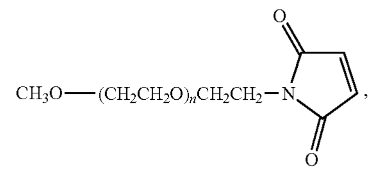

mPEG-MAL, 5kDa

V681, which has a thiol-containing cysteine residue, is dissolved in buffer. To this peptide solution is added a 3-5 fold molar excess of mPEG-MAL, 5 kDa. The mixture is stirred at room temperature under an inert atmosphere for several hours. Analysis of the reaction mixture reveals successful conjugation of this peptide.

Using this same approach, other conjugates are prepared using mPEG-MAL having other weight average molecular weights.

d) mPEG-N$^{ter}$-V681-Via mPEG-SMB

An mPEG-N-Hydroxysuccinimide is obtained having a molecular weight of 5 kDa and having the basic structure shown below:

(mPEG-Succinimidyl α-Methylbutanoate Derivative, 5kDa ("mPEG-SMB"))

mPEG-SMB, 5 kDa, stored at −20° C. under argon, is warmed to ambient temperature. A five-fold excess (relative to the amount of the peptide) of the warmed mPEG-SMB is dissolved in buffer to form a 10% reagent solution. The 10% reagent solution is quickly added to the aliquot of a stock V681 peptide solution and mixed well. After the addition of the mPEG-SMB, the pH of the reaction mixture is determined and adjusted to 6.7 to 6.8 using conventional techniques. To allow for coupling of the mPEG-SMB to the peptide via an amide linkage, the reaction solution is stirred for several hours (e.g., 5 hours) at room temperature in the dark or stirred overnight at 3-8° C. in a cold room, thereby resulting in a conjugate solution. The reaction is quenched with a 20-fold molar excess (with respect to the peptide) of Tris buffer.

Using this same approach, other conjugates are prepared using mPEG derivatives having other weight-average molecular weights that also bear an N-hydroxysuccinimide moiety.

e) V681-Glu(O-mPEG)

An illustrative polymeric reagent, mPEG-$NH_2$ reagent is covalently attached to the Glu residue of V681, to provide a Glu-conjugate form of the peptide. For coupling to the Glu residue, a protected V681 peptide is prepared and purified according to standard automated peptide synthesis techniques known to those skilled in the art. Deprotection of the Glu(OBz) residue ($H_2$/Pd) yields the free-Glu carboxylate for subsequent coupling. mPEG-$NH_2$ 20 kDa, stored at −20° C. under argon, is warmed to ambient temperature. The reaction is performed at room temperature. A 5-fold molar excess of mPEG-$NH_2$, PyBOP (benzotriazol-1-yloxy)tripyrrolidinonophosphonium hexafluorophosphate), and 1-hydroxybenzotriazole (HOBt) are used, based upon absolute peptide content. The mPEG-$NH_2$, PyBOP, HOBt are weighed into a glass vial containing a magnetic stirrer bar. A solution of Prot3-V681 peptide is prepared in N, N-dimethylformamide is added and the mixture is stirred using a magnetic stirrer until the mPEG-$NH_2$ is fully dissolved. The stirring speed is reduced and the reaction is allowed to proceed to formation of conjugate product. The conjugate solution is then analyzed by SDS-PAGE and RP-HPLC (C18) to determine the extent of Prot3-V681-(Glu-O-mPEG) conjugate formation. The remaining protecting groups are removed under standard deprotection conditions to yield the V681-Glu(O-mPEG) conjugate.

Using this same approach, other conjugates are prepared using mPEG derivatives having other weight-average molecular weights that also bear an amino moiety.

Example V2

PEGylation of V681(V13AD) with [mPEG2-NHS-20K]

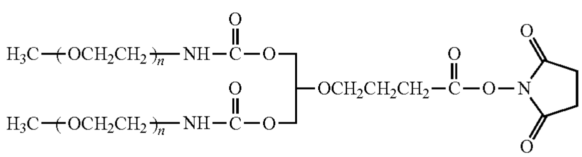

A stock solution of 4 mg/mL V681(V13AD) was prepared in water. The peptide stock solution was diluted 1:1 in 50 mM sodium phosphate, pH 7.4, resulting in a peptide concentration of 2 mg/mL. Immediately before a PEGylation reaction was initiated, a 14 mg/mL stock solution of mPEG2-NHS-20K was prepared in 2 mM HCl. This PEG reagent forms stable bonds with amine groups. To initiate a reaction, the PEG stock solution and 2 mg/mL peptide solution were brought to 25° C. and then mixed in equal volumes. The reaction mixture was stirred for 1 hour at 25° C. after which the reaction was quenched with 100 mM glycine in 2 mM HCl (10 mM final glycine concentration).

The mono-PEGylated conjugate was purified from the reaction mixture by cation exchange chromatography using SP Sepharose HP media (GE Healthcare). The resin was packed in an XK 26/10 column (GE). Buffer A was 20 mM sodium phosphate buffer, pH 7.4, and Buffer B was 20 mM sodium phosphate, 1M NaCl, pH 7.4. The resin was washed in buffer B and equilibrated in buffer A before sample loading. After loading, the resin was washed in buffer A for 2 column volumes and the PEGylated and nonPEGylated peptides were eluted using a linear gradient of 0-100% B in 10 column volumes at a flow rate of 5 mL/min.

Fractions collected during cation exchange chromatography were analyzed using reversed-phase HPLC. The mobile phases were: A, 0.1% TFA in water and B, 0.85% TFA in acetonitrile. An Agilent Poroshell 300-SB-C8 column was used with a flow rate of 0.2 ml/min and a column temperature of 50° C. Detection was carried out at 280 nm. The column was equilibrated in 0% B and conjugate separation was achieved using the gradient timetable shown in Table V2.1.

| TIME (MIN) | % MOBILE PHASE A | % MOBILE PHASE B |
|---|---|---|
| 0.00 | 100.0 | 0.0 |
| 5.00 | 100.0 | 0.0 |
| 10 | 70.0 | 30.0 |
| 20.00 | 30.0 | 70.0 |
| 21 | 20.0 | 80.0 |
| 25 | 20.0 | 80.0 |
| 30 | 100.0 | 0.0 |

Fractions containing pure [mono]-[mPEG2-20K]-[V681 (V13AD)] as determined by RP-HPLC and SDS-PAGE were pooled and concentrated over a reversed phase CG71S column. The column was washed with 0.5% acetic acid in acetonitrile and equilibrated with 0.5% acetic acid before loading. After loading, the column was washed with 0.5% acetic acid and the PEGylated peptide was eluted with 0.5% acetic acid in acetonitrile. The fractions containing pure mono-PEGylated peptide were collected, lyophilized and stored at −80° C.

A typical cation-exchange chromatogram is shown in FIG. 103. SDS-PAGE analysis of V681 (V13AD) and purified [mono]-[mPEG2-20K]-[V681 (V13AD)] conjugate is shown in FIG. 104. RP-HPLC analysis of the purified conjugate is shown in FIG. 105, and MALDI-TOF analysis of the purified conjugate is shown in FIG. 106. The purity of the mono-PEG-conjugate was >95% by SDS-PAGE analysis and >98% by RP-HPLC analysis. The mass as determined by MALDI-TOF was within the expected range. FIG. 103. Typical cation-exchange purification profile of [mPEG2-NHS-20K]-[V681(V13AD)]. The mono-PEGylated conjugate is indicated in a gray box and labeled B5-C2. The di-PEGylated conjugate did not bind to the resin. The blue line represents absorbance at 280 nm and the red line represents absorbance at 215 nm. FIG. 104. SDS-PAGE (4-12% Bis-Tris-Nu-PAGE, Invitrogen) analysis of V681 (V13AD) PEGylation and purification on the SP ion-exchange column. FIG. 105. Purity analysis of [mono]-[mPEG2-NHS 20K]-[V681(V13AD)] conjugate by reverse phase HPLC. The purity of the purified conjugate was determined to be NLT 95% at 280 nm. 1.0% of the sample eluted at 15.9 min which corresponds to the nonPEGylated peptide. The peak at 13 minutes contains column-derived species and is not specific to the sample. FIG. 106. MALDI-TOF spectra for [mono]-[mPEG2-NHS 20K]-[V681 (V13AD)]. The major peak at 20.2 kD represents the molecular weight of monomeric [mono]-[mPEG2-NHS 20K]-[V681(V13AD)] conjugate.

Example V3

PEGylation of V681(V13AD) with [mPEG-SMB-30K]

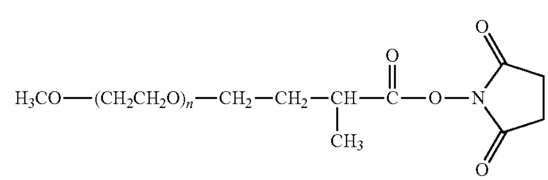

A stock solution of 4 mg/mL V681(V13AD) was prepared in water. The peptide stock solution was diluted 1:1 in 50 mM sodium phosphate, pH 7.4, resulting in a peptide concentration of 2 mg/mL. Immediately before a PEGylation reaction was initiated, a 20 mg/mL stock solution of mPEG-SMB-30K was prepared in 2 mM HCl. This PEG reagent forms stable bonds with amine groups. To initiate a reaction, the PEG stock solution and 2 mg/mL peptide solution were brought to 25° C. and then mixed in equal volumes. The reaction mixture was stirred for 1 hour at 25° C. after which the reaction was quenched with 100 mM glycine in 2 mM HCl (10 mM final glycine concentration).

The mono-PEGylated conjugate was purified from the reaction mixture by cation exchange chromatography using SP Sepharose HP media (GE Healthcare). The resin was packed in an XK 26/10 column (GE). Buffer A was 20 mM sodium phosphate buffer, pH 7.4, and Buffer B was 20 mM sodium phosphate, 1M NaCl, pH 7.4. The resin was washed in buffer B and equilibrated in buffer A before sample loading. After loading, the resin was washed in buffer A for 2 column volumes and the PEGylated and nonPEGylated peptides were eluted using a linear gradient of 0-100% B in 10 column volumes at a flow rate of 5 mL/min.

Fractions collected during cation exchange chromatography were analyzed using reversed-phase HPLC. The mobile phases were: A, 0.1% TFA in water and B, 0.85% TFA in acetonitrile. An Agilent Poroshell 300-SB-C8 column was used with a flow rate of 0.2 ml/min and a column temperature of 50° C. Detection was carried out at 280 nm. The column was equilibrated in 0% B and conjugate separation was achieved using the gradient timetable shown in Table V3.1.

| TIME (MIN) | % MOBILE PHASE A | % MOBILE PHASE B |
|---|---|---|
| 0.00 | 100.0 | 0.0 |
| 5.00 | 100.0 | 0.0 |
| 10 | 70.0 | 30.0 |
| 20.00 | 30.0 | 70.0 |
| 21 | 20.0 | 80.0 |
| 25 | 20.0 | 80.0 |
| 30 | 100.0 | 0.0 |

Fractions containing pure [mono]-[mPEG-SMB-30K]-[V681(V13AD)] as determined by RP-HPLC and SDS-PAGE were pooled and concentrated over a reversed phase CG71S column. The column was washed with 0.5% acetic acid in acetonitrile and equilibrated with 0.5% acetic acid before loading. After loading, the column was washed with 0.5% acetic acid and the PEGylated peptide was eluted with 0.5% acetic acid in acetonitrile. The fractions containing pure PEGylated peptide were collected, lyophilized and stored at −80° C.

Figure 107:
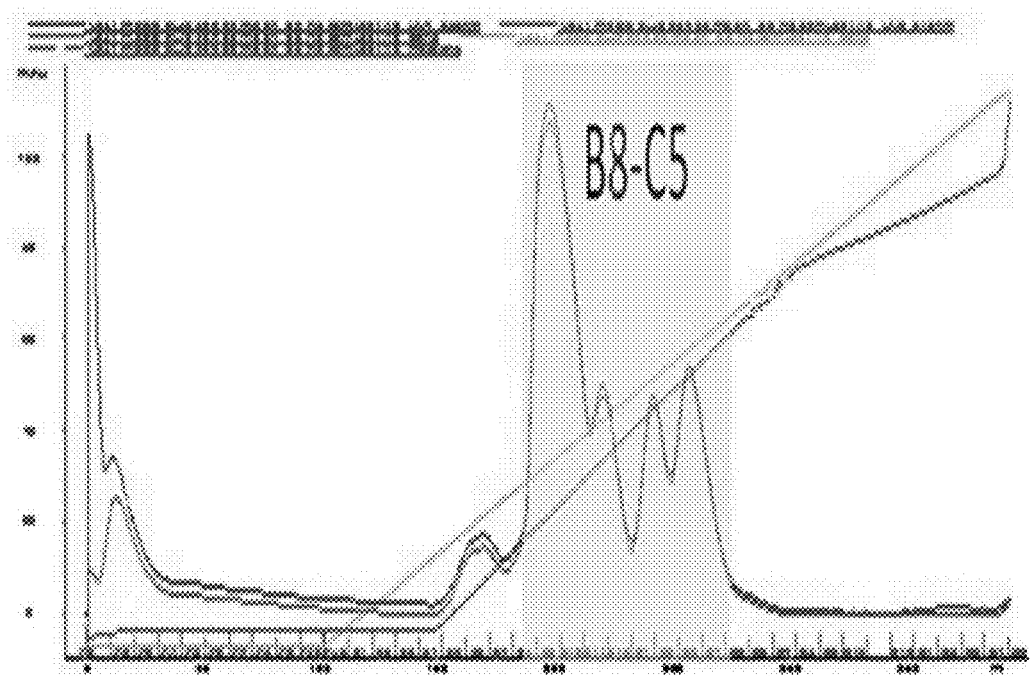
FIG. 107. Typical cation-exchange purification profile of [mPEG-SMB-30K]-[V681(V13AD)].
Figure 108:
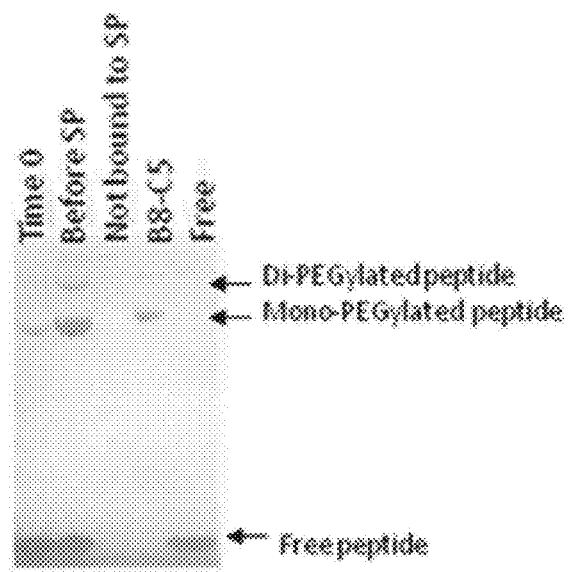
FIG. 108. SDS-PAGE analysis of V681(V13AD) PEGylation and purification on the SP ion-exchange column.
Figure 109:
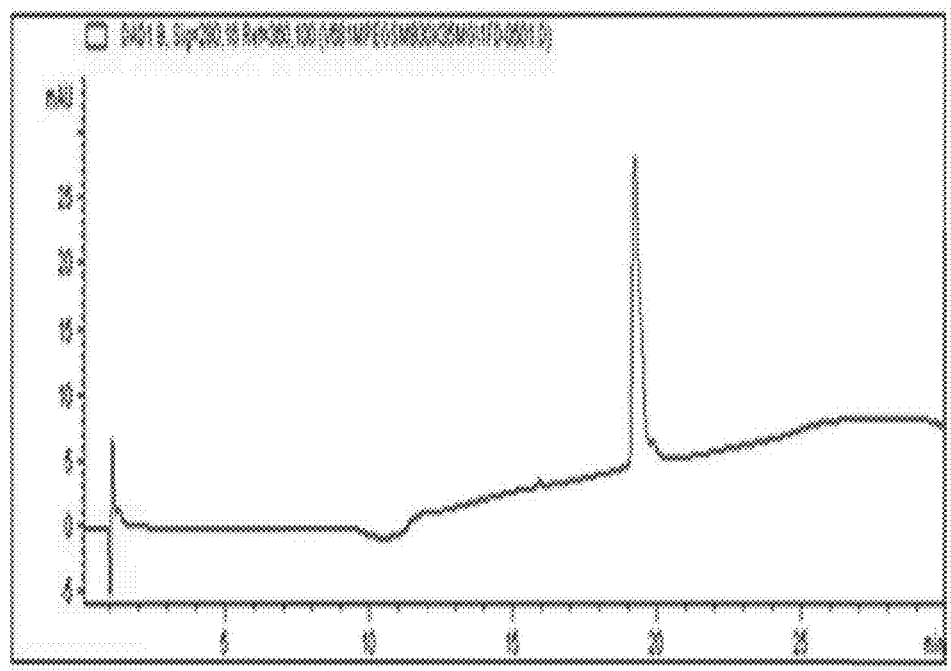
FIG. 109. Purity analysis of [mono]-[mPEG-SMB-30K]-[V681(V13AD)] conjugate by reverse phase HPLC.
Figure 110:
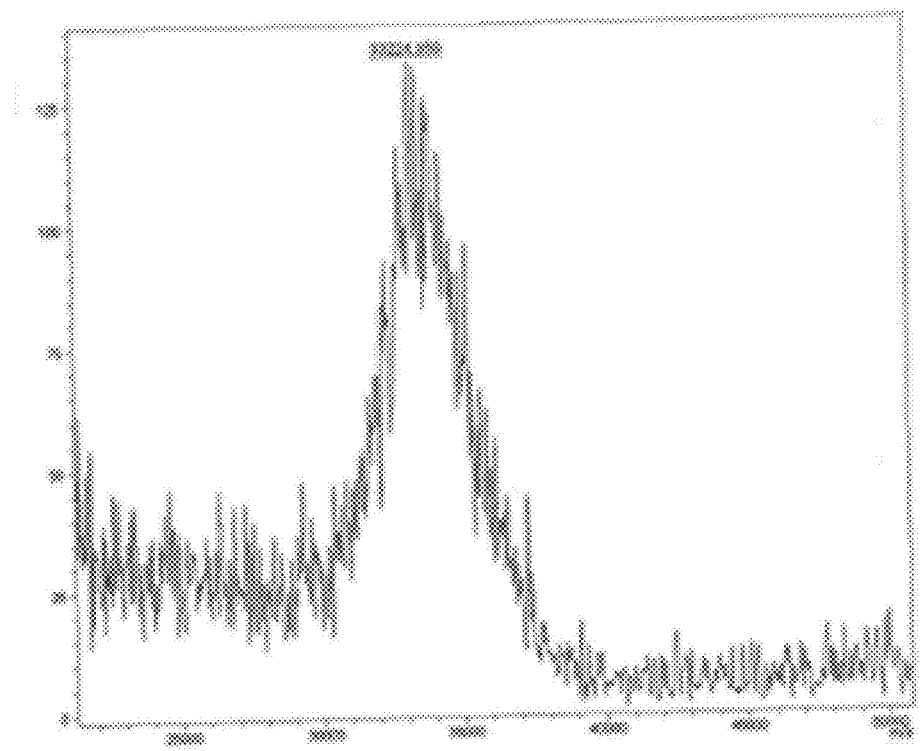
FIG. 110. MALDI-TOF spectra for [mono]-[mPEG-SMB 30K]-[V681(V13AD)].

A typical cation-exchange chromatogram is shown in FIG. 107. SDS-PAGE analysis of V681 (V13AD) and purified [mono]-[mPEG-SMB-30K]-[V681 (V13AD)] conjugate is shown in FIG. 108. RP-HPLC analysis of the purified conjugate is shown in FIG. 109, and MALDI-TOF analysis of the purified conjugate is shown in FIG. 110. FIG. 107. Typical cation-exchange purification profile of [mPEG-SMB-30K]-[V681(V13AD)]. The mono-PEGylated conjugate is indicated in B5-C2. The di-PEGylated conjugate did not bind to the resin. The blue line represents absorbance at 280 nm and the red line represents absorbance at 215 nm. FIG. 108. SDS-PAGE (4-12% Bis-Tris-Nu-PAGE, Invitrogen) analysis of V681(V13AD) PEGylation and purification on the SP ion-exchange column. FIG. 109. Purity analysis of [mono]-[mPEG-SMB-30K]-[V681(V13AD)] conjugate by reverse phase HPLC. The purity of the purified conjugate was determined to be NLT 95% at 280 nm. 1.0% of the sample eluted at 15.9 min which corresponds to the non-PEGylated peptide. The peak at 13 minutes contains column-derived species and is not specific to the sample. FIG. 110. MALDI-TOF spectra for [mono]-[mPEG-SMB 30K]-[V681(V13AD)]. The major peak at 33.9 KDa represents the molecular weight of monomeric [mono]-[mPEG-SMB 30K]-[V681(V13AD)] conjugate.

Example V4

Compare pharmacokinetics of non-releasable SMB-30K-V681 (V13AD)), and NHS-20K-V681 (V13AD)), with (parent V681 (V13AD)).

Study Design and Conduct

Procedure: Nine (9) adult male Sprague-Dawley rats with indwelling jugular vein and carotid artery catheters (JVC/CAC) (Charles River Labs, Hollister, Calif.) were utilized for this study. The weight range of the animals was 311-346 grams. All animals were food fasted overnight. Prior to dosing the rats were weighed, the tails and cage cards were labeled for identification and the doses were calculated. Anesthesia was induced and maintained with 3.0-5.0% isoflurane. The JVC and CAC were externalized, flushed with HEP/saline (10 IU/mL HEP/mL saline), plugged, and labeled to identify the jugular vein and carotid artery. The predose sample was collected from the JVC. When all of the animals had recovered from anesthesia and the predose samples were processed, the animals were dosed, intravenously (IV) via the JVC using a 1 mL syringe containing the appropriate test article, the dead volume of the catheter was flushed with 0.9% saline to ensure the animals received the correct dose. Following a single IV dose, blood samples were collected into EDTA microtainers containing 75 μL of protease inhibitor cocktail at 0 (pre-dose collected as described above), 2, 10, 30 minutes and at 1, 2, 4, 8, 24 hrs via the carotid artery catheter and processed as stated in the protocol. Following the last collection point, the animals were euthanized.

Bioanalytical Analysis:

Pharmacokinetic Analyses: Noncompartmental PK data analysis and report preparation was completed by Research Biology at Nektar Therapeutics at San Carlos, Calif. Individual plasma concentration data are listed and summarized in Appendix A1.1-1.3. PK analysis was performed using WinNonlin (Version 5.2, Mountain View, Calif.-94014). Concentrations in plasma that were below LLOQ were replaced with zeros prior to generating Tables and PK analysis. The following PK parameters were estimated using plasma concentration-time profile of each animal:

| | |
|---|---|
| $C_0$ | Extrapolated concentration to time "zero" |
| $C_{max}$ | Maximum (peak) concentration |
| $AUC_{all}$ | Area under the concentration-time from zero to time of last concentration value |
| $T_{1/2(Z)}$ | Terminal elimination half-life |
| $AUC_{inf}$ | Area under the concentration-time from zero to time infinity |
| $T_{max}$ | Time to reach maximum or peak concentration following administration |
| CL | Total body clearance |
| $V_z$ | Volume of distribution based on terminal phase |
| $V_{ss}$ | Volume of distribution at steady state |
| MRT | Mean residence time |

Figure 111:
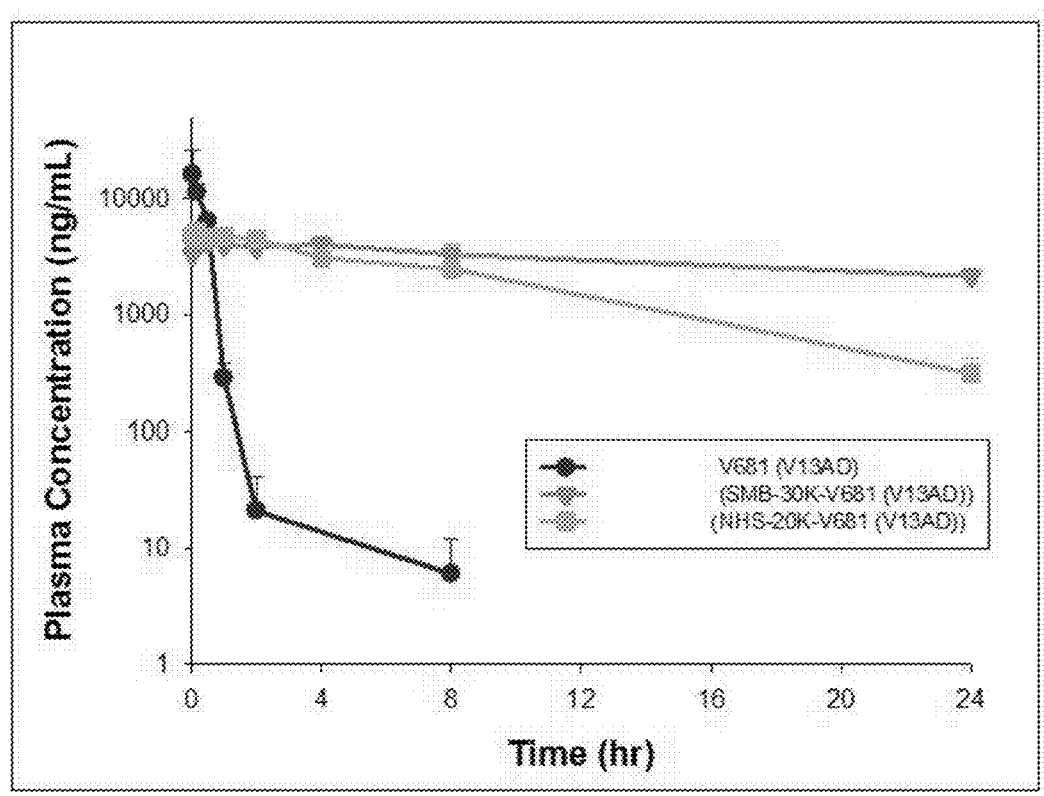
FIG. 111 shows the mean plasma concentration-time profiles for V681 (V13AD), SMB-30K-V681 (V13AD), and NHS-20K-V681 (V13AD).
Figure 112:
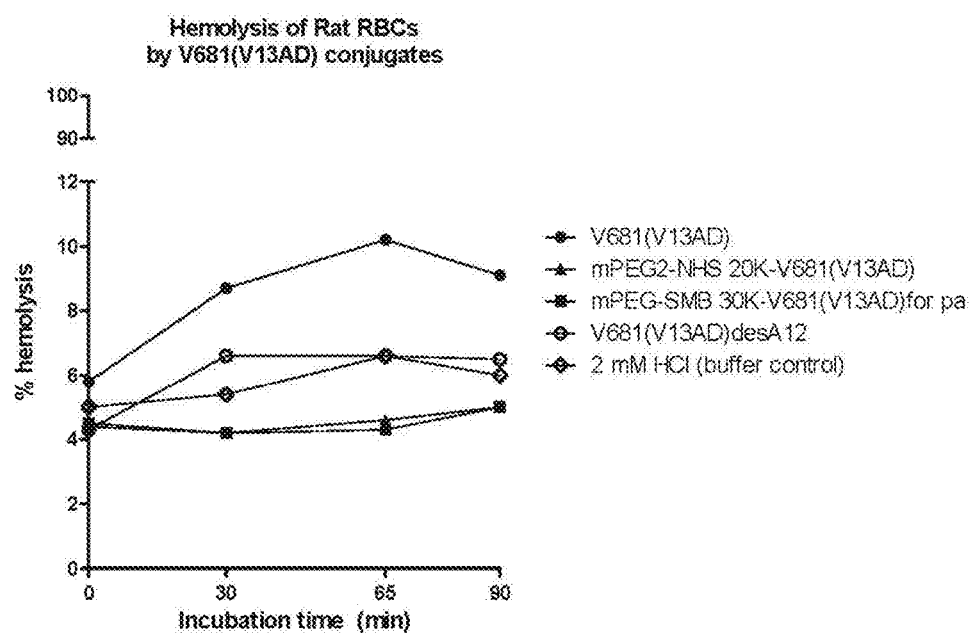
FIG. 112. Hemolysis relative to the 100% hemolysis produced by 0.25% Triton X-100.

FIG. 111 shows the mean plasma concentration-time profiles for V681 (V13AD), SMB-30K-V681 (V13AD), and NHS-20K-V681 (V13AD), observed in this study. Both SMB-30K-V681 (V13AD), and NHS-20K-V681 (V13AD) are non-releasable PEGylated conjugates and were shown to have slower declining profiles and higher systemic exposure compared to the native V681 (V13AD). A very low but detectable level of V681 (V13AD) was observed in the first few timepoints (2-30 minutes) after SMB-30K-V681 (V13AD), and NHS-20K-V681 (V13AD), administration.

Table V4.1 summarizes the PK parameters of V681 (V13AD), SMB-30K-V681 (V13AD), and NHS-20K-V681 (V13AD) following equivalent protein mass of 1.0 mg/kg administered intravenously into rats. Based on the observed data, SMB-30K-V681 (V13AD), and NHS-20K-V681 (V13AD), had significant longer mean $t_{1/2}$ compared with V681 (V13AD). The mean AUC of SMB-30K-V681 (V13AD), and NHS-20K-V681 (V13AD), were 123 and 24 times of V681 (V13AD), respectively.

TABLE V4.1

| Compound | $C_{max}$ (ng/mL) | $T_{1/2}$ (hr) | $AUC_{INF}$ (μg · hr/mL) | MRT (hr) | CL (mL/hr/kg) | $V_{ss}$ (mL/kg) |
|---|---|---|---|---|---|---|
| V681 (V13AD) | 16500 ± 9670 | 0.61 ± 0.39 | 7.21 ± 1.43 | 0.33 ± 0.08 | 142 ± 26 | 47.7 ± 18.0 |
| SMB-30K-V681 (V13AD) | 4380 ± 505 | 26.6 ± 12.5 | 158 ± 43 | 38.3 ± 18.2 | 6.6 ± 1.6 | 235 ± 50 |
| NHS-20K-V681 (V13AD) | 5210 ± 211 | 5.8 ± 1.0 | 53.0 ± 1.1 | 7.6 ± 1.1 | 18.9 ± 0.39 | 143 ± 23.7 |

Example V5

Hemolysis assay. Approximately 10 mL of blood was drawn from one adult rat into Na Heparin tube and kept in ice until use. Red blood cells were washed three times with 10 mL of cold DPBS ((−) $CaCl_2$ and (−) $MgCl_2$) and collected by sequential centrifugation at 3,000 g for 5 min at 4° C. Pellets of red blood cells were resuspended with DPBS ((−) $CaCl_2$ and (−) $MgCl_2$) and the total volume was brought up to initial volume of blood drawn. One mL of resuspended red blood cells was resuspended with 49 mL of DPBS ((−) $CaCl_2$ and (−) $MgCl_2$). Incubation mixture was prepared by 400 fold dilution of stock solution of test compounds with final volume of 800 μl. Final concentration of test compounds was equimolar to that of respective unconjugated compounds. Hemolysis incubation was done at 37° C. with mild agitation.

For releasable conjugates, test compounds were preincubated in 1×PBS at 37° C. prior to hemolysis assay. Incubation mixture was centrifuged at 3,000 g for 5 min at 4° C., and the absorbance at 550 nm was read from supernatant. The percent of hemolysis was calculated relative to the 100% hemolysis produced by 0.25% Triton X-100.

| Compounds | Description | Note |
|---|---|---|
| V681(V13AD) | Native peptide | |
| mPEG2-NHS 20K-V681(V13AD) | V681(V13AD) conjugate with a stable linker | |
| mPEG-SMB 30K-V681(V13AD) | V681(V13AD) conjugate with a stable linker | |
| mPEG2-NHS 20K-gly | PEG moiety of mPEG2-NHS 20K-V681(V13AD) | |
| mPEG-SMB 30K-gly | PEG moiety of mPEG-SMB 30K-V681(V13AD) | |
| V681(V13AD)desA12 | | |
| 2 mM HCl | | Buffer control |
| Matrix control | | Matrix control |
| TritonX-100 | Detergent | Positive control |

For V681(V13AD), hemolytic effects were almost eliminated by PEG conjugation with a stable linker mPEG2-NHS 20K-V681(V13AD), and mPEG-SMB 30K-V681(V13AD)] (FIG. 112).

Example C-PEP2

PEGylation of C-Peptide(S20C) with [mPEG-Ru-MAL-30K]

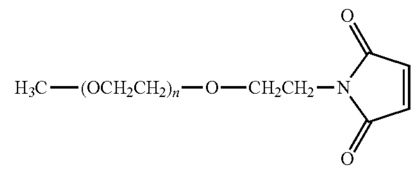

A stock solution of 4 mg/mL C-peptide(S20C) was prepared in water. The peptide stock solution was diluted 1:1 in 20 mM sodium citrate, pH 5, resulting in a peptide concentration of 2 mg/mL. Immediately before a PEGylation reaction was initiated, an 80 mg/mL stock solution of mPEG-ru-MAL-30K was prepared in 2 mM HCl. This PEG reagent forms stable bonds with thiol groups. To initiate a reaction, the PEG stock solution and 2 mg/mL peptide solution were brought to 25° C. and then mixed in equal volumes. The reaction mixture was stirred for 16 hours at 25° C.

The mono-PEGylated conjugate was purified from the reaction mixture by anion exchange chromatography using Q HP Sepharose HP media (GE Healthcare). The resin was packed in an XK 16/10 column (GE). Buffer A was 20 mM HEPES, pH 7.0, and Buffer B was 20 mM HEPES, pH 7.0, 1M NaCl. The resin was washed in buffer B and equilibrated in buffer A prior to sample loading. After loading, the resin was washed with 2 column volumes buffer A and the PEGylated and nonPEGylated peptides were eluted using a linear gradient of 0-100% B in 5 column volumes at a flow rate of 3 mL/min.

Fractions collected during anion exchange chromatography were analyzed using reversed-phase HPLC. The mobile phases were: A, 0.1% TFA in water and B, 0.85% TFA in acetonitrile. An Agilent Poroshell 300-SB-C8 column was used with a flow rate of 0.2 ml/min and a column temperature of 50° C. Detection was carried out at 215 nm. The column was equilibrated in 0% B and conjugate separation was achieved using the gradient timetable shown in Table C-PEP2.1.

TABLE C-PEP2.1

| RP-HPLC timetable | | |
|---|---|---|
| TIME (MIN) | % MOBILE PHASE A | % MOBILE PHASE B |
| 0.00 | 100.0 | 0.0 |
| 5.00 | 70.0 | 30.0 |

TABLE C-PEP2.1-continued

| RP-HPLC timetable | | |
|---|---|---|
| TIME (MIN) | % MOBILE PHASE A | % MOBILE PHASE B |
| 15.00 | 40.0 | 60.0 |
| 20.00 | 20.0 | 80.0 |

Fractions containing pure [mono]-[mPEG-ru-MAL-30K]-[C-peptide(S20C)] as determined by analytical RP-HPLC were pooled and concentrated over a reversed phase CG71S column. The column was washed with 0.5% acetic acid in acetonitrile and equilibrated with 0.5% acetic acid prior to sample loading. After loading, the column was washed with 0.5% acetic acid and the PEGylated peptide was eluted with 0.5% acetic acid in acetonitrile. Fractions containing PEGylated peptide were collected, lyophilized and stored at −80° C.

A typical anion-exchange chromatogram is shown in FIG. 1.1. RP-HPLC analysis of purified [mono]-[mPEG-ru-MAL-30K]-[C-peptide(S20C)] is shown in FIG. 1.2 and MALDI-TOF analysis of the purified conjugate is shown in FIG. 1.3. The purity of the mono-PEG-conjugate was >98% by RP-HPLC analysis. The mass as determined by MALDI-TOF was within the expected range.

Figure 113:
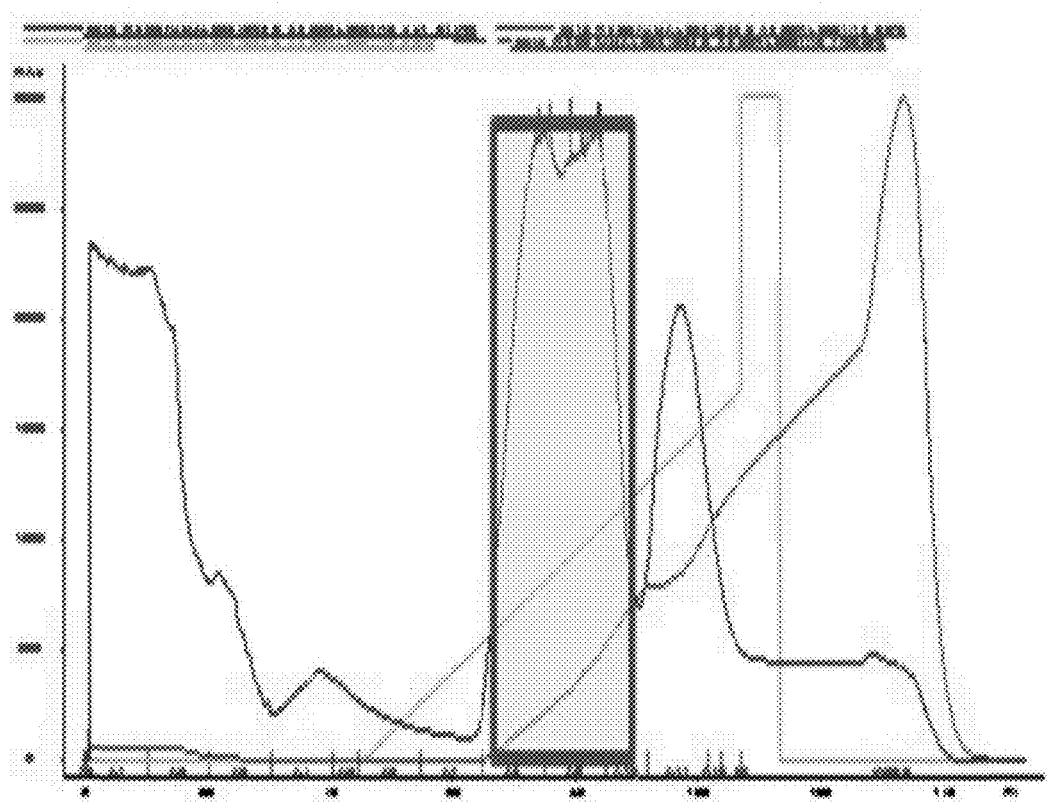
FIG. 113. Typical anion-exchange chromatography profile of [[mono]-[mPEG-ru-MAL-30K]-[C-peptide(S20C)].

FIG. 113. Typical anion-exchange chromatography profile of [[mono]-[mPEG-ru-MAL-30K]-[C-peptide(S20C)]. The mono-PEGylated conjugate is indicated in the grey box. The blue line represents absorbance at 215 nm.

Figure 114:
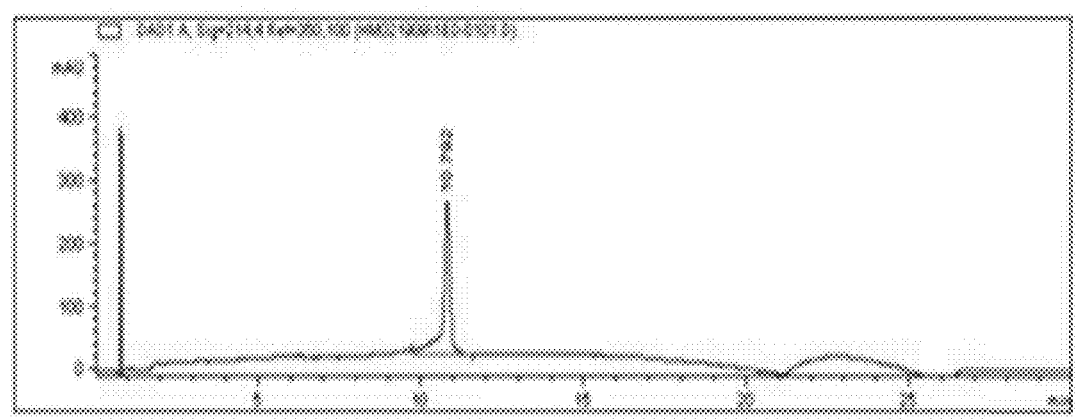
FIG. 114. Purity analysis of [[mono]-[mPEG-ru-MAL-30K]-[C-peptide(S20C)] by reversed phase HPLC.

FIG. 114. Purity analysis of [[mono]-[mPEG-ru-MAL-30K]-[C-peptide(S20C)] by reversed phase HPLC. The purity of the purified conjugate was determined to be NLT 95% at 215 nm.

Figure 115:
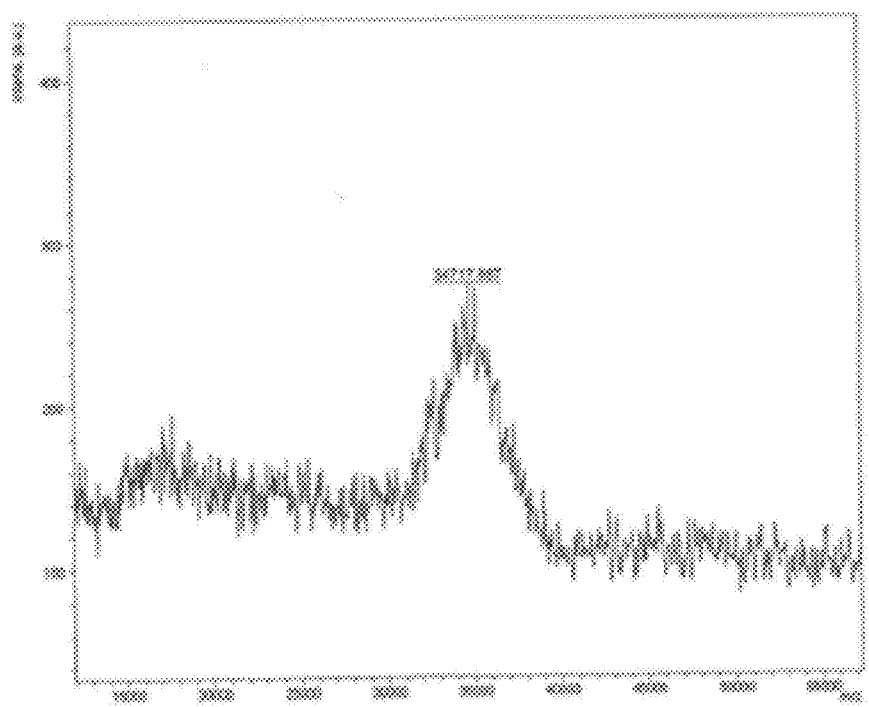
FIG. 115. MALDI-TOF spectrum for [mono]-[mPEG-ru-MAL-30K]-[C-peptide(S20C)].

FIG. 115. MALDI-TOF spectrum for [mono]-[mPEG-ru-MAL-30K]-[C-peptide(S20C)]. The major peak at 34.7 kD represents the molecular weight of monomeric [mono]-[mPEG-ru-MAL-30K]-[C-peptide(S20C)].

Example C-PEP3

PEGylation of C-Peptide(S20C) with [mPEG-Butyraldehyde-30K]

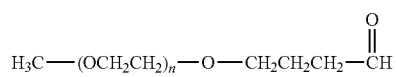

A stock solution of 4 mg/mL C-peptide(S20C) was prepared in water. The peptide stock solution was diluted 1:1 in 20 mM sodium citrate, pH 6, resulting in a peptide concentration of 2 mg/mL. Immediately before a PEGylation reaction was initiated, a 60 mg/mL stock solution of mPEG-Butyraldehyde-30K was prepared in 2 mM HCl. This PEG reagent forms stable bonds with amine groups. To initiate a reaction, the PEG stock solution and 2 mg/mL peptide solution were brought to 25° C. and then mixed in equal volumes. The reaction mixture was stirred for 1 hour at 25° C. After 1 hour, 10 mM sodium cyanoborohydride (final concentration) was added and the reaction was mixed for a further 16 hours at 25° C. After 16 hours, 100 mM glycine in 2 mM HCl was added (10 mM final glycine concentration).

The mono-PEGylated conjugate was purified from the reaction mixture by anion exchange chromatography using Q HP Sepharose HP media (GE Healthcare). The resin was packed in an XK 16/10 column (GE). Buffer A was 20 mM HEPES, pH 7.0, and Buffer B was 20 mM HEPES, pH 7.0, 1M NaCl. The resin was washed in buffer B and equilibrated in buffer A prior to sample loading. After loading, the resin was washed with 2 column volumes buffer A and the PEGylated and nonPEGylated peptides were eluted using a linear gradient of 0-100% B in 5 column volumes at a flow rate of 5 mL/min.

Fractions collected during anion exchange chromatography were analyzed using reversed-phase HPLC. The mobile phases were: A, 0.1% TFA in water and B, 0.85% TFA in acetonitrile. An Agilent Poroshell 300-SB-C8 column was used with a flow rate of 0.2 ml/min and a column temperature of 50° C. Detection was carried out at 215 nm. The column was equilibrated in 0% B and conjugate separation was achieved using the gradient timetable shown in Table C-PEP3.1.

TABLE C-PEP3.1

| RP-HPLC timetable | | |
|---|---|---|
| TIME (MIN) | % MOBILE PHASE A | % MOBILE PHASE B |
| 0.00 | 100.0 | 0.0 |
| 5.00 | 100.0 | 0.0 |
| 10.00 | 70.0 | 30.0 |
| 20.00 | 30.0 | 70.0 |
| 21.00 | 20.0 | 80.0 |
| 25.00 | 20.0 | 80.0 |

Fractions containing pure [mono]-[mPEG-Butyraldehyde-30K]-[C-peptide(S20C)] as determined by analytical RP-HPLC were pooled and concentrated over a reversed phase CG71S column. The column was washed with 0.5% acetic acid in acetonitrile and equilibrated with 0.5% acetic acid prior to sample loading. After loading, the column was washed with 0.5% acetic acid and the PEGylated peptide was eluted with 0.5% acetic acid in acetonitrile. Fractions containing PEGylated peptide were collected, lyophilized and stored at −80° C.

A typical anion-exchange chromatogram is shown in FIG. 1.1. RP-HPLC analysis of purified [mono]-[mPEG-Butyraldehyde-30K]-[C-peptide(S20C)] is shown in FIG. 1.2 and MALDI-TOF analysis of the purified conjugate is shown in FIG. 1.3. The purity of the mono-PEG-conjugate was >98% by RP-HPLC analysis. The mass as determined by MALDI-TOF was within the expected range.

Figure 116:
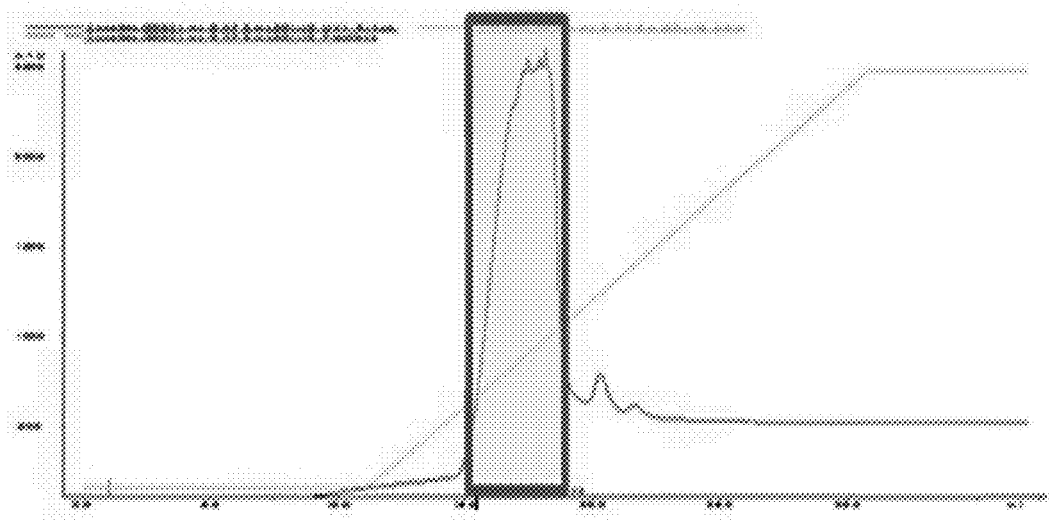
FIG. 116. Typical anion-exchange chromatography profile of [[mono]-[mPEG-Butyraldehyde-30K]-[C-peptide (S20C)].

FIG. 116. Typical anion-exchange chromatography profile of [[mono]-[mPEG-Butyraldehyde-30K]-[C-peptide(S20C)]. The mono-PEGylated conjugate is indicated in the grey box. The blue line represents absorbance at 215 nm.

Figure 117:
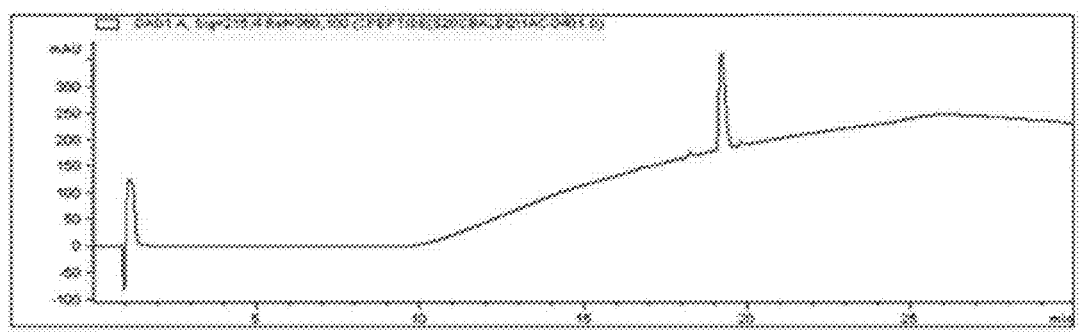
FIG. 117. Purity analysis of [mono]-[mPEG-Butyraldehyde-30K]-[C-peptide(S20C)] by reversed phase HPLC.

FIG. 117. Purity analysis of [mono]-[mPEG-Butyraldehyde-30K]-[C-peptide(S20C)] by reversed phase HPLC. The purity of the purified conjugate was determined to be NLT 95% at 215 nm.

Figure 118:
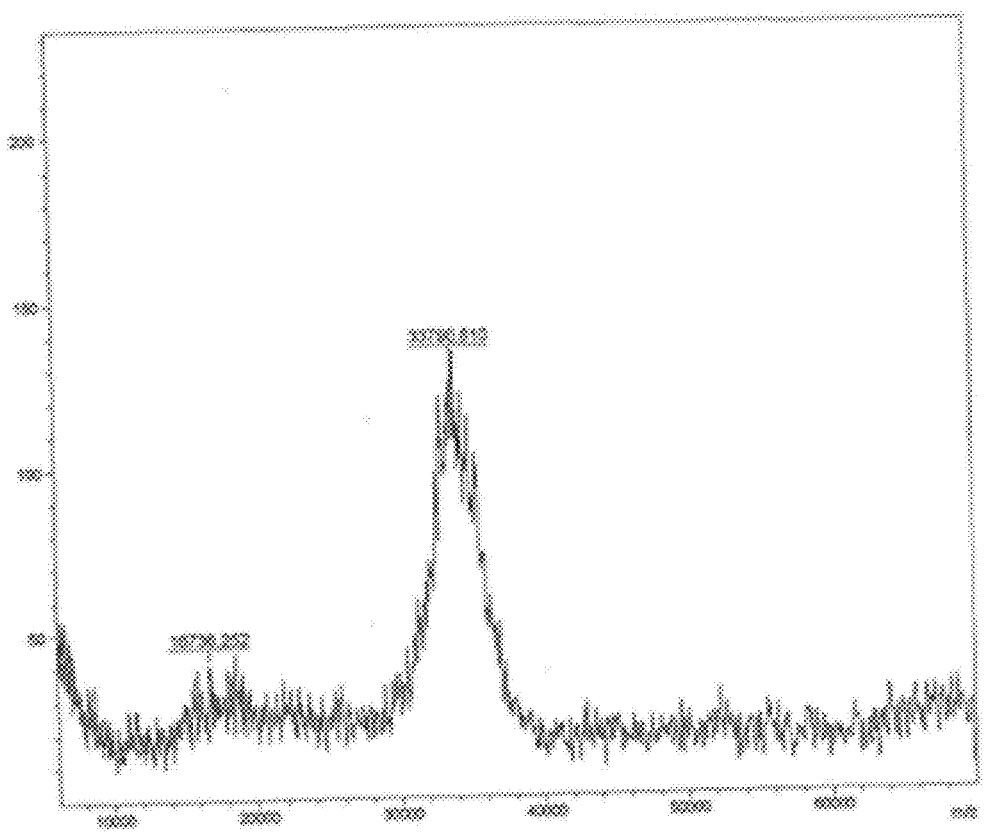
FIG. 118. MALDI-TOF spectrum for [mono]-[mPEG-Butyraldehyde-30K]-[C-peptide(S20C)].

FIG. 118. MALDI-TOF spectrum for [mono]-[mPEG-Butyraldehyde-30K]-[C-peptide(S20C)]. The major peak at 33.8 kD represents the molecular weight of monomeric [mono]-[mPEG-Butyraldehyde-30K]-[C-peptide(S20C)].

Example C-PEP4

PEGylation of C-Peptide(S20C) with [C2-PEG2-FMOC-NHS-40K]

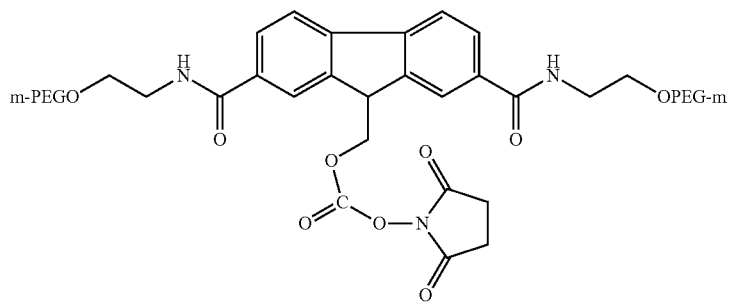

A stock solution of 2 mg/mL C-peptide(S20C) was prepared in 20 mM HCl. Immediately before a PEGylation reaction was initiated, a 56 mg/mL stock solution of C2-PEG2-FMOC-NHS-40K was prepared in 20 mM HCl. This PEG reagent forms reversible bonds with amine groups. To initiate a reaction, the two stock solutions were brought to 25° C. and then mixed in equal volumes. 1M sodium bicarbonate, pH 10.0, was immediately added (32 mM final concentration) and the reaction mixture was mixed for 10 minutes at 25° C. The reaction was quenched and the pH was lowered to 6.0 by the addition of 100 mM glycine in 100 mM HCl (10 mM final glycine concentration). After quenching, the mixture was diluted 4-fold with 10 mM ammonium acetate, pH 5.

The mono-PEGylated conjugate was purified from the reaction mixture by anion exchange chromatography using Q HP Sepharose media (GE Healthcare). The resin was packed in an XK 26/10 column (GE). Buffer A was 10 mM ammonium acetate, pH 5, and Buffer B was 10 mM ammonium acetate, pH 5, 1M NaCl. The resin was washed in buffer B and equilibrated in buffer A prior to sample loading. After loading, the resin was washed with 2 column volumes buffer A and the PEGylated and nonPEGylated peptides were eluted using a linear gradient of 0-100% B in 10 column volumes at a flow rate of 8 mL/min.

Fractions collected during anion exchange chromatography were analyzed using reversed-phase HPLC. The mobile phases were: A, 0.1% TFA in water and B, 0.85% TFA in acetonitrile. An Agilent Poroshell 300-SB-C8 column was used with a flow rate of 0.2 ml/min and a column temperature of 50° C. Detection was carried out at 215 nm and 313 nm. The column was equilibrated in 0% B and conjugate separation was achieved using the gradient timetable shown in Table C-PEP4.1.

| TIME (MIN) | % MOBILE PHASE A | % MOBILE PHASE B |
|---|---|---|
| 0.00 | 100.0 | 0.0 |
| 5.00 | 100.0 | 0.0 |

-continued

| TIME (MIN) | % MOBILE PHASE A | % MOBILE PHASE B |
|---|---|---|
| 10.00 | 70.0 | 30.0 |
| 20.00 | 30.0 | 70.0 |
| 21.00 | 20.0 | 80.0 |
| 25.00 | 20.0 | 80.0 |
| 30.00 | 100.0 | 0.0 |

Fractions containing pure [mono]-[C2-PEG2-FMOC-40K]-[C-peptide(S20C)] as determined by analytical RP-HPLC were pooled and concentrated over a reversed phase CG71S column. The column was washed with 0.5% acetic acid in acetonitrile and equilibrated with 0.5% acetic acid prior to sample loading. After loading, the column was washed with 0.5% acetic acid and the PEGylated peptide was eluted with 0.5% acetic acid in acetonitrile. Fractions containing PEGylated peptide fractions were collected, lyophilized and stored at −80° C.

Figure 119:
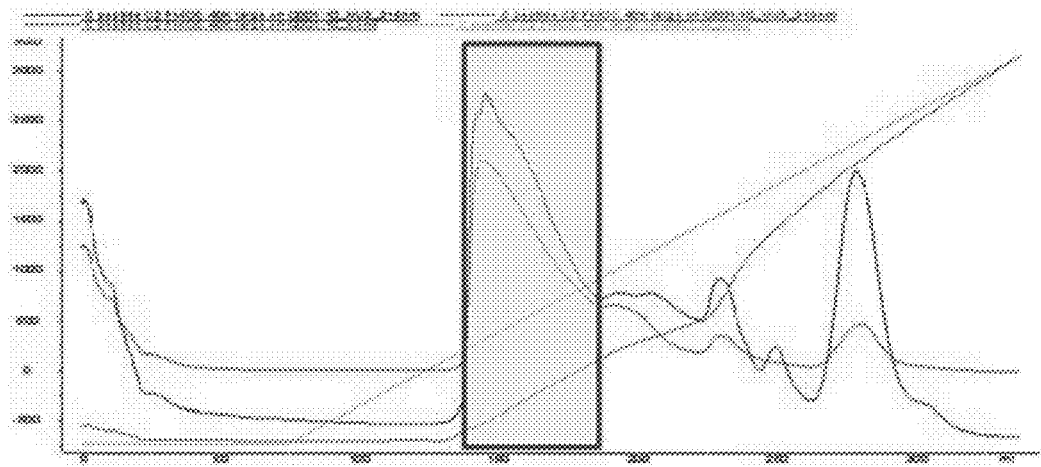
FIG. 119. Typical anion-exchange chromatography profile of [mono]-[C2-PEG2-FMOC-40K]-[C-peptide(S20C)].

A typical anion-exchange chromatogram is shown in FIG. 119. RP-HPLC analysis of [mono]-[C2-PEG2-FMOC-40K]-[C-peptide(S20C)] is shown in FIG. 120, and MALDI-TOF analysis of the purified conjugate is shown in FIG. 121.

The purity of the mono-PEG-conjugate was >98% by RP-HPLC analysis. The mass as determined by MALDI-TOF was within the expected range.

FIG. 119. Typical anion-exchange chromatography profile of [mono]-[C2-PEG2-FMOC-40K]-[C-peptide(S20C)]. The mono-PEGylated conjugate is indicated in the grey box. The blue line represents absorbance at 215 nm and the red line represents absorbance at 313 nm.

Figure 120:
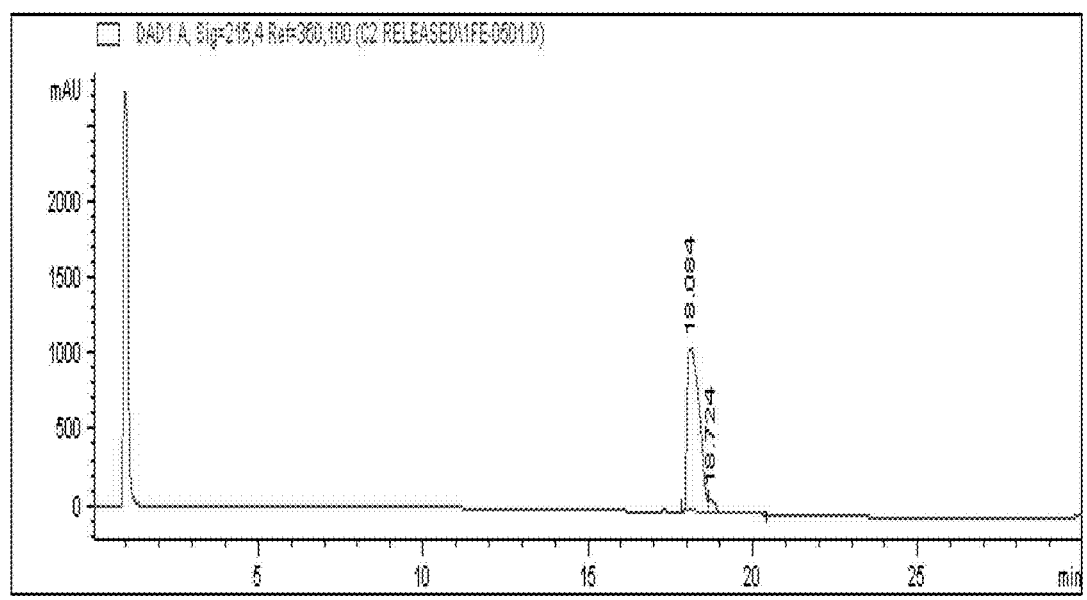
FIG. 120. Purity analysis of [[mono]-[C2-PEG2-FMOC-40K]-[C-peptide(S20C)] by reversed phase HPLC.
Figure 121:
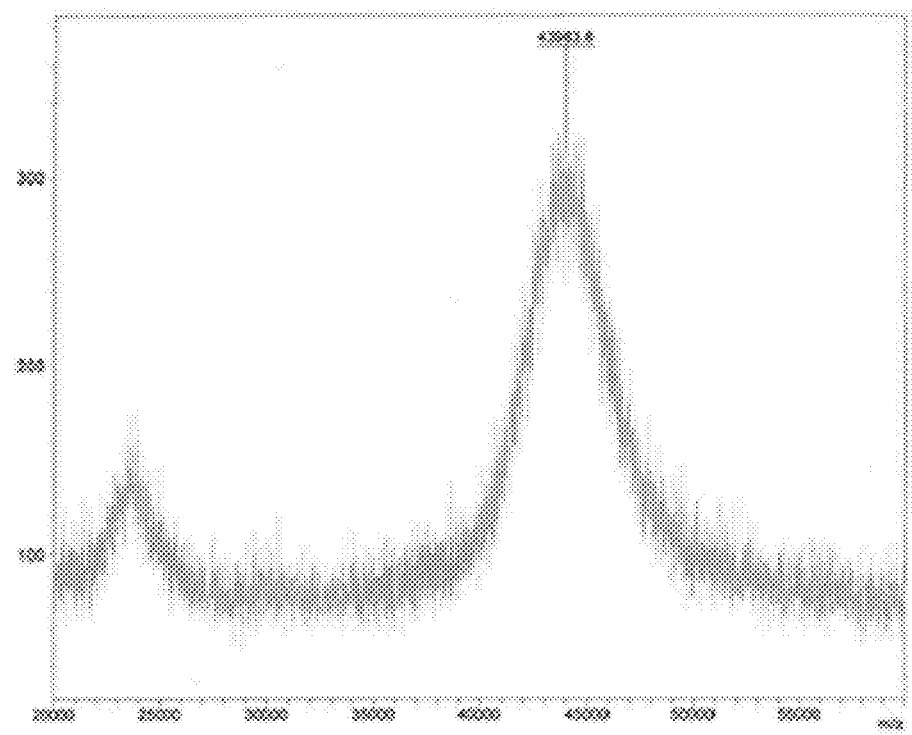
FIG. 121. MALDI-TOF spectrum for [mono]-[C2-PEG2-FMOC-40K]-[C-peptide(S20C)].

FIG. 120. Purity analysis of [[mono]-[C2-PEG2-FMOC-40K]-[C-peptide(S20C)] by reversed phase HPLC.

FIG. 121. MALDI-TOF spectrum for [mono]-[C2-PEG2-FMOC-40K]-[C-peptide(S20C)]. The major peak at 44.0 kD represents the molecular weight of monomeric [mono]-[mPEG-CAC-PEG2-FMOC-40K]-[C-peptide(S20C)].

Example C-PEP5

PEGylation of C-Peptide(S20C) with [CAC-PEG2-FMOC-NHS-40K]

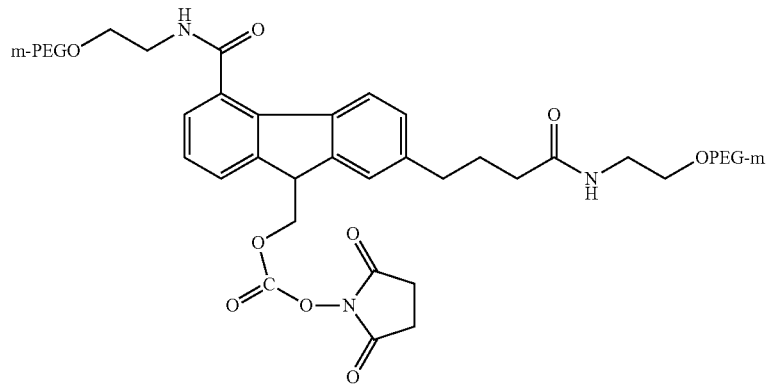

A stock solution of 4 mg/mL C-peptide(S20C) was prepared in water. The peptide stock solution was diluted 1:1 in 1M HEPES, pH 7.0, resulting in a peptide concentration of 2 mg/mL. Immediately before a PEGylation reaction was initiated, a 128 mg/mL stock solution of CAC-PEG2-FMOC-NHS-40K was prepared in 2 mM HCl. This PEG reagent forms reversible bonds with amine and thiol groups. To initiate a reaction, the PEG stock solution and 2 mg/mL peptide solution were brought to 25° C. and then mixed in equal volumes. The reaction mixture was stirred for 3 hours at 25° C. After 3 hours, 100 mM Glycine in 2 mM HCl was added (10 mM final glycine concentration).

The mono-PEGylated conjugate was purified from the reaction mixture by anion exchange chromatography using Q HP Sepharose HP media (GE Healthcare). The resin was packed in an XK 26/10 column (GE). Buffer A was 10 mM HEPES, pH 7.0, and Buffer B was 10 mM HEPES, pH 7.0, 1M NaCl. The resin was washed in buffer B and equilibrated in buffer A prior to sample loading. After loading, the resin was washed with 2 column volumes buffer A and the PEGylated and nonPEGylated peptides were eluted using a linear gradient of 0-100% B in 10 column volumes at a flow rate of 7 mL/min.

Fractions collected during anion exchange chromatography were analyzed using reversed-phase HPLC. The mobile phases were: A, 0.1% TFA in water and B, 0.85% TFA in acetonitrile. An Agilent Poroshell 300-SB-C8 column was used with a flow rate of 0.2 ml/min and a column temperature of 50° C. Detection was carried out at 215 nm and 313 nm. The column was equilibrated in 0% B and conjugate separation was achieved using the gradient timetable shown in Table C-PEP5.1.

| TIME (MIN) | % MOBILE PHASE A | % MOBILE PHASE B |
|---|---|---|
| 0.00 | 100.0 | 0.0 |
| 5.00 | 100.0 | 0.0 |
| 10.00 | 70.0 | 30.0 |
| 20.00 | 30.0 | 70.0 |
| 21.00 | 20.0 | 80.0 |
| 25.00 | 20.0 | 80.0 |

Fractions containing pure [mono]-[CAC-PEG2-FMOC-40K]-[C-peptide(S20C)] as determined by analytical RP-HPLC were pooled and concentrated over a reversed phase CG71S column. The column was washed with 0.5% acetic acid in acetonitrile and equilibrated with 0.5% acetic acid prior to loading. After loading, the column was washed with 0.5% acetic acid and the PEGylated peptide was eluted with 0.5% acetic acid in acetonitrile. Fractions containing PEGylated peptide were collected, lyophilized and stored at −80° C.

Figure 122:
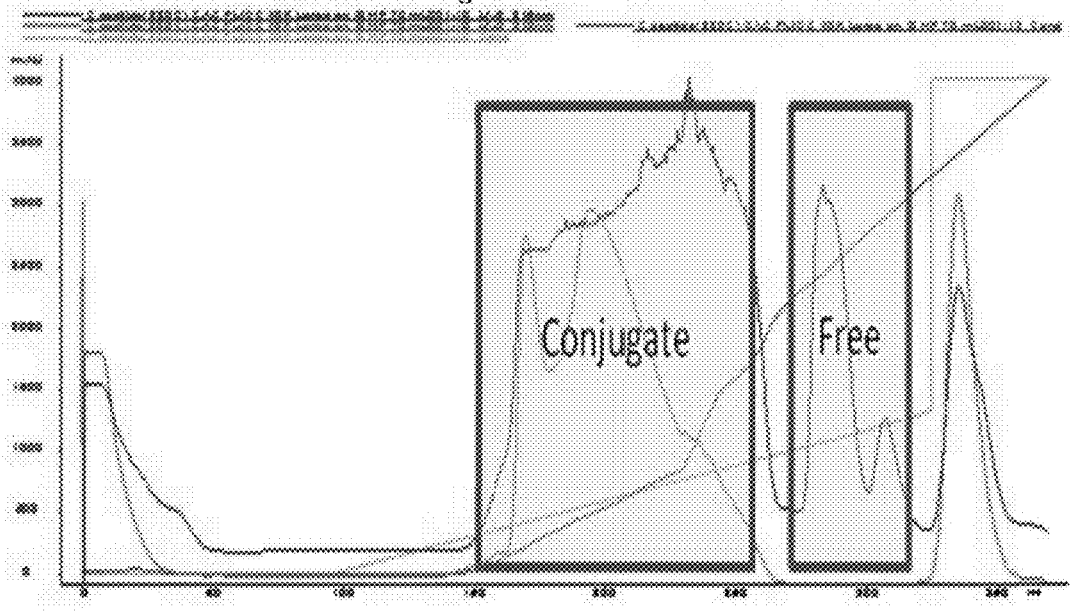
FIG. 122. Typical anion-exchange purification profile of [mono]-[CAC-PEG2-FMOC-40K]-[C-peptide(S20C)].

A typical anion-exchange chromatogram is shown in FIG. 122. RP-HPLC analysis of [mono]-[CAC-PEG2-FMOC-40K]-[C-peptide(S20C)] is shown in FIG. 123 and MALDI-TOF analysis of the purified conjugate is shown in FIG. C-PEP5.3.

The purity of the mono-PEG-conjugate was >98% by RP-HPLC analysis. The mass as determined by MALDI-TOF was within the expected range.

FIG. 122. Typical anion-exchange purification profile of [[mono]-[CAC-PEG2-FMOC-40K]-[C-peptide(S20C)].
The mono-PEGylated conjugate and nonPEGylated peptide (Free) are indicated in grey boxes. The blue line represents absorbance at 215 nm and the purple line represents absorbance at 313 nm.

FIG. 123. Purity analysis of [mono]-[CAC-PEG2-FMOC-40K]-[C-peptide(S20C)] by reversed phase HPLC. No Free peptide was detected. The first peak contains monoconjugated peptide and the second peak contains primarily di-conjugated peptide in which the N-terminal amine and cysteine thiol groups are both conjugated.

Example C-PEP6

Conjugation of C-Peptide(S20C) with Dextran Tetraethyleneglycol-Butyraldehyde 40K

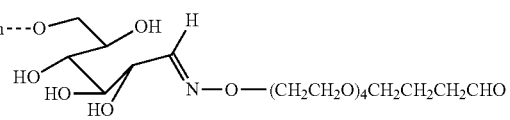

Stock solutions of 2 mg/mL C-peptide(S20C) and 200 mg/mL dextran tetra ethylene glycol (TEG)-butyraldehyde 40K, both in 500 mM HEPES, pH 7.0, were prepared. To initiate a reaction, both stock solutions were brought to 25° C. and then mixed in equal volumes. The reaction mixture was stirred at 25° C. After 1 hour reaction, 10 mM sodium cyanoborohydride (final concentration) was added and the reaction was allowed to proceed for an additional 16 hours.

The dextran-C-peptide(S20C) conjugate was purified from the reaction mixture by anion-exchange chromatography using Q HP Sepharose resin (GE Healthcare). Upon completion of the conjugation reaction, the reaction mixture was diluted 2-fold with water and loaded onto a column packed with the Sepharose resin. Buffer A was 10 mM HEPES, pH 7.0, and buffer B was 10 mM HEPES, pH 7.0, 1.0 M NaCl. The resin was washed with buffer B and equilibrated with buffer A prior to sample loading. After loading, the column was washed with 2 CV buffer A. Conjugated and nonconjugated peptides were eluted in a linear gradient of 0-100% buffer B in 10 CV at a flow rate of 8 mL/min.

Fraction II collected during chromatography with Q HP Sepharose was diluted 10-fold with water and re-loaded onto the Q column in order to concentrate the conjugate. The conjugate was eluted with 100% buffer B.

Fractions collected during both anion exchange chromatography runs were analyzed using reversed-phase HPLC.

absorbance at 215 nm. FIG. 125. Concentration of fraction II from the anion-exchange chromatogram shown in FIG. 1.1 by a second anion-exchange chromatography run. The blue line represents absorbance at 215 nm. FIG. 126. Purity analysis of [[mono]-[Dextran-40K]-[C-peptide(S20C)] by reversed phase HPLC. The purity of the purified conjugate was determined to be NLT 93% at 215 nm. FIG. 127. MALDI-TOF spectrum for [mono]-[Dextran-40K]-[C-peptide(S20C)]. The peaks at 43.2 kDa and 22.0 kDa agree with molecular weights of the single and double charged forms of the conjugated peptide.

Example OGF2

PEGylation of Opioid Growth Factor (OGF) with [mPEG2-CAC-FMOC-NHS-40K]

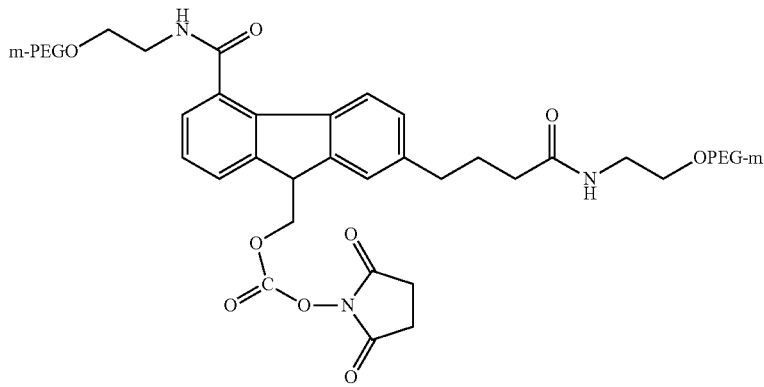

The mobile phases were: A, 0.1% TFA in water and B, 0.85% TFA in acetonitrile. An Agilent Poroshell 300-SB-C8 column was used with a flow rate of 0.2 ml/min and a column temperature of 50° C. Detection was carried out at 215 nm. The column was equilibrated in 0% B and conjugate separation was achieved using the gradient timetable shown in Table C-PEP6.1.

| Time (min) | % Mobile phase A | % Mobile phase B |
|---|---|---|
| 0.00 | 100.0 | 0.0 |
| 5.00 | 70.0 | 30.0 |
| 15.00 | 40.0 | 60.0 |
| 20.00 | 20.0 | 80.0 |

The concentrated purified conjugate collected from the second anion exchange chromatography run was dialyzed against water and frozen at −80° C. Typical anion-exchange chromatograms of the reaction mixture and Fraction II are shown in FIG. 124 and FIG. 125, respectively. RP-HPLC analysis of purified [mono]-[Dextran-40K]-[C-peptide (S20C)] is shown in FIG. 126 and MALDI-TOF analysis of the purified conjugate is shown in FIG. 127.

The purity of the mono-dextran conjugate was >93% by RP-HPLC analysis. The mass as determined by MALDI-TOF was within the expected range. FIG. 124 Typical anion-exchange chromatography profile of dextran-butryal-dehyde-40K-C-peptide(S20C). Fractions containing the conjugate are indicated in box II. The blue line represents Stock solutions of 2.0 mg/mL OGF and 200 mG/mL mPEG2-CAC-FMOC-NHS-40K were prepared in 2 mM HCl. To initiate a reaction, the two stock solutions and a 0.5 M MES, pH 6.0, stock solution were brought to 25° C. and the three stock solutions were mixed (PEG reagent added last) to give final concentrations of 1.25 mg/mL OGF (2.2 mM), 20 mM MES and a 1.25-fold molar excess of OGF over mPEG2-CAC-FMOC-NHS-40K. After 3 hours at 25° C. the reaction was quenched with 100 mM glycine in 100 mM HCl (10 mM final glycine concentration) for 10 minutes. The quenched reaction mixture was diluted with deionized sterile $H_2O$ until the conductivity of the diluted reaction mixture was below 0.5 mS/cm, and the pH was then adjusted to 6.0 with 1 M $NaHCO_3/Na_2CO_3$, pH 10.0.

The mono-PEGylated conjugate was purified from the diluted reaction mixture by anion exchange chromatography using a column packed with Q-HP media (GE Healthcare) and reversed phase chromatography using a column packed with CG17S media (Rohm Haas) on an AKTA Explorer 100 system (GE Healthcare). The AKTA Explorer plumbing system and both columns were sanitized with 1 M HCl and 1 M NaOH before use. The diluted reaction mixture was first loaded onto the Q-HP column that had been equilibrated with 15 column volumes of 20 mM MES, pH 6.0. Unreacted OGF but not mono-[mPEG2-CAC-FMOC-40K]-[OGF] and unreacted PEG bound to the Q-HP resin and the conjugate and unreacted PEG were collected in the column void fraction. Glacial acidic acid was added to the void fraction to a final concentration of 5% (v/v) and the mixture was loaded onto the CG-71S column that had been equilibrated with 5% acetic acid/95% H₂O (v/v) (Solvent A). After sample loading, the column was washed with 10 column volumes Solvent A to remove unreacted PEG. The conjugate was eluted with a linear gradient from 100% A to 20% A/80% B [Solvent B was 5% acetic acid/95% acetonitrile (v/v)] over 10 column volumes with a linear flow rate of 90 cm/hour.

Fractions collected during reverse phase chromatography were analyzed using analytical reversed-phase HPLC. The mobile phases were: A, 0.09% TFA in water, and B, 0.04% TFA in acetonitrile. An Agilent Poroshell SB-300 C8 column (2.1 mm×75 mm) was used with a flow rate of 0.5 ml/min and a column temperature of 60° C. Detection was carried out at 280 nm. The column was equilibrated in 0% B and conjugate separation was achieved using the gradient timetable shown in Table OGF2.1.

| Time (min) | % Mobile phase A | % Mobile phase B |
|---|---|---|
| 0.00 | 100.0 | 0.0 |
| 3.00 | 100.0 | 0.0 |
| 5.00 | 80.0 | 20.0 |
| 16.00 | 40.0 | 60.0 |
| 19.00 | 40.0 | 60.0 |
| 25.00 | 20.0 | 80.0 |
| 28.00 | 20.0 | 80.0 |

Fractions containing pure mono-[mPEG2-CAC-FMOC-40K]-[OGF] as determined by analytical RP-HPLC were pooled, lyophilized and stored at −80° C. A typical CG71S reversed phase chromatogram is shown in FIG. OGF2.1. RP-HPLC analysis of the purified conjugate is shown in FIG. 129, and MALDI-TOF analysis of the purified conjugate is shown in FIG. 130. The purity of the mono-PEG-conjugate was 100% by RP-HPLC analysis. The mass as determined by MALDI-TOF was within the expected range. FIG. 128. Typical CG71S reversed phase purification profile of mono-[mPEG2-CAC-FMOC-40K]-[OGF]. The mono-PEGylated conjugate and unreacted PEG are indicated. FIG. 129. Purity analysis of [mono]-[CAC-PEG2-FOMC-40K]-[OGF] by reversed phase HPLC. The purity of the purified conjugate is determined to be 100% at 280 nm. FIG. 130. MALDI-TOF spectrum of purified mono-[mPEG2-FMOC-CAC-40K]-[OGF]. The peak at 41997.4 Da is within the expected range for the molecular weight of the mono-PEG-conjugate. The very weak signal is due to the absence of a positive charge on the conjugate.

Example OGF3

PEGylation of Opioid Growth Factor (OGF) with [mPEG2-C2-FMOC-NHS-40K]

Stock solutions of 2.0 mg/mL OGF and 200 mG/mL mPEG2-C2-FMOC-NHS-40K were prepared in 2 mM HCl. To initiate a reaction, the two stock solutions and a 0.5 M MES, pH 6.0, stock solution were brought to 25° C. and the three stock solutions were mixed (PEG reagent added last) to give final concentrations of 1.25 mg/mL OGF (2.2 mM), 20 mM MES and a 1.25-fold molar excess of OGF over mPEG2-C2-FMOC-NHS-40K. After 3 hours at 25° C. the reaction was quenched with 100 mM glycine in 100 mM HCl (10 mM final glycine concentration) for 10 minutes. The quenched reaction mixture was diluted with deionized sterile H₂O until the conductivity of the diluted reaction mixture was below 0.5 mS/cm, and the pH was then adjusted to 6.0 with 1 M NaHCO₃/Na₂CO₃, pH 10.0.

The mono-PEGylated conjugate was purified from the diluted reaction mixture by anion exchange chromatography using a column packed with Q-HP media (GE Healthcare) and reversed phase chromatography using a column packed with CG17S media (Rohm Haas) on an AKTA Explorer 100 system (GE Healthcare). The AKTA Explorer plumbing system and both columns were sanitized with 1 M HCl and 1 M NaOH before use. The diluted reaction mixture was first loaded onto the Q-HP column that had been equilibrated with 15 column volumes of 20 mM MES, pH 6.0. Unreacted OGF but not mono-[mPEG2-C2-FMOC-40K]-[OGF] and unreacted PEG bound to the Q-HP resin and the conjugate and unreacted PEG were collected in the column void fraction. Glacial acidic acid was added to the void fraction to a final concentration of 5% (v/v) and the mixture was loaded onto the CG-71S column that had been equilibrated with 10 column volumes of 5% acetic acid/95% H₂O (v/v) (Solvent A). After sample loading, the column was washed with 6 column volumes 5% acetic acid/20% ethanol/75% H₂O (v/v/v) to elute unreacted PEG. The conjugate was eluted with a linear gradient from 100% A to 100% B [Solvent B was 5% acetic acid/95% acetonitrile (v/v)] over 10 column volume with a linear flow rate of 90 cm/hour.

Fractions collected during reverse phase chromatography were analyzed using analytical reversed-phase HPLC. The mobile phases were: A, 0.09% TFA in water, and B, 0.04% TFA in acetonitrile. An Agilent Poroshell SB-300 C8 column (2.1 mm×75 mm) was used with a flow rate of 0.5 ml/min and a column temperature of 60° C. Detection was carried out at 280 nm. The column was equilibrated in 0% B and conjugate separation was achieved using the gradient timetable shown in Table OGF3.1.

| Time (min) | % Mobile phase A | % Mobile phase B |
|---|---|---|
| 0.00 | 100.0 | 0.0 |
| 3.00 | 100.0 | 0.0 |
| 5.00 | 80.0 | 20.0 |

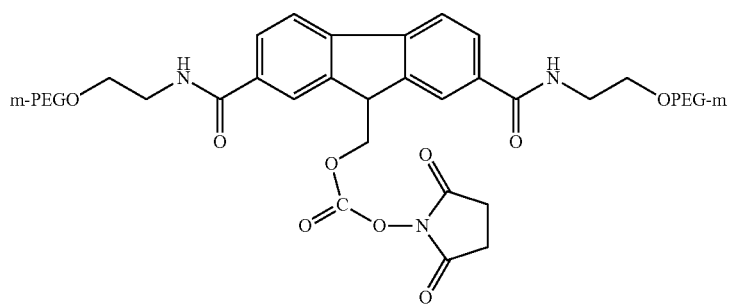

-continued

| Time (min) | % Mobile phase A | % Mobile phase B |
|---|---|---|
| 16.00 | 40.0 | 60.0 |
| 19.00 | 40.0 | 60.0 |
| 25.00 | 20.0 | 80.0 |
| 28.00 | 20.0 | 80.0 |

Fractions containing pure mono-[mPEG2-C2-FMOC-40K]-[OGF] as determined by analytical RP-HPLC were pooled, lyophilized and stored at −80° C. A typical CG71S reversed phase chromatogram is shown in FIG. 131. RP-HPLC analysis of the purified conjugate is shown in FIG. 132, and MALDI-TOF analysis of the purified conjugate is shown in FIG. 133. The purity of the mono-[mPEG2-C2-FMOC-40K]-[OGF] was 97.1% by RP-HPLC analysis. The mass as determined by MALDI-TOF was within the expected range. FIG. 131. Typical CG71S reverse phase purification profile of mono-[mPEG2-C2-FMOC-40K]-[OGF]. The mono-PEGylated conjugate and unreacted PEG are indicated. The resin was overloaded upon sample loading and mono-[mPEG2-C2-FMOC-40K]-[OGF] was found in the void fraction. The void fraction containing the conjugate was reloaded onto the CG71S column and the conjugate was eluted in a second reversed phase chromatography run (data not shown). FIG. 132. Purity analysis of mono-[mPEG2-FMOC-C2-40K]-[OGF] by reversed phase HPLC. The purity of the purified conjugate is determined to be 97.1% at 280 nm. The peak at 8.15 minutes is OGF. FIG. 133. MALDI-TOF spectrum of purified mono-[mPEG2-FMOC-C2-40K]-[OGF]. The peak at 41322.1 Da is within the expected range for the molecular weight of the mono-PEG-conjugate. The very weak signal is due to the absence of a positive charge on the conjugate.

Example OGF4

PEGylation of Opioid Growth Factor (OGF) with [mPEG-Butyraldehyde-30K]

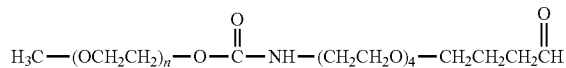

Stock solutions of 2.0 mg/mL OGF and 200 mG/mL mPEG-Butyraldehyde-30K were prepared in 2 mM HCl. To initiate a reaction, the two stock solutions and a 1 M HEPES, pH 7.0, stock solution were brought to 25° C. and the three stock solutions were mixed (PEG reagent added last) to give final concentrations of 1.25 mg/mL OGF (2.2 mM), 20 mM HEPES and a 1.25-fold molar excess of OGF over mPEG-Butyraldehyde-30K. After 15 minute reaction at 25° C., a 50-fold molar excess of $NaBH_3CN$ over PEG was added, and the reaction was allowed to continue for an additional 16 hours at 25° C. After 16 hr 15 min total reaction time, the reaction was quenched with 100 mM glycine in 100 mM HCl (10 mM final glycine concentration) for 10 minutes. The reaction mixture was diluted with deionized sterile $H_2O$ until the conductivity of the diluted reaction mixture was below 0.5 mS/cm, and the pH was then adjusted to 7.0 with 1 M $NaHCO_3/Na_2CO_3$, pH 10.0.

The mono-PEGylated conjugate was purified from the diluted reaction mixture by anion exchange chromatography using a column packed with Q-HP media (GE Healthcare) and reversed phase chromatography using a column packed with CG17S media (Rohm Haas) on an AKTA Explorer 100 system (GE Healthcare). The AKTA Explorer plumbing system and both columns were sanitized with 1 M HCl and 1 M NaOH before use. The diluted reaction mixture was first loaded onto the Q-HP column that had been equilibrated with 15 column volumes of 20 mM HEPES, pH 7.0. Unreacted OGF but not mono-[mPEG-Butyraldehyde-30K]-[OGF] and unreacted PEG bound to the Q-HP resin and the conjugate and unreacted PEG were collected in the column void fraction. Glacial acidic acid was added to the void fraction to a final concentration of 5% (v/v) and the mixture was loaded onto the CG-71S column that had been equilibrated with 5% acetic acid/95% $H_2O$ (v/v) (Solvent A). After sample loading, the column was washed with 10 column volumes Solvent A to remove unreacted PEG. The conjugate was eluted with a linear gradient from 100% A to 20% A/80% B [Solvent B was 5% acetic acid/95% acetonitrile (v/v)] over 20 column volumes with a linear flow rate of 90 cm/hour.

Fractions collected during reverse phase chromatography were analyzed using analytical reversed-phase HPLC. The mobile phases were: A, 0.09% TFA in water, and B, 0.04% TFA in acetonitrile. An Agilent Poroshell SB-300 C8 column (2.1 mm×75 mm) was used with a flow rate of 0.5 ml/min and a column temperature of 60° C. Detection was carried out at 280 nm. The column was equilibrated in 0% B and conjugate separation was achieved using the gradient timetable shown in Table OGF4.1.

| Time (min) | % Mobile phase A | % Mobile phase B |
|---|---|---|
| 0.00 | 100.0 | 0.0 |
| 3.00 | 100.0 | 0.0 |
| 5.00 | 80.0 | 20.0 |
| 16.00 | 40.0 | 60.0 |
| 19.00 | 40.0 | 60.0 |
| 25.00 | 20.0 | 80.0 |
| 28.00 | 20.0 | 80.0 |

Fractions containing pure mono-[mPEG-ButALD-30K]-[OGF] as determined by analytical RP-HPLC were pooled, lyophilized and stored at −80° C. A typical CG71S reversed phase chromatogram is shown in FIG. 134. RP-HPLC analysis of the purified conjugate is shown in FIG. 135. The purity of the mono-[mPEG-ButALD-FMOC-30K]-[OGF] was 95.3% by RP-HPLC analysis. FIG. 134. Typical CG71S reversed phase purification profile of mono-[mPEG-Butyraldehyde-30K]-[OGF]. The mono-PEGylated conjugate is indicated. The resin was overloaded upon sample loading and mono-[mPEG-Butyraldehyde-30K]-[OGF] was found in the void fraction. The void fraction containing the conjugate was reloaded onto the CG71S column and the conjugate was eluted in a second reversed phase chromatography run (data not shown). FIG. 135. Purity analysis of mono-[mPEG-ButyrAldehyde-30K]-[OGF] by reversed phase HPLC. The purity of the purified conjugate is determined to be 95.3% at 280 nm. The peak with retention time at 1.69 minutes was acetic acid derived from CG71S reversed phase chromatography.

Example OGF5

PEGylation of Opioid Growth Factor (OGF) with [mPEG-Epoxide-5K]

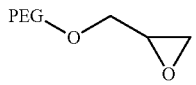

Stock solutions of 2.0 mg/mL OGF and 200 mG/mL mPEG-epoxide-5K were prepared in 2 mM HCl. To initiate a reaction, the two stock solutions and a 0.5 M MES, pH 6.0, stock solution were brought to 25° C. and the three stock solutions were mixed (PEG reagent added last) to give final concentrations of 1.25 mg/mL OGF (2.2 mM), 20 mM MES and a 1.25-fold molar excess of OGF over mPEG-epoxide-5K over OGF. After 15 hours at 25° C. the reaction was quenched with 100 mM glycine in 100 mM HCl (10 mM final glycine concentration) for 10 minutes. The quenched reaction mixture was diluted with deionized sterile $H_2O$ until the conductivity of the diluted reaction mixture was below 0.5 mS/cm, and the pH was then adjusted to 6.0 with 1 M $NaHCO_3/Na_2CO_3$, pH 10.0.

The mono-PEGylated conjugate was purified from the diluted reaction mixture by anion exchange chromatography using a column packed with Q-HP media (GE Healthcare) and reversed phase chromatography using a column packed with CG17S media (Rohm Haas) on an AKTA Explorer 100 system (GE Healthcare). The AKTA Explorer plumbing system and both columns were sanitized with 1 M HCl and 1 M NaOH before use. The diluted reaction mixture was first loaded onto the Q-HP column that had been equilibrated with 15 column volumes of 20 mM MES, pH 6.0. Unreacted OGF but not mono-[mPEG2-CAC-FMOC-40K]-[OGF] and unreacted PEG bound to the Q-HP resin and the conjugate and unreacted PEG were collected in the column void fraction. Glacial acidic acid was added to the void fraction to a final concentration of 5% (v/v) and the mixture was loaded onto the CG-71S column that had been equilibrated with 5% acetic acid/95% $H_2O$ (v/v) (Solvent A). After sample loading, the column was washed with 10 column volumes Solvent A to remove unreacted PEG. The conjugate was eluted with a linear gradient from 100% A to 20% A/80% B [Solvent B was 5% acetic acid/95% acetonitrile (v/v)] over 10 column volumes with a linear flow rate of 90 cm/hour.

Fractions collected during reverse phase chromatography were analyzed using analytical reversed-phase HPLC. The mobile phases were: A, 0.09% TFA in water, and B, 0.04% TFA in acetonitrile. An Agilent Poroshell SB-300 C8 column (2.1 mm×75 mm) was used with a flow rate of 0.5 ml/min and a column temperature of 60° C. Detection was carried out at 280 nm. The column was equilibrated in 0% B and conjugate separation was achieved using the gradient timetable shown in Table OGF5.1.

| Time (min) | % Mobile phase A | % Mobile phase B |
|---|---|---|
| 0.00 | 100.0 | 0.0 |
| 3.00 | 100.0 | 0.0 |
| 5.00 | 80.0 | 20.0 |
| 16.00 | 40.0 | 60.0 |
| 19.00 | 40.0 | 60.0 |
| 25.00 | 20.0 | 80.0 |
| 28.00 | 20.0 | 80.0 |

Fractions containing pure mono-[mPEG-epoxide-5K]-[OGF] as determined by analytical RP-HPLC were pooled, lyophilized and stored at −80° C. A typical GC71S reversed phase chromatogram is shown in FIG. 136. RP-HPLC analysis of the purified conjugate is shown in FIG. 137. The purity of the mono-[mPEG-epoxide-5K]-[OGF] was 100% by RP-HPLC analysis. FIG. 136. Typical CG71S reversed phase purification profile of mono-[mPEG-epoxide-5K]-[OGF]. The mono-PEGylated conjugate is indicated. FIG. 137. Purity analysis of mono-[mPEG-epoxide-5K]-[OGF] by reversed phase HPLC. The purity of the purified conjugate is determined to be 100% at 280 nm.

Example OGF6

PEGylation of Opioid Growth Factor (OGF) with [mPEG-Butyraldehyde-10K]

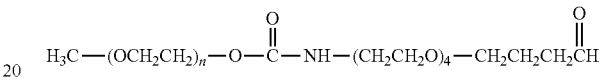

Stock solutions of 2.0 mg/mL OGF and 200 mG/mL mPEG-Butyraldehyde-10K were prepared in 2 mM HCl. To initiate a reaction, the two stock solutions and a 1 M HEPES, pH 7.0, stock solution were brought to 25° C. and the three stock solutions were mixed (PEG reagent added last) to give final concentrations of 1.25 mg/mL OGF (2.2 mM), 20 mM HEPES and a 1.25-fold molar excess of OGF over mPEG-Butyraldehyde-10K. After 15 minute reaction at 25° C., a 50-fold molar excess of $NaBH_3CN$ over PEG was added, and the reaction was allowed to continue for an additional 6 hours at 25° C. After 6 hr 15 min total reaction time, the reaction was quenched with 100 mM glycine in 100 mM HCl (10 mM final glycine concentration) for 10 minutes. The reaction mixture was diluted with deionized sterile $H_2O$ until the conductivity of the diluted reaction mixture was below 0.5 mS/cm, and the pH was then adjusted to 7.0 with 1 M $NaHCO_3/Na_2CO_3$, pH 10.0.

The mono-PEGylated conjugate was purified from the diluted reaction mixture by anion exchange chromatography using a column packed with Q-HP media (GE Healthcare) and reversed phase chromatography using a column packed with CG17S media (Rohm Haas) on an AKTA Explorer 100 system (GE Healthcare). The AKTA Explorer plumbing system and both columns were sanitized with 1 M HCl and 1 M NaOH before use. The diluted reaction mixture was first loaded onto the Q-HP column that had been equilibrated with 15 column volumes of 20 mM HEPES, pH 7.0. Unreacted OGF but not mono-[mPEG-Butyraldehyde-10K]-[OGF] and unreacted PEG bound to the Q-HP resin and the conjugate and unreacted PEG were collected in the column void fraction. Glacial acidic acid was added to the void fraction to a final concentration of 5% (v/v) and the mixture was loaded onto the CG-71S column that had been equilibrated with 5% acetic acid/95% $H_2O$ (v/v) (Solvent A). After sample loading, the column was washed with 10 column volumes Solvent A to remove unreacted PEG. The conjugate was eluted with a linear gradient from 100% A to 20% A/80% B [Solvent B was 5% acetic acid/95% acetonitrile (v/v)] over 20 column volumes with a linear flow rate of 90 cm/hour.

Fractions collected during reversed phase chromatography were analyzed using analytical reversed-phase HPLC. The mobile phases were: A, 0.09% TFA in water, and B, 0.04% TFA in acetonitrile. An Agilent Poroshell SB-300 C8 column (2.1 mm×75 mm) was used with a flow rate of 0.5 ml/min and a column temperature of 60° C. Detection was carried out at 280 nm. The column was equilibrated in 0% B and conjugate separation was achieved using the gradient timetable shown.

| Time (mm) | % Mobile phase A | % Mobile phase B |
|---|---|---|
| 0.00 | 100.0 | 0.0 |
| 3.00 | 100.0 | 0.0 |
| 5.00 | 80.0 | 20.0 |
| 16.00 | 40.0 | 60.0 |
| 19.00 | 40.0 | 60.0 |
| 25.00 | 20.0 | 80.0 |
| 28.00 | 20.0 | 80.0 |

Fractions containing pure mono-[mPEG-ButALD-10K]-[OGF] as determined by analytical RP-HPLC were pooled, lyophilized and stored at −80° C. A typical CG71S reversed phase chromatogram is shown in FIG. 138. RP-HPLC analysis of the purified conjugate is shown in FIG. 139. The purity of the mono-[mPEG-ButALD-FMOC-10K]-[OGF] was 100% by RP-HPLC analysis. FIG. 138. Typical CG71S reversed phase purification profile of mono-[mPEG-Butyraldehyde-10K]-[OGF]. The mono-PEGylated conjugate is indicated. The resin was overloaded upon sample loading and mono-[mPEG-Butyraldehyde-10K]-[OGF] was found in the void fraction. The void fraction containing the conjugate was reloaded onto the CG71S column and the conjugate was eluted in a second reversed phase chromatography run. FIG. 139. Purity analysis of mono-[mPEG-ButyrAldehyde-10K]-[OGF] by reversed phase HPLC. The purity of the purified conjugate is determined to be 100% at 280 nm. The peak with retention time at 1.7 minutes was acetic acid derived from CG71S reversed phase chromatography.

Example OGF7

Radioligand Competition Binding Assay for OGF Series at Mu and Delta Opioid Receptors.

The binding affinities of OGF (control) and PEG-OGF releasable conjugates were evaluated using radioligand binding assays in membranes prepared from CHO-K1 cells expressing recombinant human μ or δ opioid receptors.

Competition binding experiments were conducted by incubating membrane protein to equilibrium in triplicate in the presence of a fixed concentration of radioligand and increasing concentrations (0.01 nM to 10 μM) of test compound in 100 μL final volume. The radioligands used were specific for each receptor type, and the assay conditions are described in Table OGF7.2. Following incubations, the membranes were rapidly filtered through GF/B filter plate (presoaked with 0.5% polyethyleneimine), washed four times with cold 50 mM Tris-HCl, pH 7.5, and the bound radioactivity was then measured. Non-specific binding was measured in the presence of excess naloxone (100 μM); this value was subtracted from the total binding to yield the specific binding at each test concentration.

For the releasable PEG-OGF conjugates, the receptor-binding activity of both released OGF and PEG-OGF (unreleased) conjugates was tested. The test compounds were stored under acidic condition to stabilize the PEG conjugation. To test the activity of PEG-OGF conjugates, the sample was diluted on the day of the assay. To test the activity of released OGF, two samples were prepared prior to the assay based on pre-determined release rates (refer to Table OGF7.3); one sample was diluted 10-fold in assay buffer (pre-incubated under physiological-like conditions for a period until ~50% of OGF was estimated to be released) and the other sample was diluted 5-fold in 800 mM lysine solution, pH 10.0 (pre-incubated under forced release conditions for less than 24 hours until ~95% of OGF was estimated to be released).

$IC_{50}$ (concentration of test compound required to inhibit 50% of specific binding) values were obtained from non-linear regression analysis of dose-response curves, using GraphPad's Prism 5.01 software, and were calculated for those compounds that showed >50% inhibition of specific binding at the highest concentration tested. $K_i$ (affinity of test compound) was obtained using the Cheng Prusoff correction using experimental $K_d$ (affinity of radioligand) values that were previously determined under these assay conditions.

The binding affinities of OGF and PEG-OGF conjugates are shown in Table OGF7.1. Opioid growth factor displayed similar, high affinity (1.3-2.0 nM) for human μ and δ opioid receptors.

Since the releasable conjugates were pre-incubated, OGF was also pre-incubated for the maximum period to test the activity of the peptide itself under the pre-incubation treatment conditions. As shown in FIG. 140, OGF remained stable following pre-incubation under physiological-like (160 hours at 37° C., pH 7.5) and forced release conditions (16 hours at 37° C., pH 10.0). Pre-incubated OGF displayed similar, high affinity for μ and δ opioid receptors when compared to the control prepared on the day of the assay (Table OGF7.1).

Following pre-incubation of mono-mPEG2-CAC-40K-OGF for 160 hours and mono-mPEG2-C2-40K-OGF for 68 hours under physiological-like conditions, affinity for μ and δ opioid receptors was increased (compared to PEG-OGF conjugates prepared on the day of the assay) and regained (FIG. 141); OGF released from these conjugates retained receptor binding activity as shown by <9-fold loss in affinity relative to OGF. Similarly, both PEG-OGF conjugates treated under forced release conditions displayed release of active OGF and high affinity binding to μ and δ opioid receptors as shown by <4-fold loss in affinity relative to OGF.

The mono-mPEG2-CAC-40K-OGF conjugate displayed much lower affinity for both receptors; reduction in affinity was 135 to 150-folds less relative to OGF. The mono-mPEG2-C2-40K-OGF conjugate displayed a 2-fold reduction in affinity at the μ opioid and δ opioid receptor; this slight loss in affinity suggests that the mono-mPEG2-C2-40K linker may have been unstable and resulted in faster release of OGF under the assay conditions.

For the free PEGs (CAC-40K-fulvene and C2-40K-fulvene), affinity for μ and δ opioid receptors was not seen as expected. As shown in FIG. 142, binding affinity could not be determined for the free PEGs since >50% inhibition of specific binding was not achieved up to the highest test concentration (10 μM). FIG. 140. Competition binding assay of OGF at human (A) μ opioid and (B) δ opioid receptors: effects of incubation treatment conditions. Data presented as mean (±SEM) percent specific binding. FIG. 141. Competition binding assay of OGF and PEG-OGF conjugates (released and unreleased) at human (A) μ opioid and (B) δ opioid receptors. Data presented as mean (±SEM) percent specific binding. FIG. 142. Competition binding assay of OGF and free PEGs at human (A) μ opioid and (B) δ opioid receptors. Data presented as mean (±SEM) percent specific binding.

TABLE OGF7.1

Summary of binding affinities for OGF, PEG-OGF conjugates, and free PEG.

| Compound | μ Opioid Receptor Ki (nM) | μ Opioid Receptor Fold Change Relative to OGF | δ Opioid Receptor Ki (nM) | δ Opioid Receptor Fold Change Relative to OGF |
|---|---|---|---|---|
| OGF | 1.5 | 1.0 | 1.8 | 1.0 |
| OGF (Pre-incubated) | 1.3 | 0.8 | 1.7 | 1.0 |
| Mono-mPEG2-FMOC-CAC-40K-OGF (Pre-incubated) | 10.8 | 7.2 | 15.2 | 8.6 |
| Mono-mPEG2-FMOC-C2-40K-OGF (Pre-incubated) | 4.3 | 2.9 | 3.5 | 2.0 |
| CAC-40K-fulvene (Free PEG) | Not obtained | Not obtained | Not obtained | Not obtained |
| C2-40K-fulvene (Free PEG) | Not obtained | Not obtained | Not obtained | Not obtained |
| OGF (Forced release) | 1.3 | 0.9 | 2.0 | 1.1 |
| Mono-mPEG2-FMOC-CAC-40K-OGF (Forced release) | 5.8 | 3.9 | 6.5 | 3.7 |
| Mono-mPEG2-FMOC-C2-40K-OGF (Forced release) | 3.3 | 2.2 | 3.2 | 1.8 |
| Mono-mPEG2-FMOC-CAC-40K-OGF | 223.9 | 149.9 | 237.3 | 134.6 |
| Mono-mPEG2-FMOC-C2-40K-OGF | 3.2 | 2.2 | 2.6 | 1.5 |

Not obtained = $K_i$ values could not be determined since >50% inhibition of specific binding was not achieved at the highest concentration tested.

TABLE OGF7.2

Assay conditions.

| Receptor | Receptor Source | Membrane Protein | Radioligand | $K_d$ | Non-specific binding | Methods |
|---|---|---|---|---|---|---|
| μ Opioid | Human recombinant CHO-K1 cells | 5 μg/well | [$^3$H] Naloxone (5 nM) | 2.0 nM | Naloxone (100 μM) | Reaction in 50 mM Tris-HCl (pH 7.5) at 25° C. for 1 h on plate shaker |
| δ Opioid | Human recombinant CHO-K1 cells | 15 μg/well | [$^3$H] DPDPE (5 nM) | 3.0 nM | Naloxone (100 μM) | Reaction in 50 mM Tris-HCl (pH 7.5), 5 mM $MgCl_2$, 0.1% BSA at 25° C. for 1 h on plate shaker |

TABLE OGF7.3

Compounds.

| Compound | MW (Da) | Stock conc. based on peptide (mg/mL) | Storage buffer | OGF Release rate | Pre-incubation condition | Forced release condition |
|---|---|---|---|---|---|---|
| OGF | 574 | 2.0 | 100 mM HEPES | — | 160 h in 50 mM Tris-HCl, 5 mM MgCl2, 0.1% BSA, pH 7.5 at 37° C. | 16 h in 800 mM lysine, pH 10.0 at 37° C. |
| Mono-mPEG2-FMOC-CAC-40K-OGF; releasable PEG | 41,332 | 4.4 | 2 mM HCl | 7.7% after 68 h at 37° C. in 150 mM Pi + 150 mM NaCl, pH 7.4. 95% within 24 h in 200 mM lysine, pH 10.0 | 160 h in 50 mM Tris-HCl, 5 mM MgCl2, 0.1% BSA, pH 7.5 at 37° C. | 16 h in 800 mM lysine, pH 10.0 at 37° C. |

TABLE OGF7.3-continued

| Compound | MW (Da) | Stock conc. based on peptide (mg/mL) | Storage buffer | OGF Release rate | Pre-incubation condition | Forced release condition |
|---|---|---|---|---|---|---|
| Mono-mPEG2-FMOC-C2-40K-OGF; Releasable | 41,332 | 5.0 | 2 mM HCl | 46% after 48 h at 37° C. in 150 mM Pi + 150 mM NaCl, pH 7.4. 97.8% within 24 h in 200 mM lysine, pH 10.0 | 68 h in 50 mM Tris-HCl, 5 mM MgCl2, 0.1% BSA, pH 7.5 at 37° C. | 16 h in 800 mM lysine, pH 10.0 at 37° C. |

Figure 3:
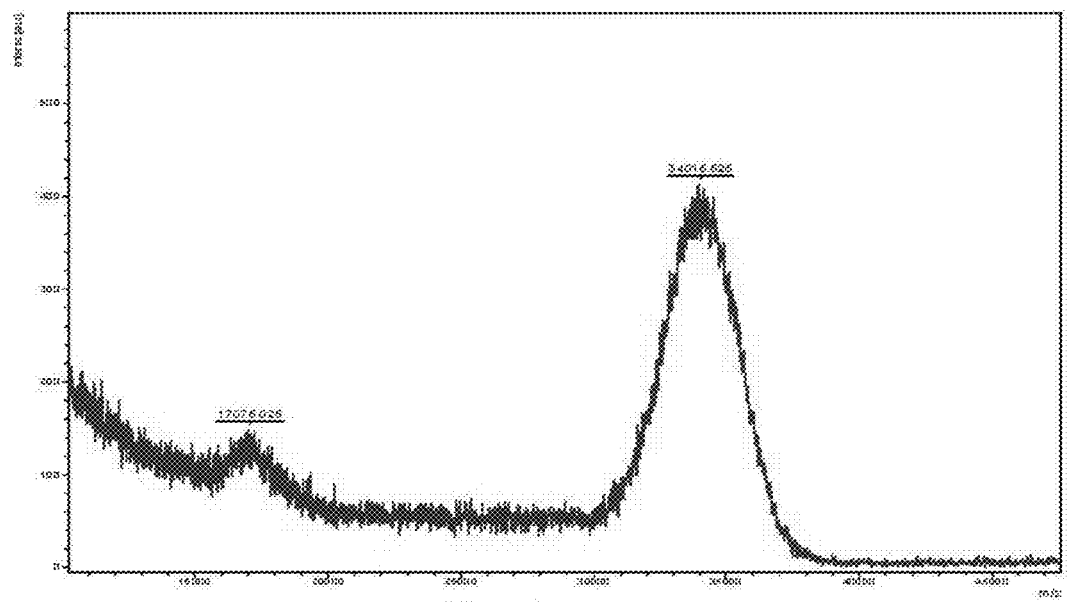
FIG. 3 MALDI-TOF spectrum of purified [mono]-[mPEG-ButyrALD-30K]-[Kisspeptin-13].

FIG. 140. Competition binding assay of OGF at human (A) μ opioid and (B) δ opioid receptors: effects of incubation treatment conditions. FIG. 141. Competition binding assay of OGF and PEG-OGF conjugates (released and unreleased) at human (A) μ opioid and (B) δ opioid receptors. FIG. 3. Competition binding assay of OGF and free PEGs at human (A) μ opioid and (B) δ opioid receptors.

Example INS1

Conjugation of Insulin with Dextran Tetraethylene Glycol-ButyrALD-40K

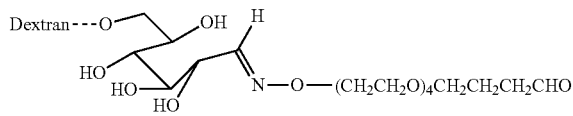

Insulin contains three primary amine groups, all of which can undergo a reductive amination reaction with dextran tetraethylene glycol-butyrALD-40K (dextran-butyrALD-40K). Reactions of insulin with dextran-butyrALD-40K therefore produce a mixture of mono-, di- and tri-conjugated peptides. The relative yields of the mono-, di- and tri-conjugated peptides depend primarily on the molar ratios of insulin and the dextran reagent used in the reactions and the reaction conditions (e.g., reaction time and temperature). The relative yield of the mono-conjugated peptide was determined to be very low unless reaction conditions were selected in which the majority of the insulin remained unreacted. In order to increase the relative and absolute yields of mono-conjugated insulin, a fraction of the amine groups on the peptide were blocked by acetylation prior to reacting the peptide and the dextran reagent. This example will describe the conjugation of both partially acetylated and non-acetylated insulin.

Conjugation of Partially Acetylated Insulin with Dextran-butyrALD-40K

Stock solutions of 2.5 mg/mL (430 μM) insulin, 2.24 mg/mL (8.62 mM) sulfo-N-hydroxysuccinimide (NHS)-acetate, and 138 mg/mL (3.45 mM) dextran-butyrALD-40K were prepared in DMSO/TEA (95%:5%, v/v), DMSO, and DMSO/TEA (99.35%:0.65%, v/v), respectively. To initiate an acetylation reaction of insulin, in which a fraction of the amine groups on the peptide are acetylated, the insulin and sulfo-NHS-acetate stock solutions were brought to ambient temperature and mixed at a 4:1 ratio (v/v). After 30 min acetylation reaction with stirring, conjugation of the peptide with dextran-butyrALD-40K was initiated by the drop-wise addition of an equal volume of dextran stock solution to the acetylation reaction mixture under vigorous stirring. Tween-20 was then added to a final concentration of 0.05% (v/v) and the reaction mixture was brought to 37° C. with stirring. 20 min after Tween-20 addition, 1 M sodium cyanoborohydride was added to a final concentration of 17 mM and the reaction was allowed to proceed with continued stirring for an additional 20 hours at 37° C.

Dextran-butyrALD-40K-insulin was purified from the reaction mixture by anion-exchange chromatography using Q Sepharose FF (GE Healthcare). Upon completion of the conjugation reaction, the reaction mixture was diluted 1:3 with 20 mM HEPES (pH 7) and the mixture was loaded onto a column packed with Q Sepharose FF resin. Purification buffers were as follows: Buffer A: 20 mM HEPES (pH 7), and Buffer B: 20 mM HEPES, 1.0 M sodium chloride (pH 7). The resin was washed with Buffer B and equilibrated with Buffer A prior to sample loading. After loading, the resin was washed with 10 column volumes Buffer A. Conjugated and nonconjugated peptides were eluted using a two-step gradient consisting of 0 to 25% Buffer B over 25 column volumes and 25% to 75% Buffer B over 5 column volumes at a flow rate of 90 cm/h (FIG. 143). FIG. 143 Typical anion-exchange chromatography profile of the conjugation reaction mixture with partially acetylated insulin. Fractions containing less substituted conjugates are indicated in the grey box. Fractions containing lower molecular weight, less substituted conjugates were identified by SDS-PAGE (FIG. 144). FIG. 144 SDS-PAGE (4-12% Bis-Tris-Nu-PAGE, Invitrogen) analysis of fractions containing dextran-butyrALD-40K-insulin collected from anion-exchange chromatography. The fractions represented in the lanes within the box on the gel image correspond to the fractions in the grey box in FIG. 143. Dextran perturbs the gel migration of the dextran-peptide conjugates and the conjugates' band locations are not indicative of the conjugates' sizes. The molecular weights of the standards are indicated in kDa.

Fractions containing less substituted conjugates (denoted by the boxes in FIGS. 1 and 2) were pooled, diluted 10-fold with 20 mM HEPES, pH 7 (Buffer A), and applied to a second column packed with Q Sepharose FF resin for sample concentration. The resin was washed with Buffer B and equilibrated with Buffer A prior to sample loading. Dextran-butyrALD-40K-insulin was eluted using a linear gradient of 0-75% Buffer B over 3 column volumes at a flow rate of 90 cm/h (FIG. 145).

FIG. 145 Concentration of purified dextran-butyrALD-40K-insulin by anion-exchange chromatography. Fractions containing dextran-butyrALD-40K-insulin are indicated by the grey box. The peak eluting at 2350-2400 mL contains residual nonconjugated insulin that was co-purified with the conjugate from the first anion-exchange chromatography run.

Fractions containing concentrated dextran-butyrALD-40K-insulin (denoted by the grey box in FIG. 145) were pooled and lyophilized. SDS-PAGE analysis of the pooled fractions indicated the presence of a significant amount of nonconjugated insulin (FIG. 146, Lane 1). The nonconjugated insulin can be removed by selective precipitation of the conjugate from a water/DMSO solution (50/50, v/v) through the addition of an organic solvent (for example, acetonitrile). Dextran-butyrALD-40K-insulin is less soluble than nonconjugated insulin in organic solvents and precipitates upon addition of an organic solvent.

Figure 4:
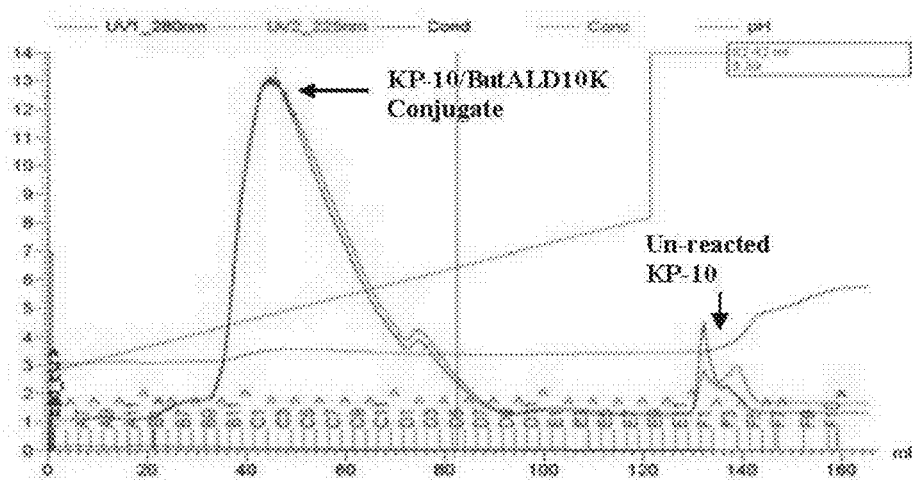
FIG. 4. Typical reversed phase purification profile of [mono]-[mPEG-ButyAldehyde-10K]-[Kisspeptin-10].
Figure 5:
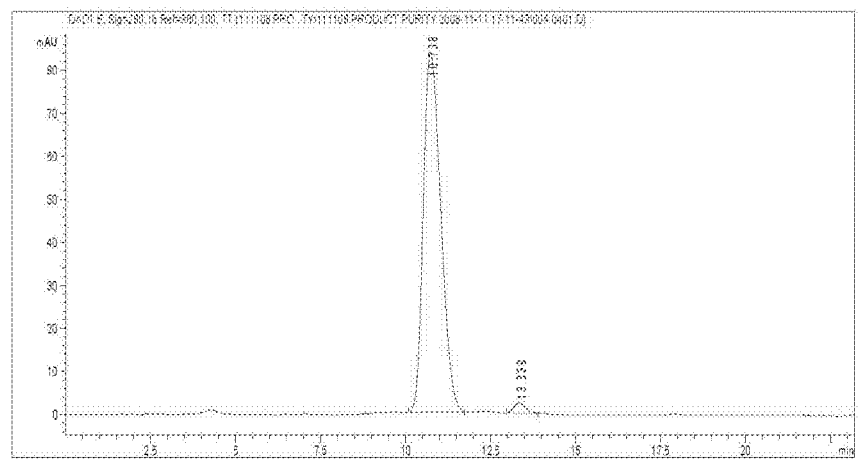
FIG. 5 Purity analysis of mono-[ButyrAldehyde-10K]-[Kisspeptin-10] by Reversed Phase HPLC.
Figure 6:
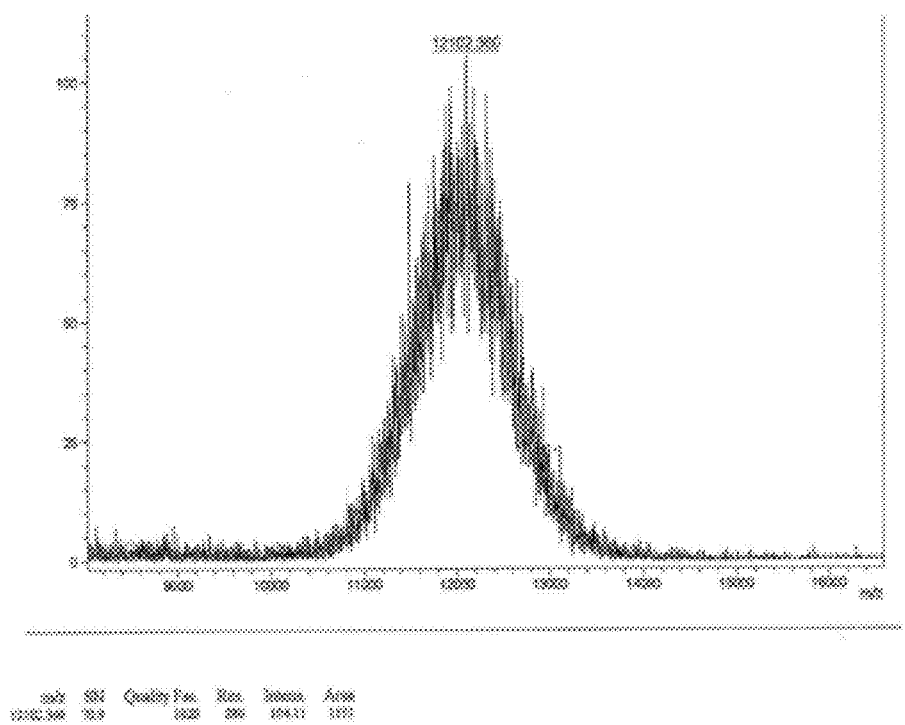
FIG. 6. MALDI-TOF spectrum of purified mono-[mPEG-butyraldehyde-10k]-[Kisspeptin-10].

Lyophilized dextran-butyrALD-40K-insulin was dissolved in water to a peptide concentration of 2 mg/mL. An equal volume of DMSO was added to the solution and after thorough mixing acetonitrile was added drop-wise until the composition of the mixture was 25% water, 25% DMSO, and 50% acetonitrile (v/v/v). Precipitated conjugated insulin was collected by centrifugation and re-dissolved in water. The final concentration of nonconjugated insulin in the re-dissolved product was reduced to less than 1% of the total peptide amount (FIG. 4, Lane 2). FIG. 146. SDS-PAGE (4-12% Bis-Tris-Nu-PAGE, Invitrogen) analysis of purified dextran-butyrALD-40K-insulin. Lane 1: Dextran-butyrALD-40K-insulin purified and concentrated by anion-exchange chromatography. Lane 2: Purified and concentrated dextran-butyrALD-40K-insulin after precipitation with acetonitrile. The molecular weights of the standards are indicated in kDa. The re-dissolved conjugate was lyophilized and stored at −80° C.

Conjugation of Non-Acetylated Insulin with Dextran-butyrALD-40K

Stock solutions of 2 mg/ml insulin and 42/mL dextran-butyrALD-40K were prepared in DMSO/TEA (95%:5%, v/v). To initiate a reaction, both stock solutions were brought to ambient temperature and then mixed in equal volumes. After 5 min reaction with stirring at ambient temperature, 1 M sodium cyanoborohydride was added to a final concentration of 20 mM and the reaction was allowed to proceed with continued stir for 22 hours at ambient temperature.

Dextran-butyrALD-40K-insulin was purified from the reaction mixture by anion-exchange chromatography using Q Sepharose FF (GE Healthcare). Upon completion of the conjugation reaction, the reaction mixture was diluted 15-fold with 20 mM HEPES (pH 7) and the mixture was loaded onto a column packed with Q Sepharose FF resin. Purification buffers were as follows: Buffer A: 20 mM HEPES (pH 7), and Buffer B: 20 mM HEPES, 1.0 M sodium chloride (pH 7). The resin was washed with Buffer B and equilibrated with Buffer A prior to sample loading. After loading, the resin was washed with 5 column volumes Buffer A. Conjugated and nonconjugated peptides were eluted using a linear gradient of 0-100% Buffer B over 10 column volumes at a flow rate of 150 cm/h (FIG. 147). FIG. 147 Typical anion-exchange chromatography profile of the conjugation reaction mixture with non-acetylated insulin. The conjugated and non-conjugated (free) peptides are indicated. The blue line represents absorbance at 280 nm.

Fractions containing dextran-butyraldehyde-40K-insulin were pooled, dialyzed against water, lyophilized and stored at −80° C. Removal of nonconjugated insulin from the conjugate sample can be performed by selective conjugate precipitation with an organic solvent as described in the previous section describing the conjugation of partially acetylated insulin with dextran-butyrALD-40K.

Example INS2

Receptor binding: In vitro binding of the Insulin-dextran conjugate. The in vitro affinity of the insulin-dextran conjugate for the insulin receptor was evaluated using radioligand binding assays in CHO cells that stably express the recombinant human insulin receptor (CHO-hIR). The CHO-hIR cell line was previously generated and characterized. CHO-hIR cells were plated in 24 well plates and washed with assay buffer containing 120 mM NaCl, 5 mM KCl, 1.2 mM MgSO$_4$, 9 mM Glucose, 10 mM HEPES, 0.5% BSA, pH 8.0. Competition binding assays were conducted by incubating CHO-hIR cells with increasing concentrations of insulin, dextran insulin and glycine dextran and a fixed concentration (100 pM) of $^{125}$I-labelled recombinant human insulin for 4 hours at 4° C. Cells were washed to remove unbound ligands, solubilized with 0.2 N NaOH and bound radioactivity was counted using a gamma counter. Non-specific binding was measured in the presence of excess cold insulin and subtraction of this value from the total binding yielded the specific binding at each test compound concentration. IC$_{50}$ values were obtained from non-linear regression analysis of specific binding versus concentration curves.

Results: The results of the in vitro competition binding assay are shown in FIG. 148. Insulin and the Dextran-TEG-butyrlaldehyde-40K acetyl insulin conjugate bound to the insulin receptor with IC$_{50}$ values of 4.3 nM and 174.9 nM respectively. Dextran conjugation thus resulted in a 40-fold reduction in the binding affinity of insulin. The dextran itself did not display specific binding to the insulin receptor at concentrations up to 1 μM. The insulin-dextran conjugate was 98% pure and contained up to 2% of free and acetylated insulin. It is possible that the specific binding observed with the insulin-dextran conjugate could be result of the free insulin in the sample.

Example INS3

Effect of Dextran Conjugated Insulin on the Blood Glucose Levels in the Db/Db Diabetic Mice Dextran conjugated insulin 250 ug/mouse was administered by i.p. injection into diabetic mouse that had elevated blood glucose levels. At different time points after dosing blood glucose levels were measured.

PBS saline solution and Dextran equivalent dose were administrated as negative controls. Insulin 50 ug/mouse was injected as positive control. Insulin 5 ug/mouse was also given to a group of db/db mice (to test if the 2% free insulin in the 250 ug Dextran-insulin prep; ~5 ug; would have any effect).

PBS and Dextran injections did not decrease db/db mice glucose levels throughout the whole study.

Dextran-Insulin injections dramatically decreased db/db mice glucose levels by ~40-60% at 1 hr and 2 hr after administrations. However this effect could be due to the free insulin that was in the conjugate preparation. Dextran- Insulin group did show slightly prolonged effect compared to 5 ug/mouse insulin injections. (table INS3.1 and FIG. 149). Table INS3.1: Glucose levels in db/db mice after compound administration. Blood glucose levels in mg/dL were expressed in Mean and SEM (standard error). FIG. 149. Glucose levels after compound administration (0-8 hr).

| Time (hr) | PBS (N = 4) Mean | SEM | Dex-Ins 250 ug (N = 4) Mean | SEM | Ins 50 ug (N = 5) Mean | SEM | Ins 5 ug (N = 5) Mean | SEM | Dextran 1.75 mg (N = 5) Mean | SEM |
|---|---|---|---|---|---|---|---|---|---|---|
| 0 | 486 | 51 | 495 | 32 | 445 | 29 | 510 | 37 | 485 | 31 |
| 1 | 528 | 54 | 263 | 39 | 210 | 16 | 265 | 51 | 565 | 32 |
| 2 | 582 | 9 | 192 | 36 | 150 | 15 | 352 | 60 | 565 | 22 |
| 4 | 597 | 1 | 462 | 30 | 550 | 25 | 587 | 9 | 562 | 27 |
| 8 | 577 | 14 | 494 | 10 | 558 | 23 | 538 | 30 | 540 | 36 |
| 24 | 560 | 24 | 517 | 24 | 541 | 19 | 538 | 36 | 531 | 40 |

What is claimed is:

1. A conjugate having the structure:

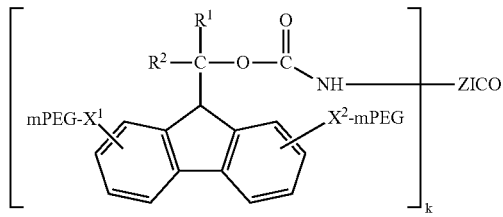

where:
mPEG is $CH_3O-(CH_2CH_2O)_n CH_2CH_2-$;
n is an integer from 10 to 1800;
$R^1$ is H or lower alkyl;
$R^2$ is H or lower alkyl;
$X^1$ and $X^2$ are each independently $-NH-C(O)-CH_2-O-$, $-NH-C(O)-(CH_2)_q-O-$, $-NH-C(O)-(CH_2)_q-CO-NH-$, $-NH-C(O)-(CH_2)_q-$, or $-C(O)-NH-$;
q is 2, 3, 4, or 5;
~NH-ZICO is an amino group of a ziconotide moiety; and
k is 1, 2, or 3.

2. The conjugate of claim 1, wherein the ziconotide moiety is prepared by chemical synthesis.

3. The conjugate of claim 1, wherein mPEG has a weight-average molecular weight in a range of from about 2,000 Daltons to about 50,000 Daltons.

4. The conjugate of claim 3, wherein mPEG has a weight-average molecular weight in a range of from about 5,000 Daltons to about 40,000 Daltons.

5. The conjugate of claim 1, wherein ~NH-ZICO is at an amino-terminal amino acid of the ziconotide moiety.

6. The conjugate of claim 1, wherein ~NH-ZICO is at an epsilon amino group of an internal lysine amino acid of the ziconotide moiety.

7. The conjugate of claim 1, prepared using a polymeric reagent selected from the following:

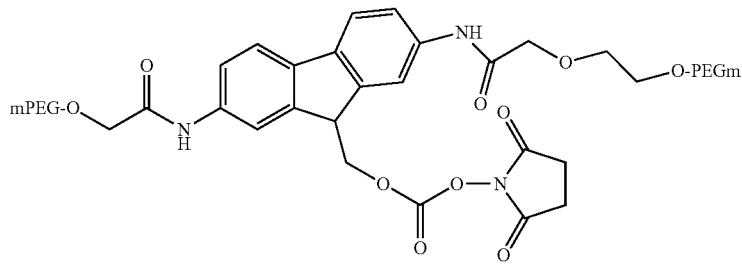

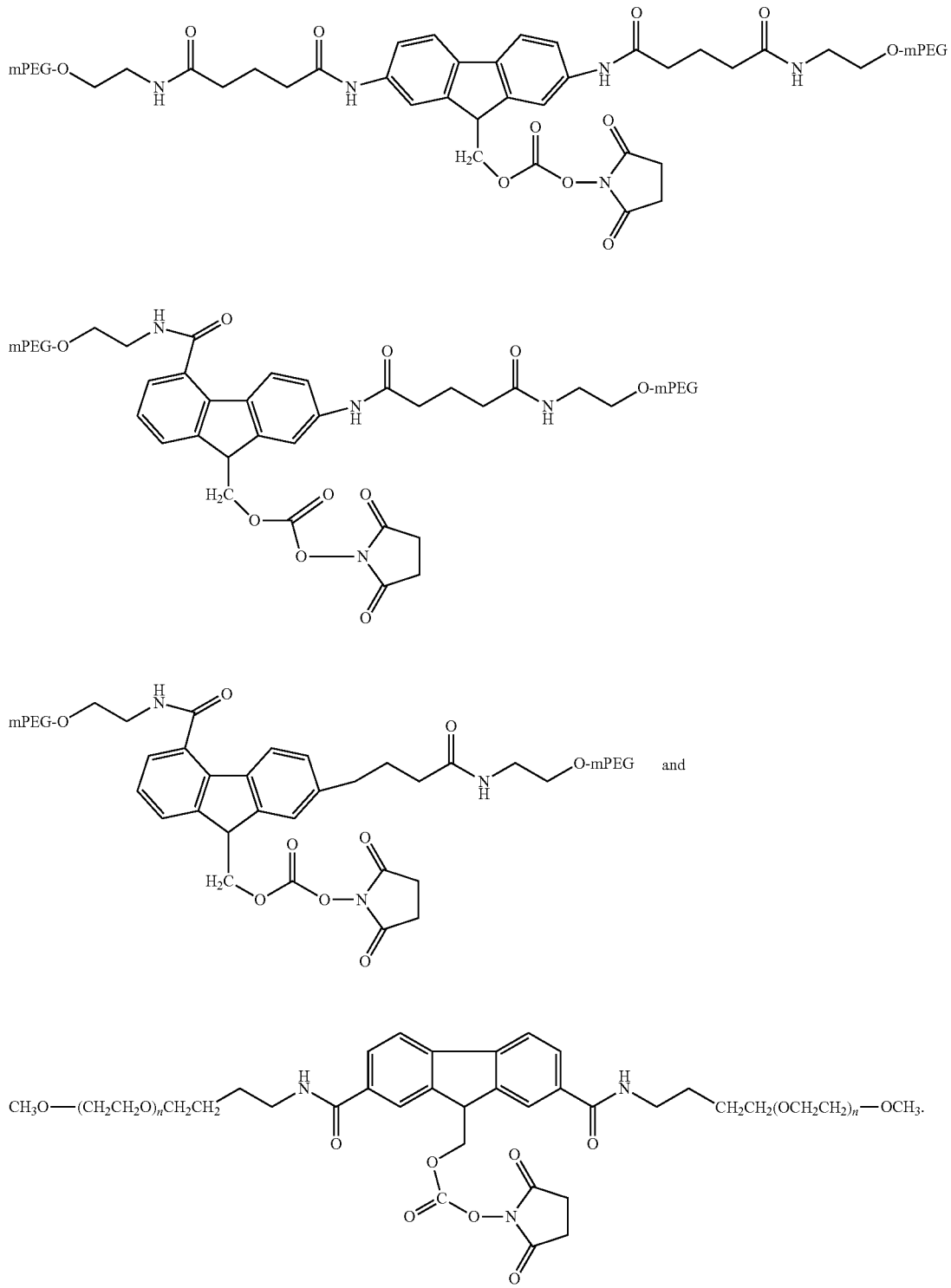

8. The conjugate according to claim 1, wherein the ziconotide comprises the amino acid sequence of SEQ ID NO: 264.

9. A pharmaceutical composition comprising the conjugate of claim 1 and a pharmaceutically acceptable excipient.

10. A method of treatment comprising administering the conjugate of claim 1 to a subject in need thereof.

11. The conjugate of claim 1, having a structure selected from:

513 514
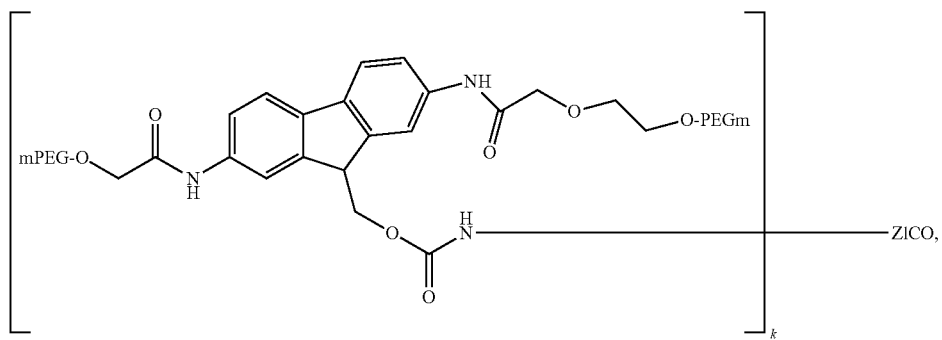
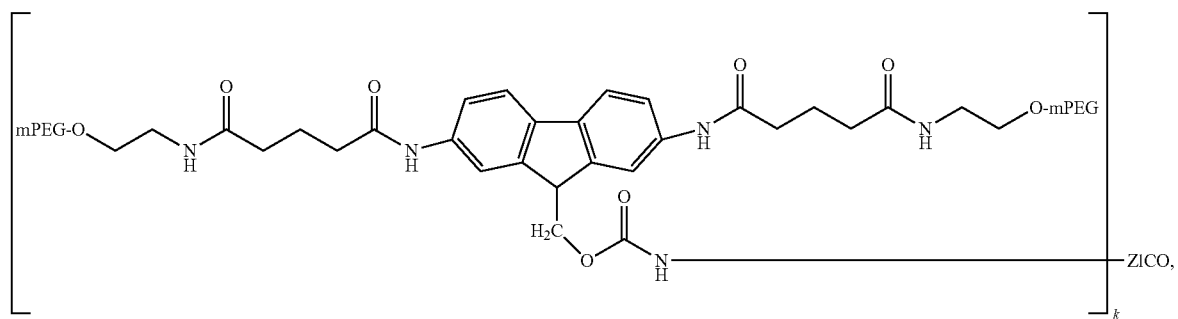
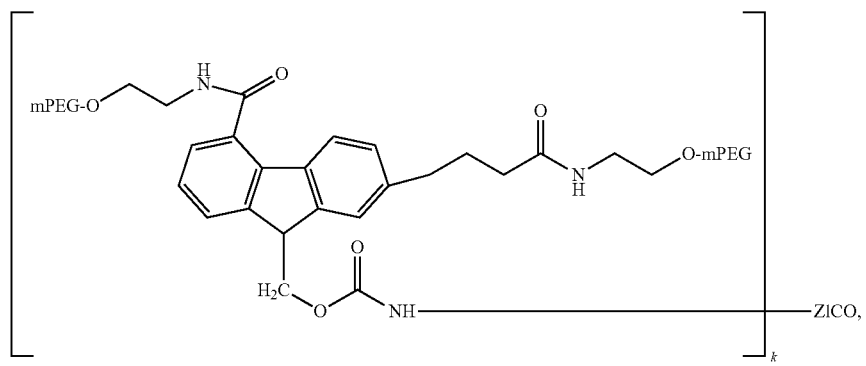
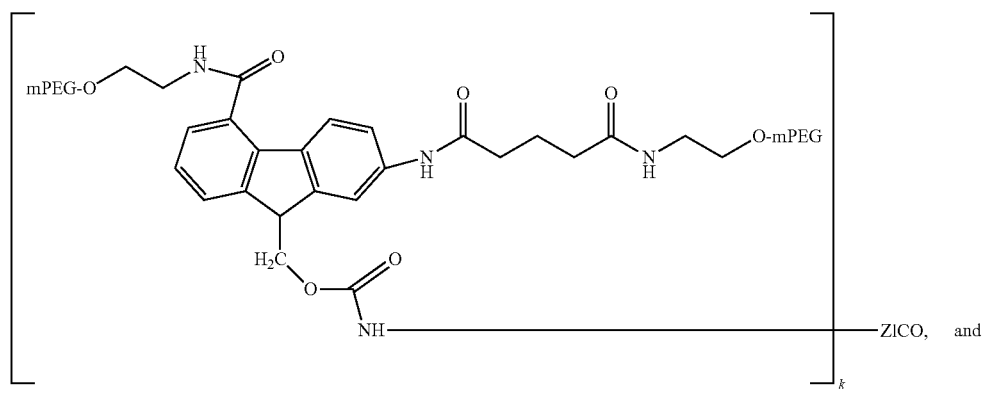

-continued
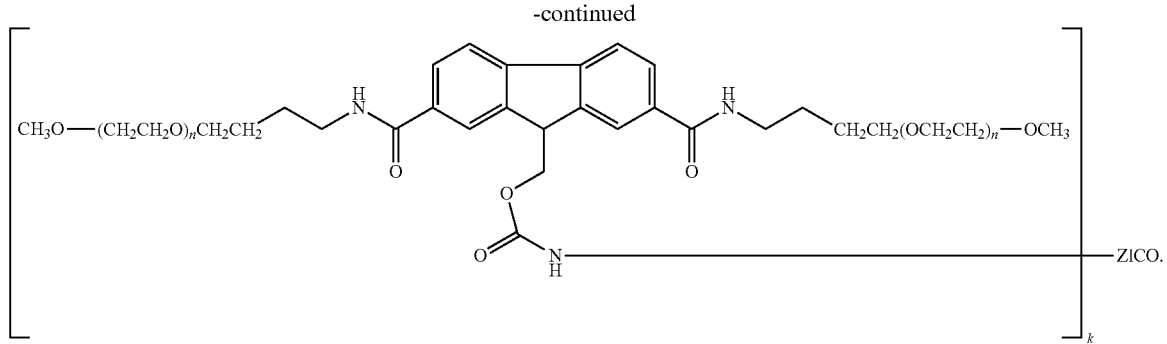
12. The conjugate of claim 1, wherein k is 1.
* * * * *

SEQUENCE LISTING

<160> NUMBER OF SEQ ID NOS: 301

<210> SEQ ID NO 1
<211> LENGTH: 28
<212> TYPE: PRT
<213> ORGANISM: Homo sapiens

<400> SEQUENCE: 1

Ser Leu Arg Arg Ser Ser Cys Phe Gly Gly Arg Met Asp Arg Ile Gly
1               5                   10                  15

Ala Gln Ser Gly Leu Gly Cys Asn Ser Phe Arg Tyr
            20                  25

<210> SEQ ID NO 2
<211> LENGTH: 10
<212> TYPE: PRT
<213> ORGANISM: Homo sapiens

<400> SEQUENCE: 2

Tyr Gly Gly Phe Leu Arg Lys Tyr Pro Lys
1               5                   10

<210> SEQ ID NO 3
<211> LENGTH: 110
<212> TYPE: PRT
<213> ORGANISM: Homo sapiens

<400> SEQUENCE: 3

Met Ala Leu Trp Met Arg Leu Leu Pro Leu Leu Ala Leu Leu Ala Leu
1               5                   10                  15

Trp Gly Pro Asp Pro Ala Ala Ala Phe Val Asn Gln His Leu Cys Gly
            20                  25                  30

Ser His Leu Val Glu Ala Leu Tyr Leu Val Cys Gly Glu Arg Gly Phe
        35                  40                  45

Phe Tyr Thr Pro Lys Thr Arg Arg Glu Ala Glu Asp Leu Gln Val Gly
    50                  55                  60

Gln Val Glu Leu Gly Gly Gly Pro Gly Ala Gly Ser Leu Gln Pro Leu
65                  70                  75                  80

Ala Leu Glu Gly Ser Leu Gln Lys Arg Gly Ile Val Glu Gln Cys Cys
                85                  90                  95

Thr Ser Ile Cys Ser Leu Tyr Gln Leu Glu Asn Tyr Cys Asn
            100                 105                 110

<210> SEQ ID NO 4
<211> LENGTH: 70

```
<212> TYPE: PRT
<213> ORGANISM: Homo sapiens

<400> SEQUENCE: 4

Met Ala Leu Trp Met Arg Leu Leu Pro Leu Leu Ala Leu Leu Ala Leu
1               5                   10                  15

Trp Gly Pro Asp Pro Ala Ala Ala Phe Val Asn Gln His Leu Cys Gly
            20                  25                  30

Ser His Leu Val Glu Ala Leu Tyr Leu Val Cys Gly Glu Arg Gly Phe
        35                  40                  45

Phe Tyr Thr Pro Lys Thr Arg Arg Glu Ala Glu Asp Leu Gln Val Gly
    50                  55                  60

Gln Val Glu Leu Gly Gly
65              70

<210> SEQ ID NO 5
<211> LENGTH: 40
<212> TYPE: PRT
<213> ORGANISM: Homo sapiens

<400> SEQUENCE: 5

Gly Pro Gly Ala Gly Ser Leu Gln Pro Leu Ala Leu Glu Gly Ser Leu
1               5                   10                  15

Gln Lys Arg Gly Ile Val Glu Gln Cys Cys Thr Ser Ile Cys Ser Leu
            20                  25                  30

Tyr Gln Leu Glu Asn Tyr Cys Asn
        35                  40

<210> SEQ ID NO 6
<211> LENGTH: 82
<212> TYPE: PRT
<213> ORGANISM: Homo sapiens

<400> SEQUENCE: 6

Gly Ser Gly Leu Thr Asn Ile Lys Thr Glu Gly Ile Ser Glu Val Lys
1               5                   10                  15

Met Asp Ala Glu Phe Arg His Asp Ser Gly Tyr Glu Val His His Gln
            20                  25                  30

Lys Leu Val Phe Phe Ala Glu Asp Val Gly Ser Asn Lys Gly Ala Ile
        35                  40                  45

Ile Gly Leu Met Val Gly Gly Val Val Ile Ala Thr Val Ile Ile Ile
    50                  55                  60

Thr Leu Val Met Leu Lys Lys Gln Tyr Thr Ser Asn His His Gly Val
65                  70                  75                  80

Val Glu

<210> SEQ ID NO 7
<211> LENGTH: 434
<212> TYPE: PRT
<213> ORGANISM: Homo sapiens

<400> SEQUENCE: 7

Met Glu Ser Glu Ser Glu Ser Gly Ala Ala Asp Thr Pro Pro Leu
1               5                   10                  15

Glu Thr Leu Ser Phe His Gly Asp Glu Ile Ile Glu Val Val Glu
            20                  25                  30

Leu Asp Pro Gly Pro Pro Asp Pro Asp Leu Ala Gln Glu Met Glu
        35                  40                  45
```

Asp Val Asp Phe Glu Glu Glu Glu Glu Gly Asn Glu Gly
    50              55                  60

Trp Val Leu Glu Pro Gln Glu Gly Val Val Gly Ser Met Glu Gly Pro
65              70                  75                  80

Asp Asp Ser Glu Val Thr Phe Ala Leu His Ser Ala Ser Val Phe Cys
                85                  90                  95

Val Ser Leu Asp Pro Lys Thr Asn Thr Leu Ala Val Thr Gly Gly Glu
            100                 105                 110

Asp Asp Lys Ala Phe Val Trp Arg Leu Ser Asp Gly Glu Leu Leu Phe
                115                 120                 125

Glu Cys Ala Gly His Lys Asp Ser Val Thr Cys Ala Gly Phe Ser His
    130                 135                 140

Asp Ser Thr Leu Val Ala Thr Gly Asp Met Ser Gly Leu Leu Lys Val
145                 150                 155                 160

Trp Gln Val Asp Thr Lys Glu Glu Val Trp Ser Phe Glu Ala Gly Asp
                165                 170                 175

Leu Glu Trp Met Glu Trp His Pro Arg Ala Pro Val Leu Leu Ala Gly
                180                 185                 190

Thr Ala Asp Gly Asn Thr Trp Met Trp Lys Val Pro Asn Gly Asp Cys
                195                 200                 205

Lys Thr Phe Gln Gly Pro Asn Cys Pro Ala Thr Cys Gly Arg Val Leu
                210                 215                 220

Pro Asp Gly Lys Arg Ala Val Val Gly Tyr Glu Asp Gly Thr Ile Arg
225                 230                 235                 240

Ile Trp Asp Leu Lys Gln Gly Ser Pro Ile His Val Leu Lys Gly Thr
                245                 250                 255

Glu Gly His Gln Gly Pro Leu Thr Cys Val Ala Ala Asn Gln Asp Gly
                260                 265                 270

Ser Leu Ile Leu Thr Gly Ser Val Asp Cys Gln Ala Lys Leu Val Ser
                275                 280                 285

Ala Thr Thr Gly Lys Val Val Gly Val Phe Arg Pro Glu Thr Val Ala
                290                 295                 300

Ser Gln Pro Ser Leu Gly Glu Gly Glu Glu Ser Glu Ser Asn Ser Val
305                 310                 315                 320

Glu Ser Leu Gly Phe Cys Ser Val Met Pro Leu Ala Ala Val Gly Tyr
                325                 330                 335

Leu Asp Gly Thr Leu Ala Ile Tyr Asp Leu Ala Thr Gln Thr Leu Arg
                340                 345                 350

His Gln Cys Gln His Gln Ser Gly Ile Val Gln Leu Leu Trp Glu Ala
                355                 360                 365

Gly Thr Ala Val Val Tyr Thr Cys Ser Leu Asp Gly Ile Val Arg Leu
                370                 375                 380

Trp Asp Ala Arg Thr Gly Arg Leu Leu Thr Asp Tyr Arg Gly His Thr
385                 390                 395                 400

Ala Glu Ile Leu Asp Phe Ala Leu Ser Lys Asp Ala Ser Leu Val Val
                405                 410                 415

Thr Thr Ser Gly Asp His Lys Ala Lys Val Phe Cys Val Gln Arg Pro
                420                 425                 430

Asp Arg

<210> SEQ ID NO 8
<211> LENGTH: 39
<212> TYPE: PRT
<213> ORGANISM: Artificial Sequence -continued

```
<220> FEATURE:
<221> NAME/KEY: source
<223> OTHER INFORMATION: /note="Description of Artificial Sequence:
      Synthetic polypeptide"

<400> SEQUENCE: 8

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser
        35

<210> SEQ ID NO 9
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (1)..(1)
<223> OTHER INFORMATION: /note="N-term acetylated"
<220> FEATURE:
<221> NAME/KEY: misc_feature
<222> LOCATION: (25)..(25)
<223> OTHER INFORMATION: /note="C-term amidated"

<400> SEQUENCE: 9

Ala Thr Gln Arg Leu Ala Asn Glu Leu Val Arg Leu Gln Thr Tyr Pro
1               5                   10                  15

Arg Thr Asn Val Gly Ser Asn Thr Tyr
            20                  25

<210> SEQ ID NO 10
<211> LENGTH: 267
<212> TYPE: PRT
<213> ORGANISM: Homo sapiens

<400> SEQUENCE: 10

Met Pro Arg Ser Cys Cys Ser Arg Ser Gly Ala Leu Leu Leu Ala Leu
1               5                   10                  15

Leu Leu Gln Ala Ser Met Glu Val Arg Gly Trp Cys Leu Glu Ser Ser
            20                  25                  30

Gln Cys Gln Asp Leu Thr Thr Glu Ser Asn Leu Leu Glu Cys Ile Arg
        35                  40                  45

Ala Cys Lys Pro Asp Leu Ser Ala Glu Thr Pro Met Phe Pro Gly Asn
    50                  55                  60

Gly Asp Glu Gln Pro Leu Thr Glu Asn Pro Arg Lys Tyr Val Met Gly
65                  70                  75                  80

His Phe Arg Trp Asp Arg Phe Gly Arg Arg Asn Ser Ser Ser Ser Gly
                85                  90                  95

Ser Ser Gly Ala Gly Gln Lys Arg Glu Asp Val Ser Ala Gly Glu Asp
            100                 105                 110

Cys Gly Pro Leu Pro Glu Gly Gly Pro Glu Pro Arg Ser Asp Gly Ala
        115                 120                 125

Lys Pro Gly Pro Arg Glu Gly Lys Arg Ser Tyr Ser Met Glu His Phe
    130                 135                 140

Arg Trp Gly Lys Pro Val Gly Lys Lys Arg Arg Pro Val Lys Val Tyr
145                 150                 155                 160
```

```
Pro Asn Gly Ala Glu Asp Ser Ala Glu Ala Phe Pro Leu Glu Phe
                165                 170                 175

Lys Arg Glu Leu Thr Gly Gln Arg Leu Arg Glu Gly Asp Gly Pro Asp
            180                 185                 190

Gly Pro Ala Asp Asp Gly Ala Gly Ala Gln Ala Asp Leu Glu His Ser
        195                 200                 205

Leu Leu Val Ala Ala Glu Lys Lys Asp Glu Gly Pro Tyr Arg Met Glu
    210                 215                 220

His Phe Arg Trp Gly Ser Pro Pro Lys Asp Lys Arg Tyr Gly Gly Phe
225                 230                 235                 240

Met Thr Ser Glu Lys Ser Gln Thr Pro Leu Val Thr Leu Phe Lys Asn
                245                 250                 255

Ala Ile Ile Lys Asn Ala Tyr Lys Lys Gly Glu
            260                 265

<210> SEQ ID NO 11
<211> LENGTH: 35
<212> TYPE: PRT
<213> ORGANISM: Human immunodeficiency virus type 1

<400> SEQUENCE: 11

Cys Thr Arg Pro Ser Asn Asn Thr Arg Lys Ser Ile Pro Val Gly Pro
1               5                   10                  15

Gly Lys Ala Leu Tyr Ala Thr Gly Ala Ile Ile Gly Asn Ile Arg Gln
            20                  25                  30

Ala His Cys
        35

<210> SEQ ID NO 12
<211> LENGTH: 508
<212> TYPE: PRT
<213> ORGANISM: Human immunodeficiency virus type 1

<400> SEQUENCE: 12

Met Gly Ala Arg Ala Ser Val Leu Ser Gly Gly Lys Leu Asp Lys Trp
1               5                   10                  15

Glu Lys Ile Arg Leu Arg Pro Gly Gly Lys Lys Thr Tyr Gln Leu Lys
            20                  25                  30

His Ile Val Trp Ala Ser Arg Glu Leu Glu Arg Phe Ala Val Asn Pro
        35                  40                  45

Gly Leu Leu Glu Thr Gly Gly Cys Lys Gln Ile Leu Val Gln Leu
    50                  55                  60

Gln Pro Ser Leu Gln Thr Gly Ser Glu Glu Leu Lys Ser Leu Tyr Asn
65                  70                  75                  80

Ala Val Ala Thr Leu Tyr Cys Val His Gln Gly Ile Glu Val Arg Asp
                85                  90                  95

Thr Lys Glu Ala Leu Asp Lys Ile Glu Glu Glu Gln Asn Lys Ser Lys
            100                 105                 110

Lys Lys Ala Gln Gln Ala Ala Ala Asp Thr Gly Asn Ser Ser Gln Val
        115                 120                 125

Ser Gln Asn Tyr Pro Ile Val Gln Asn Leu Gln Gly Gln Met Val His
    130                 135                 140

Gln Ala Ile Ser Pro Arg Thr Leu Asn Ala Trp Val Lys Val Ile Glu
145                 150                 155                 160

Glu Lys Ala Phe Ser Pro Glu Val Ile Pro Met Phe Ser Ala Leu Ser
                165                 170                 175
```

Glu Gly Ala Thr Pro Gln Asp Leu Asn Thr Met Leu Asn Thr Val Gly
                180                 185                 190

Gly His Gln Ala Ala Met Gln Met Leu Lys Glu Thr Ile Asn Glu Glu
            195                 200                 205

Ala Ala Glu Trp Asp Arg Leu His Pro Ala His Ala Gly Pro Asn Ala
210                 215                 220

Pro Gly Gln Met Arg Glu Pro Arg Gly Ser Asp Ile Ala Gly Thr Thr
225                 230                 235                 240

Ser Thr Leu Gln Glu Gln Ile Gly Trp Met Thr Ser Asn Pro Pro Val
            245                 250                 255

Pro Val Gly Glu Ile Tyr Lys Arg Trp Ile Ile Leu Gly Leu Asn Lys
            260                 265                 270

Ile Val Arg Met Tyr Ser Pro Val Ser Ile Leu Asp Ile Arg Gln Gly
            275                 280                 285

Pro Lys Glu Pro Phe Arg Asp Tyr Val Asp Arg Phe Tyr Lys Thr Leu
            290                 295                 300

Arg Ala Glu Gln Ala Ser Gln Asp Val Lys Asn Trp Met Thr Glu Thr
305                 310                 315                 320

Leu Leu Val Gln Asn Ala Asn Pro Asp Cys Lys Thr Ile Leu Lys Ala
            325                 330                 335

Leu Gly Pro Ala Ala Thr Leu Glu Glu Met Met Thr Ala Cys Gln Gly
            340                 345                 350

Val Gly Gly Pro Ser His Lys Ala Arg Ile Leu Ala Glu Ala Met Ser
            355                 360                 365

Gln Val Thr Ser Pro Ala Asn Ile Met Met Gln Arg Gly Asn Phe Arg
            370                 375                 380

Asn Gln Arg Lys Thr Ile Lys Cys Phe Asn Cys Gly Lys Glu Gly His
385                 390                 395                 400

Leu Ala Arg His Cys Arg Ala Pro Arg Lys Lys Gly Cys Trp Lys Cys
            405                 410                 415

Gly Arg Glu Gly His Gln Met Lys Asp Cys Thr Glu Arg Gln Ala Asn
            420                 425                 430

Phe Leu Gly Lys Ile Trp Pro Ser His Lys Gly Arg Pro Gly Asn Phe
            435                 440                 445

Leu Gln Ser Arg Pro Glu Pro Thr Ala Pro Pro Glu Glu Ser Phe Arg
            450                 455                 460

Phe Gly Glu Glu Thr Thr Thr Pro Pro Gln Lys Gln Glu Pro Leu Pro
465                 470                 475                 480

Ser Gln Lys Gln Glu Thr Ile Asp Lys Asp Leu Tyr Pro Leu Ala Ser
            485                 490                 495

Leu Lys Ser Leu Phe Gly Asn Asp Pro Ser Leu Gln
            500                 505

<210> SEQ ID NO 13
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 13

Asn Leu Arg Ile Ala Leu Arg
1               5

<210> SEQ ID NO 14
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 14

Arg Leu Ala Ile Arg Leu Asn
1               5

<210> SEQ ID NO 15
<211> LENGTH: 40
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 15

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
                20                  25                  30

Gly Leu Met Val Gly Gly Val Val
            35                  40

<210> SEQ ID NO 16
<211> LENGTH: 42
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 16

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
                20                  25                  30

Gly Leu Met Val Gly Gly Val Val Ile Ala
            35                  40

<210> SEQ ID NO 17
<211> LENGTH: 202
<212> TYPE: PRT
<213> ORGANISM: Homo sapiens

<400> SEQUENCE: 17

Met Lys Val Leu Ala Ala Gly Val Val Pro Leu Leu Leu Val Leu His
1               5                   10                  15

Trp Lys His Gly Ala Gly Ser Pro Leu Pro Ile Thr Pro Val Asn Ala
                20                  25                  30

Thr Cys Ala Ile Arg His Pro Cys His Asn Asn Leu Met Asn Gln Ile
            35                  40                  45

Arg Ser Gln Leu Ala Gln Leu Asn Gly Ser Ala Asn Ala Leu Phe Ile
        50                  55                  60

Leu Tyr Tyr Thr Ala Gln Gly Glu Pro Phe Pro Asn Asn Leu Asp Lys
65                  70                  75                  80

```
Leu Cys Gly Pro Asn Val Thr Asp Phe Pro Pro Phe His Ala Asn Gly
                85                  90                  95

Thr Glu Lys Ala Lys Leu Val Glu Leu Tyr Arg Ile Val Val Tyr Leu
            100                 105                 110

Gly Thr Ser Leu Gly Asn Ile Thr Arg Asp Gln Lys Ile Leu Asn Pro
            115                 120                 125

Ser Ala Leu Ser Leu His Ser Lys Leu Asn Ala Thr Ala Asp Ile Leu
            130                 135                 140

Arg Gly Leu Leu Ser Asn Val Leu Cys Arg Leu Cys Ser Lys Tyr His
145                 150                 155                 160

Val Gly His Val Asp Val Thr Tyr Gly Pro Asp Thr Ser Gly Lys Asp
                165                 170                 175

Val Phe Gln Lys Lys Leu Gly Cys Gln Leu Leu Gly Lys Tyr Lys
            180                 185                 190

Gln Ile Ile Ala Val Leu Ala Gln Ala Phe
            195                 200
```

<210> SEQ ID NO 18
<211> LENGTH: 382
<212> TYPE: PRT
<213> ORGANISM: Homo sapiens

<400> SEQUENCE: 18

```
Met Asp Phe Gly Leu Ala Leu Leu Leu Ala Gly Leu Leu Gly Leu Leu
1               5                   10                  15

Leu Gly Gln Ser Leu Gln Val Lys Pro Leu Gln Val Glu Pro Pro Glu
            20                  25                  30

Pro Val Val Ala Val Ala Leu Gly Ala Ser Arg Gln Leu Thr Cys Arg
            35                  40                  45

Leu Ala Cys Ala Asp Arg Gly Ala Ser Val Gln Trp Arg Gly Leu Asp
    50                  55                  60

Thr Ser Leu Gly Ala Val Gln Ser Asp Thr Gly Arg Ser Val Leu Thr
65                  70                  75                  80

Val Arg Asn Ala Ser Leu Ser Ala Ala Gly Thr Arg Val Cys Val Gly
                85                  90                  95

Ser Cys Gly Gly Arg Thr Phe Gln His Thr Val Gln Leu Leu Val Tyr
            100                 105                 110

Ala Phe Pro Asp Gln Leu Thr Val Ser Pro Ala Ala Leu Val Pro Gly
            115                 120                 125

Asp Pro Glu Val Ala Cys Thr Ala His Lys Val Thr Pro Val Asp Pro
            130                 135                 140

Asn Ala Leu Ser Phe Ser Leu Leu Val Gly Gly Gln Glu Leu Glu Gly
145                 150                 155                 160

Ala Gln Ala Leu Gly Pro Glu Val Gln Glu Glu Glu Glu Glu Pro Gln
                165                 170                 175

Gly Asp Glu Asp Val Leu Phe Arg Val Thr Glu Arg Trp Arg Leu Pro
            180                 185                 190

Pro Leu Gly Thr Pro Val Pro Pro Ala Leu Tyr Cys Gln Ala Thr Met
            195                 200                 205

Arg Leu Pro Gly Leu Glu Leu Ser His Arg Gln Ala Ile Pro Val Leu
            210                 215                 220

His Ser Pro Thr Ser Pro Glu Pro Pro Asp Thr Thr Ser Pro Glu Ser
225                 230                 235                 240

Pro Asp Thr Thr Ser Pro Glu Ser Pro Asp Thr Thr Ser Gln Glu Pro
```

```
                          245                 250                 255
Pro Asp Thr Thr Ser Pro Glu Pro Pro Asp Lys Thr Ser Pro Glu Pro
                260                 265                 270

Ala Pro Gln Gln Gly Ser Thr His Thr Pro Arg Ser Pro Gly Ser Thr
            275                 280                 285

Arg Thr Arg Arg Pro Glu Ile Ser Gln Ala Gly Pro Thr Gln Gly Glu
        290                 295                 300

Val Ile Pro Thr Gly Ser Ser Lys Pro Ala Gly Asp Gln Leu Pro Ala
305                 310                 315                 320

Ala Leu Trp Thr Ser Ser Ala Val Leu Gly Leu Leu Leu Ala Leu
                325                 330                 335

Pro Thr Tyr His Leu Trp Lys Arg Cys Arg His Leu Ala Glu Asp Asp
                340                 345                 350

Thr His Pro Pro Ala Ser Leu Arg Leu Leu Pro Gln Val Ser Ala Trp
                355                 360                 365

Ala Gly Leu Arg Gly Thr Gly Gln Val Gly Ile Ser Pro Ser
            370                 375                 380

<210> SEQ ID NO 19
<211> LENGTH: 74
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 19

Asp Thr Thr Val Ser Glu Pro Ala Pro Ser Cys Val Thr Leu Tyr Gln
1               5                   10                  15

Ser Trp Arg Tyr Ser Gln Ala Asp Asn Gly Cys Ala Glu Thr Val Thr
            20                  25                  30

Val Lys Val Val Tyr Glu Asp Asp Thr Glu Gly Leu Cys Tyr Ala Val
        35                  40                  45

Ala Pro Gly Gln Ile Thr Thr Val Gly Asp Gly Tyr Ile Gly Ser His
    50                  55                  60

Gly His Ala Arg Tyr Leu Ala Arg Cys Leu
65                  70

<210> SEQ ID NO 20
<211> LENGTH: 151
<212> TYPE: PRT
<213> ORGANISM: Homo sapiens

<400> SEQUENCE: 20

Met Ser Ser Phe Ser Thr Thr Thr Val Ser Phe Leu Leu Leu Leu Ala
1               5                   10                  15

Phe Gln Leu Leu Gly Gln Thr Arg Ala Asn Pro Met Tyr Asn Ala Val
            20                  25                  30

Ser Asn Ala Asp Leu Met Asp Phe Lys Asn Leu Leu Asp His Leu Glu
        35                  40                  45

Glu Lys Met Pro Leu Glu Asp Glu Val Val Pro Pro Gln Val Leu Ser
    50                  55                  60

Asp Pro Asn Glu Glu Ala Gly Ala Ala Leu Ser Pro Leu Pro Glu Val
65                  70                  75                  80

Pro Pro Trp Thr Gly Glu Val Ser Pro Ala Gln Arg Asp Gly Gly Ala
                85                  90                  95
```

```
Leu Gly Arg Gly Pro Trp Asp Ser Ser Asp Arg Ser Ala Leu Leu Lys
            100                 105                 110

Ser Lys Leu Arg Ala Leu Leu Thr Ala Pro Arg Ser Leu Arg Arg Ser
        115                 120                 125

Ser Cys Phe Gly Gly Arg Met Asp Arg Ile Gly Ala Gln Ser Gly Leu
        130                 135                 140

Gly Cys Asn Ser Phe Arg Tyr
145                 150

<210> SEQ ID NO 21
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 21

Thr Thr Ser Gln Val Arg Pro Arg
1               5

<210> SEQ ID NO 22
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 22

Val Lys Thr Thr Ser Gln Val Arg Pro Arg
1               5                   10

<210> SEQ ID NO 23
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 23

Ser Gln Val Arg Pro Arg
1               5

<210> SEQ ID NO 24
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 24

Val Arg Pro Arg
1

<210> SEQ ID NO 25
<211> LENGTH: 11
<212> TYPE: PRT
<213> ORGANISM: Artificial Sequence
<220> FEATURE:
<221> NAME/KEY: source
```

-continued

```
<223> OTHER INFORMATION: /note="Description of Artificial Sequence:
      Synthetic peptide"

<400> SEQUENCE: 25

Thr Thr Ser Gln Val Arg Pro Arg His Ile Thr
1               5                   10

<210> SEQ ID NO 26
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 26

Thr Thr Ser Gln Val
1               5

<210> SEQ ID NO 27
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 27

Thr Ser Gln Val Arg
1               5

<210> SEQ ID NO 28
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 28

Thr Thr Ser Gly Ile His Pro Lys
1               5

<210> SEQ ID NO 29
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 29

Glu Gly Pro Trp Leu Glu Glu Glu Glu
1               5

<210> SEQ ID NO 30
<211> LENGTH: 84
<212> TYPE: PRT
<213> ORGANISM: Hirudinaria manillensis

<400> SEQUENCE: 30

Met Phe Ser Leu Lys Leu Phe Val Val Phe Leu Ala Val Cys Ile Cys
1               5                   10                  15
```

```
Val Ser Gln Ala Val Ser Tyr Thr Asp Cys Thr Glu Ser Gly Gln Asn
            20                  25                  30

Tyr Cys Leu Cys Val Gly Gly Asn Leu Cys Gly Gly Gly Lys His Cys
        35                  40                  45

Glu Met Asp Gly Ser Gly Asn Lys Cys Val Asp Gly Glu Gly Thr Pro
    50                  55                  60

Lys Pro Lys Ser Gln Thr Glu Gly Asp Phe Glu Glu Ile Pro Asp Glu
65                  70                  75                  80

Asp Ile Leu Asn

<210> SEQ ID NO 31
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 31

Tyr Ala Gly Ala Val Val Asn Asp Leu
1               5

<210> SEQ ID NO 32
<211> LENGTH: 100
<212> TYPE: PRT
<213> ORGANISM: Homo sapiens

<400> SEQUENCE: 32

Met Lys Leu Leu Ala Ala Thr Val Leu Leu Leu Thr Ile Cys Ser Leu
1               5                   10                  15

Glu Gly Ala Leu Val Arg Arg Gln Ala Lys Glu Pro Cys Val Glu Ser
            20                  25                  30

Leu Val Ser Gln Tyr Phe Gln Thr Val Thr Asp Tyr Gly Lys Asp Leu
        35                  40                  45

Met Glu Lys Val Lys Ser Pro Glu Leu Gln Ala Glu Ala Lys Ser Tyr
    50                  55                  60

Phe Glu Lys Ser Lys Glu Gln Leu Thr Pro Leu Ile Lys Lys Ala Gly
65                  70                  75                  80

Thr Glu Leu Val Asn Phe Leu Ser Tyr Phe Val Glu Leu Gly Thr His
                85                  90                  95

Pro Ala Thr Gln
            100

<210> SEQ ID NO 33
<211> LENGTH: 338
<212> TYPE: PRT
<213> ORGANISM: Mycobacterium bovis

<400> SEQUENCE: 33

Met Gln Leu Val Asp Arg Val Arg Gly Ala Val Thr Gly Met Ser Arg
1               5                   10                  15

Arg Leu Val Val Gly Ala Val Gly Ala Ala Leu Val Ser Gly Leu Val
            20                  25                  30

Gly Ala Val Gly Gly Thr Ala Thr Ala Gly Ala Phe Ser Arg Pro Gly
        35                  40                  45

Leu Pro Val Glu Tyr Leu Gln Val Pro Ser Pro Ser Met Gly Arg Asp
    50                  55                  60

Ile Lys Val Gln Phe Gln Ser Gly Gly Ala Asn Ser Pro Ala Leu Tyr
```

```
                65                  70                  75                  80
Leu Leu Asp Gly Leu Arg Ala Gln Asp Phe Ser Gly Trp Asp Ile
                    85                  90                  95
Asn Thr Pro Ala Phe Glu Trp Tyr Asp Gln Ser Gly Leu Ser Val Val
                100                 105                 110
Met Pro Val Gly Gly Gln Ser Ser Phe Tyr Ser Asp Trp Tyr Gln Pro
                115                 120                 125
Ala Cys Gly Lys Ala Gly Cys Gln Thr Tyr Lys Trp Glu Thr Phe Leu
                130                 135                 140
Thr Ser Glu Leu Pro Gly Trp Leu Gln Ala Asn Arg His Val Lys Pro
145                 150                 155                 160
Thr Gly Ser Ala Val Val Gly Leu Ser Met Ala Ala Ser Ser Ala Leu
                    165                 170                 175
Thr Leu Ala Ile Tyr His Pro Gln Gln Phe Val Tyr Ala Gly Ala Met
                180                 185                 190
Ser Gly Leu Leu Asp Pro Ser Gln Ala Met Gly Pro Thr Leu Ile Gly
                195                 200                 205
Leu Ala Met Gly Asp Ala Gly Gly Tyr Lys Ala Ser Asp Met Trp Gly
                210                 215                 220
Pro Lys Glu Asp Pro Ala Trp Gln Arg Asn Asp Pro Leu Leu Asn Val
225                 230                 235                 240
Gly Lys Leu Ile Ala Asn Asn Thr Arg Val Trp Val Tyr Cys Gly Asn
                    245                 250                 255
Gly Lys Pro Ser Asp Leu Gly Gly Asn Asn Leu Pro Ala Lys Phe Leu
                260                 265                 270
Glu Gly Phe Val Arg Thr Ser Asn Ile Lys Phe Gln Asp Ala Tyr Asn
                275                 280                 285
Ala Gly Gly Gly His Asn Gly Val Phe Asp Phe Pro Asp Ser Gly Thr
                290                 295                 300
His Ser Trp Glu Tyr Trp Gly Ala Gln Leu Asn Ala Met Lys Pro Asp
305                 310                 315                 320
Leu Gln Arg Ala Leu Gly Ala Thr Pro Asn Thr Gly Pro Ala Pro Gln
                    325                 330                 335
Gly Ala

<210> SEQ ID NO 34
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (3)..(3)
<223> OTHER INFORMATION: (NH(CH2)4CO)2-Asp

<400> SEQUENCE: 34

Phe Pro Asp Phe Glu Pro Ile Pro Leu
1               5

<210> SEQ ID NO 35
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
```

```
            Synthetic peptide"
<220> FEATURE:
<221> NAME/KEY: MOD_RES
<222> LOCATION: (1)..(1)
<223> OTHER INFORMATION: Pyro-Glu
<220> FEATURE:
<221> NAME/KEY: misc_feature
<222> LOCATION: (14)..(14)
<223> OTHER INFORMATION: /note=C-term amidated"

<400> SEQUENCE: 35

Glu Gln Arg Leu Gly Asn Gln Trp Ala Val Gly His Leu Leu
1               5                   10

<210> SEQ ID NO 36
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 36

Leu Asp Val Pro
1

<210> SEQ ID NO 37
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(2)
<223> OTHER INFORMATION: Alpha-Glu
<220> FEATURE:
<221> NAME/KEY: MOD_RES
<222> LOCATION: (10)..(11)
<223> OTHER INFORMATION: Alpha-Asp

<400> SEQUENCE: 37

Gly Glu Pro Pro Pro Gly Lys Pro Ala Asp Asp Ala Gly Leu
1               5                   10

<210> SEQ ID NO 38
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: 5-oxo-Pro
<220> FEATURE:
<221> NAME/KEY: misc_feature
<222> LOCATION: (14)..(14)
<223> OTHER INFORMATION: /note="C-term amidated"

<400> SEQUENCE: 38

Pro Gln Arg Leu Gly Asn Gln Trp Ala Val Gly His Leu Met
1               5                   10

<210> SEQ ID NO 39
<211> LENGTH: 32
```

<212> TYPE: PRT
<213> ORGANISM: Homo sapiens

<400> SEQUENCE: 39

Ser Pro Lys Met Val Gln Gly Ser Gly Cys Phe Gly Arg Lys Met Asp
1               5                   10                  15

Arg Ile Ser Ser Ser Ser Gly Leu Gly Cys Lys Val Leu Arg Arg His
            20                  25                  30

<210> SEQ ID NO 40
<211> LENGTH: 37
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 40

Gly Leu Ser Lys Gly Cys Phe Gly Leu Lys Leu Asp Arg Ile Gly Ser
1               5                   10                  15

Met Ser Gly Leu Gly Cys Pro Ser Leu Arg Asp Pro Arg Pro Asn Ala
            20                  25                  30

Pro Ser Thr Ser Ala
        35

<210> SEQ ID NO 41
<211> LENGTH: 31
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 41

Glu Ala Glu Asp Leu Gln Val Gly Gln Val Glu Leu Gly Gly Gly Pro
1               5                   10                  15

Gly Ala Gly Ser Leu Gln Pro Leu Ala Leu Glu Gly Ser Leu Gln
            20                  25                  30

<210> SEQ ID NO 42
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 42

Asn Leu Gly Val
1

<210> SEQ ID NO 43
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Tyr(SO3)

<400> SEQUENCE: 43

Tyr Met Gly Trp Met Asp
1               5

<210> SEQ ID NO 44
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 44

Thr Tyr Ile Cys Glu Val Glu Asp Gln Lys Glu Glu
1               5                   10

<210> SEQ ID NO 45
<211> LENGTH: 180
<212> TYPE: PRT
<213> ORGANISM: Homo sapiens

<400> SEQUENCE: 45

Met Gly Ile Pro Met Gly Lys Ser Met Leu Val Leu Leu Thr Phe Leu
1               5                   10                  15

Ala Phe Ala Ser Cys Cys Ile Ala Ala Tyr Arg Pro Ser Glu Thr Leu
                20                  25                  30

Cys Gly Gly Glu Leu Val Asp Thr Leu Gln Phe Val Cys Gly Asp Arg
            35                  40                  45

Gly Phe Tyr Phe Ser Arg Pro Ala Ser Arg Val Ser Arg Arg Ser Arg
    50                  55                  60

Gly Ile Val Glu Glu Cys Cys Phe Arg Ser Cys Asp Leu Ala Leu Leu
65                  70                  75                  80

Glu Thr Tyr Cys Ala Thr Pro Ala Lys Ser Glu Arg Asp Val Ser Thr
                85                  90                  95

Pro Pro Thr Val Leu Pro Asp Asn Phe Pro Arg Tyr Pro Val Gly Lys
            100                 105                 110

Phe Phe Gln Tyr Asp Thr Trp Lys Gln Ser Thr Gln Arg Leu Arg Arg
        115                 120                 125

Gly Leu Pro Ala Leu Leu Arg Ala Arg Arg Gly His Val Leu Ala Lys
    130                 135                 140

Glu Leu Glu Ala Phe Arg Glu Ala Lys Arg His Arg Pro Leu Ile Ala
145                 150                 155                 160

Leu Pro Thr Gln Asp Pro Ala His Gly Gly Ala Pro Pro Glu Met Ala
                165                 170                 175

Ser Asn Arg Lys
            180

<210> SEQ ID NO 46
<211> LENGTH: 37
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: misc_feature
<222> LOCATION: (37)..(37)
<223> OTHER INFORMATION: /note="C-term amidated"

<400> SEQUENCE: 46

```
Ala Cys Asp Thr Ala Thr Cys Val Thr His Arg Leu Ala Gly Leu Leu
1               5                   10                  15

Ser Arg Ser Gly Gly Val Val Lys Asn Asn Phe Val Pro Thr Asn Val
            20                  25                  30

Gly Ser Lys Ala Phe
            35

<210> SEQ ID NO 47
<211> LENGTH: 622
<212> TYPE: PRT
<213> ORGANISM: Homo sapiens

<400> SEQUENCE: 47

Met Ala His Val Arg Gly Leu Gln Leu Pro Gly Cys Leu Ala Leu Ala
1               5                   10                  15

Ala Leu Cys Ser Leu Val His Ser Gln His Val Phe Leu Ala Pro Gln
            20                  25                  30

Gln Ala Arg Ser Leu Leu Gln Arg Val Arg Arg Ala Asn Thr Phe Leu
        35                  40                  45

Glu Glu Val Arg Lys Gly Asn Leu Glu Arg Glu Cys Val Glu Glu Thr
50                  55                  60

Cys Ser Tyr Glu Glu Ala Phe Glu Ala Leu Glu Ser Ser Thr Ala Thr
65                  70                  75                  80

Asp Val Phe Trp Ala Lys Tyr Thr Ala Cys Glu Thr Ala Arg Thr Pro
                85                  90                  95

Arg Asp Lys Leu Ala Ala Cys Leu Glu Gly Asn Cys Ala Glu Gly Leu
            100                 105                 110

Gly Thr Asn Tyr Arg Gly His Val Asn Ile Thr Arg Ser Gly Ile Glu
        115                 120                 125

Cys Gln Leu Trp Arg Ser Arg Tyr Pro His Lys Pro Glu Ile Asn Ser
130                 135                 140

Thr Thr His Pro Gly Ala Asp Leu Gln Glu Asn Phe Cys Arg Asn Pro
145                 150                 155                 160

Asp Ser Ser Thr Thr Gly Pro Trp Cys Tyr Thr Thr Asp Pro Thr Val
                165                 170                 175

Arg Arg Gln Glu Cys Ser Ile Pro Val Cys Gly Gln Asp Gln Val Thr
            180                 185                 190

Val Ala Met Thr Pro Arg Ser Glu Gly Ser Ser Val Asn Leu Ser Pro
        195                 200                 205

Pro Leu Glu Gln Cys Val Pro Asp Arg Gly Gln Gln Tyr Gln Gly Arg
210                 215                 220

Leu Ala Val Thr Thr His Gly Leu Pro Cys Leu Ala Trp Ala Ser Ala
225                 230                 235                 240

Gln Ala Lys Ala Leu Ser Lys His Gln Asp Phe Asn Ser Ala Val Gln
                245                 250                 255

Leu Val Glu Asn Phe Cys Arg Asn Pro Asp Gly Asp Glu Glu Gly Val
            260                 265                 270

Trp Cys Tyr Val Ala Gly Lys Pro Gly Asp Phe Gly Tyr Cys Asp Leu
        275                 280                 285

Asn Tyr Cys Glu Glu Ala Val Glu Glu Thr Gly Asp Gly Leu Asp
290                 295                 300

Glu Asp Ser Asp Arg Ala Ile Glu Gly Arg Thr Ala Thr Ser Glu Tyr
305                 310                 315                 320

Gln Thr Phe Phe Asn Pro Arg Thr Phe Gly Ser Gly Glu Ala Asp Cys
```

```
                     325                 330                 335
Gly Leu Arg Pro Leu Phe Glu Lys Lys Ser Leu Glu Asp Lys Thr Glu
            340                 345                 350

Arg Glu Leu Leu Glu Ser Tyr Ile Asp Gly Arg Ile Val Glu Gly Ser
            355                 360                 365

Asp Ala Glu Ile Gly Met Ser Pro Trp Gln Val Met Leu Phe Arg Lys
    370                 375                 380

Ser Pro Gln Glu Leu Leu Cys Gly Ala Ser Leu Ile Ser Asp Arg Trp
385                 390                 395                 400

Val Leu Thr Ala Ala His Cys Leu Leu Tyr Pro Pro Trp Asp Lys Asn
                405                 410                 415

Phe Thr Glu Asn Asp Leu Leu Val Arg Ile Gly Lys His Ser Arg Thr
            420                 425                 430

Arg Tyr Glu Arg Asn Ile Glu Lys Ile Ser Met Leu Glu Lys Ile Tyr
            435                 440                 445

Ile His Pro Arg Tyr Asn Trp Arg Glu Asn Leu Asp Arg Asp Ile Ala
    450                 455                 460

Leu Met Lys Leu Lys Lys Pro Val Ala Phe Ser Asp Tyr Ile His Pro
465                 470                 475                 480

Val Cys Leu Pro Asp Arg Glu Thr Ala Ala Ser Leu Leu Gln Ala Gly
                485                 490                 495

Tyr Lys Gly Arg Val Thr Gly Trp Gly Asn Leu Lys Glu Thr Trp Thr
            500                 505                 510

Ala Asn Val Gly Lys Gly Gln Pro Ser Val Leu Gln Val Val Asn Leu
            515                 520                 525

Pro Ile Val Glu Arg Pro Val Cys Lys Asp Ser Thr Arg Ile Arg Ile
    530                 535                 540

Thr Asp Asn Met Phe Cys Ala Gly Tyr Lys Pro Asp Glu Gly Lys Arg
545                 550                 555                 560

Gly Asp Ala Cys Glu Gly Asp Ser Gly Gly Pro Phe Val Met Lys Ser
                565                 570                 575

Pro Phe Asn Asn Arg Trp Tyr Gln Met Gly Ile Val Ser Trp Gly Glu
            580                 585                 590

Gly Cys Asp Arg Asp Gly Lys Tyr Gly Phe Tyr Thr His Val Phe Arg
            595                 600                 605

Leu Lys Lys Trp Ile Gln Lys Val Ile Asp Gln Phe Gly Glu
    610                 615                 620

<210> SEQ ID NO 48
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (8)..(8)
<223> OTHER INFORMATION: Alpha-Asp
<220> FEATURE:
<221> NAME/KEY: MOD_RES
<222> LOCATION: (14)..(14)
<223> OTHER INFORMATION: Alpha-Glu

<400> SEQUENCE: 48

Leu Gln Asn Arg Arg Gly Leu Asp Leu Leu Phe Leu Lys Glu Gly Gly
1               5                   10                  15
```

```
<210> SEQ ID NO 49
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 49

Thr Thr Ser Gln Val Arg Pro
1               5

<210> SEQ ID NO 50
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (7)..(7)
<223> OTHER INFORMATION: Penicillaminyl-Thr

<400> SEQUENCE: 50

Phe Cys Tyr Trp Arg Thr Thr
1               5

<210> SEQ ID NO 51
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 51

Cys Val Phe Met
1

<210> SEQ ID NO 52
<211> LENGTH: 32
<212> TYPE: PRT
<213> ORGANISM: Homo sapiens

<400> SEQUENCE: 52

Cys Gly Asn Leu Ser Thr Cys Met Leu Gly Thr Tyr Thr Gln Asp Phe
1               5                   10                  15

Asn Lys Phe His Thr Phe Pro Gln Thr Ala Ile Gly Val Gly Ala Pro
            20                  25                  30

<210> SEQ ID NO 53
<211> LENGTH: 32
<212> TYPE: PRT
<213> ORGANISM: Salmo salar
<220> FEATURE:
<221> NAME/KEY: misc_feature
<222> LOCATION: (32)..(32)
<223> OTHER INFORMATION: /note="C-term amidated"

<400> SEQUENCE: 53

Cys Ser Asn Leu Ser Thr Cys Val Leu Gly Lys Leu Ser Gln Glu Leu
1               5                   10                  15

His Lys Leu Gln Thr Tyr Pro Arg Thr Asn Thr Gly Ser Gly Thr Pro
```

```
                    20                  25                  30
```

<210> SEQ ID NO 54
<211> LENGTH: 60
<212> TYPE: PRT
<213> ORGANISM: Dendroaspis polylepis polylepis

<400> SEQUENCE: 54

```
Arg Ile Cys Tyr Ile His Lys Ala Ser Leu Pro Arg Ala Thr Lys Thr
1               5                   10                  15

Cys Val Glu Asn Thr Cys Tyr Lys Met Phe Ile Arg Thr Gln Arg Glu
                20                  25                  30

Tyr Ile Ser Glu Arg Gly Cys Gly Cys Pro Thr Ala Met Trp Pro Tyr
            35                  40                  45

Gln Thr Glu Cys Cys Lys Gly Asp Arg Cys Asn Lys
        50                  55                  60
```

<210> SEQ ID NO 55
<211> LENGTH: 320
<212> TYPE: PRT
<213> ORGANISM: Homo sapiens

<400> SEQUENCE: 55

```
Met Ala Gln Val Leu Arg Gly Thr Val Thr Asp Phe Pro Gly Phe Asp
1               5                   10                  15

Glu Arg Ala Asp Ala Glu Thr Leu Arg Lys Ala Met Lys Gly Leu Gly
                20                  25                  30

Thr Asp Glu Glu Ser Ile Leu Thr Leu Leu Thr Ser Arg Ser Asn Ala
            35                  40                  45

Gln Arg Gln Glu Ile Ser Ala Ala Phe Lys Thr Leu Phe Gly Arg Asp
        50                  55                  60

Leu Leu Asp Asp Leu Lys Ser Glu Leu Thr Gly Lys Phe Glu Lys Leu
65                  70                  75                  80

Ile Val Ala Leu Met Lys Pro Ser Arg Leu Tyr Asp Ala Tyr Glu Leu
                85                  90                  95

Lys His Ala Leu Lys Gly Ala Gly Thr Asn Glu Lys Val Leu Thr Glu
            100                 105                 110

Ile Ile Ala Ser Arg Thr Pro Glu Glu Leu Arg Ala Ile Lys Gln Val
        115                 120                 125

Tyr Glu Glu Glu Tyr Gly Ser Ser Leu Glu Asp Asp Val Val Gly Asp
    130                 135                 140

Thr Ser Gly Tyr Tyr Gln Arg Met Leu Val Val Leu Leu Gln Ala Asn
145                 150                 155                 160

Arg Asp Pro Asp Ala Gly Ile Asp Glu Ala Gln Val Glu Gln Asp Ala
                165                 170                 175

Gln Ala Leu Phe Gln Ala Gly Glu Leu Lys Trp Gly Thr Asp Glu Glu
            180                 185                 190

Lys Phe Ile Thr Ile Phe Gly Thr Arg Ser Val Ser His Leu Arg Lys
        195                 200                 205

Val Phe Asp Lys Tyr Met Thr Ile Ser Gly Phe Gln Ile Glu Glu Thr
    210                 215                 220

Ile Asp Arg Glu Thr Ser Gly Asn Leu Glu Gln Leu Leu Leu Ala Val
225                 230                 235                 240

Val Lys Ser Ile Arg Ser Ile Pro Ala Tyr Leu Ala Glu Thr Leu Tyr
                245                 250                 255

Tyr Ala Met Lys Gly Ala Gly Thr Asp Asp His Thr Leu Ile Arg Val
```

```
                    260                 265                 270
Met Val Ser Arg Ser Glu Ile Asp Leu Phe Asn Ile Arg Lys Glu Phe
            275                 280                 285

Arg Lys Asn Phe Ala Thr Ser Leu Tyr Ser Met Ile Lys Gly Asp Thr
        290                 295                 300

Ser Gly Asp Tyr Lys Lys Ala Leu Leu Leu Leu Cys Gly Glu Asp Asp
305                 310                 315                 320

<210> SEQ ID NO 56
<211> LENGTH: 31
<212> TYPE: PRT
<213> ORGANISM: Sus scrofa

<400> SEQUENCE: 56

Ser Trp Leu Ser Lys Thr Ala Lys Lys Leu Glu Asn Ser Ala Lys Lys
1               5                   10                  15

Arg Ile Ser Glu Gly Ile Ala Ile Ala Ile Gln Gly Gly Pro Arg
            20                  25                  30

<210> SEQ ID NO 57
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (3)..(3)
<223> OTHER INFORMATION: N-methyl-Val
<220> FEATURE:
<221> NAME/KEY: misc_feature
<222> LOCATION: (5)..(5)
<223> OTHER INFORMATION: /note="C-term amidated"

<400> SEQUENCE: 57

Val Val Val Pro Pro
1               5

<210> SEQ ID NO 58
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Pyro-Glu
<220> FEATURE:
<221> NAME/KEY: MOD_RES
<222> LOCATION: (4)..(4)
<223> OTHER INFORMATION: Tyr(SO3H)
<220> FEATURE:
<221> NAME/KEY: misc_feature
<222> LOCATION: (10)..(10)
<223> OTHER INFORMATION: /note="C-term amidated"

<400> SEQUENCE: 58

Glu Gln Asp Tyr Thr Gly Trp Met Asp Phe
1               5                   10

<210> SEQ ID NO 59
<211> LENGTH: 41
<212> TYPE: PRT
```

<213> ORGANISM: Artificial Sequence
<220> FEATURE:
<221> NAME/KEY: source
<223> OTHER INFORMATION: /note="Description of Artificial Sequence:
     Synthetic polypeptide"

<400> SEQUENCE: 59

```
Ser Gln Glu Pro Pro Ile Ser Leu Asp Leu Thr Phe His Leu Leu Arg
1               5                   10                  15
Glu Val Leu Glu Met Thr Lys Ala Asp Gln Leu Ala Gln Gln Ala His
            20                  25                  30
Ser Asn Arg Lys Leu Leu Asp Ile Ala
        35                  40
```

<210> SEQ ID NO 60
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic peptide"
<220> FEATURE:
<221> NAME/KEY: MOD_RES
<222> LOCATION: (1)..(1)
<223> OTHER INFORMATION: Beta-Ala

<400> SEQUENCE: 60

```
Ala Arg Gly Phe Phe
1               5
```

<210> SEQ ID NO 61
<211> LENGTH: 41
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic polypeptide"
<220> FEATURE:
<221> NAME/KEY: MOD_RES
<222> LOCATION: (26)..(26)
<223> OTHER INFORMATION: Alph-Glu

<400> SEQUENCE: 61

```
Met Thr Leu Thr Val Gln Ala Arg Gln Leu Leu Ser Gln Ile Val Gln
1               5                   10                  15
Gln Gln Asn Asn Leu Leu Arg Ala Ile Glu Ala Gln Gln His Leu Leu
            20                  25                  30
Gln Leu Thr Val Trp Gly Ile Lys Gln
        35                  40
```

<210> SEQ ID NO 62
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic peptide"

<400> SEQUENCE: 62

```
Arg Gly Asp Ser
1
```

<210> SEQ ID NO 63
<211> LENGTH: 17

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 63

Tyr Gly Gly Phe Leu Arg Arg Ile Arg Pro Lys Leu Lys Trp Asp Asn
1               5                   10                  15

Gln

<210> SEQ ID NO 64
<211> LENGTH: 94
<212> TYPE: PRT
<213> ORGANISM: Homo sapiens

<400> SEQUENCE: 64

Met Arg Thr Leu Ala Ile Leu Ala Ala Ile Leu Leu Val Ala Leu Gln
1               5                   10                  15

Ala Gln Ala Glu Pro Leu Gln Ala Arg Ala Asp Glu Val Ala Ala Ala
            20                  25                  30

Pro Glu Gln Ile Ala Ala Asp Ile Pro Glu Val Val Ser Leu Ala
        35                  40                  45

Trp Asp Glu Ser Leu Ala Pro Lys His Pro Gly Ser Arg Lys Asn Met
50                  55                  60

Asp Cys Tyr Cys Arg Ile Pro Ala Cys Ile Ala Gly Glu Arg Arg Tyr
65                  70                  75                  80

Gly Thr Cys Ile Tyr Gln Gly Arg Leu Trp Ala Phe Cys Cys
                85                  90

<210> SEQ ID NO 65
<211> LENGTH: 60
<212> TYPE: PRT
<213> ORGANISM: Ornithodoros moubata

<400> SEQUENCE: 65

Ser Asp Asp Lys Cys Gln Gly Arg Pro Met Tyr Gly Cys Arg Glu Asp
1               5                   10                  15

Asp Asp Ser Val Phe Gly Trp Thr Tyr Asp Ser Asn His Gly Gln Cys
            20                  25                  30

Trp Lys Gly Ser Tyr Cys Lys His Arg Arg Gln Pro Ser Asn Tyr Phe
        35                  40                  45

Ala Ser Gln Gln Glu Cys Arg Asn Thr Cys Gly Ala
    50                  55                  60

<210> SEQ ID NO 66
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (7)..(7)
<223> OTHER INFORMATION: N2-methyl-Arg

<400> SEQUENCE: 66

Tyr Gly Gly Phe Leu Arg Arg
1               5
```

```
<210> SEQ ID NO 67
<211> LENGTH: 60
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 67

Glu Ala Met His Ser Phe Cys Ala Phe Lys Ala Asp Asp Gly Pro Cys
1               5                   10                  15

Arg Ala Ala His Pro Arg Trp Phe Phe Asn Ile Phe Thr Arg Gln Cys
            20                  25                  30

Glu Glu Phe Ile Tyr Gly Gly Cys Glu Gly Asn Gln Asn Arg Phe Glu
        35                  40                  45

Ser Leu Glu Glu Cys Lys Lys Met Cys Thr Arg Asp
    50                  55                  60

<210> SEQ ID NO 68
<211> LENGTH: 21
<212> TYPE: PRT
<213> ORGANISM: Homo sapiens

<400> SEQUENCE: 68

Met Arg Ala Ser Ser Phe Leu Ile Val Val Val Phe Leu Ile Ala Gly
1               5                   10                  15

Thr Leu Val Leu Glu
            20

<210> SEQ ID NO 69
<211> LENGTH: 57
<212> TYPE: PRT
<213> ORGANISM: Homo sapiens

<400> SEQUENCE: 69

Ala Gln Glu Pro Val Lys Gly Pro Val Ser Thr Lys Pro Gly Ser Cys
1               5                   10                  15

Pro Ile Ile Leu Ile Arg Cys Ala Met Leu Asn Pro Pro Asn Arg Cys
            20                  25                  30

Leu Lys Asp Thr Asp Cys Pro Gly Ile Lys Lys Cys Cys Glu Gly Ser
        35                  40                  45

Cys Gly Met Ala Cys Phe Val Pro Gln
    50                  55

<210> SEQ ID NO 70
<211> LENGTH: 31
<212> TYPE: PRT
<213> ORGANISM: Homo sapiens
<220> FEATURE:
<221> NAME/KEY: misc_feature
<222> LOCATION: (31)..(31)
<223> OTHER INFORMATION: /note="C-term amidated"

<400> SEQUENCE: 70

Ser Asn Leu Ser Thr Asn Val Leu Gly Lys Leu Ser Gln Glu Leu His
1               5                   10                  15

Lys Leu Gln Thr Tyr Pro Arg Thr Asn Val Gly Ala Gly Thr Pro
            20                  25                  30

<210> SEQ ID NO 71
<211> LENGTH: 12
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: 5-oxo-Pro
<220> FEATURE:
<221> NAME/KEY: misc_feature
<222> LOCATION: (12)..(12)
<223> OTHER INFORMATION: /note="C-term amidated"

<400> SEQUENCE: 71

Pro Pro Ser Lys Asp Ala Phe Ala Ile Gly Leu Met
1               5                   10

<210> SEQ ID NO 72
<211> LENGTH: 31
<212> TYPE: PRT
<213> ORGANISM: Homo sapiens

<400> SEQUENCE: 72

Tyr Gly Gly Phe Met Thr Ser Glu Lys Ser Gln Thr Pro Leu Val Thr
1               5                   10                  15

Leu Phe Lys Asn Ala Ile Ile Lys Asn Ala Tyr Lys Lys Gly Glu
            20                  25                  30

<210> SEQ ID NO 73
<211> LENGTH: 482
<212> TYPE: PRT
<213> ORGANISM: Homo sapiens

<400> SEQUENCE: 73

Met Ala Ala Leu Met Thr Pro Gly Thr Gly Ala Pro Pro Ala Pro Gly
1               5                   10                  15

Asp Phe Ser Gly Glu Gly Ser Gln Gly Leu Pro Asp Pro Ser Pro Glu
            20                  25                  30

Pro Lys Gln Leu Pro Glu Leu Ile Arg Met Lys Arg Asp Gly Gly Arg
        35                  40                  45

Leu Ser Glu Ala Asp Ile Arg Gly Phe Val Ala Ala Val Val Asn Gly
    50                  55                  60

Ser Ala Gln Gly Ala Gln Ile Gly Ala Met Leu Met Ala Ile Arg Leu
65                  70                  75                  80

Arg Gly Met Asp Leu Glu Glu Thr Ser Val Leu Thr Gln Ala Leu Ala
                85                  90                  95

Gln Ser Gly Gln Gln Leu Glu Trp Pro Glu Ala Trp Arg Gln Gln Leu
            100                 105                 110

Val Asp Lys His Ser Thr Gly Gly Val Gly Asp Lys Val Ser Leu Val
        115                 120                 125

Leu Ala Pro Ala Leu Ala Ala Cys Gly Cys Lys Val Pro Met Ile Ser
    130                 135                 140

Gly Arg Gly Leu Gly His Thr Gly Gly Thr Leu Asp Lys Leu Glu Ser
145                 150                 155                 160

Ile Pro Gly Phe Asn Val Ile Gln Ser Pro Glu Gln Met Gln Val Leu
                165                 170                 175

Leu Asp Gln Ala Gly Cys Cys Ile Val Gly Gln Ser Glu Gln Leu Val
            180                 185                 190

Pro Ala Asp Gly Ile Leu Tyr Ala Ala Arg Asp Val Thr Ala Thr Val
```

```
            195                 200                 205
Asp Ser Leu Pro Leu Ile Thr Ala Ser Ile Leu Ser Lys Lys Leu Val
    210                 215                 220

Glu Gly Leu Ser Ala Leu Val Val Asp Val Lys Phe Gly Gly Ala Ala
225                 230                 235                 240

Val Phe Pro Asn Gln Glu Gln Ala Arg Glu Leu Ala Lys Thr Leu Val
                245                 250                 255

Gly Val Gly Ala Ser Leu Gly Leu Arg Val Ala Ala Leu Thr Ala
                260                 265                 270

Met Asp Lys Pro Leu Gly Arg Cys Val Gly His Ala Leu Glu Val Glu
            275                 280                 285

Glu Ala Leu Leu Cys Met Asp Gly Ala Gly Pro Pro Asp Leu Arg Asp
    290                 295                 300

Leu Val Thr Thr Leu Gly Gly Ala Leu Leu Trp Leu Ser Gly His Ala
305                 310                 315                 320

Gly Thr Gln Ala Gln Gly Ala Ala Arg Val Ala Ala Leu Asp Asp
                325                 330                 335

Gly Ser Ala Leu Gly Arg Phe Glu Arg Met Leu Ala Ala Gln Gly Val
                340                 345                 350

Asp Pro Gly Leu Ala Arg Ala Leu Cys Ser Gly Ser Pro Ala Glu Arg
            355                 360                 365

Arg Gln Leu Leu Pro Arg Ala Arg Glu Gln Glu Leu Leu Ala Pro
    370                 375                 380

Ala Asp Gly Thr Val Glu Leu Val Arg Ala Leu Pro Leu Ala Leu Val
385                 390                 395                 400

Leu His Glu Leu Gly Ala Gly Arg Ser Arg Ala Gly Glu Pro Leu Arg
                405                 410                 415

Leu Gly Val Gly Ala Glu Leu Leu Val Asp Val Gly Arg Leu Arg
                420                 425                 430

Arg Gly Thr Pro Trp Leu Arg Val His Arg Asp Gly Pro Ala Leu Ser
            435                 440                 445

Gly Pro Gln Ser Arg Ala Leu Gln Glu Ala Leu Val Leu Ser Asp Arg
    450                 455                 460

Ala Pro Phe Ala Ala Pro Ser Pro Phe Ala Glu Leu Val Leu Pro Pro
465                 470                 475                 480

Gln Gln

<210> SEQ ID NO 74
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (5)..(5)
<223> OTHER INFORMATION: /note="C-term amidated"

<400> SEQUENCE: 74

Gly Asp Trp Pro Cys
1               5

<210> SEQ ID NO 75
<211> LENGTH: 5
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic peptide"

<400> SEQUENCE: 75

Gln His Asn Pro Arg
1               5

<210> SEQ ID NO 76
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 76

Gly Arg Gly Asp Ser
1               5

<210> SEQ ID NO 77
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 77

Tyr Tyr Trp Ile Gly Ile Arg
1               5

<210> SEQ ID NO 78
<211> LENGTH: 92
<212> TYPE: PRT
<213> ORGANISM: Homo sapiens

<400> SEQUENCE: 78

Met Lys Pro Ile Gln Lys Leu Leu Ala Gly Leu Ile Leu Leu Thr Trp
1               5                   10                  15

Cys Val Glu Gly Cys Ser Ser Gln His Trp Ser Tyr Gly Leu Arg Pro
                20                  25                  30

Gly Gly Lys Arg Asp Ala Glu Asn Leu Ile Asp Ser Phe Gln Glu Ile
            35                  40                  45

Val Lys Glu Val Gly Gln Leu Ala Glu Thr Gln Arg Phe Glu Cys Thr
    50                  55                  60

Thr His Gln Pro Arg Ser Pro Leu Arg Asp Leu Lys Gly Ala Leu Glu
65                  70                  75                  80

Ser Leu Ile Glu Glu Glu Thr Gly Gln Lys Lys Ile
                85                  90

<210> SEQ ID NO 79
<211> LENGTH: 44
<212> TYPE: PRT
<213> ORGANISM: Homo sapiens

<400> SEQUENCE: 79

Met Pro Leu Trp Val Phe Phe Phe Val Ile Leu Thr Leu Ser Asn Ser
1               5                   10                  15

Ser His Cys Ser Pro Pro Pro Pro Leu Thr Leu Arg Met Arg Arg Tyr
                20                  25                  30
```

Ala Asp Ala Ile Phe Thr Asn Ser Tyr Arg Lys Val
        35                  40

<210> SEQ ID NO 80
<211> LENGTH: 107
<212> TYPE: PRT
<213> ORGANISM: Homo sapiens

<400> SEQUENCE: 80

Met Pro Leu Trp Val Phe Phe Phe Val Ile Leu Thr Leu Ser Asn Ser
1               5                   10                  15

Ser His Cys Ser Pro Pro Pro Leu Thr Leu Arg Met Arg Arg Tyr
            20                  25                  30

Ala Asp Ala Ile Phe Thr Asn Ser Tyr Arg Lys Val Leu Gly Gln Leu
        35                  40                  45

Ser Ala Arg Lys Leu Leu Gln Asp Ile Met Ser Arg Gln Gln Gly Glu
    50                  55                  60

Ser Asn Gln Glu Arg Gly Ala Arg Ala Arg Leu Gly Arg Gln Val Asp
65                  70                  75                  80

Ser Met Trp Ala Glu Gln Lys Gln Met Glu Leu Glu Ser Ile Leu Val
                85                  90                  95

Ala Leu Leu Gln Lys His Arg Asn Ser Gln Gly
            100                 105

<210> SEQ ID NO 81
<211> LENGTH: 123
<212> TYPE: PRT
<213> ORGANISM: Homo sapiens

<400> SEQUENCE: 81

Met Ala Arg Gly Ser Ala Leu Leu Leu Ala Ser Leu Leu Leu Ala Ala
1               5                   10                  15

Ala Leu Ser Ala Ser Ala Gly Leu Trp Ser Pro Ala Lys Glu Lys Arg
            20                  25                  30

Gly Trp Thr Leu Asn Ser Ala Gly Tyr Leu Leu Gly Pro His Ala Val
        35                  40                  45

Gly Asn His Arg Ser Phe Ser Asp Lys Asn Gly Leu Thr Ser Lys Arg
    50                  55                  60

Glu Leu Arg Pro Glu Asp Asp Met Lys Pro Gly Ser Phe Asp Arg Ser
65                  70                  75                  80

Ile Pro Glu Asn Asn Ile Met Arg Thr Ile Ile Glu Phe Leu Ser Phe
                85                  90                  95

Leu His Leu Lys Glu Ala Gly Ala Leu Asp Arg Leu Leu Asp Leu Pro
            100                 105                 110

Ala Ala Ala Ser Ser Glu Asp Ile Glu Arg Ser
        115                 120

<210> SEQ ID NO 82
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (7)..(7)
<223> OTHER INFORMATION: /note="C-term amidated"

-continued

```
<400> SEQUENCE: 82

Glu Ala Tyr Gly Tyr Met Asp
1               5

<210> SEQ ID NO 83
<211> LENGTH: 180
<212> TYPE: PRT
<213> ORGANISM: Homo sapiens

<400> SEQUENCE: 83

Met Lys Ser Ile Tyr Phe Val Ala Gly Leu Phe Val Met Leu Val Gln
1               5                   10                  15

Gly Ser Trp Gln Arg Ser Leu Gln Asp Thr Glu Glu Lys Ser Arg Ser
            20                  25                  30

Phe Ser Ala Ser Gln Ala Asp Pro Leu Ser Asp Pro Asp Gln Met Asn
        35                  40                  45

Glu Asp Lys Arg His Ser Gln Gly Thr Phe Thr Ser Asp Tyr Ser Lys
    50                  55                  60

Tyr Leu Asp Ser Arg Arg Ala Gln Asp Phe Val Gln Trp Leu Met Asn
65                  70                  75                  80

Thr Lys Arg Asn Arg Asn Asn Ile Ala Lys Arg His Asp Glu Phe Glu
                85                  90                  95

Arg His Ala Glu Gly Thr Phe Thr Ser Asp Val Ser Ser Tyr Leu Glu
            100                 105                 110

Gly Gln Ala Ala Lys Glu Phe Ile Ala Trp Leu Val Lys Gly Arg Gly
        115                 120                 125

Arg Arg Asp Phe Pro Glu Glu Val Ala Ile Val Glu Glu Leu Gly Arg
    130                 135                 140

Arg His Ala Asp Gly Ser Phe Ser Asp Glu Met Asn Thr Ile Leu Asp
145                 150                 155                 160

Asn Leu Ala Ala Arg Asp Phe Ile Asn Trp Leu Ile Gln Thr Lys Ile
                165                 170                 175

Thr Asp Arg Lys
            180

<210> SEQ ID NO 84
<211> LENGTH: 29
<212> TYPE: PRT
<213> ORGANISM: Homo sapiens

<400> SEQUENCE: 84

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr
            20                  25

<210> SEQ ID NO 85
<211> LENGTH: 92
<212> TYPE: PRT
<213> ORGANISM: Homo sapiens

<400> SEQUENCE: 85

Met Lys Pro Ile Gln Lys Leu Leu Ala Gly Leu Ile Leu Leu Thr Trp
1               5                   10                  15

Cys Val Glu Gly Cys Ser Ser Gln His Trp Ser Tyr Gly Leu Arg Pro
            20                  25                  30

Gly Gly Lys Arg Asp Ala Glu Asn Leu Ile Asp Ser Phe Gln Glu Ile
        35                  40                  45
```

```
Val Lys Glu Val Gly Gln Leu Ala Glu Thr Gln Arg Phe Glu Cys Thr
        50                  55                  60

Thr His Gln Pro Arg Ser Pro Leu Arg Asp Leu Lys Gly Ala Leu Glu
 65                  70                  75                  80

Ser Leu Ile Glu Glu Thr Gly Gln Lys Lys Ile
                85                  90

<210> SEQ ID NO 86
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: 5-oxo-His
<220> FEATURE:
<221> NAME/KEY: misc_feature
<222> LOCATION: (9)..(9)
<223> OTHER INFORMATION: /note="C-term amidated"

<400> SEQUENCE: 86

His Trp Ser Tyr Gly Leu Arg Pro Gly
1               5

<210> SEQ ID NO 87
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 87

Arg Gly Gly Leu Cys Tyr Cys Arg Gly Arg Phe Cys Val Cys Val Gly
1               5                   10                  15

<210> SEQ ID NO 88
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(2)
<223> OTHER INFORMATION: (4R)-4-hydroxy-Pro

<400> SEQUENCE: 88

Phe Pro Arg Gly
1

<210> SEQ ID NO 89
<211> LENGTH: 140
<212> TYPE: PRT
<213> ORGANISM: Homo sapiens

<400> SEQUENCE: 89

Met Gly Phe Gln Lys Phe Ser Pro Phe Leu Ala Leu Ser Ile Leu Val
1               5                   10                  15

Leu Leu Gln Ala Gly Ser Leu His Ala Ala Pro Phe Arg Ser Ala Leu
```

```
                    20                  25                  30
Glu Ser Ser Pro Ala Asp Pro Ala Thr Leu Ser Glu Asp Glu Ala Arg
                35                  40                  45
Leu Leu Leu Ala Ala Leu Val Gln Asp Tyr Val Gln Met Lys Ala Ser
 50                  55                  60
Glu Leu Glu Gln Glu Gln Arg Glu Gly Ser Ser Leu Asp Ser Pro
 65                  70                  75                  80
Arg Ser Lys Arg Cys Gly Asn Leu Ser Thr Cys Met Leu Gly Thr Tyr
                85                  90                  95
Thr Gln Asp Phe Asn Lys Phe His Thr Phe Pro Gln Thr Ala Ile Gly
                100                 105                 110
Val Gly Ala Pro Gly Lys Lys Arg Asp Met Ser Ser Asp Leu Glu Arg
            115                 120                 125
Asp His Arg Pro His Val Ser Met Pro Gln Ala Asn
        130                 135                 140

<210> SEQ ID NO 90
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 90

Arg Met Phe Arg Tyr
1               5

<210> SEQ ID NO 91
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (6)..(6)
<223> OTHER INFORMATION: (3S,4S)-4-amino-5-cyclohexyl-3-hydroxypentanoic
      acid
<220> FEATURE:
<221> NAME/KEY: misc_feature
<222> LOCATION: (8)..(8)
<223> OTHER INFORMATION: /note=C-term amidated"

<400> SEQUENCE: 91

Val His Pro Phe His Xaa Leu Phe
1               5

<210> SEQ ID NO 92
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (3)..(3)
<223> OTHER INFORMATION: Alpha-Asp

<400> SEQUENCE: 92

Phe Leu Asp Val Pro Ala Ala Lys
```

```
<210> SEQ ID NO 93
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 93

Pro Val Thr Lys Pro Gln
1               5

<210> SEQ ID NO 94
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (6)..(6)
<223> OTHER INFORMATION: /note="C-term amidated"

<400> SEQUENCE: 94

Ser Ile Lys Val Ala Val
1               5

<210> SEQ ID NO 95
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 95

Tyr Ile Gly Ser Arg
1               5

<210> SEQ ID NO 96
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 96

Ile Leu Arg Trp Pro Trp Trp Pro Trp Arg Arg
1               5                   10

<210> SEQ ID NO 97
<211> LENGTH: 304
<212> TYPE: PRT
<213> ORGANISM: Homo sapiens

<400> SEQUENCE: 97

Met Gly Asn His Ala Gly Lys Arg Glu Leu Asn Ala Glu Lys Ala Ser
1               5                   10                  15

Thr Asn Ser Glu Thr Asn Arg Gly Glu Ser Glu Lys Lys Arg Asn Leu
            20                  25                  30
```

```
Gly Glu Leu Ser Arg Thr Thr Ser Glu Asp Asn Glu Val Phe Gly Glu
            35                  40                  45

Ala Asp Ala Asn Gln Asn Asn Gly Thr Ser Ser Gln Asp Thr Ala Val
 50                  55                  60

Thr Asp Ser Lys Arg Thr Ala Asp Pro Lys Asn Ala Trp Gln Asp Ala
 65                  70                  75                  80

His Pro Ala Asp Pro Gly Ser Arg Pro His Leu Ile Arg Leu Phe Ser
                85                  90                  95

Arg Asp Ala Pro Gly Arg Glu Asp Asn Thr Phe Lys Asp Arg Pro Ser
            100                 105                 110

Glu Ser Asp Glu Leu Gln Thr Ile Gln Glu Asp Ser Ala Ala Thr Ser
            115                 120                 125

Glu Ser Leu Asp Val Met Ala Ser Gln Lys Arg Pro Ser Gln Arg His
            130                 135                 140

Gly Ser Lys Tyr Leu Ala Thr Ala Ser Thr Met Asp His Ala Arg His
145                 150                 155                 160

Gly Phe Leu Pro Arg His Arg Asp Thr Gly Ile Leu Asp Ser Ile Gly
                165                 170                 175

Arg Phe Phe Gly Gly Asp Arg Gly Ala Pro Lys Arg Gly Ser Gly Lys
            180                 185                 190

Asp Ser His His Pro Ala Arg Thr Ala His Tyr Gly Ser Leu Pro Gln
            195                 200                 205

Lys Ser His Gly Arg Thr Gln Asp Glu Asn Pro Val Val His Phe Phe
210                 215                 220

Lys Asn Ile Val Thr Pro Arg Thr Pro Pro Ser Gln Gly Lys Gly
225                 230                 235                 240

Arg Gly Leu Ser Leu Ser Arg Phe Ser Trp Gly Ala Glu Gly Gln Arg
                245                 250                 255

Pro Gly Phe Gly Tyr Gly Gly Arg Ala Ser Asp Tyr Lys Ser Ala His
            260                 265                 270

Lys Gly Phe Lys Gly Val Asp Ala Gln Gly Thr Leu Ser Lys Ile Phe
            275                 280                 285

Lys Leu Gly Gly Arg Asp Ser Arg Ser Gly Ser Pro Met Ala Arg Arg
            290                 295                 300

<210> SEQ ID NO 98
<211> LENGTH: 197
<212> TYPE: PRT
<213> ORGANISM: Homo sapiens

<400> SEQUENCE: 98

Met Gly Asn His Ala Gly Lys Arg Glu Leu Asn Ala Glu Lys Ala Ser
1               5                   10                  15

Thr Asn Ser Glu Thr Asn Arg Gly Glu Ser Glu Lys Lys Arg Asn Leu
            20                  25                  30

Gly Glu Leu Ser Arg Thr Thr Ser Glu Asp Asn Glu Val Phe Gly Glu
            35                  40                  45

Ala Asp Ala Asn Gln Asn Asn Gly Thr Ser Ser Gln Asp Thr Ala Val
 50                  55                  60

Thr Asp Ser Lys Arg Thr Ala Asp Pro Lys Asn Ala Trp Gln Asp Ala
 65                  70                  75                  80

His Pro Ala Asp Pro Gly Ser Arg Pro His Leu Ile Arg Leu Phe Ser
                85                  90                  95

Arg Asp Ala Pro Gly Arg Glu Asp Asn Thr Phe Lys Asp Arg Pro Ser
```

```
                100              105              110
Glu Ser Asp Glu Leu Gln Thr Ile Gln Glu Asp Ser Ala Ala Thr Ser
            115                  120             125
Glu Ser Leu Asp Val Met Ala Ser Gln Lys Arg Pro Ser Gln Arg His
        130                 135             140
Gly Ser Lys Tyr Leu Ala Thr Ala Ser Thr Met Asp His Ala Arg His
145                 150             155                 160
Gly Phe Leu Pro Arg His Arg Asp Thr Gly Ile Leu Asp Ser Ile Gly
                165             170             175
Arg Phe Phe Gly Gly Asp Arg Gly Ala Pro Lys Arg Gly Ser Gly Lys
            180             185             190
Val Ser Ser Glu Glu
        195

<210> SEQ ID NO 99
<211> LENGTH: 197
<212> TYPE: PRT
<213> ORGANISM: Homo sapiens

<400> SEQUENCE: 99

Met Ala Ser Gln Lys Arg Pro Ser Gln Arg His Gly Ser Lys Tyr Leu
1               5                   10                  15
Ala Thr Ala Ser Thr Met Asp His Ala Arg His Gly Phe Leu Pro Arg
            20                  25                  30
His Arg Asp Thr Gly Ile Leu Asp Ser Ile Gly Arg Phe Phe Gly Gly
        35                  40                  45
Asp Arg Gly Ala Pro Lys Arg Gly Ser Gly Lys Val Pro Trp Leu Lys
    50                  55                  60
Pro Gly Arg Ser Pro Leu Pro Ser His Ala Arg Ser Gln Pro Gly Leu
65                  70                  75                  80
Cys Asn Met Tyr Lys Asp Ser His His Pro Ala Arg Thr Ala His Tyr
                85                  90                  95
Gly Ser Leu Pro Gln Lys Ser His Gly Arg Thr Gln Asp Glu Asn Pro
            100                 105                 110
Val Val His Phe Phe Lys Asn Ile Val Thr Pro Arg Thr Pro Pro Pro
        115                 120                 125
Ser Gln Gly Lys Gly Arg Gly Leu Ser Leu Ser Arg Phe Ser Trp Gly
    130                 135                 140
Ala Glu Gly Gln Arg Pro Gly Phe Gly Tyr Gly Gly Arg Ala Ser Asp
145                 150                 155                 160
Tyr Lys Ser Ala His Lys Gly Phe Lys Gly Val Asp Ala Gln Gly Thr
                165                 170                 175
Leu Ser Lys Ile Phe Lys Leu Gly Gly Arg Asp Ser Arg Ser Gly Ser
            180                 185                 190
Pro Met Ala Arg Arg
        195

<210> SEQ ID NO 100
<211> LENGTH: 22
<212> TYPE: PRT
<213> ORGANISM: Homo sapiens

<400> SEQUENCE: 100

Met Ala Ser Gln Lys Arg Pro Ser Gln Arg His Gly Ser Lys Tyr Leu
1               5                   10                  15
Ala Thr Ala Ser Thr Met
```

20

<210> SEQ ID NO 101
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 101

Gly Pro Leu Ala
1

<210> SEQ ID NO 102
<211> LENGTH: 4
<212> TYPE: PRT
<213> ORGANISM: Homo sapiens

<400> SEQUENCE: 102

Asn Ala Gly Ala
1

<210> SEQ ID NO 103
<211> LENGTH: 487
<212> TYPE: PRT
<213> ORGANISM: Homo sapiens

<400> SEQUENCE: 103

Met Arg Glu Asn Met Ala Arg Gly Pro Cys Asn Ala Pro Arg Trp Ala
1               5                   10                  15

Ser Leu Met Val Leu Val Ala Ile Gly Thr Ala Val Thr Ala Ala Val
                20                  25                  30

Asn Pro Gly Val Val Val Arg Ile Ser Gln Lys Gly Leu Asp Tyr Ala
            35                  40                  45

Ser Gln Gln Gly Thr Ala Ala Leu Gln Lys Glu Leu Lys Arg Ile Lys
        50                  55                  60

Ile Pro Asp Tyr Ser Asp Ser Phe Lys Ile Lys His Leu Gly Lys Gly
65                  70                  75                  80

His Tyr Ser Phe Tyr Ser Met Asp Ile Arg Glu Phe Gln Leu Pro Ser
                85                  90                  95

Ser Gln Ile Ser Met Val Pro Asn Val Gly Leu Lys Phe Ser Ile Ser
            100                 105                 110

Asn Ala Asn Ile Lys Ile Ser Gly Lys Trp Lys Ala Gln Lys Arg Phe
        115                 120                 125

Leu Lys Met Ser Gly Asn Phe Asp Leu Ser Ile Glu Gly Met Ser Ile
    130                 135                 140

Ser Ala Asp Leu Lys Leu Gly Ser Asn Pro Thr Ser Gly Lys Pro Thr
145                 150                 155                 160

Ile Thr Cys Ser Ser Cys Ser Ser His Ile Asn Ser Val His Val His
                165                 170                 175

Ile Ser Lys Ser Lys Val Gly Trp Leu Ile Gln Leu Phe His Lys Lys
            180                 185                 190

Ile Glu Ser Ala Leu Arg Asn Lys Met Asn Ser Gln Val Cys Glu Lys
        195                 200                 205

Val Thr Asn Ser Val Ser Ser Glu Leu Gln Pro Tyr Phe Gln Thr Leu
    210                 215                 220

Pro Val Met Thr Lys Ile Asp Ser Val Ala Gly Ile Asn Tyr Gly Leu

```
                   225                 230                 235                 240
     Val Ala Pro Pro Ala Thr Thr Ala Glu Thr Leu Asp Val Gln Met Lys
                     245                 250                 255

Gly Glu Phe Tyr Ser Glu Asn His His Asn Pro Pro Phe Ala Pro
                     260                 265                 270

Pro Val Met Glu Phe Pro Ala Ala His Asp Arg Met Val Tyr Leu Gly
                 275                 280                 285

Leu Ser Asp Tyr Phe Phe Asn Thr Ala Gly Leu Val Tyr Gln Glu Ala
                 290                 295                 300

Gly Val Leu Lys Met Thr Leu Arg Asp Asp Met Ile Pro Lys Glu Ser
     305                 310                 315                 320

Lys Phe Arg Leu Thr Thr Lys Phe Phe Gly Thr Phe Leu Pro Glu Val
                     325                 330                 335

Ala Lys Lys Phe Pro Asn Met Lys Ile Gln Ile His Val Ser Ala Ser
                     340                 345                 350

Thr Pro Pro His Leu Ser Val Gln Pro Thr Gly Leu Thr Phe Tyr Pro
                     355                 360                 365

Ala Val Asp Val Gln Ala Phe Ala Val Leu Pro Asn Ser Ser Leu Ala
                 370                 375                 380

Ser Leu Phe Leu Ile Gly Met His Thr Thr Gly Ser Met Glu Val Ser
     385                 390                 395                 400

Ala Glu Ser Asn Arg Leu Val Gly Glu Leu Lys Leu Asp Arg Leu Leu
                     405                 410                 415

Leu Glu Leu Lys His Ser Asn Ile Gly Pro Phe Pro Val Glu Leu Leu
                     420                 425                 430

Gln Asp Ile Met Asn Tyr Ile Val Pro Ile Leu Val Leu Pro Arg Val
                 435                 440                 445

Asn Glu Lys Leu Gln Lys Gly Phe Pro Leu Pro Thr Pro Ala Arg Val
                 450                 455                 460

Gln Leu Tyr Asn Val Val Leu Gln Pro His Gln Asn Phe Leu Leu Phe
     465                 470                 475                 480

Gly Ala Asp Val Val Tyr Lys
                     485

<210> SEQ ID NO 104
<211> LENGTH: 31
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Alpha-Glu
<220> FEATURE:
<221> NAME/KEY: MOD_RES
<222> LOCATION: (9)..(9)
<223> OTHER INFORMATION: Alpha-Asp
<220> FEATURE:
<221> NAME/KEY: MOD_RES
<222> LOCATION: (15)..(15)
<223> OTHER INFORMATION: Alpha-Glu
<220> FEATURE:
<221> NAME/KEY: MOD_RES
<222> LOCATION: (20)..(20)
<223> OTHER INFORMATION: N6-N-(1-oxohexadecyl)-gamma-Glu
<220> FEATURE:
<221> NAME/KEY: MOD_RES
<222> LOCATION: (22)..(22)
<223> OTHER INFORMATION: Alpha-Glu

<400> SEQUENCE: 104

His Ala Glu Gly Thr Phe Thr Ser Asp Val Ser Ser Tyr Leu Glu Gly
```

```
                1               5                   10                  15
Gln Ala Ala Glu Lys Glu Phe Ile Ala Trp Leu Val Arg Gly Arg
            20                  25                  30
```

<210> SEQ ID NO 105
<211> LENGTH: 70
<212> TYPE: PRT
<213> ORGANISM: Homo sapiens

<400> SEQUENCE: 105

```
Ser Phe Lys Ile Lys His Leu Gly Lys Gly His Tyr Ser Phe Tyr Ser
1               5                   10                  15
Met Asp Ile Arg Glu Phe Gln Leu Pro Ser Ser Gln Ile Ser Met Val
            20                  25                  30
Pro Asn Val Gly Leu Lys Phe Ser Ile Ser Asn Ala Asn Ile Lys Ile
        35                  40                  45
Ser Gly Lys Trp Lys Ala Gln Lys Arg Phe Leu Lys Met Ser Gly Asn
    50                  55                  60
Phe Asp Leu Ser Ile Glu
65                  70
```

<210> SEQ ID NO 106
<211> LENGTH: 70
<212> TYPE: PRT
<213> ORGANISM: Homo sapiens

<400> SEQUENCE: 106

```
Gly Met Ser Ile Ser Ala Asp Leu Lys Leu Gly Ser Asn Pro Thr Ser
1               5                   10                  15
Gly Lys Pro Thr Ile Thr Cys Ser Ser Cys Ser Ser His Ile Asn Ser
            20                  25                  30
Val His Val His Ile Ser Lys Ser Lys Val Gly Trp Leu Ile Gln Leu
        35                  40                  45
Phe His Lys Lys Ile Glu Ser Ala Leu Arg Asn Lys Met Asn Ser Gln
    50                  55                  60
Val Cys Glu Lys Val Thr
65                  70
```

<210> SEQ ID NO 107
<211> LENGTH: 21
<212> TYPE: PRT
<213> ORGANISM: Homo sapiens

<400> SEQUENCE: 107

```
Cys Leu Gly Val Gly Ser Cys Asn Asp Phe Ala Gly Cys Gly Tyr Ala
1               5                   10                  15
Ile Val Cys Phe Trp
            20
```

<210> SEQ ID NO 108
<211> LENGTH: 70
<212> TYPE: PRT
<213> ORGANISM: Homo sapiens

<400> SEQUENCE: 108

```
Asn Ser Val Ser Ser Glu Leu Gln Pro Tyr Phe Gln Thr Leu Pro Val
1               5                   10                  15
Met Thr Lys Ile Asp Ser Val Ala Gly Ile Asn Tyr Gly Leu Val Ala
            20                  25                  30
```

```
Pro Pro Ala Thr Thr Ala Glu Thr Leu Asp Val Gln Met Lys Gly Glu
            35                  40                  45
Phe Tyr Ser Glu Asn His His Asn Pro Pro Phe Ala Pro Pro Val
 50                  55                  60
Met Glu Phe Pro Ala Ala
 65                  70

<210> SEQ ID NO 109
<211> LENGTH: 70
<212> TYPE: PRT
<213> ORGANISM: Homo sapiens

<400> SEQUENCE: 109

His Asp Arg Met Val Tyr Leu Gly Leu Ser Asp Tyr Phe Phe Asn Thr
 1               5                  10                  15
Ala Gly Leu Val Tyr Gln Glu Ala Gly Val Leu Lys Met Thr Leu Arg
                20                  25                  30
Asp Asp Met Ile Pro Lys Glu Ser Lys Phe Arg Leu Thr Thr Lys Phe
            35                  40                  45
Phe Gly Thr Phe Leu Pro Glu Val Ala Lys Lys Phe Pro Asn Met Lys
 50                  55                  60
Ile Gln Ile His Val Ser
 65                  70

<210> SEQ ID NO 110
<211> LENGTH: 70
<212> TYPE: PRT
<213> ORGANISM: Homo sapiens

<400> SEQUENCE: 110

Ala Ser Thr Pro Pro His Leu Ser Val Gln Pro Thr Gly Leu Thr Phe
 1               5                  10                  15
Tyr Pro Ala Val Asp Val Gln Ala Phe Ala Val Leu Pro Asn Ser Ser
                20                  25                  30
Leu Ala Ser Leu Phe Leu Ile Gly Met His Thr Thr Gly Ser Met Glu
            35                  40                  45
Val Ser Ala Glu Ser Asn Arg Leu Val Gly Leu Lys Leu Asp Arg
 50                  55                  60
Leu Leu Leu Glu Leu Lys
 65                  70

<210> SEQ ID NO 111
<211> LENGTH: 67
<212> TYPE: PRT
<213> ORGANISM: Homo sapiens

<400> SEQUENCE: 111

His Ser Asn Ile Gly Pro Phe Pro Val Glu Leu Leu Gln Asp Ile Met
 1               5                  10                  15
Asn Tyr Ile Val Pro Ile Leu Val Leu Pro Arg Val Asn Glu Lys Leu
                20                  25                  30
Gln Lys Gly Phe Pro Leu Pro Thr Pro Ala Arg Val Gln Leu Tyr Asn
            35                  40                  45
Val Val Leu Gln Pro His Gln Asn Phe Leu Leu Phe Gly Ala Asp Val
 50                  55                  60
Val Tyr Lys
 65
```

```
<210> SEQ ID NO 112
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 112

Gly Glu Pro Pro Pro Gly Lys Pro Ala Asp Asp Ala Gly Leu Val
1               5                   10                  15

<210> SEQ ID NO 113
<211> LENGTH: 6
<212> TYPE: PRT
<213> ORGANISM: Homo sapiens

<400> SEQUENCE: 113

Asp Leu Gln Val Phe Val
1               5

<210> SEQ ID NO 114
<211> LENGTH: 5
<212> TYPE: PRT
<213> ORGANISM: Homo sapiens

<400> SEQUENCE: 114

Gly Glu Lys Lys Asp
1               5

<210> SEQ ID NO 115
<211> LENGTH: 5
<212> TYPE: PRT
<213> ORGANISM: Homo sapiens

<400> SEQUENCE: 115

Ala Thr His Glu Ser
1               5

<210> SEQ ID NO 116
<211> LENGTH: 6
<212> TYPE: PRT
<213> ORGANISM: Homo sapiens

<400> SEQUENCE: 116

Cys Leu Pro Val Ser Gly
1               5

<210> SEQ ID NO 117
<211> LENGTH: 6
<212> TYPE: PRT
<213> ORGANISM: Homo sapiens

<400> SEQUENCE: 117

Leu Pro Val Ser Gly Ser
1               5

<210> SEQ ID NO 118
<211> LENGTH: 6
<212> TYPE: PRT
<213> ORGANISM: Homo sapiens

<400> SEQUENCE: 118

Pro Cys His Ala Pro Pro
1               5
```

```
<210> SEQ ID NO 119
<211> LENGTH: 8
<212> TYPE: PRT
<213> ORGANISM: Homo sapiens

<400> SEQUENCE: 119

Gly Gly His Asp Leu Glu Ser Gly
1               5

<210> SEQ ID NO 120
<211> LENGTH: 6
<212> TYPE: PRT
<213> ORGANISM: Homo sapiens

<400> SEQUENCE: 120

Asp Asp Leu Gln Val Phe
1               5

<210> SEQ ID NO 121
<211> LENGTH: 5
<212> TYPE: PRT
<213> ORGANISM: Homo sapiens

<400> SEQUENCE: 121

Pro Leu Thr Ser Gly
1               5

<210> SEQ ID NO 122
<211> LENGTH: 8
<212> TYPE: PRT
<213> ORGANISM: Homo sapiens

<400> SEQUENCE: 122

Leu Ile His Phe Glu Glu Gly Val
1               5

<210> SEQ ID NO 123
<211> LENGTH: 7
<212> TYPE: PRT
<213> ORGANISM: Homo sapiens

<400> SEQUENCE: 123

Gly Glu Phe Ser Tyr Asp Ser
1               5

<210> SEQ ID NO 124
<211> LENGTH: 7
<212> TYPE: PRT
<213> ORGANISM: Homo sapiens

<400> SEQUENCE: 124

His Ala Pro Pro Leu Thr Ser
1               5

<210> SEQ ID NO 125
<211> LENGTH: 7
<212> TYPE: PRT
<213> ORGANISM: Homo sapiens

<400> SEQUENCE: 125

Asp Leu Glu Ser Gly Glu Phe
1               5
```

```
<210> SEQ ID NO 126
<211> LENGTH: 8
<212> TYPE: PRT
<213> ORGANISM: Homo sapiens

<400> SEQUENCE: 126

Gly Glu Phe Ser Val Cys Asp Ser
1               5

<210> SEQ ID NO 127
<211> LENGTH: 10
<212> TYPE: PRT
<213> ORGANISM: Homo sapiens

<400> SEQUENCE: 127

Lys Lys Gly Glu Phe Ser Val Ala Asp Ser
1               5                   10

<210> SEQ ID NO 128
<211> LENGTH: 9
<212> TYPE: PRT
<213> ORGANISM: Homo sapiens

<400> SEQUENCE: 128

Lys Lys Gly Glu Phe Tyr Cys Ser Arg
1               5

<210> SEQ ID NO 129
<211> LENGTH: 13
<212> TYPE: PRT
<213> ORGANISM: Homo sapiens

<400> SEQUENCE: 129

Gly Leu Arg Val Arg Val Trp Asn Gly Lys Phe Pro Lys
1               5                   10

<210> SEQ ID NO 130
<211> LENGTH: 16
<212> TYPE: PRT
<213> ORGANISM: Homo sapiens

<400> SEQUENCE: 130

Gly Val Ala Phe Glu Glu Ala Pro Asp His Ser Phe Phe Leu Phe
1               5                   10                  15

<210> SEQ ID NO 131
<211> LENGTH: 7
<212> TYPE: PRT
<213> ORGANISM: Homo sapiens

<400> SEQUENCE: 131

Gly Gly His Asp Leu Ser Gly
1               5

<210> SEQ ID NO 132
<211> LENGTH: 8
<212> TYPE: PRT
<213> ORGANISM: Homo sapiens

<400> SEQUENCE: 132

Gly Gly His Asp Leu Glu Ser Gly
1               5

<210> SEQ ID NO 133
<211> LENGTH: 14
```

```
<212> TYPE: PRT
<213> ORGANISM: Homo sapiens

<400> SEQUENCE: 133

Gly Gly His Asp Leu Glu Ser Gly Glu Phe Ser Tyr Asp Ser
1               5                   10

<210> SEQ ID NO 134
<211> LENGTH: 14
<212> TYPE: PRT
<213> ORGANISM: Homo sapiens

<400> SEQUENCE: 134

Gly Gly Ser Asp Leu Ser Gly Glu Phe Ser Val Cys Asp Ser
1               5                   10

<210> SEQ ID NO 135
<211> LENGTH: 15
<212> TYPE: PRT
<213> ORGANISM: Homo sapiens

<400> SEQUENCE: 135

Gly Gly Ser Asp Leu Ser Gly Gly Glu Phe Ser Val Cys Asp Ser
1               5                   10                  15

<210> SEQ ID NO 136
<211> LENGTH: 15
<212> TYPE: PRT
<213> ORGANISM: Homo sapiens

<400> SEQUENCE: 136

Gly Gly Ser Asp Leu Ser Gly Gly Glu Phe Ser Val Ala Asp Ser
1               5                   10                  15

<210> SEQ ID NO 137
<211> LENGTH: 14
<212> TYPE: PRT
<213> ORGANISM: Homo sapiens

<400> SEQUENCE: 137

Gly Gly Ser Asp Leu Ser Gly Glu Phe Ser Val Ala Asp Ser
1               5                   10

<210> SEQ ID NO 138
<211> LENGTH: 6
<212> TYPE: PRT
<213> ORGANISM: Homo sapiens

<400> SEQUENCE: 138

Glu Thr Leu Gln Phe Arg
1               5

<210> SEQ ID NO 139
<211> LENGTH: 8
<212> TYPE: PRT
<213> ORGANISM: Homo sapiens

<400> SEQUENCE: 139

Lys Lys Glu Thr Leu Gln Phe Arg
1               5

<210> SEQ ID NO 140
<211> LENGTH: 8
<212> TYPE: PRT
<213> ORGANISM: Homo sapiens
```

<400> SEQUENCE: 140

Glu Thr Leu Gln Phe Arg Lys Lys
1               5

<210> SEQ ID NO 141
<211> LENGTH: 9
<212> TYPE: PRT
<213> ORGANISM: Homo sapiens

<400> SEQUENCE: 141

Lys Ala Ser Thr Thr Thr Asn Tyr Thr
1               5

<210> SEQ ID NO 142
<211> LENGTH: 13
<212> TYPE: PRT
<213> ORGANISM: Homo sapiens

<400> SEQUENCE: 142

Ala Leu Lys Arg Gln Gly Arg Thr Leu Tyr Gly Phe Gly
1               5                   10

<210> SEQ ID NO 143
<211> LENGTH: 8
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Sarcosine

<400> SEQUENCE: 143

Xaa Arg Val Tyr Val His Pro Ala
1               5

<210> SEQ ID NO 144
<211> LENGTH: 60
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 144

Arg Lys Arg Gly Arg Gln Thr Tyr Thr Arg Tyr Gln Thr Leu Glu Leu
1               5                   10                  15

Glu Lys Glu Phe His Phe Asn Arg Tyr Leu Thr Arg Arg Arg Arg Ile
            20                  25                  30

Glu Ile Ala His Ala Leu Cys Leu Thr Glu Arg Gln Ile Lys Ile Trp
        35                  40                  45

Phe Gln Asn Arg Arg Met Lys Trp Lys Lys Glu Asn
    50                  55                  60

<210> SEQ ID NO 145
<211> LENGTH: 38
<212> TYPE: PRT
<213> ORGANISM: Homo sapiens

<400> SEQUENCE: 145

Arg Arg Arg Pro Arg Pro Pro Tyr Leu Pro Arg Pro Arg Pro Pro Pro
1               5                   10                  15

Phe Phe Pro Pro Arg Leu Pro Pro Arg Ile Pro Pro Gly Phe Pro Pro

```
                20                  25                  30
Arg Phe Pro Pro Arg Phe
            35

<210> SEQ ID NO 146
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Alpha-Glu
<220> FEATURE:
<221> NAME/KEY: MOD_RES
<222> LOCATION: (5)..(5)
<223> OTHER INFORMATION: Alpha-Asp
<220> FEATURE:
<221> NAME/KEY: MOD_RES
<222> LOCATION: (7)..(7)
<223> OTHER INFORMATION: S-(acetylamino)methyl-Cys
<220> FEATURE:
<221> NAME/KEY: MOD_RES
<222> LOCATION: (8)..(8)
<223> OTHER INFORMATION: Alpha-Glu
<220> FEATURE:
<221> NAME/KEY: MOD_RES
<222> LOCATION: (10)..(10)
<223> OTHER INFORMATION: S-(acetylamino)methyl-Cys
<220> FEATURE:
<221> NAME/KEY: MOD_RES
<222> LOCATION: (12)..(12)
<223> OTHER INFORMATION: S-(acetylamino)methyl-Cys
<220> FEATURE:
<221> NAME/KEY: MOD_RES
<222> LOCATION: (14)..(14)
<223> OTHER INFORMATION: Alpha-Glu

<400> SEQUENCE: 146

Glu Trp Gln Thr Asp Asn Cys Glu Thr Cys Thr Cys Tyr Glu
1               5                   10

<210> SEQ ID NO 147
<211> LENGTH: 116
<212> TYPE: PRT
<213> ORGANISM: Homo sapiens

<400> SEQUENCE: 147

Met Leu Ser Cys Arg Leu Gln Cys Ala Leu Ala Ala Leu Ser Ile Val
1               5                   10                  15

Leu Ala Leu Gly Cys Val Thr Gly Ala Pro Ser Asp Pro Arg Leu Arg
                20                  25                  30

Gln Phe Leu Gln Lys Ser Leu Ala Ala Ala Ala Gly Lys Gln Glu Leu
            35                  40                  45

Ala Lys Tyr Phe Leu Ala Glu Leu Leu Ser Glu Pro Asn Gln Thr Glu
        50                  55                  60

Asn Asp Ala Leu Glu Pro Glu Asp Leu Ser Gln Ala Ala Glu Gln Asp
65                  70                  75                  80

Glu Met Arg Leu Glu Leu Gln Arg Ser Ala Asn Ser Asn Pro Ala Met
                85                  90                  95

Ala Pro Arg Glu Arg Lys Ala Gly Cys Lys Asn Phe Phe Trp Lys Thr
            100                 105                 110

Phe Thr Ser Cys
            115
```

<210> SEQ ID NO 148
<211> LENGTH: 176
<212> TYPE: PRT
<213> ORGANISM: Homo sapiens

<400> SEQUENCE: 148

Met Gln Arg Arg Leu Val Gln Gln Trp Ser Val Ala Val Phe Leu Leu
1               5                   10                  15

Ser Tyr Ala Val Pro Ser Cys Gly Arg Ser Val Glu Gly Leu Ser Arg
            20                  25                  30

Arg Leu Lys Arg Ala Val Ser Glu His Gln Leu Leu His Asp Lys Gly
        35                  40                  45

Lys Ser Ile Gln Asp Leu Arg Arg Arg Phe Phe Leu His His Leu Ile
    50                  55                  60

Ala Glu Ile His Thr Ala Glu Ile Arg Ala Thr Ser Glu Val Ser Pro
65                  70                  75                  80

Asn Ser Lys Pro Ser Pro Asn Thr Lys Asn His Pro Val Phe Gly Ser
                85                  90                  95

Asp Asp Glu Gly Arg Tyr Leu Thr Gln Glu Thr Asn Lys Val Glu Thr
            100                 105                 110

Tyr Lys Glu Gln Pro Leu Lys Thr Pro Gly Lys Lys Lys Gly Lys
        115                 120                 125

Pro Gly Lys Arg Lys Glu Gln Glu Lys Lys Arg Arg Thr Arg Ser
    130                 135                 140

Ala Trp Leu Asp Ser Gly Val Thr Gly Ser Gly Leu Glu Gly Asp His
145                 150                 155                 160

Leu Ser Asp Thr Ser Thr Thr Ser Leu Glu Leu Asp Ser Arg Arg His
                165                 170                 175

<210> SEQ ID NO 149
<211> LENGTH: 34
<212> TYPE: PRT
<213> ORGANISM: Homo sapiens

<400> SEQUENCE: 149

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe

<210> SEQ ID NO 150
<211> LENGTH: 35
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: misc_feature
<222> LOCATION: (1)..(1)
<223> OTHER INFORMATION: /note="N-term acetlyated"
<220> FEATURE:
<221> NAME/KEY: MOD_RES
<222> LOCATION: (10)..(11)
<223> OTHER INFORMATION: Alpha-Glu
<220> FEATURE:
<221> NAME/KEY: MOD_RES
<222> LOCATION: (17)..(17)
<223> OTHER INFORMATION: Alpha-Glu

```
<220> FEATURE:
<221> NAME/KEY: MOD_RES
<222> LOCATION: (20)..(20)
<223> OTHER INFORMATION: Alpha-Glu
<220> FEATURE:
<221> NAME/KEY: MOD_RES
<222> LOCATION: (22)..(22)
<223> OTHER INFORMATION: Alpha-Glu
<220> FEATURE:
<221> NAME/KEY: MOD_RES
<222> LOCATION: (25)..(25)
<223> OTHER INFORMATION: Alpha-Glu
<220> FEATURE:
<221> NAME/KEY: MOD_RES
<222> LOCATION: (27)..(27)
<223> OTHER INFORMATION: Alpha-Asp

<400> SEQUENCE: 150

Tyr Thr Ser Leu Ile His Ser Leu Ile Glu Glu Ser Gln Asn Gln Gln
1               5                   10                  15

Glu Lys Asn Glu Gln Glu Leu Leu Glu Leu Asp Lys Trp Ala Ser Leu
                20                  25                  30

Trp Asn Trp
        35

<210> SEQ ID NO 151
<211> LENGTH: 5
<212> TYPE: PRT
<213> ORGANISM: Homo sapiens

<400> SEQUENCE: 151

Ala Arg Pro Ala Lys
1               5

<210> SEQ ID NO 152
<211> LENGTH: 37
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 152

Lys Cys Asn Thr Ala Thr Cys Ala Thr Gln Arg Leu Ala Asn Phe Leu
1               5                   10                  15

Val His Ser Ser Asn Asn Phe Gly Ala Ile Leu Ser Ser Thr Asn Val
                20                  25                  30

Gly Ser Asn Thr Tyr
        35

<210> SEQ ID NO 153
<211> LENGTH: 30
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: misc_feature
<222> LOCATION: (1)..(1)
<223> OTHER INFORMATION: /note="N-term acetylated"
<220> FEATURE:
<221> NAME/KEY: MOD_RES
<222> LOCATION: (3)..(3)
<223> OTHER INFORMATION: Alpha-Asp
<220> FEATURE:
<221> NAME/KEY: MOD_RES
```

```
<222> LOCATION: (8)..(8)
<223> OTHER INFORMATION: Alpha-Glu
<220> FEATURE:
<221> NAME/KEY: MOD_RES
<222> LOCATION: (17)..(17)
<223> OTHER INFORMATION: Norleu
<220> FEATURE:
<221> NAME/KEY: MOD_RES
<222> LOCATION: (25)..(25)
<223> OTHER INFORMATION: Alpha-Asp

<400> SEQUENCE: 153

His Ser Asp Ala Val Phe Thr Glu Asn Tyr Thr Lys Leu Arg Lys Gln
1               5                   10                  15

Leu Ala Ala Lys Lys Tyr Leu Asn Asp Leu Lys Lys Gly Gly
            20                  25                  30

<210> SEQ ID NO 154
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 154

Leu Lys Arg Met Pro
1               5

<210> SEQ ID NO 155
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Pyro-Glu

<400> SEQUENCE: 155

Glu Glu Asp Cys Lys
1               5

<210> SEQ ID NO 156
<211> LENGTH: 43
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (4)..(4)
<223> OTHER INFORMATION: Alpha-Glu
<220> FEATURE:
<221> NAME/KEY: MOD_RES
<222> LOCATION: (13)..(13)
<223> OTHER INFORMATION: Alpha-Glu
<220> FEATURE:
<221> NAME/KEY: MOD_RES
<222> LOCATION: (26)..(26)
<223> OTHER INFORMATION: Alpha-Glu

<400> SEQUENCE: 156

Met Phe Leu Glu Ala Ile Pro Met Ser Ile Pro Pro Glu Val Lys Phe
1               5                   10                  15
```

```
Asn Lys Pro Phe Val Phe Leu Met Ile Glu Gln Asn Thr Lys Ser Pro
            20                  25                  30

Leu Phe Met Gly Lys Val Val Asn Pro Thr Gln
        35                  40
```

<210> SEQ ID NO 157
<211> LENGTH: 7
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Isoval
<220> FEATURE:
<221> NAME/KEY: MOD_RES
<222> LOCATION: (3)..(3)
<223> OTHER INFORMATION: Norleu
<220> FEATURE:
<221> NAME/KEY: MOD_RES
<222> LOCATION: (4)..(4)
<223> OTHER INFORMATION: Statin residue
<220> FEATURE:
<221> NAME/KEY: MOD_RES
<222> LOCATION: (6)..(6)
<223> OTHER INFORMATION: Statin residue

<400> SEQUENCE: 157

```
Val Phe Leu Xaa Ala Xaa Lys
1               5
```

<210> SEQ ID NO 158
<211> LENGTH: 32
<212> TYPE: PRT
<213> ORGANISM: Salmo salar

<400> SEQUENCE: 158

```
Cys Ser Asn Leu Ser Thr Cys Val Leu Gly Lys Leu Ser Gln Glu Leu
1               5                   10                  15

His Lys Leu Gln Thr Tyr Pro Arg Thr Asn Thr Gly Ser Gly Thr Pro
            20                  25                  30
```

<210> SEQ ID NO 159
<211> LENGTH: 29
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (29)..(29)
<223> OTHER INFORMATION: /note="C-term amidated"

<400> SEQUENCE: 159

```
Tyr Ala Asp Ala Ile Phe Thr Asn Ser Tyr Arg Lys Val Leu Gly Gln
1               5                   10                  15

Leu Ser Ala Arg Lys Leu Leu Gln Asp Ile Met Ser Arg
            20                  25
```

<210> SEQ ID NO 160
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

```
<400> SEQUENCE: 160

His Ser Asp Gly Thr Phe
1               5

<210> SEQ ID NO 161
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 161

Lys Leu Leu Leu Leu Lys Leu Leu Leu Lys Leu Leu Leu Leu Lys
1               5                   10                  15

Leu Leu Leu Leu
            20

<210> SEQ ID NO 162
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 162

Trp Ala Gly Gly Asp Ala Ser Gly Glu
1               5

<210> SEQ ID NO 163
<211> LENGTH: 108
<212> TYPE: PRT
<213> ORGANISM: Homo sapiens

<400> SEQUENCE: 163

Met Pro Leu Trp Val Phe Phe Val Ile Leu Thr Leu Ser Asn Ser
1               5                   10                  15

Ser His Cys Ser Pro Pro Pro Leu Thr Leu Arg Met Arg Arg Tyr
                20                  25                  30

Ala Asp Ala Ile Phe Thr Asn Ser Tyr Arg Lys Val Leu Gly Gln Leu
                35                  40                  45

Ser Ala Arg Lys Leu Leu Gln Asp Ile Met Ser Arg Gln Gln Gly Glu
        50                  55                  60

Ser Asn Gln Glu Arg Gly Ala Arg Ala Arg Leu Gly Arg Gln Val Asp
65              70                  75                  80

Ser Met Trp Ala Glu Gln Lys Gln Met Glu Leu Glu Ser Ile Leu Val
                85                  90                  95

Ala Leu Leu Gln Lys His Ser Arg Asn Ser Gln Gly
                100                 105

<210> SEQ ID NO 164
<211> LENGTH: 70
<212> TYPE: PRT
<213> ORGANISM: Homo sapiens

<400> SEQUENCE: 164

Met Pro Leu Trp Val Phe Phe Val Ile Leu Thr Leu Ser Asn Ser
1               5                   10                  15
```

```
Ser His Cys Ser Pro Pro Pro Leu Thr Leu Arg Met Arg Arg Tyr
            20              25                  30

Ala Asp Ala Ile Phe Thr Asn Ser Tyr Arg Lys Val Leu Gly Gln Leu
                35              40                  45

Ser Ala Arg Lys Leu Leu Gln Asp Ile Met Ser Arg Gln Gln Gly Glu
 50                  55                  60

Ser Asn Gln Glu Arg Gly
 65              70

<210> SEQ ID NO 165
<211> LENGTH: 38
<212> TYPE: PRT
<213> ORGANISM: Homo sapiens

<400> SEQUENCE: 165

Ala Arg Ala Arg Leu Gly Arg Gln Val Asp Ser Met Trp Ala Glu Gln
 1               5                  10                  15

Lys Gln Met Glu Leu Glu Ser Ile Leu Val Ala Leu Leu Gln Lys His
                20                  25                  30

Ser Arg Asn Ser Gln Gly
            35

<210> SEQ ID NO 166
<211> LENGTH: 200
<212> TYPE: PRT
<213> ORGANISM: Homo sapiens

<400> SEQUENCE: 166

Met Ala Ser Leu Tyr Val Gly Asp Leu His Pro Glu Val Thr Glu Ala
 1               5                  10                  15

Met Leu Tyr Glu Lys Phe Ser Pro Ala Gly Pro Ile Leu Ser Ile Arg
                20                  25                  30

Ile Cys Arg Asp Lys Ile Thr Arg Arg Ser Leu Gly Tyr Ala Tyr Val
            35                  40                  45

Asn Tyr Gln Gln Pro Val Asp Ala Lys Arg Ala Leu Glu Thr Leu Asn
 50                  55                  60

Phe Asp Val Ile Lys Gly Arg Pro Val Arg Ile Met Trp Ser Gln Arg
 65                  70                  75                  80

Asp Pro Ser Leu Arg Lys Ser Gly Val Gly Asn Val Phe Ile Lys Asn
                85                  90                  95

Leu Gly Lys Thr Ile Asp Asn Lys Ala Leu Tyr Asn Ile Phe Ser Ala
            100                 105                 110

Phe Gly Asn Ile Leu Ser Cys Lys Val Ala Cys Asp Glu Lys Gly Pro
        115                 120                 125

Lys Gly Tyr Gly Phe Val His Phe Gln Lys Gln Glu Ser Ala Glu Arg
    130                 135                 140

Ala Ile Asp Val Met Asn Gly Met Phe Leu Asn Tyr Arg Lys Ile Phe
145                 150                 155                 160

Val Gly Arg Phe Lys Ser His Lys Glu Arg Glu Ala Glu Arg Gly Ala
                165                 170                 175

Trp Ala Arg Gln Ser Thr Ser Ala Asp Val Lys Asp Phe Glu Glu Asp
                180                 185                 190

Thr Asp Glu Glu Ala Thr Leu Arg
            195                 200

<210> SEQ ID NO 167
<211> LENGTH: 17
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 167

Arg Arg Trp Cys Tyr Arg Lys Cys Tyr Lys Gly Tyr Cys Tyr Arg Lys
1               5                   10                  15

Cys

<210> SEQ ID NO 168
<211> LENGTH: 8
<212> TYPE: PRT
<213> ORGANISM: Homo sapiens

<400> SEQUENCE: 168

Leu Glu Asp Gly Pro Lys Phe Leu
1               5

<210> SEQ ID NO 169
<211> LENGTH: 30
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 169

Lys Ser Ser Gln Tyr Ile Lys Ala Asn Ser Lys Phe Ile Gly Ile Thr
1               5                   10                  15

Glu Ala Ala Ala Phe Leu Pro Ser Asp Phe Phe Pro Ser Val
            20                  25                  30

<210> SEQ ID NO 170
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (6)..(6)
<223> OTHER INFORMATION: Alpha-Asp
<220> FEATURE:
<221> NAME/KEY: MOD_RES
<222> LOCATION: (7)..(7)
<223> OTHER INFORMATION: O-methyl-Tyr

<400> SEQUENCE: 170

Cys Asn Pro Arg Gly Asp Tyr Arg
1               5

<210> SEQ ID NO 171
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 171

Gly Gly Gly Lys
```

```
<210> SEQ ID NO 172
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (12)..(12)
<223> OTHER INFORMATION: /note="C-term amidated"

<400> SEQUENCE: 172

Gly Gly Gly Cys Tyr Phe Gln Asn Cys Pro Lys Gly
1               5                   10

<210> SEQ ID NO 173
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 173

Gln Glu Asp Leu Ile Asp Val
1               5

<210> SEQ ID NO 174
<211> LENGTH: 214
<212> TYPE: PRT
<213> ORGANISM: Mus musculus

<400> SEQUENCE: 174

Met Glu Pro Gly Leu Trp Leu Leu Gly Leu Thr Val Thr Ser Ala
1               5                   10                  15

Ala Gly Leu Val Pro Cys Pro Gln Ser Gly Asp Ser Gly Arg Ala Ser
                20                  25                  30

Val Ser Gln Gly Pro Pro Glu Ala Gly Ser Glu Arg Gly Cys Glu Glu
            35                  40                  45

Thr Val Ala Gly Pro Gly Glu Arg Ile Val Ser Pro Thr Val Ala Leu
        50                  55                  60

Pro Ala Gln Pro Glu Ser Ala Gly Gln Glu Arg Ala Pro Gly Arg Ser
65                  70                  75                  80

Gly Lys Gln Glu Asp Lys Gly Leu Pro Ala His His Arg Pro Arg Arg
                85                  90                  95

Cys Thr Cys Phe Thr Tyr Lys Asp Lys Glu Cys Val Tyr Tyr Cys His
            100                 105                 110

Leu Asp Ile Ile Trp Ile Asn Thr Pro Glu Gln Thr Val Pro Tyr Gly
        115                 120                 125

Leu Ser Asn Tyr Arg Glu Ser Leu Arg Gly Lys Arg Ser Leu Gly Pro
    130                 135                 140

Val Pro Glu Ser Ser Gln Pro Ser Pro Trp Thr Arg Leu Arg Cys Thr
145                 150                 155                 160

Cys Met Gly Ala Asp Asp Lys Ala Cys Ala His Phe Cys Ala Arg Thr
                165                 170                 175

Arg Asp Val Thr Ser Tyr Ser Gly Arg Ala Glu Arg Pro Ala Ala Glu
            180                 185                 190
```

Glu Met Arg Glu Thr Gly Gly Pro Arg Gln Arg Leu Met Ser Arg Thr
    195                 200                 205

Asp Lys Ala His Arg Pro
    210

<210> SEQ ID NO 175
<211> LENGTH: 356
<212> TYPE: PRT
<213> ORGANISM: Homo sapiens

<400> SEQUENCE: 175

Met Ala Ala Glu Gly Trp Ile Trp Arg Trp Gly Trp Gly Arg Arg Cys
1               5                   10                  15

Leu Gly Arg Pro Gly Leu Leu Gly Pro Gly Pro Gly Thr Thr Pro
            20                  25                  30

Leu Phe Leu Leu Leu Leu Gly Ser Val Thr Ala Asp Ile Thr Asp
        35                  40                  45

Gly Asn Ser Glu His Leu Lys Arg Glu His Ser Leu Ile Lys Pro Tyr
    50                  55                  60

Gln Gly Val Gly Ser Ser Met Pro Leu Trp Asp Phe Gln Gly Ser
65                  70                  75                  80

Thr Met Leu Thr Ser Gln Tyr Val Arg Leu Thr Pro Asp Glu Arg Ser
                85                  90                  95

Lys Glu Gly Ser Ile Trp Asn His Gln Pro Cys Phe Leu Lys Asp Trp
            100                 105                 110

Glu Met His Val His Phe Lys Val His Gly Thr Gly Lys Lys Asn Leu
        115                 120                 125

His Gly Asp Gly Ile Ala Leu Trp Tyr Thr Arg Asp Arg Leu Val Pro
    130                 135                 140

Gly Pro Val Phe Gly Ser Lys Asp Asn Phe His Gly Leu Ala Ile Phe
145                 150                 155                 160

Leu Asp Thr Tyr Pro Asn Asp Glu Thr Thr Glu Arg Val Phe Pro Tyr
                165                 170                 175

Ile Ser Val Met Val Asn Asn Gly Ser Leu Ser Tyr Asp His Ser Lys
            180                 185                 190

Asp Gly Arg Trp Thr Glu Leu Ala Gly Cys Thr Ala Asp Phe Arg Asn
        195                 200                 205

Arg Asp His Asp Thr Phe Leu Ala Val Arg Tyr Ser Arg Gly Arg Leu
    210                 215                 220

Thr Val Met Thr Asp Leu Glu Asp Lys Asn Glu Trp Lys Asn Cys Ile
225                 230                 235                 240

Asp Ile Thr Gly Val Arg Leu Pro Thr Gly Tyr Tyr Phe Gly Ala Ser
                245                 250                 255

Ala Gly Thr Gly Asp Leu Ser Asp Asn His Asp Ile Ile Ser Met Lys
            260                 265                 270

Leu Phe Gln Leu Met Val Glu His Thr Pro Asp Glu Glu Ser Ile Asp
        275                 280                 285

Trp Thr Lys Ile Glu Pro Ser Val Asn Phe Leu Lys Ser Pro Lys Asp
    290                 295                 300

Asn Val Asp Asp Pro Thr Gly Asn Phe Arg Ser Gly Pro Leu Thr Gly
305                 310                 315                 320

Trp Arg Val Phe Leu Leu Leu Cys Ala Leu Leu Gly Ile Val Val
                325                 330                 335

Cys Ala Val Val Gly Ala Val Val Phe Gln Lys Arg Gln Glu Arg Asn

```
                    340                 345                 350
Lys Arg Phe Tyr
        355

<210> SEQ ID NO 176
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (8)..(8)
<223> OTHER INFORMATION: /note="C-term amidated"

<400> SEQUENCE: 176

Thr Asp Ser Phe Val Gly Leu Met
1               5

<210> SEQ ID NO 177
<211> LENGTH: 8
<212> TYPE: PRT
<213> ORGANISM: Homo sapiens

<400> SEQUENCE: 177

Lys Pro Gly Glu Pro Gly Pro Lys
1               5

<210> SEQ ID NO 178
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 178

Gly Ser His Lys
1

<210> SEQ ID NO 179
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 179

Ala Ser His Lys
1

<210> SEQ ID NO 180
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 180

Leu Ser His Lys
1
```

```
<210> SEQ ID NO 181
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 181

Thr Ser His Lys
1

<210> SEQ ID NO 182
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 182

Tyr Ser His Lys
1

<210> SEQ ID NO 183
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 183

Pro Ser His Lys
1

<210> SEQ ID NO 184
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Pyro-Glu

<400> SEQUENCE: 184

Glu Ser His Lys
1

<210> SEQ ID NO 185
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 185

Trp Ser His Lys
1
```

```
<210> SEQ ID NO 186
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(2)
<223> OTHER INFORMATION: Hydroxy-Pro

<400> SEQUENCE: 186

Pro Pro Gly Ala Gly
1               5

<210> SEQ ID NO 187
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 187

Trp Ala Ser Gly Asn
1               5

<210> SEQ ID NO 188
<211> LENGTH: 8
<212> TYPE: PRT
<213> ORGANISM: Homo sapiens

<400> SEQUENCE: 188

Asp Ala Asp Pro Arg Gln Tyr Ala
1               5

<210> SEQ ID NO 189
<211> LENGTH: 518
<212> TYPE: PRT
<213> ORGANISM: Homo sapiens

<400> SEQUENCE: 189

Met Ser Cys Val Lys Leu Trp Pro Ser Gly Ala Pro Ala Pro Leu Val
1               5                   10                  15

Ser Ile Glu Glu Leu Glu Asn Gln Glu Leu Val Gly Lys Gly Gly Phe
                20                  25                  30

Gly Thr Val Phe Arg Ala Gln His Arg Lys Trp Gly Tyr Asp Val Ala
            35                  40                  45

Val Lys Ile Val Asn Ser Lys Ala Ile Ser Arg Glu Val Lys Ala Met
        50                  55                  60

Ala Ser Leu Asp Asn Glu Phe Val Leu Arg Leu Glu Gly Val Ile Glu
65                  70                  75                  80

Lys Val Asn Trp Asp Gln Asp Pro Lys Pro Ala Leu Val Thr Lys Phe
                85                  90                  95

Met Glu Asn Gly Ser Leu Ser Gly Leu Leu Gln Ser Gln Cys Pro Arg
                100                 105                 110

Pro Trp Pro Leu Leu Cys Arg Leu Leu Lys Glu Val Val Leu Gly Met
            115                 120                 125

Phe Tyr Leu His Asp Gln Asn Pro Val Leu Leu His Arg Asp Leu Lys
```

```
                130             135             140
Pro Ser Asn Val Leu Leu Asp Pro Glu Leu His Val Lys Leu Ala Asp
145                 150                 155                 160

Phe Gly Leu Ser Thr Phe Gln Gly Gly Ser Gln Ser Gly Thr Gly Ser
                165                 170                 175

Gly Glu Pro Gly Gly Thr Leu Gly Tyr Leu Ala Pro Glu Leu Phe Val
            180                 185                 190

Asn Val Asn Arg Lys Ala Ser Thr Ala Ser Asp Val Tyr Ser Phe Gly
        195                 200                 205

Ile Leu Met Trp Ala Val Leu Ala Gly Arg Glu Val Glu Leu Pro Thr
    210                 215                 220

Glu Pro Ser Leu Val Tyr Glu Ala Val Cys Asn Arg Gln Asn Arg Pro
225                 230                 235                 240

Ser Leu Ala Glu Leu Pro Gln Ala Gly Pro Glu Thr Pro Gly Leu Glu
                245                 250                 255

Gly Leu Lys Glu Leu Met Gln Leu Cys Trp Ser Ser Glu Pro Lys Asp
            260                 265                 270

Arg Pro Ser Phe Gln Glu Cys Leu Pro Lys Thr Asp Glu Val Phe Gln
        275                 280                 285

Met Val Glu Asn Asn Met Asn Ala Ala Val Ser Thr Val Lys Asp Phe
    290                 295                 300

Leu Ser Gln Leu Arg Ser Ser Asn Arg Arg Phe Ser Ile Pro Glu Ser
305                 310                 315                 320

Gly Gln Gly Gly Thr Glu Met Asp Gly Phe Arg Arg Thr Ile Glu Asn
                325                 330                 335

Gln His Ser Arg Asn Asp Val Met Val Ser Glu Trp Leu Asn Lys Leu
            340                 345                 350

Asn Leu Glu Glu Pro Pro Ser Ser Val Pro Lys Lys Cys Pro Ser Leu
        355                 360                 365

Thr Lys Arg Ser Arg Ala Gln Glu Glu Gln Val Pro Gln Ala Trp Thr
    370                 375                 380

Ala Gly Thr Ser Ser Asp Ser Met Ala Gln Pro Gln Thr Pro Glu
385                 390                 395                 400

Thr Ser Thr Phe Arg Asn Gln Met Pro Ser Pro Thr Ser Thr Gly Thr
                405                 410                 415

Pro Ser Pro Gly Pro Arg Gly Asn Gln Gly Ala Glu Arg Gln Gly Met
            420                 425                 430

Asn Trp Ser Cys Arg Thr Pro Glu Pro Asn Pro Val Thr Gly Arg Pro
        435                 440                 445

Leu Val Asn Ile Tyr Asn Cys Ser Gly Val Gln Val Gly Asp Asn Asn
    450                 455                 460

Tyr Leu Thr Met Gln Thr Thr Ala Leu Pro Thr Trp Gly Leu Ala
465                 470                 475                 480

Pro Ser Gly Lys Gly Arg Gly Leu Gln His Pro Pro Val Gly Ser
                485                 490                 495

Gln Glu Gly Pro Lys Asp Pro Glu Ala Trp Ser Arg Pro Gln Gly Trp
            500                 505                 510

Tyr Asn His Ser Gly Lys
            515

<210> SEQ ID NO 190
<211> LENGTH: 19
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic peptide"

<400> SEQUENCE: 190

Gly Tyr Tyr Trp Ser Trp Ile Arg Gln Pro Pro Gly Lys Gly Glu Glu
1               5                   10                  15

Trp Ile Gly

<210> SEQ ID NO 191
<211> LENGTH: 82
<212> TYPE: PRT
<213> ORGANISM: Homo sapiens

<400> SEQUENCE: 191

Gly Ser Gly Leu Thr Asn Ile Lys Thr Glu Ile Ser Glu Val Lys
1               5                   10                  15

Met Asp Ala Glu Phe Arg His Asp Ser Gly Tyr Glu Val His His Gln
                20                  25                  30

Lys Leu Val Phe Phe Ala Glu Asp Val Gly Ser Asn Lys Gly Ala Ile
            35                  40                  45

Ile Gly Leu Met Val Gly Gly Val Val Ile Ala Thr Val Ile Ile Ile
50                  55                  60

Thr Leu Val Met Leu Lys Lys Gln Tyr Thr Ser Asn His His Gly Val
65                  70                  75                  80

Val Glu

<210> SEQ ID NO 192
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (10)..(10)
<223> OTHER INFORMATION: /note="C-term amidated"

<400> SEQUENCE: 192

Leu Arg Ala His Ala Val Asp Val Asn Gly
1               5                   10

<210> SEQ ID NO 193
<211> LENGTH: 9
<212> TYPE: PRT
<213> ORGANISM: Homo sapiens

<400> SEQUENCE: 193

Leu Leu Pro Gly Gly Arg Pro Tyr Arg
1               5

<210> SEQ ID NO 194
<211> LENGTH: 359
<212> TYPE: PRT
<213> ORGANISM: Homo sapiens

<400> SEQUENCE: 194

Met Ile Leu Asn Ser Ser Thr Glu Asp Gly Ile Lys Arg Ile Gln Asp
1               5                   10                  15

Asp Cys Pro Lys Ala Gly Arg His Asn Tyr Ile Phe Val Met Ile Pro
```

```
                20              25              30
Thr Leu Tyr Ser Ile Ile Phe Val Val Gly Ile Phe Gly Asn Ser Leu
                35                  40                  45
Val Val Ile Val Ile Tyr Phe Tyr Met Lys Leu Lys Thr Val Ala Ser
                50                  55                  60
Val Phe Leu Leu Asn Leu Ala Leu Ala Asp Leu Cys Phe Leu Leu Thr
 65                  70                  75                  80
Leu Pro Leu Trp Ala Val Tyr Thr Ala Met Glu Tyr Arg Trp Pro Phe
                 85                  90                  95
Gly Asn Tyr Leu Cys Lys Ile Ala Ser Ala Ser Val Ser Phe Asn Leu
                100                 105                 110
Tyr Ala Ser Val Phe Leu Leu Thr Cys Leu Ser Ile Asp Arg Tyr Leu
                115                 120                 125
Ala Ile Val His Pro Met Lys Ser Arg Leu Arg Arg Thr Met Leu Val
                130                 135                 140
Ala Lys Val Thr Cys Ile Ile Ile Trp Leu Leu Ala Gly Leu Ala Ser
145                 150                 155                 160
Leu Pro Ala Ile Ile His Arg Asn Val Phe Phe Ile Glu Asn Thr Asn
                165                 170                 175
Ile Thr Val Cys Ala Phe His Tyr Glu Ser Gln Asn Ser Thr Leu Pro
                180                 185                 190
Ile Gly Leu Gly Leu Thr Lys Asn Ile Leu Gly Phe Leu Phe Pro Phe
                195                 200                 205
Leu Ile Ile Leu Thr Ser Tyr Thr Leu Ile Trp Lys Ala Leu Lys Lys
                210                 215                 220
Ala Tyr Glu Ile Gln Lys Asn Lys Pro Arg Asn Asp Asp Ile Phe Lys
225                 230                 235                 240
Ile Ile Met Ala Ile Val Leu Phe Phe Phe Ser Trp Ile Pro His
                245                 250                 255
Gln Ile Phe Thr Phe Leu Asp Val Leu Ile Gln Leu Gly Ile Ile Arg
                260                 265                 270
Asp Cys Arg Ile Ala Asp Ile Val Asp Thr Ala Met Pro Ile Thr Ile
                275                 280                 285
Cys Ile Ala Tyr Phe Asn Asn Cys Leu Asn Pro Leu Phe Tyr Gly Phe
                290                 295                 300
Leu Gly Lys Lys Phe Lys Arg Tyr Phe Leu Gln Leu Leu Lys Tyr Ile
305                 310                 315                 320
Pro Pro Lys Ala Lys Ser His Ser Asn Leu Ser Thr Lys Met Ser Thr
                325                 330                 335
Leu Ser Tyr Arg Pro Ser Asp Asn Val Ser Ser Ser Thr Lys Lys Pro
                340                 345                 350
Ala Pro Cys Phe Glu Val Glu
                355

<210> SEQ ID NO 195
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 195

Ile Leu Arg Trp Pro Trp Pro Trp Arg Arg
1               5                   10
```

<210> SEQ ID NO 196
<211> LENGTH: 109
<212> TYPE: PRT
<213> ORGANISM: Homo sapiens

<400> SEQUENCE: 196

Met Arg Gly Ala Leu Leu Val Ala Leu Leu Val Thr Gln Ala Leu
1               5                   10                  15

Gly Val Lys Met Ala Glu Thr Cys Pro Ile Phe Tyr Asp Val Phe Phe
            20                  25                  30

Ala Val Ala Asn Gly Asn Glu Leu Leu Leu Asp Leu Ser Leu Thr Lys
            35                  40                  45

Val Asn Ala Thr Glu Pro Glu Arg Thr Ala Met Lys Lys Ile Gln Asp
50                  55                  60

Cys Tyr Val Glu Asn Gly Leu Ile Ser Arg Val Leu Asp Gly Leu Val
65              70                  75                  80

Met Thr Thr Ile Ser Ser Lys Asp Cys Met Gly Glu Ala Val Gln
                85                  90                  95

Asn Thr Val Glu Asp Leu Lys Leu Asn Thr Leu Gly Arg
            100                 105

<210> SEQ ID NO 197
<211> LENGTH: 138
<212> TYPE: PRT
<213> ORGANISM: Homo sapiens

<400> SEQUENCE: 197

Met Asn Ser Leu Val Ser Trp Gln Leu Leu Leu Phe Leu Cys Ala Thr
1               5                   10                  15

His Phe Gly Glu Pro Leu Glu Lys Val Ala Ser Val Gly Asn Ser Arg
            20                  25                  30

Pro Thr Gly Gln Gln Leu Glu Ser Leu Gly Leu Leu Ala Pro Gly Glu
        35                  40                  45

Gln Ser Leu Pro Cys Thr Glu Arg Lys Pro Ala Ala Thr Ala Arg Leu
50                  55                  60

Ser Arg Arg Gly Thr Ser Leu Ser Pro Pro Glu Ser Ser Gly Ser
65              70                  75                  80

Pro Gln Gln Pro Gly Leu Ser Ala Pro His Ser Arg Gln Ile Pro Ala
                85                  90                  95

Pro Gln Gly Ala Val Leu Val Gln Arg Glu Lys Asp Leu Pro Asn Tyr
            100                 105                 110

Asn Trp Asn Ser Phe Gly Leu Arg Phe Gly Lys Arg Glu Ala Ala Pro
        115                 120                 125

Gly Asn His Gly Arg Ser Ala Gly Arg Gly
    130                 135

<210> SEQ ID NO 198
<211> LENGTH: 422
<212> TYPE: PRT
<213> ORGANISM: Homo sapiens

<400> SEQUENCE: 198

Met Ser Thr Ser Tyr Gly Cys Phe Trp Arg Phe Ile His Gly Ile
1               5                   10                  15

Gly Arg Ser Gly Asp Ile Ser Ala Val Gln Pro Lys Ala Gly Ser
            20                  25                  30

Ser Leu Leu Asn Lys Ile Thr Asn Ser Leu Val Leu Asp Ile Ile Lys
            35                  40                  45

Leu Ala Gly Val His Thr Val Ala Asn Cys Phe Val Val Pro Met Ala
 50                  55                  60

Thr Gly Met Ser Leu Thr Leu Cys Phe Leu Thr Leu Arg His Lys Arg
 65                  70                  75                  80

Pro Lys Ala Lys Tyr Ile Ile Trp Pro Arg Ile Asp Gln Lys Ser Cys
                 85                  90                  95

Phe Lys Ser Met Ile Thr Ala Gly Phe Glu Pro Val Val Ile Glu Asn
            100                 105                 110

Val Leu Glu Gly Asp Glu Leu Arg Thr Asp Leu Lys Ala Val Glu Ala
        115                 120                 125

Lys Val Gln Glu Leu Gly Pro Asp Cys Ile Leu Cys Ile His Ser Thr
130                 135                 140

Thr Ser Cys Phe Ala Pro Arg Val Pro Asp Arg Leu Glu Glu Leu Ala
145                 150                 155                 160

Val Ile Cys Ala Asn Tyr Asp Ile Pro His Ile Val Asn Asn Ala Tyr
                165                 170                 175

Gly Val Gln Ser Ser Lys Cys Met His Leu Ile Gln Gln Gly Ala Arg
            180                 185                 190

Val Gly Arg Ile Asp Ala Phe Val Gln Ser Leu Asp Lys Asn Phe Met
        195                 200                 205

Val Pro Val Gly Gly Ala Ile Ile Ala Gly Phe Asn Asp Ser Phe Ile
210                 215                 220

Gln Glu Ile Ser Lys Met Tyr Pro Gly Arg Ala Ser Ala Ser Pro Ser
225                 230                 235                 240

Leu Asp Val Leu Ile Thr Leu Leu Ser Leu Gly Ser Asn Gly Tyr Lys
                245                 250                 255

Lys Leu Leu Lys Glu Arg Lys Glu Met Phe Ser Tyr Leu Ser Asn Gln
            260                 265                 270

Ile Lys Lys Leu Ser Glu Ala Tyr Asn Glu Arg Leu Leu His Thr Pro
        275                 280                 285

His Asn Pro Ile Ser Leu Ala Met Thr Leu Lys Thr Leu Asp Glu His
290                 295                 300

Arg Asp Lys Ala Val Thr Gln Leu Gly Ser Met Leu Phe Thr Lys Gln
305                 310                 315                 320

Val Ser Gly Ala Arg Val Val Pro Leu Gly Ser Met Gln Thr Val Ser
                325                 330                 335

Gly Tyr Thr Phe Arg Gly Phe Met Ser His Thr Asn Asn Tyr Pro Cys
            340                 345                 350

Ala Tyr Leu Asn Ala Ala Ser Ala Ile Gly Met Lys Met Gln Asp Val
        355                 360                 365

Asp Leu Phe Ile Asn Arg Leu Asp Arg Cys Leu Lys Ala Val Arg Lys
370                 375                 380

Glu Arg Ser Lys Glu Ser Asp Asp Asn Tyr Asp Lys Thr Glu Asp Val
385                 390                 395                 400

Asp Ile Glu Glu Met Ala Leu Lys Leu Asp Asn Val Leu Leu Asp Thr
                405                 410                 415

Tyr Gln Asp Ala Ser Ser
            420

<210> SEQ ID NO 199
<211> LENGTH: 246
<212> TYPE: PRT

<213> ORGANISM: Homo sapiens

<400> SEQUENCE: 199

Met Thr Leu Ile Glu Gly Val Gly Asp Glu Val Thr Val Leu Phe Ser
1               5                   10                  15

Val Leu Ala Cys Leu Leu Val Leu Ala Leu Ala Trp Val Ser Thr His
            20                  25                  30

Thr Ala Glu Gly Gly Asp Pro Leu Pro Gln Pro Ser Gly Thr Pro Thr
        35                  40                  45

Pro Ser Gln Pro Ser Ala Ala Met Ala Ala Thr Asp Ser Met Arg Gly
    50                  55                  60

Glu Ala Pro Gly Ala Glu Thr Pro Ser Leu Arg His Arg Gly Gln Ala
65                  70                  75                  80

Ala Gln Pro Glu Pro Ser Thr Gly Phe Thr Ala Thr Pro Pro Ala Pro
                85                  90                  95

Asp Ser Pro Gln Glu Pro Leu Val Leu Arg Leu Lys Phe Leu Asn Asp
            100                 105                 110

Ser Glu Gln Val Ala Arg Ala Trp Pro His Asp Thr Ile Gly Ser Leu
        115                 120                 125

Lys Arg Thr Gln Phe Pro Gly Arg Glu Gln Gln Val Arg Leu Ile Tyr
130                 135                 140

Gln Gly Gln Leu Leu Gly Asp Asp Thr Gln Thr Leu Gly Ser Leu His
145                 150                 155                 160

Leu Pro Pro Asn Cys Val Leu His Cys His Val Ser Thr Arg Val Gly
                165                 170                 175

Pro Pro Asn Pro Pro Cys Pro Pro Gly Ser Glu Pro Gly Pro Ser Gly
            180                 185                 190

Leu Glu Ile Gly Ser Leu Leu Leu Pro Leu Leu Leu Leu Leu Leu Leu
        195                 200                 205

Leu Leu Trp Tyr Cys Gln Ile Gln Tyr Arg Pro Phe Phe Pro Leu Thr
    210                 215                 220

Ala Thr Leu Gly Leu Ala Gly Phe Thr Leu Leu Leu Ser Leu Leu Ala
225                 230                 235                 240

Phe Ala Met Tyr Arg Pro
                245

<210> SEQ ID NO 200
<211> LENGTH: 39
<212> TYPE: PRT
<213> ORGANISM: Homo sapiens
<220> FEATURE:
<221> NAME/KEY: misc_feature
<222> LOCATION: (39)..(39)
<223> OTHER INFORMATION: /note="C-term amidated"

<400> SEQUENCE: 200

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 201
<211> LENGTH: 177
<212> TYPE: PRT
<213> ORGANISM: Homo sapiens

<400> SEQUENCE: 201

Met Gln Arg Arg Leu Val Gln Gln Trp Ser Val Ala Val Phe Leu Leu
1               5                   10                  15

Ser Tyr Ala Val Pro Ser Cys Gly Arg Ser Val Glu Gly Leu Ser Arg
            20                  25                  30

Arg Leu Lys Arg Ala Val Ser Glu His Gln Leu Leu His Asp Lys Gly
        35                  40                  45

Lys Ser Ile Gln Asp Leu Arg Arg Arg Phe Phe Leu His His Leu Ile
    50                  55                  60

Ala Glu Ile His Thr Ala Glu Ile Arg Ala Thr Ser Glu Val Ser Pro
65                  70                  75                  80

Asn Ser Lys Pro Ser Pro Asn Thr Lys Asn His Pro Val Arg Phe Gly
                85                  90                  95

Ser Asp Asp Glu Gly Arg Tyr Leu Thr Gln Thr Asn Lys Val Glu
            100                 105                 110

Thr Tyr Lys Glu Gln Pro Leu Lys Thr Pro Gly Lys Lys Lys Gly
            115                 120                 125

Lys Pro Gly Lys Arg Lys Glu Gln Glu Lys Lys Arg Arg Thr Arg
    130                 135                 140

Ser Ala Trp Leu Asp Ser Gly Val Thr Gly Ser Gly Leu Glu Gly Asp
145                 150                 155                 160

His Leu Ser Asp Thr Ser Thr Thr Ser Leu Glu Leu Asp Ser Arg Arg
                165                 170                 175

His

<210> SEQ ID NO 202
<211> LENGTH: 36
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: misc_feature
<222> LOCATION: (36)..(36)
<223> OTHER INFORMATION: /note="C-term amidated"

<400> SEQUENCE: 202

Met Cys Met Pro Cys Phe Thr Thr Asp His Gln Met Ala Arg Lys Cys
1               5                   10                  15

Asp Asp Cys Cys Gly Gly Lys Gly Arg Gly Lys Cys Tyr Gly Pro Gln
            20                  25                  30

Cys Leu Cys Arg
        35

<210> SEQ ID NO 203
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (1)..(1)
<223> OTHER INFORMATION: /note="N-term acetylated"
<220> FEATURE:
<221> NAME/KEY: misc_feature
<222> LOCATION: (12)..(12)
<223> OTHER INFORMATION: /note="C-term amidated"

```
<400> SEQUENCE: 203

Arg Tyr Tyr Arg Trp Lys Lys Lys Lys Lys
1               5                   10

<210> SEQ ID NO 204
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 204

Cys Thr Thr His Trp Gly Phe Thr Leu Cys
1               5                   10

<210> SEQ ID NO 205
<211> LENGTH: 97
<212> TYPE: PRT
<213> ORGANISM: Homo sapiens

<400> SEQUENCE: 205

Met Val Phe Val Arg Arg Pro Trp Pro Ala Leu Thr Thr Val Leu Leu
1               5                   10                  15

Ala Leu Leu Val Cys Leu Gly Ala Leu Val Asp Ala Tyr Pro Ile Lys
            20                  25                  30

Pro Glu Ala Pro Arg Glu Asp Ala Ser Pro Glu Glu Leu Asn Arg Tyr
        35                  40                  45

Tyr Ala Ser Leu Arg His Tyr Leu Asn Leu Val Thr Arg Gln Arg Tyr
    50                  55                  60

Gly Lys Arg Asp Gly Pro Asp Thr Leu Leu Ser Lys Thr Phe Phe Pro
65                  70                  75                  80

Asp Gly Glu Asp Arg Pro Val Arg Ser Arg Ser Glu Gly Pro Asp Leu
                85                  90                  95

Trp

<210> SEQ ID NO 206
<211> LENGTH: 8
<212> TYPE: PRT
<213> ORGANISM: Homo sapiens

<400> SEQUENCE: 206

Asn Ala Pro Val Ser Ile Pro Gln
1               5

<210> SEQ ID NO 207
<211> LENGTH: 711
<212> TYPE: PRT
<213> ORGANISM: Homo sapiens

<400> SEQUENCE: 207

Met Ala Glu Arg Glu Ser Gly Leu Gly Gly Ala Ala Ser Pro
1               5                   10                  15

Pro Ala Ala Ser Pro Phe Leu Gly Leu His Ile Ala Ser Pro Pro Asn
            20                  25                  30

Phe Arg Leu Thr His Asp Ile Ser Leu Glu Glu Phe Glu Asp Glu Asp
        35                  40                  45

Leu Ser Glu Ile Thr Asp Glu Cys Gly Ile Ser Leu Gln Cys Lys Asp
    50                  55                  60
```

-continued

```
Thr Leu Ser Leu Arg Pro Pro Arg Ala Gly Leu Ser Ala Gly Gly
 65                  70                  75                  80

Gly Gly Ala Gly Ser Arg Leu Gln Ala Glu Met Leu Gln Met Asp Leu
             85                  90                  95

Ile Asp Ala Thr Gly Asp Thr Pro Gly Ala Glu Asp Asp Glu Asp
             100                 105                 110

Asp Asp Glu Glu Arg Ala Ala Arg Arg Pro Gly Ala Gly Pro Pro Lys
             115                 120                 125

Ala Glu Ser Gly Gln Glu Pro Ala Ser Arg Gly Gln Gly Gln Ser Gln
 130                 135                 140

Gly Gln Ser Gln Gly Pro Gly Ser Gly Asp Thr Tyr Arg Pro Lys Arg
 145                 150                 155                 160

Pro Thr Thr Leu Asn Leu Phe Pro Gln Val Pro Arg Ser Gln Asp Thr
                 165                 170                 175

Leu Asn Asn Asn Ser Leu Gly Lys Lys His Ser Trp Gln Asp Arg Val
                 180                 185                 190

Ser Arg Ser Ser Ser Pro Leu Lys Thr Gly Glu Gln Thr Pro Pro His
     195                 200                 205

Glu His Ile Cys Leu Ser Asp Glu Leu Pro Pro Gln Ser Gly Pro Ala
 210                 215                 220

Pro Thr Thr Asp Arg Gly Thr Ser Thr Asp Ser Pro Cys Arg Arg Ser
 225                 230                 235                 240

Thr Ala Thr Gln Met Ala Pro Pro Gly Gly Pro Pro Ala Ala Pro Pro
                 245                 250                 255

Gly Gly Arg Gly His Ser His Arg Asp Arg Ile His Tyr Gln Ala Asp
                 260                 265                 270

Val Arg Leu Glu Ala Thr Glu Glu Ile Tyr Leu Thr Pro Val Gln Arg
     275                 280                 285

Pro Pro Asp Ala Ala Glu Pro Thr Ser Ala Phe Leu Pro Pro Thr Glu
 290                 295                 300

Ser Arg Met Ser Val Ser Ser Asp Pro Asp Pro Ala Ala Tyr Pro Ser
 305                 310                 315                 320

Thr Ala Gly Arg Pro His Pro Ser Ile Ser Glu Glu Glu Glu Gly Phe
                 325                 330                 335

Asp Cys Leu Ser Ser Pro Glu Arg Ala Glu Pro Pro Gly Gly Gly Trp
                 340                 345                 350

Arg Gly Ser Leu Gly Glu Pro Pro Pro Pro Arg Ala Ser Leu Ser
                 355                 360                 365

Ser Asp Thr Ser Ala Leu Ser Tyr Asp Ser Val Lys Tyr Thr Leu Val
     370                 375                 380

Val Asp Glu His Ala Gln Leu Glu Leu Val Ser Leu Arg Pro Cys Phe
 385                 390                 395                 400

Gly Asp Tyr Ser Asp Glu Ser Asp Ser Ala Thr Val Tyr Asp Asn Cys
                 405                 410                 415

Ala Ser Val Ser Ser Pro Tyr Glu Ser Ala Ile Gly Glu Glu Tyr Glu
                 420                 425                 430

Glu Ala Pro Arg Pro Gln Pro Ala Cys Leu Ser Glu Asp Ser Thr
                 435                 440                 445

Pro Asp Glu Pro Asp Val His Phe Ser Lys Lys Phe Leu Asn Val Phe
 450                 455                 460

Met Ser Gly Arg Ser Arg Ser Ser Ala Glu Ser Phe Gly Leu Phe
 465                 470                 475                 480
```

```
Ser Cys Ile Ile Asn Gly Glu Glu Gln Glu Gln Thr His Arg Ala Ile
                485                 490                 495

Phe Arg Phe Val Pro Arg His Glu Asp Glu Leu Glu Leu Glu Val Asp
            500                 505                 510

Asp Pro Leu Leu Val Glu Leu Gln Ala Glu Asp Tyr Trp Tyr Glu Ala
            515                 520                 525

Tyr Asn Met Arg Thr Gly Ala Arg Gly Val Phe Pro Ala Tyr Tyr Ala
            530                 535                 540

Ile Glu Val Thr Lys Glu Pro Glu His Met Ala Ala Leu Ala Lys Asn
545                 550                 555                 560

Ser Asp Trp Val Asp Gln Phe Arg Val Lys Phe Leu Gly Ser Val Gln
                565                 570                 575

Val Pro Tyr His Lys Gly Asn Asp Val Leu Cys Ala Ala Met Gln Lys
            580                 585                 590

Ile Ala Thr Thr Arg Arg Leu Thr Val His Phe Asn Pro Pro Ser Ser
            595                 600                 605

Cys Val Leu Glu Ile Ser Val Arg Gly Val Lys Ile Gly Val Lys Ala
            610                 615                 620

Asp Asp Ser Gln Glu Ala Lys Gly Asn Lys Cys Ser His Phe Phe Gln
625                 630                 635                 640

Leu Lys Asn Ile Ser Phe Cys Gly Tyr His Pro Lys Asn Asn Lys Tyr
                645                 650                 655

Phe Gly Phe Ile Thr Lys His Pro Ala Asp His Arg Phe Ala Cys His
            660                 665                 670

Val Phe Val Ser Glu Asp Ser Thr Lys Ala Leu Ala Glu Ser Val Gly
            675                 680                 685

Arg Ala Phe Gln Gln Phe Tyr Lys Gln Phe Val Glu Tyr Thr Cys Pro
            690                 695                 700

Thr Glu Asp Ile Tyr Leu Glu
705                 710

<210> SEQ ID NO 208
<211> LENGTH: 710
<212> TYPE: PRT
<213> ORGANISM: Homo sapiens

<400> SEQUENCE: 208

Met Ala Glu Arg Glu Ser Gly Gly Leu Gly Gly Gly Ala Ala Ser Pro
1               5                   10                  15

Pro Ala Ser Pro Phe Leu Gly Leu His Ile Ala Ser Pro Pro Asn
            20                  25                  30

Phe Arg Leu Thr His Asp Ile Ser Leu Glu Glu Phe Glu Asp Glu Asp
            35                  40                  45

Leu Ser Glu Ile Thr Asp Glu Cys Gly Ile Ser Leu Gln Cys Lys Asp
            50                  55                  60

Thr Leu Ser Leu Arg Pro Pro Arg Ala Gly Leu Leu Ser Ala Gly Gly
65                  70                  75                  80

Gly Gly Ala Gly Ser Arg Leu Gln Ala Glu Met Leu Gln Met Asp Leu
                85                  90                  95

Ile Asp Ala Thr Gly Asp Thr Pro Gly Ala Glu Asp Asp Glu Asp Asp
            100                 105                 110

Asp Asp Glu Glu Arg Ala Ala Arg Arg Pro Gly Ala Gly Pro Pro Lys
            115                 120                 125

Ala Glu Ser Gly Gln Glu Pro Ala Ser Arg Gly Gln Gly Gln Ser Gln
            130                 135                 140
```

```
Gly Gln Ser Gln Gly Pro Gly Ser Gly Asp Thr Tyr Arg Pro Lys Arg
145                 150                 155                 160

Pro Thr Thr Leu Asn Leu Phe Pro Gln Val Pro Arg Ser Gln Asp Thr
            165                 170                 175

Leu Asn Asn Ser Leu Gly Lys Lys His Ser Trp Gln Asp Arg Val
        180                 185                 190

Ser Arg Ser Ser Ser Pro Leu Lys Thr Gly Glu Gln Thr Pro Pro His
    195                 200                 205

Glu His Ile Cys Leu Ser Asp Glu Leu Pro Pro Gln Ser Gly Pro Ala
210                 215                 220

Pro Thr Thr Asp Arg Gly Thr Ser Thr Asp Ser Pro Cys Arg Arg Ser
225                 230                 235                 240

Thr Ala Thr Gln Met Ala Pro Pro Gly Gly Pro Pro Ala Ala Pro Pro
                245                 250                 255

Gly Gly Arg Gly His Ser His Arg Asp Arg Ile His Tyr Gln Ala Asp
                260                 265                 270

Val Arg Leu Glu Ala Thr Glu Ile Tyr Leu Thr Pro Val Gln Arg
    275                 280                 285

Pro Pro Asp Ala Ala Glu Pro Thr Ser Ala Phe Leu Pro Pro Thr Glu
    290                 295                 300

Ser Arg Met Ser Val Ser Ser Asp Pro Asp Pro Ala Ala Tyr Pro Ser
305                 310                 315                 320

Thr Ala Gly Arg Pro His Pro Ser Ile Ser Glu Glu Glu Gly Phe
                325                 330                 335

Asp Cys Leu Ser Ser Pro Glu Arg Ala Glu Pro Pro Gly Gly Gly Trp
                340                 345                 350

Arg Gly Ser Leu Gly Glu Pro Pro Pro Pro Arg Ala Ser Leu Ser
        355                 360                 365

Ser Asp Thr Ser Ala Leu Ser Tyr Asp Ser Val Lys Tyr Thr Leu Val
    370                 375                 380

Val Asp Glu His Ala Gln Leu Glu Leu Val Ser Leu Arg Pro Cys Phe
385                 390                 395                 400

Gly Asp Tyr Ser Asp Glu Ser Asp Ser Ala Thr Val Tyr Asp Asn Cys
                405                 410                 415

Ala Ser Val Ser Ser Pro Tyr Glu Ser Ala Ile Gly Glu Glu Tyr Glu
                420                 425                 430

Glu Ala Pro Arg Pro Gln Pro Pro Ala Cys Leu Ser Glu Asp Ser Thr
            435                 440                 445

Pro Asp Glu Pro Asp Val His Phe Ser Lys Lys Phe Leu Asn Val Phe
            450                 455                 460

Met Ser Gly Arg Ser Arg Ser Ser Ala Glu Ser Phe Gly Leu Phe
465                 470                 475                 480

Ser Cys Ile Ile Asn Gly Glu Glu Gln Glu Gln Thr His Arg Ala Ile
                485                 490                 495

Phe Arg Phe Val Pro Arg His Glu Asp Glu Leu Glu Leu Glu Val Asp
                500                 505                 510

Asp Pro Leu Leu Val Glu Leu Gln Ala Glu Asp Tyr Trp Tyr Glu Ala
            515                 520                 525

Tyr Asn Met Arg Thr Gly Ala Arg Gly Val Phe Pro Ala Tyr Tyr Ala
        530                 535                 540

Ile Glu Val Thr Lys Glu Pro Glu His Met Ala Ala Leu Ala Lys Asn
545                 550                 555                 560
```

```
Ser Asp Trp Val Asp Gln Phe Arg Val Lys Phe Leu Gly Ser Val Gln
                565                 570                 575

Val Pro Tyr His Lys Gly Asn Asp Val Leu Cys Ala Ala Met Gln Lys
            580                 585                 590

Ile Ala Thr Thr Arg Arg Leu Thr Val His Phe Asn Pro Pro Ser Ser
        595                 600                 605

Cys Val Leu Glu Ile Ser Val Arg Gly Val Lys Gly Val Lys Ala Asp
    610                 615                 620

Asp Ser Gln Glu Ala Lys Gly Asn Lys Cys Ser His Phe Phe Gln Leu
625                 630                 635                 640

Lys Asn Ile Ser Phe Cys Gly Tyr His Pro Lys Asn Asn Lys Tyr Phe
                645                 650                 655

Gly Phe Ile Thr Lys His Pro Ala Asp His Arg Phe Ala Cys His Val
            660                 665                 670

Phe Val Ser Glu Asp Ser Thr Lys Ala Leu Ala Glu Ser Val Gly Arg
        675                 680                 685

Ala Phe Gln Gln Phe Tyr Lys Gln Phe Val Glu Tyr Thr Cys Pro Thr
    690                 695                 700

Glu Asp Ile Tyr Leu Glu
705                 710

<210> SEQ ID NO 209
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 209

Tyr Gly Phe Gly Gly
1               5

<210> SEQ ID NO 210
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 210

Tyr Cys Trp Ser Gln Tyr Leu Cys Tyr
1               5

<210> SEQ ID NO 211
<211> LENGTH: 28
<212> TYPE: PRT
<213> ORGANISM: Homo sapiens

<400> SEQUENCE: 211

His Ser Asp Ala Val Phe Thr Asp Asn Tyr Thr Arg Leu Arg Lys Gln
1               5                   10                  15

Met Ala Val Lys Lys Tyr Leu Asn Ser Ile Leu Asn
            20                  25

<210> SEQ ID NO 212
<211> LENGTH: 9
<212> TYPE: PRT
<213> ORGANISM: Homo sapiens
```

<400> SEQUENCE: 212

Ser Ala Leu Leu Arg Ser Ile Pro Ala
1               5

<210> SEQ ID NO 213
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 213

Leu Glu Glu Lys Lys Gly Asn Tyr Val Val Thr Asp His Cys
1               5                   10

<210> SEQ ID NO 214
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 214

Asn Phe Gly Ala Ile Leu
1               5

<210> SEQ ID NO 215
<211> LENGTH: 312
<212> TYPE: PRT
<213> ORGANISM: Homo sapiens

<400> SEQUENCE: 215

Met Ala Lys Val Phe Ser Phe Ile Leu Val Thr Thr Ala Leu Thr Met
1               5                   10                  15

Gly Arg Glu Ile Ser Ala Leu Glu Asp Cys Ala Gln Glu Gln Met Arg
            20                  25                  30

Leu Arg Ala Gln Val Arg Leu Leu Glu Thr Arg Val Lys Gln Gln Gln
        35                  40                  45

Val Lys Ile Lys Gln Leu Leu Gln Glu Asn Glu Val Gln Phe Leu Asp
    50                  55                  60

Lys Gly Asp Glu Asn Thr Val Ile Asp Leu Gly Ser Lys Arg Gln Tyr
65                  70                  75                  80

Ala Asp Cys Ser Glu Ile Phe Asn Asp Gly Tyr Lys Leu Ser Gly Phe
                85                  90                  95

Tyr Lys Ile Lys Pro Leu Gln Ser Pro Ala Glu Phe Ser Val Tyr Cys
            100                 105                 110

Asp Met Ser Asp Gly Gly Gly Trp Thr Val Ile Gln Arg Arg Ser Asp
        115                 120                 125

Gly Ser Glu Asn Phe Asn Arg Gly Trp Lys Asp Tyr Glu Asn Gly Phe
    130                 135                 140

Gly Asn Phe Val Gln Lys His Gly Glu Tyr Trp Leu Gly Asn Lys Asn
145                 150                 155                 160

Leu His Phe Leu Thr Thr Gln Glu Asp Tyr Thr Leu Lys Ile Asp Leu
                165                 170                 175

Ala Asp Phe Glu Lys Asn Ser Arg Tyr Ala Gln Tyr Lys Asn Phe Lys
            180                 185                 190

```
Val Gly Asp Glu Lys Asn Phe Tyr Glu Leu Asn Ile Gly Glu Tyr Ser
        195                 200                 205

Gly Thr Ala Gly Asp Ser Leu Ala Gly Asn Phe His Pro Glu Val Gln
    210                 215                 220

Trp Trp Ala Ser His Gln Arg Met Lys Phe Ser Thr Trp Asp Arg Asp
225                 230                 235                 240

His Asp Asn Tyr Glu Gly Asn Cys Ala Glu Asp Gln Ser Gly Trp
            245                 250                 255

Trp Phe Asn Arg Cys His Ser Ala Asn Leu Asn Gly Val Tyr Tyr Ser
                260                 265                 270

Gly Pro Tyr Thr Ala Lys Thr Asp Asn Gly Ile Val Trp Tyr Thr Trp
            275                 280                 285

His Gly Trp Trp Tyr Ser Leu Lys Ser Val Val Met Lys Ile Arg Pro
        290                 295                 300

Asn Asp Phe Ile Pro Asn Val Ile
305                 310

<210> SEQ ID NO 216
<211> LENGTH: 64
<212> TYPE: PRT
<213> ORGANISM: Homo sapiens

<400> SEQUENCE: 216

Met Ala Lys Val Phe Ser Phe Ile Leu Val Thr Thr Ala Leu Thr Met
1               5                   10                  15

Gly Arg Glu Ile Ser Ala Leu Glu Asp Cys Ala Gln Glu Gln Met Arg
            20                  25                  30

Leu Arg Ala Gln Val Arg Leu Leu Glu Thr Arg Val Lys Gln Gln Gln
        35                  40                  45

Val Lys Ile Lys Gln Leu Leu Gln Glu Asn Glu Val Gln Phe Leu Asp
    50                  55                  60

<210> SEQ ID NO 217
<211> LENGTH: 19
<212> TYPE: PRT
<213> ORGANISM: Vibrio cholerae

<400> SEQUENCE: 217

Asn Leu Ile Asp Cys Cys Glu Ile Cys Cys Asn Pro Ala Cys Phe Gly
1               5                   10                  15

Cys Leu Asn

<210> SEQ ID NO 218
<211> LENGTH: 83
<212> TYPE: PRT
<213> ORGANISM: Laticauda semifasciata

<400> SEQUENCE: 218

Met Lys Thr Leu Leu Leu Thr Leu Val Val Thr Ile Val Cys Leu
1               5                   10                  15

Asp Leu Gly Tyr Thr Arg Ile Cys Phe Asn His Gln Ser Ser Gln Pro
            20                  25                  30

Gln Thr Thr Lys Thr Cys Ser Pro Gly Glu Ser Ser Cys Tyr Asn Lys
        35                  40                  45

Gln Trp Ser Asp Phe Arg Gly Thr Ile Ile Glu Arg Gly Cys Gly Cys
    50                  55                  60

Pro Thr Val Lys Pro Gly Ile Lys Leu Ser Cys Cys Glu Ser Glu Val
```

```
                65                  70                  75                  80

Cys Asn Asn

<210> SEQ ID NO 219
<211> LENGTH: 141
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 219

Met Ser Asn Lys Lys Ile Ile Lys Ile Ile Lys Leu Gln Ile Pro Gly
1               5                   10                  15

Gly Lys Ala Asn Pro Ala Pro Ile Gly Pro Ala Leu Gly Ala Ala
            20                  25                  30

Gly Val Asn Ile Met Gly Phe Cys Lys Glu Phe Asn Ala Ala Thr Gln
        35                  40                  45

Asp Arg Pro Gly Asp Leu Leu Pro Val Val Ile Thr Val Tyr Ser Asp
    50                  55                  60

Lys Thr Phe Ser Phe Val Met Lys Gln Ser Pro Val Ser Ser Leu Ile
65                  70                  75                  80

Lys Lys Ala Leu Gly Leu Glu Ser Gly Ser Lys Ile Pro Asn Arg Asn
                85                  90                  95

Lys Val Gly Lys Leu Thr Arg Ala Gln Ile Thr Val Ile Ala Glu Gln
            100                 105                 110

Lys Met Lys Asp Met Asp Val Val Leu Leu Glu Ser Ala Glu Arg Met
        115                 120                 125

Val Glu Gly Thr Ala Arg Ser Met Gly Val Asp Val Glu
    130                 135                 140

<210> SEQ ID NO 220
<211> LENGTH: 172
<212> TYPE: PRT
<213> ORGANISM: Mus musculus

<400> SEQUENCE: 220

Met Ser Val Pro Glu Pro Pro Pro Asp Gly Val Leu Thr Gly Pro
1               5                   10                  15

Ser Asp Ser Leu Glu Ala Gly Glu Pro Thr Pro Gly Leu Ser Asp Thr
            20                  25                  30

Ser Pro Asp Glu Gly Leu Ile Glu Asp Phe Pro Val Asp Asp Arg Ala
        35                  40                  45

Val Glu His Leu Val Gly Gly Leu Leu Ser His Tyr Leu Pro Asp Leu
    50                  55                  60

Gln Arg Ser Lys Arg Ala Leu Gln Glu Leu Thr Gln Asn Gln Val Val
65                  70                  75                  80

Leu Leu Asp Thr Leu Glu Gln Glu Ile Ser Lys Phe Lys Glu Cys His
                85                  90                  95

Ser Met Leu Asp Ile Asn Ala Leu Phe Thr Glu Ala Lys His Tyr His
            100                 105                 110

Ala Lys Leu Val Thr Ile Arg Lys Glu Met Leu Leu His Glu Lys
        115                 120                 125

Thr Ser Lys Leu Lys Lys Arg Ala Leu Lys Leu Gln Gln Lys Arg Gln
    130                 135                 140

Arg Glu Glu Leu Glu Arg Glu Gln Gln Arg Glu Lys Glu Phe Glu Arg
```

```
                    145                 150                 155                 160
Glu Lys Gln Leu Thr Ala Lys Pro Ala Lys Arg Thr
                165                 170

<210> SEQ ID NO 221
<211> LENGTH: 90
<212> TYPE: PRT
<213> ORGANISM: Human immunodeficiency virus type 1

<400> SEQUENCE: 221

Lys Leu Thr Pro Leu Cys Val Thr Leu Asn Cys Thr Asp Leu Asp Leu
1               5                   10                  15

Arg Asn Thr Thr Asn Asn Thr Thr Glu Glu Arg Gly Glu Met Lys
            20                  25                  30

Asn Cys Ser Phe Asn Ile Thr Thr Asn Ile Arg Asp Arg Tyr Gln Lys
        35                  40                  45

Glu Tyr Ala Leu Phe Tyr Lys Leu Asp Val Ile Pro Ile Lys Glu Asp
    50                  55                  60

Asn Thr Ser Asp Asn Thr Ser Tyr Arg Leu Ile Ser Cys Asn Thr Ser
65                  70                  75                  80

Val Ile Thr Gln Ala Cys Pro Lys Ile Ser
                85                  90

<210> SEQ ID NO 222
<211> LENGTH: 191
<212> TYPE: PRT
<213> ORGANISM: Bubalus bubalis

<400> SEQUENCE: 222

Ala Phe Pro Ala Met Ser Leu Ser Ser Leu Phe Ala Asn Ala Val Leu
1               5                   10                  15

Arg Ala Gln His Leu His Gln Leu Ala Ala Asp Thr Phe Lys Glu Phe
            20                  25                  30

Glu Arg Thr Tyr Ile Pro Glu Gly Gln Arg Tyr Ser Ile Gln Asn Thr
        35                  40                  45

Gln Val Ala Phe Cys Phe Ser Glu Thr Ile Pro Ala Pro Thr Gly Lys
    50                  55                  60

Asn Glu Ala Gln Gln Lys Ser Asp Leu Glu Leu Leu Arg Ile Ser Leu
65                  70                  75                  80

Leu Leu Ile Gln Ser Trp Leu Gly Pro Leu Gln Phe Leu Ser Arg Val
                85                  90                  95

Phe Thr Asn Ser Leu Val Phe Gly Thr Ser Asp Arg Val Tyr Glu Lys
            100                 105                 110

Leu Lys Asp Leu Glu Glu Gly Ile Leu Ala Leu Met Arg Glu Leu Glu
        115                 120                 125

Asp Gly Thr Pro Arg Ala Gly Gln Ile Leu Lys Arg Thr Tyr Asp Lys
    130                 135                 140

Phe Asp Thr Asn Met Arg Ser Asp Asp Ala Leu Leu Lys Asn Tyr Gly
145                 150                 155                 160

Leu Leu Ser Cys Phe Arg Lys Asp Leu His Lys Thr Glu Thr Tyr Leu
                165                 170                 175

Arg Val Met Lys Cys Arg Arg Phe Gly Glu Ala Ser Cys Ala Phe
            180                 185                 190

<210> SEQ ID NO 223
<211> LENGTH: 14
<212> TYPE: PRT
```

```
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 223

Leu Ser Glu Asn Asp Glu Trp Thr Gln Asp Arg Ala Lys Pro
1               5                   10

<210> SEQ ID NO 224
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 224

Asn Pro Phe Pro Thr Trp Arg Lys Arg Pro Gly
1               5                   10

<210> SEQ ID NO 225
<211> LENGTH: 134
<212> TYPE: PRT
<213> ORGANISM: Homo sapiens

<400> SEQUENCE: 225

Met Asp Pro Gln Thr Ala Pro Ser Arg Ala Leu Leu Leu Leu Leu Phe
1               5                   10                  15

Leu His Leu Ala Phe Leu Gly Gly Arg Ser His Pro Leu Gly Ser Pro
            20                  25                  30

Gly Ser Ala Ser Asp Leu Glu Thr Ser Gly Leu Gln Glu Gln Arg Asn
        35                  40                  45

His Leu Gln Gly Lys Leu Ser Glu Leu Gln Val Glu Gln Thr Ser Leu
    50                  55                  60

Glu Pro Leu Gln Glu Ser Pro Arg Pro Thr Gly Val Trp Lys Ser Arg
65                  70                  75                  80

Glu Val Ala Thr Glu Gly Ile Arg Gly His Arg Lys Met Val Leu Tyr
                85                  90                  95

Thr Leu Arg Ala Pro Arg Ser Pro Lys Met Val Gln Gly Ser Gly Cys
            100                 105                 110

Phe Gly Arg Lys Met Asp Arg Ile Ser Ser Ser Ser Gly Leu Gly Cys
        115                 120                 125

Lys Val Leu Arg Arg His
    130

<210> SEQ ID NO 226
<211> LENGTH: 87
<212> TYPE: PRT
<213> ORGANISM: Heloderma suspectum

<400> SEQUENCE: 226

Met Lys Ile Ile Leu Trp Leu Cys Val Phe Gly Leu Phe Leu Ala Thr
1               5                   10                  15

Leu Phe Pro Ile Ser Trp Gln Met Pro Val Glu Ser Gly Leu Ser Ser
            20                  25                  30

Glu Asp Ser Ala Ser Ser Glu Ser Phe Ala Ser Lys Ile Lys Arg His
        35                  40                  45

Gly Glu Gly Thr Phe Thr Ser Asp Leu Ser Lys Gln Met Glu Glu Glu
```

```
                   50                  55                  60
Ala Val Arg Leu Phe Ile Glu Trp Leu Lys Asn Gly Gly Pro Ser Ser
 65                  70                  75                  80

Gly Ala Pro Pro Ser Gly
                 85

<210> SEQ ID NO 227
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 227

His Gly Val Ser Gly His Gly Gln His Gly Val His Gly
 1               5                  10

<210> SEQ ID NO 228
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (1)..(1)
<223> OTHER INFORMATION: /note="N-term acetylated"
<220> FEATURE:
<221> NAME/KEY: misc_feature
<222> LOCATION: (9)..(9)
<223> OTHER INFORMATION: /note="C-term amidated"

<400> SEQUENCE: 228

Lys Trp Arg Arg Trp Val Arg Trp Ile
 1               5

<210> SEQ ID NO 229
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 229

Lys Phe His Glu Lys His His Ser His Arg Gly Tyr
 1               5                  10

<210> SEQ ID NO 230
<211> LENGTH: 51
<212> TYPE: PRT
<213> ORGANISM: Homo sapiens

<400> SEQUENCE: 230

Met Lys Phe Phe Val Phe Ala Leu Ile Leu Ala Leu Met Leu Ser Met
 1               5                  10                  15

Thr Gly Ala Asp Ser His Ala Lys Arg His His Gly Tyr Lys Arg Lys
                20                  25                  30

Phe His Glu Lys His His Ser His Arg Gly Tyr Arg Ser Asn Tyr Leu
             35                  40                  45

Tyr Asp Asn
```

-continued

```
<210> SEQ ID NO 231
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 231

Met Gln Cys Asn Ser
1               5

<210> SEQ ID NO 232
<211> LENGTH: 390
<212> TYPE: PRT
<213> ORGANISM: Homo sapiens

<400> SEQUENCE: 232

Met Pro Pro Ser Gly Leu Arg Leu Leu Pro Leu Leu Leu Pro Leu Leu
1               5                   10                  15

Trp Leu Leu Val Leu Thr Pro Gly Arg Pro Ala Ala Gly Leu Ser Thr
            20                  25                  30

Cys Lys Thr Ile Asp Met Glu Leu Val Lys Arg Lys Arg Ile Glu Ala
        35                  40                  45

Ile Arg Gly Gln Ile Leu Ser Lys Leu Arg Leu Ala Ser Pro Pro Ser
    50                  55                  60

Gln Gly Glu Val Pro Pro Gly Pro Leu Pro Glu Ala Val Leu Ala Leu
65                  70                  75                  80

Tyr Asn Ser Thr Arg Asp Arg Val Ala Gly Glu Ser Ala Glu Pro Glu
                85                  90                  95

Pro Glu Pro Glu Ala Asp Tyr Tyr Ala Lys Glu Val Thr Arg Val Leu
            100                 105                 110

Met Val Glu Thr His Asn Glu Ile Tyr Asp Lys Phe Lys Gln Ser Thr
        115                 120                 125

His Ser Ile Tyr Met Phe Phe Asn Thr Ser Glu Leu Arg Glu Ala Val
    130                 135                 140

Pro Glu Pro Val Leu Leu Ser Arg Ala Glu Leu Arg Leu Leu Arg Leu
145                 150                 155                 160

Lys Leu Lys Val Glu Gln His Val Glu Leu Tyr Gln Lys Tyr Ser Asn
                165                 170                 175

Asn Ser Trp Arg Tyr Leu Ser Asn Arg Leu Leu Ala Pro Ser Asp Ser
            180                 185                 190

Pro Glu Trp Leu Ser Phe Asp Val Thr Gly Val Val Arg Gln Trp Leu
        195                 200                 205

Ser Arg Gly Gly Glu Ile Glu Gly Phe Arg Leu Ser Ala His Cys Ser
    210                 215                 220

Cys Asp Ser Arg Asp Asn Thr Leu Gln Val Asp Ile Asn Gly Phe Thr
225                 230                 235                 240

Thr Gly Arg Arg Gly Asp Leu Ala Thr Ile His Gly Met Asn Arg Pro
                245                 250                 255

Phe Leu Leu Leu Met Ala Thr Pro Leu Glu Arg Ala Gln His Leu Gln
            260                 265                 270

Ser Ser Arg His Arg Arg Ala Leu Asp Thr Asn Tyr Cys Phe Ser Ser
        275                 280                 285
```

```
Thr Glu Lys Asn Cys Cys Val Arg Gln Leu Tyr Ile Asp Phe Arg Lys
            290                 295                 300

Asp Leu Gly Trp Lys Trp Ile His Glu Pro Lys Gly Tyr His Ala Asn
305                 310                 315                 320

Phe Cys Leu Gly Pro Cys Pro Tyr Ile Trp Ser Leu Asp Thr Gln Tyr
                325                 330                 335

Ser Lys Val Leu Ala Leu Tyr Asn Gln His Asn Pro Gly Ala Ser Ala
            340                 345                 350

Ala Pro Cys Cys Val Pro Gln Ala Leu Glu Pro Leu Pro Ile Val Tyr
            355                 360                 365

Tyr Val Gly Arg Lys Pro Lys Val Glu Gln Leu Ser Asn Met Ile Val
    370                 375                 380

Arg Ser Cys Lys Cys Ser
385                 390

<210> SEQ ID NO 233
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 233

Cys Asn Gly Arg Cys Gly
1               5

<210> SEQ ID NO 234
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 234

Val Pro Val Asp
1

<210> SEQ ID NO 235
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 235

Val Pro Asp Pro Arg
1               5

<210> SEQ ID NO 236
<211> LENGTH: 348
<212> TYPE: PRT
<213> ORGANISM: Homo sapiens

<400> SEQUENCE: 236

Met Leu Gln Thr Lys Asp Leu Ile Trp Thr Leu Phe Phe Leu Gly Thr
1               5                   10                  15

Ala Val Ser Leu Gln Val Asp Ile Val Pro Ser Gln Gly Glu Ile Ser
            20                  25                  30
```

Val Gly Glu Ser Lys Phe Phe Leu Cys Gln Val Ala Gly Asp Ala Lys
            35                  40                  45

Asp Lys Asp Ile Ser Trp Phe Ser Pro Asn Gly Glu Lys Leu Thr Pro
 50                  55                  60

Asn Gln Gln Arg Ile Ser Val Val Trp Asn Asp Asp Ser Ser Ser Thr
 65                  70                  75                  80

Leu Thr Ile Tyr Asn Ala Asn Ile Asp Asp Ala Gly Ile Tyr Lys Cys
                85                  90                  95

Val Val Thr Gly Glu Asp Gly Ser Glu Ser Glu Ala Thr Val Asn Val
            100                 105                 110

Lys Ile Phe Gln Lys Leu Met Phe Lys Asn Ala Pro Thr Pro Gln Glu
            115                 120                 125

Phe Arg Glu Gly Glu Asp Ala Val Ile Val Cys Asp Val Val Ser Ser
130                 135                 140

Leu Pro Pro Thr Ile Ile Trp Lys His Lys Gly Arg Asp Val Ile Leu
145                 150                 155                 160

Lys Lys Asp Val Arg Phe Ile Phe Leu Ser Asn Asn Tyr Leu Pro Ile
                165                 170                 175

Pro Gly Ile Lys Lys Thr Asp Glu Gly Thr Tyr Arg Cys Glu Gly Arg
            180                 185                 190

Ile Leu Ala Arg Gly Glu Ile Asn Phe Asn Asp Ile Gln Val Ile Val
            195                 200                 205

Asn Val Pro Pro Thr Ile Gln Ala Arg Gln Asn Ile Val Asn Ala Thr
 210                 215                 220

Ala Asn Leu Gly Gln Ser Val Thr Leu Val Cys Asp Ala Glu Gly Phe
225                 230                 235                 240

Pro Gly Pro Thr Met Ser Trp Thr Lys Asp Gly Glu Gln Ile Glu Gln
                245                 250                 255

Glu Glu His Asp Glu Lys Tyr Leu Phe Ser Asp Asp Ser Ser His Leu
            260                 265                 270

Thr Ile Lys Lys Val Asp Lys Asn His Glu Ala Glu Asn Ile Cys Ile
            275                 280                 285

Ala Glu Asn Lys Val Gly Glu Gln Asp Ala Thr Ile His Leu Lys Val
            290                 295                 300

Phe Ala Lys Pro Gln Ile Thr Tyr Val Glu Asp Gln Thr Ala Met Glu
305                 310                 315                 320

Leu Ala Glu Gln Val Ile Leu Thr Val Glu Ala Ser Gly Asp His Ile
                325                 330                 335

Pro Tyr Ile Thr Trp Trp Thr Ser Thr Trp Gln Ile
            340                 345

<210> SEQ ID NO 237
<211> LENGTH: 153
<212> TYPE: PRT
<213> ORGANISM: Homo sapiens

<400> SEQUENCE: 237

Met Val Ala Thr Lys Thr Phe Ala Leu Leu Leu Ser Leu Phe Leu
1               5                   10                  15

Ala Val Gly Leu Gly Glu Lys Lys Glu Gly His Phe Ser Ala Leu Pro
            20                  25                  30

Ser Leu Pro Val Gly Ser His Ala Lys Val Ser Ser Pro Gln Pro Arg
            35                  40                  45

Gly Pro Arg Tyr Ala Glu Gly Thr Phe Ile Ser Asp Tyr Ser Ile Ala

Met Asp Lys Ile His Gln Gln Asp Phe Val Asn Trp Leu Leu Ala Gln
65                  70                  75                  80

Lys Gly Lys Lys Asn Asp Trp Lys His Asn Ile Thr Gln Arg Glu Ala
                85                  90                  95

Arg Ala Leu Glu Leu Ala Ser Gln Ala Asn Arg Lys Glu Glu Glu Ala
            100                 105                 110

Val Glu Pro Gln Ser Ser Pro Ala Lys Asn Pro Ser Asp Glu Asp Leu
        115                 120                 125

Leu Arg Asp Leu Leu Ile Gln Glu Leu Leu Ala Cys Leu Leu Asp Gln
    130                 135                 140

Thr Asn Leu Cys Arg Leu Arg Ser Arg
145                 150

<210> SEQ ID NO 238
<211> LENGTH: 24
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 238

Glu Leu Tyr Ser Ala Leu Ala Asn Lys Cys Cys His Val Gly Cys Thr
1               5                   10                  15

Lys Arg Ser Leu Ala Arg Phe Cys
            20

<210> SEQ ID NO 239
<211> LENGTH: 28
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 239

Asp Ser Trp Met Glu Glu Val Ile Lys Leu Cys Gly Arg Glu Leu Val
1               5                   10                  15

Arg Ala Gln Ile Ala Ile Cys Gly Met Ser Thr Ser
            20                  25

<210> SEQ ID NO 240
<211> LENGTH: 31
<212> TYPE: PRT
<213> ORGANISM: Homo sapiens

<400> SEQUENCE: 240

Glu Ala Glu Asp Leu Gln Val Gly Gln Val Glu Leu Gly Gly Gly Pro
1               5                   10                  15

Gly Ala Gly Ser Leu Gln Pro Leu Ala Leu Glu Gly Ser Leu Gln
            20                  25                  30

<210> SEQ ID NO 241
<211> LENGTH: 80
<212> TYPE: PRT
<213> ORGANISM: Homo sapiens

<400> SEQUENCE: 241

Met Asp Lys Phe Trp Trp His Ala Ala Trp Gly Leu Cys Leu Val Pro

```
                1               5                  10                 15
Leu Ser Leu Ala Gln Ile Asp Leu Asn Ile Thr Cys Arg Phe Ala Gly
                20                 25                 30

Val Phe His Val Glu Lys Asn Gly Arg Tyr Ser Ile Ser Arg Thr Glu
        35                 40                 45

Ala Ala Asp Leu Cys Lys Ala Phe Asn Ser Thr Leu Pro Thr Met Ala
    50                 55                 60

Gln Met Glu Lys Ala Leu Ser Ile Gly Phe Glu Thr Cys Ser Ser Thr
65                  70                 75                 80
```

<210> SEQ ID NO 242
<211> LENGTH: 83
<212> TYPE: PRT
<213> ORGANISM: Bitis arietans

<400> SEQUENCE: 242

```
Ser Pro Pro Val Cys Gly Asn Lys Ile Leu Glu Gln Gly Glu Asp Cys
1               5                  10                 15

Asp Cys Gly Ser Pro Ala Asn Cys Gln Asp Arg Cys Cys Asn Ala Ala
            20                 25                 30

Thr Cys Lys Leu Thr Pro Gly Ser Gln Cys Asn Tyr Gly Glu Cys Cys
        35                 40                 45

Asp Gln Cys Arg Phe Lys Lys Ala Gly Thr Val Cys Arg Ile Ala Arg
    50                 55                 60

Gly Asp Trp Asn Asp Asp Tyr Cys Thr Gly Lys Ser Ser Asp Cys Pro
65                  70                 75                 80

Trp Asn His
```

<210> SEQ ID NO 243
<211> LENGTH: 50
<212> TYPE: PRT
<213> ORGANISM: Homo sapiens

<400> SEQUENCE: 243

```
Met Glu Cys Glu Ser Gly Pro Cys Cys Arg Asn Cys Lys Phe Leu Lys
1               5                  10                 15

Glu Gly Thr Ile Cys Lys Arg Ala Arg Gly Asp Asp Leu Asp Asp Tyr
            20                 25                 30

Cys Asn Gly Lys Thr Cys Asp Cys Pro Arg Asn Pro His Lys Gly Pro
        35                 40                 45

Ala Thr
    50
```

<210> SEQ ID NO 244
<211> LENGTH: 82
<212> TYPE: PRT
<213> ORGANISM: Homo sapiens

<400> SEQUENCE: 244

```
Glu Ala Ser Trp Lys Pro Arg Ser Gln Gln Pro Asp Ala Pro Leu Gly
1               5                  10                 15

Thr Gly Ala Asn Arg Asp Leu Glu Leu Pro Trp Leu Glu Gln Gln Gly
            20                 25                 30

Pro Ala Ser His His Arg Arg Gln Leu Gly Pro Gln Gly Pro Pro His
        35                 40                 45

Leu Val Ala Asp Pro Ser Lys Lys Gln Gly Pro Trp Leu Glu Glu Glu
    50                 55                 60
```

Glu Glu Ala Tyr Gly Trp Met Asp Phe Gly Arg Ser Ala Glu Asp
65                  70                  75                  80

Glu Asn

<210> SEQ ID NO 245
<211> LENGTH: 23
<212> TYPE: PRT
<213> ORGANISM: Human herpesvirus 1

<400> SEQUENCE: 245

Met Gly Gly Ala Ala Ala Arg Leu Gly Ala Val Ile Leu Phe Val Val
1               5                   10                  15

Ile Val Gly Leu His Gly Val
            20

<210> SEQ ID NO 246
<211> LENGTH: 12
<212> TYPE: PRT
<213> ORGANISM: Homo sapiens

<400> SEQUENCE: 246

Leu Tyr Glu Asn Lys Pro Arg Arg Pro Tyr Ile Leu
1               5                   10

<210> SEQ ID NO 247
<211> LENGTH: 176
<212> TYPE: PRT
<213> ORGANISM: Homo sapiens

<400> SEQUENCE: 247

Met Lys Val Leu Leu Cys Asp Leu Leu Leu Ser Leu Phe Ser Ser
1               5                   10                  15

Val Phe Ser Ser Cys Gln Arg Asp Cys Leu Thr Cys Gln Glu Lys Leu
                20                  25                  30

His Pro Ala Leu Asp Ser Phe Asp Leu Glu Val Cys Ile Leu Glu Cys
            35                  40                  45

Glu Glu Lys Val Phe Pro Ser Pro Leu Trp Thr Pro Cys Thr Lys Val
        50                  55                  60

Met Ala Arg Ser Ser Trp Gln Leu Ser Pro Ala Ala Pro Glu His Val
65                  70                  75                  80

Ala Ala Ala Leu Tyr Gln Pro Arg Ala Ser Glu Met Gln His Leu Arg
                85                  90                  95

Arg Met Pro Arg Val Arg Ser Leu Phe Gln Glu Gln Glu Glu Pro Glu
                100                 105                 110

Pro Gly Met Glu Glu Ala Gly Glu Met Glu Gln Lys Gln Leu Gln Lys
            115                 120                 125

Arg Phe Gly Gly Phe Thr Gly Ala Arg Lys Ser Ala Arg Lys Leu Ala
        130                 135                 140

Asn Gln Lys Arg Phe Ser Glu Phe Met Arg Gln Tyr Leu Val Leu Ser
145                 150                 155                 160

Met Gln Ser Ser Gln Arg Arg Arg Thr Leu His Gln Asn Gly Asn Val
                165                 170                 175

<210> SEQ ID NO 248
<211> LENGTH: 37
<212> TYPE: PRT
<213> ORGANISM: Homo sapiens

<400> SEQUENCE: 248

-continued

```
His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala
            35

<210> SEQ ID NO 249
<211> LENGTH: 49
<212> TYPE: PRT
<213> ORGANISM: Sus scrofa

<400> SEQUENCE: 249

Gly Trp Pro Gln Ala Pro Ala Met Asp Gly Ala Gly Lys Thr Gly Ala
1               5                   10                  15

Glu Glu Ala Gln Pro Pro Glu Gly Lys Gly Ala Arg Glu His Ser Arg
            20                  25                  30

Gln Glu Glu Glu Glu Glu Thr Ala Gly Ala Pro Gln Gly Leu Phe Arg
            35                  40                  45

Gly

<210> SEQ ID NO 250
<211> LENGTH: 185
<212> TYPE: PRT
<213> ORGANISM: Homo sapiens

<400> SEQUENCE: 250

Met Pro Arg Leu Phe Leu Phe His Leu Leu Glu Phe Cys Leu Leu Leu
1               5                   10                  15

Asn Gln Phe Ser Arg Ala Val Ala Ala Lys Trp Lys Asp Asp Val Ile
            20                  25                  30

Lys Leu Cys Gly Arg Glu Leu Val Arg Ala Gln Ile Ala Ile Cys Gly
            35                  40                  45

Met Ser Thr Trp Ser Lys Arg Ser Leu Ser Gln Glu Asp Ala Pro Gln
    50                  55                  60

Thr Pro Arg Pro Val Ala Glu Ile Val Pro Ser Phe Ile Asn Lys Asp
65                  70                  75                  80

Thr Glu Thr Ile Ile Ile Met Leu Glu Phe Ile Ala Asn Leu Pro Pro
                85                  90                  95

Glu Leu Lys Ala Ala Leu Ser Glu Arg Gln Pro Ser Leu Pro Glu Leu
            100                 105                 110

Gln Gln Tyr Val Pro Ala Leu Lys Asp Ser Asn Leu Ser Phe Glu Glu
            115                 120                 125

Phe Lys Lys Leu Ile Arg Asn Arg Gln Ser Glu Ala Ala Asp Ser Asn
130                 135                 140

Pro Ser Glu Leu Lys Tyr Leu Gly Leu Asp Thr His Ser Gln Lys Lys
145                 150                 155                 160

Arg Arg Pro Tyr Val Ala Leu Phe Glu Lys Cys Cys Leu Ile Gly Cys
                165                 170                 175

Thr Lys Arg Ser Leu Ala Lys Tyr Cys
            180                 185

<210> SEQ ID NO 251
<211> LENGTH: 27
<212> TYPE: PRT
<213> ORGANISM: Homo sapiens

<400> SEQUENCE: 251
```

His Ser Asp Gly Thr Phe Thr Ser Glu Leu Ser Arg Leu Arg Glu Gly
1               5                   10                  15

Ala Arg Leu Gln Arg Leu Leu Gln Gly Leu Val
            20                  25

<210> SEQ ID NO 252
<211> LENGTH: 207
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 252

Met Ala Pro Phe Glu Pro Leu Ala Ser Gly Ile Leu Leu Leu Leu Trp
1               5                   10                  15

Leu Ile Ala Pro Ser Arg Ala Cys Thr Cys Val Pro Pro His Pro Gln
            20                  25                  30

Thr Ala Phe Cys Asn Ser Asp Leu Val Ile Arg Ala Lys Phe Val Gly
        35                  40                  45

Thr Pro Glu Val Asn Gln Thr Thr Leu Tyr Gln Arg Tyr Glu Ile Lys
    50                  55                  60

Met Thr Lys Met Tyr Lys Gly Phe Gln Ala Leu Gly Asp Ala Ala Asp
65                  70                  75                  80

Ile Arg Phe Val Tyr Thr Pro Ala Met Glu Ser Val Cys Gly Tyr Phe
                85                  90                  95

His Arg Ser His Asn Arg Ser Glu Glu Phe Leu Ile Ala Gly Lys Leu
            100                 105                 110

Gln Asp Gly Leu Leu His Ile Thr Thr Cys Ser Phe Val Ala Pro Trp
        115                 120                 125

Asn Ser Leu Ser Leu Ala Gln Arg Arg Gly Phe Thr Lys Thr Tyr Thr
    130                 135                 140

Val Gly Cys Glu Glu Cys Thr Val Phe Pro Cys Leu Ser Ile Pro Cys
145                 150                 155                 160

Lys Leu Gln Ser Gly Thr His Cys Leu Trp Thr Asp Gln Leu Leu Gln
                165                 170                 175

Gly Ser Glu Lys Gly Phe Gln Ser Arg His Leu Ala Cys Leu Pro Arg
            180                 185                 190

Glu Pro Gly Leu Cys Thr Trp Gln Ser Leu Arg Ser Gln Ile Ala
        195                 200                 205

<210> SEQ ID NO 253
<211> LENGTH: 74
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 253

Asp Thr Thr Val Ser Glu Pro Ala Pro Ser Cys Val Thr Leu Tyr Gln
1               5                   10                  15

Ser Trp Arg Tyr Ser Gln Ala Asp Asn Gly Cys Ala Gln Thr Val Thr
            20                  25                  30

Val Lys Val Val Tyr Glu Asp Asp Thr Glu Gly Leu Cys Tyr Ala Val
        35                  40                  45

```
Ala Pro Gly Gln Ile Thr Thr Val Gly Asp Gly Tyr Ile Gly Ser His
            50                  55                  60
Gly His Ala Arg Tyr Leu Ala Arg Cys Leu
 65                  70
```

<210> SEQ ID NO 254
<211> LENGTH: 44
<212> TYPE: PRT
<213> ORGANISM: Homo sapiens

<400> SEQUENCE: 254

```
Met Ser Asp Lys Pro Asp Met Ala Glu Ile Glu Lys Phe Asp Lys Ser
 1               5                  10                  15
Lys Leu Lys Lys Thr Glu Thr Gln Glu Lys Asn Pro Leu Pro Ser Lys
                20                  25                  30
Glu Thr Ile Glu Gln Glu Lys Gln Ala Gly Glu Ser
            35                  40
```

<210> SEQ ID NO 255
<211> LENGTH: 32
<212> TYPE: PRT
<213> ORGANISM: Rana tigrina

<400> SEQUENCE: 255

```
Thr Ala Pro Arg Ser Leu Arg Arg Ser Ser Cys Phe Gly Gly Arg Met
 1               5                  10                  15
Asp Arg Ile Gly Ala Gln Ser Gly Leu Gly Cys Asn Ser Phe Arg Tyr
                20                  25                  30
```

<210> SEQ ID NO 256
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 256

```
Gly Ser Arg Ala His Ser Ser His Leu Lys
 1               5                  10
```

<210> SEQ ID NO 257
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 257

```
Glu Leu Lys Cys Tyr Thr Cys Lys Glu Pro Met Thr Ser Ala Ala Cys
 1               5                  10                  15
```

<210> SEQ ID NO 258
<211> LENGTH: 4
<212> TYPE: PRT
<213> ORGANISM: Homo sapiens

<400> SEQUENCE: 258

```
Asp Ala His Lys
 1
```

-continued

```
<210> SEQ ID NO 259
<211> LENGTH: 38
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 259

Lys Met Val Gln Gly Ser Gly Cys Phe Gly Arg Lys Met Asp Ile Ser
1               5                   10                  15

Ser Ser Ser Gly Leu Gly Cys Pro Ser Leu Arg Asp Pro Arg Pro Asn
            20                  25                  30

Ala Pro Ser Thr Ser Ala
        35

<210> SEQ ID NO 260
<211> LENGTH: 54
<212> TYPE: PRT
<213> ORGANISM: Homo sapiens
<220> FEATURE:
<221> NAME/KEY: misc_feature
<222> LOCATION: (54)..(54)
<223> OTHER INFORMATION: /note="C-term amidated"

<400> SEQUENCE: 260

Gly Thr Ser Leu Ser Pro Pro Glu Ser Ser Gly Ser Pro Gln Gln
1               5                   10                  15

Pro Gly Leu Ser Ala Pro His Ser Arg Gln Ile Pro Ala Pro Gln Gly
            20                  25                  30

Ala Val Leu Val Gln Arg Glu Lys Asp Leu Pro Asn Tyr Asn Trp Asn
        35                  40                  45

Ser Phe Gly Leu Arg Phe
    50

<210> SEQ ID NO 261
<211> LENGTH: 14
<212> TYPE: PRT
<213> ORGANISM: Homo sapiens
<220> FEATURE:
<221> NAME/KEY: misc_feature
<222> LOCATION: (14)..(14)
<223> OTHER INFORMATION: /note="C-term amidated"

<400> SEQUENCE: 261

Asp Leu Pro Asn Tyr Asn Trp Asn Ser Phe Gly Leu Arg Phe
1               5                   10

<210> SEQ ID NO 262
<211> LENGTH: 13
<212> TYPE: PRT
<213> ORGANISM: Homo sapiens
<220> FEATURE:
<221> NAME/KEY: misc_feature
<222> LOCATION: (13)..(13)
<223> OTHER INFORMATION: /note="C-term amidated"

<400> SEQUENCE: 262

Leu Pro Asn Tyr Asn Trp Asn Ser Phe Gly Leu Arg Phe
1               5                   10

<210> SEQ ID NO 263
<211> LENGTH: 10
<212> TYPE: PRT
<213> ORGANISM: Homo sapiens
```

-continued

```
<220> FEATURE:
<221> NAME/KEY: misc_feature
<222> LOCATION: (10)..(10)
<223> OTHER INFORMATION: /note="C-term amidated"

<400> SEQUENCE: 263

Tyr Asn Trp Asn Ser Phe Gly Leu Arg Phe
1               5                   10

<210> SEQ ID NO 264
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (1)..(16)
<223> OTHER INFORMATION: /note="Disulfide bridge"
<220> FEATURE:
<221> NAME/KEY: misc_feature
<222> LOCATION: (8)..(20)
<223> OTHER INFORMATION: /note="Disulfide bridge"
<220> FEATURE:
<221> NAME/KEY: misc_feature
<222> LOCATION: (15)..(25)
<223> OTHER INFORMATION: /note="Disulfide bridge"
<220> FEATURE:
<221> NAME/KEY: misc_feature
<222> LOCATION: (25)..(25)
<223> OTHER INFORMATION: /note="C-term amidated"

<400> SEQUENCE: 264

Cys Lys Gly Lys Gly Ala Lys Cys Ser Arg Leu Met Tyr Asp Cys Cys
1               5                   10                  15

Thr Gly Ser Cys Arg Ser Gly Lys Cys
            20                  25

<210> SEQ ID NO 265
<211> LENGTH: 18
<212> TYPE: PRT
<213> ORGANISM: Sus scrofa
<220> FEATURE:
<221> NAME/KEY: misc_feature
<222> LOCATION: (18)..(18)
<223> OTHER INFORMATION: /note="C-term amidated"

<400> SEQUENCE: 265

Arg Gly Gly Arg Leu Cys Tyr Cys Arg Arg Arg Phe Cys Val Cys Val
1               5                   10                  15

Gly Arg

<210> SEQ ID NO 266
<211> LENGTH: 26
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (1)..(1)
<223> OTHER INFORMATION: /note="N-term acetylated"
<220> FEATURE:
<221> NAME/KEY: misc_feature
<222> LOCATION: (26)..(26)
<223> OTHER INFORMATION: /note="C-term amidated"
```

```
<400> SEQUENCE: 266

Lys Trp Lys Ser Phe Leu Lys Thr Phe Lys Ser Ala Val Lys Thr Val
1               5                   10                  15

Leu His Thr Ala Leu Lys Ala Ile Ser Ser
            20                  25

<210> SEQ ID NO 267
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 267

Lys Trp Lys Ser Phe Leu Lys Thr Phe Lys Ser Val Lys Thr Val Leu
1               5                   10                  15

His Thr Ala Leu Lys Ala Ile Ser Ser
            20                  25

<210> SEQ ID NO 268
<211> LENGTH: 26
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 268

Lys Trp Lys Ser Phe Leu Lys Thr Phe Lys Ser Ala Lys Lys Thr Val
1               5                   10                  15

Leu His Thr Ala Leu Lys Ala Ile Ser Ser
            20                  25

<210> SEQ ID NO 269
<211> LENGTH: 26
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 269

Lys Trp Lys Ser Phe Leu Lys Thr Phe Lys Ser Ala Lys Lys Lys Val
1               5                   10                  15

Leu His Thr Ala Leu Lys Ala Ile Ser Ser
            20                  25

<210> SEQ ID NO 270
<211> LENGTH: 33
<212> TYPE: PRT
<213> ORGANISM: Homo sapiens

<400> SEQUENCE: 270

His Ala Asp Gly Ser Phe Ser Asp Glu Met Asn Thr Ile Leu Asp Asn
1               5                   10                  15

Leu Ala Ala Arg Asp Phe Ile Asn Trp Leu Ile Gln Thr Lys Ile Thr
            20                  25                  30

Asp
```

<210> SEQ ID NO 271
<211> LENGTH: 33
<212> TYPE: PRT
<213> ORGANISM: Homo sapiens

<400> SEQUENCE: 271

His Gly Asp Gly Ser Phe Ser Asp Glu Met Asn Thr Ile Leu Asp Asn
1               5                   10                  15

Leu Ala Ala Arg Asp Phe Ile Asn Trp Leu Ile Gln Thr Lys Ile Thr
            20                  25                  30

Asp

<210> SEQ ID NO 272
<211> LENGTH: 34
<212> TYPE: PRT
<213> ORGANISM: Homo sapiens

<400> SEQUENCE: 272

His Gly Asp Gly Ser Phe Ser Asp Glu Met Asn Thr Ile Leu Asp Asn
1               5                   10                  15

Leu Ala Ala Arg Asp Phe Ile Asn Trp Leu Ile Gln Thr Lys Ile Thr
            20                  25                  30

Asp Cys

<210> SEQ ID NO 273
<211> LENGTH: 16
<212> TYPE: PRT
<213> ORGANISM: Homo sapiens

<400> SEQUENCE: 273

Leu Arg Ile Val Gln Cys Ala Ser Val Glu Gly Ser Cys Gly Phe Tyr
1               5                   10                  15

<210> SEQ ID NO 274
<211> LENGTH: 16
<212> TYPE: PRT
<213> ORGANISM: Homo sapiens
<220> FEATURE:
<221> NAME/KEY: misc_feature
<222> LOCATION: (1)..(1)
<223> OTHER INFORMATION: /note="N-term acetylated"

<400> SEQUENCE: 274

Leu Arg Ile Val Gln Cys Ala Lys Val Glu Gly Ser Cys Gly Phe Tyr
1               5                   10                  15

<210> SEQ ID NO 275
<211> LENGTH: 17
<212> TYPE: PRT
<213> ORGANISM: Homo sapiens
<220> FEATURE:
<221> NAME/KEY: misc_feature
<222> LOCATION: (1)..(1)
<223> OTHER INFORMATION: /note="N-term acetylated"

<400> SEQUENCE: 275

Leu Arg Ile Val Gln Cys Ala Ser Val Glu Gly Ser Cys Gly Phe Tyr
1               5                   10                  15

Lys

<210> SEQ ID NO 276
<211> LENGTH: 31
<212> TYPE: PRT
<213> ORGANISM: Homo sapiens

```
<400> SEQUENCE: 276

Glu Ala Glu Asp Leu Gln Val Gly Gln Val Glu Leu Gly Gly Gly Pro
1               5                   10                  15

Gly Ala Gly Ser Leu Gln Pro Leu Ala Leu Glu Gly Ser Leu Gln
            20                  25                  30

<210> SEQ ID NO 277
<211> LENGTH: 16
<212> TYPE: PRT
<213> ORGANISM: Sus scrofa

<400> SEQUENCE: 277

Arg Gly Gly Arg Leu Cys Tyr Cys Arg Arg Phe Cys Ile Cys Val
1               5                   10                  15

<210> SEQ ID NO 278
<211> LENGTH: 19
<212> TYPE: PRT
<213> ORGANISM: Sus scrofa

<400> SEQUENCE: 278

Arg Gly Gly Gly Leu Cys Tyr Cys Arg Arg Phe Cys Val Cys Val
1               5                   10                  15

Gly Arg Gly

<210> SEQ ID NO 279
<211> LENGTH: 19
<212> TYPE: PRT
<213> ORGANISM: Sus scrofa

<400> SEQUENCE: 279

Arg Gly Gly Arg Leu Cys Tyr Cys Arg Gly Trp Ile Cys Phe Cys Val
1               5                   10                  15

Gly Arg Gly

<210> SEQ ID NO 280
<211> LENGTH: 19
<212> TYPE: PRT
<213> ORGANISM: Sus scrofa

<400> SEQUENCE: 280

Arg Gly Gly Arg Leu Cys Tyr Cys Arg Pro Arg Phe Cys Val Cys Val
1               5                   10                  15

Gly Arg Gly

<210> SEQ ID NO 281
<211> LENGTH: 149
<212> TYPE: PRT
<213> ORGANISM: Sus scrofa

<400> SEQUENCE: 281

Met Glu Thr Gln Arg Ala Ser Leu Cys Leu Gly Arg Trp Ser Leu Trp
1               5                   10                  15

Leu Leu Leu Leu Gly Leu Val Val Pro Ser Ala Ser Ala Gln Ala Leu
            20                  25                  30

Ser Tyr Arg Glu Ala Val Leu Arg Ala Val Asp Arg Leu Asn Glu Gln
            35                  40                  45

Ser Ser Glu Ala Asn Leu Tyr Arg Leu Leu Glu Leu Asp Gln Pro Pro
        50                  55                  60
```

-continued

Lys Ala Asp Glu Asp Pro Gly Thr Pro Lys Pro Val Ser Phe Thr Val
65                  70                  75                  80

Lys Glu Thr Val Cys Pro Arg Pro Thr Arg Gln Pro Pro Glu Leu Cys
                85                  90                  95

Asp Phe Lys Glu Asn Gly Arg Val Lys Gln Cys Val Gly Thr Val Thr
            100                 105                 110

Leu Asp Gln Ile Lys Asp Pro Leu Asp Ile Thr Cys Asn Glu Val Gln
        115                 120                 125

Gly Val Arg Gly Arg Leu Cys Tyr Cys Arg Pro Arg Phe Cys Val
    130                 135                 140

Cys Val Gly Arg Gly
145

<210> SEQ ID NO 282
<211> LENGTH: 5
<212> TYPE: PRT
<213> ORGANISM: Homo sapiens

<400> SEQUENCE: 282

Glu Gly Ser Leu Cys
1               5

<210> SEQ ID NO 283
<211> LENGTH: 5
<212> TYPE: PRT
<213> ORGANISM: Homo sapiens

<400> SEQUENCE: 283

Tyr Gly Gly Phe Met
1               5

<210> SEQ ID NO 284
<211> LENGTH: 9
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Tyr(SO3)
<220> FEATURE:
<221> NAME/KEY: MOD_RES
<222> LOCATION: (7)..(7)
<223> OTHER INFORMATION: Norleu

<400> SEQUENCE: 284

Arg Asp Tyr Thr Gly Trp Leu Asp Phe
1               5

<210> SEQ ID NO 285
<211> LENGTH: 13
<212> TYPE: PRT
<213> ORGANISM: Homo sapiens

<400> SEQUENCE: 285

Tyr Gly Gly Phe Leu Arg Arg Ile Arg Pro Lys Leu Lys
1               5                   10

<210> SEQ ID NO 286
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

```
<400> SEQUENCE: 286

Arg Ser Ser Cys Phe Gly Gly Arg Met Asp Arg Ile Gly Ala Gln Ser
1               5                   10                  15

Gly Leu Gly Cys Asn Ser Phe Arg Tyr
            20                  25

<210> SEQ ID NO 287
<211> LENGTH: 37
<212> TYPE: PRT
<213> ORGANISM: Homo sapiens

<400> SEQUENCE: 287

Glu Val Val Pro Pro Gln Val Leu Ser Asp Pro Asn Glu Glu Ala Gly
1               5                   10                  15

Ala Ala Leu Ser Pro Leu Pro Glu Val Pro Pro Trp Thr Gly Glu Val
            20                  25                  30

Ser Pro Ala Gln Arg
        35

<210> SEQ ID NO 288
<211> LENGTH: 65
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 288

Val Val Tyr Thr Asp Cys Thr Glu Ser Gly Gln Asn Leu Cys Leu Cys
1               5                   10                  15

Glu Gly Ser Asn Val Cys Gly Gln Gly Asn Lys Cys Ile Leu Gly Ser
            20                  25                  30

Asp Gly Glu Lys Asn Gln Cys Val Thr Gly Glu Gly Thr Pro Lys Pro
        35                  40                  45

Gln Ser His Asn Asp Gly Asp Phe Glu Glu Ile Pro Glu Glu Tyr Leu
    50                  55                  60

Gln
65

<210> SEQ ID NO 289
<211> LENGTH: 14
<212> TYPE: PRT
<213> ORGANISM: Homo sapiens

<400> SEQUENCE: 289

Ala Leu Lys Arg Gln Gly Arg Thr Leu Tyr Gly Phe Gly Gly
1               5                   10

<210> SEQ ID NO 290
<211> LENGTH: 5
<212> TYPE: PRT
<213> ORGANISM: Homo sapiens

<400> SEQUENCE: 290

Tyr Gly Phe Gly Gly
1               5

<210> SEQ ID NO 291
<211> LENGTH: 11
<212> TYPE: PRT
```

```
<213> ORGANISM: Homo sapiens
<220> FEATURE:
<221> NAME/KEY: misc_feature
<222> LOCATION: (1)..(1)
<223> OTHER INFORMATION: /note="N-term acetylated"

<400> SEQUENCE: 291

Ala Ser Gln Lys Arg Pro Ser Gln Arg His Gly
1               5                   10

<210> SEQ ID NO 292
<211> LENGTH: 11
<212> TYPE: PRT
<213> ORGANISM: Homo sapiens
<220> FEATURE:
<221> NAME/KEY: misc_feature
<222> LOCATION: (1)..(1)
<223> OTHER INFORMATION: /note="N-term acetylated"

<400> SEQUENCE: 292

Ala Ser Gln Tyr Arg Pro Ser Gln Arg His Gly
1               5                   10

<210> SEQ ID NO 293
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Pyro-Glu
<220> FEATURE:
<221> NAME/KEY: misc_feature
<222> LOCATION: (10)..(10)
<223> OTHER INFORMATION: /note="C-term amidated"

<400> SEQUENCE: 293

Glu His Trp Ser Tyr Gly Leu Arg Pro Gly
1               5                   10

<210> SEQ ID NO 294
<211> LENGTH: 15
<212> TYPE: PRT
<213> ORGANISM: Phodopus sp.

<400> SEQUENCE: 294

Gly Leu His Asp Pro Ser His Gly Thr Leu Pro Asn Gly Ser Gly
1               5                   10                  15

<210> SEQ ID NO 295
<211> LENGTH: 41
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 295

Ile Val Leu Ser Leu Asp Val Pro Ile Gly Leu Leu Gln Ile Leu Leu
1               5                   10                  15

Glu Gln Ala Arg Ala Arg Ala Ala Arg Glu Gln Ala Thr Thr Asn Ala
            20                  25                  30

Arg Ile Leu Ala Arg Val Gly His Cys
```

```
<210> SEQ ID NO 296
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (8)..(8)
<223> OTHER INFORMATION: /note="C-term amidated"

<400> SEQUENCE: 296

Lys Pro Ser Ser Pro Pro Glu Glu
1               5

<210> SEQ ID NO 297
<211> LENGTH: 23
<212> TYPE: PRT
<213> ORGANISM: Homo sapiens
<220> FEATURE:
<221> NAME/KEY: misc_feature
<222> LOCATION: (23)..(23)
<223> OTHER INFORMATION: /note="C-term amidated"

<400> SEQUENCE: 297

Phe Asn Ala Pro Phe Asp Val Gly Ile Lys Leu Ser Gly Val Gln Tyr
1               5                   10                  15

Gln Gln His Ser Gln Ala Leu
            20

<210> SEQ ID NO 298
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(2)
<223> OTHER INFORMATION: Lys(Et)

<400> SEQUENCE: 298

Gly Lys Pro Arg
1

<210> SEQ ID NO 299
<211> LENGTH: 22
<212> TYPE: PRT
<213> ORGANISM: Homo sapiens

<400> SEQUENCE: 299

Gly Leu Ser Lys Gly Cys Phe Gly Leu Lys Leu Asp Arg Ile Gly Ser
1               5                   10                  15

Met Ser Gly Leu Gly Cys
            20

<210> SEQ ID NO 300
<211> LENGTH: 49
<212> TYPE: PRT
<213> ORGANISM: Homo sapiens

<400> SEQUENCE: 300
```

```
Tyr Leu Tyr Gln Trp Leu Gly Ala Pro Val Pro Tyr Pro Asp Pro Leu
1               5                   10                  15

Glu Pro Arg Arg Glu Val Cys Glu Leu Asn Pro Asp Cys Asp Glu Leu
            20                  25                  30

Ala Asp His Ile Gly Phe Gln Glu Ala Tyr Arg Arg Phe Tyr Gly Pro
        35                  40                  45

Val

<210> SEQ ID NO 301
<211> LENGTH: 31
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 301

Glu Ala Glu Asp Leu Gln Val Gly Gln Val Leu Glu Gly Gly Gly Pro
1               5                   10                  15

Gly Ala Gly Cys Leu Gln Pro Leu Ala Leu Glu Gly Ser Leu Gln
            20                  25                  30
```